(12) United States Patent
Bhattacharjee et al.

(10) Patent No.: US 10,947,237 B2
(45) Date of Patent: Mar. 16, 2021

(54) ANTIMICROBIAL COMPOUNDS AND METHODS OF MAKING AND USING THE SAME

(71) Applicant: BIOVERSYS AG, Basel (CH)

(72) Inventors: Ashoke Bhattacharjee, Cheshire, CT (US); Erin M. Duffy, Deep River, CT (US); Zoltan F. Kanyo, North Haven, CT (US); Somenath Chowdhury, New Haven, CT (US); Vinay Thakur, New Haven, CT (US); Wan Lau, New Haven, CT (US)

(73) Assignee: BIOVERSYS AG, Basel (CH)

( * ) Notice: Subject to any disclaimer, the term of this patent is extended or adjusted under 35 U.S.C. 154(b) by 0 days.

(21) Appl. No.: 15/557,007

(22) PCT Filed: Mar. 11, 2016

(86) PCT No.: PCT/US2016/022216
§ 371 (c)(1),
(2) Date: Sep. 8, 2017

(87) PCT Pub. No.: WO2016/145417
PCT Pub. Date: Sep. 15, 2016

(65) Prior Publication Data
US 2018/0065966 A1 Mar. 8, 2018

Related U.S. Application Data

(60) Provisional application No. 62/131,751, filed on Mar. 11, 2015.

(51) Int. Cl.
*A61K 31/5025* (2006.01)
*C07D 471/04* (2006.01)
*C07D 487/04* (2006.01)

(52) U.S. Cl.
CPC ......... *C07D 487/04* (2013.01); *C07D 471/04* (2013.01)

(58) Field of Classification Search
CPC . A61K 31/5025; C07D 471/04; C07D 487/04
See application file for complete search history.

(56) References Cited

U.S. PATENT DOCUMENTS

| | | | |
|---|---|---|---|
| 2,624,731 A | 1/1953 | Hitchings et al. | |
| 3,673,184 A | 6/1972 | Minami | |
| 3,980,781 A | 9/1976 | Snell et al. | |
| 4,000,138 A | 12/1976 | Snell et al. | |
| 4,361,557 A | 11/1982 | Nagabhushan | |
| 4,522,811 A | 6/1985 | Eppstein et al. | |
| 4,971,965 A | 11/1990 | Ono et al. | |
| 5,208,141 A | 5/1993 | Ikesu et al. | |
| 5,434,257 A | 7/1995 | Matteucci et al. | |
| 5,567,844 A | 10/1996 | Jommi et al. | |
| 5,763,263 A | 6/1998 | Dehlinger | |
| 5,763,588 A | 6/1998 | Matteucci et al. | |
| 5,766,855 A | 6/1998 | Buchardt et al. | |
| 5,958,930 A | 9/1999 | Gangjee | |
| 6,028,183 A | 2/2000 | Lin et al. | |
| 6,110,925 A | 8/2000 | Williams et al. | |
| 6,162,925 A | 12/2000 | Williams et al. | |
| 6,617,332 B1 | 9/2003 | Brands et al. | |
| 6,875,764 B1 | 4/2005 | Muzi et al. | |
| 7,282,327 B2 | 10/2007 | McGall et al. | |
| 9,023,843 B2 | 5/2015 | Duffy et al. | |
| 9,193,731 B2 | 11/2015 | Duffy et al. | |
| 9,216,979 B2 | 12/2015 | Duffy et al. | |
| 9,221,827 B2 | 12/2015 | Duffy et al. | |
| 9,573,962 B2 | 2/2017 | Duffy et al. | |
| 9,937,183 B2* | 4/2018 | Kanyo ................ | A61K 31/519 |
| 2002/0016297 A1 | 2/2002 | Linde, II et al. | |
| 2002/0193385 A1 | 12/2002 | Chambers et al. | |
| 2003/0158403 A1 | 8/2003 | Manoharan et al. | |
| 2004/0176390 A1 | 9/2004 | Blumberg et al. | |
| 2005/0153992 A1 | 7/2005 | Tsutsumi et al. | |
| 2006/0014743 A1 | 1/2006 | Boojamra et al. | |
| 2006/0100224 A1 | 5/2006 | Svenstrup et al. | |
| 2006/0189631 A1 | 8/2006 | Ruiz et al. | |
| 2007/0206054 A1 | 9/2007 | Watanbe | |
| 2008/0221095 A1 | 9/2008 | Gege et al. | |
| 2008/0255164 A1 | 10/2008 | Albert et al. | |
| 2010/0190747 A1 | 7/2010 | Suzuki et al. | |
| 2010/0249126 A1 | 9/2010 | Burger et al. | |
| 2015/0274752 A1 | 10/2015 | Duffy et al. | |
| 2016/0214988 A1 | 7/2016 | Kanyo et al. | |

(Continued)

FOREIGN PATENT DOCUMENTS

| | | |
|---|---|---|
| CN | 1871240 | 11/2006 |
| CN | 101535311 | 9/2009 |
| CN | 102712647 | 10/2012 |

(Continued)

OTHER PUBLICATIONS

CAS Registry No. 104461-93-0, 1 page, Sep. 27, 1986.
CAS Registry No. 104461-98-5, 1 page, Sep. 27, 1986.
CAS Registry No. 104462-00-2, 1 page, Sep. 27, 1986.
CAS Registry No. 104462-09-1, 1 page, Sep. 27, 1986.
CAS Registry No. 104462-19-3, 1 page, Sep. 27, 1986.
CAS Registry No. 104462-26-2, 1 page, Sep. 27, 1986.
CAS Registry No. 1050590-82-3, 1 page, Sep. 19, 2008.
CAS Registry No. 144841-25-8, 1 page, Dec. 10, 1992.
CAS Registry No. 144841-26-9, 1 page, Dec. 10, 1992.
CAS Registry No. 144841-27-0, 1 page, Dec. 10, 1992.
CAS Registry No. 144841-28-1, 1 page, Dec. 10, 1992.
CAS Registry No. 144841-42-9, 1 page, Dec. 10, 1992.

(Continued)

*Primary Examiner* — Brenda L Coleman
(74) *Attorney, Agent, or Firm* — Brown Rudnick LLP; Thomas C. Meyers

(57) ABSTRACT

The present disclosure relates generally to the field of antimicrobial compounds and to methods of making and using them. These compounds are useful for treating, preventing, reducing the risk of, and delaying the onset of microbial infections in humans and animals.

46 Claims, No Drawings

(56) References Cited

U.S. PATENT DOCUMENTS

2016/0220568 A1   8/2016  Kanyo et al.
2018/0334439 A1  11/2018  Duffy

FOREIGN PATENT DOCUMENTS

| | | |
|---|---|---|
| DE | 3446812 | 6/1986 |
| DE | 10061537 | 6/2002 |
| DE | 10061538 | 6/2002 |
| DE | 10061541 | 6/2002 |
| DE | 10061542 | 6/2002 |
| DE | 10133277 | 1/2003 |
| DE | 10141271 | 3/2003 |
| EP | 0339596 | 11/1989 |
| EP | 1113008 | 7/2001 |
| JP | S42025913 | 9/1965 |
| JP | S5959688 | 4/1984 |
| JP | 61091184 | 5/1986 |
| JP | H03215488 | 1/1990 |
| JP | 04077488 | 3/1992 |
| JP | H04153647 | 5/1992 |
| JP | H09506859 | 7/1997 |
| JP | H10503759 | 4/1998 |
| JP | 2001522369 | 11/2001 |
| JP | 2001522860 | 11/2001 |
| JP | 2003155287 | 8/2002 |
| JP | 2004533406 | 11/2004 |
| JP | 2004537503 | 12/2004 |
| JP | 2005504020 | 2/2005 |
| JP | 2005526058 | 9/2005 |
| JP | 2007270087 | 10/2007 |
| JP | 2008222557 | 9/2008 |
| JP | S5821681 | 10/2015 |
| JP | 2016529325 | 9/2016 |
| KR | 20060118416 | 11/2006 |
| TW | 424090 | 3/2001 |
| TW | 99135283 | 10/2010 |
| TW | 201124417 | 7/2011 |
| WO | WO1994026722 | 11/1994 |
| WO | WO1995029894 | 11/1995 |
| WO | WO1997001562 | 1/1997 |
| WO | WO1998049177 | 11/1998 |
| WO | WO1999007685 | 2/1999 |
| WO | WO1999024452 | 5/1999 |
| WO | WO2000012484 | 3/2000 |
| WO | WO2001030749 | 5/2001 |
| WO | WO2001060825 | 8/2001 |
| WO | WO2002032920 | 4/2002 |
| WO | WO2002048138 | 6/2002 |
| WO | WO2002061110 | 8/2002 |
| WO | WO2002074773 | 9/2002 |
| WO | WO2002097134 | 12/2002 |
| WO | WO2003004602 | 1/2003 |
| WO | WO2003072574 | 9/2003 |
| WO | WO2004080466 | 9/2004 |
| WO | WO2005019228 | 3/2005 |
| WO | WO2005037801 | 4/2005 |
| WO | WO2006002627 | 1/2006 |
| WO | WO2007014308 | 2/2007 |
| WO | WO2007069923 | 6/2007 |
| WO | WO2007084786 | 7/2007 |
| WO | WO2007101871 | 9/2007 |
| WO | WO2008004796 | 1/2008 |
| WO | WO2008030119 | 3/2008 |
| WO | WO2008082440 | 7/2008 |
| WO | WO2008104279 | 9/2008 |
| WO | WO2008143729 | 11/2008 |
| WO | WO2008150406 | 12/2008 |
| WO | WO2008154642 | 12/2008 |
| WO | WO2008156610 | 12/2008 |
| WO | WO2009074812 | 6/2009 |
| WO | WO2009113828 | 10/2009 |
| WO | WO2010101951 | 9/2010 |
| WO | WO2011017319 | 2/2011 |
| WO | WO2011045415 | 4/2011 |
| WO | WO2011047319 | 4/2011 |
| WO | WO2011047323 | 4/2011 |
| WO | WO2012125832 | 9/2012 |
| WO | WO2012173689 | 12/2012 |
| WO | WO2015035421 | 3/2015 |
| WO | WO2015035426 | 3/2015 |

OTHER PUBLICATIONS

CAS Registry No. 54535-57-8, 1 page, Nov. 16, 1984.
CAS Registry No. 752259-90-8, 1 page, Sep. 27, 2004.
CAS Registry No. 845295-22-9, 1 page, Mar. 11, 2005.
CAS Registry No. 845295-53-6, 1 page, Mar. 11, 2005.
CAS Registry No. 860260-10-2, 1 page, Aug. 15, 2015.
Extended European Search Report in Application No. 18162332.3, dated Aug. 8, 2018, 8 pages.
Extended European Search Report in Application No. 18166144.8, dated Oct. 26, 2018.
Mosselhi et al., "Synthesis and antimicrobial activity of imidazo- and pyrimido [2, 1-f]-theophyllines", Monatshefte fuer Chemie, vo., 139, No. 7, 825-834, 2008.
Aguilar et al., "Toward a library synthesis of the natural dipeptide antibiotic TAN 1057 A, B," Molecules. Jun. 30, 2002; 7(6):469-474.
Housman et al., "In Vitro Evaluation of Novel Compounds against Selected Resistant Pseudomonas aeruginosa Isolates," *Antimicrobial Agents and Chemotherapy* 2012, vol. 56(3) p. 1646-1649.
Angelino et al., "On the oxidation of N-methyl and N-benzylpyrimidin-2-and-4-ones by rabbit liver aldehyde oxidase," Journal of heterocyclic chemistry. 1984; 21:749-752.
Anonymous: "U.S. Government Lists of 1-12 Bioterrorism Agents and Diseases", Biosecurity and Biodefense Resource, Jan. 1, 2007 (Jan. 1, 2007), XP055352854, Retrieved from the Internet:URL:https://fas.org/biosecurity/resource/lists.htm [retrieved on Mar. 8, 2017].
Ausín et al., "Synthesis of amino-and guanidino-G-clamp PNA monomers," Organic letters. Nov. 14, 2002; 4(23):4073-4075.
Babic et al., "What's new in antibiotic resistance? Focus on beta-lactamases," Drug resistance updates. Jun. 30, 2006; 9(3):142-156.
Bandow et al., "Proteomic approach to understanding antibiotic action," Antimicrobial agents and chemotherapy. Mar. 1, 2003; 47(3):948-955.
Banker et al, "Modern Pharmaceutices, 3ed.," Marcel Dekker, New York. 1996, pp. 451 and 596.
Bassetti et al., "New antibiotics for bad bugs: where are we," Ann Clin Microbiol Antimicrob. Aug. 28, 2013; 12(1):22.
Becker, "Antimicrobial drugs," Anesth Prog. 2013 Fall;60(3):111-122; quiz 123.
Stengel et al., Biochemistry, 2009, vol. 48(31), pp. 7547-7555.
Belov et al., "First enantioselective synthesis of the novel antiinfective TAN-1057A via its aminomethyl-substituted dihydropyrimidinone heterocycle," Tetrahedron. Aug. 23, 2004; 60(35):7579-7589.
Palchykovska et al., Biopolymers and Cell, 2009, 25(6), pp. 491-499.
Berlinck, "Natural guanidine derivatives," Natural Product Reports. 1999; 16(3):339-365.
Böddeker et al., "Characterization of a novel antibacterial agent that inhibits bacterial translation,"RNA. Sep. 1, 2002; 8(09):1120-1128.
Bondock et al., "Synthesis and antimicrobial activity of some new heterocycles incorporating antipyrine moiety," European journal of medicinal chemistry. Oct. 31, 2008; 43(10):2122-2129.
Brackmann et al., "Titanium-mediated cyclopropanation of N, N-dibenzylcarboxamides towards functionally substituted 2-(1'-aminocyclopropyl) acetic acidsl," Synthesis. 2005(12):2008-2014.
Brands et al., "Dihydropyrimidinones—a new class of anti-Staphylococcal antibiotics," Bioorganic & medicinal chemistry letters. Jan. 20, 2003; 13(2):241-245.
Brands et al., "Novel antibiotics for the treatment of gram-positive bacterial infections," Journal of medicinal chemistry. Sep. 12, 2002; 45(19):4246-4253.
Brands et al., "Pyrimidinone antibiotics—heterocyclic analogues with improved antibacterial spectrum," Bioorganic & medicinal chemistry letters. Aug. 18, 2003; 13(16):2641-2645.
Budĕsínský et al., "[5-Aryl-pyrimidines. 3. 5-Aryl-isocytosines and 5-aryl-4-thio-isocytosines]," Cesk Farm., 15(8):432-437, Oct. 1966.

(56) References Cited

OTHER PUBLICATIONS

Budesinsky et al., Cesko-Slovenska Farmacie (1966), 15(8), 432-7; CA 67:90756, 1967. CAPLUS Abstract provided, 3 pages.
Cahn and Ingold, "131. Specification of configuration about quadricovalent asymmetric atoms," Journal of the Chemical Society (Resumed). 1951:612-622.
Cahn et al., "Specification of Molecular Chirality" Angew. Chem. Int. Ed. Engl., 5(4):385-415, Apr. 1966.
Cahn et al., "The specification of asymmetric configuration in organic chemistry," Experientia. Mar. 1, 1956; 12(3):81-94.
Cahn. "An Introduction to the Sequence Rule: A System for the Specification of Absolute Configuration," J. Chem. Educ. 1964; 41(3):116-125.
CAS Registry No. 1056628-47-7, 1 page, Oct. 3, 2008.
CAS Registry No. 1056628-57-9, 2 pages, 2008.
CAS Registry No. 1056628-60-4, 2 pages, 2008.
CAS Registry No. 646521-61-1, 2 pages, 2003.
CAS Registry No. 646521-62-2, "(2R,4S,5R)-2-[2-(N-benzoylamino)-4-oxo-3,4-dihydropyrimidin-5-yl]-4-hydroxy-5-hydroxymethyl pyrrolidine," 3 pages, 2005.
CAS Registry No. 646521-63-3, "(2R,4S,5R)-N-[(9-fluorenylmethoxy)carbonyl]-2-[2-(N-benzoylamino)-4-oxo-3,4-dihydropyrimidin-5-yl]-4-hydroxy-5-hydroxymethyl pyrrolidine," 2 pages, 2005.
CAS Registry No. 646521-64-4, "(2R,4S,5R)-N-[(9-fluorenylmethoxy)carbonyl]-2-[2-(N-benzoylamino)-4-oxo-3,4-dihydropyrimidin-5-yl]-5-[(4,4'-dimethoxy)triphenylmethyl]-oxymethyl-4-hydroxy pyrrolidine," 2 pages, 2005.
CAS Registry No. 646521-65-5, 2 pages, Feb. 5, 2004.
CAS Registry No. 667411-76-9, "2-benzoylamino-5-[2'-deoxy-3',5'-bis-O-(tert-butyldimethylsilyl)-β-D-erythro-pent-2-enofuranosyl]-3Hpyrimidin-4-one," 3 pages, 2003.
CAS Registry No. 667411-77-0, "N4-benzoyl-2'-deoxypseudoisocytidine," 3 pages, 2003.
CAS Registry No. 667411-78-1, 3 pages, 2003.
CAS Registry No. 667411-79-2, 1 page, Mar. 25, 2004.
CAS Registry No. 751437-20-4, 1 page, Sep. 24, 2004.
CAS Registry No. 646521-58-6, "(2R,5R)-N-(benzyloxy)carbonyl-2-[2-(N-benzoylamino)-4-oxo-3,4-dihydropyrimidin-5-yl]-4-[(tertbutyl)dimethylsilyl]oxy-5-[(tert-butyl)dimethylsilyl]oxymethyl-aza-cyclopent-3-ene," 3 pages, 2003.
Champney et al., "TAN-1057A: a translational inhibitor with a specific inhibitory effect on 50S ribosomal subunit formation," Current microbiology. Nov. 1, 2001; 43(5):340-345.
Chemical Abstracts Accession No. 1967:490756, 3 pages, 1966.
Chemical Abstracts Accession No. 2004:353887, 1 page, 2004.
Chou et al., "Quantitative analysis of dose-effect relationships: the combined effects of multiple drugs or enzyme inhibitors," Advances in enzyme regulation. Dec. 31, 1984; 22:27-55.
Chu, Chung K. et al., Journal of Heterocyclic Chemistry, 1986, 23(6), 1621-4.
Chu et al., "Nucleosides XCII. A facile synthesis of 5-(β-d-ribofuranosyl)-isocytosine (ψ-isocytidine)," J Heterocycl Chem., Jan. 1, 1975;12(4):817-818.
Chu, "Acyclopyrimidine C-nucleosides. Synthesis of acyclopseudoisocytidine and its derivatives," J. Heterocyclic Chem., 21: 9-11, 1984.
Corriere, M.D., et al, MRSA: An Evolving Pathogen: Disease-A-Month, vol. 54 pp. 751-755. Published 2008.
Debaene et al., "Expanding the scope of PNA-encoded libraries: divergent synthesis of libraries targeting cysteine, serine and metalloproteases as well as tyrosine phosphatases," Tetrahedron. Jul. 9, 2007; 63(28):6577-6586.
Dermer, "Another anniversary for the war on cancer," Nature Biotechnology. Mar. 1, 1994; 12(3):320.
Dyer et al., "Carbamates and Ureas Derived from Amino- and Oxopyrimidines," Journal of Organic Chemistry 27:982-985 (1962).
European Search Report for Application No. 10824203.3, dated May 31, 2013, 9 pages.
European Search Report for Application No. 10824204.1, dated Apr. 17, 2013, 5 pages.
European Search Report for Application No. 10824207.4, dated Apr. 17, 2013, 9 pages.
Extended European Search Report for Application No. 14841546.6, dated Apr. 28, 2017, 10 pages.
European Search Report for Application No. 12756938.2 dated Nov. 20, 2014, 5 pages.
European Search Report for Application No. 12799934 dated Aug. 12, 2014, 7 pages.
Fattori et al., "Drug-eluting stents in vascular intervention," The Lancet. Jan. 18, 2003; 361(9353):247-249.
Franceschi et al., "Structure-based drug design meets the ribosome," Biochemical pharmacology. Mar. 30, 2006; 71(7):1016-1025.
Freshney et al.,Culture of Animal Cells, A Manual of Basic Technique, Alan R. Liss, Inc., 1983, New York, p. 4.
Funabashi et al., "A new anti-MRSA dipeptide, TAN-1057 A," Tetrahedron. Jan. 1, 1993; 49(1):13-28.
Gangjee et al., "Synthesis of classical, three-carbon-bridged 5-substituted furo[2,3-d]pyrimidine and 6-substituted pyrrolo[2,3-d]pyrimidine analogues as antifolates," J Med Chem., 47(27):6893-6901, Dec. 30, 2004.
Gnad et al., "Synthesis and applications of β-aminocarboxylic acids containing a cyclopropan ring," Chemical reviews. Apr. 9, 2003; 103(4):1603-1624.
Gold et al., "Antimicrobial-drug resistance," New England Journal of Medicine. Nov. 7, 1996; 335(19):1445-1453.
Häberli et al., "Pyrrolidino-DNA," Nucleosides Nucleotides Nucleic Acids. May-Aug. 2003; 22(5-8):1187-1189.
Hershfield et al., "Antibacterial Activity of Novel RX-04 Compounds Against Biodefense Pathogens," Poster F-1522, 52nd ICAAC, 2012.
Housman et al., "In Vitro Evaluation of Rib-X Novel Compounds Against Selected Resistant Pseudomonas aeruginosa Isolates," Antimicrob. Agents Chemother., 05944, Dec. 27, 2011, 17 pages.
Hudson et al., "Fluorescent 7-deazapurine derivatives from 5-iodocytosine via a tandem cross-coupling-annulation reaction with terminal alkynes," Synlett. 2004(13):2400-2402.
Hudson et al., "Nucleobase modified peptide nucleic acid," Nucleosides, Nucleotides and Nucleic Acids. Oct. 1, 2003; 22(5-8):1029-1033.
Hudson et al., Canadian Journal of Chemistry, 86(11): 1026-1029, 2008.
International Preliminary Report on Patentability for PCT/US2010/052922, dated Apr. 17, 2012, 8 pages.
International Preliminary Report on Patentability for PCT/US2010/052924, dated Apr. 17, 2012, 6 pages.
International Preliminary Report on Patentability for PCT/US2010/052928, dated Apr. 17, 2012, 7 pages.
International Preliminary Report on Patentability for PCT/US2012/029234, dated Sep. 17, 2013, 8 pages.
International Preliminary Report on Patentability for PCT/US2012/032994, dated Oct. 15, 2013, 8 pages.
International Preliminary Report on Patentability for PCT/US2016/022216, dated Sep. 21, 2017, 13 pages.
International Preliminary Report on Patentability for PCT/US2014/054860, dated Mar. 24, 2016, 9 pages.
International Search Report and Written Opinion for Application No. PCT/US2010/052928, dated Jun. 28, 2011, 9 pages.
International Search Report for Application No. PCT/US2010/052924, dated Jun. 28, 2011, 4 pages.
International Search Report for Application No. PCT/US2012/029234, dated Sep. 12, 2012, 3 pages.
International Search Report for PCT/US2010/052922 dated Jun. 28, 2011, 5 pages.
International Search Report for PCT/US2012/032994, dated Feb. 1, 2013, 4 pages.
Indian Journal of Chemistry, Section B: Organic Chemistry Including Medicinal Chemistry, 1992, 31B(2), pp. 105-108.
International Search Report in PCT/US2014/054860, dated Dec. 8, 2014, 4 pages.
JACS, 2009, 131(12), pp. 4288-4293.

(56) References Cited

OTHER PUBLICATIONS

International Search Report and Written Opinion in PCT/US2014/054869, dated Oct. 29, 2014, 13 pages.
International Search Report and Written Opinion in PCT/US2016/022216, dated Jun. 17, 2016, 19 pages.
Tawain Office Action in Application No. 104131806, dated Jul. 4, 2017, 56 pages.
Japanese Office Action in Japanese Application No. 2016-37911, dated Feb. 7, 2017, 17 pages.
Janeba et al., "Synthesis and Biological Evaluation of Acyclic 3-[(2-Hydroxyethoxy) methyl] Analogues of Antiviral Furo- and Pyrrolo [2,3-d] pyrimidine Nucleosides". J Med Chem, Jul. 14, 2005; 14:48(14): 4690-6.
Katayama et al., "TAN-1057 AD, new antibiotics with potent antibacterial activity against methicillin-resistant *Staphylococcus aureus*. Taxonomy, fermentation and biological activity," The Journal of antibiotics. 1993; 46(4):606-613.
Kawahara et al., "Computer-Aided Molecular Design of Hydrogen Bond Equivalents of Nucleobases: Theoretical Study of Substituent Effects on the Hydrogen Bond Energies of Nucleobase Pairs," European Journal of Organic Chemistry. Jul. 1, 2003; 2003(14):2577-2584.
Kint et al., "New-found fundamentals of bacterial persistence," Trends in microbiology. Dec. 31, 2012;20(12):577-585.
Kordes et al., "Preparation of Cyclopropane Analogues of the Natural AntibioticTAN 1057 A/B," European journal of organic chemistry. Jul. 1, 2005; 2005(14):3008-3016.
Kosegi et al., JP 61091184; CA: 105:208920, 1986. CAPLUS Abstract provided.
Laufersweiler et al., "Synthesis and evaluation of tricyclic pyrrolopyrimidinones as dipeptide mimetics. Inhibition of interleukin-1β-converting enzyme," Bioorganic & medicinal chemistry letters. Oct. 1, 2005; 15(19):4322-4326.
Limburg et al., "Ribosomal alterations contribute to bacterial resistance against the dipeptide antibiotic TAN 1057," Antimicrobial agents and chemotherapy. Feb. 1, 2004; 48(2):619-622.
Lin et al., "Assembly of the TAN-1057 A/B heterocycle from a dehydroalanine precursor,"Synthesis, 2000(14):2127-2130, 2000.
Lin et al., "Tricyclic 2'-deoxycytidine analogs: syntheses and incorporation into oligodeoxynucleotides which have enhanced binding to complementary RNA," Journal of the American Chemical Society. Apr. 1995; 117(13):3873-3874.
Liu et al., "Recent advances in the stereoselective synthesis of β-amino acids," Tetrahedron. Sep. 30, 2002; 58(40):7991-8035.
Lowy, "Antimicrobial resistance: the example of *Staphylococcus aureus*," Journal of Clinical Investigation. May 1, 2003;111(9):1265.
Lukin et al, "Rationalizing the strength of hydrogen-bonded complexes. Ab initio HF and DFT studies," The Journal of Physical Chemistry A. Jul. 25, 2002;106(29):6775-6782.
Magiorakos et al., "Multidrug-resistant, extensively drug-resistant and pandrug-resistant bacteria: an international expert proposal for interim standard definitions for acquired resistance," Clinical Microbiology and Infection. Mar. 1, 2012; 18(3):268-281.
Maguire, "Inhibition of bacterial ribosome assembly: a suitable drug target?" Microbiology and Molecular Biology Reviews. Mar. 1, 2009;73(1):22-35.
Matsuda et al., "Nucleosides. 120. Syntheses of 2'-deoxy-. psi.-isocytidine and 2'-deoxy-1-methyl-. psi.-uridine from. psi.-uridine," The Journal of Organic Chemistry. Aug. 1981;46(18):3603-3609.
Matsuda et al., Journal of Organic Chemistry (1981), 46(18), 3603-9; CA: 95:98205, 1981. CAPLUS Abstract provided.
Mayer et al., "Synthesis and triplex forming properties of pyrrolidino pseudoisocytidine containing oligodeoxynucleotides," Organic & biomolecular chemistry. 2005;3(9):1653-1658.
Merriam-Webster: Definition of Prophylaxis, 2017.
Mishra et al., "Dry Media Synthesis of Novel Pyrrolo-pyrimidines," Journal of Nepal Chemical Society. 2010; 25:83-88.
Golovan et al., Mikrobiologichnii Zhurnal, 2010, 72(2), pp. 36-42.

Miyaura et al., "A new stereospecific cross-coupling by the palladium-catalyzed reaction of 1-alkenylboranes with 1-alkenyl or 1-alkynyl halides," Tetrahedron Letters. Dec. 31, 1979; 20(36):3437-3440.
Moellering, "Linezolid: the first oxazolidinone antimicrobial," Annals of internal medicine. Jan. 21, 2003; 138(2):135-142.
Morice, "A new era in the treatment of coronary disease?" European heart journal. Feb. 1, 2003;24(3):209-211.
National Center for Biotechnology Information. PubChem Compound Database; CID=1112068, create date Jul. 10, 2005, 10 pages.
National Center for Biotechnology Information. PubChem Compound Database; CID=23522053, create date Dec. 6, 2007, 11 pages.
Nett, "The chemistry of gliding bacteria," Natural product reports. 2007; 24(6):1245-1261.
Orner et al., "The guanidinium group in molecular recognition: design and synthetic approaches," Journal of inclusion phenomena and macrocyclic chemistry. Dec. 1, 2001; 41(1-4):141-147.
Otteneder et al., PNAS, 2006, 103(17), pp. 6665-6669.
Ortega et al., "Binding affinities of oligonucleotides and PNAs containing phenoxazine and G-clamp cytosine analogues are unusually sequence-dependent," Organic letters. Oct. 25, 2007; 9(22):4503-4506.
Paterson et al., "Extended-spectrum β-lactamases: a clinical update," Clinical microbiology reviews. Oct. 1, 2005;18(4):657-686.
Phillips, "Reactivity of 5-Bromoisocytosine with Some Amines," Journal of the American Chemical Society. Aug. 1953;75(16):4092.
Phillips, A. P., Journal of the American Chemical Society (1953), 75, 4092; CA 49:42634, 1955. CAPLUS Abstract provided, 1 page.
Pohl, "Zur Kenntnis des Dicyandiamids," [Investigations from the Organic Chemistry Laboratory of the Technical University of Dresden], Journal für Praktische Chemie., 77(1):533-548, May 14, 1908 [English machine translation], 30 pages.
Rajeev et al., "High-affinity peptide nucleic acid oligomers containing tricyclic cytosine analogues," Organic letters. Dec. 12, 2002; 4(25):4395-4398.
Ravin et al., "Preformulation," Remington's Pharm. Sci., Chapter 75, 1435-1450 (1990).
Rehm et al., "*Staphylococcus aureus*: methicillin-susceptible *S. aureus* to methicillin-resistant *S. aureus* and vancomycin-resistant *S. aureus*," Clinical Infectious Diseases. Sep. 15, 2010;51(Supplement 2):S176-S182.
Reigan et al., "Synthesis and enzymatic evaluation of xanthine oxidase-activated prodrugs based on inhibitors of thymidine phosphorylase," Bioorganic & medicinal chemistry letters. Nov. 1, 2004; 14(21):5247-5250.
Remington's Pharmaceutical Sciences, 18th ed. (Mack Publishing Company, 1990) Table of Contents p. xv, and chapter 75 pp. 1435-1450.
Rival et al., "Synthesis and antibacterial activity of some imidazo[1,2-a]pyrimidine derivatives," Chem Pharm Bull (Tokyo)., 40(5):1170-1176, May 1992.
Šála et al., "Synthesis of racemic 2-hydroxy-4-and 2-hydroxy-5-(hydroxymethyl) cyclohexane pyrimidine C-nucleoside analogues," Collection of Czechoslovak chemical communications, 69(4): 918-932, 2004.
Sala et al., Collection of Czechoslovak Chemical Communications (2004), 69(4), Abstract provided. 918-932; CA: 141:314551, 2004. CAPLUS Abstract provided, 3 pages.
Sanders et al., "Disease-related misassembly of membrane proteins," Annu. Rev. Biophys. Biomol. Struct. Jun. 9, 2004; 33:25-51.
Sato et al., "A Convenient Route to 5'-Modified Pseudoisocytidines and 2-Thiopseudouridines," Chemistry Letters. 1978; 7(11):1297-1300.
Sato et al., Chemistry Letters (1978), (11), 1297-300; CA 90:87793, 1979. CAPLUS Abstract provided, 4 pages.
Sato et al., Tetrahedron Letters (1979), (31), 2897-900; CA 92:164211, 1980. CAPLUS Abstract provided, 2 pages.
Shaffer, "The challenge of antibiotic-resistant *Staphylococcus*: lessons from hospital nurseries in the mid-20th century," The Yale journal of biology and medicine. Jun. 2013; 86(2):261.
Singh, "Confronting the challenges of discovery of novel antibacterial agents," Bioorganic & medicinal chemistry letters. Aug. 15, 2014; 24(16):3683-3689.

(56) References Cited

OTHER PUBLICATIONS

Sniady et al., "Zinc-catalyzed cycloisomerizations. Synthesis of substituted furans and furopyrimidine nucleosides," The Journal of organic chemistry. Jul. 3, 2008; 73(15):5881-5889.
Sokolov et al., "Total Synthesis of TAN-1057 A/B, a New Dipeptide Antibiotic from *Flexibacter* sp. PK-74," European journal of organic chemistry. May 1, 1998; 1998(5):777-783.
Stoss et al., "Novel pyrimidine and pyrimido[1, 2-a]pyrimidine derivatives. By-products of a guanidine based thymine synthesis," Journal of Heterocyclic Chemistry, 28(2):231-236, Feb./Mar. 1991.
Supplementary European Search Report in European Application No. EP14841940, dated Mar. 8, 2017, 5 pages.
Theuretzbacher et al., "Update on antibacterial and antifungal drugs—can we master the resistance crisis?" Current opinion in pharmacology. Oct. 31, 2011; 11(5):429-432.
Toutouzas et al., "Sirolimus-eluting stents: a review of experimental and clinical findings," Zeitschrift für Kardiologie. Jul. 1, 2002; 91(3):49-57.
Tsiodras et al., "Linezolid resistance in a clinical isolate of *Staphylococcus aureus*," The Lancet. Jul. 21, 2001;358(9277):207-8.
Wang et al., "A highly enantioselective hetero-Diels-Alder reaction of aldehydes with Danishefsky's diene catalyzed by chiral titanium (IV) 5, 5', 6, 6', 7, 7', 8, 8'-octahydro-1, 1'-bi-2-naphthol complexes," The Journal of organic chemistry. Apr. 5, 2002;67(7):2175-2182.
Wang, TW 424090; CA: 138:205080, 2003. CAPLUS Abstract provided, 1 page.
Williams et al., "Synthesis and antimicrobial evaluation of TAN-1057 A/B analogs," The Journal of antibiotics. 1998; 51(2):189-201.
Wilson, "The A-Z of bacterial translation inhibitors. Critical Reviews in Biochemistry and Molecular Biology," Dec. 1, 2009; 44(6):393-433.
Wojciechowski et al., "Exceptional Fluorescence and Hybridization Properties of a Phenylpyrrolocytosine in Peptide Nucleic Acid," InNucleic Acids Symposium Series Sep. 1, 2008 (vol. 52, No. 1, pp. 401-402). Oxford University Press.
Wojciechowski et al., "Peptide nucleic acid containing a meta-substituted phenylpyrrolocytosine exhibits a fluorescence response and increased binding affinity toward RNA," Organic Letters. Sep. 29, 2009; 11(21):4878-4881.
Wojciechowski, "Fluorescence and hybridization properties of peptide nucleic acid containing a substituted phenylpyrrolocytosine designed to engage guanine with an additional H-bond," Journal of the American Chemical Society. Aug. 30, 2008; 130(38):12574-12575.
Wolff Manfred E. "Burger's Medicinal Chemistry, 5ed, Part 1", John Wiley & Sons, 1995, pp. 975-977.
Xu et al., "A new and convergent synthesis for 2, 5-diamino-tetrahydropyrimidones," Tetrahedron letters. Mar. 17, 2003; 44(12):2601-2604.
Xu et al., "SAR studies on dihydropyrimidinone antibiotics," Bioorganic & medicinal chemistry letters. Mar. 15, 2011; 21(6):1670-1674.
Yuan et al., "Total synthesis of the anti methicillin-resistant *Staphylococcus aureus* peptide antibiotics TAN-1057A-D," Journal of the American Chemical Society. Dec. 10, 1997; 119(49):11777-11784.
Zhang et al., "A facile construction of the 3, 6-diamino-1, 2, 3, 4-tetrahydropyridine-4-one scaffold: synthesis of N-3 to carbon replacement analog of TAN-1057A/B," Tetrahedron letters. Apr. 30, 2007; 48(18):3273-3275.
Zhang et al., "A new approach to the 2, 5-diamino-5, 6-dihydro-1H-Pyrimidine-4-one derivatives: synthesis of TAN-1057A/B and analogs," Tetrahedron letters. Jul. 28, 2003; 44(31):5871-5873.
Zhou et al., "Design at the atomic level: design of biaryloxazolidinones as potent orally active antibiotics," Bioorg Med Chem Lett., 18(23):6175-6178, Epub Oct. 7, 2008.
Zhou et al., "Design at the atomic level: generation of novel hybrid biaryloxazolidinones as promising new antibiotics," Bioorg Med Chem Lett., 18(23):6179-6183, Epub Oct. 7, 2008.
Perin et al., Bulletin de la Societe Chimique de France 1964, vol. 8, p. 1877-1880 (English translation).

European Search Report issued in European Patent Application No. 10824207.4-1452 dated Jul. 24, 2017.
Zeitschrift fuer Analytische Chemie 1976, vol. 281 p. 302.
Australian Office Action in Australian Application No. 2016266048, dated Jun. 26, 2017.
Zanatta, N. et al, Synthesis, 2006, 14, 2305-2312.
Kovigin, Yu. A. et al, Izvestiya Vysshikh Uchebnykh Zavedenii, Khimiya i Khimicheskaya Tekhnologiya, 2005, 48(1 ), 59-60 (No English Translation).
Anwar, H.F. et al, Journal of Chemical Research, 2005, 29-31.
Matteucci, M.D. et al, Tetrahedron Letters, 1996, 37(29), 5057-5060.
LaMattina, J.L. et al, Tetrahedron, 1988, 44(11), 3073-3078.
Sato, Y. et al, Yakugaku Zasshi, 1970, 90(5), 618-28.
Abdel-Fattah, A. M. et al., "New synthesis of imidazo [1,2-a]- and pyrimido [1,2-a] pyrimidines", Phosphorus, Sulfur and Silicon and the Related Elements, 1992, vol. 70, No. 1, pp. 67-73.
Abdel-Megid, Mohamed, Nitrogen bridgehead compounds, facile synthesis of bioactive cyanopyrimido [1,2-a]pyrimidinones, Pharmazie, 2000, vol. 55, No. 4, pp. 263-268.
Angier, Robert et al., "Alkylation of 2-amino-4-hydroxypyrimidines with acrylonitrile and with dimethyl sulfate: Two pyrimido [1,2-a] pryimidinediones", Journal of Organic Chemistry, 1961, vol. 26, pp. 1891-1895.
Australian Examination Report in Australian Application No. 2016266048, dated Jun. 6, 2018.
Canadian Office Action in Application No. 2,777,734, dated Jul. 27, 2018,6 pages.
CAS RN: 221555-28-8, STN Entry Date Apr. 22, 1999.
CAS RN: 359851-13-1, STN Entry Date Oct. 3, 2001.
CAS RN: 55662-33-4, STN Entry Date Nov. 16, 1984.
Chinese Examination Report in Chinese Application No. CPCH1660525P, dated Nov. 1, 2017, 10 pages.
De Cat et al., "Heterocyclic derivatives of pyrimidobenzimidazoles. II", Bulletin des Societes Chimiques Beiges, 60, pp. 69-75, 1951.
Extended European Search Report in Application No. 16762682.9, dated Jul. 20, 2018, 7 pages.
Flamm, R. K. et al., "In Vitro Activity of RX-P873 against Enterobacteriaceae, Pseudomonas aeruginosa, and Acinetobacter baumanii", Antimicrobial Agents and Chemotherapy, vol. 59, No. 4, pp. 2280-2285, 2015.
Hanessian et al., "On the binding site of quinolone antibacterials. An attempt to probe the Shen model", Bioorganic & Medicinal Chemistry Letters, 6(19), pp. 2333-2338, 1996.
Japanese Office Action in Application No. 2016/015912, dated Aug. 27, 2018, 6 pages.
Japanese Office Action in Japanese Application No. 2016/540938, dated Jun. 19, 2018, 11 pages.
Japanese Office Action in Japanese Application No. 2017/148521, dated Mar. 27, 2018, 8 pages.
Japanese Office Action in Japanese Application No. 2017/148530, dated Mar. 30, 2017, 6 pages.
Jokic et al., "The synthesis of novel 6,5- and 6,6-membered fused heterocyclic compounds derived from thymine", Nucleosides, Nucleotides & Nucleic Acids, vol. 19, No. 9, pp. 1381-1396, 2000.
Mexican Office Action in Mexican Application No. MX/a/2013/012015, dated Apr. 11, 2012, 3 pages.
Minami, Shinsaku et al., "Pyrido [2,3-d] pyrimidine antibacterial agents. I. 8-alkyl-5,8-dihydro-5-oxopyrido[2,3-d]-pryimidine-6-carboxylic acids and related compounds", Chemical & Pharmaceutical Bulletin, 1971, vol. 19, No. 7, pp. 1482-1486.
Minamoto, K. et al., J. Chem. Soc. Perkin Trans. I, 1988, 2955-2961.
Morimoto et al., "Successful management of severe L-asparaginase-associated pancreatits by continuous regional arterial infusion of protease inhibitor and antibiotiv", Cancer, 113(6), pp. 1362-1369, 2008.
Sandrini et al., "Deoxyribonucleoside kinases activate nucleoside antibiotics in severely pathogenic bacteria", Antimicrobial Agents and Chemotherapy, 51(8), pp. 2726-2732, 2007.

* cited by examiner

ANTIMICROBIAL COMPOUNDS AND METHODS OF MAKING AND USING THE SAME

CLAIM OF PRIORITY

This application is a National Stage application under 35 U.S.C. § 371 of International Application No. PCT/US2016/022216, filed Mar. 11, 2016, which claims the benefit of U.S. Provisional Application No. 62/131,751, filed Mar. 11, 2015. The entire contents of the foregoing are hereby incorporated by reference.

BACKGROUND

Since the discovery of penicillin in the 1920s and streptomycin in the 1940s, many new compounds have been discovered or specifically designed for use as antibiotic agents. It was once thought that infectious diseases could be completely controlled or eradicated with the use of such therapeutic agents. However, such views have been challenged because strains of cells or microorganisms resistant to currently effective therapeutic agents continue to evolve. Almost every antibiotic agent developed for clinical use has ultimately encountered problems with the emergence of resistant bacteria. For example, resistant strains of Gram-positive bacteria such as methicillin-resistant staphylococci, penicillin-resistant streptococci, and vancomycin-resistant enterococci have developed. Resistant bacteria can cause serious and even fatal results for infected patients. See, e.g., Lowry, F. D. "Antimicrobial Resistance: The Example of *Staphylococcus aureus*," *J. Clin. Invest.*, vol. 111, no. 9, pp. 1265-1273 (2003); and Gold, H. S. and Moellering, R. C., Jr., "Antimicrobial-Drug Resistance," *N. Engl. J. Med.*, vol. 335, pp. 1445-53 (1996).

The discovery and development of new antibacterial agents have been for decades a major focus of many pharmaceutical companies. Nonetheless, in more recent years there has been an exodus from this area of research and drug development resulting in very few new antibiotics entering the market. This lack of new antibiotics is particularly disturbing, especially at a time when bacterial resistance to current therapies is increasing both in the hospital and community settings.

One approach to developing new antimicrobial compounds is to design modulators, for example, inhibitors, of bacterial ribosome function. By modulating or inhibiting bacterial ribosome function, antimicrobial compounds could interfere with essential processes such as RNA translation and protein synthesis, thereby providing an antimicrobial effect. In fact, some antibiotic compounds such as erythromycin, clindamycin, and linezolid are known to bind to the ribosome.

SUMMARY OF THE INVENTION

The present disclosure relates generally to the field of antimicrobial compounds and to methods of making and using them. These compounds and tautomers thereof are useful for treating, preventing, reducing the risk of, or delaying the onset of microbial infections in humans and animals. The present disclosure also provides pharmaceutically acceptable salts, esters, and prodrugs of these compounds and tautomers.

In one aspect, the present disclosure provides a compound of Formula (A):

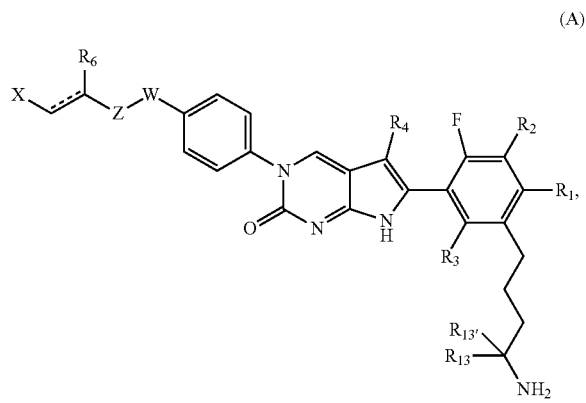

(A)

or a tautomer thereof, or a pharmaceutically acceptable salt, or ester of said compound or tautomer, wherein:

----- is a single or a double bond;

X is —NHC(NH)NH$_2$, —CH$_2$NH$_2$, —CH$_2$NHC(NH) NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH) heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the (C$_1$-C$_4$)alkyl, cycloalkyl, heterocycloalkyl and heteroaryl are optionally substituted with one or more R$_7$;

Z is O, CH$_2$, NR$_{11}$, or S(O)$_p$;

W is N(R$_5$) or C(R$_5$)(R$_{5'}$);

R$_1$ is H, (C$_1$-C$_4$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, heterocycloalkyl, halogen, or —NO$_2$, wherein the (C$_1$-C$_4$) alkyl, (C$_2$-C$_4$)alkenyl, and heterocycloalkyl are optionally substituted with one or more R$_{12}$; or R$_1$ and R$_2$ together with the carbon atoms to which they are attached form a (C$_3$-C$_7$)cycloalkyl or heterocycloalkyl;

R$_2$ is —F, —Cl, —CF$_3$, —SCF$_3$, or —OCF$_3$;

R$_3$ is H or —NO$_2$;

R$_4$ is H, (C$_1$-C$_3$)alkyl, (C$_2$-C$_3$)alkenyl, halogen, or —NO$_2$;

R$_5$ is H or —CH$_3$;

R$_{5'}$ is H; or

R$_6$ is H, (C$_1$-C$_3$)alkyl, (C$_2$-C$_3$)alkenyl, (C$_1$-C$_3$)haloalkyl, —CH$_2$NHC(NH)NH$_2$, —CH$_2$NHC(NH)(C$_1$-C$_3$)alkyl, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NHheterocycloalkyl, —(CH$_2$)$_n$heteroaryl, or —CH$_2$NHheteroaryl, wherein the heteroaryl and heterocycloalkyl are optionally substituted with one or more R$_8$; or R$_5$ and R$_6$ together with the carbon atoms to which they are attached and the Z atom connecting said two carbon atoms, form a (C$_5$-C$_6$)cycloalkyl or a 5- to 6-membered heterocycloalkyl ring containing 1-3 heteroatoms optionally substituted with one or more R$_9$; or when W is N(R$_5$), R$_6$ and W together with the Z atom connecting W and the carbon atom to which R$_6$ is attached, form a 5- to 6-membered heterocycloalkyl ring containing 1-3 heteroatoms optionally substituted with one or more $R_9$;

at least one of $R_5$ and $R_6$ is not H;

each $R_7$ is independently $(C_1-C_3)$alkyl, halogen, oxo, —OH, or —$NH_2$;

each $R_8$ is independently $(C_1-C_3)$alkyl, $(C_1-C_3)$alkoxy, halogen, oxo, —$NH_2$, or —$NHR_{10}$;

each $R_9$ is independently $(C_1-C_3)$alkyl, $(C_2-C_4)$alkenyl, —$NH_2$, —$NHC(NH)NH_2$, —$NHC(NH)(C_1-C_3)$alkyl, —$CH_2$heteroaryl, —NHheterocycloalkyl, or —NHheteroaryl, wherein the $(C_1-C_3)$alkyl is optionally substituted with one or more substituents independently selected from —$NHC(NH)NH_2$, —OH, and —$NH_2$;

each $R_{10}$ is independently —$CH_2$aryl optionally substituted with $(C_1-C_3)$alkoxy or halogen;

$R_{11}$ is H, —$NHC(NH)NH_2$, —C(O)H, —$C(O)(C_1-C_4)$alkyl, —$C(O)O(C_1-C_4)$alkyl, $(C_1-C_4)$alkyl, $(C_3-C_6)$cycloalkyl, or heterocycloalkyl, wherein the $(C_1-C_4)$alkyl is optionally substituted with one or more substituents independently selected from —OH, $(C_1-C_3)$alkoxy, —$NH_2$, and —$NHC(NH)NH_2$;

each $R_{12}$ is independently selected from $(C_1-C_3)$alkoxy, $(C_1-C_3)$haloalkyl, $(C_1-C_3)$ hydroxyalkyl, halogen, —OH, —$NH_2$, —$NH(C_1-C_4)$alkyl, —$N((C_1-C_4)$alkyl$)_2$, and oxo;

$R_{13}$ is —$CH_3$, —$CH=CH_2$, —$CF_3$, —$CH_2F$, or —$CH_2OH$;

$R_{13'}$ is H or —$CH_3$;

n is 1 or 2;

each p is independently 0, 1, or 2; and provided that when Z is NH, X is —$CH_2NHC(NH)NH_2$ or —$CH_2NH_2$, $R_1$ is H or F, $R_3$ is H, $R_5$ is methyl, and $R_6$ is H, then $R_4$ is $(C_1-C_3)$alkyl, $(C_2-C_3)$alkenyl, F, I, or —$NO_2$.

In one aspect, the present disclosure relates to a compound of Formula (I):

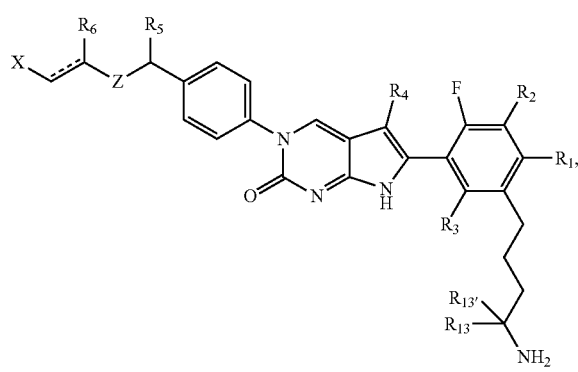

or a tautomer thereof, or a pharmaceutically acceptable salt, or ester of said compound or tautomer wherein:

⁃⁃⁃⁃⁃ is a single or a double bond;

X is —$NHC(NH)NH_2$, —$CH_2NH_2$, —$CH_2NHC(NH)NH_2$, —$CH_2NHCH_2C(O)CH_3$, —$CH_2NHC(NH)(C_1-C_4)$alkyl, —$CH_2NHC(NH)(C_3-C_7)$cycloalkyl, —$CH_2NHC(NH)$heteroaryl, heteroaryl, —$CH_2$heteroaryl, —$NHCH_2$heteroaryl, —$CH_2NH$heteroaryl, —CH(OH)heteroaryl, —$CH_2$heterocycloalkyl, —$NHCH_2$heterocycloalkyl, or —$CH_2NH$heterocycloalkyl, wherein the $(C_1-C_4)$alkyl, cycloalkyl, heterocycloalkyl and heteroaryl are optionally substituted with one or more $R_7$;

Z is O, $CH_2$, $NR_{11}$, or $S(O)_p$;

$R_1$ is H, $(C_1-C_4)$alkyl, $(C_2-C_4)$alkenyl, $(C_2-C_4)$alkynyl, $(C_1-C_3)$alkoxy, $(C_1-C_3)$haloalkyl, —$O(C_1-C_3)$haloalkyl, heterocycloalkyl, halogen, —$NO_2$, wherein the $(C_1-C_4)$alkyl, $(C_2-C_4)$alkenyl, and heterocycloalkyl are optionally substituted with one or more $R_{12}$; or $R_1$ and $R_2$ together with the carbon atoms to which they are attached form a $(C_3-C_7)$cycloalkyl or heterocycloalkyl;

$R_2$ is —F, —Cl, —$CF_3$, —$SCF_3$, or —$OCF_3$;

$R_3$ is H or —$NO_2$;

$R_4$ is H, $(C_1-C_3)$alkyl, $(C_2-C_3)$alkenyl, halogen, or —$NO_2$;

$R_5$ is H or —$CH_3$;

$R_6$ is H, $(C_1-C_3)$alkyl, $(C_2-C_3)$alkenyl, $(C_1-C_3)$haloalkyl, —$CH_2NHC(NH)NH_2$, —$(CH_2)_nOH$, —$CH_2S(O)_pNH_2$, —$CH_2NH(C_1-C_3)$alkyl, —$CH_2C(O)NH_2$, —$(CH_2)_nNH_2$, —$CH_2$heterocycloalkyl, —$CH_2NH_2$heterocycloalkyl, —$(CH_2)_n$heteroaryl, or —$CH_2NH_2$heteroaryl, wherein the heteroaryl and heterocycloalkyl is optionally substituted with one or more $R_8$; or $R_5$ and $R_6$ together with the carbon atoms to which they are attached and the Z atom connecting said two carbon atoms, form a $(C_5-C_6)$cycloalkyl or a 5- to 6-membered heterocycloalkyl ring containing 1-3 heteroatoms optionally substituted with one or more $R_9$;

at least one of $R_5$ and $R_6$ is not H;

each $R_7$ is independently $(C_1-C_3)$alkyl, halogen, oxo, —OH, or —$NH_2$;

each $R_8$ is independently $(C_1-C_3)$alkyl, $(C_1-C_3)$alkoxy, halogen, oxo, —$NH_2$, or —$NHR_{10}$;

each $R_9$ is independently $(C_1-C_3)$alkyl, $(C_2-C_4)$alkenyl, —$NH_2$, —$NH_2C(NH)NH_2$, —$NH_2C(NH)(C_1-C_3)$alkyl, —$CH_2$heteroaryl, NHheterocycloalkyl, or —NHheteroaryl, wherein the $(C_1-C_3)$alkyl is optionally substituted with one or more substituents independently selected from —OH and —$NH_2$;

each $R_{10}$ is independently —$CH_2$aryl optionally substituted with $(C_1-C_3)$alkoxy or halogen;

$R_{11}$ is H, —$NHC(NH)NH_2$, —C(O)H, —$C(O)(C_1-C_4)$alkyl, —$C(O)O(C_1-C_4)$alkyl, $(C_1-C_4)$alkyl, $(C_3-C_6)$cycloalkyl, or heterocycloalkyl, wherein the $(C_1-C_4)$alkyl is optionally substituted with one or more substituents independently selected from —OH, $(C_1-C_3)$alkoxy, —$NH_2$, and —$NHC(NH)NH_2$;

each $R_{12}$ is independently selected from $(C_1-C_3)$alkoxy, $(C_1-C_3)$haloalkyl, $(C_1-C_3)$ hydroxyalkyl, halogen, —OH, —$NH_2$, —$NH(C_1-C_4)$alkyl, —$N((C_1-C_4)$alkyl$)_2$, and oxo;

$R_{13}$ is —$CH_3$, —$CH=CH_2$, —$CF_3$, —$CH_2F$, or —$CH_2OH$;

$R_{13'}$ is H or —$CH_3$;

n is 1 or 2;

each p is independently 0, 1, or 2; and provided that when Z is NH, X is —$CH_2NHC(NH)NH_2$ or —$CH_2NH_2$, $R_1$ is H, $R_3$ is H, $R_5$ is methyl, and $R_6$ is H, then $R_4$ is $(C_1-C_3)$alkyl, $(C_2-C_3)$alkenyl, halogen, or —$NO_2$.

In one aspect, the present disclosure provides a compound of Formula B:

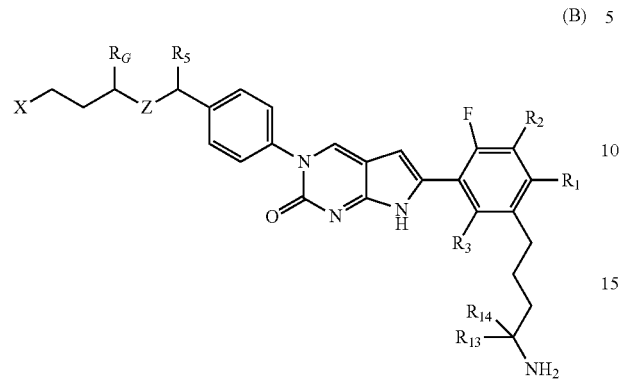

(B)

or a tautomer thereof, or a pharmaceutically acceptable salt, or ester of said compound or tautomer wherein:

X is —NHC(NH)NH$_2$, —NHC(O)NH$_2$, —NHC(NH)(C$_1$-C$_3$)alkyl, —NHS(O)$_2$(C$_1$-C$_3$)alkyl, or heterocycloalkyl;

Z is O, CH$_2$, or NR$_{11}$.

R$_1$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN, or —NO$_2$, wherein the (C$_1$-C$_3$)alkyl, (C$_2$-C$_4$)alkenyl, and (C$_1$-C$_3$)alkoxy are optionally substituted with one or more R$_{12}$;

R$_2$ is halogen, (C$_1$-C$_3$)haloalkyl, —S(C$_1$-C$_3$)haloalkyl, or —O(C$_1$-C$_3$)haloalkyl;

R$_3$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN, or —NO$_2$, wherein the (C$_1$-C$_3$)alkyl, (C$_2$-C$_4$)alkenyl, and (C$_1$-C$_3$)alkoxy are optionally substituted with one or more R$_{12}$;

R$_5$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN or —NO$_2$, wherein the (C$_1$-C$_3$)alkyl, (C$_2$-C$_4$)alkenyl and (C$_1$-C$_3$)alkoxy are optionally substituted with one or more R$_{12}$;

R$_G$ is (C$_1$-C$_3$)alkyl, (C$_2$-C$_3$)alkenyl, (C$_2$-C$_4$)alkynyl, (C$_1$-C$_3$)alkoxy, (C$_1$-C$_3$)haloalkyl, or —O(C$_1$-C$_3$)haloalkyl, wherein the (C$_1$-C$_3$)alkyl is optionally substituted with at least one —NHC(NH)NH$_2$, —NHC(NH)(C$_1$-C$_3$)alkyl, (C$_1$-C$_3$)alkoxy, halogen, —OH, —S(O)$_2$NH$_2$, C(O)NH$_2$, —NH$_2$, —NH(C$_1$-C$_3$)alkyl, or —N((C$_1$-C$_3$)alkyl)$_2$;

R$_{11}$ is H or (C$_1$-C$_4$)alkyl;

each R$_{12}$ is independently selected from halogen, (C$_1$-C$_3$) alkoxy, —OH, —NH$_2$, —NH(C$_1$-C$_3$)alkyl, —N((C$_1$-C$_3$) alkyl)$_2$, and oxo;

R$_{13}$ is H, (C$_1$-C$_3$)alkyl, (C$_2$-C$_4$)alkenyl, (C$_2$-C$_4$)alkynyl, —(C$_3$-C$_5$)cycloalkyl, (C$_1$-C$_3$)alkoxy, (C$_1$-C$_3$)haloalkyl, (C$_1$-C$_3$) hydroxyalkyl, —O(C$_1$-C$_3$)haloalkyl, halogen, CN or —NO$_2$, wherein the (C$_1$-C$_3$)alkyl, (C$_2$-C$_4$)alkenyl, and (C$_1$-C$_3$)alkoxy are optionally substituted with one or more R$_{12}$; and R$_{14}$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN, or —NO$_2$.

In one aspect the present disclosure provides a compound of Formula B-1:

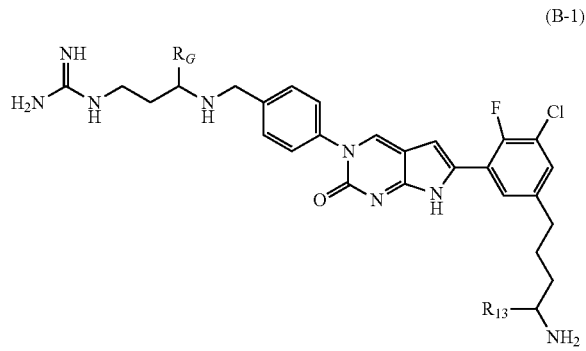

(B-1)

In one aspect the present disclosure provides a compound of Formula B-2:

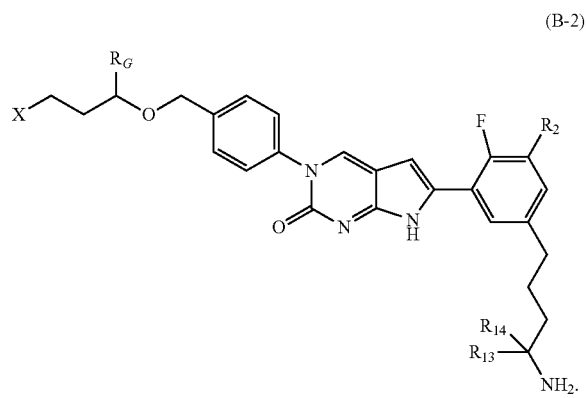

(B-2)

In one aspect the present disclosure provides a compound of Formula C:

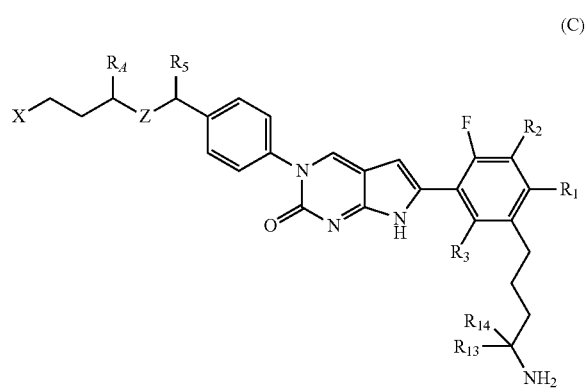

(C)

or a tautomer thereof, or a pharmaceutically acceptable salt, or ester of said compound or tautomer, wherein:

X is —NHC(NH)NH$_2$, —NHC(O)NH$_2$, —NHC(O)(C$_1$-C$_3$)alkyl, or —NHC(NH)(C$_1$-C$_3$)alkyl;

Z is O, CH$_2$, or NR$_{11}$.

R$_1$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN or —NO$_2$, wherein the (C$_1$-C$_3$)alkyl, (C$_2$-C$_4$)alkenyl, and (C$_1$-C$_3$)alkoxy are optionally substituted with one or more R$_{12}$;

R$_2$ is halogen, (C$_1$-C$_3$)haloalkyl, —S(C$_1$-C$_3$)haloalkyl, or —O(C$_1$-C$_3$)haloalkyl;

R$_3$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN, or —NO$_2$, wherein the (C$_1$-C$_3$)alkyl, (C$_2$-C$_4$)alkenyl, and (C$_1$-C$_3$)alkoxy are optionally substituted with one or more R$_{12}$;

R$_5$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN, or —NO$_2$, wherein the (C$_1$-C$_3$)alkyl, (C$_2$-C$_4$)alkenyl, and (C$_1$-C$_3$)alkoxy are optionally substituted with one or more R$_{12}$;

R$_4$ is heteroaryl, (C$_1$-C$_3$)alkylene-NH-heteroaryl or (C$_1$-C$_3$)alkylene-heteroaryl, each of which is optionally substituted with at least one R$_{12}$;

R$_{11}$ is H or (C$_1$-C$_3$)alkyl;

each R$_{12}$ is independently selected from halogen, (C$_1$-C$_3$)alkyl, (C$_1$-C$_3$)alkoxy, —OH, —NH$_2$, —NH(C$_1$-C$_3$)alkyl, —N((C$_1$-C$_3$)alkyl)$_2$, and oxo;

R$_{13}$ is H, (C$_1$-C$_3$)alkyl, (C$_2$-C$_4$)alkenyl, (C$_2$-C$_4$)alkynyl, —(C$_3$-C$_5$)cycloalkyl, (C$_1$-C$_3$)alkoxy, (C$_1$-C$_3$)haloalkyl, (C$_1$-C$_3$) hydroxyalkyl, —O(C$_1$-C$_3$)haloalkyl, halogen, CN, or —NO$_2$, wherein the (C$_1$-C$_3$)alkyl, (C$_2$-C$_4$)alkenyl, and (C$_1$-C$_3$)alkoxy are optionally substituted with one or more R$_{12}$; and R$_{14}$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN, or —NO$_2$.

In one aspect the present disclosure provides a compound of Formula C-1:

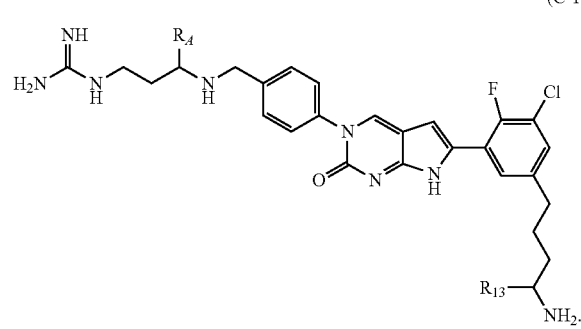

(C-1)

In one aspect the present disclosure provides a compound of Formula C-2:

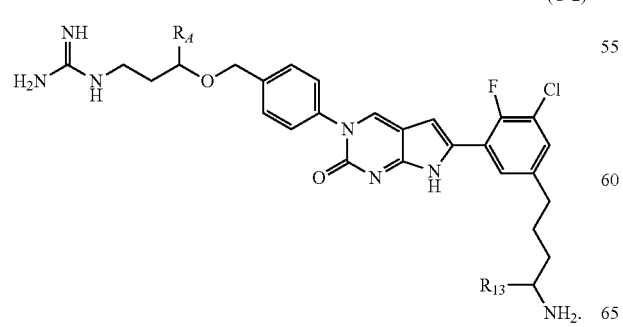

(C-2)

In another aspect, the present disclosure relates to a compound of Formula (II):

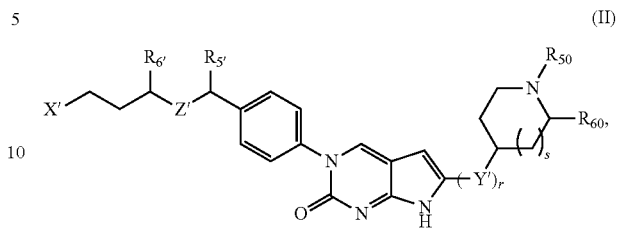

(II)

or a tautomer thereof, or a pharmaceutically acceptable salt, or ester of said compound or tautomer, wherein:

X' is —NHC(NH)NH$_2$, —NHC(NH)CH$_3$, —NHheteroaryl, or —heteroaryl;

each Y' is independently CH$_2$ or NH;

Z' is O, NH, or CH$_2$;

R$_{5'}$ is H or CH$_3$;

R$_{6'}$ is (C$_1$-C$_3$)alkyl, (C$_2$-C$_3$)alkenyl, or (C$_1$-C$_3$)haloalkyl, wherein the alkyl is optionally substituted with one or more substituents independently selected from halogen, —NHC(NH)NH$_2$, and —NHheteroaryl; or R$_{5'}$ and R$_{6'}$ together with the carbon atoms to which they are attached and the Z atom connecting said two carbon atoms, form a 6-membered heterocycloalkyl ring containing 1-3 heteroatoms optionally substituted with one or more R$_{101}$;

R$_{50}$ is H or —C(NH)NH$_2$;

R$_{60}$ is H or (C$_1$-C$_5$)alkyl, wherein the alkyl optionally substituted with one or more substituents independently selected from (C$_1$-C$_2$)alkyl, (C$_2$-C$_4$)alkenyl, (C$_1$-C$_2$)haloalkyl, (C$_1$-C$_2$) hydroxyalkyl, and —NH$_2$;

each R$_{101}$ is independently selected from (C$_1$-C$_3$)alkyl, (C$_2$-C$_3$)alkenyl, halogen, —NH$_2$, and —NHheteroaryl wherein the alkyl is optionally substituted with one or more substituents independently selected from —NH$_2$ and —NHC(NH)NH$_2$;

r is 0, 1, 2, or 3; and s is 0 or 1.

Another aspect of the present disclosure relates to a compound of Formula (III):

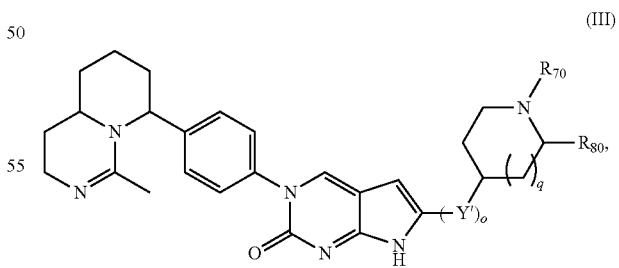

(III)

or a tautomer thereof, or a pharmaceutically acceptable salt, or ester of said compound or tautomer, wherein:

each Y' is independently CH$_2$ or NH$_2$;

R$_{70}$ is H or —C(NH)NH$_2$;

R$_{80}$ is H or (C$_1$-C$_5$)alkyl, wherein the alkyl optionally substituted with one or more substituents independently selected from $(C_1-C_2)$alkyl, $(C_2-C_4)$alkenyl, $(C_1-C_2)$haloalkyl, $(C_1-C_2)$ hydroxyalkyl, and —NH$_2$;

o is 0, 1, 2, or 3; and q is 0 or 1.

In another aspect, the present disclosure relates to a pharmaceutical composition comprising a pharmaceutically acceptable carrier and a compound of the present disclosure or a tautomer thereof, or a pharmaceutically acceptable salt, or ester of said compound or tautomer.

In another aspect, the present disclosure relates to a method of treating a microbial infection comprising administering to a subject in need thereof an effective amount of a compound of the present disclosure, or a tautomer thereof, or a pharmaceutically acceptable salt, or ester of said compound or tautomer.

In another aspect, the present disclosure relates to a method of preventing a microbial infection comprising administering to a subject in need thereof an effective amount of a compound of the present disclosure, or a tautomer thereof, or a pharmaceutically acceptable salt, or ester of said compound or tautomer.

In yet another aspect, the present disclosure relates to a method of reducing the risk of a microbial infection comprising administering to a subject in need thereof an effective amount of a compound of the present disclosure, or a tautomer thereof, or a pharmaceutically acceptable salt, or ester of said compound or tautomer.

In another aspect, the present disclosure relates to a method of delaying the onset of a microbial infection comprising administering to a subject in need thereof an effective amount of a compound of the present disclosure, or a tautomer thereof, or a pharmaceutically acceptable salt, or ester of said compound or tautomer.

In another aspect, the present disclosure relates to the use of a compound of the present disclosure, or a tautomer thereof, or a pharmaceutically acceptable salt, or ester of said compound or tautomer, in the manufacture of a medicament for treating, preventing, or reducing a microbial infection in a subject.

In yet another aspect, the present disclosure relates to a compound for use in a method for treating, preventing, reducing the risk of, and/or delaying the onset of a microbial infection in a subject, wherein the compound is selected from a compound of the present disclosure, or a tautomer thereof, or a pharmaceutically acceptable salt, or ester of said compound or tautomer.

In addition, the disclosure provides methods of synthesizing the foregoing compounds and tautomers thereof, and pharmaceutically acceptable salts, esters and prodrugs of said compounds and tautomers. Following synthesis, an effective amount of one or more of the compounds or tautomers thereof, or pharmaceutically acceptable salts, esters or prodrugs of said compounds or tautomers can be formulated with a pharmaceutically acceptable carrier for administration to a human or animal for use as antimicrobial agents, particularly as antibacterial agents. In certain embodiments, the compounds of the present disclosure are useful for treating, preventing, reducing the risk of, or delaying the onset of microbial infections or for the manufacture of a medicament for treating, preventing, reducing the risk of, or delaying the onset of microbial infections.

Accordingly, the compounds or tautomers thereof, or pharmaceutically acceptable salts, esters, or prodrugs of said compounds or tautomers or their formulations can be administered, for example, via oral, parenteral, intravenous, otic, ophthalmic, nasal, or topical routes, to provide an effective amount of the compound or tautomer thereof, or pharmaceutically acceptable salt, ester or prodrug of said compound or tautomer to the human or animal.

The foregoing and other aspects and embodiments of the disclosure can be more fully understood by reference to the following detailed description and claims.

DETAILED DESCRIPTION OF THE INVENTION

The present disclosure utilizes a structure based drug design approach for discovering and developing new antimicrobial agents. This approach starts with a high resolution X-ray crystal of a ribosome to design new classes of antimicrobial compounds having specific chemical structures, ribosome binding characteristics, and antimicrobial activity. This structure based drug discovery approach is described in the following publication: Franceschi, F. and Duffy, E. M., "Structure-based drug design meets the ribosome", *Biochemical Pharmacology*, vol. 71, pp. 1016-1025 (2006).

Based on this structure based drug design approach, the present disclosure describes new chemical classes of antimicrobial compounds useful for treating bacterial infections in humans and animals. Without being limited by theories, these compounds are believed to inhibit bacterial ribosome function by binding to the ribosome. By taking advantage of these ribosome binding sites, the antimicrobial compounds of the present disclosure can provide better activity, especially against resistant strains of bacteria, than currently available antibiotic compounds.

The present disclosure therefore fills an important ongoing need for new antimicrobial agents, particularly for antimicrobial agents, having activity against resistant pathogenic bacterial organisms.

The present disclosure provides a family of compounds or tautomers thereof, that can be used as antimicrobial agents, more particularly as antibacterial agents.

The present disclosure also includes pharmaceutically acceptable salts, esters, and prodrugs of said compounds and tautomers.

The compounds or tautomers thereof, or pharmaceutically acceptable salts, esters, or prodrugs of said compounds or tautomers disclosed herein can have asymmetric centers. Compounds or tautomers thereof, or pharmaceutically acceptable salts, esters, or prodrugs of said compounds or tautomers of the present disclosure containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds or tautomers thereof, or pharmaceutically acceptable salts, esters, or prodrugs of said compounds or tautomers disclosed herein, and all such stable isomers are contemplated in the present disclosure. Cis and trans geometric isomers of the compounds or tautomers thereof, or pharmaceutically acceptable salts, esters, or prodrugs of said compounds or tautomers of the present disclosure are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds or tautomers thereof, or pharmaceutically acceptable salts, esters, or prodrugs of said compounds or tautomers of the present disclosure and intermediates made herein are considered to be part of the present disclosure. All tautomers of shown or described compounds are also considered to be part of the present disclosure. Furthermore, the disclosure also includes metabolites of the compounds disclosed herein.

The disclosure also comprehends isotopically-labeled compounds or tautomers thereof, or pharmaceutically acceptable salts, esters, or prodrugs of said compounds or tautomers, which are identical to those recited in formulae of the disclosure, but for the replacement of one or more atoms by an atom having an atomic mass or mass number different from the atomic mass or mass number most commonly found in nature. Examples of isotopes that can be incorporated into compounds or tautomers thereof, or pharmaceutically acceptable salts, esters, or prodrugs of said compounds or tautomers of the disclosure include isotopes of hydrogen, carbon, nitrogen, fluorine, such as $^3H$, $^{11}C$, $^{14}C$ and $^{18}F$.

The compounds of the present disclosure or tautomers thereof, or pharmaceutically acceptable salts, esters, or prodrugs of said compounds or tautomers that contain the aforementioned isotopes and/or isotopes of other atoms are within the scope of the present disclosure. Isotopically-labeled compounds or tautomers thereof, or pharmaceutically acceptable salts, esters, or prodrugs of said compounds or tautomers of the present disclosure, for example, those into which radioactive isotopes such as $^3H$ and $^{14}C$ are incorporated, are useful in drug and/or substrate tissue distribution assays. Tritium, i.e., $^3H$, and carbon-14, i.e., $^{14}C$, isotopes are are particularly preferred due to their ease of preparation and detectability. $^{11}C$ and $^{18}F$ isotopes are particularly useful in PET (positron emission tomography). PET is useful in brain imaging. Further, substitution with heavier isotopes such as deuterium, i.e., $^2H$, can afford certain therapeutic advantages resulting from greater metabolic stability, i.e., increased in vivo half-life or reduced dosage requirements and, hence, may be preferred in some circumstances. Isotopically labeled compounds or tautomers thereof, or pharmaceutically acceptable salts, esters, or prodrugs of said compounds or tautomers having a formula of the disclosed herein can generally be prepared as described in the procedures, Schemes and/or in the Examples disclosed herein, by substituting a non-isotopically labeled reagent with a readily available isotopically labeled reagent. In one embodiment, the compounds or tautomers thereof, or pharmaceutically acceptable salts, esters, or prodrugs of said compounds or tautomers disclosed herein are not isotopically labeled.

When any variable (e.g., R) occurs more than one time in any constituent or formulae of the disclosed herein, its definition at each occurrence is independent of its definition at every other occurrence. Thus, for example, if a group is shown to be substituted with one or more R moieties, then R at each occurrence is selected independently from the definition of R. Also, combinations of substituents and/or variables are permissible, but only if such combinations result in stable compounds within a designated atom's normal valence.

A chemical structure showing a dotted line representation for a chemical bond indicates that the bond is optionally present. For example, a dotted line drawn next to a solid single bond indicates that the bond can be either a single bond or a double bond.

When a bond to a substituent is shown to cross a bond connecting two atoms in a ring, then such substituent can be bonded to any atom on the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

In cases wherein compounds of the present disclosure, or tautomers thereof, or pharmaceutically acceptable salts, esters, or prodrugs of said compounds or tautomers thereof, contain nitrogen atoms, these, where appropriate, can be converted to N-oxides by treatment with an oxidizing agent (e.g., meta-chloroperoxybenzoic acid (mCPBA) and/or hydrogen peroxides). Thus, shown and claimed nitrogen atoms are considered to cover both the shown nitrogen and its N-oxide (N→O) derivative, as appropriate. In some embodiments, the present disclosure relates to N-oxides of the compounds or tautomers thereof, or pharmaceutically acceptable salts, esters, or prodrugs of said compounds or tautomers disclosed herein.

One approach to developing improved anti-proliferative and anti-infective agents is to provide modulators (for example, inhibitors) of ribosome function.

Ribosomes are ribonucleoproteins, which are present in both prokaryotes and eukaryotes. Ribosomes are the cellular organelles responsible for protein synthesis. During gene expression, ribosomes translate the genetic information encoded in a messenger RNA into protein (Garrett et al. (2000) "*The Ribosome: Structure, Function, Antibiotics and Cellular Interactions*," American Society for Microbiology, Washington, D.C.).

Ribosomes comprise two nonequivalent ribonucleoprotein subunits. The larger subunit (also known as the "large ribosomal subunit") is about twice the size of the smaller subunit (also known as the "small ribosomal subunit"). The small ribosomal subunit binds messenger RNA (mRNA) and mediates the interactions between mRNA and transfer RNA (tRNA) anticodons on which the fidelity of translation depends. The large ribosomal subunit catalyzes peptide bond formation, i.e., the peptidyl-transferase reaction of protein synthesis, and includes, at least, three different tRNA binding sites known as the aminoacyl, peptidyl, and exit sites. The aminoacyl site or A-site accommodates the incoming aminoacyl-tRNA that is to contribute its amino acid to the growing peptide chain. Also, the A space of the A-site is important. The peptidyl site or P-site accommodates the peptidyl-tRNA complex, i.e., the tRNA with its amino acid that is part of the growing peptide chain. The exit or E-site accommodates the deacylated tRNA after it has donated its amino acid to the growing polypeptide chain.

1. Definitions

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. A compound with one chiral center has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J., Chem. Educ.* 1964, 41, 116).

"Geometric isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however, as a result of recent advances in chromatography techniques, it has been possible to separate mixtures of two atropic isomers in select cases.

Some compounds of the present disclosure can exist in a tautomeric form which is also intended to be encompassed within the scope of the present disclosure. "Tautomers" refers to compounds whose structures differ markedly in the arrangement of atoms, but which exist in easy and rapid equilibrium. It is to be understood that compounds of present disclosure may be depicted as different tautomers. It should also be understood that when compounds have tautomeric forms, all tautomeric forms are intended to be within the scope of the disclosure, and the naming of the compounds does not exclude any tautomeric form.

The compounds, pharmaceutically acceptable salts, esters and prodrugs of the present disclosure can exist in one or more tautomeric forms, including the enol and imine form, and the keto and enamine form and geometric isomers and mixtures thereof. All such tautomeric forms are included within the scope of the present disclosure. Tautomers exist as mixtures of a tautomeric set in solution. In solid form, usually one tautomer predominates. Even though one tautomer may be described, the present disclosure includes all tautomers of the compounds disclosed herein.

A tautomer is one of two or more structural isomers that exist in equilibrium and are readily converted from one isomeric form to another. This reaction results in the formal migration of a hydrogen atom accompanied by a shift of adjacent conjugated double bonds. In solutions where tautomerization is possible, a chemical equilibrium of the tautomers can be reached. The exact ratio of the tautomers depends on several factors, including temperature, solvent, and pH. The concept of tautomers that are interconvertible by tautomerizations is called tautomerism.

Of the various types of tautomerism that are possible, two are commonly observed. In keto-enol tautomerism, a simultaneous shift of electrons and a hydrogen atom occurs. Ring-chain tautomerism, exhibited by glucose and other sugars, arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs include: ketone-enol, amide-nitrile, lactam-lactim, amide-imidic acid tautomerism in heterocyclic rings (e.g., in the nucleobases guanine, thymine, and cytosine), amine-enamine and enamine-enamine. Examples below are included for illustrative purposes, and the present disclosure is not limited to the examples:

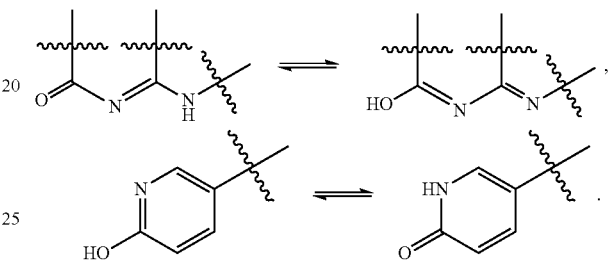

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate over another crystal form. Crystal polymorphs of the compounds can be prepared by crystallization under different conditions.

The term "substituted," as used herein, means that any one or more hydrogens on the designated atom, usually a carbon, oxygen, or nitrogen atom, is replaced with a selection from the indicated group, provided that the designated atom's normal valency is not exceeded, and that the substitution results in a stable compound. When a substituent is keto or oxo (i.e., =O), then 2 hydrogens on the atom are replaced. Ring double bonds, as used herein, are double bonds that are formed between two adjacent ring atoms (e.g., C=C, C=N, N=N, etc.). Substituents can include, for example, —($C_{1-9}$ alkyl) optionally substituted with one or more of hydroxyl, —$NH_2$, —NH($C_{1-3}$ alkyl), and —N($C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxyl) optionally substituted with one or more of halide, hydroxyl, —$NH_2$, —NH($C_{1-3}$ alkyl), and —N($C_{1-3}$ alkyl)$_2$; —OPO(OH)$_2$; a phosphonate [such as —PO(OH)$_2$ and —PO(OR')$_2$]; —OPO(OR')R''; —NRR'; —C(O)NRR'; —C(NR)NR'R''; —C(NR')R''; a cyano; a nitro; an azido; —SH; —S—R; —OSO$_2$(OR); a sulfonate [such as —SO$_2$(OH) and —SO$_2$(OR)]; —SO$_2$NR'R''; and —SO$_2$R; in which each occurrence of R, R' and R'' are independently selected from H, —($C_{1-9}$ alkyl), $C_{6-10}$ aryl optionally substituted with from 1-3R''', 5-10 membered heteroaryl having from 1-4 heteroatoms independently selected from N, O, and S and optionally substituted with from 1-3 R''', $C_{3-7}$ carbocyclyl optionally substituted with from 1-3 R''', and 3-8 membered heterocyclyl having from 1-4 heteroatoms independently selected from N, O, and S and optionally substituted with from 1-3 R'''; wherein each R''' is independently selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

As used herein, "alkyl" is intended to include both branched and straight-chain saturated aliphatic hydrocarbon groups having the specified number of carbon atoms. For example $C_{1-4}$ is intended to include $C_1$, $C_2$, $C_3$, and $C_4$ $C_{1-6}$ alkyl is intended to include $C_1$, $C_2$, $C_3$, $C_4$, $C_5$, and $C_6$ alkyl groups and $C_{1-8}$ is intended to include $C_1$, $C_2$, $C_3$, $C_4$, $C_5$, $C_6$, $C_7$, and $C_8$. Some examples of alkyl include, but are not limited to, methyl, ethyl, n-propyl, i-propyl, n-butyl, s-butyl, t-butyl, n-pentyl, s-pentyl, n-hexyl, n-heptyl, and n-octyl.

As used herein, "alkenyl" is intended to include hydrocarbon chains of either straight or branched configuration and one or more unsaturated carbon-carbon bonds that can occur in any stable point along the chain, such as ethenyl and propenyl. For example $C_{2-6}$ alkenyl is intended to include $C_2$, $C_3$, $C_4$, $C_5$, and $C_6$ alkenyl groups and $C_{2-8}$ alkenyl is intended to include $C_2$, $C_3$, $C_4$, $C_5$, $C_6$, $C_7$, and $C_8$.

As used herein, "alkynyl" is intended to include hydrocarbon chains of either straight or branched configuration and one or more triple carbon-carbon bonds that can occur in any stable point along the chain, such as ethynyl and propynyl. For example, $C_{2-6}$ alkynyl is intended to include $C_2$, $C_3$, $C_4$, $C_5$, and $C_6$ alkynyl groups and $C_{2-8}$ alkynyl is intended to include $C_2$, $C_3$, $C_4$, $C_5$, $C_6$, $C_7$, and $C_8$.

As used herein, "alkylene" is intended to include moieties which are diradicals, i.e., having two points of attachment. A non-limiting example of such an alkylene moiety is —$CH_2CH_2$—, i.e., a $C_2$ alkyl group that is covalently bonded via each terminal carbon atom to the remainder of the molecule. The alkylene diradicals are also known as "alkylenyl" radicals. Alkylene groups can be saturated or unsaturated (e.g., containing —CH=CH— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms). Some examples of alkylene groups include, but are not limited to, methylene, ethylene, n-propylene, iso-propylene, n-butylene, iso-butylene, sec-butylene, tert-butylene, n-pentylene, iso-pentylene, sec-pentylene, and neo-pentylene.

As used herein, "cycloalkyl" is intended to include saturated or unsaturated nonaromatic ring groups, such as cyclopropyl, cyclobutyl, or cyclopentyl. $C_{3-8}$ cycloalkyl is intended to include $C_3$, $C_4$, $C_5$, $C_6$, $C_7$, and $C_8$ cycloalkyl groups. Cycloalkyls may include multiple spiro- or fused rings.

As used herein, the term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "amine" or "amino" refers to unsubstituted —$NH_2$ unless otherwise specified.

The term "alkylamino" as used herein refers to an amino or —$NH_2$ group where one of the hydrogens have been replaced with an alkyl group, as defined herein above, i.e., —NH(alkyl). Example of alkylamino groups include, but are not limited to, methylamino (i.e., —NH($CH_3$)), ethylamino, propylamino, iso-propylamino, butylamino, sec-butylamino, tert-butylamino, etc.

The term "dialkylamino" as used herein refers to an amino or —$NH_2$ group where both of the hydrogens have been replaced with alkyl groups, as defined herein above, i.e., —N(alkyl)$_2$. The alkyl groups on the amino group can be the same or different alkyl groups. Example of alkylamino groups include, but are not limited to, dimethylamino (i.e., —N($CH_3$)$_2$), diethylamino, dipropylamino, diiso-propylamino, di-n-butylamino, di-sec-butylamino, di-tert-butylamino, methyl(ethyl)amino, methyl(butyl)amino, etc.

As used herein, "halo" or "halogen" refers to fluoro, chloro, bromo, and iodo substituents.

As used herein, "haloalkyl" is intended to include both branched and straight-chain saturated aliphatic hydrocarbon groups having the specified number of carbon atoms, substituted with one or more halogen (for example —$C_vF_wH_{2v-w+1}$ wherein v=1 to 3 and w=1 to (2v+1)). Examples of haloalkyl include, but are not limited to, trifluoromethyl, trichloromethyl, pentafluoroethyl, and pentachloroethyl.

The term "haloalkoxy" as used herein refers to an alkoxy group, as defined herein, which is substituted one or more halogen. Examples of haloalkoxy groups include, but are not limited to, trifluoromethoxy, difluoromethoxy, pentafluoroethoxy, trichloromethoxy, etc.

As used herein, "haloalkenyl" is intended to include both branched and straight-chain unsaturated hydrocarbon groups having the specified number of carbon atoms, substituted with one or more halogen. Examples of haloalkyl include, but are not limited to, —CH═CHF, —CH═CHCl, —CH═CF$_2$, —CH═CCl$_2$, CH$_2$CH═CHF, CH$_2$CH═CHCl, CH$_2$CH═CF$_2$, and CH$_2$CH═CCl$_2$.

As used herein, "alkoxyl" or "alkoxy" refers to an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "alkylthio" refers to an alkyl group as defined above with the indicated number of carbon atoms attached through a sulfur bridge. $C_{1-6}$ alkylthio, is intended to include $C_1$, $C_2$, $C_3$, $C_4$, $C_5$, and $C_6$ alkylthio groups. $C_{1-8}$ alkylthio, is intended to include $C_1$, $C_2$, $C_3$, $C_4$, $C_5$, $C_6$, $C_7$, and $C_8$ alkylthio groups.

As used herein, "aryl" includes groups with aromaticity, including "conjugated," or multicyclic systems with at least one aromatic ring and do not contain any heteroatom in the ring structure. Aryl may be monocyclic or polycyclic (e.g., having 2, 3 or 4 fused rings). The term "Cn-m aryl" refers to an aryl group having from n to m ring carbon atoms. In some embodiments, aryl groups have from 6 to 10 carbon atoms. In some embodiments, the aryl group is phenyl or naphthyl.

As used herein, the term "aromatic heterocycle", "aromatic heterocyclic" or "heteroaryl" ring is intended to mean a stable 5, 6, 7, 8, 9, 10, 11, or 12-membered monocyclic or bicyclic aromatic ring which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic aromatic heterocyclic or heterocycle or heteroaryl rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and S(O)$_p$, wherein p=1 or 2). In certain compounds, the total number of S and O atoms in the aromatic heterocycle is not more than 1.

Examples of aromatic heterocycles, aromatic heterocyclics or heteroaryls include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, benzooxadiazoly, carbazolyl, 4aH-carbazolyl, carbolinyl, cinnolinyl, furazanyl, imidazolyl, imidazolonyl, 1H-indazolyl, indolizinyl, indolyl, 3H-indolyl, isobenzofuranyl, isochromanyl, isoindazolyl, isoindolyl, isoquinolinyl, isothiazolyl, isoxazolyl, methylbenztriazolyl, methylfuranyl, methylimidazolyl, methylthiazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, phenanthridinyl, phenanthrolinyl, phenazinyl, phenothiazinyl, phenoxathinyl, phenoxazinyl, phthalazinyl, pteridinyl, purinyl, pyrazinyl, pyrazolyl, pyridazinyl, pyridooxazolyl, pyridoimidazolyl, pyridothiazolyl, pyridinyl, pyridinonyl, pyridyl, pyrimidinyl, 2H-pyrrolyl, pyrrolyl, quinazolinyl, quinolinyl, 4H-quinolizinyl, quinoxalinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, triazolopyrimidinyl, 1,2,3-triazolyl, 1,2,4-triazolyl, 1,2,5-triazolyl, and 1,3,4-triazolyl.

The term "hydroxyalkyl" means an alkyl group as defined above, where the alkyl group is substituted with one or more OH groups. Examples of hydroxyalkyl groups include HO—CH$_2$—, HO—CH$_2$—CH$_2$— and CH$_3$—CH(OH)—.

The term "cyano" as used herein means a substituent having a carbon atom joined to a nitrogen atom by a triple bond, i.e., C≡N.

As used herein, "oxo" is means a "═O" group.

As used herein, the phrase "pharmaceutically acceptable" refers to those compounds or tautomers thereof, or salts, esters, or prodrugs thereof, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds or tautomers thereof, wherein the parent compound or a tautomer thereof, is modified by making of the acid or base salts thereof of the parent compound or a tautomer thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound, or a tautomer thereof, formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present disclosure can be synthesized from the parent compound or a tautomer thereof, that contains a basic or acidic moiety by conventional chemical methods. Generally, such pharmaceutically acceptable salts can be prepared by reacting the free acid or base forms of these compounds or tautomers thereof with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., USA, p. 1445 (1990).

Since prodrugs are known to enhance numerous desirable qualities of pharmaceuticals (e.g., solubility, bioavailability, manufacturing, etc.), the compounds or tautomers thereof of the present disclosure can be delivered in prodrug form. Thus, the present disclosure is intended to cover prodrugs of the presently claimed compounds or tautomers thereof, methods of delivering the same, and compositions containing the same. "Prodrugs" are intended to include any covalently bonded carriers that release an active parent drug of the present disclosure in vivo when such prodrug is administered to a mammalian subject. Prodrugs of the present disclosure are prepared by modifying functional groups present in the compound or a tautomer thereof in such a way that the modified functional groups are cleaved, either in routine manipulation or in vivo, to the release, form, or produce the parent compound or a tautomer thereof. Prodrugs include compounds or tautomers thereof of the present disclosure wherein a hydroxy, amino, or sulfhydryl group is bonded to any group to produce a prodrug of the compound or tautomer thereof that when administered to a mammalian subject is cleaved to form a free hydroxyl, free amino, or free sulfhydryl group, respectively. Examples of prodrugs include, but are not limited to, acetate, formate, and benzoate derivatives of alcohol and amine functional groups in the compounds of the present disclosure.

As used herein, "stable compound" and "stable structure" are meant to indicate a compound that is sufficiently robust to survive isolation to a useful degree of purity from a reaction mixture, and formulation into an efficacious therapeutic agent.

As used herein, the term "patient", as used herein, means the human or animal (in the case of an animal, more typically a mammal) subject that would be subjected to a surgical or invasive medical procedure. Such patient or subject could be considered to be in need of the methods of treating, reducing the risk of or preventing the infection due to a surgical procedure or an invasive medical procedure. Such patient or subject can also be considered to be in need of peri-operative prophylaxis.

As used herein, the term "treating" means to provide a therapeutic intervention to cure or ameliorate an infection. In some embodiments, "treating" refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

As used herein, the term "preventing", as used herein means, to completely or almost completely stop an infection from occurring, for example when the patient or subject is predisposed to an infection or at risk of contracting an infection. Preventing can also include inhibiting, i.e., arresting the development, of an infection.

As used herein, the term "reducing the risk of", as used herein, means to lower the likelihood or probability of an infection occurring, for example when the patient or subject is predisposed to an infection or at risk of contracting an infection.

As used herein, "unsaturated" refers to compounds having at least one degree of unsaturation (e.g., at least one multiple bond) and includes partially and fully unsaturated compounds.

As used herein, the term "effective amount" refers to an amount of a compound or a tautomer thereof, or a pharmaceutically acceptable salt, ester, or prodrug of said compound or tautomer (including combinations of compounds and/or tautomers thereof, and/or pharmaceutically acceptable salts, esters, or prodrugs of said compound or tautomer) of the present disclosure that is effective when administered alone or in combination as an antimicrobial agent. For example, an effective amount refers to an amount of the compound or tautomer thereof, or a pharmaceutically acceptable salt, ester, or prodrug said compound or tautomer that is present in a composition, a formulation or on a medical device given to a recipient patient or subject sufficient to elicit biological activity, for example, anti-infective activity, such as e.g., anti-microbial activity, anti-bacterial activity, anti-fungal activity, anti-viral activity, or anti-parasitic activity.

The term "prophylactically effective amount" means an amount of a compound or a tautomer of said compound or tautomer, or a pharmaceutically acceptable salt, ester, or prodrug of said compound or tautomer (including combinations of compounds and/or tautomers thereof, and/or pharmaceutically acceptable salts, esters, or prodrugs thereof), of the present disclosure that is effective prophylactically when administered alone or in combination as an antimicrobial agent. For example, a prophylactically effective amount refers to an amount of the compound or tautomer thereof, or a pharmaceutically acceptable salt, ester, or prodrug of said compound or tautomer that is present in a composition, a formulation, or on a medical device given to a recipient patient or subject sufficient to prevent or reduce the risk of an infection due to a surgical procedure or an invasive medical procedure.

In the specification, the singular forms also include the plural, unless the context clearly dictates otherwise. Unless defined otherwise, all technical and scientific terms used herein have the same meaning as commonly understood by one of ordinary skill in the art to which this disclosure belongs. In the case of conflict, the present specification will control. As used herein, "mammal" refers to human and non-human patients.

As used herein, the term "therapeutically effective amount" refers to an amount of a compound or a tautomer thereof or a pharmaceutically acceptable salt, ester, or prodrug of said compound or tautomer, (also including combinations of compounds and/or tautomers thereof, and/or pharmaceutically acceptable salts, esters, or prodrugs or said compounds or tautomers), of the present disclosure that is effective when administered alone or in combination as an antimicrobial agent. For example, a therapeutically effective amount refers to an amount of the compound or tautomer thereof, or a pharmaceutically acceptable salt, ester, or prodrug of said compound or tautomer that is present in a composition, a formulation, or on a medical device given to a recipient patient or subject in an amount sufficient to elicit biological activity, for example, anti-microbial activity, anti-fungal activity, anti-viral activity, anti-parasitic activity, anti-diarrheal activity, and/or anti-proliferative activity. In one aspect, the combination of compounds and/or tautomers thereof, and/or pharmaceutically acceptable salts, esters, or prodrugs or said compounds or tautomers is a synergistic combination. Synergy, as described, for example, by Chou and Talalay, *Adv. Enzyme Regul.* vol. 22, pp. 27-55 (1984), occurs when the effect of the compounds or tautomers thereof or pharmaceutically acceptable salts, esters, or prodrugs of said compounds or tautomers when administered in combination is greater than the additive effect of the compounds or tautomers thereof, or pharmaceutically acceptable salts, esters, or prodrugs of said compounds or tautomers when administered alone as a single agent. In general, a synergistic effect is most clearly demonstrated at sub-optimal concentrations of the compounds or tautomers thereof, or pharmaceutically acceptable salts, esters, or prodrugs of said compounds or tautomers. Synergy can be in terms of lower cytotoxicity, increased anti-proliferative and/or anti-infective effect, or some other beneficial effect of the combination compared with the individual components.

As used herein, the term ESBL is extended spectrum beta-lactamase. The term KPC is *Klebsiella pneumonia* carbapenemase.

As used herein, the term acute bacterial skin and skin structure infection (ABSSSI) encompasses complicated skin and skin structure infections (cSSSI) and complication skin and soft tissue infections (cSSTI), which have been used interchangeably. The terms uncomplicated skin and skin structure infections (uCSSSI) and uncomplicated skin and soft tissue infections (uCSSTI) have been used interchangeably.

As used herein, the term "spp." is the abbreviation for species.

As used herein, the term "formulae of the disclosure" or "formulae disclosed herein" includes one or more of the Formulae: A, B, B-1, B-2, C, C-1, C-2, I, Ia, Ib, Ic, Id, Ie, Ig, Ih, Ii, Il, Im, In, II, IIa, IIb, IIc, IId, IIe, IIf, III, IIIa, IV, V, VI, and VII As used herein, the term "compound of the disclosure" or "compound disclosed herein" includes one or more compounds of the formulae of the disclosure or a compound explicitly disclosed herein.

All percentages and ratios used herein, unless otherwise indicated, are by weight.

Throughout the description, where compositions are described as having, including, or comprising specific components, or where processes are described as having, including, or comprising specific process steps, it is contemplated that compositions of the present disclosure also consist essentially of, or consist of, the recited components, and that the processes of the present disclosure also consist essentially of, or consist of, the recited processing steps. Further, it should be understood that the order of steps or order for performing certain actions are immaterial so long as the invention remains operable. Moreover, two or more steps or actions can be conducted simultaneously.

2. Compounds of the Disclosure

In one aspect, the present disclosure provides a compound of Formula (A):

(A)

or a tautomer thereof, or a pharmaceutically acceptable salt, or ester of said compound or tautomer, wherein:

----- is a single or a double bond;

X is $-NHC(NH)NH_2$, $-CH_2NH_2$, $-CH_2NHC(NH)NH_2$, $-CH_2NHCH_2C(O)CH_3$, $-CH_2NHC(NH)(C_1-C_4)$alkyl, $-CH_2NHC(NH)(C_3-C_7)$cycloalkyl, $-CH_2NHC(NH)$heteroaryl, heteroaryl, $-CH_2$heteroaryl, $-NHCH_2$heteroaryl, $-CH_2NH$heteroaryl, $-CH(OH)$heteroaryl, $-CH_2$heterocycloalkyl, $-NHCH_2$heterocycloalkyl, or $-CH_2NH$heterocycloalkyl, wherein the $(C_1-C_4)$alkyl, cycloalkyl, heterocycloalkyl and heteroaryl are optionally substituted with one or more $R_7$;

Z is O, $CH_2$, $NR_{11}$, or $S(O)_p$;

W is $N(R_5)$ or $C(R_5)(R_{5'})$;

$R_1$ is H, $(C_1-C_4)$alkyl, $(C_2-C_4)$alkenyl, $(C_2-C_4)$alkynyl, $(C_1-C_3)$alkoxy, $(C_1-C_3)$haloalkyl, $-O(C_1-C_3)$haloalkyl, heterocycloalkyl, halogen, or $-NO_2$, wherein the $(C_1-C_4)$alkyl, $(C_2-C_4)$alkenyl, and heterocycloalkyl are optionally substituted with one or more $R_{12}$; or $R_1$ and $R_2$ together with the carbon atoms to which they are attached form a $(C_3-C_7)$cycloalkyl or heterocycloalkyl;

$R_2$ is $-F$, $-Cl$, $-CF_3$, $-SCF_3$, or $-OCF_3$;

$R_3$ is H or $-NO_2$;

$R_4$ is H, $(C_1-C_3)$alkyl, $(C_2-C_3)$alkenyl, halogen, or $-NO_2$;

$R_5$ is H or $-CH_3$;

$R_{5'}$ is H; or $R_6$ is H, $(C_1-C_3)$alkyl, $(C_2-C_3)$alkenyl, $(C_1-C_3)$haloalkyl, $-CH_2NHC(NH)NH_2$, $-CH_2NHC(NH)(C_1-C_3)$alkyl, $-(CH_2)_nOH$, $-CH_2S(O)_pNH_2$, $-CH_2NH(C_1-C_3)$alkyl, $-CH_2C(O)NH_2$, $-(CH_2)_nNH_2$, $-CH_2$heterocycloalkyl, $-CH_2NH$heterocycloalkyl, $-(CH_2)_n$heteroaryl, or $-CH_2NH$heteroaryl, wherein the heteroaryl and heterocycloalkyl is optionally substituted with one or more $R_8$; or $R_5$ and $R_6$ together with the carbon atoms to which they are attached and the Z atom connecting said two carbon atoms, form a $(C_5-C_6)$cycloalkyl or a 5- to 6-membered heterocycloalkyl ring containing 1-3 heteroatoms optionally substituted with one or more $R_9$; or when W is $N(R_5)$, $R_6$ and W together with the Z atom connecting W and the carbon atom to which $R_6$ is attached, form a 5- to 6-membered heterocycloalkyl ring containing 1-3 heteroatoms optionally substituted with one or more $R_9$;

at least one of $R_5$ and $R_6$ is not H;

each $R_7$ is independently $(C_1-C_3)$alkyl, halogen, oxo, $-OH$, or $-NH_2$;

each $R_8$ is independently $(C_1-C_3)$alkyl, $(C_1-C_3)$alkoxy, halogen, oxo, $-NH_2$, or $-NHR_{10}$;

each $R_9$ is independently $(C_1-C_3)$alkyl, $(C_2-C_4)$alkenyl, $-NH_2$, $-NHC(NH)NH_2$, $-NHC(NH)(C_1-C_3)$alkyl, $-CH_2$heteroaryl, $-NH$heterocycloalkyl, or $-NH$heteroaryl, wherein the $(C_1-C_3)$alkyl is optionally substituted with one or more substituents independently selected from $-NHC(NH)NH_2$, $-OH$ and $-NH_2$;

each $R_{10}$ is independently $-CH_2$aryl optionally substituted with $(C_1-C_3)$alkoxy or halogen;

$R_{11}$ is H, $-NHC(NH)NH_2$, $-C(O)H$, $-C(O)(C_1-C_4)$alkyl, $-C(O)O(C_1-C_4)$alkyl, $(C_1-C_4)$alkyl, $(C_3-C_6)$cycloalkyl, or heterocycloalkyl, wherein the $(C_1-C_4)$alkyl is optionally substituted with one or more substituents independently selected from $-OH$, $(C_1-C_3)$alkoxy, $-NH_2$, and $-NHC(NH)NH_2$;

each $R_{12}$ is independently selected from $(C_1-C_3)$alkoxy, $(C_1-C_3)$haloalkyl, $(C_1-C_3)$ hydroxyalkyl, halogen, $-OH$, $-NH_2$, $-NH(C_1-C_4)$alkyl, $-N((C_1-C_4)$alkyl$)_2$, and oxo;

$R_{13}$ is —CH$_3$, —CH=CH$_2$, —CF$_3$, —CH$_2$F, or —CH$_2$OH;

$R_{13'}$ is H or —CH$_3$;

n is 1 or 2;

each p is independently 0, 1, or 2; and provided that when Z is NH, X is —CH$_2$NHC(NH)NH$_2$ or —CH$_2$NH$_2$, $R_1$ is H or F, $R_3$ is H, $R_5$ is methyl, and $R_6$ is H, then $R_4$ is (C$_1$-C$_3$)alkyl, (C$_2$-C$_3$)alkenyl, F, I, or —NO$_2$.

In some embodiments of compounds of Formula (A), when Z is NH, X is —NHC(NH)NH$_2$, —CH$_2$NHC(NH)NH$_2$, —CH$_2$NHC(NH)(C$_1$-C$_3$ alkyl), or —CH$_2$NH$_2$, and $R_5$ is H or CH$_3$, then $R_6$ is not CH$_3$, —CH=CH$_2$, —(CH$_2$)$_n$NH$_2$, —(CH$_2$)$_n$OH or a group of Formula:

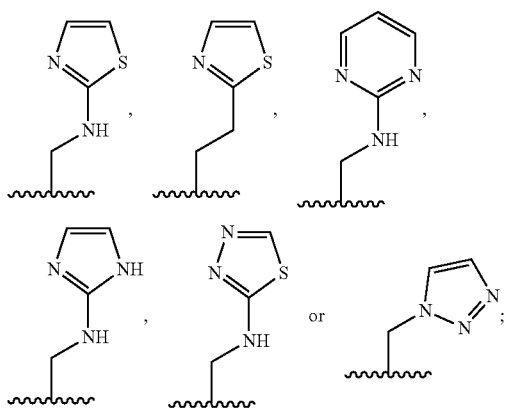

and when Z is NH, X is —NHC(NH)NH$_2$, —CH$_2$NHC(NH)CH$_3$, —CH$_2$NHC(NH)NH$_2$, —CH$_2$NH$_2$ or a group of Formula:

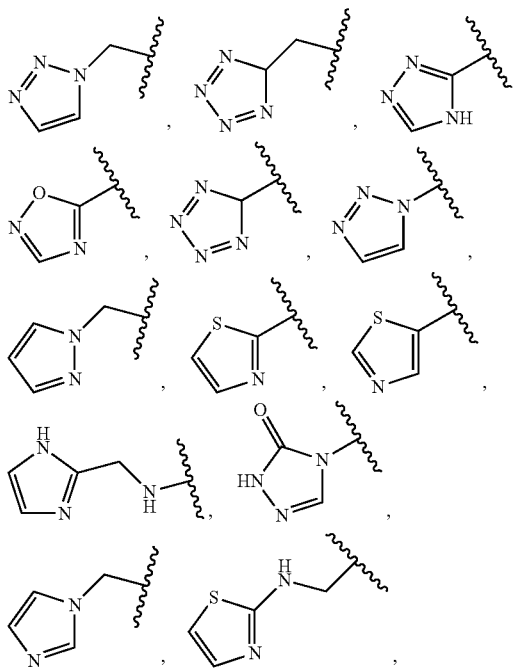

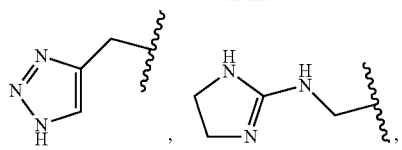

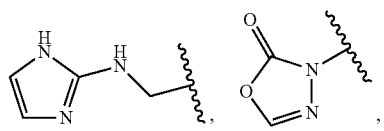

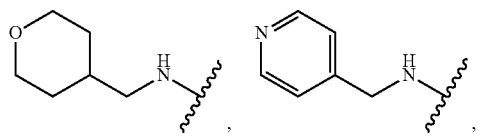

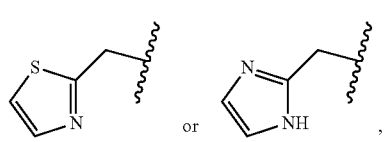

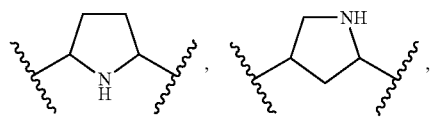

then $R_5$ and $R_6$ do not from a ring of Formula:

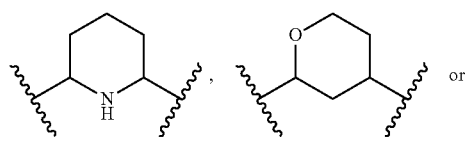

when Z is O, X is —CH$_2$NHC(N)NH$_2$, and $R_5$ is H, then $R_6$ is not a group of Formula:

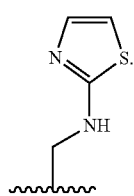

In some embodiments, a compound of Formula (A) is not a compound selected from:
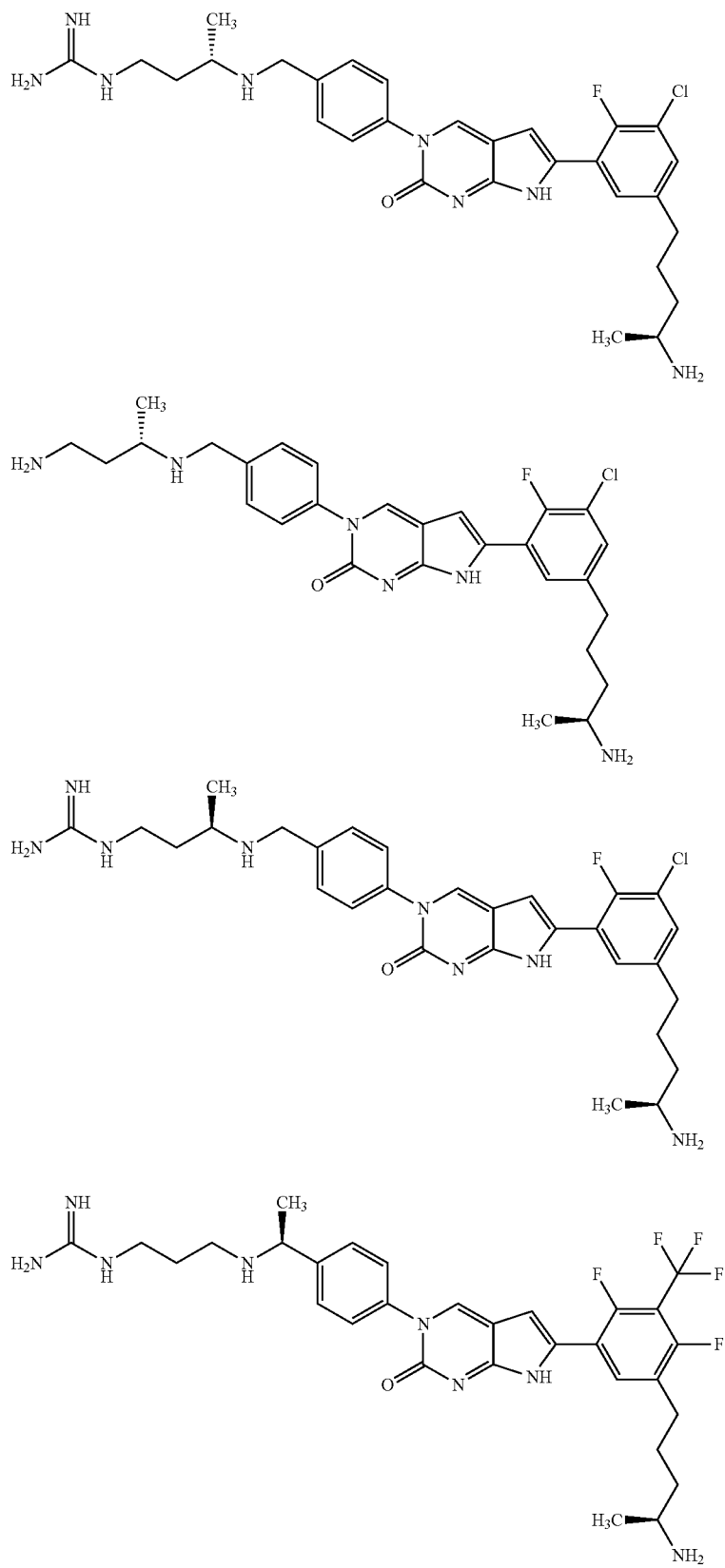

-continued
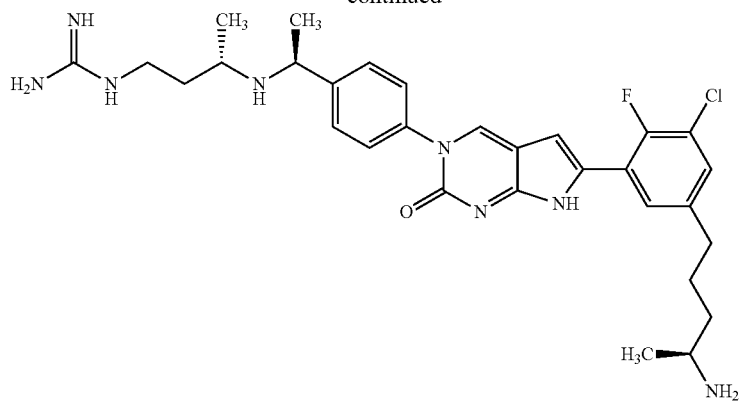
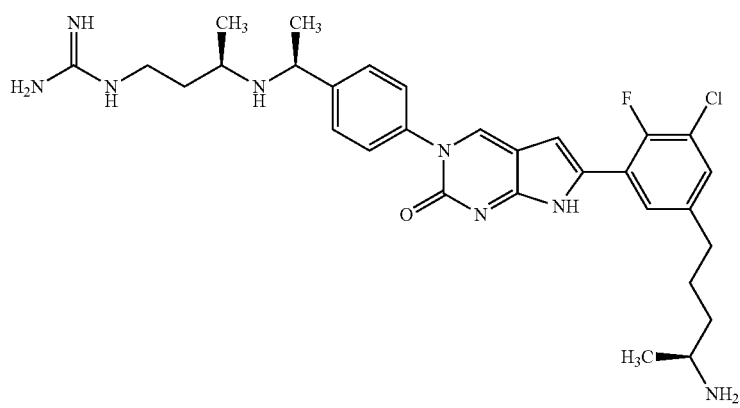
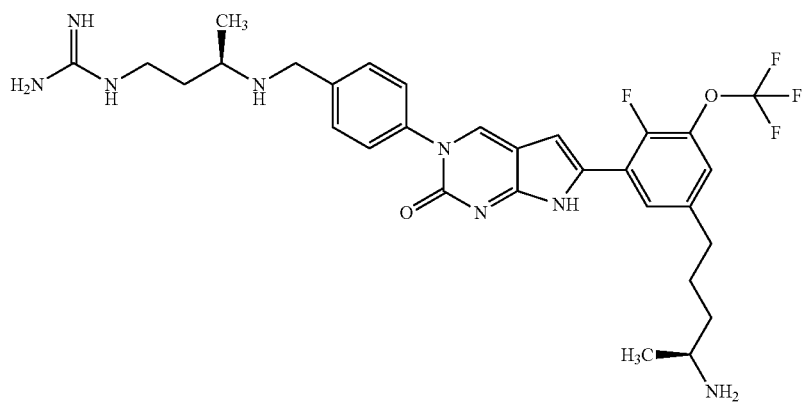
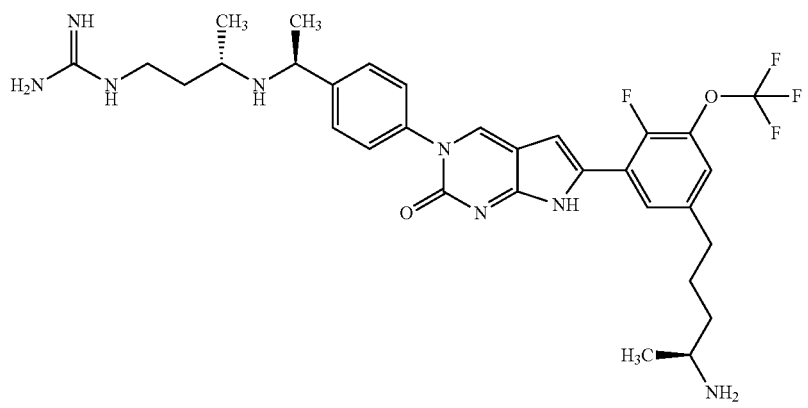

-continued
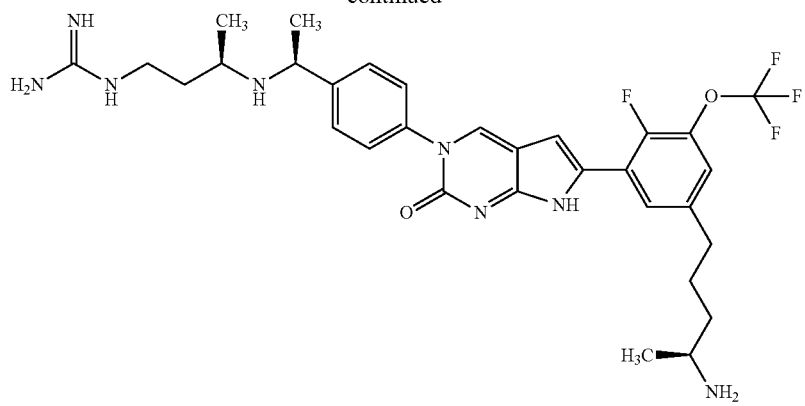
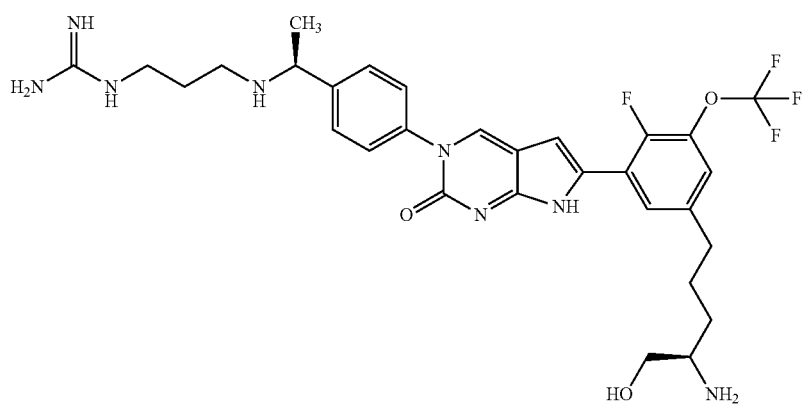
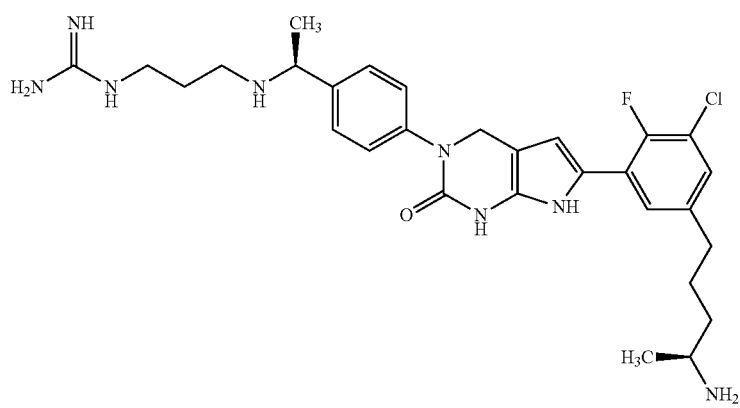
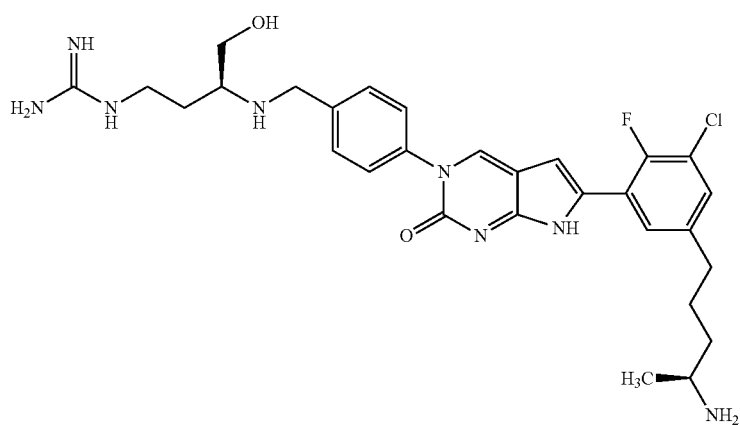

-continued
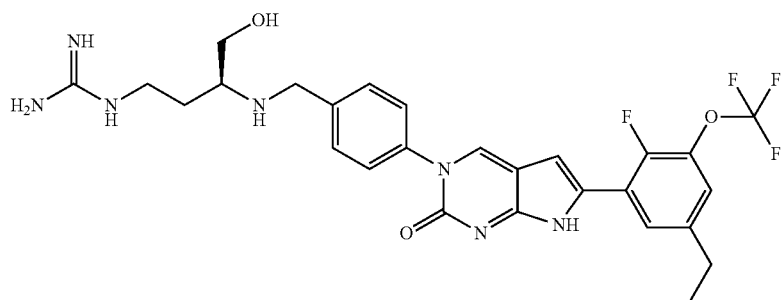
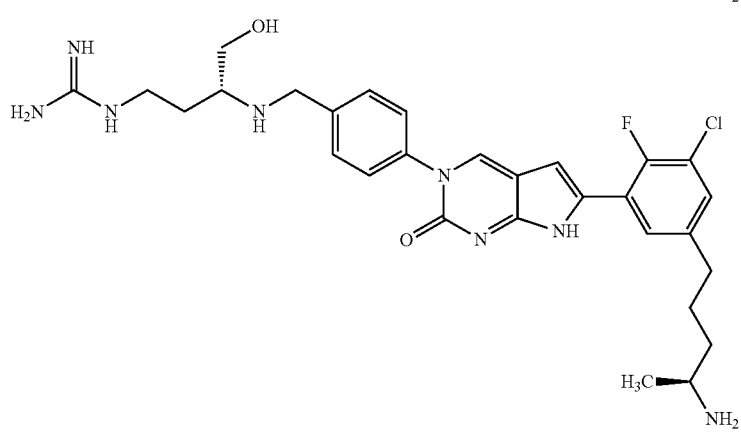
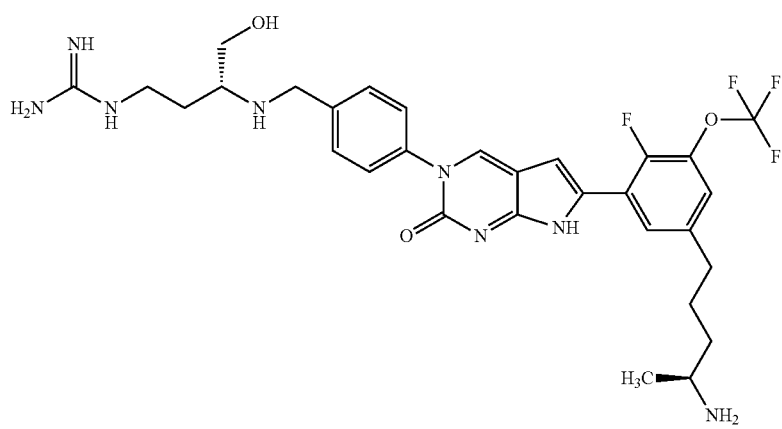
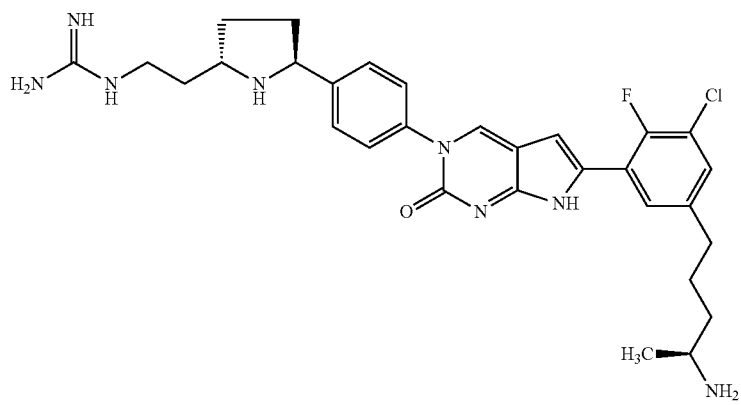

-continued
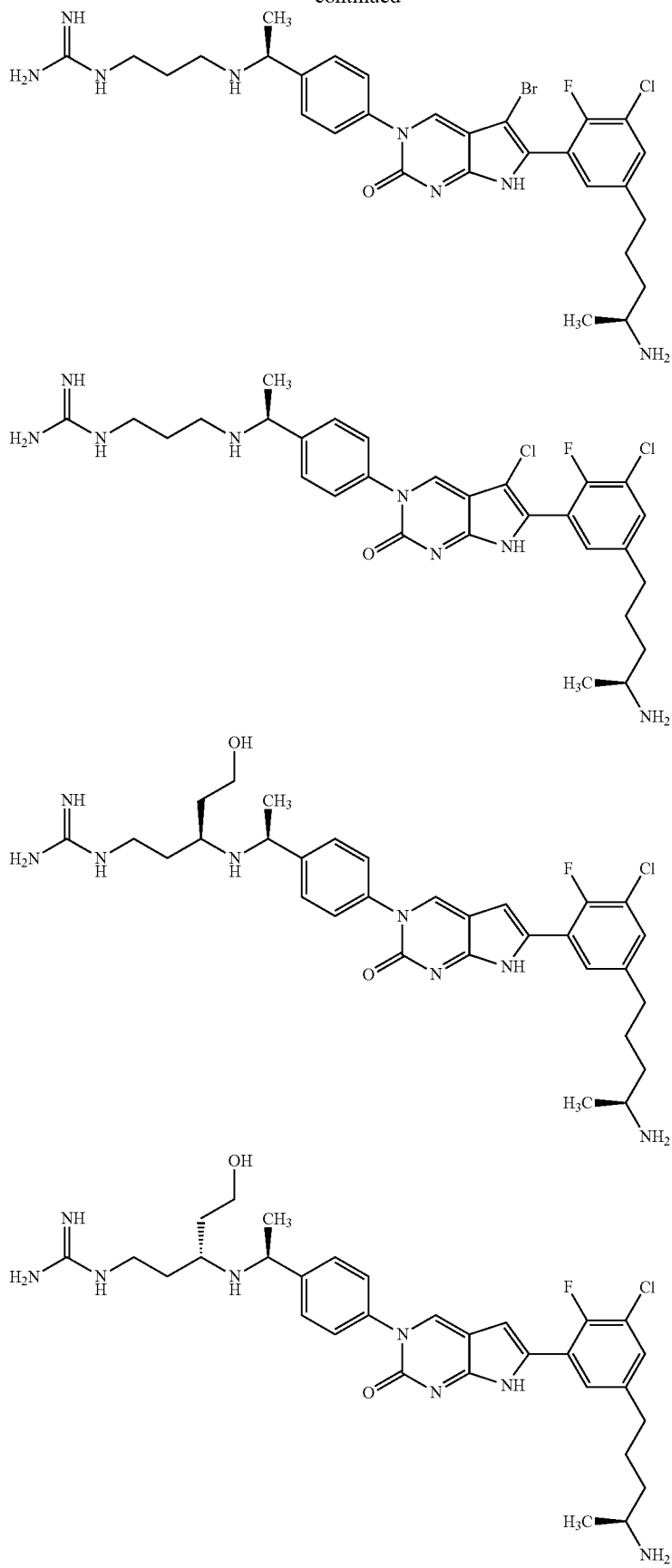

-continued
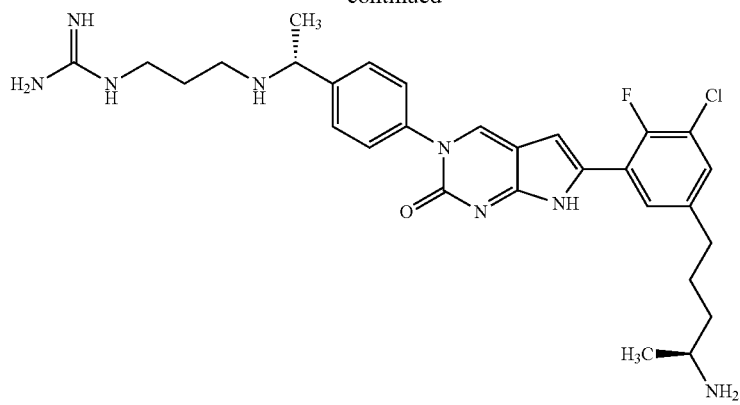
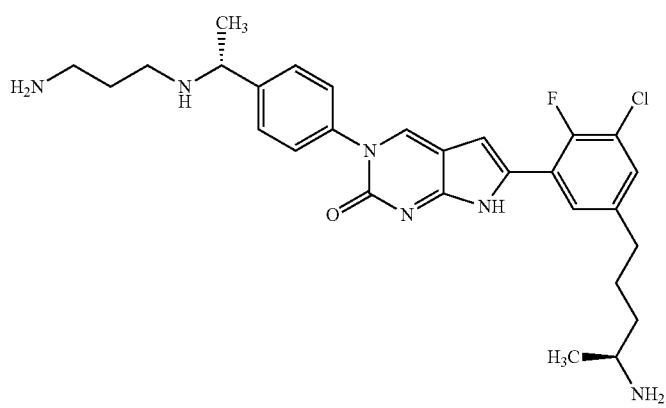
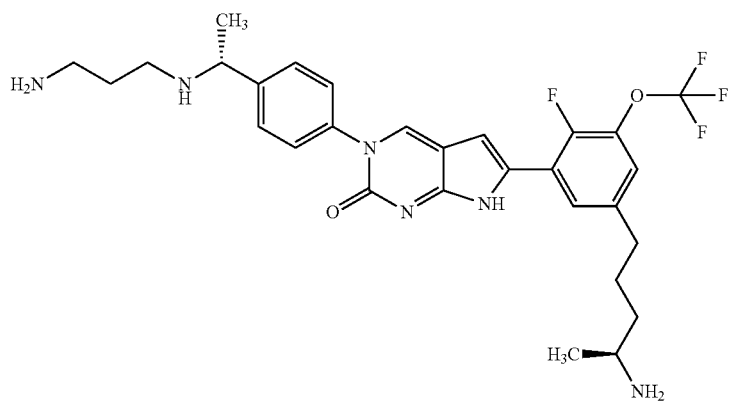
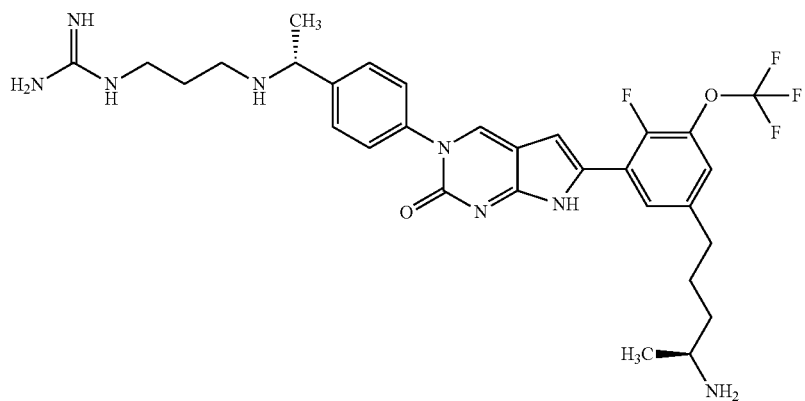

-continued
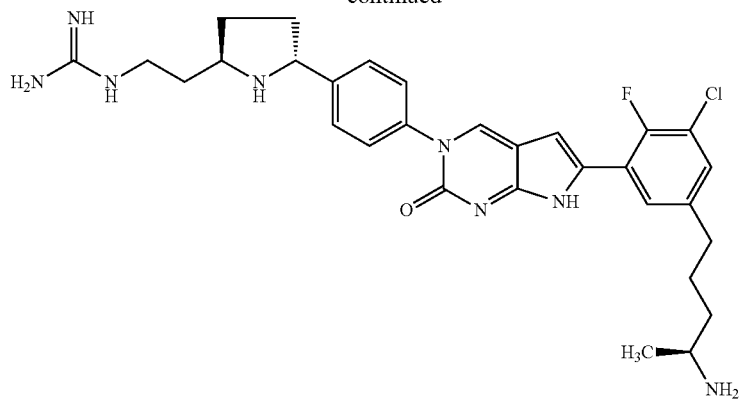
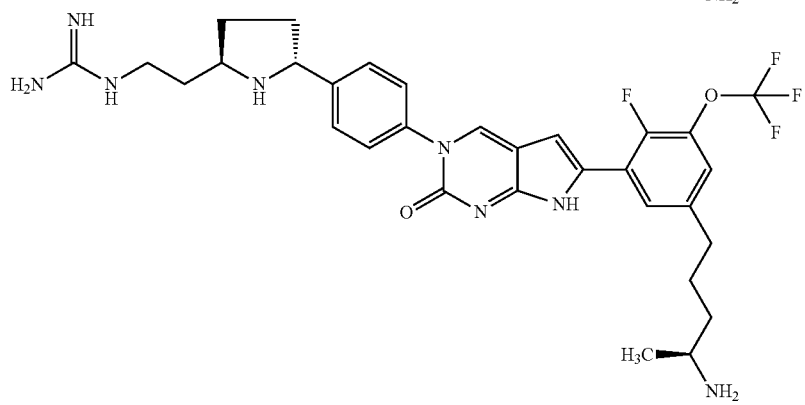
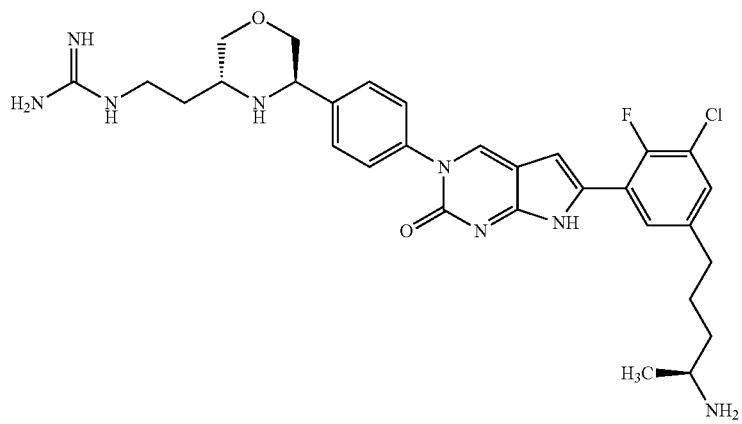
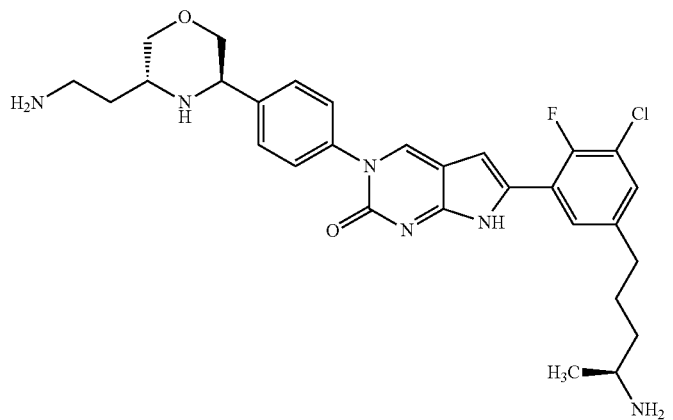

-continued
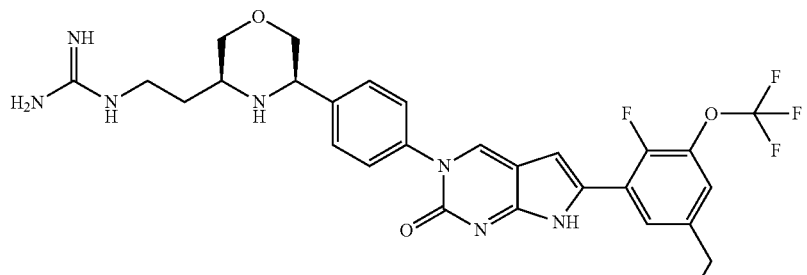
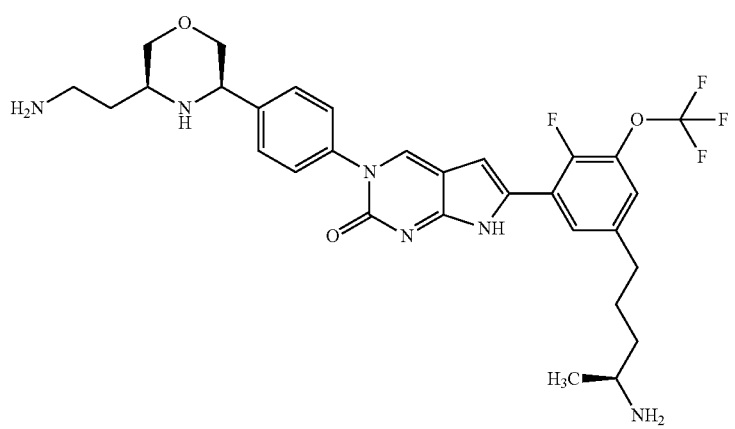
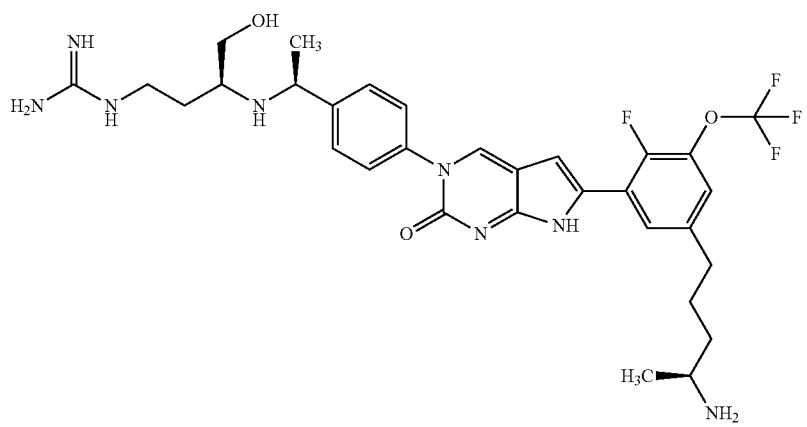
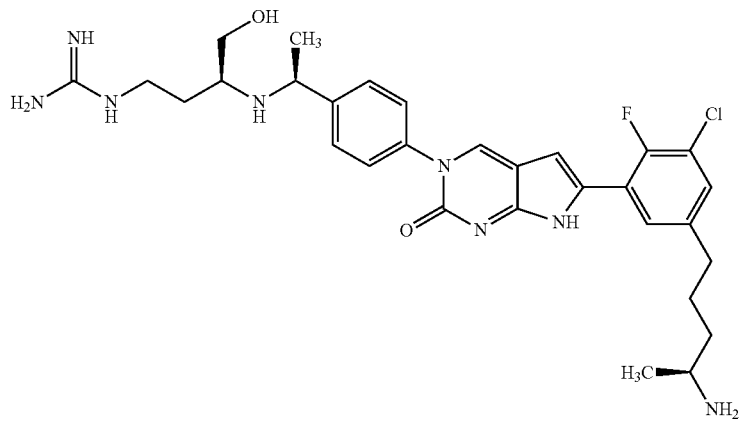

-continued
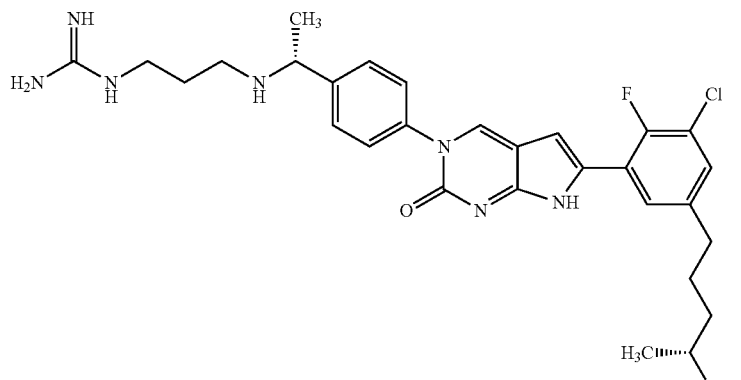
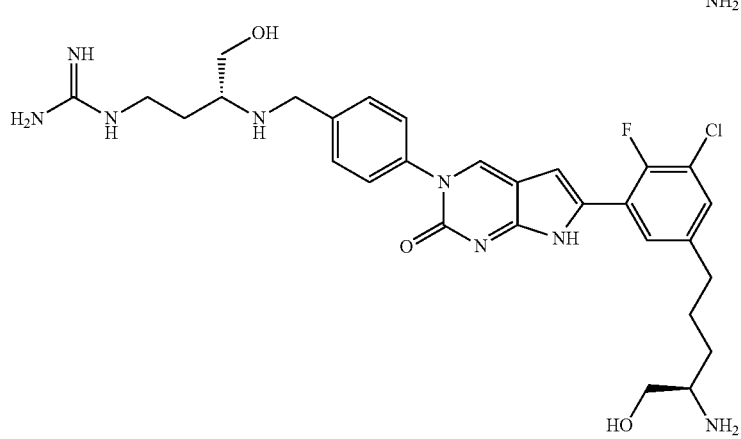
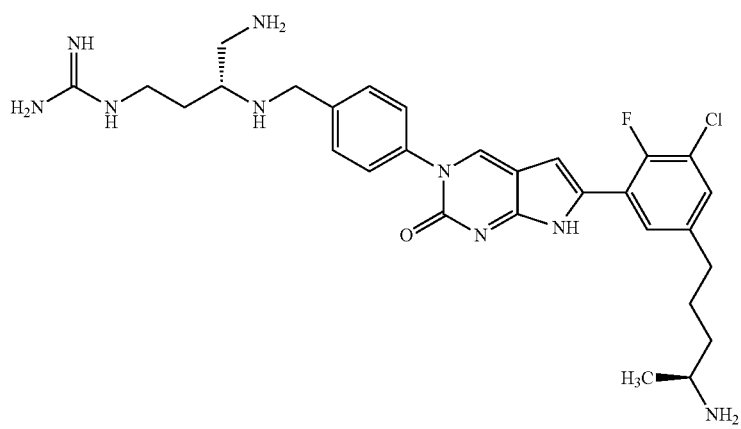
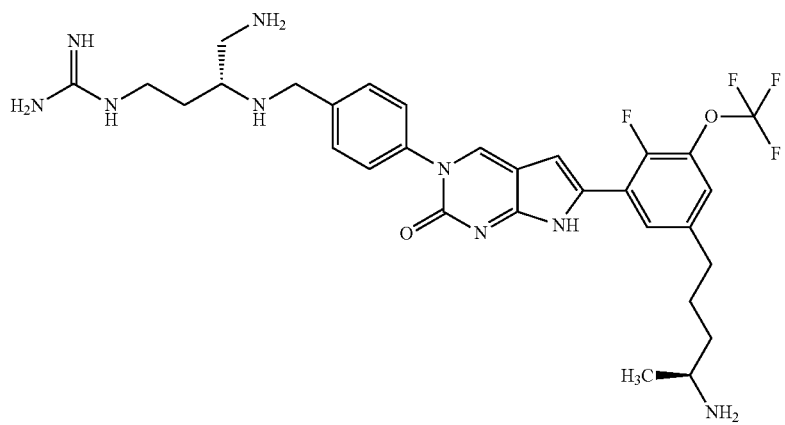

-continued
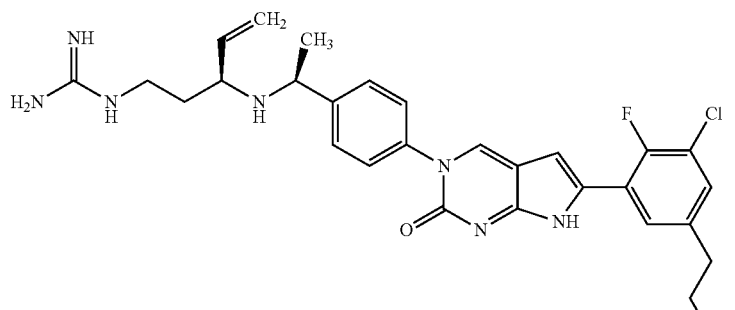
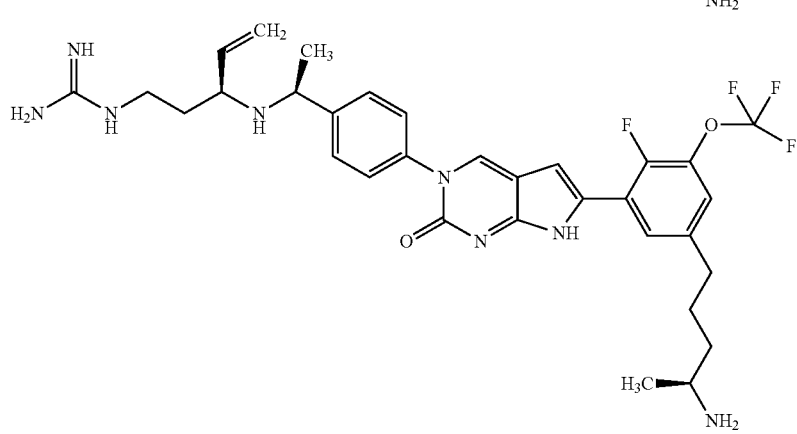
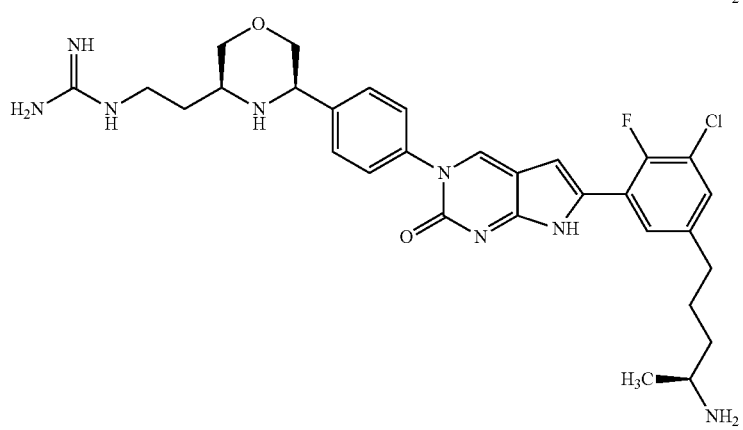
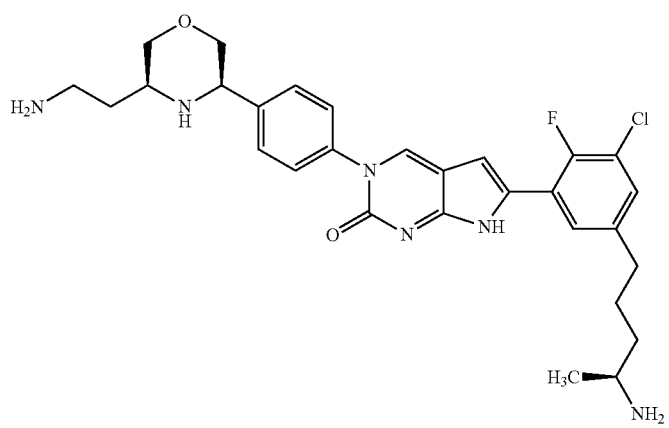

-continued
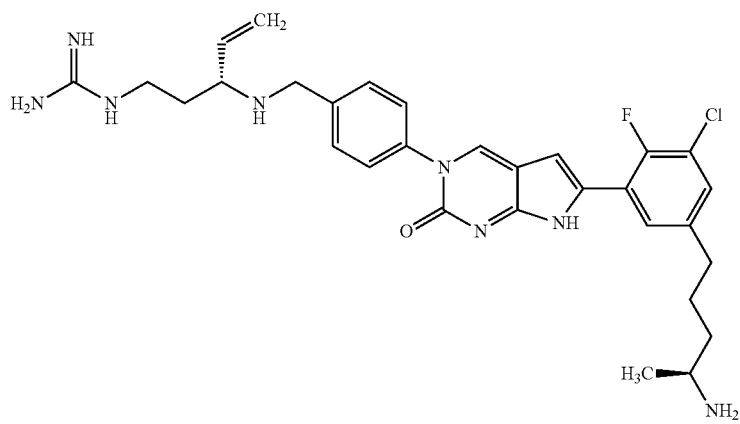
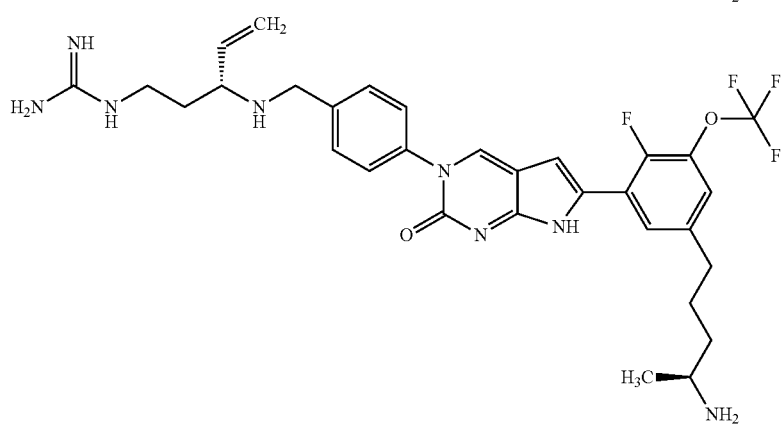
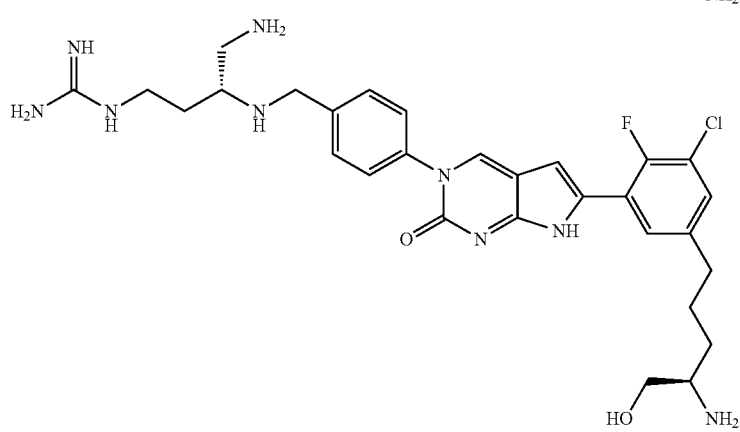
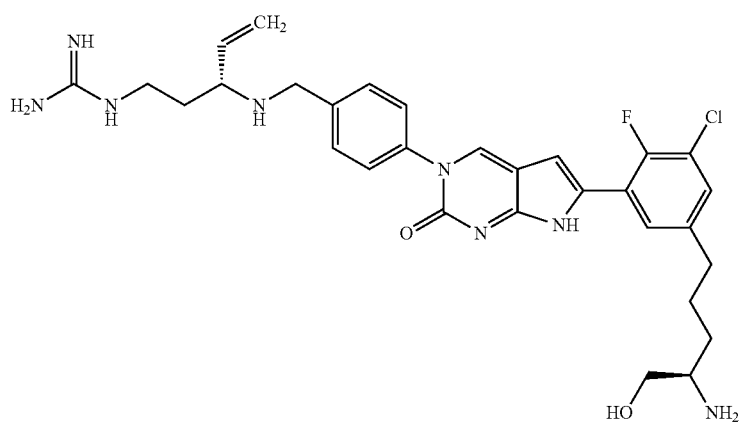

-continued
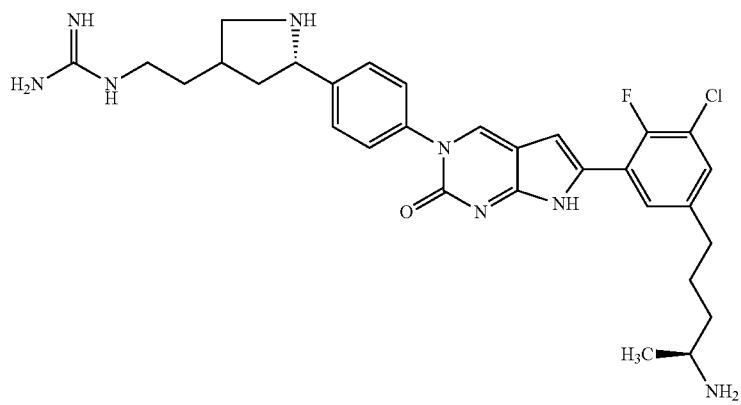
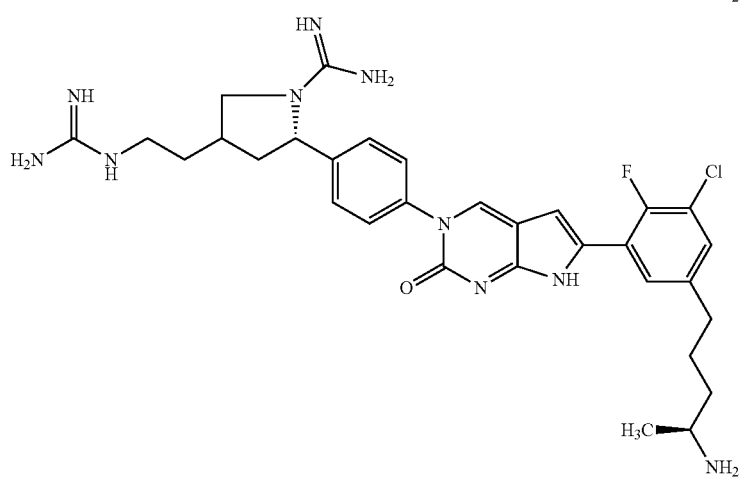
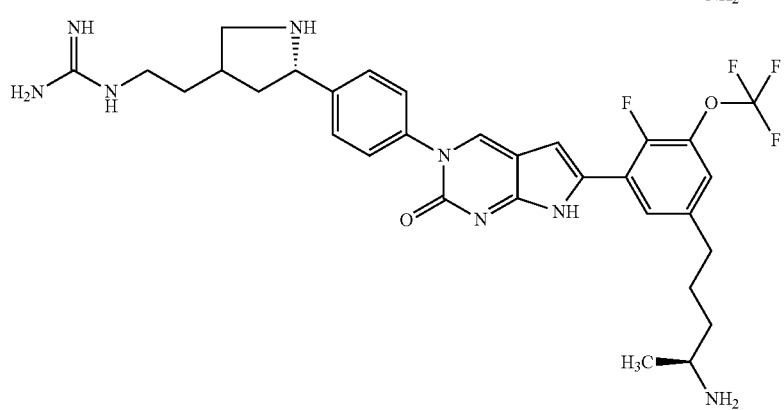
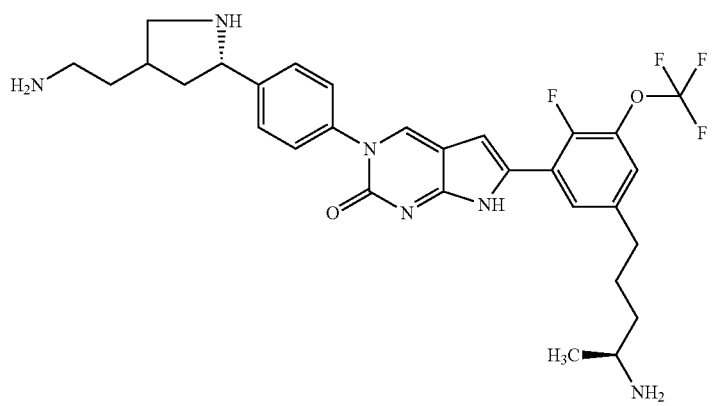

-continued
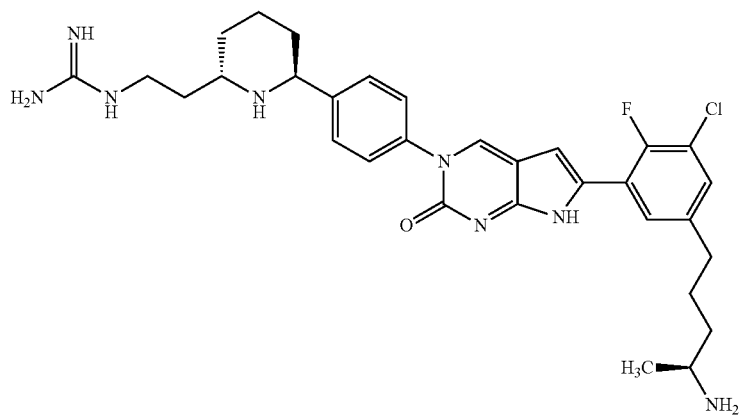
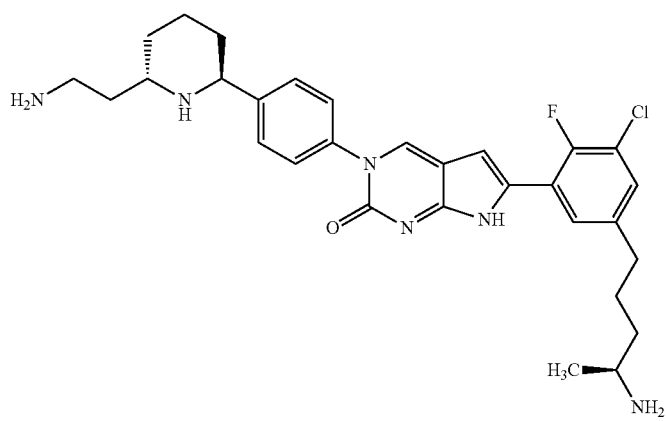
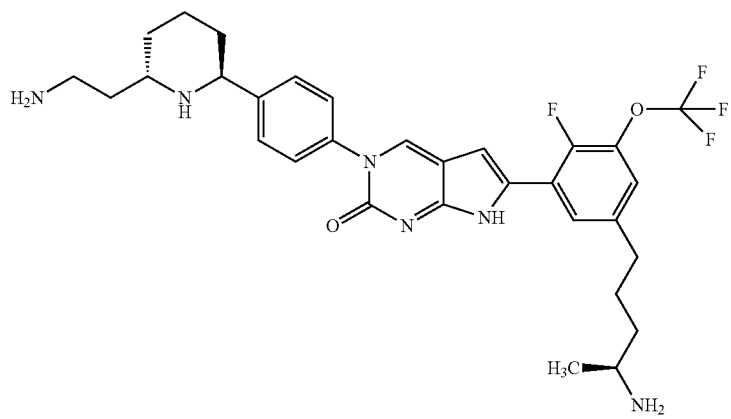
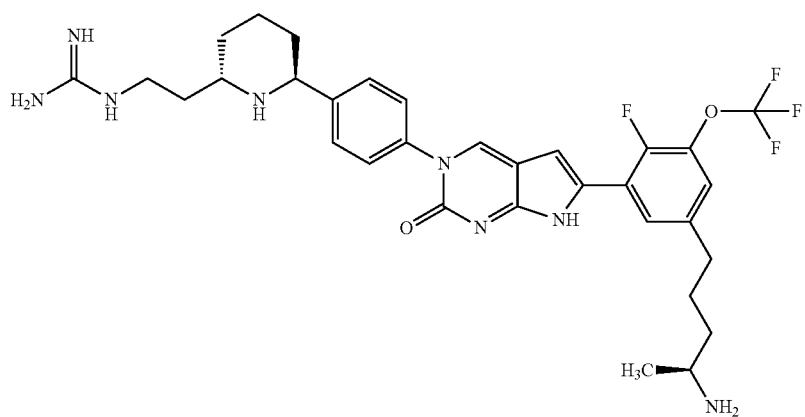

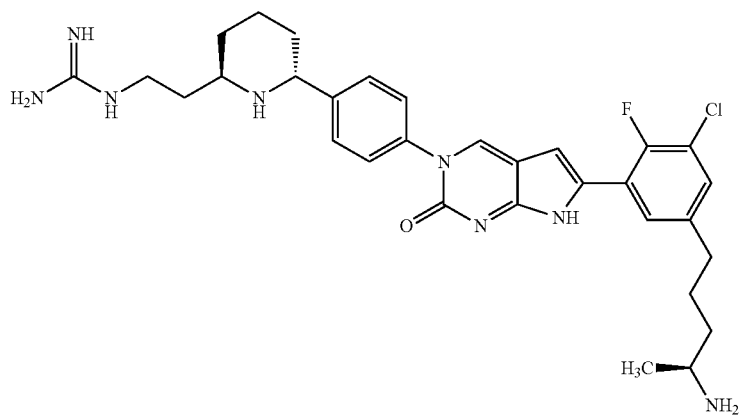
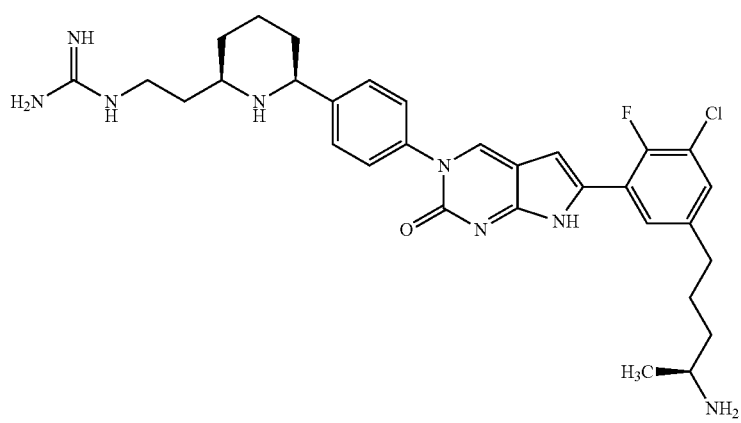
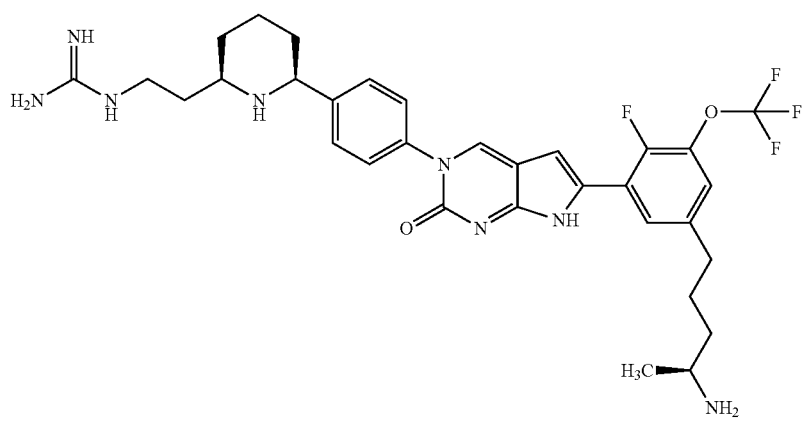
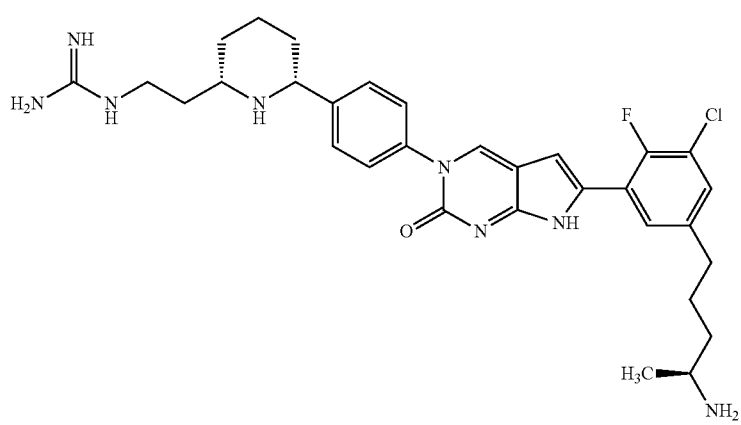

-continued
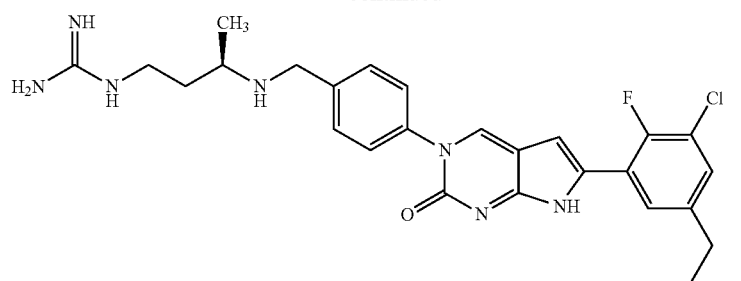
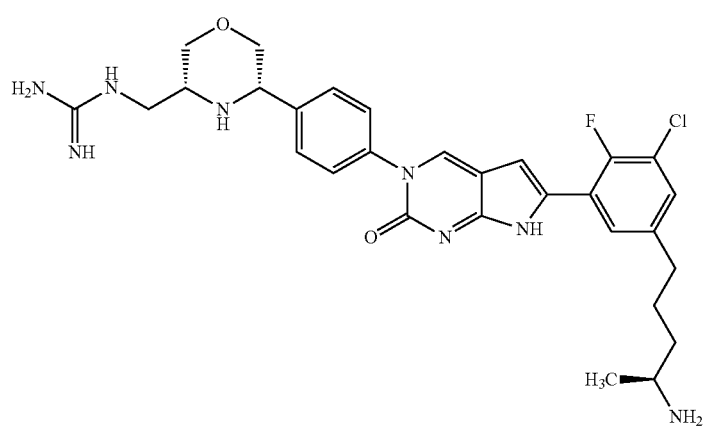
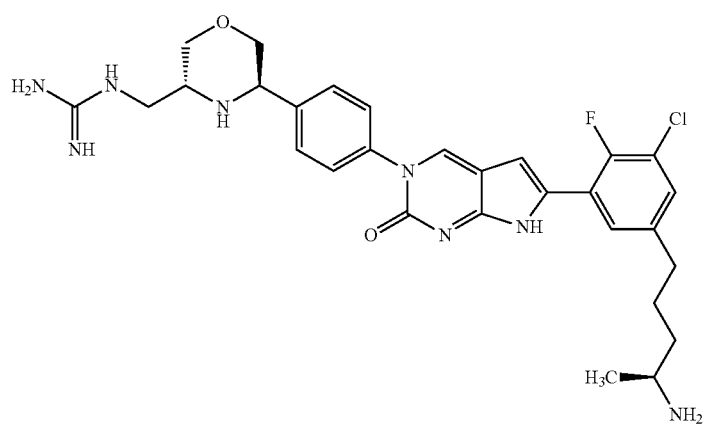
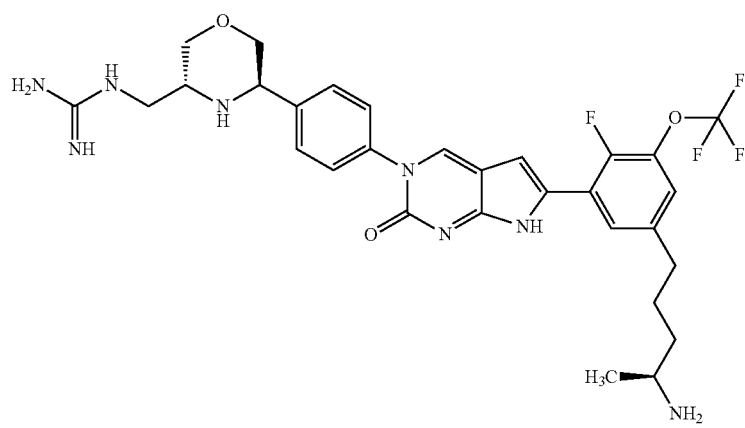

-continued
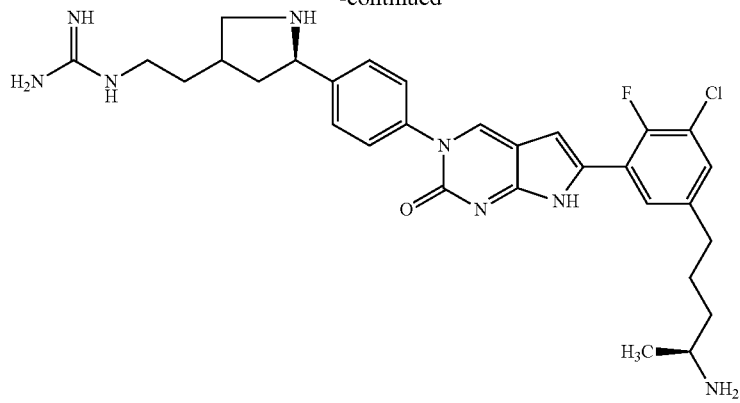
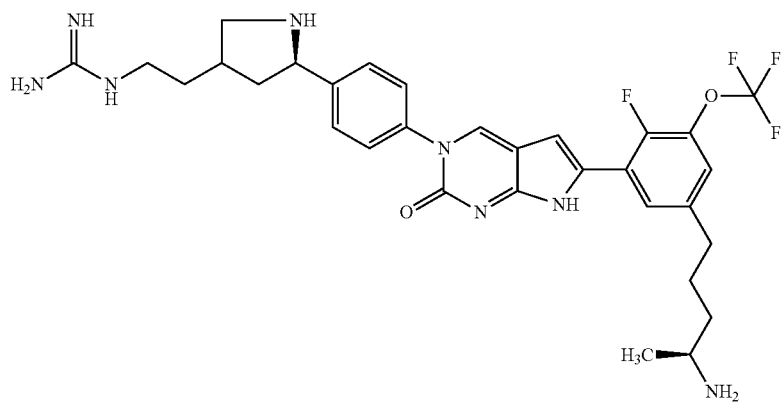
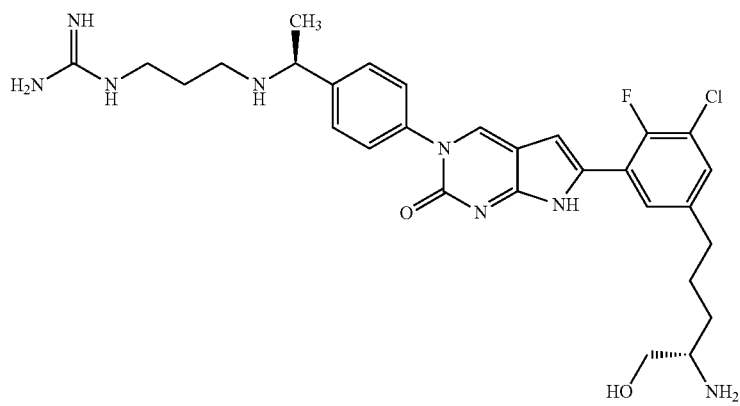
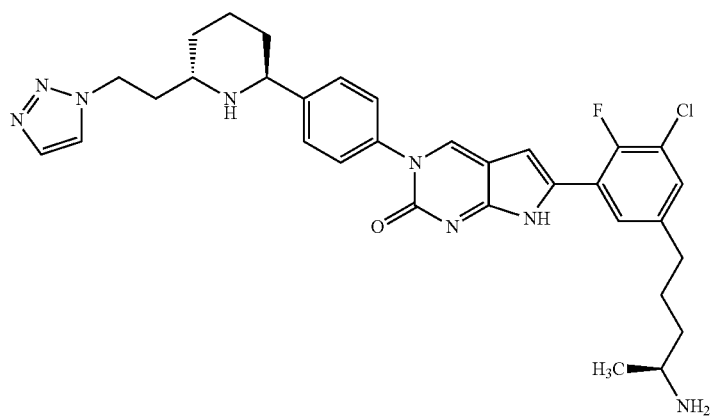

-continued
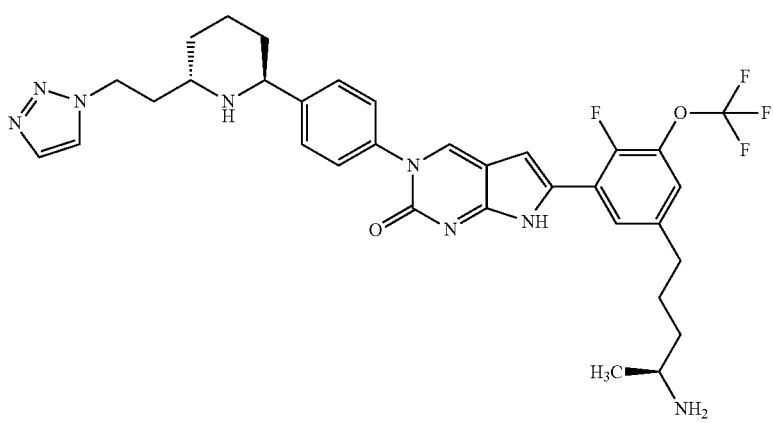
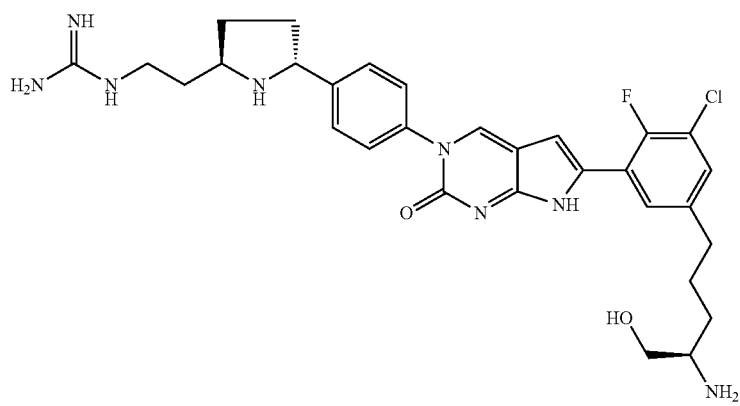
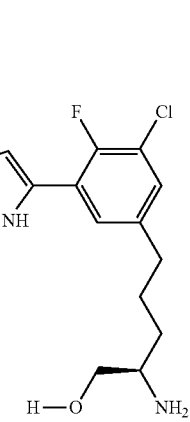
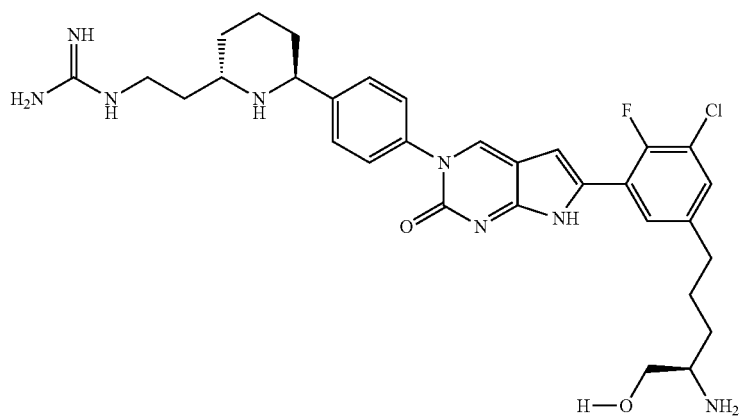

-continued
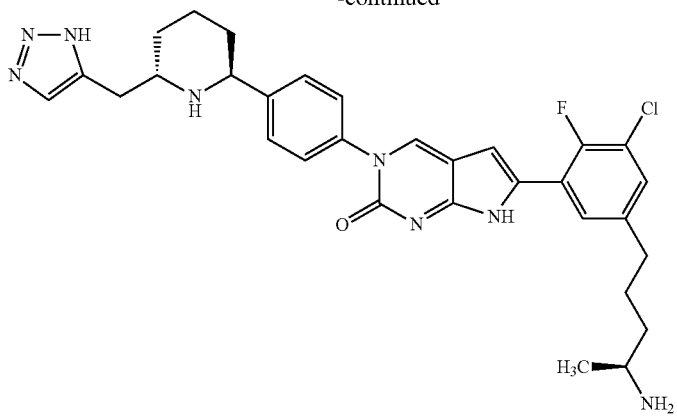
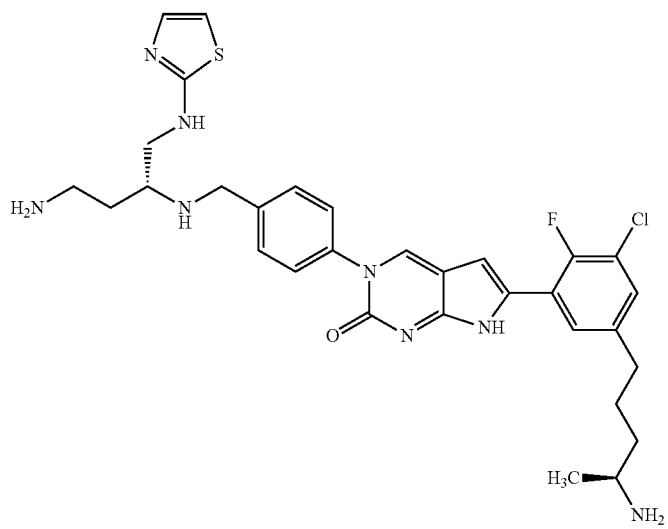
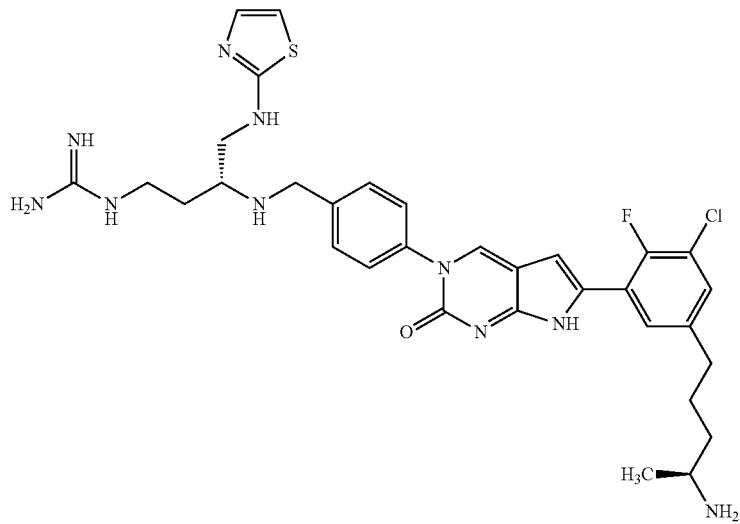

-continued
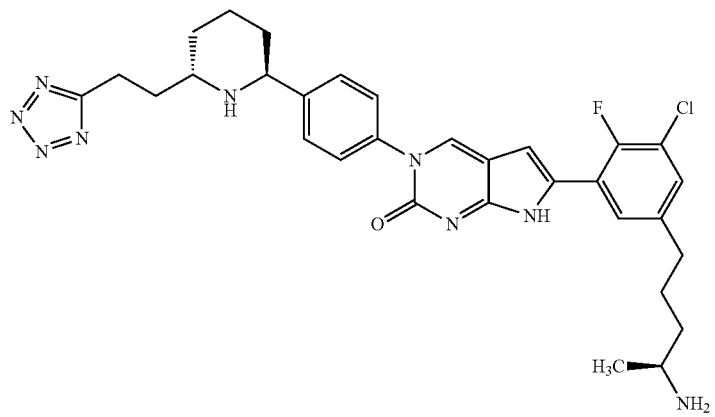
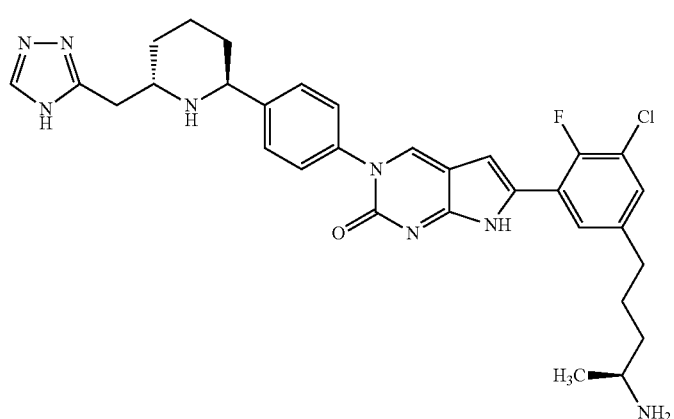
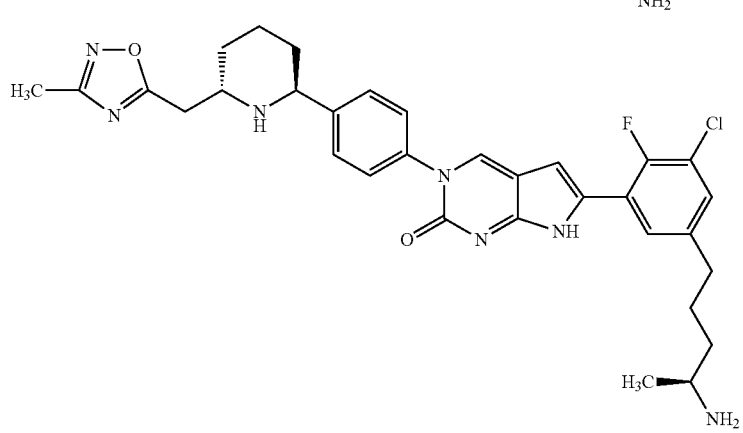
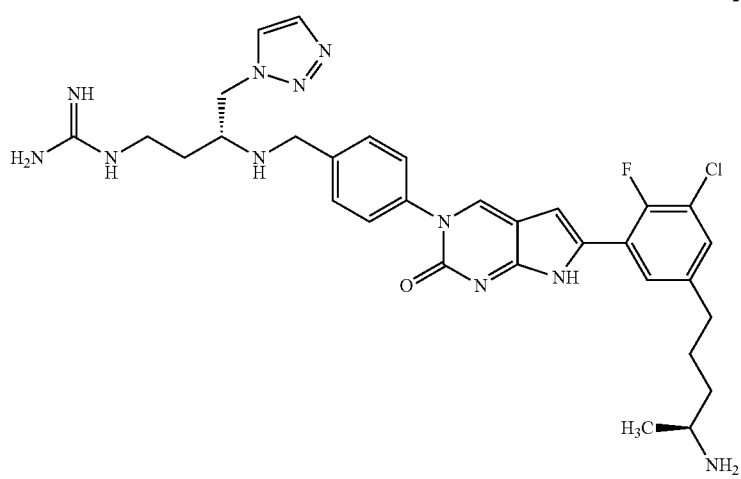

-continued
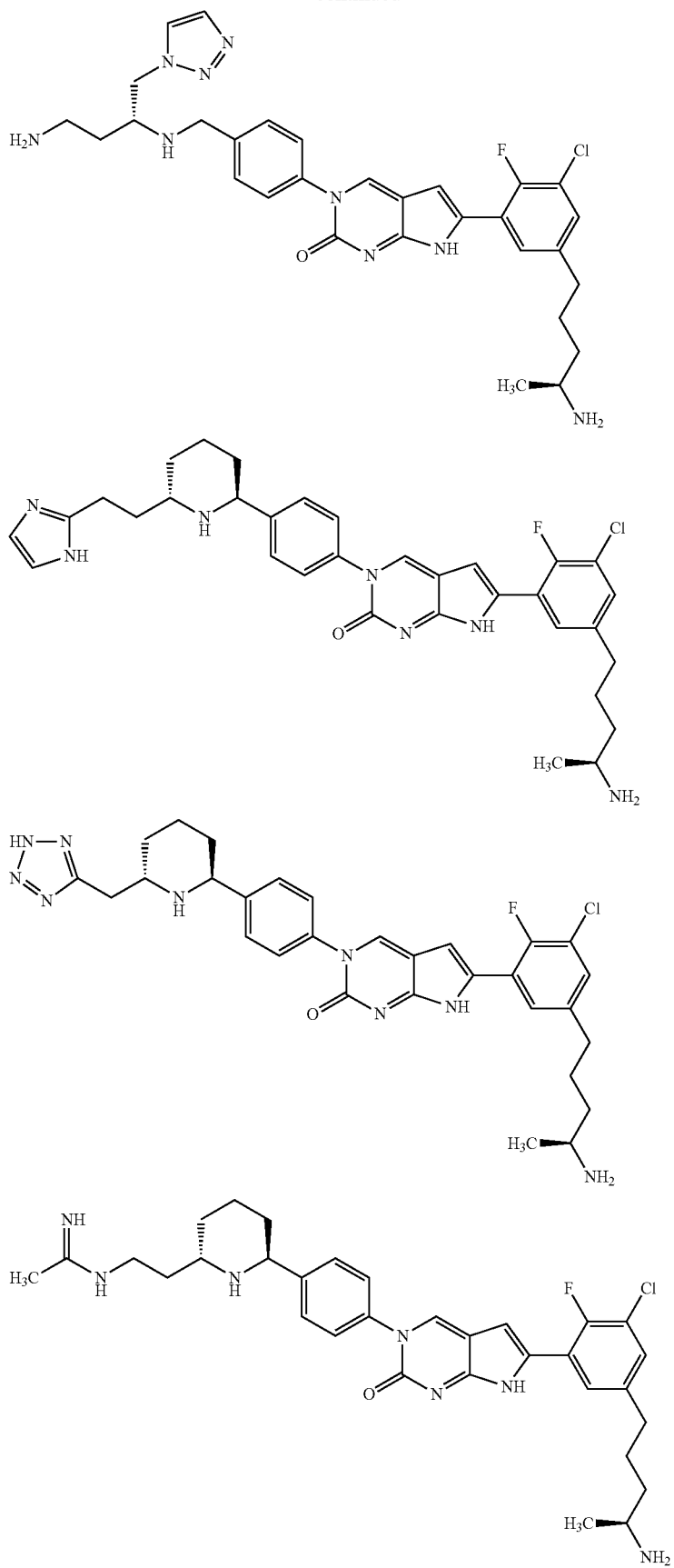 [SMILES: C[C@H](N)CCCc1cc(Cl)c(F)c(-c2cc3cn(-c4ccc(CN[C@H](CCN)Cn5ccnn5)cc4)c(=O)nc3[nH]2)c1 ; C[C@H](N)CCCc1cc(Cl)c(F)c(-c2cc3cn(-c4ccc([C@@H]5CCC[C@@H](CCc6ncc[nH]6)N5)cc4)c(=O)nc3[nH]2)c1 ; C[C@H](N)CCCc1cc(Cl)c(F)c(-c2cc3cn(-c4ccc([C@@H]5CCC[C@@H](Cc6nn[nH]n6)N5)cc4)c(=O)nc3[nH]2)c1 ; CC(=N)NCC[C@@H]1CCC[C@@H](c2ccc(-n3cc4cc(-c5cc(CCC[C@H](C)N)cc(Cl)c5F)[nH]c4nc3=O)cc2)N1]

-continued
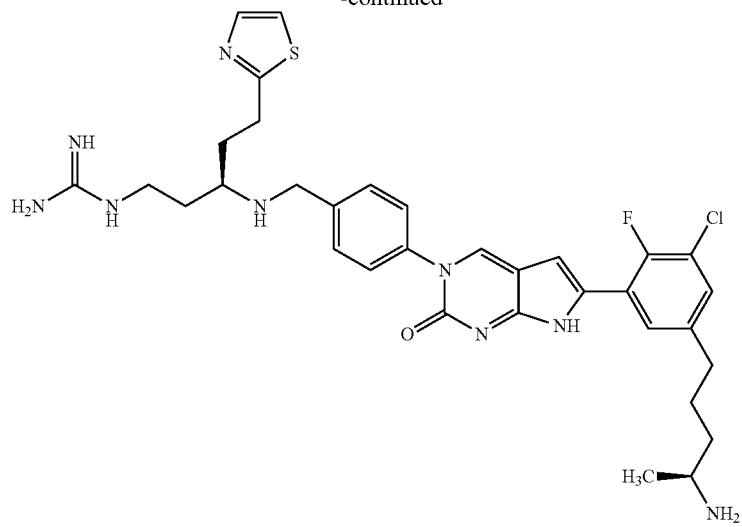
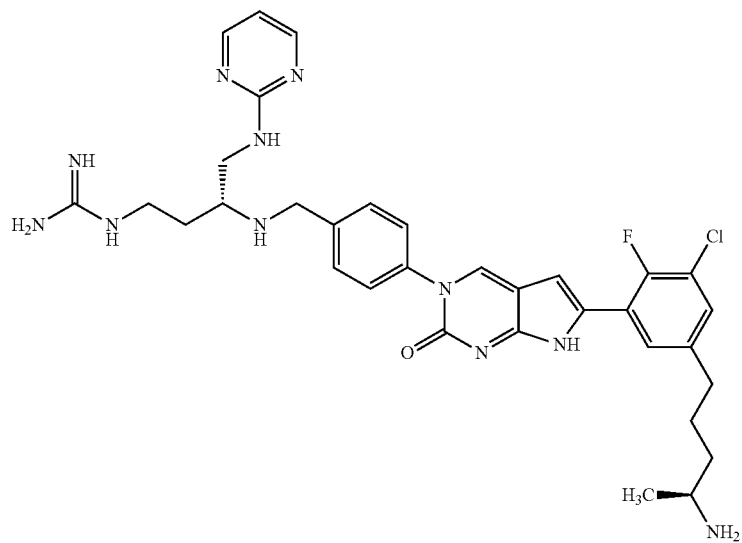
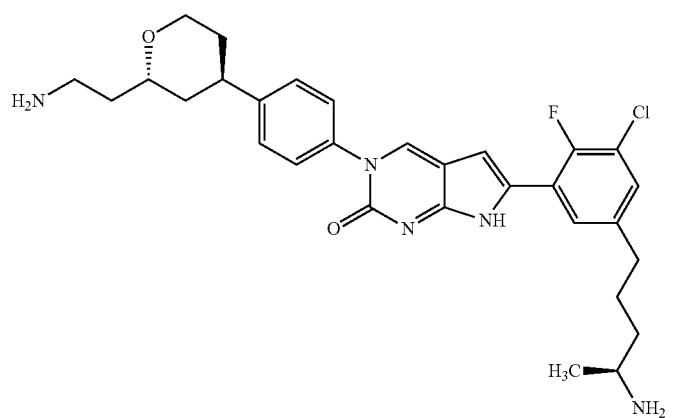

-continued
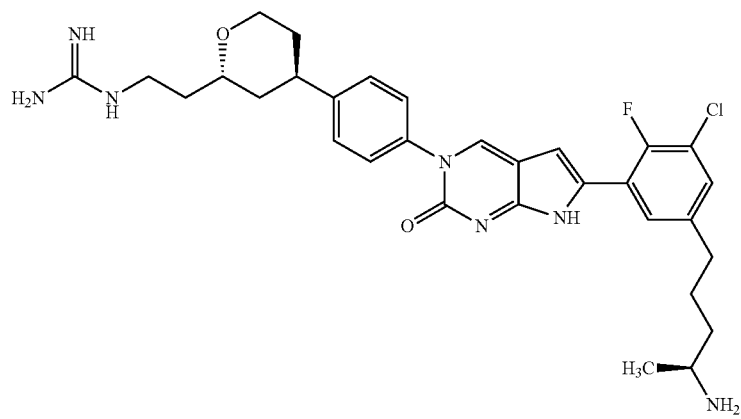
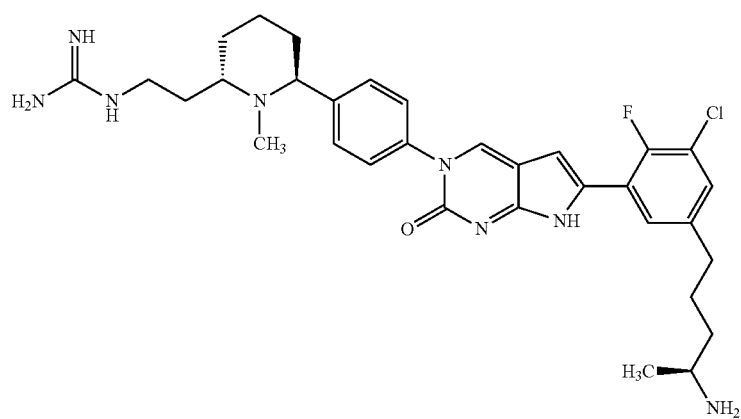
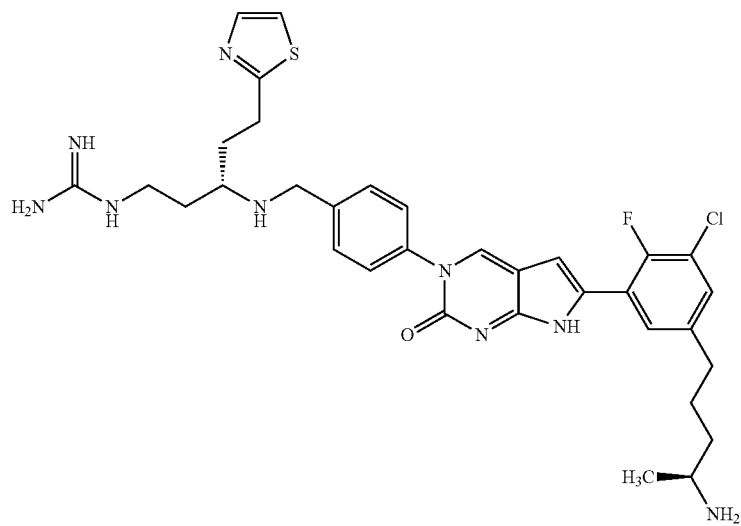

-continued
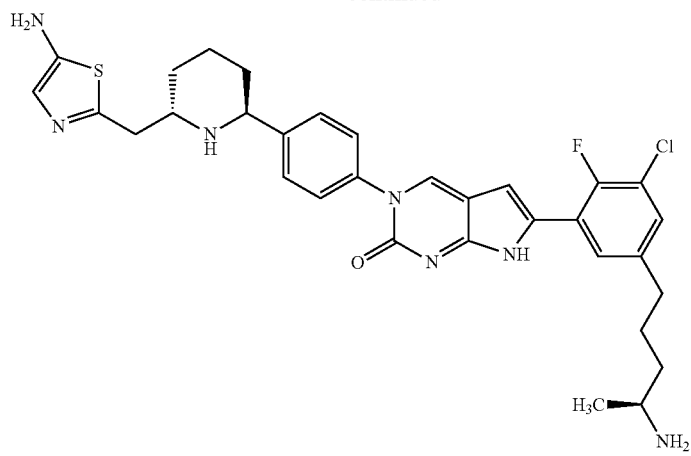
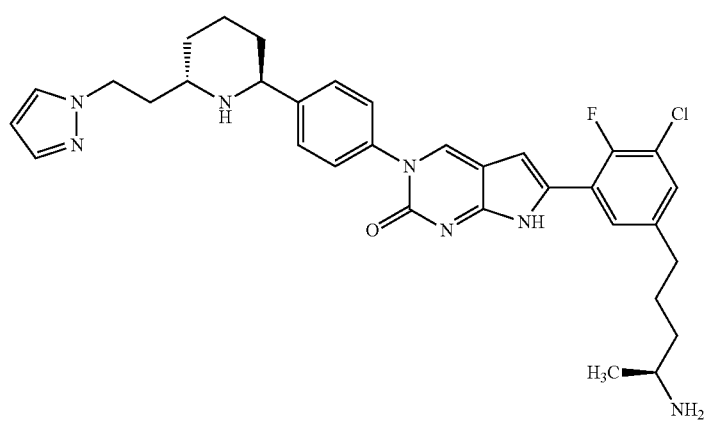
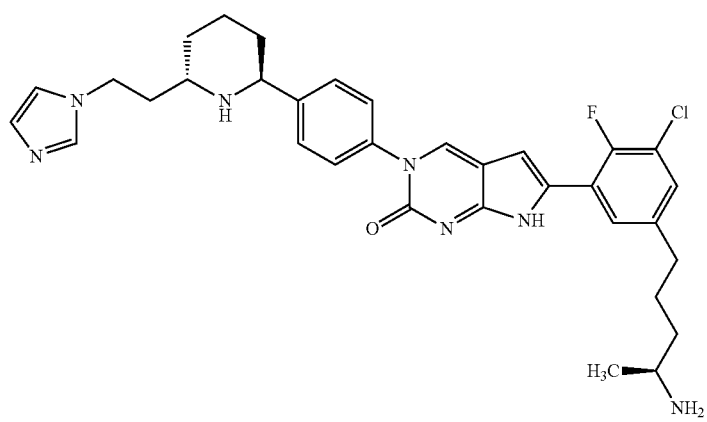

-continued
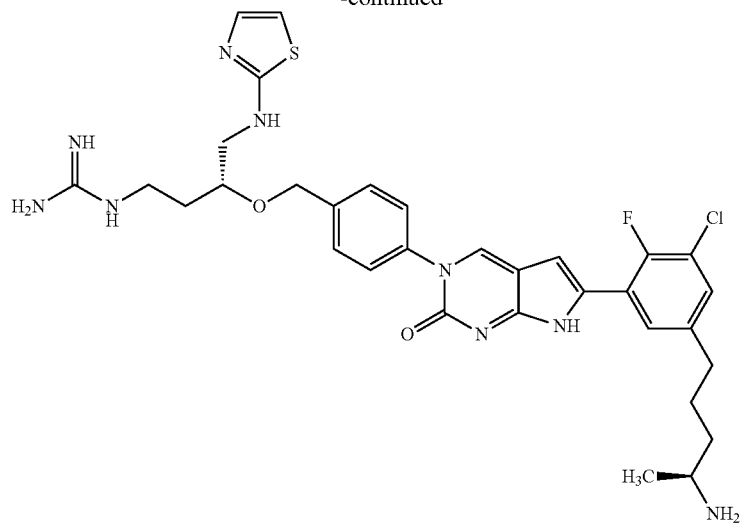
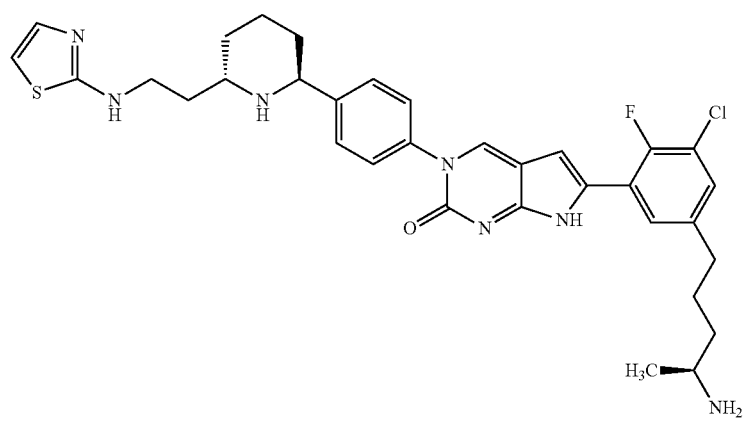
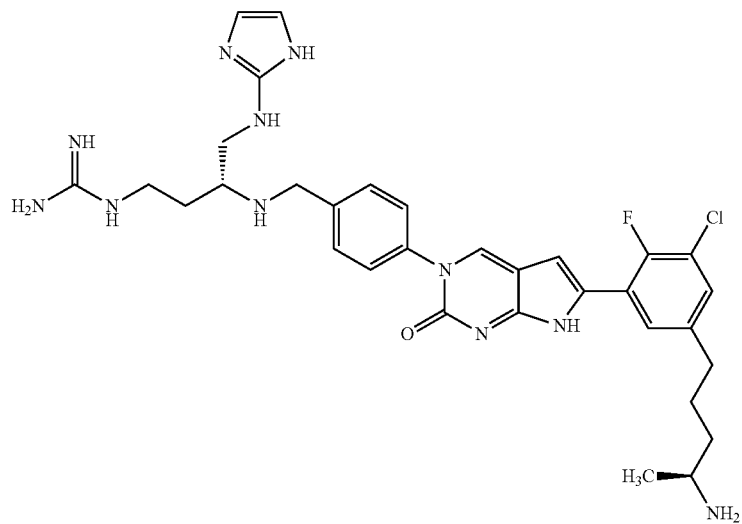

-continued
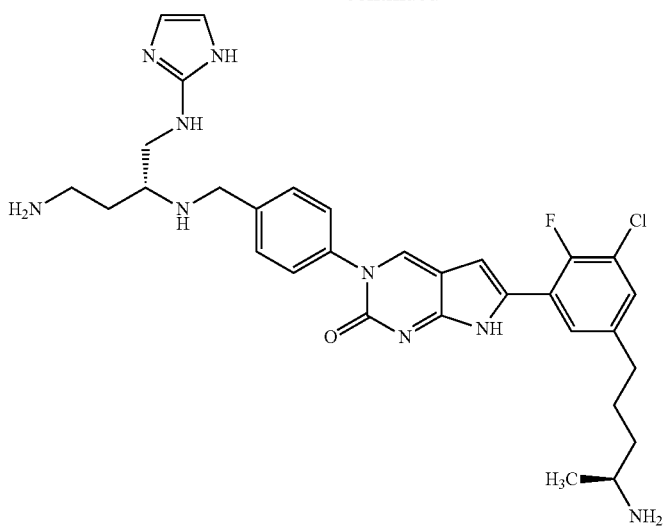
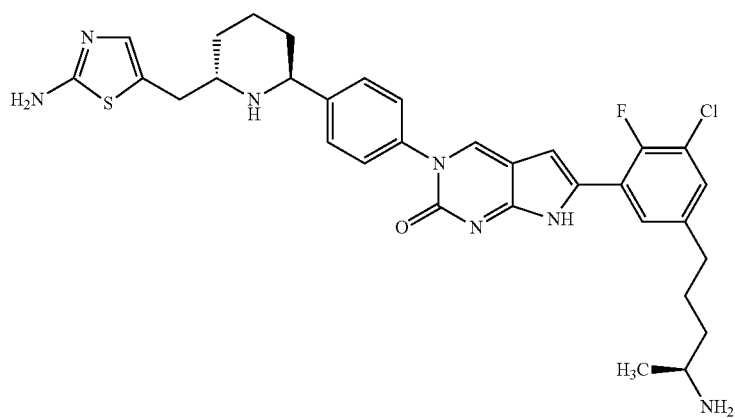
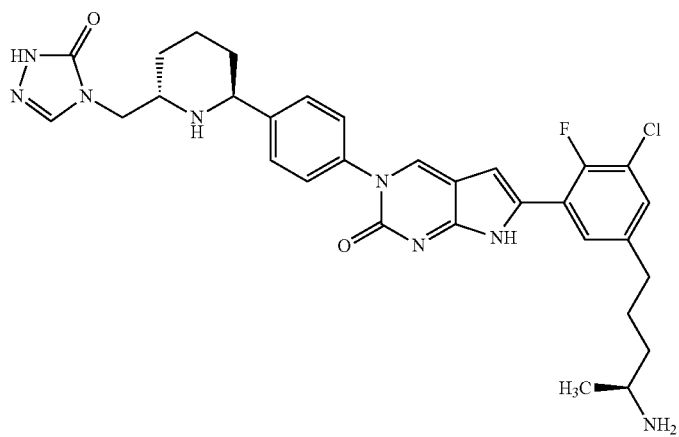

-continued
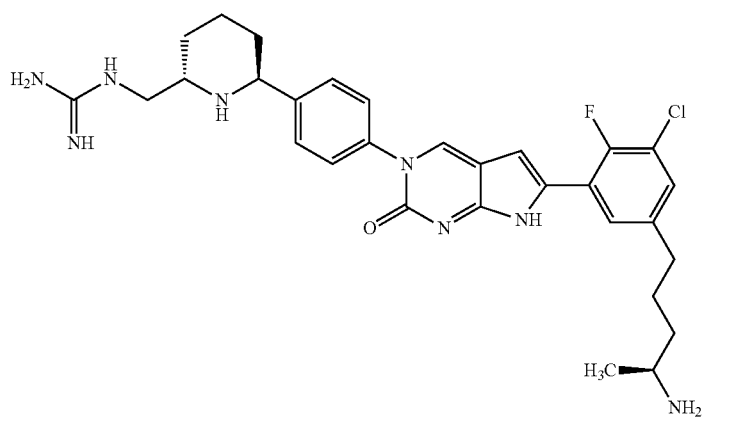
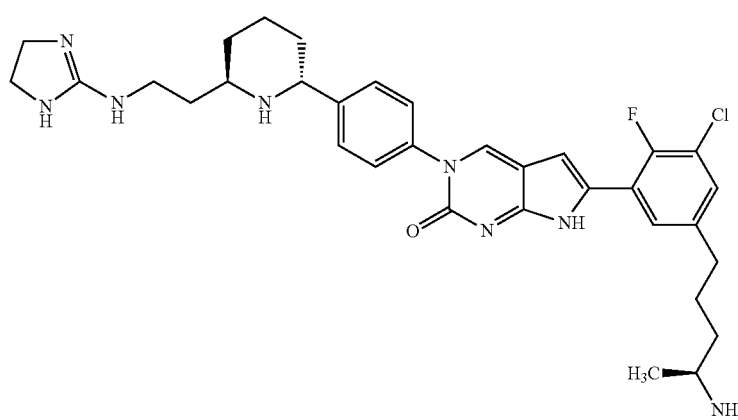
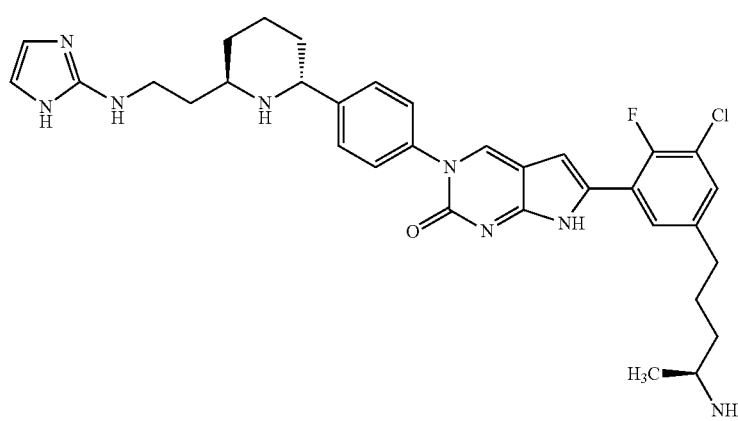
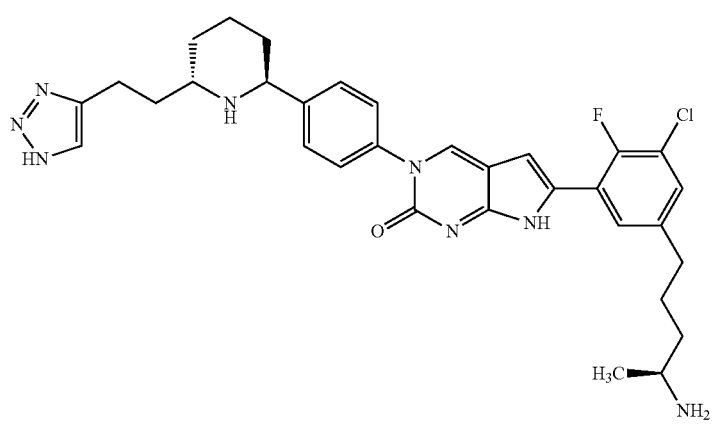

-continued
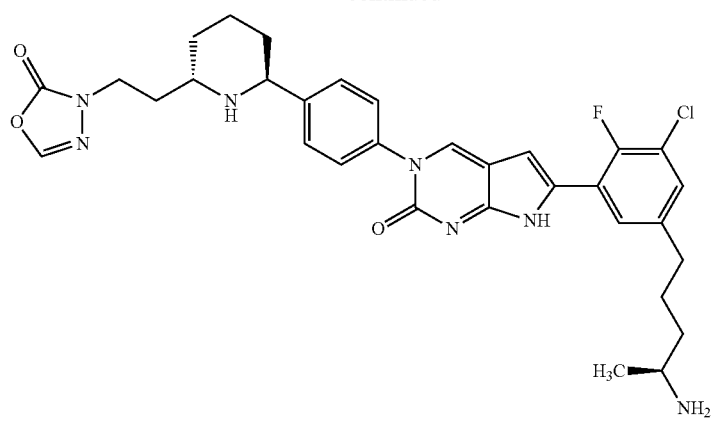
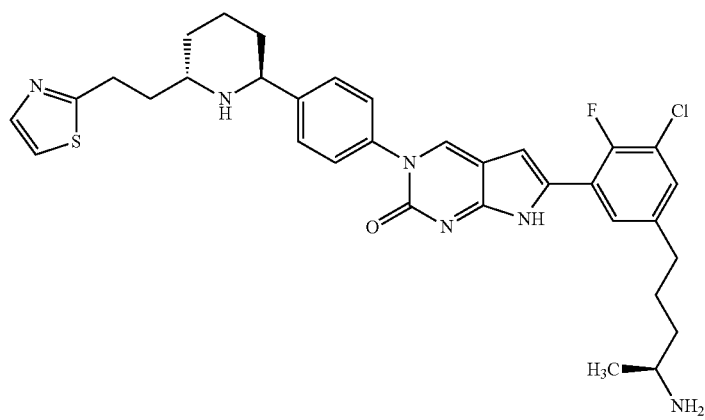
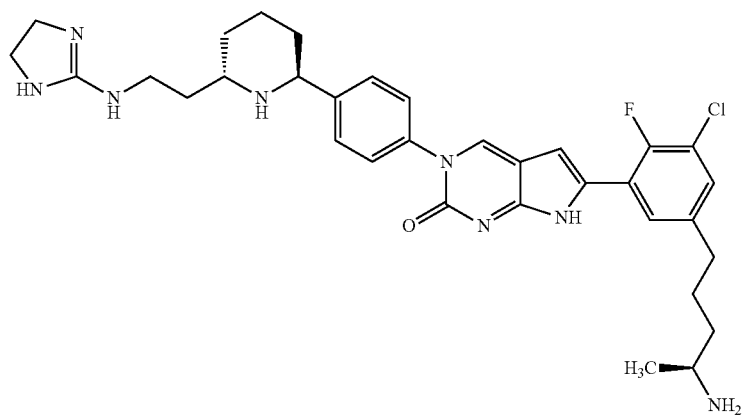
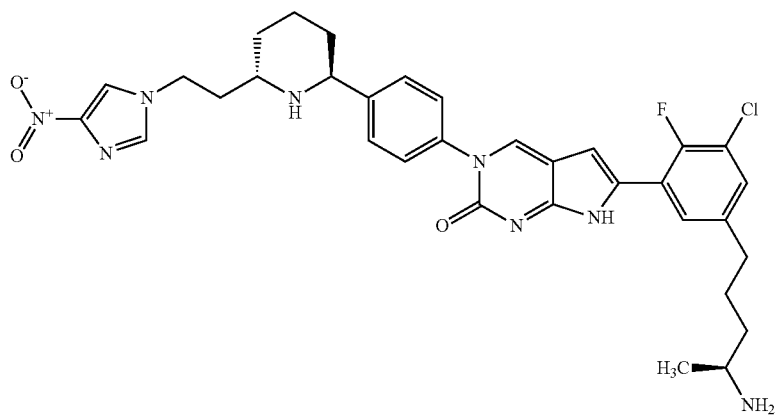

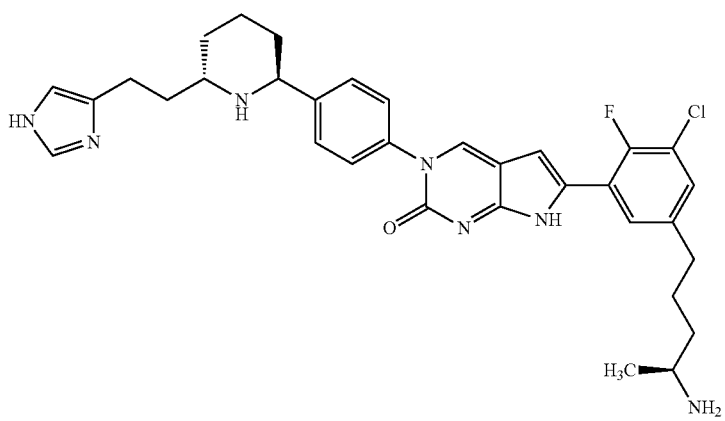
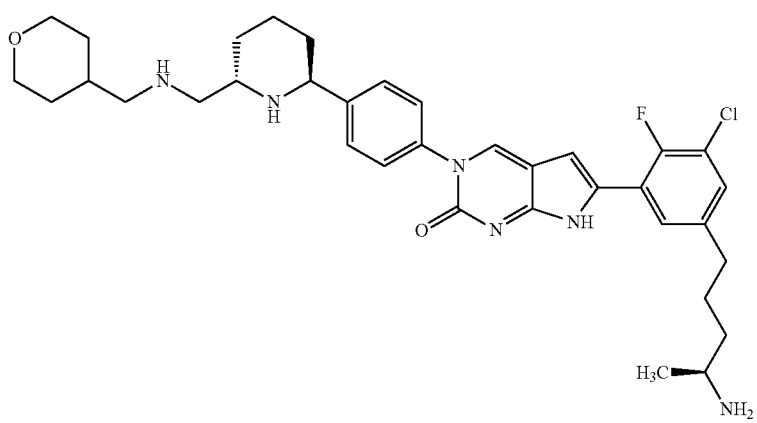
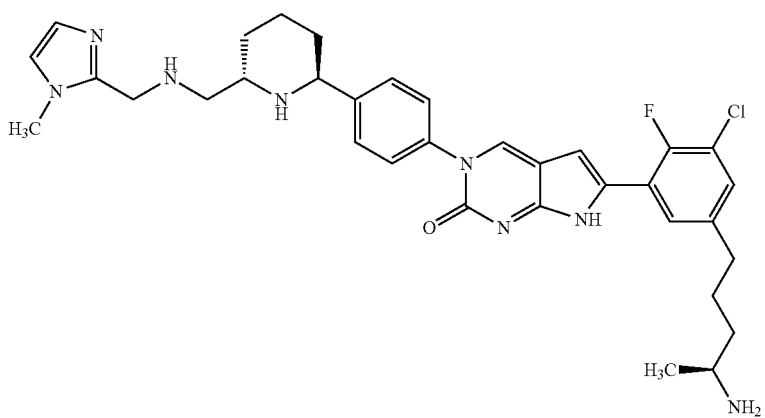
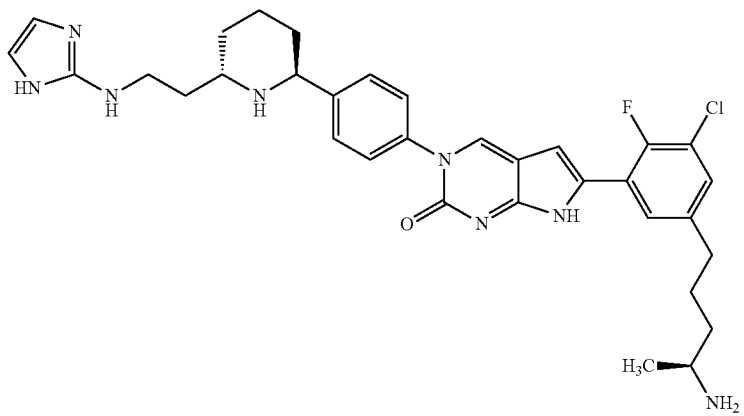

-continued
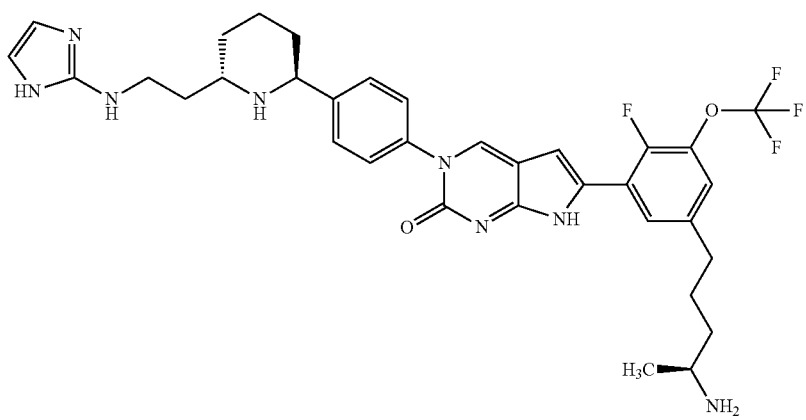
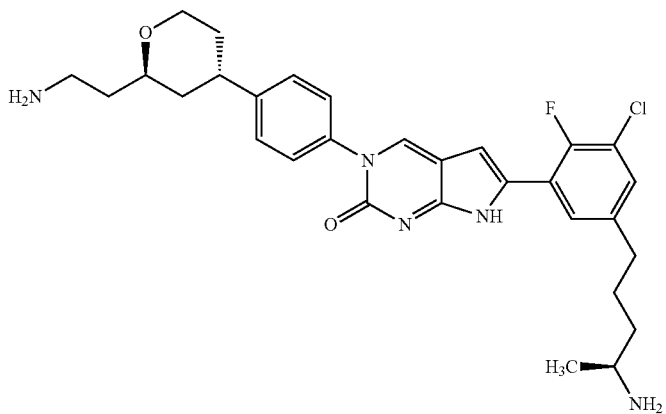
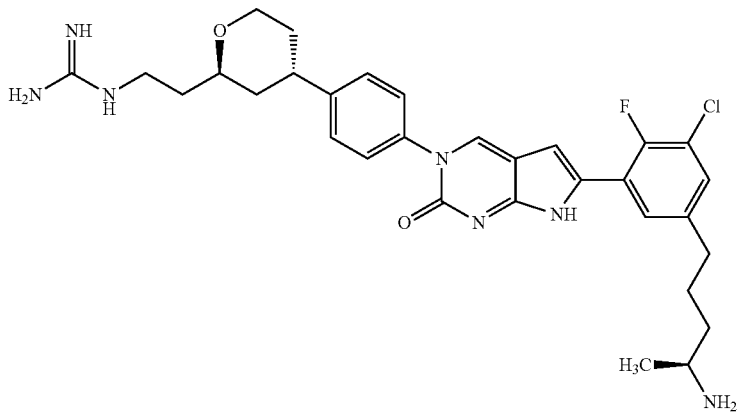
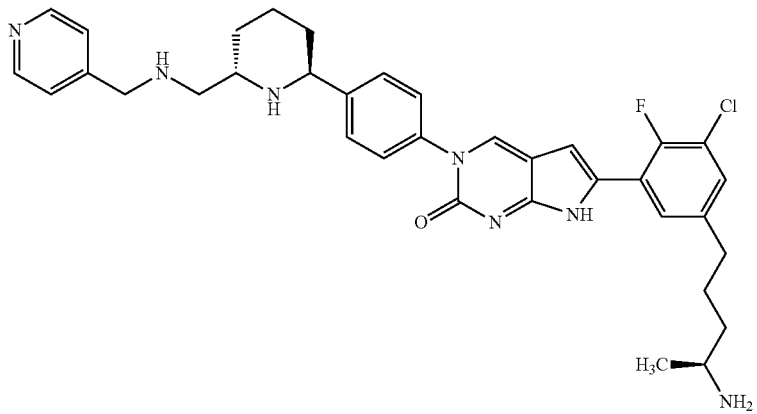

-continued
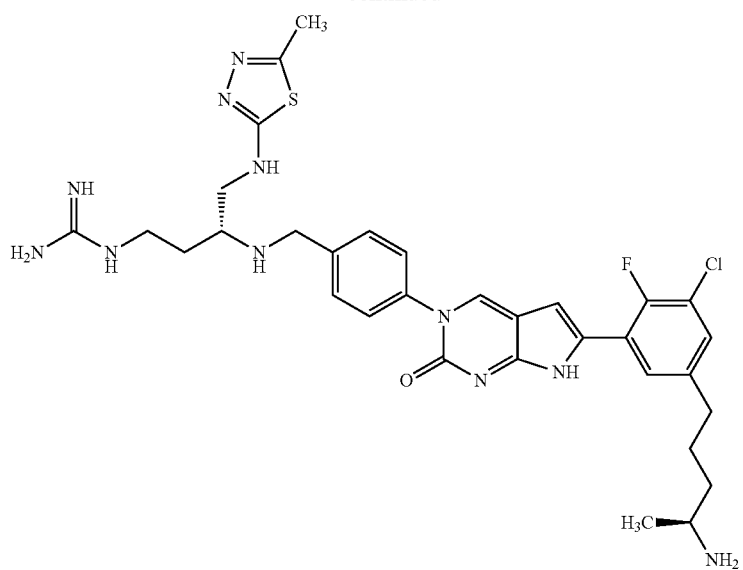
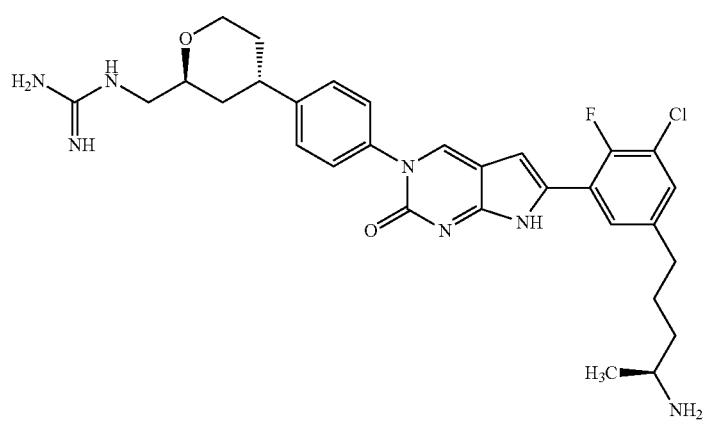
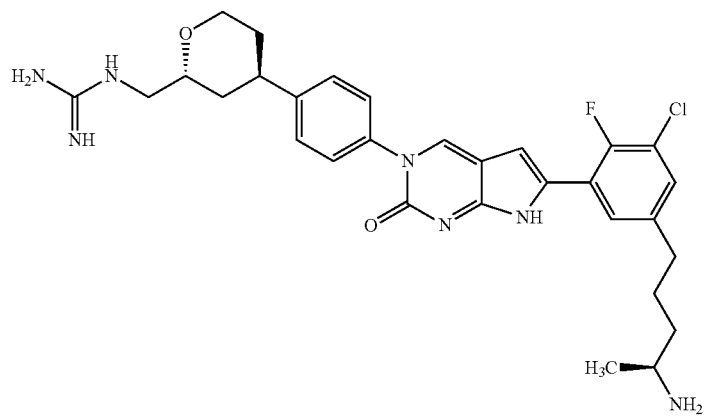

-continued
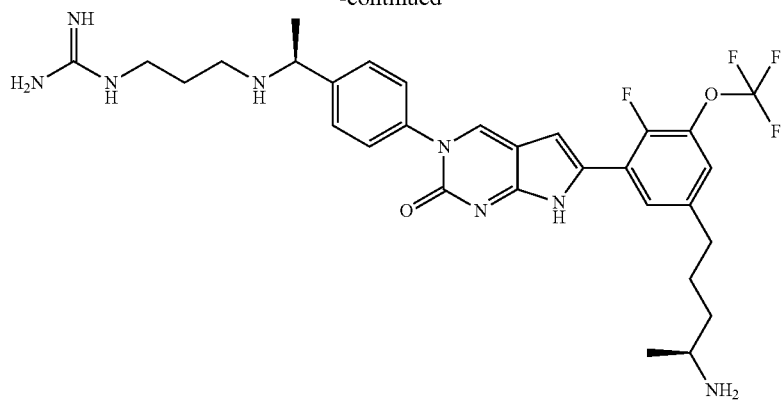
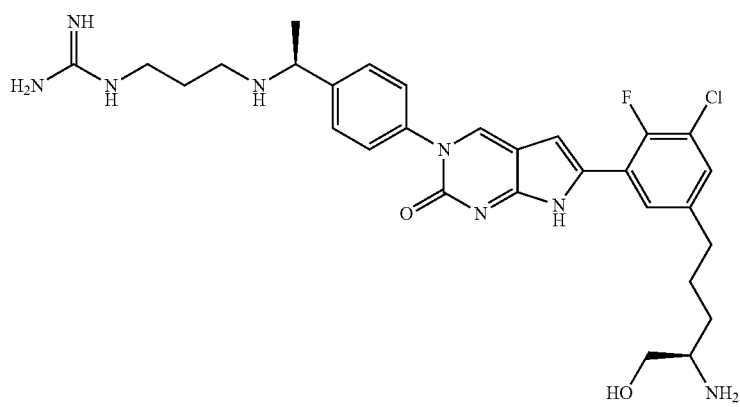
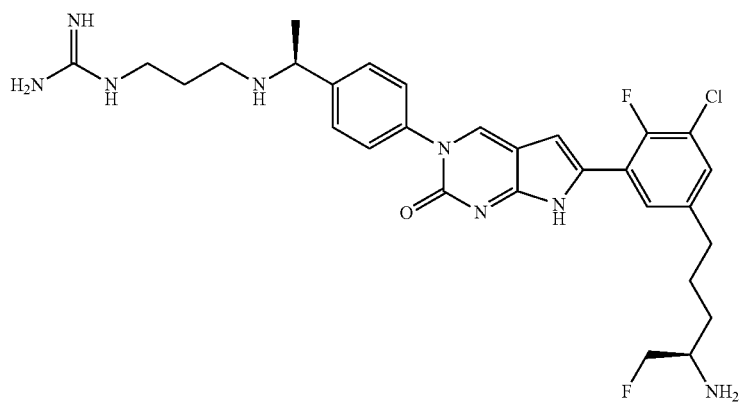
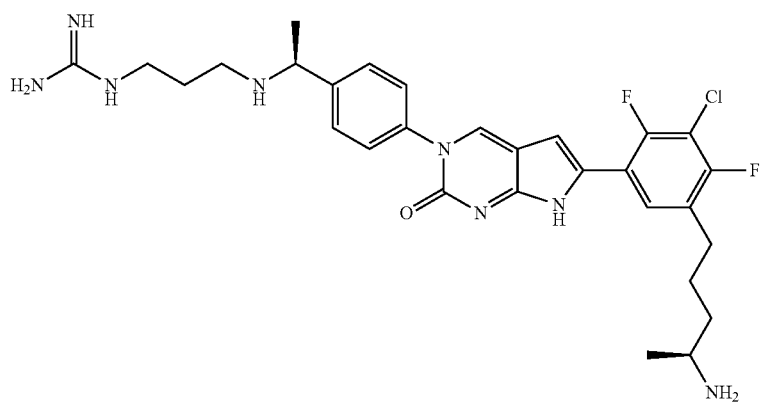

-continued
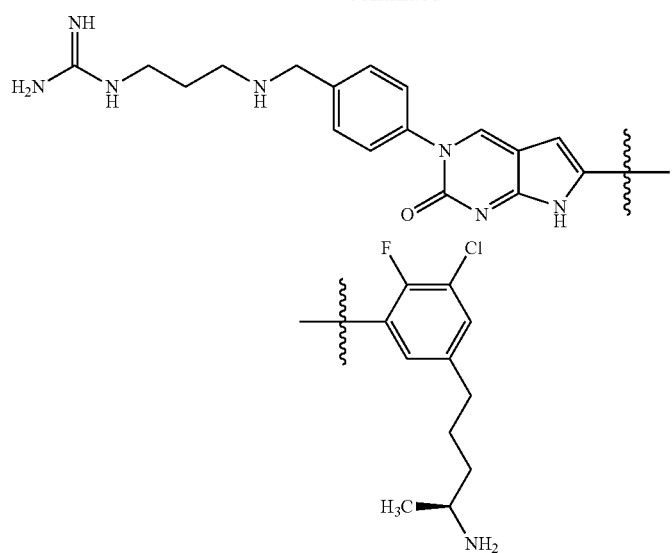
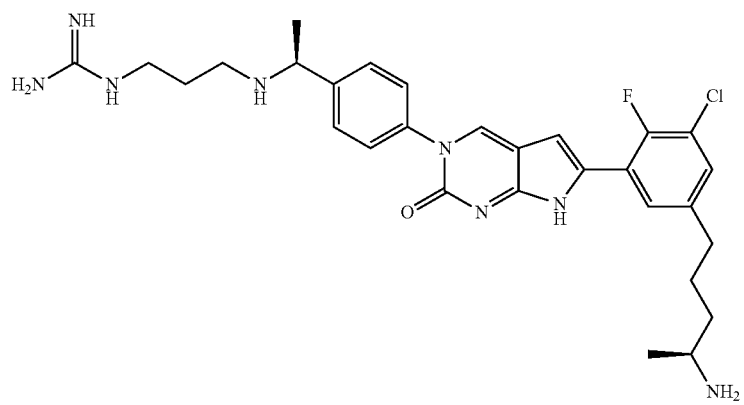
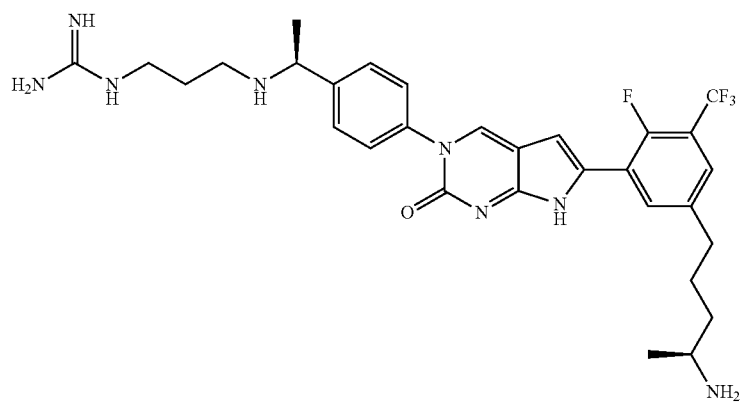

-continued
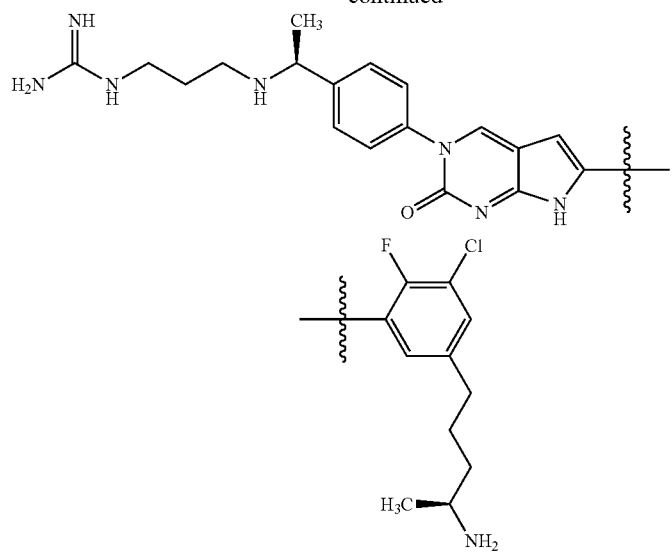
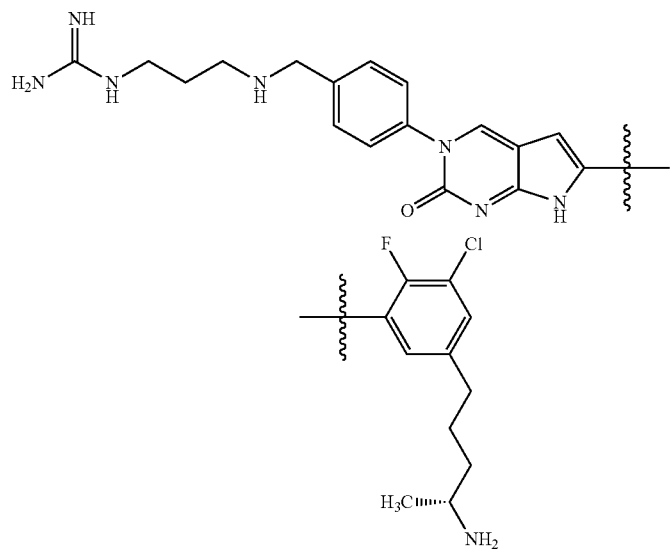
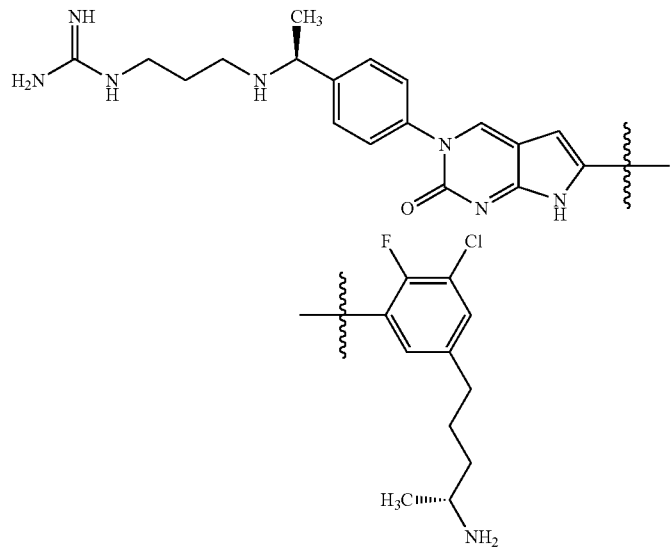

-continued
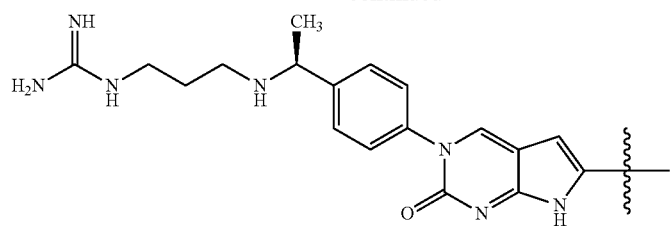
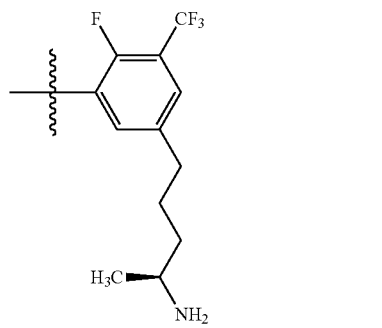
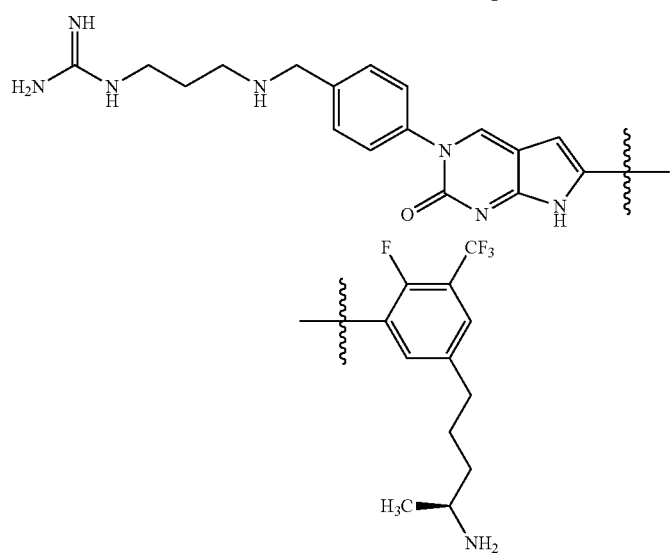
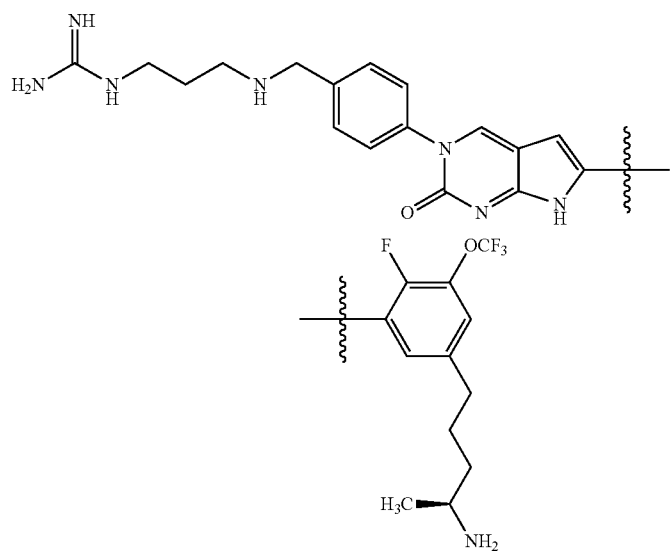

-continued
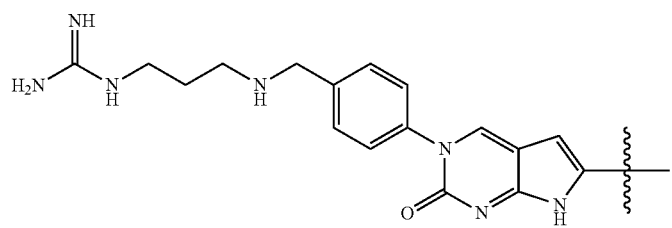
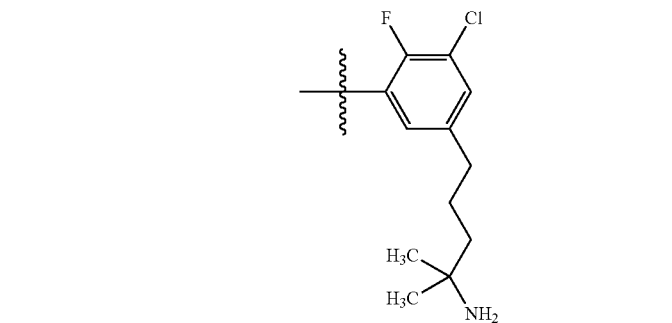
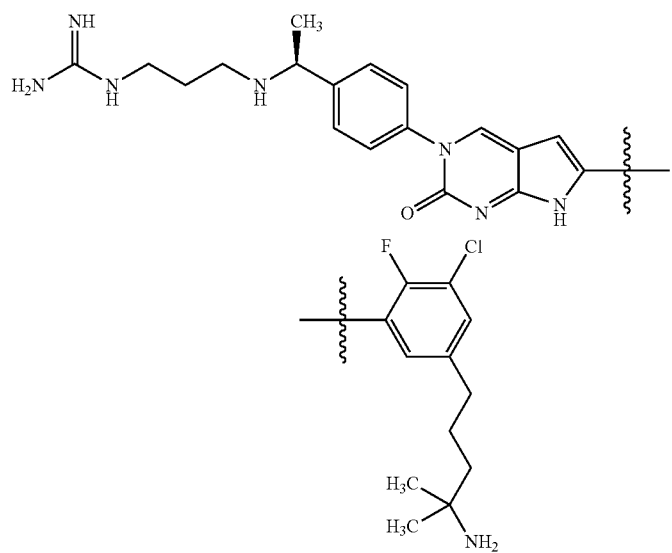
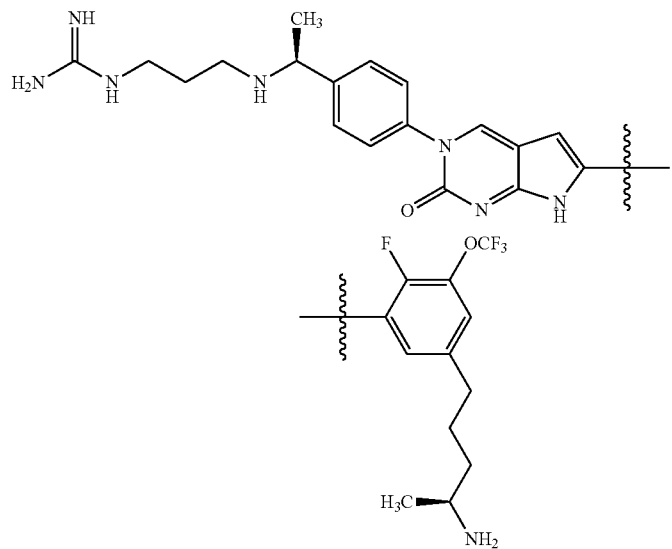

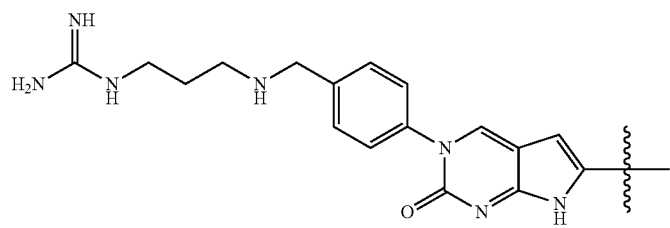
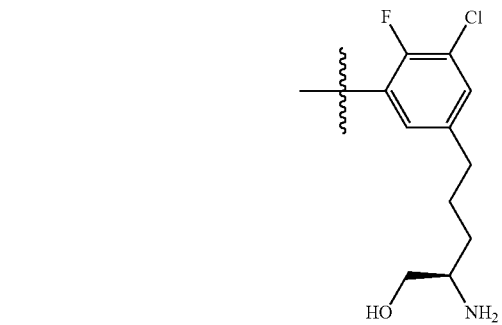
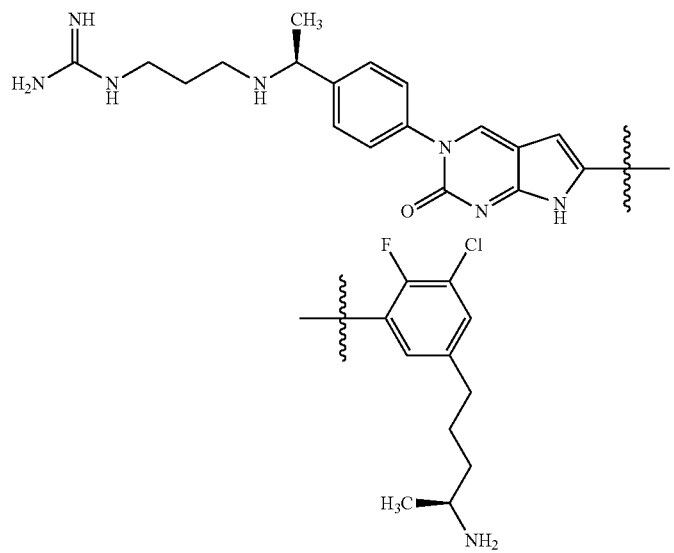
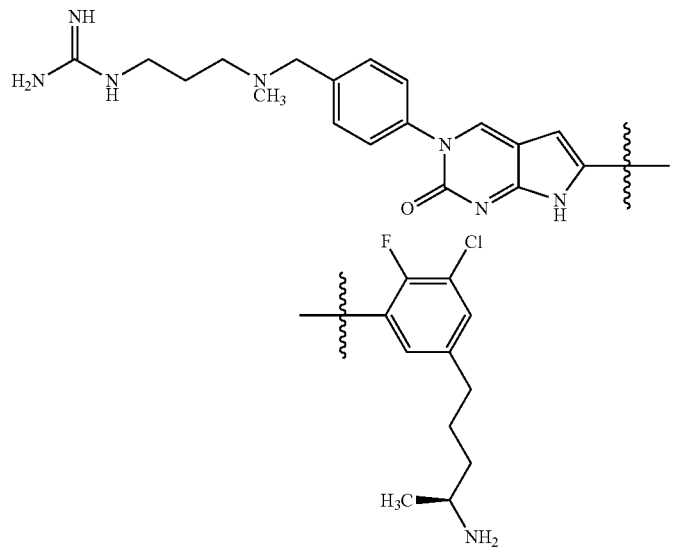

-continued
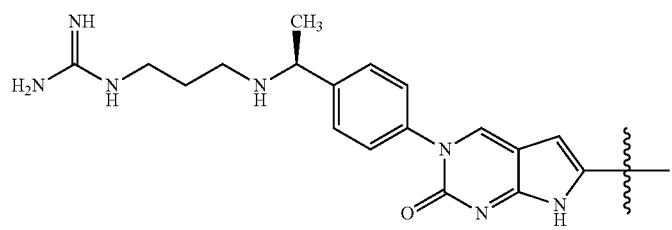
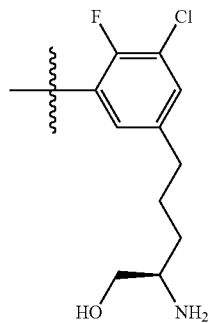
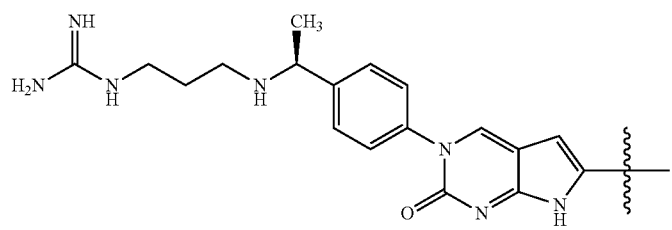
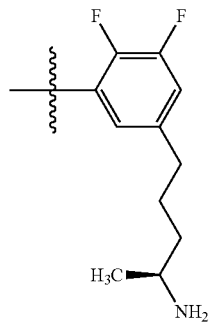
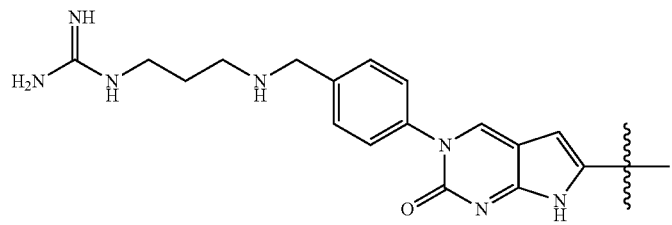
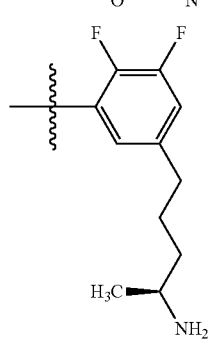

-continued
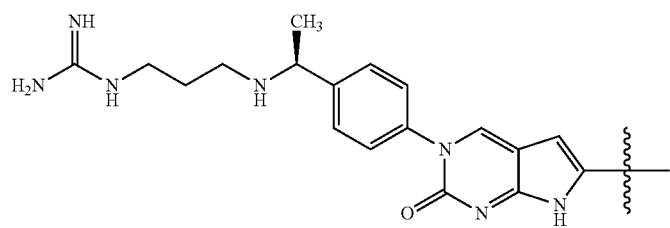
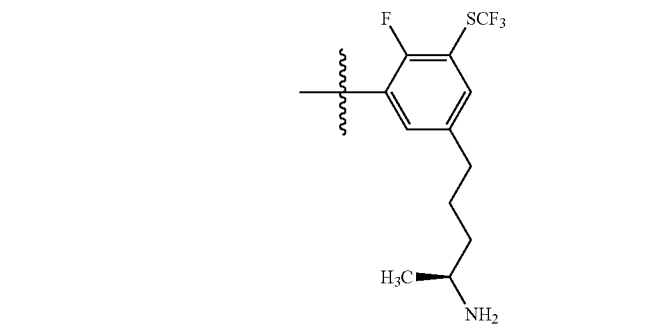
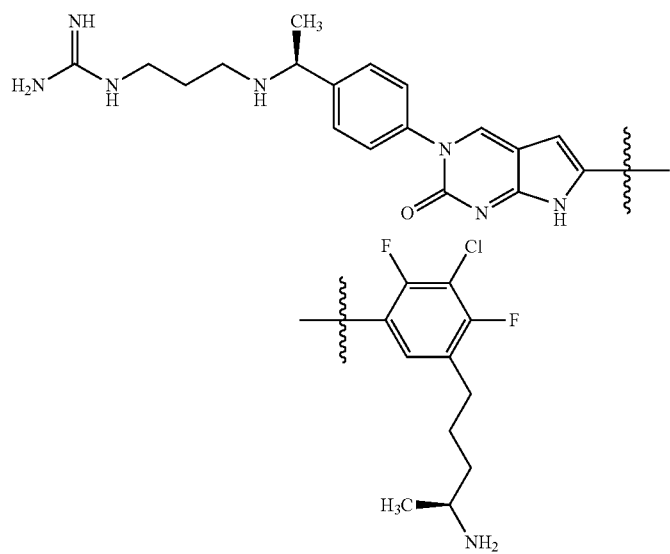
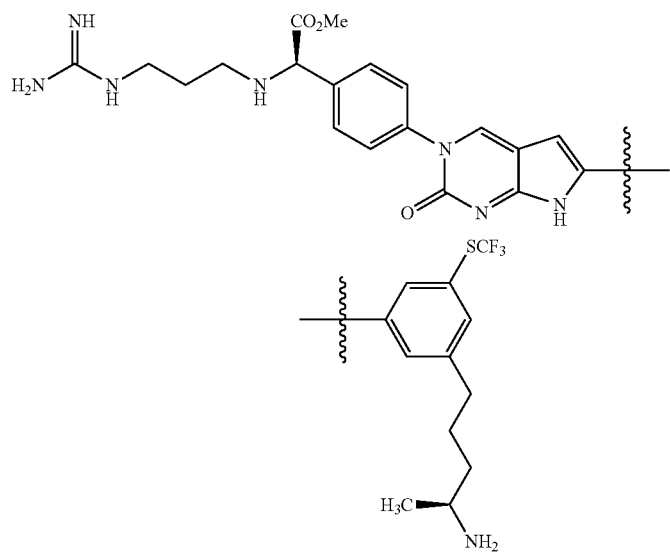

In some embodiments, the compounds of Formula (A) have Formula (I):

(I)

or a tautomer thereof, or a pharmaceutically acceptable salt, or ester of said compound or tautomer,
wherein:
===== is a single or a double bond;
X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the (C$_1$-C$_4$)alkyl, cycloalkyl, heterocycloalkyl, and heteroaryl are optionally substituted with one or more R$_7$;
Z is O, CH$_2$, NR$_{11}$1, or S(O)$_p$;
R$_1$ is H, (C$_1$-C$_4$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, heterocycloalkyl, halogen, —NO$_2$, wherein the (C$_1$-C$_4$)alkyl, (C$_2$-C$_4$)alkenyl, and heterocycloalkyl are optionally substituted with one or more R$_{12}$; or
R$_1$ and R$_2$ together with the carbon atoms to which they are attached form a (C$_3$-C$_7$)cycloalkyl or heterocycloalkyl;
R$_2$ is —F, —Cl, —CF$_3$, —SCF$_3$, or —OCF$_3$;
R$_3$ is H or —NO$_2$;
R$_4$ is H, (C$_1$-C$_3$)alkyl, (C$_2$-C$_3$)alkenyl, halogen, or —NO$_2$;
R$_5$ is H or —CH$_3$; or
R$_6$ is H, (C$_1$-C$_3$)alkyl, (C$_2$-C$_3$)alkenyl, (C$_1$-C$_3$)haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more R$_8$; or
R$_5$ and R$_6$ together with the carbon atoms to which they are attached and the Z atom connecting said two carbon atoms, form a (C$_5$-C$_6$)cycloalkyl or a 5- to 6-membered heterocycloalkyl ring containing 1-3 heteroatoms optionally substituted with one or more R$_9$;
at least one of R$_5$ and R$_6$ is not H;
each R$_7$ is independently (C$_1$-C$_3$)alkyl, halogen, oxo, —OH, or —NH$_2$;
each R$_8$ is independently (C$_1$-C$_3$)alkyl, (C$_1$-C$_3$)alkoxy, halogen, oxo, —NH$_2$, or —NHR$_{10}$;
each R$_9$ is independently (C$_1$-C$_3$)alkyl, (C$_2$-C$_4$)alkenyl, —NH$_2$, —NH$_2$C(NH)NH$_2$, —NH$_2$C(NH)(C$_1$-C$_3$)alkyl, —CH$_2$heteroaryl, —NHheterocycloalkyl, or —NHheteroaryl, wherein the (C$_1$-C$_3$)alkyl is optionally substituted with one or more substituents independently selected from —OH and —NH$_2$;
each R$_{10}$ is independently —CH$_2$aryl optionally substituted with (C$_1$-C$_3$)alkoxy or halogen;
R$_{11}$ is H, —NHC(NH)NH$_2$, —C(O)H, —C(O)(C$_1$-C$_4$)alkyl, —C(O)O(C$_1$-C$_4$)alkyl, (C$_1$-C$_4$)alkyl, (C$_3$-C$_6$)cycloalkyl, or heterocycloalkyl, wherein the (C$_1$-C$_4$)alkyl is optionally substituted with one or more substituents independently selected from —OH, (C$_1$-C$_3$)alkoxy, —NH$_2$, and —NHC(NH)NH$_2$;
each R$_{12}$ is independently selected from (C$_1$-C$_3$)alkoxy, (C$_1$-C$_3$)haloalkyl, (C$_1$-C$_3$) hydroxyalkyl, halogen, —OH, —NH$_2$, —NH(C$_1$-C$_4$)alkyl, —N((C$_1$-C$_4$)alkyl)$_2$, and oxo;
R$_{13}$ is —CH$_3$, —CH=CH$_2$, —CF$_3$, —CH$_2$F, or —CH$_2$OH;
R$_{13'}$ is H or —CH$_3$;
n is 1 or 2;
each p is independently 0, 1, or 2; and
provided that when Z is NH, X is —CH$_2$NHC(NH)NH$_2$ or —CH$_2$NH$_2$, R$_1$ is H, R$_3$ is H, R$_5$ is methyl, and R$_6$ is H, then R$_4$ is (C$_1$-C$_3$)alkyl, (C$_2$-C$_3$)alkenyl, halogen, or —NO$_2$.
In some embodiments of Formula (A) or Formula (I),
Z is O, CH$_2$, or NH;
R$_1$ is H or —NO$_2$;
R$_2$ is —Cl or —OCF$_3$;
R$_4$ is H or —NO$_2$;
R$_{11}$ is H;
R$_{13}$ is —CH$_3$; and
R$_{13'}$ is H.
In some embodiments of Formula (A) or Formula (I),
R$_6$ is H, (C$_1$-C$_3$)alkyl, (C$_2$-C$_3$)alkenyl, (C$_1$-C$_3$)haloalkyl, —CH$_2$NHC(NH)NH$_2$, —CH$_2$NHC(NH)CH$_3$, —(CH$_2$)$_n$OH, —CH$_2$S(O)$_2$NH$_2$, —CH$_2$NHCH$_2$CH$_3$, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more R$_8$.
In some embodiments of Formula (A) or Formula (I),
R$_6$ is H, (C$_1$-C$_3$)alkyl, (C$_2$-C$_3$)alkenyl, (C$_1$-C$_3$)haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$hetero aryl, or —CH$_2$NH$_2$heteroaryl, wherein the heteroaryl and heterocycloalkyl is optionally substituted with one or more R$_8$; and
provided that when Z is NH, X is —CH$_2$NHC(NH)NH$_2$ or —CH$_2$NH$_2$, R$_1$ is H, R$_3$ is H, R$_4$ is H, then R$_6$ is not H, —CH$_3$, —CH$_2$OH, —CH$_2$NH$_2$NH$_2$, or —CH=CH$_2$.
In some embodiments of Formula (A) or Formula (I),
R$_6$ is (C$_1$-C$_3$)alkyl, (C$_2$-C$_3$)alkenyl, (C$_1$-C$_3$)haloalkyl, —CH$_2$NHC(NH)NH$_2$, CH$_2$NHC(NH)CH$_3$, —CH$_2$CH$_2$OH, —CH$_2$OH, —CH$_2$S(O)$_2$NH$_2$, CH$_2$NHCH$_2$CH$_3$, —CH$_2$C(O)NH$_2$, —CH$_2$CH$_2$NH$_2$, —CH$_2$NH$_2$, or a group of Formulae:

-continued

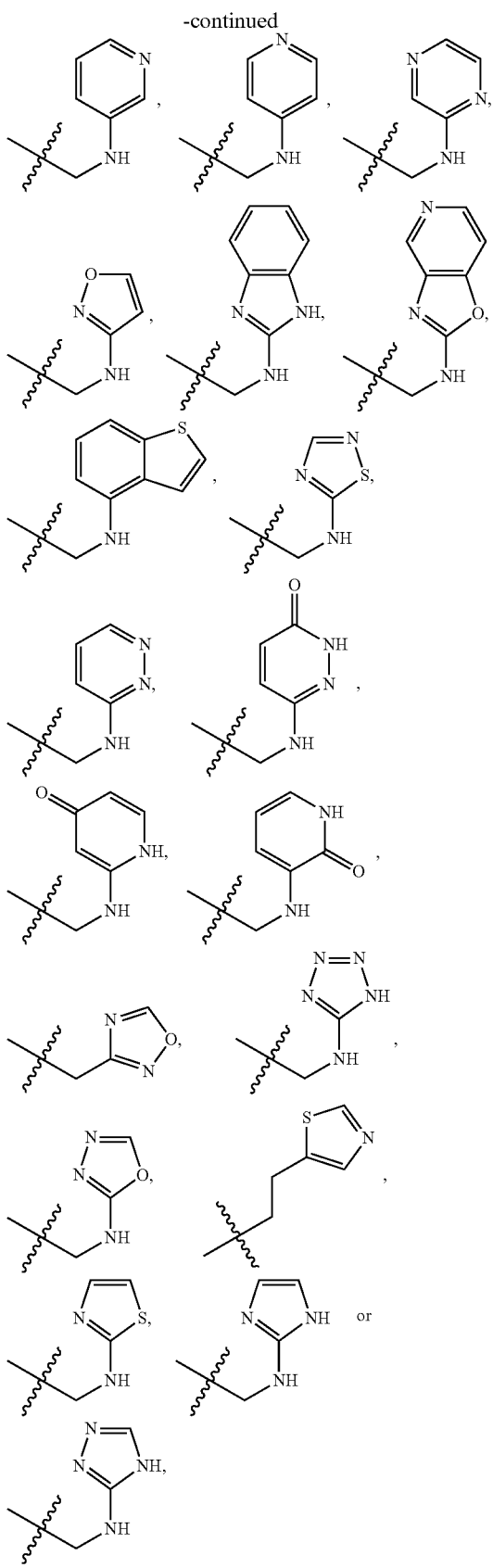

wherein any one of the Formulae is optionally substituted with one or more $R_8$.

In some embodiments of Formula (A) or Formula (I), $R_6$ is $(C_1-C_3)$alkyl, $(C_2-C_3)$alkenyl, $(C_1-C_3)$haloalkyl, —$CH_2NHC(NH)NH_2$, —$(CH_2)_nOH$, —$CH_2S(O)_pNH_2$, —$CH_2NH(C_1-C_3)$alkyl, —$CH_2C(O)NH_2$, —$(CH_2)_nNH_2$,

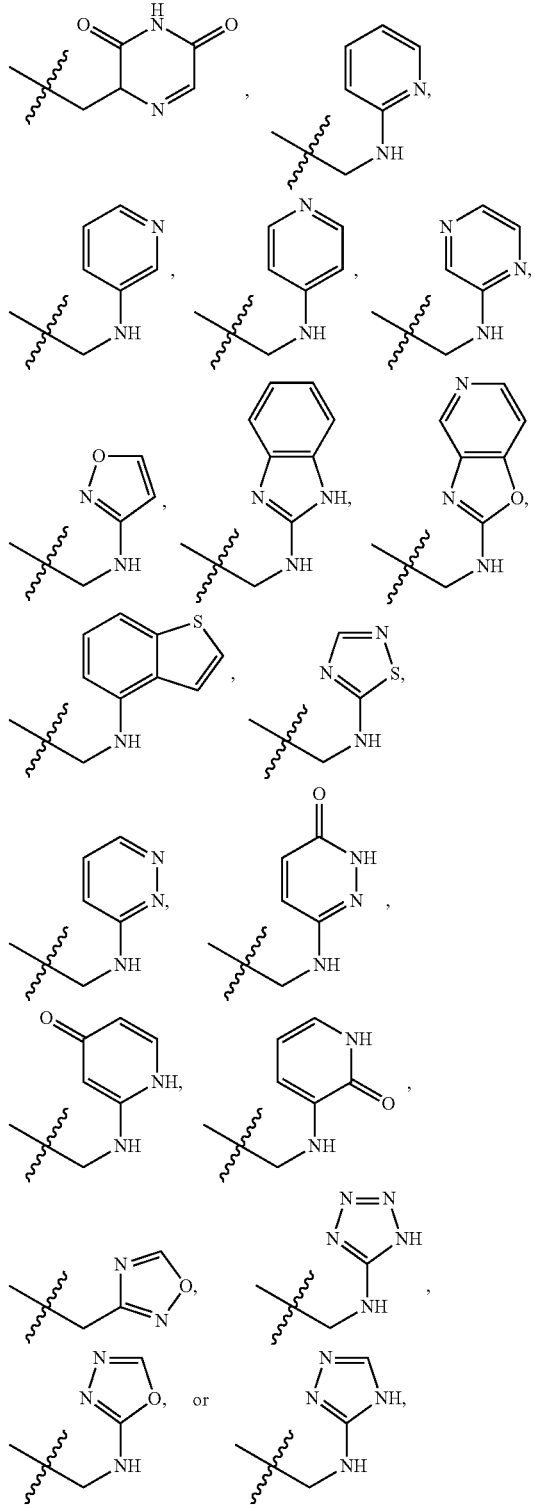

wherein the heteroaryl and heterocycloalkyl in the above structures are optionally substituted with one or more $R_8$; and provided that when Z is NH, X is —CH₂NHC(NH)NH₂ or —CH₂NH₂, R₁ is H, R₃ is H, R₄ is H, then R₆ is not (C₁-C₃)alkyl or (C₂-C₃)alkenyl.

In some embodiments of Formula (A) or Formula (I), R₆ is

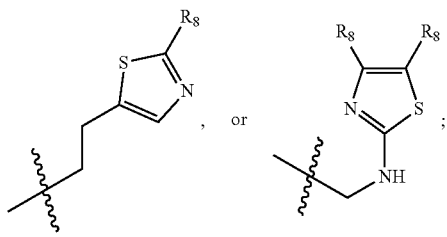

and provided that when Z is NH, X is —CH₂NHC(NH)NH₂ or —CH₂NH₂, R₁ is H, R₃ is H, R₄ is H, then R₆ is not (C₁-C₃)alkyl or (C₂-C₃)alkenyl.

In some embodiments of Formula (A) or Formula (I),

X is —CH₂NHCH₂C(O)CH₃, —CH₂NHC(NH)(C₁-C₄)alkyl, —CH₂NHC(NH)(C₃-C₇)cycloalkyl, —CH₂NHC(NH)heteroaryl, heteroaryl, —NHCH₂heteroaryl, —CH₂NHheteroaryl, —CH(OH)heteroaryl, —CH₂heterocycloalkyl, —NHCH₂heterocycloalkyl, or —CH₂NHheterocycloalkyl, wherein the (C₁-C₄)alkyl, cycloalkyl, heterocycloalkyl and heteroaryl are optionally substituted with one or more R₇;

R₁ is H;
R₃ is H;
R₄ is H;

R₅ and R₆ together with the carbon atoms to which they are attached and the Z atom connecting said two carbon atoms, form a (C₅-C₆)cycloalkyl or a 5- to 6-membered heterocycloalkyl ring containing 1-3 heteroatoms optionally substituted with one or more R₉;

provided that when Z is NH, R₁ is H, R₂ is H, R₃ is H and R₄ is H, then X is not —CH₂NHC(NH)CH₃.

In some embodiments of Formula (A) or Formula (I),

X is —CH₂NHCH₂C(O)CH₃, —CH₂NHC(NH)(C₁-C₄)alkyl, —CH₂NHC(NH)(C₃-C₇)cycloalkyl, —CH₂NHC(NH)heteroaryl, or —CH(OH)heteroaryl, wherein the (C₁-C₄)alkyl, cycloalkyl, and heteroaryl are optionally substituted with one or more R₇;

R₁ is H;
R₃ is H;
R₄ is H;

R₅ and R₆ together with the carbon atoms to which they are attached and the Z atom connecting said two carbon atoms, form a (C₅-C₆)cycloalkyl or a 5- to 6-membered heterocycloalkyl ring containing 1-3 heteroatoms optionally substituted with one or more R₉; and provided that when Z is NH, R₁ is H, R₂ is H, R₃ is H and R₄ is H, then X is not —CH₂NHC(NH)CH₃.

In some embodiments of Formula (A) or Formula (I),

X is —CH₂NHCH₂C(O)CH₃, —CH₂NHC(NH)(C₁-C₄)alkyl, —CH₂NHC(NH)(C₁-C₄)haloalkyl, —CH₂NHC(NH)(C₃-C₇)cycloalkyl, or a group of Formulae:

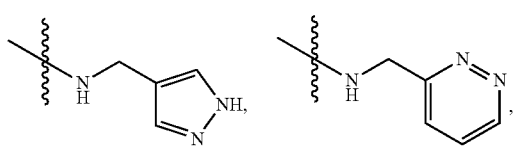

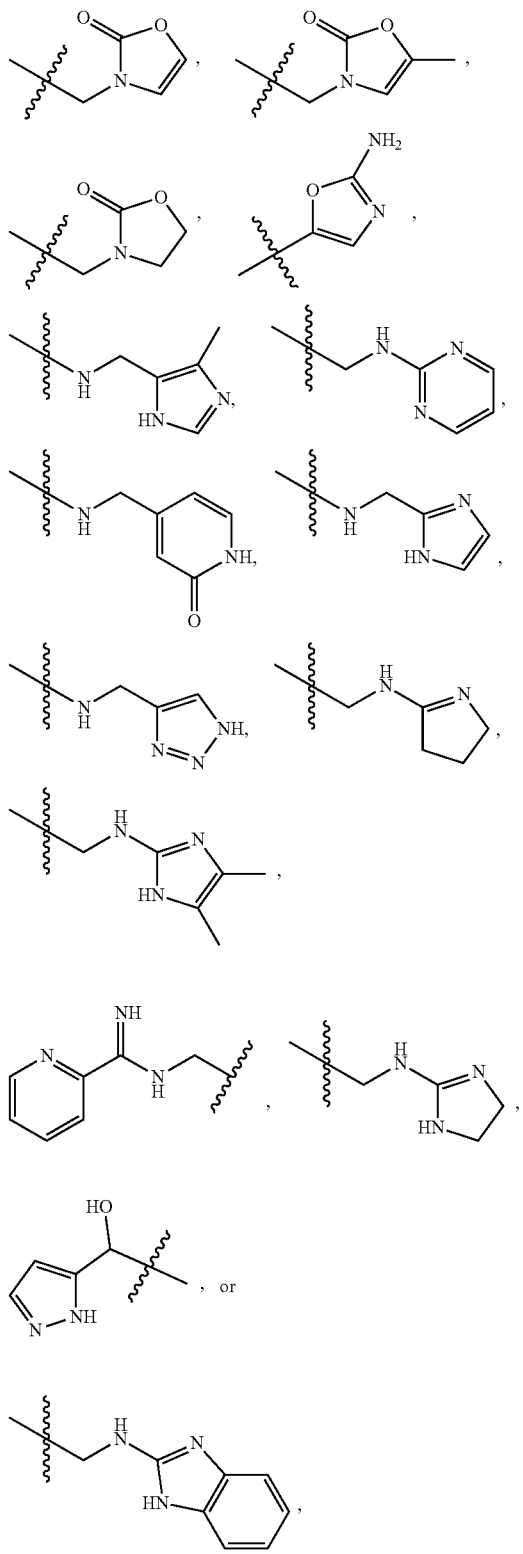

wherein the (C₁-C₄)alkyl, cycloalkyl, and any one of the Formulae are optionally substituted with one or more RT.

In some embodiments of Formula (A) or Formula (I), when Z is NH and X is —NHC(NH)NH₂, —CH₂NHC(NH)NH₂, or —CH₂NH₂, then R₅ and R₆ do not from a ring of Formula:

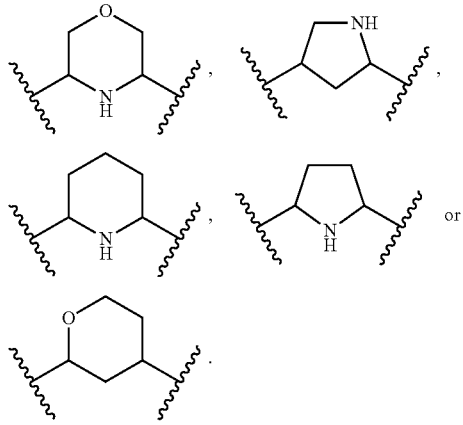

In some embodiments of Formula (A) or Formula (I), the compound is not:

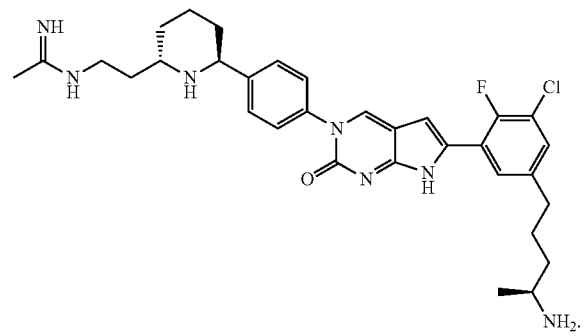 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1]

In some embodiments of Formula (A) or Formula (I), when Z is NH and X is any one of the following Formulae:

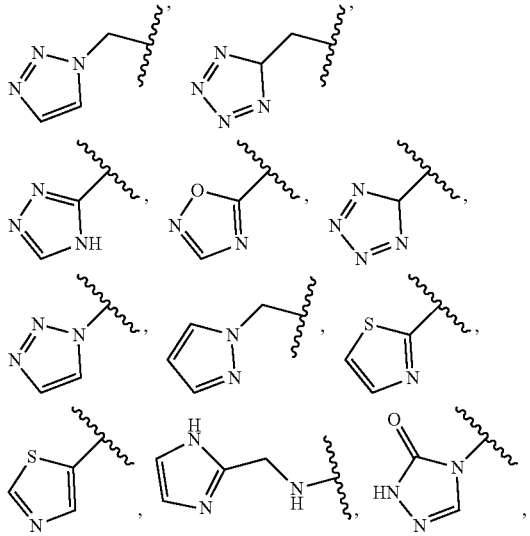

-continued

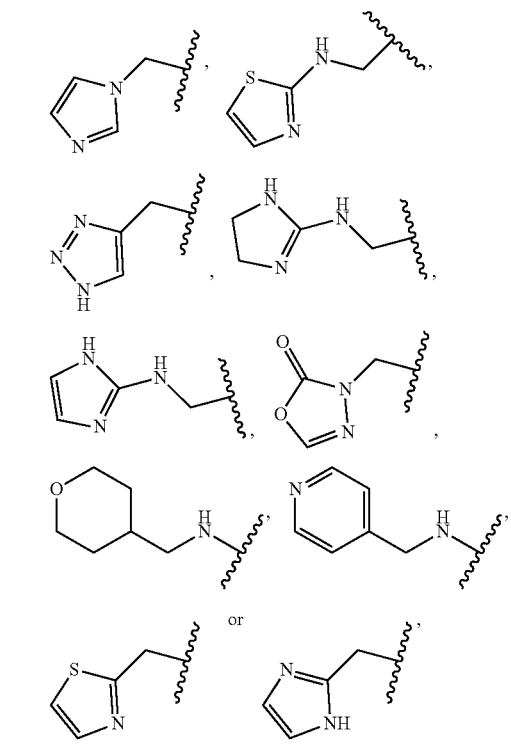

then R₅ and R₆ do not from a ring of Formula:

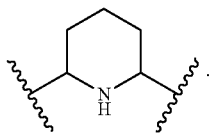 [SMILES: *C1CCCC(*)N1]

In some embodiments of Formula (A) or Formula (I) R₅ and R₆ form a ring of Formula:

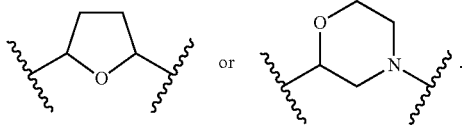 [SMILES: *C1CCC(*)O1 ; *C1CN(*)CCO1]

In some embodiments of Formula (A) or Formula (I):

X is

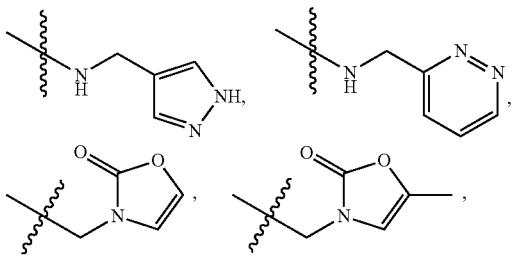

-continued

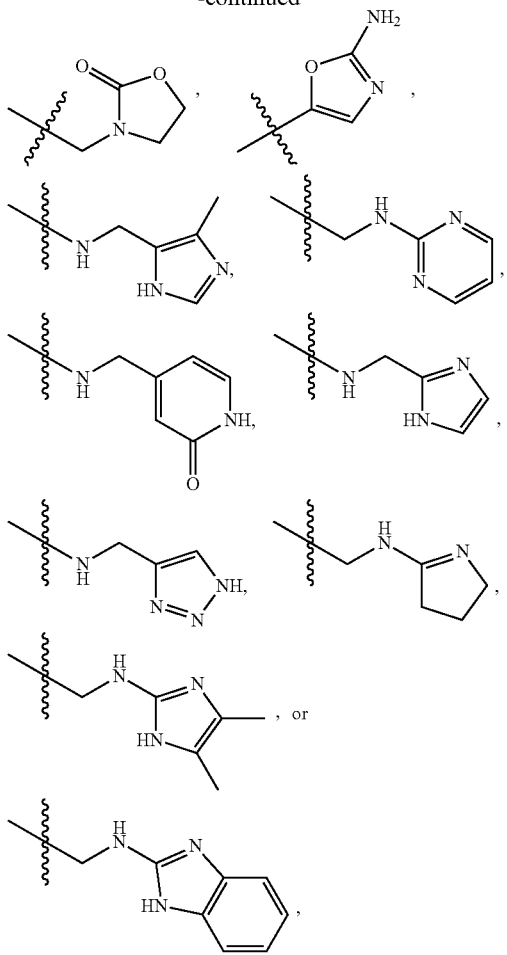

wherein the heterocycloalkyl and heteroaryl in the above structures is optionally substituted with one or more $R_7$;
$R_1$ is H;
$R_3$ is H;
$R_4$ is H;
$R_5$ and $R_6$ together with the carbon atoms to which they are attached and the Z atom connecting said two carbon atoms, form a $(C_5-C_6)$cycloalkyl or a 5- to 6-membered heterocycloalkyl ring containing 1-3 heteroatoms optionally substituted with one or more $R_9$; and
provided that when Z is NH, $R_1$ is H, $R_2$ is H, $R_3$ is H and $R_4$ is H, then X is not —$CH_2NHC(NH)CH_3$.

In some embodiments of Formula (A) or Formula (I)
Z is O;
W is $CH_2$; and
$R_6$ is $(C_1-C_3)$alkyl, $(C_2-C_3)$alkenyl, $(C_1-C_3)$haloalkyl, —$(CH_2)_nOH$, —$CH_2NHC(NH)NH_2$,
$CH_2NH_2$, $CH_2NH$heteroaryl, $CH_2N((C_1-C_3)alkyl)_2$, or —$CH_2NHC(=NH)$ $(C_1-C_3)$alkyl.

In some embodiments of Formula (A) or Formula (I)
Z is O;
W is $CH_2$; and
$R_6$ is $CH_3$, —$CH=CH_2$, $CH_2F$, —$CH_2NHC(NH)NH_2$, —$CH_2$—$N(CH_3)_2$, —$CH_2NHC(=NH)CH_3$, —$CH_2OH$, —$CH_2NH_2$, —$CH_2NH_2$thiazole, —$CH_2NH_2$imidazole or —$CH_2NH_2$pyridine, wherein said pyridine is optionally substituted with at least one F.

In some embodiments of Formula (A) or Formula (I) when X is —$CH_2NHC(NH)NH_2$, then $R_6$ is not a group of Formula:

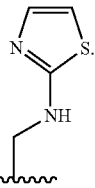

In some embodiments of Formula (A) or Formula (I)
Z is O;
$R_6$ is H, $(C_1-C_3)$alkyl, $(C_2-C_3)$alkenyl, $(C_1-C_3)$haloalkyl, —$CH_2NHC(NH)NH_2$, —$(CH_2)_nOH$, —$CH_2S(O)_pNH_2$, —$CH_2NH(C_1-C_3)$alkyl, —$CH_2C(O)NH_2$, —$(CH_2)_nNH_2$, —$CH_2$heterocycloalkyl, —$CH_2NH_2$heterocycloalkyl, —$(CH_2)_n$heteroaryl, or —$CH_2NH_2$heteroaryl, wherein the heteroaryl and heterocycloalkyl are optionally substituted with one or more $R_8$; and
at least one of $R_5$ and $R_6$ is not H.

In some embodiments of Formula (A) or Formula (I)
Z is $CH_2$;
$R_6$ is H, $(C_1-C_3)$alkyl, $(C_2-C_3)$alkenyl, $(C_1-C_3)$haloalkyl, —$CH_2NHC(NH)NH_2$, —$(CH_2)_nOH$, —$CH_2S(O)_pNH_2$, —$CH_2NH(C_1-C_3)$alkyl, —$CH_2C(O)NH_2$, —$(CH_2)_nNH_2$, —$CH_2$heterocycloalkyl, —$CH_2NH_2$heterocycloalkyl, —$(CH_2)_n$heteroaryl, or —$CH_2NH_2$heteroaryl, wherein the heteroaryl and heterocycloalkyl are optionally substituted with one or more $R_8$; and
at least one of $R_5$ and $R_6$ is not H.

In some embodiments of Formula (A) or Formula (I)
Z is NH;
$R_6$ is H, $(C_1-C_3)$alkyl, $(C_2-C_3)$alkenyl, $(C_1-C_3)$haloalkyl, —$CH_2NHC(NH)NH_2$, —$(CH_2)_nOH$, —$CH_2S(O)_pNH_2$, —$CH_2NH(C_1-C_3)$alkyl, —$CH_2C(O)NH_2$, —$(CH_2)_nNH_2$, —$CH_2$heterocycloalkyl, —$CH_2NH_2$heterocycloalkyl, —$(CH_2)_n$heteroaryl, or —$CH_2NH_2$heteroaryl, wherein the heteroaryl and heterocycloalkyl are optionally substituted with one or more $R_8$;
at least one of $R_5$ and $R_6$ is not H; and
provided that when X is —$CH_2NHC(NH)NH_2$ or —$CH_2NH_2$, $R_1$ is H, $R_3$ is H, $R_4$ is H, then $R_6$ is not H, $(C_1-C_3)$alkyl or $(C_2-C_3)$alkenyl.

In some embodiments of Formula (A) or Formula (I)
X is —$CH_2NH_2$ or —$CH_2NHC(NH)NH_2$;
Z is NH;
$R_1$ is H or —$NO_2$;
$R_2$ is —Cl or —$OCF_3$;
$R_3$ is H or —$NO_2$;
$R_4$ is —$NO_2$;
$R_5$ is H or —$CH_3$;
and $R_6$ is H.

In some embodiments of Formula (A) or Formula (I), X is —$NHC(NH)NH_2$, —$CH_2NH_2$, or —$CH_2NHC(NH)NH_2$.

In some embodiments of Formula (A) or Formula (I), X is —$CH_2NHCH_2C(O)CH_3$, —$CH_2NHC(NH)(C_1-C_4)$alkyl, —$CH_2NHC(NH)(C_3-C_7)$cycloalkyl, or —$CH_2NHC(NH)$ heteroaryl, wherein the $(C_1-C_4)$alkyl, cycloalkyl, and heteroaryl are optionally substituted with one or more $R_7$.

In some embodiments of Formula (A) or Formula (I), X is —$CH_2NHCH_2C(O)CH_3$, —$CH_2NHC(NH)(C_1-C_4)$alkyl, or —$CH_2NHC(NH)(C_3-C_7)$cycloalkyl.

In some embodiments of Formula (A) or Formula (I), X is —$CH(OH)$heteroaryl optionally substituted with one or more $R_7$.

In some embodiments of Formula (A) or Formula (I), X is

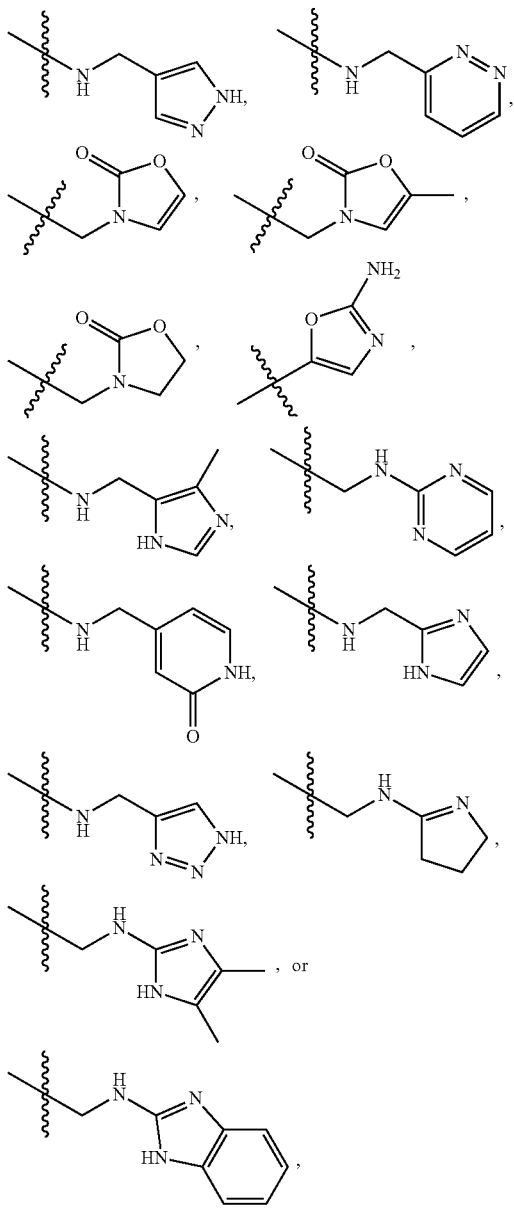

wherein each is optionally substituted with one or more $R_7$.

In some embodiments of Formula (A) or Formula (I), $R_2$ is —Cl.

In some embodiments of Formula (A) or Formula (I), $R_2$ is —Cl, —CF$_3$, —SCF$_3$, or —OCF$_3$.

In some embodiments of Formula (A) or Formula (I), $R_2$ is —Cl or —CF$_3$.

In some embodiments of Formula (A) or Formula (I), $R_2$ is —Cl, or —OCF$_3$.

In some embodiments of Formula (A) or Formula (I), $R_2$ is —Cl or —SCF$_3$.

In some embodiments of Formula (A) or Formula (I), $R_1$ is H, $R_3$ is H and $R_4$ is H.

In some embodiments of Formula (A) or Formula (I), Z is NH.

In some embodiments of Formula (A) or Formula (I), Z is O.

In some embodiments of Formula (A) or Formula (I), Z is $CH_2$.

In some embodiments of Formula (A) or Formula (I), $R_3$ is H.

In some embodiments of Formula (A) or Formula (I), $R_5$ is H.

In some embodiments of Formula (A) or Formula (I), W is $NR_5$.

In some embodiments of Formula (A) or Formula (I), W is $CHR_5$.

In some embodiments of Formula (A) or Formula (I), $R_6$ is $(C_1$-$C_3)$alkyl, $(C_2$-$C_3)$alkenyl, or $(C_1$-$C_3)$haloalkyl.

In some embodiments of Formula (A) or Formula (I), $R_6$ is $(C_1$-$C_3)$alkyl, $(C_2$-$C_3)$alkenyl, or $(C_1$-$C_3)$haloalkyl; and X is —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, or —CH$_2$NHC(NH)heteroaryl, or —CH(OH)heteroaryl, wherein the (C$_1$-C$_4$) alkyl, cycloalkyl and heteroaryl are optionally substituted with one or more $R_7$.

In some embodiments of Formula (A) or Formula (I), $R_6$ is —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, or —(CH$_2$)$_n$NH$_2$.

In some embodiments of Formula (A) or Formula (I), $R_6$ is

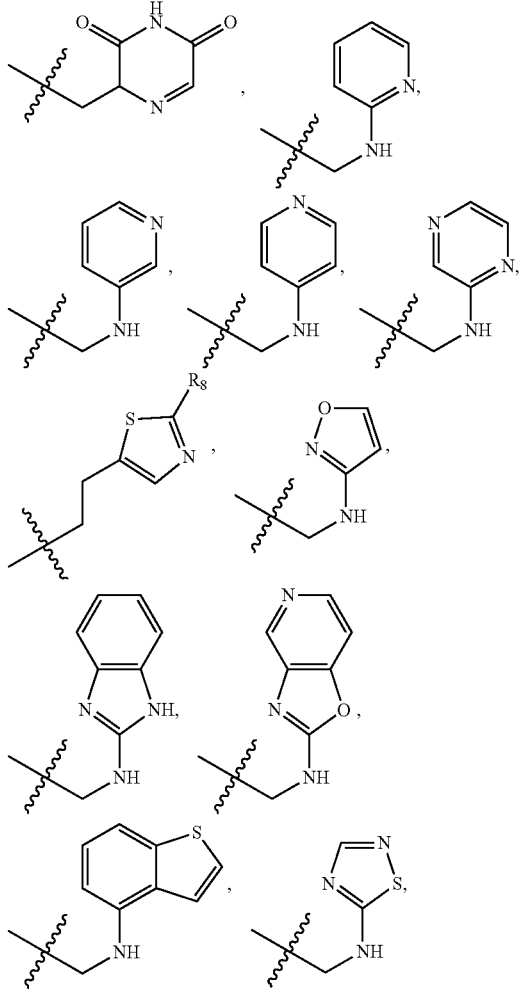

-continued

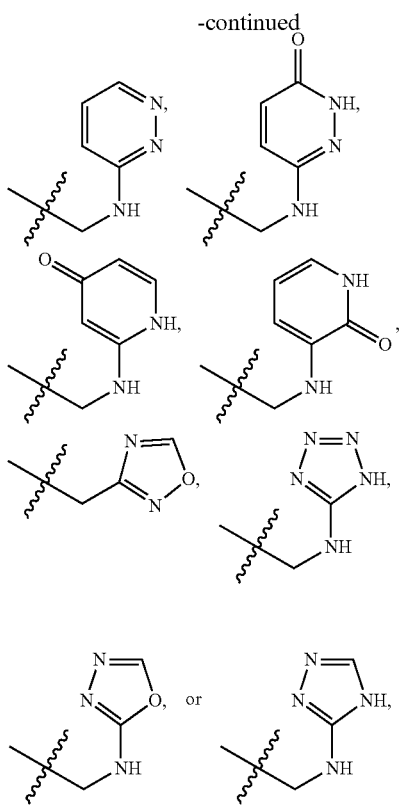

wherein the heteroaryl and heterocycloalkyl in the above structures is optionally substituted with one or more $R_8$.

In some embodiments of Formula (A) or Formula (I), $R_6$ is

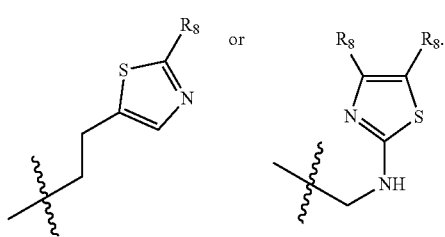

In some embodiments of Formula (A) or Formula (I), $R_9$ is independently $(C_1-C_3)$alkyl, $(C_2-C_4)$alkenyl, $-NH_2$, $-NHC(NH)NH_2$, $-NHC(NH)(C_1-C_3)$alkyl, $-CH_2$heteroaryl, $-NH$heterocycloalkyl, or $-NH$heteroaryl, wherein the $(C_1-C_3)$alkyl is optionally substituted with one or more substituents independently selected from $-NHC(NH)NH_2$, $-OH$ and $-NH_2$;

In some embodiments of Formula (A) or Formula (I), $R_9$ is H, $(C_1-C_3)$alkyl, $(C_2-C_4)$alkenyl, $-NH_2$, $-N((C_1-C_3)$alkyl$)_2$; $-C(=NH)-(C_1-C_3)$alkyl; $-C(=NH)(NH_2)$; $(C_1-C_3)$ hydroxyalkyl; $-NH_2C(=NH)NH_2$, $-NH_2C(=NH)(C_1-C_3)$alkyl, $-(C_1-C_3)$alkylene-heteroaryl, $-NH-$ heterocycloalkyl, or $-NH$-heteroaryl, wherein the $(C_1-C_3)$alkyl is optionally substituted with one or more substituents independently selected from $-OH$, $-NHC(=NH)NH_2$ and $-NH_2$.

In some embodiments of Formula (A) or Formula (I), $R_9$ is $(C_1-C_3)$alkyl substituted with one or more substituents independently selected from $-NHC(NH)NH_2$, $-OH$ and $-NH_2$.

In some embodiments of Formula (A) or Formula (I), $R_9$ is H, $(C_1-C_3)$alkyl, $(C_2-C_4)$alkenyl, $-NH_2$, $-N((C_1-C_3)$alkyl$)_2$; $-C(=NH)-(C_1-C_3)$alkyl; $-C(=NH)(NH_2)$; $(C_1-C_3)$ hydroxyalkyl; $-NH_2C(=NH)NH_2$; or $-NH_2C(=NH)(C_1-C_3)$alkyl.

In some embodiments of Formula (A) or Formula (I), $R_9$ is H, $(C_2-C_4)$alkenyl, $-NH_2$, $-N((C_1-C_3)$alkyl$)_2$; $-C(=NH)-(C_1-C_3)$alkyl; $-C(=NH)(NH_2)$; $(C_1-C_3)$ hydroxyalkyl; $-NH_2C(=NH)NH_2$; or $-NH_2C(=NH)(C_1-C_3)$alkyl.

In some embodiments of Formula (A) or Formula (I), $R_9$ is $-CH_2CH_2NHC(NH)NH_2$.

In some embodiments of Formula (A) or Formula (I), $R_9$ is $-(C_1-C_3)$alkylene-heteroaryl, $-NH$-heterocycloalkyl, or $-NH$-heteroaryl.

In some embodiments of Formula (A) or Formula (I), $R_9$ is $(C_1-C_3)$alkyl is optionally substituted with one or more substituents independently selected from $-OH$, $-NHC(=NH)NH_2$, and $-NH_2$.

In some embodiments of Formula (A) or Formula (I), $R_9$ is H, $-CH=CH_2$, $-NH_2$, $-N(CH_3)_2$; $-C(=NH)(CH_3)$; $-C(=NH)(NH_2)$; $-CH_2CH_2OH$; $-NH_2C(=NH)NH_2$, $-NH_2C(=NH)CH_3$, $-CH_2$-imidazole, $-NH$-imidazolidine, $-CH_2-NHC(=NH)NH_2$, or $-CH_2NH_2$.

In some embodiments of Formula (A) or Formula (I), $R_{11}$ is H.

In some embodiments of Formula (A) or Formula (I), $R_{11}$ is H or $(C_1-C_3)$alkyl.

In some embodiments of Formula (A) or Formula (I), $R_{11}$ is H or $CH_3$.

In some embodiments of Formula (A) or Formula (I), the compound has any one of the following Formulae:

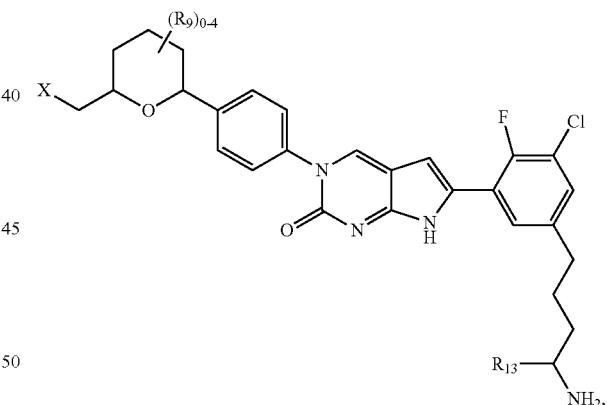

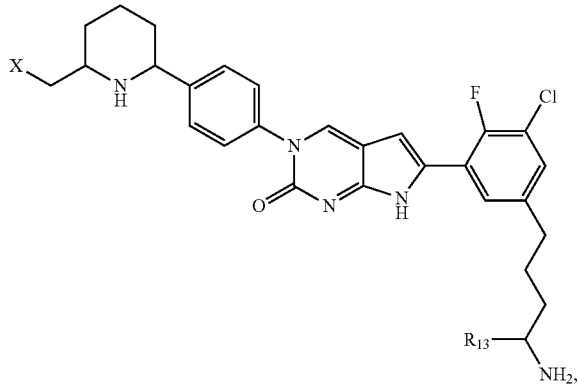

-continued
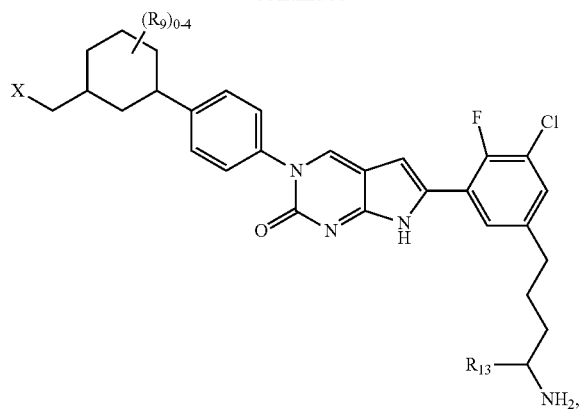
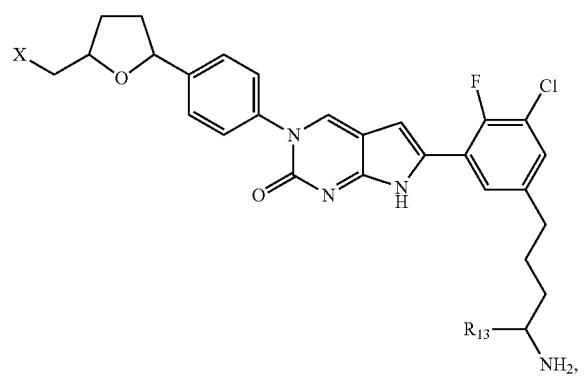
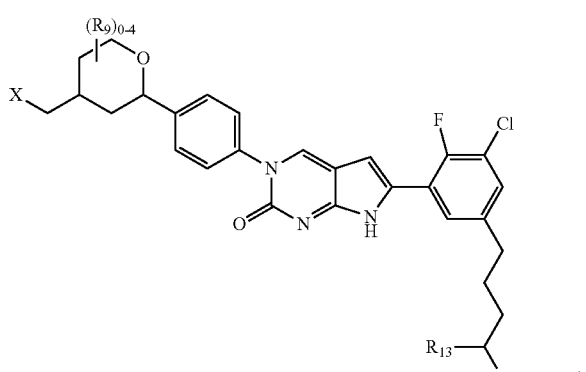
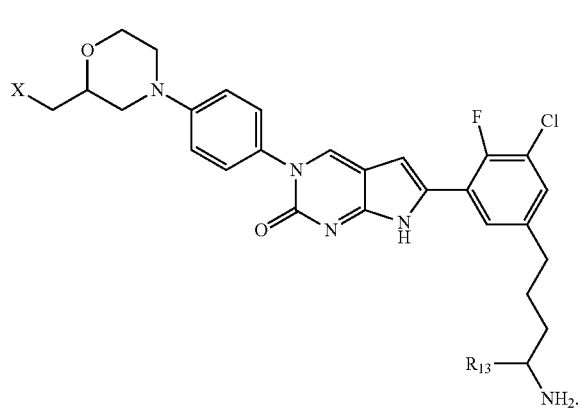
In some embodiments of Formula (A) or Formula (I), when Z is NH, X is —NHC(NH)NH$_2$, —CH$_2$NHC(NH)NH$_2$, —CH$_2$NHC(NH)(C$_1$-C$_3$ alkyl) or —CH$_2$NH$_2$, and R$_5$ is H or CH$_3$, then R$_6$ is not CH$_3$, —CH=CH$_2$, —(CH$_2$)$_n$NH$_2$, —(CH$_2$)$_n$OH or a group of Formula:
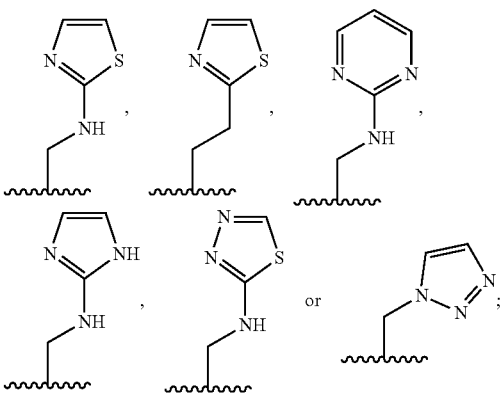
and
when Z is NH, X is —NHC(NH)NH$_2$, —CH$_2$NHC(NH)CH$_3$, —CH$_2$NHC(NH)NH$_2$, —CH$_2$NH$_2$, or a group of Formula:
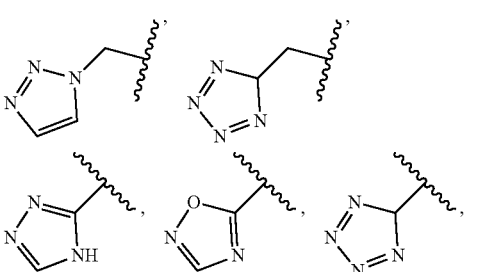
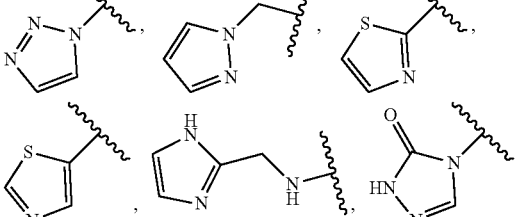
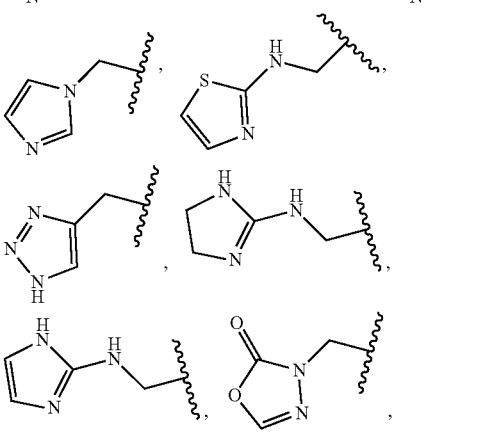

-continued

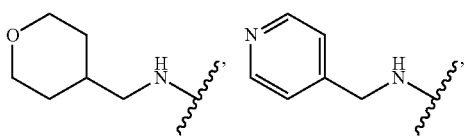

or

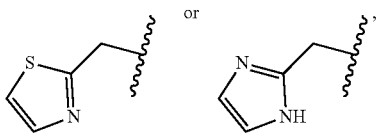

then R₅ and R₆ do not from a ring of Formula:

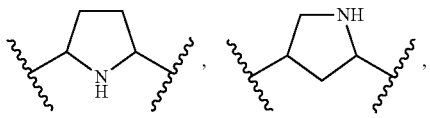

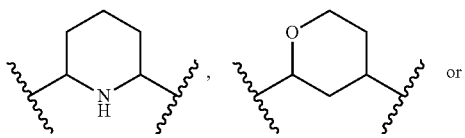

and when Z is O, X is —CH₂NHC(NH)NH₂, and R₅ is H, then R₆ is not a group of Formula:

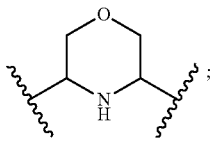

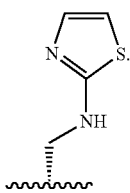

In some embodiments of Formula (A) or Formula (I), the compound of Formula A is selected from any one of compounds 1, 3-78, 81-92, 96, 97, 106-111, 119, 120, 123, 127, 128, 132-135, 137, 138, 143, 150-153 listed in Table 1.

In one aspect, the present disclosure provides a compound of Formula B:

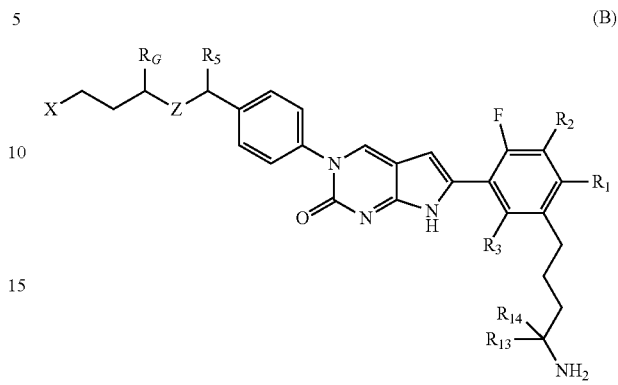

(B)

or a tautomer thereof, or a pharmaceutically acceptable salt, or ester of said compound or tautomer,
wherein:
X is —NHC(NH)NH$_2$, —NHC(O)NH$_2$, —NHC(NH)(C$_1$-C$_3$)alkyl, —NHS(O)$_2$(C$_1$-C$_3$)alkyl, or heterocycloalkyl;
Z is O, CH$_2$, or NR$_{11}$;
R$_1$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN or —NO$_2$, wherein the (C$_1$-C$_3$)alkyl, (C$_2$-C$_4$) alkenyl and (C$_1$-C$_3$)alkoxy are optionally substituted with one or more R$_{12}$;
R$_2$ is halogen, (C$_1$-C$_3$)haloalkyl, —S(C$_1$-C$_3$)haloalkyl, or —O(C$_1$-C$_3$)haloalkyl;
R$_3$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN or —NO$_2$, wherein the (C$_1$-C$_3$)alkyl, (C$_2$-C$_4$) alkenyl and (C$_1$-C$_3$)alkoxy are optionally substituted with one or more R$_{12}$;
R$_5$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN or —NO$_2$, wherein the (C$_1$-C$_3$)alkyl, (C$_2$-C$_4$) alkenyl and (C$_1$-C$_3$)alkoxy are optionally substituted with one or more R$_{12}$;
R$_G$ is (C$_1$-C$_3$)alkyl, (C$_2$-C$_3$)alkenyl, (C$_2$-C$_4$)alkynyl, (C$_1$-C$_3$)alkoxy, (C$_1$-C$_3$)haloalkyl, or —O(C$_1$-C$_3$)haloalkyl, wherein the (C$_1$-C$_3$)alkyl is optionally substituted with at least one —NHC(NH)NH$_2$, —NHC(NH)(C$_1$-C$_3$)alkyl, (C$_1$-C$_3$)alkoxy, halogen, —OH, —S(O)$_2$NH$_2$, C(O)NH$_2$, —NH$_2$, —NH(C$_1$-C$_3$)alkyl, or —N((C$_1$-C$_3$)alkyl)$_2$;
R$_{11}$ is H or (C$_1$-C$_4$)alkyl;
each R$_{12}$ is independently selected from halogen, (C$_1$-C$_3$) alkoxy, —OH, —NH$_2$, —NH(C$_1$-C$_3$)alkyl, —N((C$_1$-C$_3$) alkyl)$_2$, and oxo;
R$_{13}$ is H, (C$_1$-C$_3$)alkyl, (C$_2$-C$_4$)alkenyl, (C$_2$-C$_4$)alkynyl, —(C$_3$-C$_5$)cycloalkyl, (C$_1$-C$_3$)alkoxy, (C$_1$-C$_3$)haloalkyl, (C$_1$-C$_3$) hydroxyalkyl, —O(C$_1$-C$_3$)haloalkyl, halogen, CN, or —NO$_2$, wherein the (C$_1$-C$_3$)alkyl, (C$_2$-C$_4$)alkenyl, and (C$_1$-C$_3$)alkoxy are optionally substituted with one or more R$_{12}$; and
R$_{14}$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN, or —NO$_2$.
In some embodiments of Formula (B), X is —NHC(=NH)NH$_2$ or —NHC(NH)(C$_1$-C$_3$)alkyl.
In some embodiments of Formula (B), X is —NHC(NH)(C$_1$-C$_3$)alkyl.

In some embodiments of Formula (B), X is —NHC(=NH)NH$_2$.

In some embodiments of Formula (B), X is —NHC(NH)CH$_3$.

In some embodiments of Formula (B), X is —NHC(O)NH$_2$.

In some embodiments of Formula (B), X is a group of Formula:

[structure: imidazolidinone group with HN and N attached via wavy bond, C=O]

In some embodiments of Formula (B), Z is O or NR$_{11}$.
In some embodiments of Formula (B), Z is O or NH.
In some embodiments of Formula (B), Z is O.
In some embodiments of Formula (B), Z is NR$_{11}$.
In some embodiments of Formula (B), Z is NH.
In some embodiments of Formula (B), R$_1$ is H, halogen, or (C$_1$-C$_3$)alkyl.
In some embodiments of Formula (B), R$_1$ is F or Cl.
In some embodiments of Formula (B), R$_1$ is H.
In some embodiments of Formula (B), R$_2$ is halogen, CF$_3$, —SCF$_3$, or —OCF$_3$.
In some embodiments of Formula (B), R$_2$ is Cl or —OCF$_3$.
In some embodiments of Formula (B), R$_2$ is Cl or —SCF$_3$.
In some embodiments of Formula (B), R$_2$ is Cl.
In some embodiments of Formula (B), R$_3$ is H, halogen, or (C$_1$-C$_3$)alkyl.
In some embodiments of Formula (B), R$_3$ is F or Cl.
In some embodiments of Formula (B), R$_3$ is H.
In some embodiments of Formula (B), R$_5$ is H, —CF$_2$; —CHF$_2$; —CH$_2$OH; —CH=CH$_2$; or —CH$_3$.
In some embodiments of Formula (B), R$_5$ is H.
In some embodiments of Formula (B), R$_G$ is (C$_1$-C$_3$)alkyl, (C$_2$-C$_3$)alkenyl, (C$_1$-C$_3$)alkylene-NHC(NH)NH$_2$, (C$_1$-C$_3$)alkylene-NHC(NH)(C$_1$-C$_3$)alkyl, (C$_1$-C$_3$)haloalkyl, —(C$_1$-C$_3$) hydroxyalkyl, (C$_1$-C$_3$)alkylene-S(O)$_2$NH$_2$, (C$_1$-C$_3$)alkylene-C(O)NH$_2$, (C$_1$-C$_3$)alkylene-NH$_2$, (C$_1$-C$_3$)alkylene-NH(C$_1$-C$_3$)alkyl, or (C$_1$-C$_3$)alkylene-N((C$_1$-C$_3$)alkyl)$_2$.
In some embodiments of Formula (B), R$_G$ is CH$_3$, CH=CH$_2$, —CH$_2$—NHC(NH)NH$_2$, —CH$_2$—NHC(NH)CH$_3$, —CH$_2$F, CH$_2$CH$_2$OH, CH$_2$OH, —CH$_2$—S(O)$_2$NH$_2$, —CH$_2$—C(O)NH$_2$, —CH$_2$NH$_2$, —CH$_2$CH$_2$NH$_2$, —CH$_2$—NH-ethyl, or —CH$_2$—N(CH$_3$)$_2$.
In some embodiments of Formula (B), R$_G$ is —CH$_2$—NHC(NH)NH$_2$ or —CH$_2$—NHC(NH)CH$_3$.
In some embodiments of Formula (B), R$_G$ is —CH$_2$—NHC(NH)NH$_2$.
In some embodiments of Formula (B), R$_G$ is —CH$_2$—NHC(NH)CH$_3$.
In some embodiments of Formula (B), R$_G$ is CH$_3$, CH=CH$_2$, CH$_2$F, CH$_2$CH$_2$OH, CH$_2$OH, —CH$_2$—S(O)$_2$NH$_2$, —CH$_2$—C(O)NH$_2$, —CH$_2$NH$_2$, —CH$_2$CH$_2$NH$_2$, —CH$_2$—NH-ethyl, or —CH$_2$—N(CH$_3$)$_2$.
In some embodiments of Formula (B), R$_{11}$ is H or (C$_1$-C$_3$)alkyl.
In some embodiments of Formula (B), R$_{11}$ is H or CH$_3$.
In some embodiments of Formula (B), R$_{11}$ is H.
In some embodiments of Formula (B), R$_{13}$ is (C$_1$-C$_3$)alkyl, (C$_2$-C$_4$)alkenyl, —(C$_3$-C$_5$)cycloalkyl, (C$_1$-C$_3$)haloalkyl, (C$_1$-C$_3$)alkylene-(C$_1$-C$_3$)alkoxy, or (C$_1$-C$_3$) hydroxyalkyl.

In some embodiments of Formula (B), R$_{13}$ is CH$_3$, CH=CH$_2$, cyclopropyl, —CH$_2$F, CH$_2$OCH$_3$, or —CH$_2$OH.
In some embodiments of Formula (B), R$_{13}$ is cyclopropyl.
In some embodiments of Formula (B), R$_{13}$ is —CH=CH$_2$, —CH$_2$F, CH$_2$OCH$_3$, or —CH$_2$OH.
In some embodiments of Formula (B), R$_{13}$ is CH$_3$.
In some embodiments of Formula (B), R$_{14}$ is H or (C$_1$-C$_3$)alkyl.
In some embodiments of Formula (B), R$_{14}$ is H.
In some embodiments of Formula (B), R$_{14}$ is CH$_3$.
In some embodiments of Formula (B), R$_{13}$ is CH$_3$ and R$_{14}$ is CH$_3$.
In some embodiments of Formula (B),
Z is O or NH;
X is —NHC(NH)NH$_2$, —NHC(O)NH$_2$, —NHC(NH)CH$_3$, —NHS(O)$_2$CH$_3$, or imidazolidinone;
R$_1$ is H;
R$_2$ is halogen, CF$_3$, —SCF$_3$, or —OCF$_3$;
R$_3$ is H;
R$_5$ is H;
R$_G$ is (C$_1$-C$_3$)alkyl, (C$_2$-C$_3$)alkenyl, (C$_1$-C$_3$)alkylene-NHC(NH)NH$_2$, (C$_1$-C$_3$)alkylene-NHC(NH)(C$_1$-C$_3$)alkyl, (C$_1$-C$_3$)haloalkyl, —(C$_1$-C$_3$) hydroxyalkyl, (C$_1$-C$_3$)alkylene-S(O)$_2$NH$_2$, (C$_1$-C$_3$)alkylene-C(O)NH$_2$, (C$_1$-C$_3$)alkylene-NH$_2$, (C$_1$-C$_3$)alkylene-NH(C$_1$-C$_3$)alkyl, or (C$_1$-C$_3$)alkylene-N((C$_1$-C$_3$)alkyl)$_2$;
R$_{13}$ is (C$_1$-C$_3$)alkyl, (C$_2$-C$_4$)alkenyl, —(C$_3$-C$_5$)cycloalkyl, (C$_1$-C$_3$)haloalkyl, (C$_1$-C$_3$)alkylene-(C$_1$-C$_3$)alkoxy, or (C$_1$-C$_3$) hydroxyalkyl;
R$_{14}$ is H or (C$_1$-C$_3$)alkyl.
In some embodiments of Formula (B),
Z is O or NH;
X is —NHC(=NH)NH$_2$ or —NHC(NH)(C$_1$-C$_3$)alkyl;
R$_1$ is H;
R$_2$ is Cl or —OCF$_3$;
R$_3$ is H;
R$_5$ is H;
R$_G$ is CH$_3$, CH=CH$_2$, —CH$_2$—NHC(NH)NH$_2$, —CH$_2$—NHC(NH)CH$_3$, —CH$_2$F, CH$_2$CH$_2$OH, CH$_2$OH, —CH$_2$—S(O)$_2$NH$_2$, —CH$_2$—C(O)NH$_2$, —CH$_2$NH$_2$, —CH$_2$CH$_2$NH$_2$, —CH$_2$—NH-ethyl, or —CH$_2$—N(CH$_3$)$_2$;
R$_{13}$ is CH$_3$, CH=CH$_2$, cyclopropyl, —CH$_2$F, CH$_2$OCH$_3$, or —CH$_2$OH; and
R$_{14}$ is H or CH$_3$.
In some embodiments of Formula (B),
Z is NH;
X is —NHC(=NH)NH$_2$;
R$_1$ is H;
R$_2$ is Cl;
R$_3$ is H;
R$_5$ is H;
R$_G$ is (C$_1$-C$_3$)haloalkyl, —(C$_1$-C$_3$) hydroxyalkyl, (C$_1$-C$_3$)alkylene-NHC(NH)NH$_2$, (C$_1$-C$_3$)alkylene-NHC(NH)(C$_1$-C$_3$)alkyl, (C$_1$-C$_3$)alkylene-S(O)$_2$NH$_2$, (C$_1$-C$_3$)alkylene-C(O)NH$_2$, (C$_1$-C$_3$)alkylene-NH$_2$, or (C$_1$-C$_3$)alkylene-NH(C$_1$-C$_3$)alkyl;
R$_{13}$ is (C$_1$-C$_3$)alkyl; and
R$_{14}$ is H.
In some embodiments of Formula (B),
R$_G$ is —CH$_2$F, CH$_2$CH$_2$OH, CH$_2$OH, —CH$_2$—NHC(NH)NH$_2$, —CH$_2$—NHC(NH)CH$_3$, —CH$_2$—S(O)$_2$NH$_2$, —CH$_2$—C(O)NH$_2$, —CH$_2$NH$_2$, —CH$_2$CH$_2$NH$_2$, or —CH$_2$—NH-ethyl;
R$_{13}$ is CH$_3$; and
R$_{14}$ is H.

In some embodiments of Formula (B),
when Z is NH, X is —NHC(NH)NH$_2$ or —NHC(NH)(C$_1$-C$_3$)alkyl and R$_5$ is H or (C$_1$-C$_3$)alkyl,
then R$_G$ is not (C$_1$-C$_3$)alkyl, (C$_2$-C$_3$)alkenyl, (C$_1$-C$_3$)alkylene-NH$_2$, or —(C$_1$-C$_3$) hydroxyalkyl.

In some embodiments of Formula (B),
when Z is NH, X is —NHC(NH)NH$_2$ and R$_5$ is H,
then R$_G$ is not CH$_3$, CH=CH$_2$, CH$_2$NH$_2$, —CH$_2$CH$_2$NH$_2$, CH$_2$CH$_2$OH, or CH$_2$OH.

In some embodiments of Formula (B),
Z is NH, X is —NHC(NH)NH$_2$, and
R$_G$ is (C$_1$-C$_3$)alkylene-NHC(NH)NH$_2$, (C$_1$-C$_3$)alkylene-NHC(NH)(C$_1$-C$_3$)alkyl, (C$_1$-C$_3$)haloalkyl, (C$_1$-C$_3$)alkylene-S(O)$_2$NH$_2$, or (C$_1$-C$_3$)alkylene-C(O)NH$_2$.

In some embodiments of Formula (B),
Z is NH, X is —NHC(NH)NH$_2$, and
R$_G$ is (C$_1$-C$_3$)alkylene-NHC(NH)NH$_2$, (C$_1$-C$_3$)alkylene-NHC(NH)(C$_1$-C$_3$)alkyl, (C$_1$-C$_3$)alkylene-S(O)$_2$NH$_2$, or (C$_1$-C$_3$)alkylene-C(O)NH$_2$.

In some embodiments of Formula (B),
Z is O;
X is —NHC(NH)NH$_2$, —NHC(O)NH$_2$, —NHC(NH)(C$_1$-C$_3$)alkyl, —NHS(O)$_2$(C$_1$-C$_3$)alkyl, or heterocycloalkyl;
R$_2$ is halogen or —O(C$_1$-C$_3$)haloalkyl;
R$_3$ is H;
R$_5$ is H;
R$_G$ is (C$_1$-C$_3$)alkyl, (C$_2$-C$_3$)alkenyl, (C$_1$-C$_3$)alkylene-NHC(NH)NH$_2$, (C$_1$-C$_3$)alkylene-NHC(NH)(C$_1$-C$_3$)alkyl, (C$_1$-C$_3$)haloalkyl, —(C$_1$-C$_3$) hydroxyalkyl, (C$_1$-C$_3$)alkylene-NH$_2$, or (C$_1$-C$_3$)alkylene-N((C$_1$-C$_3$)alkyl)$_2$;
R$_{13}$ is (C$_1$-C$_3$)alkyl, (C$_2$-C$_4$)alkenyl, —(C$_3$-C$_5$)cycloalkyl, (C$_1$-C$_3$)haloalkyl, (C$_1$-C$_3$)alkylene-(C$_1$-C$_3$)alkoxy, or (C$_1$-C$_3$) hydroxyalkyl; and
R$_{14}$ is H or (C$_1$-C$_3$)alkyl.

In some embodiments of Formula (B),
Z is O;
X is —NHC(NH)NH$_2$, —NHC(O)NH$_2$, —NHC(NH)CH$_3$, —NHS(O)$_2$CH$_3$, or imidazolidinone;
R$_2$ is Cl or —OCF$_3$;
R$_3$ is H;
R$_5$ is H;
R$_G$ is CH$_3$, CH=CH$_2$, —CH$_2$—NHC(NH)NH$_2$, —CH$_2$—NHC(NH)CH$_3$, —CH$_2$F, CH$_2$CH$_2$OH, CH$_2$OH, —CH$_2$NH$_2$, —CH$_2$CH$_2$NH$_2$ or —CH$_2$—N(CH$_3$)$_2$;
R$_{13}$ is CH$_3$, CH=CH$_2$, cyclopropyl, —CH$_2$F, CH$_2$OCH$_3$ or —CH$_2$OH; and
R$_{14}$ is H or CH$_3$.

In some embodiments, compounds of Formula (B) have Formula B-1:

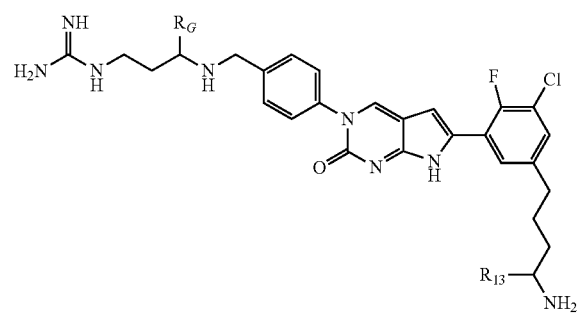

(B-1)

In some embodiments of Formula B-1, R$_{13}$ is (C$_1$-C$_3$) alkyl.

In some embodiments of Formula B-1, R$_{13}$ is CH$_3$.

In some embodiments of Formula B-1, R$_G$ is (C$_1$-C$_3$) alkyl, (C$_2$-C$_3$)alkenyl, (C$_2$-C$_4$)alkynyl, (C$_1$-C$_3$)alkoxy, (C$_1$-C$_3$)haloalkyl, or —O(C$_1$-C$_3$)haloalkyl, wherein the (C$_1$-C$_3$) alkyl is optionally substituted with at least one —NHC(NH)NH$_2$, —NHC(NH)(C$_1$-C$_3$)alkyl, (C$_1$-C$_3$)alkoxy, halogen, —OH, —S(O)$_2$NH$_2$, C(O)NH$_2$, —NH$_2$, —NH(C$_1$-C$_3$)alkyl, or —N((C$_1$-C$_3$)alkyl)$_2$; In some embodiments of Formula B-1, R$_G$ is not (C$_1$-C$_3$)alkyl, (C$_2$-C$_3$)alkenyl, (C$_1$-C$_3$)alkylene-NH$_2$, or —(C$_1$-C$_3$) hydroxyalkyl.

In some embodiments of Formula B-1, R$_G$ is not CH$_3$, CH=CH$_2$, CH$_2$NH$_2$, —CH$_2$CH$_2$NH$_2$, CH$_2$CH$_2$OH, or CH$_2$OH.

In some embodiments of Formula B-1, R$_G$ is (C$_1$-C$_3$) alkylene-NHC(NH)NH$_2$, (C$_1$-C$_3$)alkylene-NHC(NH)(C$_1$-C$_3$)alkyl, (C$_1$-C$_3$)haloalkyl, (C$_1$-C$_3$)alkylene-S(O)$_2$NH$_2$, or (C$_1$-C$_3$)alkylene-C(O)NH$_2$.

In some embodiments of Formula B-1, R$_G$ is (C$_1$-C$_3$) alkylene-NHC(NH)NH$_2$, (C$_1$-C$_3$)alkylene-NHC(NH)(C$_1$-C$_3$)alkyl, (C$_1$-C$_3$)alkylene-S(O)$_2$NH$_2$, or (C$_1$-C$_3$)alkylene-C(O)NH$_2$.

In some embodiments of Formula B-1, R$_G$ is —CH$_2$—NHC(NH)NH$_2$, —CH$_2$—NHC(NH)CH$_3$, —CH$_2$F, —CH$_2$—S(O)$_2$NH$_2$, or —CH$_2$—C(O)NH$_2$.

In some embodiments of Formula B-1, R$_G$ is —CH$_2$—NHC(NH)NH$_2$, —CH$_2$—NHC(NH)CH$_3$, —CH$_2$—S(O)$_2$NH$_2$, or —CH$_2$—C(O)NH$_2$.

In some embodiments of Formula B-1, R$_G$ is —CH$_2$—NHC(NH)NH$_2$.

In some embodiments of Formula B-1, R$_G$ is —CH$_2$—NHC(NH)CH$_3$.

In some embodiments of Formula B-1, R$_G$ is —CH$_2$—S(O)$_2$NH$_2$.

In some embodiments of Formula B-1, R$_G$ is —CH$_2$—C(O)NH$_2$.

In some embodiments, compounds of Formula (B) have Formula Formula B-2:

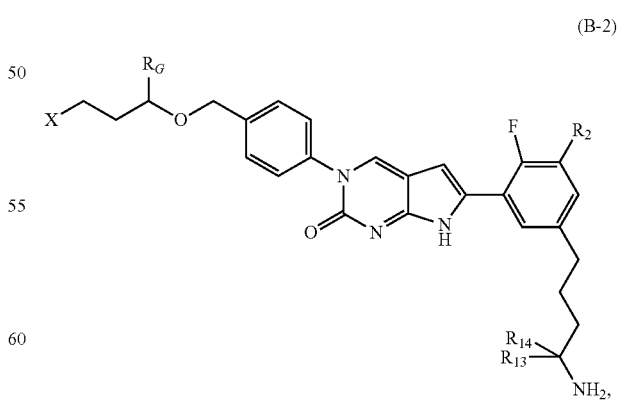

(B-2)

wherein R$_G$, X, R$_2$, R$_{13}$ and R$_{14}$ are as defined herein for Formula (B).

In some embodiments, compounds of Formula (B) have any one of the following Formulae:

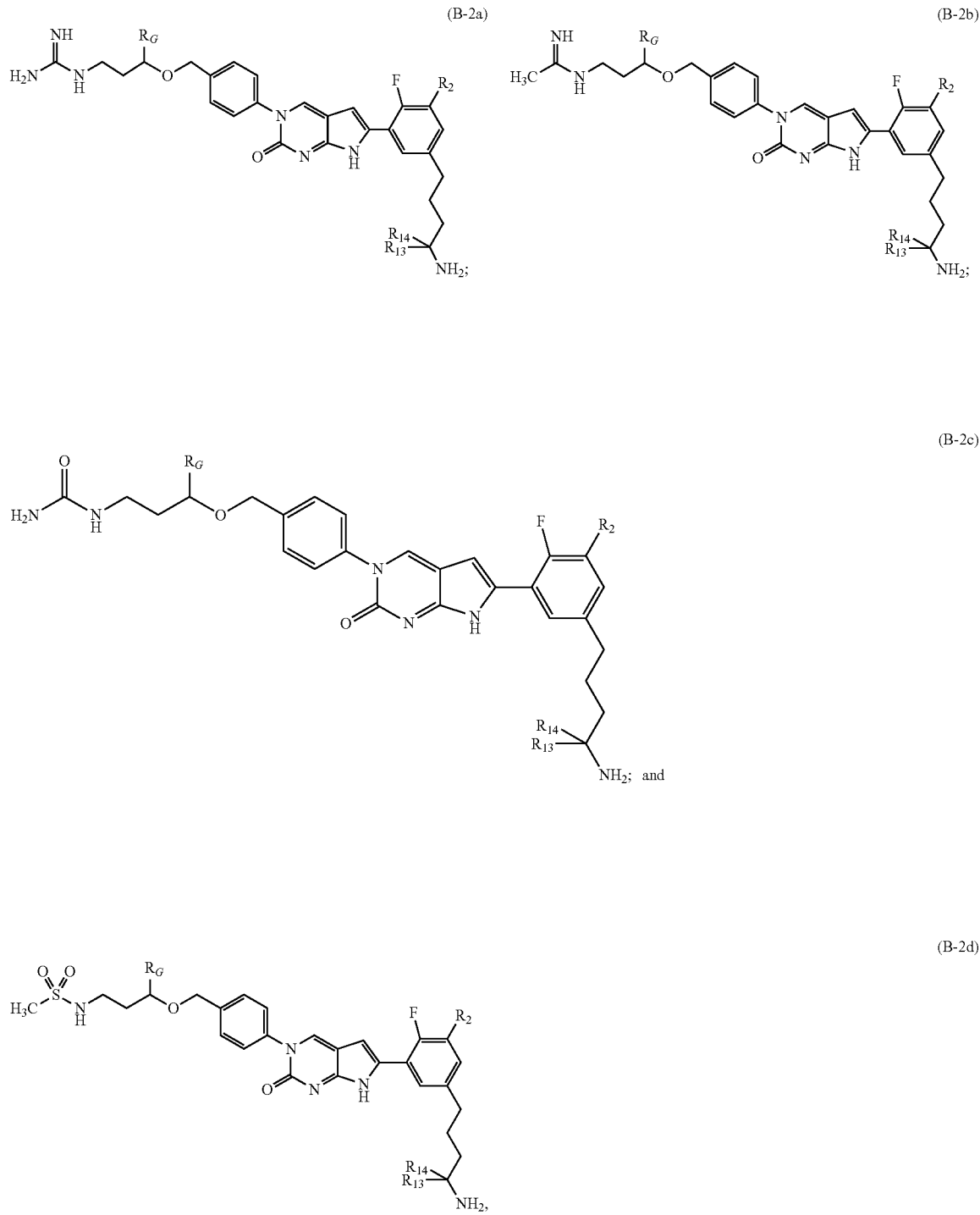

wherein $R_G$, $R_2$, $R_{13}$, and $R_{14}$ are as defined herein for Formula (B).

In some embodiments of Formula B, the compound is selected from any one of compounds 4, 13, 15, 30, 57, 61, 67, and 107 listed in Table 1.

In some embodiments of Formula B, the compound is selected from any one of compounds 59, 64, 66, 68, 71, 72, 132, and 135 listed in Table 1 and compounds 159-178 listed in Table 1a.

In one aspect, the present disclosure provides compound of Formula C:

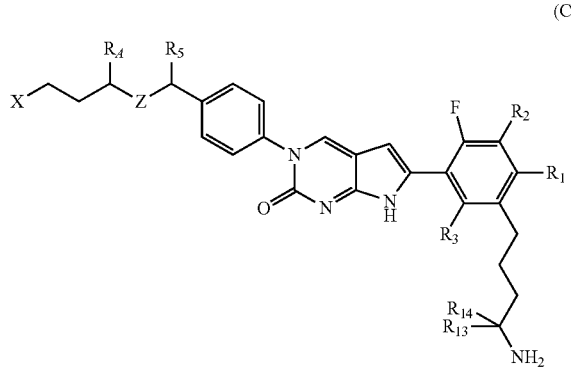

or a tautomer thereof, or a pharmaceutically acceptable salt, or ester of said compound or tautomer,
wherein:
X is —NHC(NH)NH$_2$, —NHC(O)NH$_2$, —NHC(O)(C$_1$-C$_3$)alkyl, or —NHC(NH)(C$_1$-C$_3$)alkyl;
Z is O, CH$_2$ or NR$_{11}$.
R$_1$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN, or —NO$_2$, wherein the (C$_1$-C$_3$)alkyl, (C$_2$-C$_4$)alkenyl, and (C$_1$-C$_3$)alkoxy are optionally substituted with one or more R$_{12}$;
R$_2$ is halogen, (C$_1$-C$_3$)haloalkyl, —S(C$_1$-C$_3$)haloalkyl, or —O(C$_1$-C$_3$)haloalkyl;
R$_3$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN, or —NO$_2$, wherein the (C$_1$-C$_3$)alkyl, (C$_2$-C$_4$)alkenyl, and (C$_1$-C$_3$)alkoxy are optionally substituted with one or more R$_{12}$;
R$_5$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN, or —NO$_2$, wherein the (C$_1$-C$_3$)alkyl, (C$_2$-C$_4$)alkenyl, and (C$_1$-C$_3$)alkoxy are optionally substituted with one or more R$_{12}$;
R$_4$ is heteroaryl, (C$_1$-C$_3$)alkylene-NH-heteroaryl, or (C$_1$-C$_3$)alkylene-heteroaryl, each of which is optionally substituted with at least one R$_{12}$;
R$_{11}$ is H or (C$_1$-C$_3$)alkyl;
each R$_{12}$ is independently selected from halogen, (C$_1$-C$_3$)alkyl, (C$_1$-C$_3$)alkoxy, —OH, —NH$_2$, —NH(C$_1$-C$_3$)alkyl, —N((C$_1$-C$_3$)alkyl)$_2$, and oxo;
R$_{13}$ is H, (C$_1$-C$_3$)alkyl, (C$_2$-C$_4$)alkenyl, (C$_2$-C$_4$)alkynyl, —(C$_3$-C$_5$)cycloalkyl, (C$_1$-C$_3$)alkoxy, (C$_1$-C$_3$)haloalkyl, (C$_1$-C$_3$) hydroxyalkyl, —O(C$_1$-C$_3$)haloalkyl, halogen, CN, or —NO$_2$, wherein the (C$_1$-C$_3$)alkyl, (C$_2$-C$_4$)alkenyl, and (C$_1$-C$_3$)alkoxy are optionally substituted with one or more R$_{12}$; and
R$_{14}$ is H, (C$_1$-C$_3$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, halogen, CN, or —NO$_2$.
In some embodiments of Formula (C), X is —NHC(NH)NH$_2$.
In some embodiments of Formula (C), Z is O or NH.
In some embodiments of Formula (C), Z is O.
In some embodiments of Formula (C), Z is NH.
In some embodiments of Formula (C), R$_1$ is H.
In some embodiments of Formula (C), R$_2$ is halogen.
In some embodiments of Formula (C), R$_2$ is Cl or F.
In some embodiments of Formula (C), R$_2$ is Cl.
In some embodiments of Formula (C), R$_3$ is H.
In some embodiments of Formula (C), R$_5$ is H.
In some embodiments of Formula (C), R$_4$ is (C$_1$-C$_3$)alkylene-NH-heteroaryl, or (C$_1$-C$_3$)alkylene-heteroaryl.
In some embodiments of Formula (C), R$_4$ is (C$_1$-C$_3$)alkylene-NH-heteroaryl.
In some embodiments of Formula (C), R$_4$ is CH$_2$—NH-heteroaryl.
In some embodiments of Formula (C), R$_4$ is (C$_1$-C$_3$)alkylene-heteroaryl.
In some embodiments of Formula (C), R$_4$ is CH$_2$-heteroaryl or CH$_2$CH$_2$-heteroaryl.
In some embodiments of Formula (C), R$_4$ is a group of any one of the following Formulae:

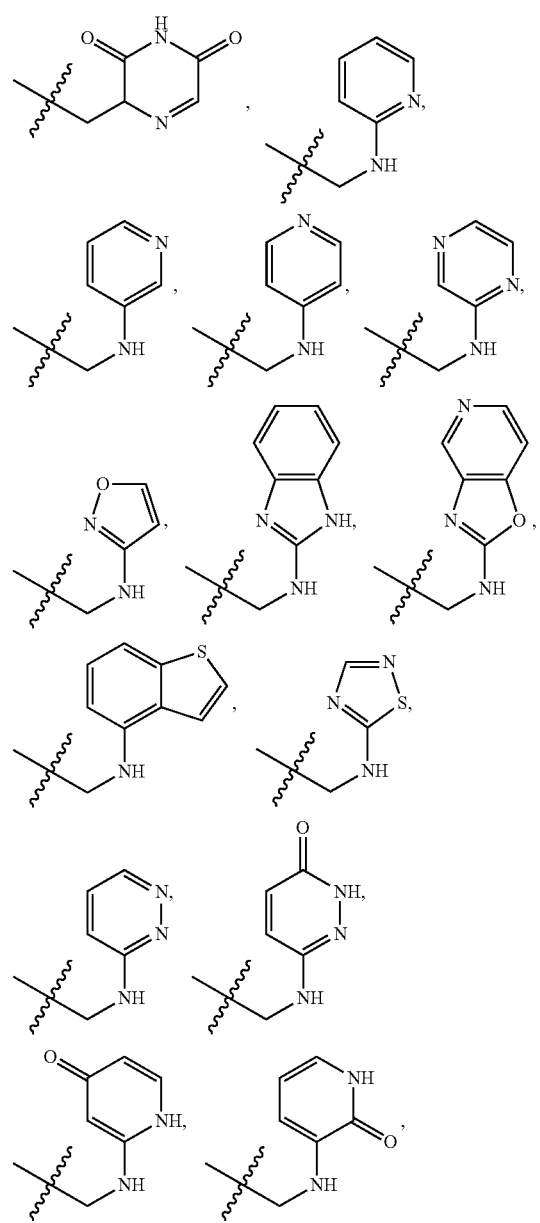

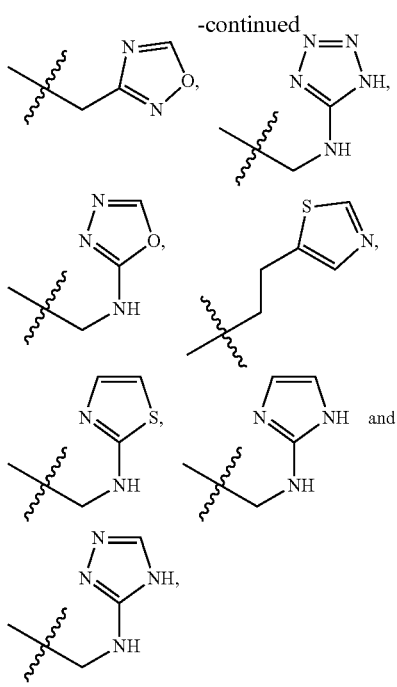

wherein each Formulae is optionally substituted with 1-4 R₁₂.

In some embodiments of Formula (C), $R_{13}$ is $(C_1-C_3)$ alkyl.

In some embodiments of Formula (C), $R_{13}$ is $CH_3$.

In some embodiments of Formula (C), $R_{14}$ is H.

In some embodiments of Formula (C), when Z is NH and X is —NHC(NH)NH₂, then $R_A$ is not a group of Formulae:

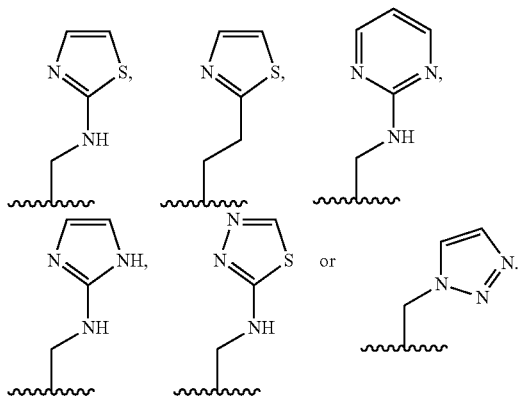

In some embodiments of Formula (C), when Z is O and X is —NHC(NH)NH₂, then $R_A$ is not a group of Formula:

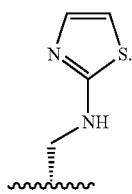

In some embodiments, compounds of Formula (C) have Formula C-1:

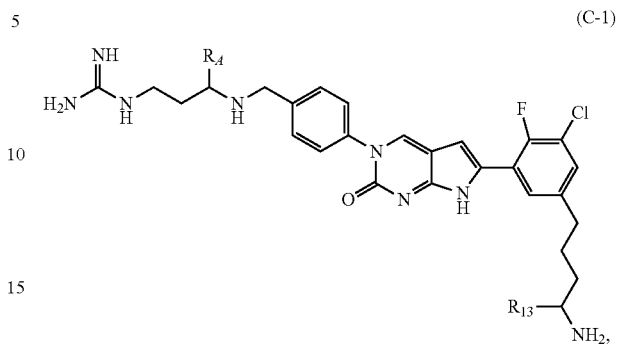

(C-1)

wherein $R_A$ and $R_{13}$ are as defined herein for Formula (C).

In some embodiments, compounds of Formula (C) have Formula C-2:

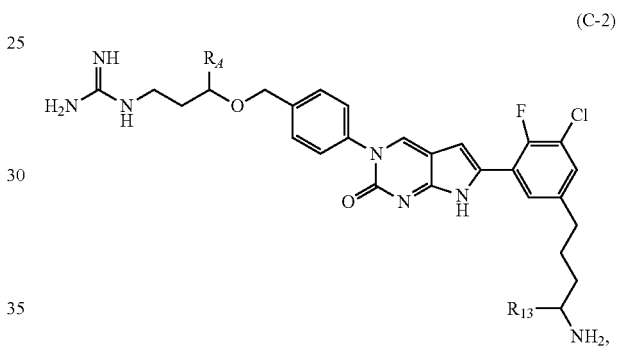

(C-2)

wherein $R_A$ and $R_{13}$ are as defined herein for Formula (C).

In some embodiments of Formula (C), the compound is selected from any one of the compounds 7, 14, 21, 24, 25, 33, 36, 37-40, 45-51, 54-56, 58, 62, 63, 65 and 106 listed in Table 1.

In some embodiments of Formula (C), the compound is selected from any one of the compounds 60, 75 and 76 listed in Table 1.

In some embodiments, the present disclosure relates to a compound having the Formula (Ia):

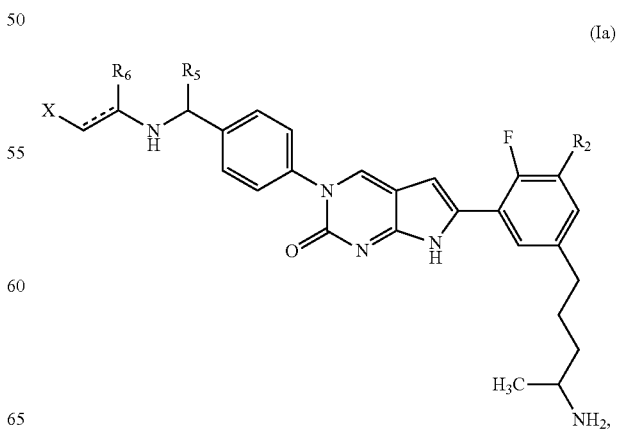

(Ia)

or a tautomer thereof, or a pharmaceutically acceptable salt, ester, or prodrug of said compound or tautomer, wherein:

X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the (C$_1$-C$_4$)alkyl, cycloalkyl, heterocycloalkyl and heteroaryl are optionally substituted with one or more R$_7$;

R$_2$ is —Cl or —OCF$_3$;

R$_5$ is H or —CH$_3$;

R$_6$ is H, (C$_1$-C$_3$)alkyl, (C$_2$-C$_3$)alkenyl, (C$_1$-C$_3$)haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more R$_8$; or R$_5$ and R$_6$ together with the carbon atoms to which they are attached and the Z atom connecting said two carbon atoms, form a (C$_5$-C$_6$)cycloalkyl or a 5- to 6-membered heterocycloalkyl ring containing 1-3 heteroatoms optionally substituted with one or more R$_9$;

at least one of R$_5$ and R$_6$ is not H;

R$_7$ is (C$_1$-C$_3$)alkyl, halogen, oxo, or —NH$_2$;

R$_8$ is (C$_1$-C$_3$)alkyl, (C$_1$-C$_3$)alkoxy, halogen, oxo, —NH$_2$, or —NHR$_{10}$;

each R$_9$ is independently (C$_1$-C$_3$)alkyl, (C$_2$-C$_4$)alkenyl, —NH$_2$, —NH$_2$C(NH)NH$_2$, —NH$_2$C(NH)(C$_1$-C$_3$)alkyl, —CH$_2$heteroaryl, —NHheterocycloalkyl, or —NH heteroaryl, wherein the (C$_1$-C$_3$)alkyl is optionally substituted with one or more substituents independently selected from —OH and —NH$_2$;

R$_{10}$ is CH$_2$ aryl optionally substituted with (C$_1$-C$_3$)alkoxy or halogen;

----- is a single or a double bond;

n is 1 or 2;

p is 0, 1, or 2; and provided that when R$_5$ is methyl, and R$_6$ is H, then X is not —CH$_2$NHC(NH)NH$_2$ or —CH$_2$NH$_2$.

In some embodiments, the present disclosure relates to a compound having the Formula (Ib):

(Ib)

or a tautomer thereof, or a pharmaceutically acceptable salt, ester, or prodrug of said compound or tautomer, wherein:

X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the (C$_1$-C$_4$)alkyl, cycloalkyl, heterocycloalkyl and heteroaryl are optionally substituted with one or more R$_7$;

R$_2$ is —Cl or —OCF$_3$;

R$_5$ is H or —CH$_3$;

R$_6$ is H, (C$_1$-C$_3$)alkyl, (C$_2$-C$_3$)alkenyl, (C$_1$-C$_3$)haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more R$_8$; or R$_5$ and R$_6$ together with the carbon atoms to which they are attached and the Z atom connecting said two carbon atoms, form a (C$_5$-C$_6$)cycloalkyl or a 5- to 6-membered heterocycloalkyl ring containing 1-3 heteroatoms optionally substituted with one or more R$_9$;

at least one of R$_5$ and R$_6$ is not H;

R$_7$ is (C$_1$-C$_3$)alkyl, halogen, oxo, or —NH$_2$;

R$_8$ is (C$_1$-C$_3$)alkyl, (C$_1$-C$_3$)alkoxy, halogen, oxo, —NH$_2$, or —NHR$_{10}$;

each R$_9$ is independently (C$_1$-C$_3$)alkyl, (C$_2$-C$_4$)alkenyl, —NH$_2$, —NH$_2$C(NH)NH$_2$, —NH$_2$C(NH)(C$_1$-C$_3$)alkyl, —CH$_2$heteroaryl, —NHheterocycloalkyl, or —NH heteroaryl, wherein the (C$_1$-C$_3$)alkyl is optionally substituted with one or more substituents independently selected from —OH and —NH$_2$;

R$_{10}$ is —CH$_2$aryl optionally substituted with (C$_1$-C$_3$) alkoxy or halogen;

----- is a single or a double bond;

n is 1 or 2; and p is 0, 1, or 2.

In some embodiments, the present disclosure relates to a compound having the Formula (Ic):

(Ic)

or a tautomer thereof, or a pharmaceutically acceptable salt, ester, or prodrug of said compound or tautomer, wherein:

X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH₂NHC(NH)(C₃-C₇)cycloalkyl, —CH₂NHC(NH)heteroaryl, heteroaryl, —CH₂heteroaryl, —NHCH₂heteroaryl, —CH₂NHheteroaryl, —CH(OH)heteroaryl, —CH₂heterocycloalkyl, —NHCH₂heterocycloalkyl, or —CH₂NHheterocycloalkyl, wherein the (C₁-C₄)alkyl, cycloalkyl, heterocycloalkyl and heteroaryl are optionally substituted with one or more R₇;

R₂ is —Cl or —OCF₃;

R₅ is H or —CH₃;

R₆ is H, (C₁-C₃)alkyl, (C₂-C₃)alkenyl, (C₁-C₃)haloalkyl, —CH₂NHC(NH)NH₂, —(CH₂)ₙOH, —CH₂S(O)ₚNH₂, —CH₂NH(C₁-C₃)alkyl, —CH₂C(O)NH₂, —(CH₂)ₙNH₂, —CH₂heterocycloalkyl, —CH₂NH₂heterocycloalkyl, —(CH₂)ₙheteroaryl, or —CH₂NH₂heteroaryl, wherein the heteroaryl and heterocycloalkyl is optionally substituted with one or more R₈; or R₅ and R₆ together with the carbon atoms to which they are attached and the Z atom connecting said two carbon atoms, form a (C₅-C₆)cycloalkyl or a 5- to 6-membered heterocycloalkyl ring containing 1-3 heteroatoms optionally substituted with one or more R₉;

at least one of R₅ and R₆ is not H;

R₇ is (C₁-C₃)alkyl, halogen, oxo, or —NH₂;

R₈ is (C₁-C₃)alkyl, (C₁-C₃)alkoxy, halogen, oxo, —NH₂, or —NHR₁₀;

each R₉ is independently (C₁-C₃)alkyl, (C₂-C₄)alkenyl, —NH₂, —NH₂C(NH)NH₂, —NH₂C(NH)(C₁-C₃)alkyl, or —NH heteroaryl, wherein the (C₁-C₃)alkyl is optionally substituted with one or more substituents independently selected from —OH and —NH₂;

R₁₀ is —CH₂aryl optionally substituted with (C₁-C₃)alkoxy or halogen;

---- is a single or a double bond;

n is 1 or 2; and p is 0, 1, or 2.

In some embodiments, the present disclosure relates to a compound having the Formula (Id):

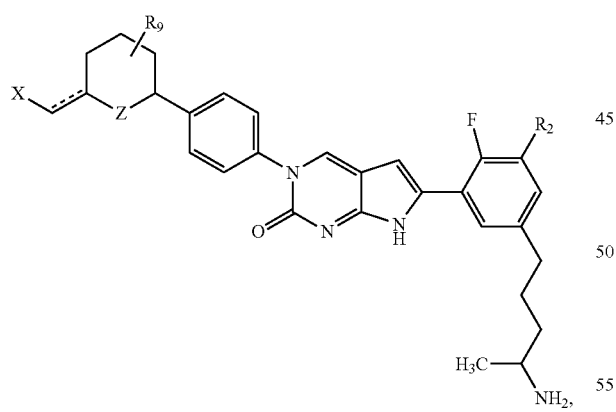

(Id)

or a tautomer thereof, or a pharmaceutically acceptable salt, ester, or prodrug of said compound or tautomer, wherein:

X is —NHC(NH)NH₂, —CH₂NH₂, —CH₂NHC(NH)NH₂, —CH₂NHCH₂C(O)CH₃, —CH₂NHC(NH)(C₁-C₄)alkyl, —CH₂NHC(NH)(C₃-C₇)cycloalkyl, —CH₂NHC(NH)heteroaryl, heteroaryl, —CH₂heteroaryl, —NHCH₂heteroaryl, —CH₂NHheteroaryl, —CH(OH)heteroaryl, —CH₂heterocycloalkyl, —NHCH₂heterocycloalkyl, or —CH₂NHheterocycloalkyl, wherein the (C₁-C₄)alkyl, cycloalkyl, heterocycloalkyl and heteroaryl are optionally substituted with one or more R₇;

Z is O, CH₂, or NH;

R₂ is —Cl or —OCF₃;

R₇ is (C₁-C₃)alkyl, halogen, oxo, or —NH₂;

R₉ is (C₁-C₃)alkyl, (C₂-C₄)alkenyl, —NH₂, —NH₂C(NH)NH₂, —NH₂C(NH)(C₁-C₃)alkyl, —CH₂heteroaryl, —NHheterocycloalkyl, or —NH heteroaryl, wherein the (C₁-C₃)alkyl is optionally substituted with one or more substituents independently selected from —OH and —NH₂; and ---- is a single or a double bond.

In some embodiments, the present disclosure relates to a compound having the Formula (Ie):

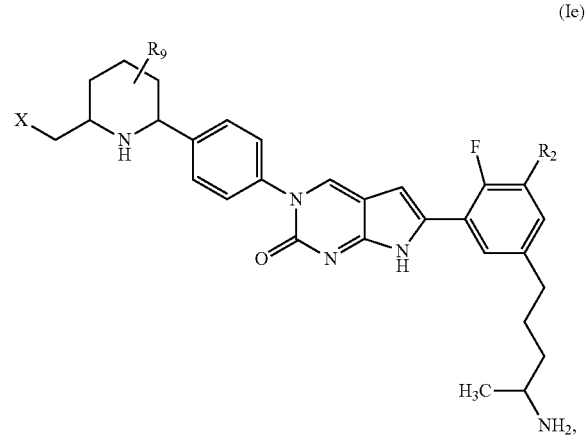

(Ie)

or a tautomer thereof, or a pharmaceutically acceptable salt, ester, or prodrug of said compound or tautomer, wherein:

X is —CH₂NHCH₂C(O)CH₃, —CH₂NHC(NH)(C₂-C₄)alkyl, —CH₂NHC(NH)(C₃-C₇)cycloalkyl, —CH₂NHC(NH)heteroaryl, —CH(OH)heteroaryl, -continued

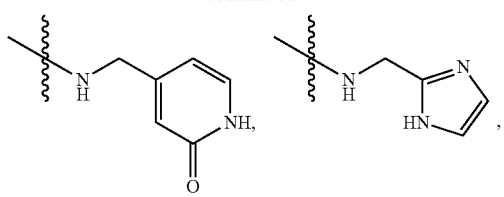

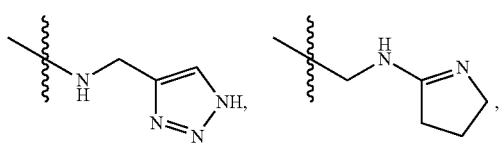

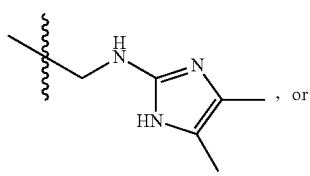

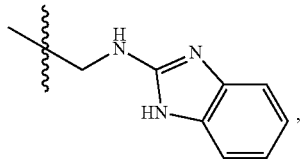

wherein the $(C_1-C_4)$alkyl, cycloalkyl, heterocycloalkyl, and heteroaryl are optionally substituted with one or more $R_7$;

$R_2$ is —Cl or —OCF$_3$;

$R_7$ is $(C_1-C_3)$alkyl, halogen, oxo, or —NH$_2$; and $R_9$ is $(C_1-C_3)$alkyl, $(C_2-C_4)$alkenyl, —NH$_2$, —NH$_2$C(NH)NH$_2$, —NH$_2$C(NH)(C$_1$-C$_3$)alkyl, —CH$_2$heteroaryl, —NHheterocycloalkyl, or —NH heteroaryl, wherein the $(C_1-C_3)$alkyl is optionally substituted with one or more substituents independently selected from —OH and —NH$_2$.

In some embodiments, the present disclosure relates to a compound having any one of the Formulae (If) or (Ig):

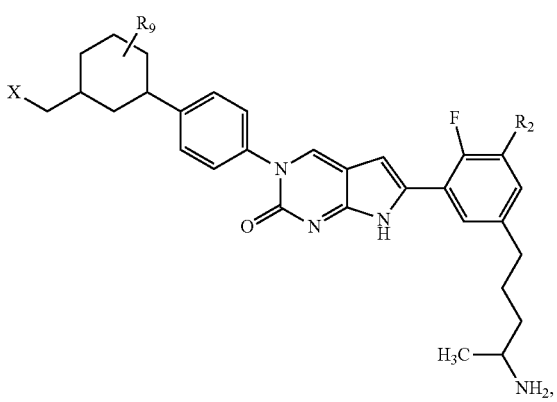

(Ig)

or a tautomer thereof, or a pharmaceutically acceptable salt, ester, or prodrug of said compound or tautomer, wherein:

X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the $(C_1-C_4)$alkyl, cycloalkyl, heterocycloalkyl and heteroaryl are optionally substituted with one or more $R_7$;

$R_2$ is —Cl or —OCF$_3$;

$R_7$ is $(C_1-C_3)$alkyl, halogen, oxo, or —NH$_2$; and $R_9$ is $(C_1-C_3)$alkyl, $(C_2-C_4)$alkenyl, —NH$_2$, —NH$_2$C(NH)NH$_2$, —NH$_2$C(NH)(C$_1$-C$_3$)alkyl, —CH$_2$heteroaryl, —NHheterocycloalkyl, or —NH heteroaryl, wherein the $(C_1-C_3)$alkyl is optionally substituted with one or more substituents independently selected from —OH and —NH$_2$.

In some embodiments, the present disclosure relates to a compound having any one of the Formulae (Ih) or (Ii):

(If)

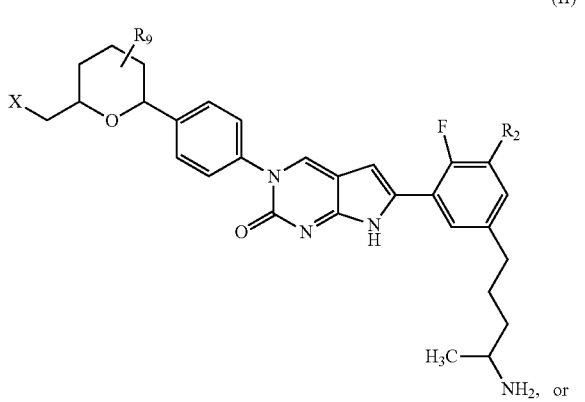

(Ih)

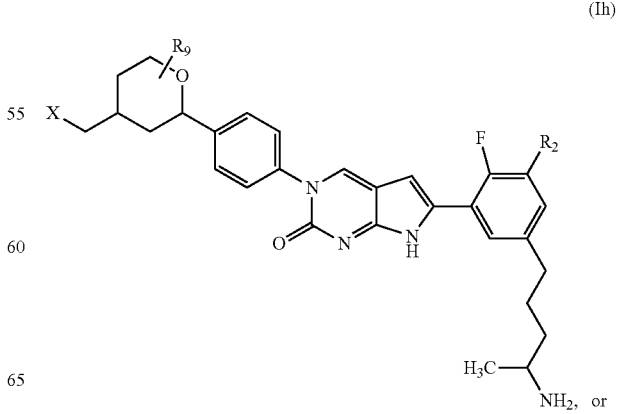

or

-continued (Ii)

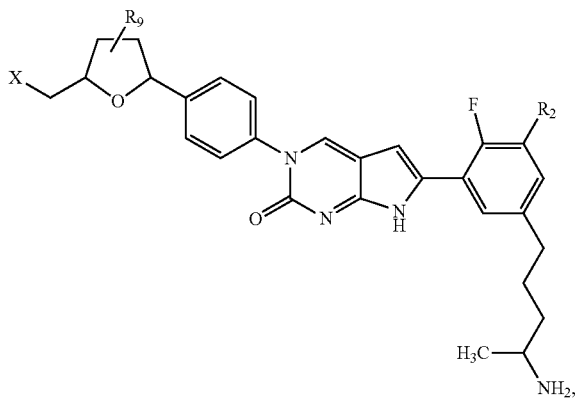

or a tautomer thereof, or a pharmaceutically acceptable salt, ester, or prodrug of said compound or tautomer, wherein:

X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, or —CH$_2$NHheteroaryl, wherein the (C$_1$-C$_4$)alkyl, cycloalkyl, heterocycloalkyl and heteroaryl are optionally substituted with one or more R$_7$;

R$_2$ is —Cl or —OCF$_3$;

R$_7$ is (C$_1$-C$_3$)alkyl, halogen, oxo, or —NH$_2$; and

R$_9$ is (C$_1$-C$_3$)alkyl, (C$_2$-C$_4$)alkenyl, —NH$_2$, —NH$_2$C(NH)NH$_2$, —NH$_2$C(NH)(C$_1$-C$_3$)alkyl, —CH$_2$heteroaryl, —NHheterocycloalkyl, or —NH heteroaryl, wherein the (C$_1$-C$_3$)alkyl is optionally substituted with one or more substituents independently selected from —OH and —NH$_2$.

In some embodiments, the present disclosure relates to a compound having the Formula (I):

(II)

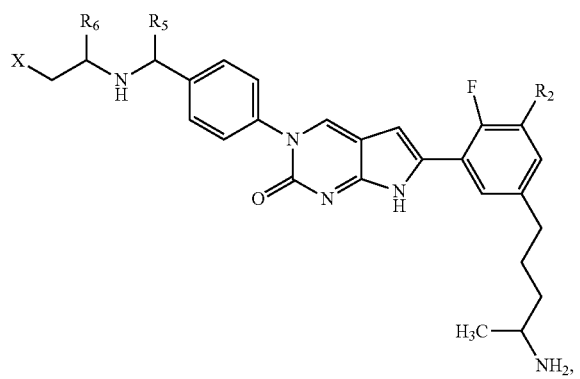

or a tautomer thereof, or a pharmaceutically acceptable salt, ester, or prodrug of said compound or tautomer, wherein:

X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —NHCH$_2$heterocycloalkyl, or —CH$_2$NHheterocycloalkyl, wherein the (C$_1$-C$_4$)alkyl, cycloalkyl, heterocycloalkyl and heteroaryl are optionally substituted with one or more R$_7$;

R$_2$ is —Cl or —OCF$_3$;

R$_5$ is H or —CH$_3$;

R$_6$ is H, (C$_1$-C$_3$)alkyl, (C$_2$-C$_3$)alkenyl, (C$_1$-C$_3$)haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more R$_8$; or R$_5$ and R$_6$ together with the carbon atoms to which they are attached and the Z atom connecting said two carbon atoms, form a (C$_5$-C$_6$)cycloalkyl or a 5- to 6-membered heterocycloalkyl ring optionally substituted with one or more R$_9$;

at least one of R$_5$ and R$_6$ is not H;

R$_7$ is (C$_1$-C$_3$)alkyl, halogen, oxo, or —NH$_2$;

R$_8$ is (C$_1$-C$_3$)alkyl, (C$_1$-C$_3$)alkoxy, halogen, oxo, —NH$_2$, or —NHR$_{10}$;

each R$_9$ is independently (C$_1$-C$_3$)alkyl, (C$_2$-C$_4$)alkenyl, —NH$_2$, —NH$_2$C(NH)NH$_2$, —NH$_2$C(NH)(C$_1$-C$_3$)alkyl, —CH$_2$heteroaryl, —NHheterocycloalkyl, or —NH heteroaryl, wherein the (C$_1$-C$_3$)alkyl is optionally substituted with one or more substituents independently selected from —OH and —NH$_2$;

R$_{10}$ is —CH$_2$aryl optionally substituted with (C$_1$-C$_3$) alkoxy or halogen;

n is 1 or 2;

p is 0, 1, or 2; and provided that when R$_5$ is methyl, and R$_6$ is H, then X is not —CH$_2$NHC(NH)NH$_2$ or —CH$_2$NH$_2$.

In some embodiments, the present disclosure relates to a compound having the Formula (Im):

(Im)

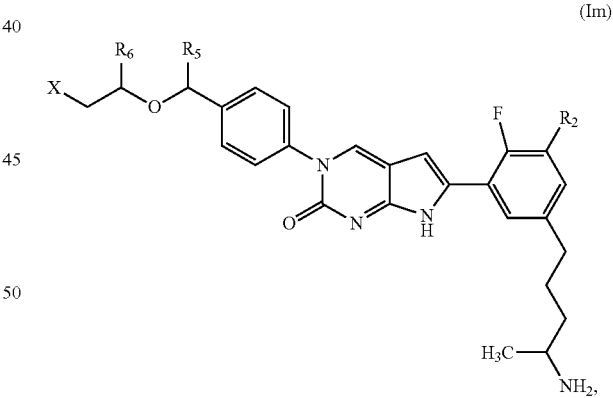

or a tautomer thereof, or a pharmaceutically acceptable salt, ester, or prodrug of said compound or tautomer, wherein:

X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the (C$_1$-C$_4$)alkyl, cycloalkyl, heterocycloalkyl and heteroaryl are optionally substituted with one or more R$_7$;

$R_2$ is —Cl or —OCF$_3$;

$R_5$ is H or —CH$_3$;

$R_6$ is H, (C$_1$-C$_3$)alkyl, (C$_2$-C$_3$)alkenyl, (C$_1$-C$_3$)haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more $R_8$; or $R_5$ and $R_6$ together with the carbon atoms to which they are attached and the Z atom connecting said two carbon atoms, form a (C$_5$-C$_6$)cycloalkyl or a 5- to 6-membered heterocycloalkyl ring optionally substituted with one or more $R_9$;

at least one of $R_5$ and $R_6$ is not H;

$R_7$ is (C$_1$-C$_3$)alkyl, halogen, oxo, or —NH$_2$;

$R_8$ is (C$_1$-C$_3$)alkyl, (C$_1$-C$_3$)alkoxy, halogen, oxo, —NH$_2$, or —NHR$_{10}$;

each $R_9$ is independently (C$_1$-C$_3$)alkyl, (C$_2$-C$_4$)alkenyl, —NH$_2$, —NH$_2$C(NH)NH$_2$, —NH$_2$C(NH)(C$_1$-C$_3$)alkyl, —CH$_2$heteroaryl, —NHheterocycloalkyl, or —NH heteroaryl, wherein the (C$_1$-C$_3$)alkyl is optionally substituted with one or more substituents independently selected from —OH and —NH$_2$;

$R_{10}$ is —CH$_2$aryl optionally substituted with (C$_1$-C$_3$) alkoxy or halogen;

n is 1 or 2; and p is 0, 1, or 2.

In some embodiments, the present disclosure relates to a compound having the Formula (In):

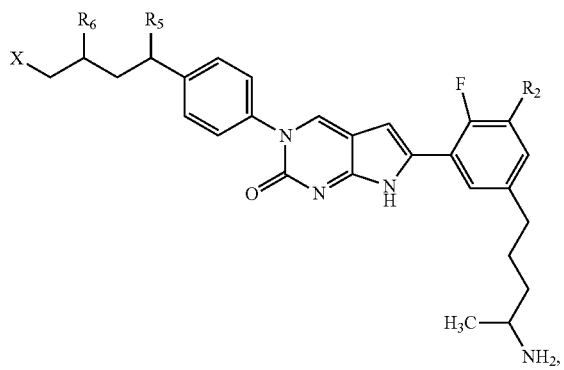

(In)

or a tautomer thereof, or a pharmaceutically acceptable salt, ester, or prodrug of said compound or tautomer, wherein:

X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the (C$_1$-C$_4$)alkyl, cycloalkyl, heterocycloalkyl and heteroaryl are optionally substituted with one or more $R_7$;

$R_2$ is —Cl or —OCF$_3$;

$R_5$ is H or —CH$_3$;

$R_6$ is H, (C$_1$-C$_3$)alkyl, (C$_2$-C$_3$)alkenyl, (C$_1$-C$_3$)haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more $R_8$; or $R_5$ and $R_6$ together with the carbon atoms to which they are attached and the Z atom connecting said two carbon atoms, form a (C$_5$-C$_6$)cycloalkyl or a 5- to 6-membered heterocycloalkyl ring optionally substituted with one or more $R_9$;

at least one of $R_5$ and $R_6$ is not H;

$R_7$ is (C$_1$-C$_3$)alkyl, halogen, oxo, or —NH$_2$;

$R_8$ is (C$_1$-C$_3$)alkyl, (C$_1$-C$_3$)alkoxy, halogen, oxo, —NH$_2$, or —NHR$_{10}$;

each $R_9$ is independently (C$_1$-C$_3$)alkyl, (C$_2$-C$_4$)alkenyl, —NH$_2$, —NH$_2$C(NH)NH$_2$, —NH$_2$C(NH)(C$_1$-C$_3$)alkyl, —CH$_2$heteroaryl, —NHheterocycloalkyl, or —NH heteroaryl, wherein the (C$_1$-C$_3$)alkyl is optionally substituted with one or more substituents independently selected from —OH and —NH$_2$;

$R_{10}$ is —CH$_2$aryl optionally substituted with (C$_1$-C$_3$) alkoxy or halogen;

n is 1 or 2; and p is 0, 1, or 2.

In another aspect, the disclosure features a compound of Formula (II):

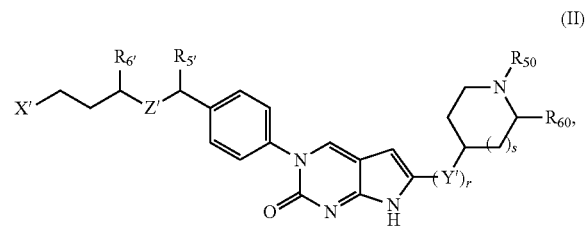

(II)

or or a tautomer thereof, or a pharmaceutically acceptable salt, or ester of said compound or tautomer, wherein:

X' is —NHC(NH)NH$_2$, —NHC(NH)CH$_3$, —NHheteroaryl, or —heteroaryl;

each Y' is independently CH$_2$ or NH;

Z' is O, NH, or CH$_2$;

$R_{5'}$ is H or —CH$_3$;

$R_{6'}$ is (C$_1$-C$_3$)alkyl, (C$_2$-C$_3$)alkenyl, or (C$_1$-C$_3$)haloalkyl, wherein the alkyl is optionally substituted with one or more substituents independently selected from halogen, —NHC(NH)NH$_2$, and —NHheteroaryl; or $R_{5'}$ and $R_{6'}$ together with the carbon atoms to which they are attached and the Z atom connecting said two carbon atoms, form a 6-membered heterocycloalkyl ring containing 1-3 heteroatoms optionally substituted with one or more $R_{101}$; or $R_{50}$ is H or —C(NH)NH$_2$;

$R_{60}$ is H or (C$_1$-C$_5$)alkyl, wherein the alkyl optionally substituted with one or more substituents independently selected from (C$_1$-C$_2$)alkyl, (C$_2$-C$_4$)alkenyl, (C$_1$-C$_2$)haloalkyl, (C$_1$-C$_2$) hydroxyalkyl, and —NH$_2$;

each $R_{101}$ is independently selected from (C$_1$-C$_3$)alkyl, (C$_2$-C$_3$)alkenyl, halogen, —NH$_2$, and —NHheteroaryl wherein the alkyl is optionally substituted with one or more substituents independently selected from —NH$_2$ and —NHC(NH)NH$_2$;

r is 0, 1, 2, or 3; and s is 0 or 1.

In some embodiments, the present disclosure relates to a compound having the Formula (IIa):

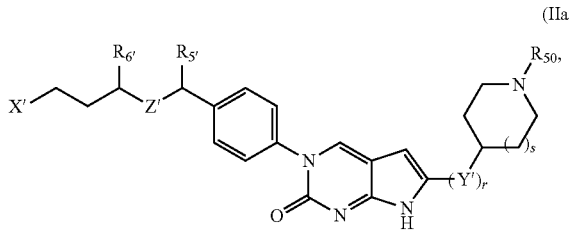

(IIa)

or or a tautomer thereof, or a pharmaceutically acceptable salt, or ester of said compound or tautomer, wherein:

X' is —NHC(NH)NH$_2$, —NHC(NH)CH$_3$, —NHheteroaryl, or —heteroaryl;

each Y' is independently CH$_2$ or NH;

Z' is O, NH, or CH$_2$;

R$_{5'}$ is H or —CH$_3$;

R$_{6'}$ is (C$_1$-C$_3$)alkyl, (C$_2$-C$_3$)alkenyl, or (C$_1$-C$_3$)haloalkyl, wherein the alkyl is optionally substituted with one or more substituents independently selected from halogen, —NHC(NH)NH$_2$, and —NHheteroaryl; or R$_{5'}$ and R$_{6'}$ together with the carbon atoms to which they are attached and the Z atom connecting said two carbon atoms, form a 6-membered heterocycloalkyl ring optionally substituted with one or more R$_{101}$; or R$_{50}$ is H or —C(NH)NH$_2$;

each R$_{101}$ is independently selected from (C$_1$-C$_3$)alkyl, (C$_2$-C$_3$)alkenyl, halogen, —NH$_2$, and —NHheteroaryl wherein the alkyl is optionally substituted with one or more substituents independently selected from —NH$_2$ and —NHC(NH)NH$_2$;

r is 0, 1, 2, or 3; and s is 0 or 1.

In some embodiments, the present disclosure relates to a compound having the Formula (IIb):

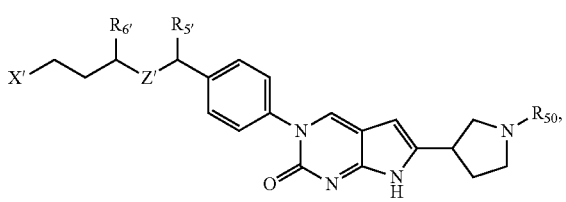

(IIb)

or or a tautomer thereof, or a pharmaceutically acceptable salt, or ester of said compound or tautomer, wherein:

X' is —NHC(NH)NH$_2$, —NHC(NH)CH$_3$, —NHheteroaryl, or —heteroaryl;

Z' is O, NH, or CH$_2$;

R$_{5'}$ is H or —CH$_3$;

R$_{6'}$ is (C$_1$-C$_3$)alkyl, (C$_2$-C$_3$)alkenyl, or (C$_1$-C$_3$)haloalkyl, wherein the alkyl is optionally substituted with one or more substituents independently selected from halogen, —NHC(NH)NH$_2$, and —NHheteroaryl; or R$_{5'}$ and R$_{6'}$ together with the carbon atoms to which they are attached and the Z atom connecting said two carbon atoms, form a 6-membered heterocycloalkyl ring optionally substituted with one or more R$_{101}$; or R$_{50}$ is H or —C(NH)NH$_2$; and each R$_{101}$ is independently selected from (C$_1$-C$_3$)alkyl, (C$_2$-C$_3$)alkenyl, halogen, —NH$_2$, and —NHheteroaryl wherein the alkyl is optionally substituted with one or more substituents independently selected from —NH$_2$ and —NHC(NH)NH$_2$.

In some embodiments, the present disclosure relates to a compound having the Formula (IIc):

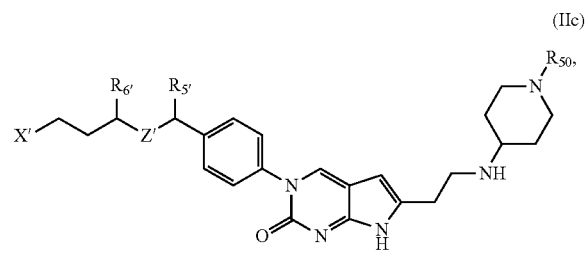

(IIc)

or or a tautomer thereof, or a pharmaceutically acceptable salt, or ester of said compound or tautomer, wherein:

X' is —NHC(NH)NH$_2$, —NHC(NH)CH$_3$, —NHheteroaryl, or —heteroaryl;

Z' is O, NH, or CH$_2$;

R$_{5'}$ is H or —CH$_3$;

R$_{6'}$ is (C$_1$-C$_3$)alkyl, (C$_2$-C$_3$)alkenyl, or (C$_1$-C$_3$)haloalkyl, wherein the alkyl is optionally substituted with one or more substituents independently selected from halogen, —NHC(NH)NH$_2$, and —NHheteroaryl; or R$_{5'}$ and R$_{6'}$ together with the carbon atoms to which they are attached and the Z atom connecting said two carbon atoms, form a 6-membered heterocycloalkyl ring optionally substituted with one or more R$_{101}$; or R$_{50}$ is H or —C(NH)NH$_2$; and each R$_{101}$ is independently selected from (C$_1$-C$_3$)alkyl, (C$_2$-C$_3$)alkenyl, halogen, —NH$_2$, and —NHheteroaryl wherein the alkyl is optionally substituted with one or more substituents independently selected from —NH$_2$ and —NHC(NH)NH$_2$.

In some embodiments, the present disclosure relates to a compound having the Formula (IId):

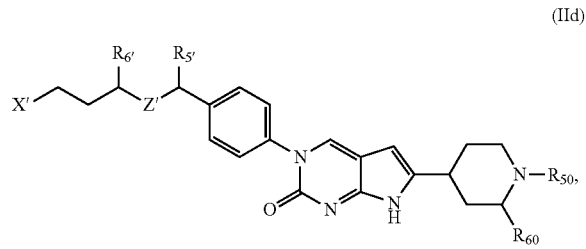

(IId)

or or a tautomer thereof, or a pharmaceutically acceptable salt, or ester of said compound or tautomer, wherein:

X' is —NHC(NH)NH$_2$, —NHC(NH)CH$_3$, —NHheteroaryl, or —heteroaryl;

Z is O, NH, or CH$_2$;

R$_{5'}$ is H or —CH$_3$;

$R_{6'}$ is $(C_1-C_3)$alkyl, $(C_2-C_3)$alkenyl, or $(C_1-C_3)$haloalkyl, wherein the alkyl is optionally substituted with one or more substituents independently selected from halogen, —NHC(NH)NH$_2$, and —NHheteroaryl; or $R_{5'}$ and $R_{6'}$ together with the carbon atoms to which they are attached and the Z atom connecting said two carbon atoms, form a 6-membered heterocycloalkyl ring optionally substituted with one or more $R_{101}$; or $R_{50}$ is H or —C(NH)NH$_2$;

$R_{60}$ is H or $(C_1-C_5)$alkyl, wherein the alkyl optionally substituted with one or more substituents independently selected from $(C_1-C_2)$alkyl, $(C_2-C_4)$alkenyl, $(C_1-C_2)$haloalkyl, $(C_1-C_2)$ hydroxyalkyl, and —NH$_2$; and each $R_{101}$ is independently selected from $(C_1-C_3)$alkyl, $(C_2-C_3)$alkenyl, halogen, —NH$_2$, and —NHheteroaryl wherein the alkyl is optionally substituted with one or more substituents independently selected from —NH$_2$ and —NHC(NH)NH$_2$.

In some embodiments, the present disclosure relates to a compound having the Formulae (IIe) or (IIf):

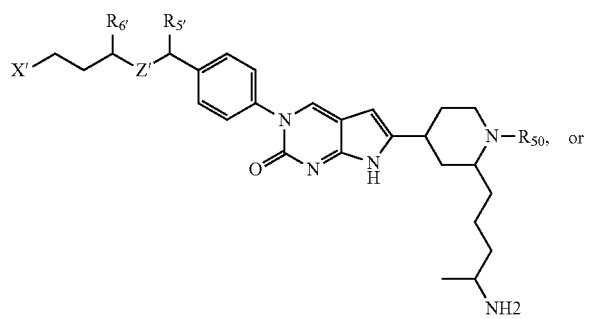

(IIe)

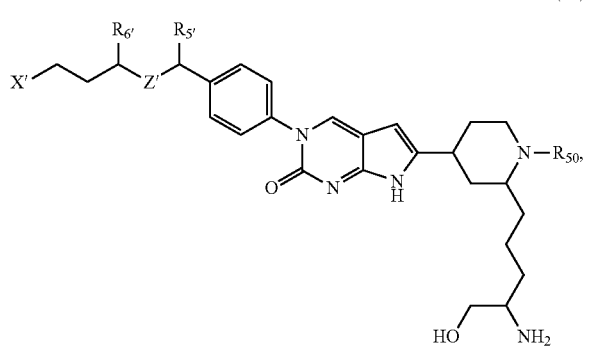

(IIf)

or a tautomer thereof, or a pharmaceutically acceptable salt, or ester of said compound or tautomer, wherein:

X' is —NHC(NH)NH$_2$, —NHC(NH)CH$_3$, —NHheteroaryl, or —heteroaryl;

Z' is O, NH, or CH$_2$;

$R_{5'}$ is H or —CH$_3$;

$R_{6'}$ is $(C_1-C_3)$alkyl, $(C_2-C_3)$alkenyl, or $(C_1-C_3)$haloalkyl, wherein the alkyl is optionally substituted with one or more substituents independently selected from halogen, —NHC(NH)NH$_2$, and —NHheteroaryl; or $R_{5'}$ and $R_{6'}$ together with the carbon atoms to which they are attached and the Z atom connecting said two carbon atoms, form a 6-membered heterocycloalkyl ring optionally substituted with one or more $R_{101}$; or $R_{50}$ is H or —C(NH)NH$_2$; and each $R_{101}$ is independently selected from $(C_1-C_3)$alkyl, $(C_2-C_3)$alkenyl, halogen, —NH$_2$, and —NHheteroaryl wherein the alkyl is optionally substituted with one or more substituents independently selected from —NH$_2$ and —NHC(NH)NH$_2$.

In one aspect, the present disclosure provides a compound of Formula:

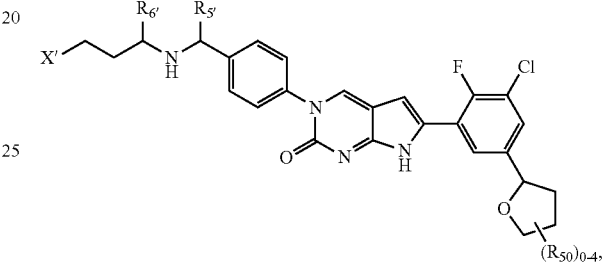

(II-g2)

wherein X', $R_{6'}$, $R_{5'}$, and $R_{80}$ are as described herein for Formula II.

In one aspect, the present disclosure provides a compound of Formula:

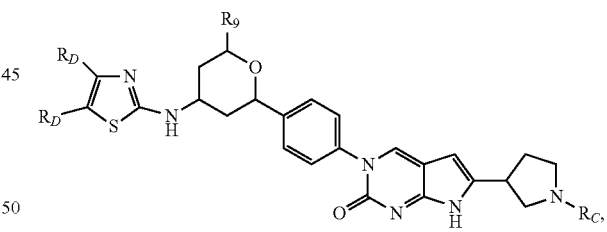

(XIa)

wherein $R_9$ is $(C_1-C_3)$alkyl, $(C_2-C_4)$alkenyl, —NH$_2$, —N$((C_1-C_3)$alkyl$)_2$; —C(=NH)—$(C_1-C_3)$alkyl; —C(=NH)(NH$_2$); $(C_1-C_3)$ hydroxyalkyl; $(C_1-C_3)$alkylene-NH$_2$C(=NH)NH$_2$, —NH$_2$C(=NH)NH$_2$, or —NH$_2$C(=NH)$(C_1-C_3)$alkyl;

$R_C$ is H, $(C_1-C_7)$alkyl, $(C_2-C_4)$alkenyl, $(C_2-C_4)$aminoalkyl, $(C_1-C_7)$haloalkyl, $(C_1-C_2)$ hydroxyalkyl, —NH$_2$, —CH$_2$NH$_2$, or —C(=NH)NH$_2$;

$R_D$ is H, $(C_1-C_7)$alkyl, $(C_2-C_4)$alkenyl, $(C_2-C_4)$aminoalkyl, $(C_1-C_7)$haloalkyl, $(C_1-C_2)$ hydroxyalkyl, —NH$_2$, —CH$_2$NH$_2$, or —C(=NH)NH$_2$;

In one aspect, the present disclosure provides a compound of Formula:

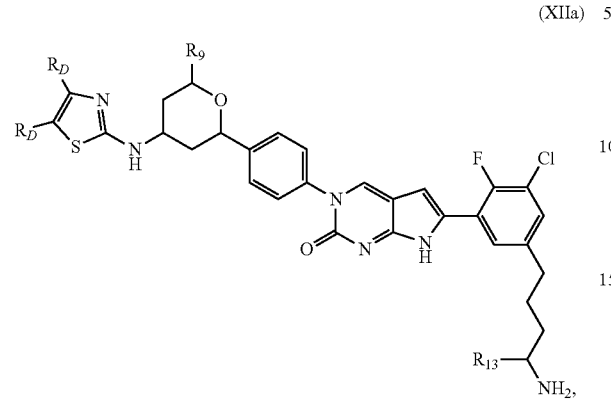
(XIIa)

wherein

R$_9$ is (C$_1$-C$_3$)alkyl, (C$_2$-C$_4$)alkenyl, —NH$_2$, —N((C$_1$-C$_3$) alkyl)$_2$; —C(=NH)—(C$_1$-C$_3$)alkyl; —C(=NH)(NH$_2$); (C$_1$-C$_3$) hydroxyalkyl; (C$_1$-C$_3$)alkylene-NH$_2$C(=NH)NH$_2$, —NH$_2$C(=NH)NH$_2$, or —NH$_2$C(=NH)(C$_1$-C$_3$)alkyl;

R$_D$ is H, (C$_1$-C$_7$)alkyl, (C$_2$-C$_4$)alkenyl, (C$_2$-C$_4$)aminoalkyl, (C$_1$-C$_7$)haloalkyl, (C$_1$-C$_2$) hydroxyalkyl, —NH$_2$, —CH$_2$NH$_2$, or —C(=NH)NH$_2$;

R$_{13}$ is selected from (C$_1$-C$_3$)alkyl, (C$_1$-C$_4$)haloalkyl, and (C$_1$-C$_4$) hydroxyalkyl.

In another aspect, the disclosure features a compound of Formula (III):

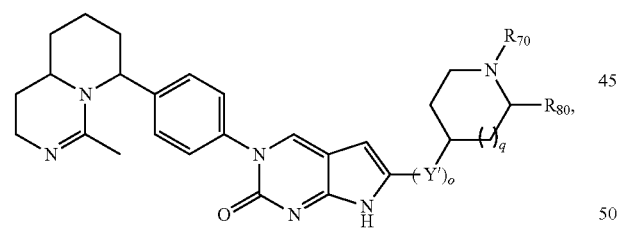
(III)

or a tautomer thereof, or a pharmaceutically acceptable salt, or ester of said compound or tautomer, wherein:

each Y' is independently CH$_2$ or NH$_2$;

R$_{70}$ is H or —C(NH)NH$_2$;

R$_{80}$ is H or (C$_1$-C$_5$)alkyl, wherein the alkyl optionally substituted with one or more substituents independently selected from (C$_1$-C$_2$)alkyl, (C$_2$-C$_4$)alkenyl, (C$_1$-C$_2$)haloalkyl, (C$_1$-C$_2$) hydroxyalkyl, and —NH$_2$;

o is 0, 1, 2, or 3; and q is 0 or 1.

In some embodiments, the present disclosure relates to a compound having the Formula (IIIa):

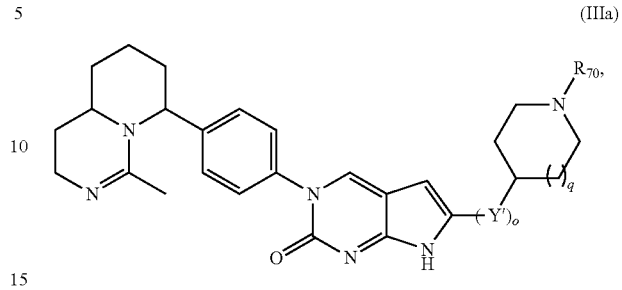
(IIIa)

or a tautomer thereof, or a pharmaceutically acceptable salt, or ester of said compound or tautomer, wherein:

each Y' is independently CH$_2$ or NH$_2$;

R$_{70}$ is H or —C(NH)NH$_2$;

o is 0, 1, 2, or 3; and q is 0 or 1.

In another aspect, the disclosure features a compound of Formula (IV):

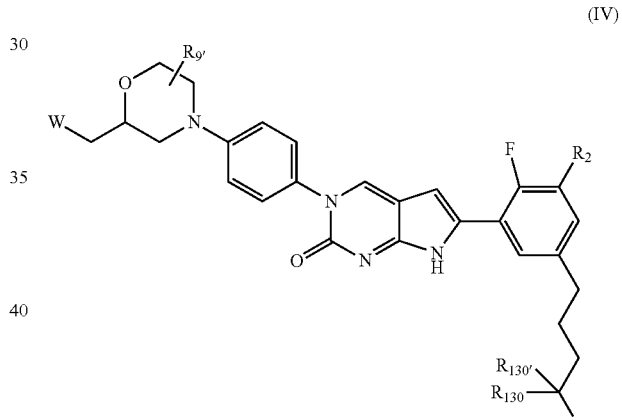
(IV)

or a tautomer thereof, or a pharmaceutically acceptable salt, or ester of said compound or tautomer, wherein:

W is —NHC(NH)NH$_2$, —CH$_2$NH$_2$, or —CH$_2$NHC(NH) NH$_2$;

R$_2$ is —F, —Cl, —CF$_3$, —SCF$_3$, or —OCF$_3$;

R$_{9'}$ is H, (C$_1$-C$_3$)alkyl, (C$_2$-C$_4$)alkenyl, —OH, or —NH$_2$;

R$_{130}$ is —CH$_3$, —CH=CH$_2$, —CF$_3$, —CH$_2$F, or —CH$_2$OH; and

R$_{130'}$ is H or —CH$_3$.

In one embodiment of Formula (IV), W is —NHC(NH) NH$_2$, —CH$_2$NH$_2$, or —CH$_2$NHC(NH)NH$_2$; R$_2$ is —Cl or —OCF$_3$; R$_{9'}$ is (C$_1$-C$_3$)alkyl, (C$_2$-C$_4$)alkenyl, —OH, or —NH$_2$; R$_{130}$ is —CH$_3$, or —CH$_2$OH; and R$_{130'}$ is H. In another embodiment of Formula (IV), W is —NHC(NH) NH$_2$, —CH$_2$NH$_2$, or —CH$_2$NHC(NH)NH$_2$; R$_2$ is —Cl or —OCF$_3$; R$_{9'}$ is H; R$_{130}$ is —CH$_3$, or —CH$_2$OH; and R$_{130'}$ is H.

In another aspect, the disclosure features a compound of Formula (V):

(V)

or a tautomer thereof, or a pharmaceutically acceptable salt, or ester of said compound or tautomer, wherein:
W' is —NHC(NH)NH$_2$, —CH$_2$NH$_2$, or —CH$_2$NHC(NH)NH$_2$;
R$_2$ is —F, —Cl, —CF$_3$, —SCF$_3$, or —OCF$_3$;
R$_{9'}$ is H or (C$_1$-C$_3$)alkyl;
R$_{140}$ is —CH$_3$, —CH=CH$_2$, —CF$_3$, —CH$_2$F, or —CH$_2$OH; and
R$_{140'}$ is H or —CH$_3$.

In one embodiment of Formula (V), W' is —NHC(NH)NH$_2$, —CH$_2$NH$_2$, or —CH$_2$NHC(NH)NH$_2$; R$_2$ is —Cl or —OCF$_3$; R$_{9'}$ is (C$_1$-C$_3$)alkyl; R$_{140}$ is —CH$_3$, or —CH$_2$OH; and R$_{140'}$ is H.

In another aspect, the disclosure features a compound of Formula (VI):

(VI)

or a tautomer thereof, or a pharmaceutically acceptable salt, or ester of said compound or tautomer, wherein:
G is —NHC(NH)NH$_2$, —CH$_2$NH$_2$, or —CH$_2$NHC(NH)NH$_2$;
R$_2$ is —F, —Cl, —CF$_3$, —SCF$_3$, or —OCF$_3$;
R$_{90}$ is (C$_1$-C$_3$)alkyl, (C$_2$-C$_3$)alkenyl, or (C$_1$-C$_3$)haloalkyl; and
R$_{91}$ is H or —CH$_3$.

In one embodiment of Formula (VI), R$_2$ is —Cl or OCF$_3$.

In another aspect, the disclosure features a compound of Formula (VII):

(VII)

or a tautomer thereof, or a pharmaceutically acceptable salt, or ester of said compound or tautomer, wherein:
W' is —NHC(NH)NH$_2$, —CH$_2$NH$_2$, or —CH$_2$NHC(NH)NH$_2$;
each J is independently CH$_2$ or NH;
R$_{150}$ is —H or —C(NH)NH$_2$;
R$_{9'}$ is H, (C$_1$-C$_3$)alkyl, (C$_2$-C$_4$)alkenyl, —OH, or —NH$_2$;
t is 0, 1, 2, or 3; and
u is 0 or 1.

In one embodiment of Formula (VII), W' is —NHC(NH)NH$_2$, —CH$_2$NH$_2$, or —CH$_2$NHC(NH)NH$_2$; each J is independently CH$_2$ or NH; R$_{150}$ is —H or —C(NH)NH$_2$; R$_{9'}$ is H; t is 0, 1, 2, or 3; and u is 0 or 1.

In some embodiments, the present disclosure relates to a compound having the Formula (I), wherein:
═══ is a single or a double bond;
X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the (C$_1$-C$_4$)alkyl, cycloalkyl, heterocycloalkyl and heteroaryl are optionally substituted with one or more R$_7$;
Z is O, CH$_2$, or NH;
R$_1$ is H or —NO$_2$;
R$_2$ is —Cl or —OCF$_3$;
R$_3$ is H or —NO$_2$;
R$_4$ is H or —NO$_2$;
R$_5$ is H or —CH$_3$; or
R$_6$ is H, (C$_1$-C$_3$)alkyl, (C$_2$-C$_3$)alkenyl, (C$_1$-C$_3$)haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more R$_8$; or
R$_5$ and R$_6$ together with the carbon atoms to which they are attached and the Z atom connecting said two carbon atoms, form a (C$_5$-C$_6$)cycloalkyl or a 5- to 6-membered heterocycloalkyl ring containing 1-3 heteroatoms optionally substituted with one or more R$_9$;
at least one of R$_5$ and R$_6$ is not H;
R$_7$ is (C$_1$-C$_3$)alkyl, halogen, oxo, or —NH$_2$;
R$_8$ is (C$_1$-C$_3$)alkyl, (C$_1$-C$_3$)alkoxy, halogen, oxo, —NH$_2$, or —NHR$_{10}$;
each R$_9$ is independently (C$_1$-C$_3$)alkyl, (C$_2$-C$_4$)alkenyl, —NH$_2$, —NH$_2$C(NH)NH$_2$, —NH$_2$C(NH)(C$_1$-C$_3$)alkyl, —CH$_2$heteroaryl, —NHheterocycloalkyl, or —NH heteroaryl, wherein the $(C_1-C_3)$alkyl is optionally substituted with one or more substituents independently selected from —OH and —NH$_2$;

$R_{10}$ is —CH$_2$aryl optionally substituted with $(C_1-C_3)$ alkoxy or halogen;

$R_{13}$ is —CH$_3$ or —CH$_2$OH;

$R_{13'}$ is H;

n is 1 or 2;

p is 0, 1, or 2; and provided that when Z is NH, X is —CH$_2$NHC(NH)NH$_2$ or —CH$_2$NH$_2$, $R_1$ is H, $R_3$ is H, $R_5$ is methyl, and $R_6$ is H, then $R_4$ is not H.

In some embodiments, the present disclosure relates to a compound having the Formula (I), wherein:

----- is a single or a double bond;

X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the $(C_1-C_4)$alkyl, cycloalkyl, heterocycloalkyl and heteroaryl are optionally substituted with one or more $R_7$;

Z is O, CH$_2$, or NH;

$R_1$ is H or —NO$_2$;

$R_2$ is —Cl or —OCF$_3$;

$R_3$ is H or —NO$_2$;

$R_4$ is H or —NO$_2$;

$R_5$ is H or —CH$_3$; or $R_6$ is H, $(C_1-C_3)$alkyl, $(C_2-C_3)$alkenyl, $(C_1-C_3)$haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more $R_8$; or $R_5$ and $R_6$ together with the carbon atoms to which they are attached and the Z atom connecting said two carbon atoms, form a $(C_5-C_6)$cycloalkyl or a 5- to 6-membered heterocycloalkyl ring containing 1-3 heteroatoms optionally substituted with one or more $R_9$; at least one of $R_5$ and $R_6$ is not H;

$R_7$ is $(C_1-C_3)$alkyl, halogen, oxo, or —NH$_2$;

$R_8$ is $(C_1-C_3)$alkyl, $(C_1-C_3)$alkoxy, halogen, oxo, —NH$_2$, or —NHR$_{10}$;

each $R_9$ is independently $(C_1-C_3)$alkyl, $(C_2-C_4)$alkenyl, —NH$_2$, —NH$_2$C(NH)NH$_2$, —NH$_2$C(NH)(C$_1$-C$_3$)alkyl, —CH$_2$heteroaryl, —NHheterocycloalkyl, or —NH heteroaryl, wherein the $(C_1-C_3)$alkyl is optionally substituted with one or more substituents independently selected from —OH and —NH$_2$;

$R_{10}$ is —CH$_2$aryl optionally substituted with $(C_1-C_3)$ alkoxy or halogen;

$R_{13}$ is —CH$_3$;

$R_{13'}$ is H;

n is 1 or 2;

p is 0, 1, or 2; and provided that when Z is NH, X is —CH$_2$NHC(NH)NH$_2$ or —CH$_2$NH$_2$, $R_1$ is H, $R_3$ is H, $R_5$ is methyl, and $R_6$ is H, then $R_4$ is not H.

In some embodiments, the present disclosure relates to a compound having the Formula (I), wherein:

----- is a single or a double bond;

X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the $(C_1-C_4)$alkyl, cycloalkyl, heterocycloalkyl and heteroaryl are optionally substituted with one or more $R_7$;

Z is O, CH$_2$, or NH;

$R_1$ is H or —NO$_2$;

$R_2$ is —Cl or —OCF$_3$;

$R_3$ is H or —NO$_2$;

$R_4$ is H or —NO$_2$;

$R_5$ is H or —CH$_3$; or $R_6$ is H, $(C_1-C_3)$alkyl, $(C_2-C_3)$alkenyl, $(C_1-C_3)$haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more $R_8$; or $R_5$ and $R_6$ together with the carbon atoms to which they are attached and the Z atom connecting said two carbon atoms, form a $(C_5-C_6)$cycloalkyl or a 5- to 6-membered heterocycloalkyl ring containing 1-3 heteroatoms optionally substituted with one or more $R_9$;

at least one of $R_5$ and $R_6$ is not H;

$R_7$ is $(C_1-C_3)$alkyl, halogen, oxo, or —NH$_2$;

$R_8$ is $(C_1-C_3)$alkyl, $(C_1-C_3)$alkoxy, halogen, oxo, —NH$_2$, or —NHR$_{10}$;

each $R_9$ is independently $(C_1-C_3)$alkyl, $(C_2-C_4)$alkenyl, —NH$_2$, —NH$_2$C(NH)NH$_2$, —NH$_2$C(NH)(C$_1$-C$_3$)alkyl, or —NH heteroaryl, wherein the $(C_1-C_3)$alkyl is optionally substituted with one or more substituents independently selected from —OH and —NH$_2$;

$R_{10}$ is —CH$_2$aryl optionally substituted with $(C_1-C_3)$ alkoxy or halogen;

$R_{13}$ is —CH$_3$;

$R_{13'}$ is H;

n is 1 or 2;

p is 0, 1, or 2; and provided that when Z is NH, X is —CH$_2$NHC(NH)NH$_2$ or —CH$_2$NH$_2$, $R_1$ is H, $R_3$ is H, $R_5$ is methyl, and $R_6$ is H, then $R_4$ is not H.

In other embodiment, the present disclosure relates to a compound having the Formula (I), wherein:

----- is a single or a double bond;

X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the $(C_1-C_4)$alkyl, cycloalkyl, heterocycloalkyl and heteroaryl are optionally substituted with one or more $R_7$;

Z is O, CH$_2$, or NH;

$R_1$ is H or —NO$_2$;

$R_2$ is —Cl or —OCF$_3$;

$R_3$ is H or —NO$_2$;

$R_4$ is H or —NO$_2$;

$R_5$ is H or —CH$_3$;

$R_6$ is H, $(C_1-C_3)$alkyl, $(C_2-C_3)$alkenyl, $(C_1-C_3)$haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more $R_8$;

at least one of $R_5$ and $R_6$ is not H;

$R_7$ is $(C_1-C_3)$alkyl, halogen, oxo, or —$NH_2$;

$R_8$ is $(C_1-C_3)$alkyl, $(C_1-C_3)$alkoxy, halogen, oxo, —$NH_2$, or —$NHR_{10}$;

$R_{10}$ is —$CH_2$aryl optionally substituted with $(C_1-C_3)$alkoxy or halogen;

n is 1 or 2;

p is 0, 1, or 2; and provided that when Z is NH, X is —$CH_2NHC(NH)NH_2$ or —$CH_2NH_2$, $R_1$ is H, $R_3$ is H, $R_4$ is H, then $R_6$ is not H, $(C_1-C_3)$alkyl or $(C_2-C_3)$alkenyl.

In some embodiments, the present disclosure relates to a compound having the Formula (I), wherein:

----- is a single or a double bond;

X is —$NHC(NH)NH_2$, —$CH_2NH_2$, —$CH_2NHC(NH)NH_2$, —$CH_2NHCH_2C(O)CH_3$, —$CH_2NHC(NH)(C_1-C_4)$alkyl, —$CH_2NHC(NH)(C_3-C_7)$cycloalkyl, —$CH_2NHC(NH)$heteroaryl, heteroaryl, —$CH_2$heteroaryl, —$NHCH_2$heteroaryl, —$CH_2NH$heteroaryl, —$CH(OH)$heteroaryl, —$CH_2$heterocycloalkyl, —$NHCH_2$heterocycloalkyl, or —$CH_2NH$heterocycloalkyl, wherein the $(C_1-C_4)$alkyl, cycloalkyl, heterocycloalkyl and heteroaryl are optionally substituted with one or more $R_7$;

Z is O, $CH_2$, or NH;

$R_1$ is H or —$NO_2$;

$R_2$ is —Cl or —$OCF_3$;

$R_3$ is H or —$NO_2$;

$R_4$ is H or —$NO_2$;

$R_5$ is H or —$CH_3$;

$R_6$ is $(C_1-C_3)$alkyl, $(C_2-C_3)$alkenyl, $(C_1-C_3)$haloalkyl, —$CH_2NHC(NH)NH_2$, —$(CH_2)_nOH$, —$CH_2S(O)_pNH_2$, —$CH_2NH(C_1-C_3)$alkyl, —$CH_2C(O)NH_2$, —$(CH_2)_nNH_2$,

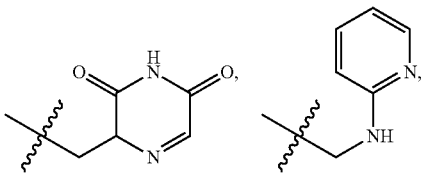

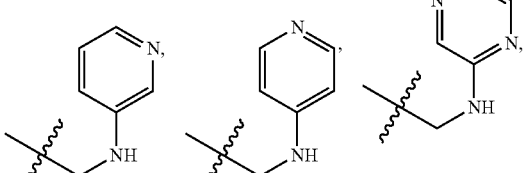

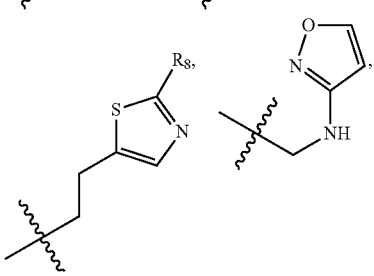

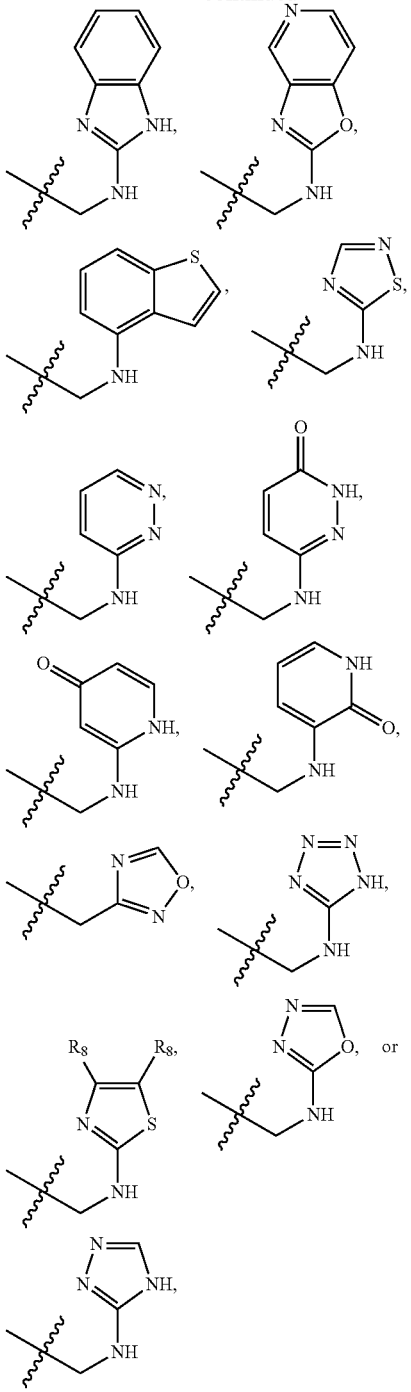

wherein each heteroaryl and heterocycloalkyl is optionally substituted with one or more R;

$R_7$ is $(C_1-C_3)$alkyl, halogen, oxo, or —$NH_2$;

$R_8$ is $(C_1-C_3)$alkyl, $(C_1-C_3)$alkoxy, halogen, —$NH_2$, or —$NHR_{10}$;

$R_{10}$ is $CH_2$aryl optionally substituted with $(C_1-C_3)$alkoxy or halogen;

n is 1 or 2;

p is O, 1, or 2; and provided that when Z is NH, X is —$CH_2NHC(NH)NH_2$ or —$CH_2NH_2$, RI is H, $R_3$ is H, $R_4$ is H, then $R_6$ is not $(C_1-C_3)$alkyl or $(C_2-C_3)$alkenyl.

In some embodiments, the present disclosure relates to a compound having the Formula (I), wherein:

----- $R_2$ is a single or a double bond;

X is —$CH_2NHCH_2C(O)CH_3$, —$CH_2NHC(NH)(C_1-C_4)$alkyl, —$CH_2NHC(NH)(C_3-C_7)$cycloalkyl, —$CH_2NHC(NH)$heteroaryl, heteroaryl, —$NHCH_2$heteroaryl, —$CH_2NH$heteroaryl, —$CH(OH)$heteroaryl, —$CH_2$heterocycloalkyl, —$NHCH_2$heterocycloalkyl, or —$CH_2NH$heterocycloalkyl, wherein the $(C_1-C_4)$alkyl, cycloalkyl, heterocycloalkyl and heteroaryl are optionally substituted with one or more $R_7$;

Z is O, $CH_2$, or NH;

RI is H;

$R_2$ is —Cl or —$OCF_3$;

$R_3$ is H;

$R_4$ is H;

$R_8$ and $R_6$ together with the carbon atoms to which they are attached and the Z atom connecting said two carbon atoms, form a $(C_5-C_6)$cycloalkyl or a 5- to 6-membered heterocycloalkyl ring optionally substituted with one or more $R_9$;

$R_7$ is $(C_1-C_3)$alkyl, halogen, oxo, or —$NH_2$; and each $R_9$ is independently $(C_1-C_3)$alkyl, $(C_2-C_4)$alkenyl, —$NH_2$, —$NH_2C(NH)NH_2$, —$NH_2C(NH)(C_1-C_3)$alkyl, —$CH_2$heteroaryl, —NHheterocycloalkyl, or —NH heteroaryl, wherein the $(C_1-C_3)$alkyl is optionally substituted with one or more substituents independently selected from —OH and —$NH_2$; and provided that when Z is NH, $R_1$ is H, $R_2$ is H, $R_3$ is H and $R_4$ is H, then X is not —$CH_2NHC(NH)CH_3$.

In some embodiments, the present disclosure relates to a compound having the Formula (I), wherein:

----- is a single or a double bond;

X is —$CH_2NHCH_2C(O)CH_3$, —$CH_2NHC(NH)(C_1-C_4)$alkyl, —$CH_2NHC(NH)(C_3-C_7)$cycloalkyl, —$CH_2NHC(NH)$heteroaryl, —$CH(OH)$heteroaryl,

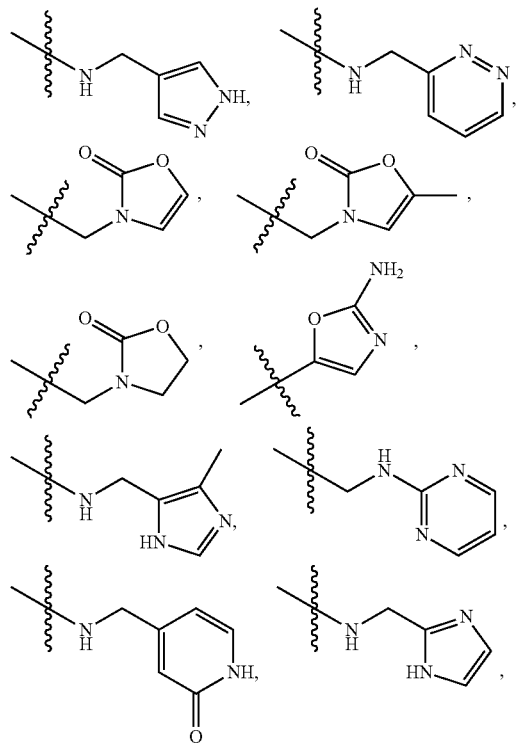

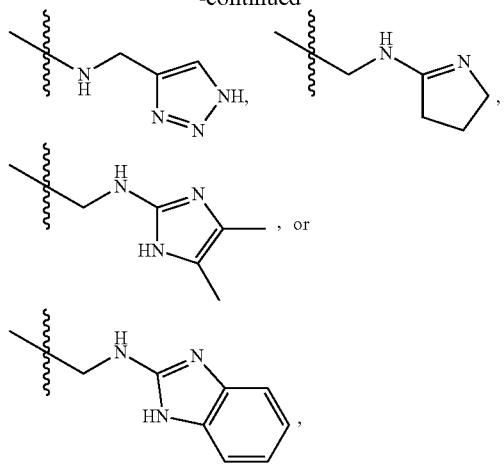

wherein the alkyl, cycloalkyl, heterocycloalkyl, and heteroaryl are optionally substituted with one or more $R_7$;

Z is O, $CH_2$, or NH;

$R_1$ is H;

$R_2$ is —Cl or —$OCF_3$;

$R_3$ is H;

$R_4$ is H;

$R_5$ and $R_6$ together with the carbon atoms to which they are attached and the Z atom connecting said two carbon atoms, form a $(C_5-C_6)$cycloalkyl or a 5- to 6-membered heterocycloalkyl ring optionally substituted with one or more $R_9$;

$R_7$ is $(C_1-C_3)$alkyl, halogen, or —$NH_2$; and each $R_9$ is independently $(C_1-C_3)$alkyl, $(C_2-C_4)$alkenyl, —$NH_2$, —$NH_2C(NH)NH_2$, —$NH_2C(NH)(C_1-C_3)$alkyl, —$CH_2$heteroaryl, —NHheterocycloalkyl, or —NH heteroaryl, wherein the $(C_1-C_3)$alkyl is optionally substituted with one or more substituents independently selected from —OH and —$NH_2$; and provided that when Z is NH, $R_1$ is H, $R_2$ is H, $R_3$ is H and $R_4$ is H, then X is not —$CH_2NHC(NH)CH_3$.

In some embodiments, the present disclosure relates to a compound having the Formula (I), wherein:

----- is a single or a double bond;

X is —$NHC(NH)NH_2$, —$CH_2NH_2$, —$CH_2NHC(NH)NH_2$, —$CH_2NHCH_2C(O)CH_3$, —$CH_2NHC(NH)(C_1-C_4)$alkyl, —$CH_2NHC(NH)(C_3-C_7)$cycloalkyl, —$CH_2NHC(NH)$heteroaryl, heteroaryl, —$CH_2$heteroaryl, —$NHCH_2$heteroaryl, —$CH_2NH$heteroaryl, —$CH(OH)$heteroaryl, —$CH_2$heterocycloalkyl, —$NHCH_2$heterocycloalkyl, or —$CH_2NH$heterocycloalkyl, wherein the alkyl, cycloalkyl, heterocycloalkyl and heteroaryl are optionally substituted with one or more $R_7$;

Z is O;

$R_1$ is H or —$NO_2$;

$R_2$ is —Cl or —$OCF_3$;

$R_3$ is H or —$NO_2$;

$R_4$ is H or —$NO_2$;

$R_5$ is H or —$CH_3$;

$R_6$ is H, $(C_1-C_3)$alkyl, $(C_2-C_3)$alkenyl, $(C_1-C_3)$haloalkyl, —$CH_2NHC(NH)NH_2$, —$(CH_2)_nOH$, —$CH_2S(O)_pNH_2$, —$CH_2NH(C_1-C_3)$alkyl, —$CH_2C(O)NH_2$, —$(CH_2)_nNH_2$, —$CH_2$heterocycloalkyl, —$CH_2NH_2$heterocycloalkyl, —$(CH_2)_n$heteroaryl, or —$CH_2NH_2$heteroaryl, wherein the heteroaryl and heterocycloalkyl is optionally substituted with one or more $R_8$;
at least one of $R_5$ and $R_6$ is not H;
$R_7$ is $(C_1-C_3)$alkyl, halogen, oxo, or —$NH_2$;
$R_8$ is $(C_1-C_3)$alkyl, $(C_1-C_3)$alkoxy, halogen, oxo, —$NH_2$, or —$NHR_{10}$;
$R_{10}$ is —$CH_2$aryl optionally substituted with $(C_1-C_3)$ alkoxy or halogen;
n is 1 or 2; and
p is 0, 1, or 2.

In some embodiments, the present disclosure relates to a compound having the Formula (I), wherein:
----- is a single or a double bond;
X is —NHC(NH)$NH_2$, —$CH_2NH_2$, —$CH_2$NHC(NH)$NH_2$, —$CH_2NHCH_2C(O)CH_3$, —$CH_2NHC(NH)(C_1-C_4)$alkyl, —$CH_2NHC(NH)(C_3-C_7)$cycloalkyl, —$CH_2NHC(NH)$heteroaryl, heteroaryl, —$CH_2$heteroaryl, —$NHCH_2$heteroaryl, —$CH_2NH$heteroaryl, —CH(OH)heteroaryl, —$CH_2$heterocycloalkyl, —$NHCH_2$heterocycloalkyl, or —$CH_2NH$heterocycloalkyl, wherein the $(C_1-C_4)$alkyl, cycloalkyl, heterocycloalkyl and heteroaryl are optionally substituted with one or more $R_7$;
Z is —$CH_2$;
$R_1$ is H or —$NO_2$;
$R_2$ is —Cl or —$OCF_3$;
$R_3$ is H or —$NO_2$;
$R_4$ is H or —$NO_2$;
$R_5$ is H or —$CH_3$;
$R_6$ is H, $(C_1-C_3)$alkyl, $(C_2-C_3)$alkenyl, $(C_1-C_3)$haloalkyl, —$CH_2NHC(NH)NH_2$, —$(CH_2)_n$OH, —$CH_2S(O)_pNH_2$, —$CH_2NH(C_1-C_3)$alkyl, —$CH_2C(O)NH_2$, —$(CH_2)_nNH_2$, —$CH_2$heterocycloalkyl, —$CH_2NH_2$heterocycloalkyl, —$(CH_2)_n$heteroaryl, or —$CH_2NH_2$heteroaryl, wherein the heteroaryl and heterocycloalkyl is optionally substituted with one or more $R_8$;
at least one of $R_5$ and $R_6$ is not H;
$R_7$ is $(C_1-C_3)$alkyl, halogen, oxo, or —$NH_2$;
$R_8$ is $(C_1-C_3)$alkyl, $(C_1-C_3)$alkoxy, halogen, oxo, —$NH_2$, or —$NHR_{10}$;
$R_{10}$ is —$CH_2$aryl optionally substituted with $(C_1-C_3)$ alkoxy or halogen;
n is 1 or 2; and
p is 0, 1, or 2.

In some embodiments, the present disclosure relates to a compound having the Formula (I), wherein:
----- is a single or a double bond;
X is —NHC(NH)$NH_2$, —$CH_2NH_2$, —$CH_2$NHC(NH)$NH_2$, —$CH_2NHCH_2C(O)CH_3$, —$CH_2NHC(NH)(C_1-C_4)$alkyl, —$CH_2NHC(NH)(C_3-C_7)$cycloalkyl, —$CH_2NHC(NH)$heteroaryl, heteroaryl, —$CH_2$heteroaryl, —$NHCH_2$heteroaryl, —$CH_2NH$heteroaryl, —CH(OH)heteroaryl, —$CH_2$heterocycloalkyl, —$NHCH_2$heterocycloalkyl, or —$CH_2NH$heterocycloalkyl, wherein the $(C_1-C_4)$alkyl, cycloalkyl, heterocycloalkyl and heteroaryl are optionally substituted with one or more $R_7$;
Z is NH;
$R_1$ is H or —$NO_2$;
$R_2$ is —Cl or —$OCF_3$;
$R_3$ is H or —$NO_2$;
$R_4$ is H or $NO_2$;
$R_5$ is H or —$CH_3$;
$R_6$ is H, $(C_1-C_3)$alkyl, $(C_2-C_3)$alkenyl, $(C_1-C_3)$haloalkyl, —$CH_2NHC(NH)NH_2$, —$(CH_2)_n$OH, —$CH_2S(O)_pNH_2$, —$CH_2NH(C_1-C_3)$alkyl, —$CH_2C(O)NH_2$, —$(CH_2)_nNH_2$, —$CH_2$heterocycloalkyl, —$CH_2NH_2$heterocycloalkyl, —$(CH_2)_n$heteroaryl, or —$CH_2NH_2$heteroaryl, wherein the heteroaryl and heterocycloalkyl is optionally substituted with one or more $R_8$;
at least one of $R_5$ and $R_6$ is not H;
$R_7$ is $(C_1-C_3)$alkyl, halogen, oxo, or —$NH_2$;
$R_8$ is $(C_1-C_3)$alkyl, $(C_1-C_3)$alkoxy, halogen, oxo, —$NH_2$, or —$NHR_{10}$;
$R_{10}$ is —$CH_2$aryl optionally substituted with $(C_1-C_3)$ alkoxy or halogen;
n is 1 or 2;
p is 0, 1, or 2; and
provided that when X is —$CH_2NHC(NH)NH_2$ or —$CH_2NH_2$, $R_1$ is H, $R_3$ is H, $R_4$ is H, then $R_6$ is not H, $(C_1-C_3)$alkyl or $(C_2-C_3)$alkenyl.

In some embodiments, the present disclosure relates to a compound having the Formula (I), wherein:
X is —$CH_2NH_2$ or —$CH_2NHC(NH)NH_2$;
Z is NH;
$R_1$ is H or —$NO_2$;
$R_2$ is —Cl or —$OCF_3$;
$R_3$ is H or —$NO_2$;
$R_4$ is —$NO_2$;
$R_5$ is H or —$CH_3$;
and $R_6$ is H.

The compounds of any of Formulae I, Ia, Ib, Ic, Id, Ie, Ig, Ih, Ii, Il, Im, In, II, IIa, IIb, IIc, IId, IIe, IIf, III, IIIa, IV, V, VI, and VII or tautomers thereof, or pharmaceutically acceptable salts, esters, or prodrugs of said compounds or tautomers, can include one or more of the following features, when applicable.

In some embodiments of the Formulae above, X is —NHC(NH)$NH_2$, —$CH_2NH_2$, —$CH_2$NHC(NH)$NH_2$, —$CH_2NHCH_2C(O)CH_3$, —$CH_2NHC(NH)(C_1-C_4)$alkyl, —$CH_2NHC(NH)(C_3-C_7)$cycloalkyl, —$CH_2NHC(NH)$heteroaryl, heteroaryl, —$CH_2$heteroaryl, —$NHCH_2$heteroaryl, —$CH_2NH$heteroaryl, —CH(OH)heteroaryl, —$CH_2$heterocycloalkyl, —$NHCH_2$heterocycloalkyl, or —$CH_2NH$heterocycloalkyl, wherein the alkyl, cycloalkyl, heterocycloalkyl and heteroaryl are optionally substituted with one or more $R_7$. In another embodiment, X is —$CH_2NHCH_2C(O)CH_3$, —$CH_2NHC(NH)(C_1-C_4)$alkyl, —$CH_2NHC(NH)(C_3-C_7)$cycloalkyl, —$CH_2NHC(NH)$heteroaryl, or —CH(OH)heteroaryl, wherein the alkyl, cycloalkyl, heterocycloalkyl, and heteroaryl are optionally substituted with one or more $R_7$. In another embodiment, X is

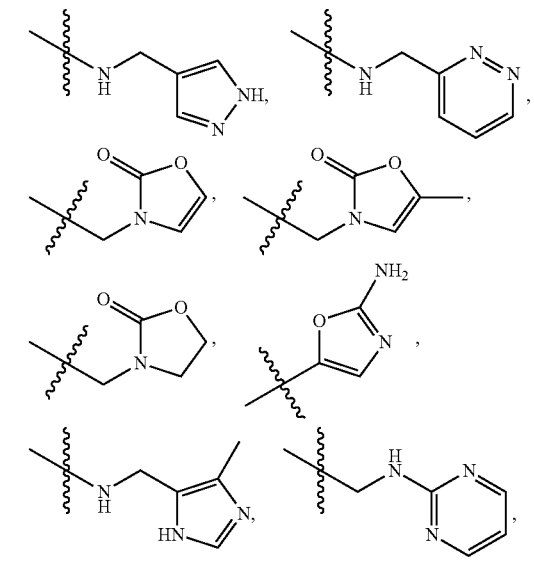

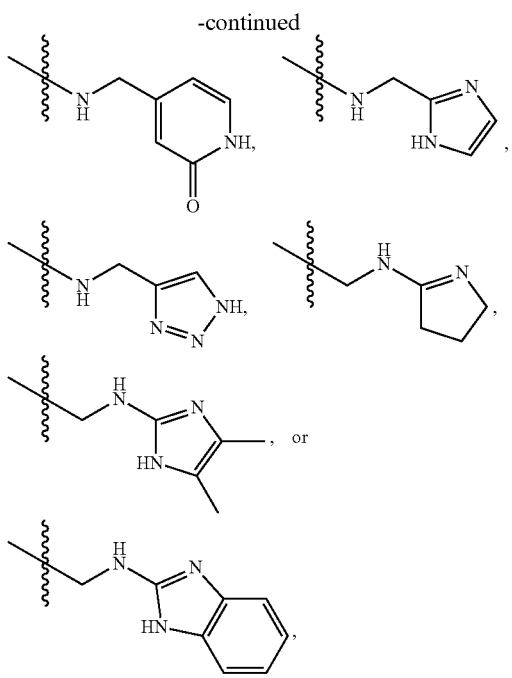

wherein each heterocycloalkyl and heteroaryl is optionally substituted with one or more $R_7$.

In some embodiments of the Formulae above, Z is O. In another embodiment, Z is $CH_2$. In yet another embodiment, Z is NH.

In some embodiments of the Formulae above, $R_1$ is H. In another embodiment, $R_1$ is $-NO_2$.

In some embodiments of the Formulae above, $R_2$ is $-F$, $-Cl$, $-CF_3$, $-SCF_3$, or $-OCF_3$. In another embodiment, $R_2$ is $-Cl$. In yet another embodiment, $R_2$ is $-OCF_3$.

In some embodiments of the Formulae above, $R_3$ is H. In another embodiment, $R_3$ is $-NO_2$.

In some embodiments of the Formulae above, $R_4$ is H. In another embodiment, $R_4$ is $-NO_2$.

In some embodiments of the Formulae above, $R_5$ is H. In another embodiment, $R_5$ is $-CH_2$. In In some embodiments of the Formulae above, $R_6$ is H, $(C_1-C_3)$alkyl, $(C_2-C_3)$alkenyl, $(C_1-C_3)$haloalkyl, $-CH_2NHC(NH)NH_2$, $-(CH_2)_nOH$, $-CH_2S(O)_pNH_2$, $-CH_2NH(C_1-C_3)$alkyl, $-CH_2C(O)NH_2$, $-(CH_2)_nNH_2$, $-CH_2$heterocycloalkyl, $-CH_2NH_2$heterocycloalkyl, $-(CH_2)_n$heteroaryl, or $-CH_2NH_2$heteroaryl, wherein the heteroaryl and heterocycloalkyl is optionally substituted with one or more $R_8$.

In another embodiment, $R_5$ and $R_6$ together with the carbon atoms to which they are attached and the Z atom connecting said two carbon atoms, form a $(C_5-C_6)$cycloalkyl or a 5- to 6-membered heterocycloalkyl ring optionally substituted with one or more $R_9$.

In some embodiments of the Formulae above, at least one of $R_5$ and $R_6$ is not H.

In some embodiments of the Formulae above, $R_7$ is $(C_1-C_3)$alkyl, halogen, oxo, or $-NH_2$. In another embodiment, $R_7$ is $(C_1-C_3)$alkyl, F, Cl, oxo, or $-NH_2$.

In some embodiments of the Formulae above, $R_8$ is $(C_1-C_3)$alkyl, $(C_1-C_3)$alkoxy, halogen, oxo, $-NH_2$, or $-NHR_{10}$.

In some embodiments of the Formulae above, $R_9$ is $(C_1-C_3)$alkyl, $(C_2-C_4)$alkenyl, $-NH_2$, $-NH_2C(NH)NH_2$, $-NH_2C(NH)(C_1-C_3)$alkyl, $-CH_2$heteroaryl, $-NH$hetero-cycloalkyl, or $-NH$ heteroaryl, wherein the $(C_1-C_3)$alkyl is optionally substituted with one or more substituents independently selected from $-OH$ and $-NH_2$. In another embodiment, $R_9$ is $(C_1-C_3)$alkyl, $(C_2-C_4)$alkenyl, $-NH_2$, $-NH_2C(NH)NH_2$, $-NH_2C(NH)(C_1-C_3)$alkyl, or $-NH$ heteroaryl, wherein the $(C_1-C_3)$alkyl is optionally substituted with one or more substituents independently selected from $-OH$ and $-NH_2$.

In some embodiments of the Formulae above, $R_{10}$ is $-CH_2$aryl optionally substituted with $(C_1-C_3)$alkoxy or halogen.

In some embodiments of the Formulae above, ----- is a double bond. In some embodiments of the Formulae above, ----- is a single bond.

In some embodiments of the Formulae above, n is 1. In another embodiment, n is 2.

In some embodiments of the Formulae above, p is 0. In another embodiment, p is 1. In yet another embodiment, p is 2.

In some embodiments of the Formulae above, when Z is NH, X is $-CH_2NHC(NH)NH_2$ or $-CH_2NH_2$, $R_1$ is H, $R_3$ is H, $R_5$ is methyl, and $R_6$ is H, then $R_4$ is not H.

In some embodiments of the Formulae above, when Z is NH, X is $-CH_2NHC(NH)NH_2$ or $-CH_2NH_2$, $R_1$ is H, $R_3$ is H, $R_5$ is methyl, and $R_6$ is H, then $R_4$ is $(C_1-C_3)$alkyl, $(C_2-C_3)$alkenyl, halogen, or $-NO_2$.

In some embodiments of the Formulae above, when Z is NH, $R_1$ is H, $R_2$ is H, $R_3$ is H and $R_4$ is H, then X is not $-CH_2NHC(NH)CH_3$.

In some embodiments of the Formulae above, when Z is NH, $R_1$ is H, $R_2$ is H, $R_3$ is H and $R_4$ is H, then X is $-CH_2NHCH_2C(O)CH_3$, $-CH_2NHC(NH)(C_1-C_4)$alkyl, $-CH_2NHC(NH)(C_3-C_7)$cycloalkyl, $-CH_2NHC(NH)$het-eroaryl, heteroaryl, $-CH_2$heteroaryl, $-NHCH_2$heteroaryl, $-CH_2NH$heteroaryl, $-CH(OH)$heteroaryl, $-CH_2$heterocycloalkyl, $-NHCH_2$heterocycloalkyl, or $-CH_2NH$heteroaryl, wherein the alkyl, cycloalkyl, heterocycloalkyl and heteroaryl are optionally substituted with one or more $R_7$. In another embodiment, when Z is NH, $R_1$ is H, $R_2$ is H, $R_3$ is H and $R_4$ is H, then X is $-CH_2NHCH_2C(O)CH_3$, $-CH_2NHC(NH)(C_2-C_4)$alkyl, $-CH_2NHC(NH)(C_3-C_7)$cycloalkyl, $-CH_2NHC(NH)$het-eroaryl, $-CH(OH)$heteroaryl,

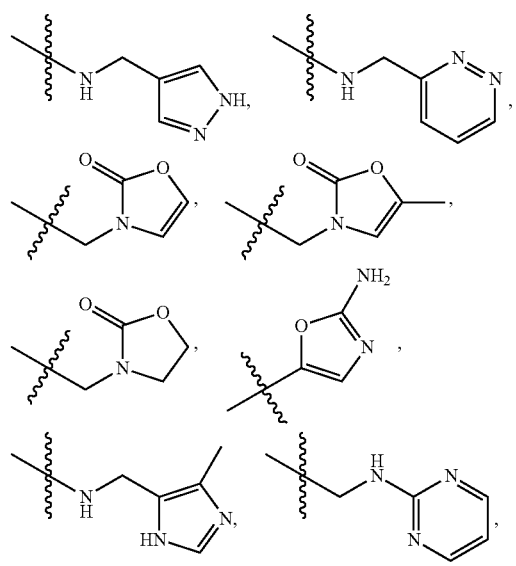

157

-continued

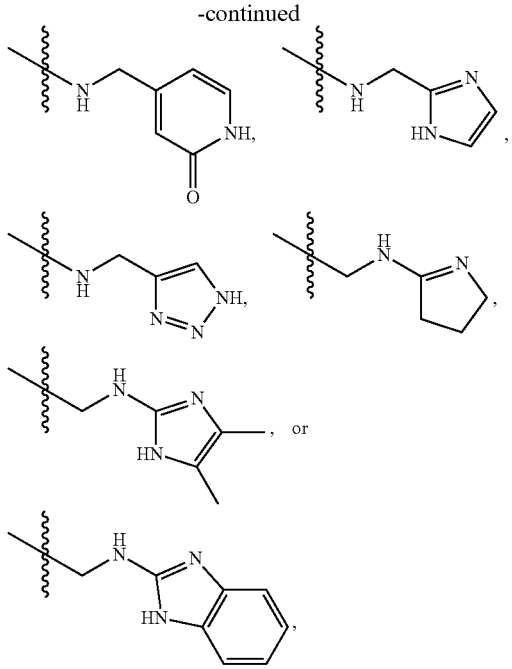

wherein the alkyl, heterocycloalkyl, and heteroaryl is optionally substituted with one or more $R_7$.

In some embodiments of the Formulae above, when Z is NH, X is —$CH_2NHCH_2C(O)CH_3$, —$CH_2NHC(NH)(C_1$-$C_4)$alkyl, —$CH_2NHC(NH)(C_3$-$C_7)$cycloalkyl, —$CH_2NHC(NH)$heteroaryl, heteroaryl, —$CH_2$heteroaryl, —$NHCH_2$heteroaryl, —$CH_2NH$heteroaryl, —$CH(OH)$heteroaryl, —$CH_2$heterocycloalkyl, —$NHCH_2$heterocycloalkyl, or —$CH_2NH$heterocycloalkyl, wherein the alkyl, cycloalkyl, heterocycloalkyl and heteroaryl are optionally substituted with one or more $R_7$. In another embodiment, when Z is NH, X is —$CH_2NHCH_2C(O)CH_3$, —$CH_2NHC(NH)(C_2$-$C_4)$alkyl, —$CH_2NHC(NH)(C_3$-$C_7)$cycloalkyl, —$CH_2NHC(NH)$heteroaryl, —$CH(OH)$heteroaryl,

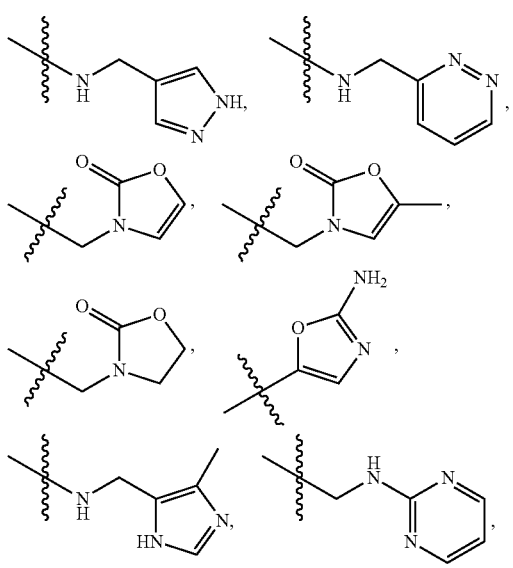

158

-continued

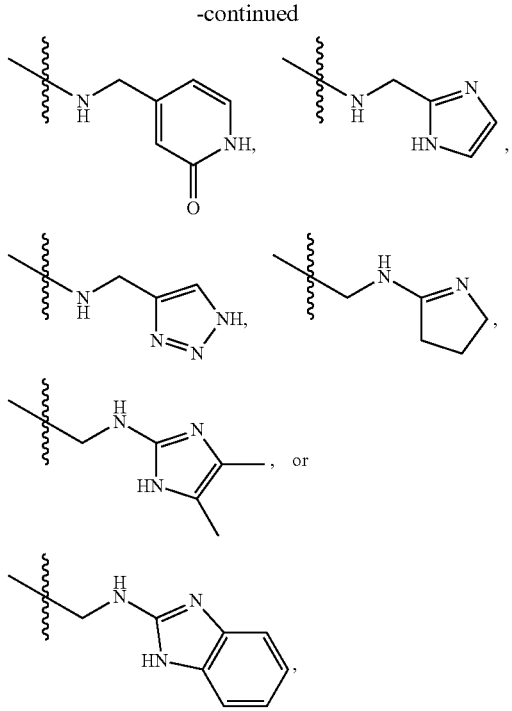

wherein the alkyl, heterocycloalkyl and heteroaryl is optionally substituted with one or more $R_7$.

In some embodiments of the Formulae above, X is —$NHC(NH)NH_2$, —$CH_2NH_2$, or —$CH_2NHC(NH)NH_2$.

In some embodiments of the Formulae above, X is —$CH_2NHCH_2C(O)CH_3$, —$CH_2NHC(NH)(C_1$-$C_4)$alkyl, —$CH_2NHC(NH)(C_3$-$C_7)$cycloalkyl, or —$CH_2NHC(NH)$heteroaryl.

In some embodiments of the Formulae above, wherein X is —$CH(OH)$heteroaryl,

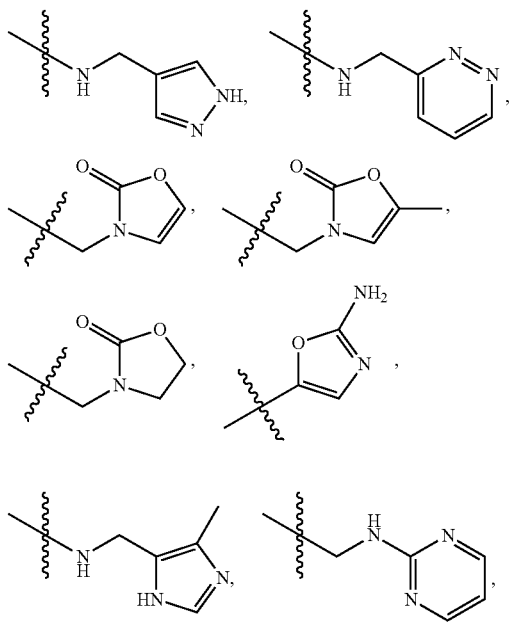

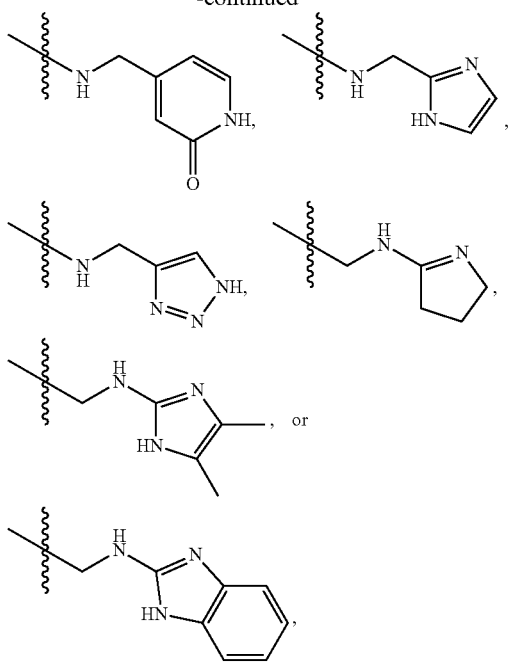
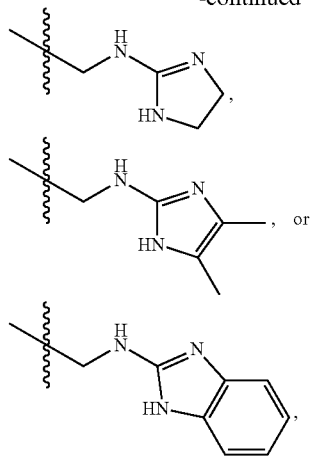

wherein each is optionally substituted with one or more $R_7$.

In some embodiments of the Formulae above, wherein X is —CH(OH)heteroaryl,

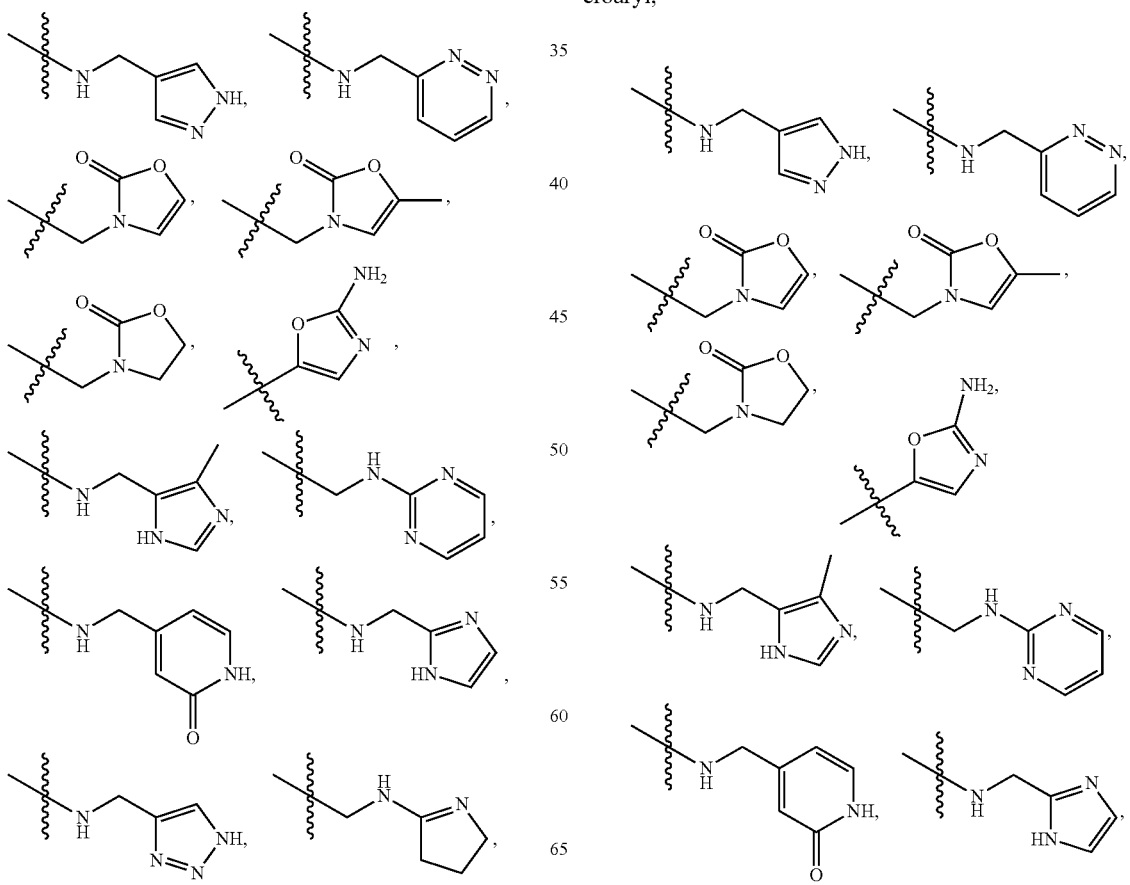

wherein each is optionally substituted with one or more $R_7$.

In some embodiments of the Formulae above, $R_2$ is —Cl.

In some embodiments of the Formulae above, $R_1$ is H, $R_3$ is H and $R_4$ is H.

In some embodiments of the Formulae above, Z is NH.

In some embodiments of the Formulae above, $R_6$ is $(C_1$-$C_3)$alkyl, $(C_2$-$C_3)$alkenyl, or $(C_1$-$C_3)$haloalkyl. In another embodiment, $R_6$ is $(C_1$-$C_3)$alkyl, $(C_2$-$C_3)$alkenyl, or $(C_1$-$C_3)$haloalkyl and X is —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, or —CH$_2$NHC(NH)heteroaryl, —CH(OH)heteroaryl,

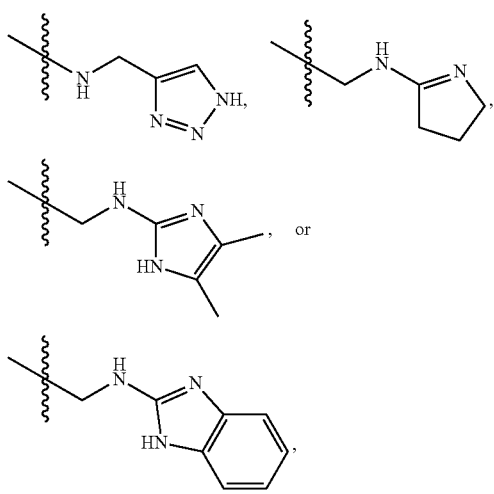

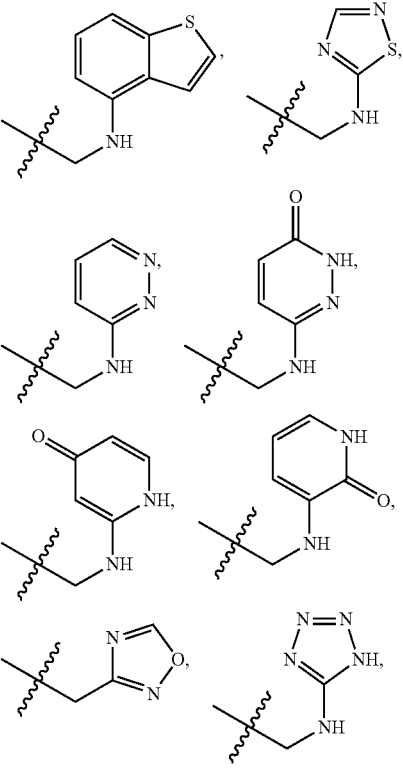

wherein the alkyl, heterocycloalkyl and heteroaryl is optionally substituted with one or more $R_7$.

In some embodiments of the Formulae above, $R_6$ is —$CH_2NHC(NH)NH_2$, —$(CH_2)_nOH$, —$CH_2S(O)_pNH_2$, —$CH_2NH(C_1-C_3)$alkyl, —$CH_2C(O)NH_2$, or —$(CH_2)_nNH_2$.

In some embodiments of the Formulae above, $R_6$ is

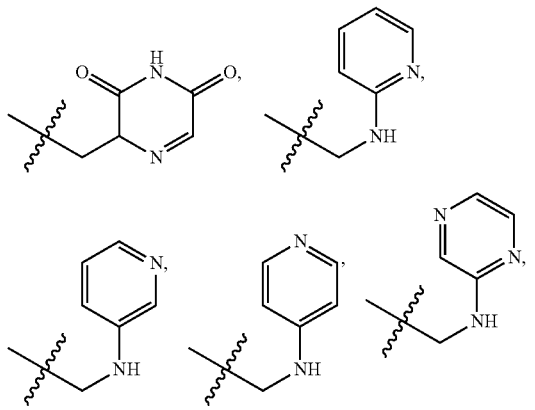

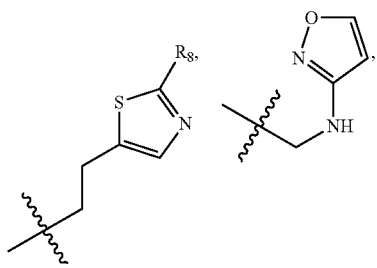

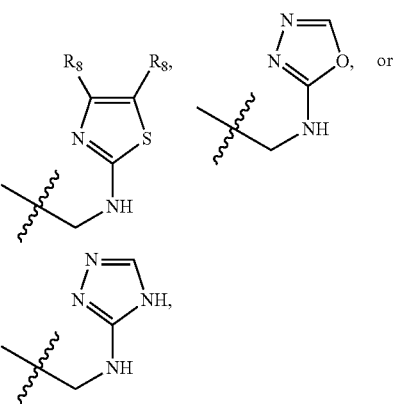

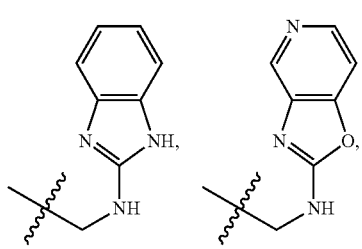

wherein each heteroaryl and heterocycloalkyl is optionally substituted with one or more $R_8$.

In some embodiments, when $R_5$ and $R_6$ together form a $(C_5-C_6)$cycloalkyl or a 5- to 6-membered heterocycloalkyl ring, Z is NH, $R_1$ is H, $R_2$ is H, $R_3$ is H and $R_4$ is H, then X is not —$CH_2NHC(NH)CH_3$. In another embodiment, $R_5$ and $R_6$ together form a $(C_5-C_6)$cycloalkyl or a 5- to 6-membered heterocycloalkyl ring, Z is NH, $R_1$ is H, $R_2$ is H, $R_3$ is H and $R_4$ is H, X is —$CH_2NHCH_2C(O)CH_3$, —$CH_2NHC(NH)(C_2-C_4)$alkyl, —$CH_2NHC(NH)(C_3-C_7)$cycloalkyl, —$CH_2NHC(NH)$heteroaryl, —$CH(OH)$heteroaryl,

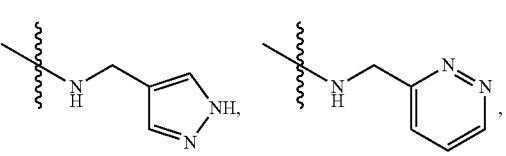

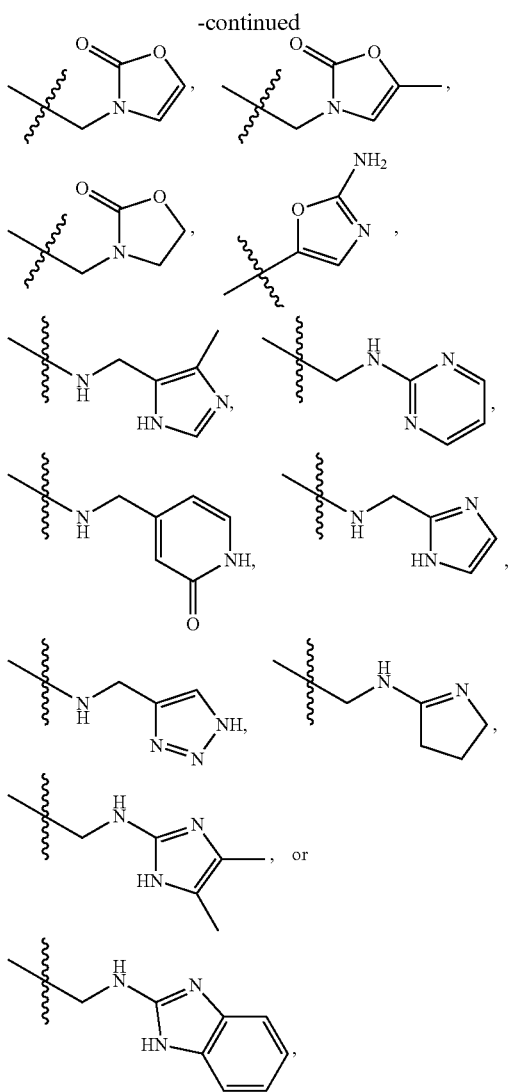

wherein the alkyl, heterocycloalkyl and heteroaryl is optionally substituted with one or more $R_7$.

In some embodiments of the Formulae above, X' is —NHC(NH)NH$_2$, —NHC(NH)CH$_3$, —NHheteroaryl, or heteroaryl. In another embodiment, X' is —NHC(NH)NH$_2$. In yet another embodiment, X' is —NHC(NH)CH$_3$. In another embodiment, X' is —NHheteroaryl. In yet another embodiment, X' is heteroaryl.

In some embodiments of the Formulae above, Y' is CH$_2$ or NH. In another embodiment, Y' is CH$_2$. In yet another embodiment, Y' is NH.

In some embodiments of the Formulae above, Z' is O, NH, or CH$_2$. In another embodiment, Z' is O. In another embodiment, Z' is NH. In yet another embodiment, Z' is CH$_2$.

In some embodiments of the Formulae above, $R_{5'}$ is H or —CH$_3$. In another embodiment, $R_{5'}$ is H. In yet another embodiment, $R_{5'}$ is —CH$_3$.

In some embodiments of the Formulae above, $R_{6'}$ is (C$_1$-C$_3$)alkyl, (C$_2$-C$_3$)alkenyl, or (C$_1$-C$_3$)haloalkyl, wherein the alkyl is optionally substituted with one or more substituents independently selected from halogen, —NHC(NH)NH$_2$, and —NHheteroaryl. In another embodiment, $R_{6'}$ is (C$_1$-C$_3$)alkyl, (C$_2$-C$_3$)alkenyl, or (C$_1$-C$_3$)haloalkyl, wherein the alkyl is optionally substituted with one to three substituents independently selected from halogen, —NHC(NH)NH$_2$, and —NHheteroaryl. In yet another embodiment, $R_{6'}$ is (C$_1$-C$_3$)alkyl, (C$_2$-C$_3$)alkenyl, or (C$_1$-C$_2$)haloalkyl, wherein the alkyl is optionally substituted with one to three substituents independently selected from halogen, —NHC(NH)NH$_2$, and —NHheteroaryl.

In another embodiment, $R_{5'}$ and $R_{6'}$ together with the carbon atoms to which they are attached and the Z atom connecting said two carbon atoms, form a 6-membered heterocycloalkyl ring containing 1-3 heteroatoms optionally substituted with one or more $R_{101}$. In yet another embodiment, $R_{5'}$ and $R_{6'}$ together with the carbon atoms to which they are attached and the Z atom connecting said two carbon atoms, form a 6-membered heterocycloalkyl ring containing 1-3 heteroatoms optionally substituted with one to three $R_{101}$.

In some embodiments of the Formulae above, $R_{50}$ is H or —C(NH)NH$_2$. In another embodiment, $R_{50}$ is H. In yet another embodiment, $R_{50}$ is H or —C(NH)NH$_2$.

In some embodiments of the Formulae above, $R_{60}$ is H or (C$_1$-C$_5$)alkyl, wherein the alkyl optionally substituted with one or more substituents independently selected from (C$_1$-C$_2$)alkyl, (C$_2$-C$_4$)alkenyl, (C$_1$-C$_2$)haloalkyl, (C$_1$-C$_2$) hydroxyalkyl, and —NH$_2$. In another embodiment, $R_{60}$ is H. In yet another embodiment, $R_{60}$ is (C$_1$-C$_5$)alkyl optionally substituted with one or more substituents independently selected from (C$_1$-C$_2$)alkyl, (C$_2$-C$_4$)alkenyl, (C$_1$-C$_2$)haloalkyl, (C$_1$-C$_2$) hydroxyalkyl, and —NH$_2$. In another embodiment, $R_{60}$ is (C$_1$-C$_5$)alkyl optionally substituted with one or more substituents independently selected from (C$_1$-C$_2$)alkyl and —NH$_2$.

In some embodiments of the Formulae above, $R_{101}$ is independently selected from (C$_1$-C$_3$)alkyl, (C$_2$-C$_3$)alkenyl, halogen, —NH$_2$, and —NHheteroaryl, wherein the alkyl is optionally substituted with one or more substituents independently selected from —NH$_2$ and —NHC(NH)NH$_2$. In another embodiment, $R_{101}$ is independently selected from (C$_1$-C$_3$)alkyl, (C$_2$-C$_3$)alkenyl, halogen, —NH$_2$, and —NHheteroaryl, wherein the alkyl is optionally substituted with one to three substituents independently selected from —NH$_2$ and —NHC(NH)NH$_2$.

In some embodiments of the Formulae above, r is 0, 1, 2, or 3. In another embodiment, r is 0. In yet another embodiment, r is 1. In yet another embodiment, r is 2. In yet another embodiment, r is 3.

In some embodiments of the Formulae above, s is 0 or 1. In another embodiment, s is 0. In yet another embodiment, s is 1.

In another embodiment, r is 0 and s is 0. In another embodiment, r is 3 and s is 1.

In some embodiments of the Formulae above, $R_{70}$ is H or —C(NH)NH$_2$. In another embodiment, $R_{70}$ is H. In yet another embodiment, $R_{70}$ is —C(NH)NH$_2$.

In some embodiments of the Formulae above, $R_{80}$ is H or (C$_1$-C$_5$)alkyl, wherein the alkyl optionally substituted with one or more substituents independently selected from (C$_1$-C$_2$)alkyl, (C$_2$-C$_4$)alkenyl, (C$_1$-C$_2$)haloalkyl, (C$_1$-C$_2$) hydroxyalkyl, and —NH$_2$. In another embodiment, $R_{80}$ is H. In yet another embodiment, $R_{80}$ is (C$_1$-C$_5$)alkyl substituted with one or more substituents independently selected from (C$_1$-C$_2$)alkyl, (C$_2$-C$_4$)alkenyl, (C$_1$-C$_2$)haloalkyl, (C$_1$-C$_2$) hydroxyalkyl, and —NH$_2$. In another embodiment, $R_{80}$ is (C$_1$-C$_5$)alkyl optionally substituted with one or more substituents independently selected from (C$_1$-C$_2$)alkyl and —NH$_2$.

In some embodiments of the Formulae above, o is 0, 1, 2, or 3. In another embodiment, o is 0. In yet another embodiment, o is 1. In another embodiment, o is 2. In yet another embodiment, o is 3.

In some embodiments of the Formulae above, q is 0 or 1. In another embodiment, q is 0. In yet another embodiment, q is 1.

In some embodiments of the Formulae above, o is 0 and q is 0. In another embodiment, o is 3 and q is 1.

In some embodiments, the present disclosure relates to a compound or a tautomer thereof, or a pharmaceutically acceptable salt, ester, or prodrug of said compound or tautomer, according to any one the compounds in Table 1 or Table 1a.

TABLE 1

| Cmpd No. | Structure | ESI, m/z [M + H]+ |
|---|---|---|
| 1 | 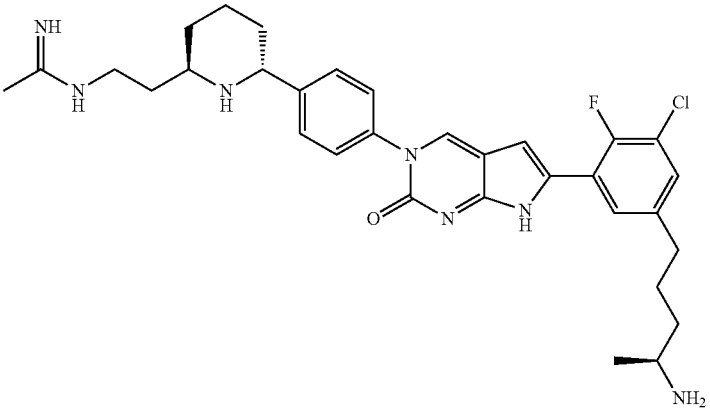 [SMILES: CC(=N)NCC[C@H]1CCC[C@H](c2ccc(-n3cc4cc(-c5cc(CCC[C@H](C)N)cc(Cl)c5F)[nH]c4nc3=O)cc2)N1] | 592.6 |
| 2 | 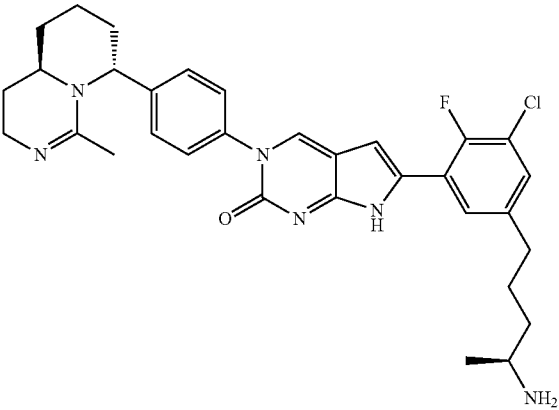 [SMILES: CC1=NCC[C@H]2CCC[C@H](c3ccc(-n4cc5cc(-c6cc(CCC[C@H](C)N)cc(Cl)c6F)[nH]c5nc4=O)cc3)N12] | 575.6 |
| 3 | 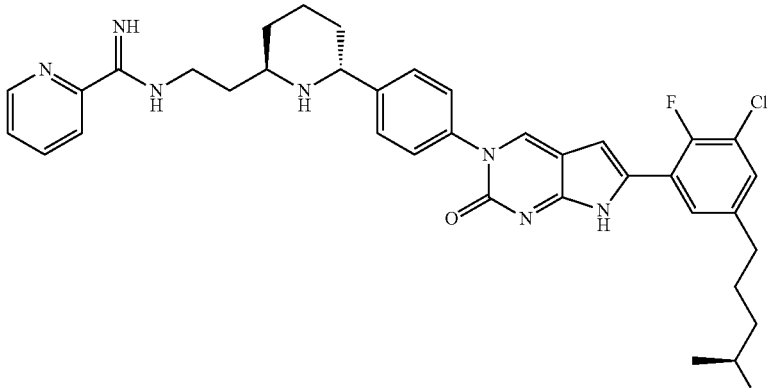 | 655.7 |

TABLE 1-continued

| Cmpd No. | Structure | ESI, m/z [M + H]+ |
|---|---|---|
| 4 | 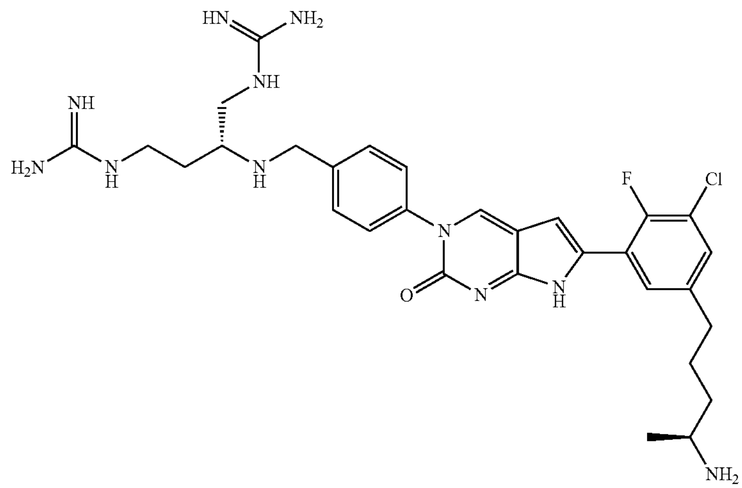 [SMILES: C[C@H](N)CCCc1cc(Cl)c(F)c(-c2cc3cn(-c4ccc(CN[C@H](CCNC(=N)N)CNC(=N)N)cc4)c(=O)nc3[nH]2)c1] | 624 |
| 5 | 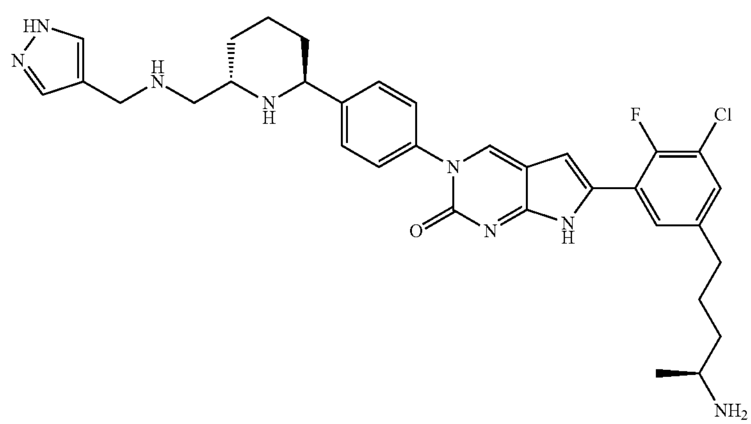 [SMILES: C[C@H](N)CCCc1cc(Cl)c(F)c(-c2cc3cn(-c4ccc([C@@H]5CCC[C@@H](CNCc6cn[nH]c6)N5)cc4)c(=O)nc3[nH]2)c1] | 617 |
| 6 | 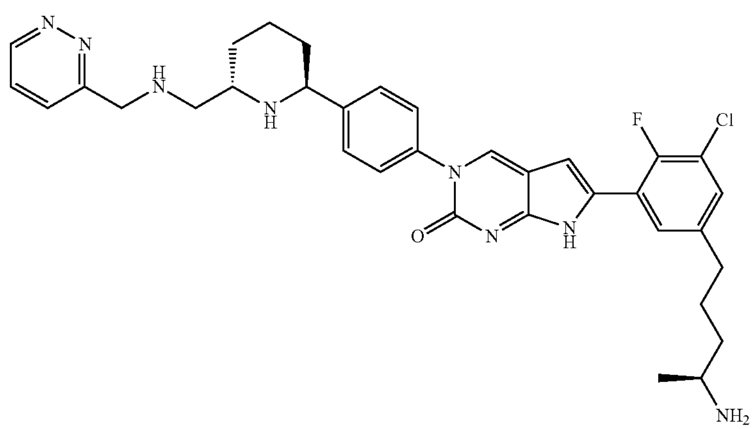 [SMILES: C[C@H](N)CCCc1cc(Cl)c(F)c(-c2cc3cn(-c4ccc([C@@H]5CCC[C@@H](CNCc6cccnn6)N5)cc4)c(=O)nc3[nH]2)c1] | 629 |

TABLE 1-continued

| Cmpd No. | Structure | ESI, m/z [M + H]+ |
|---|---|---|
| 7 | 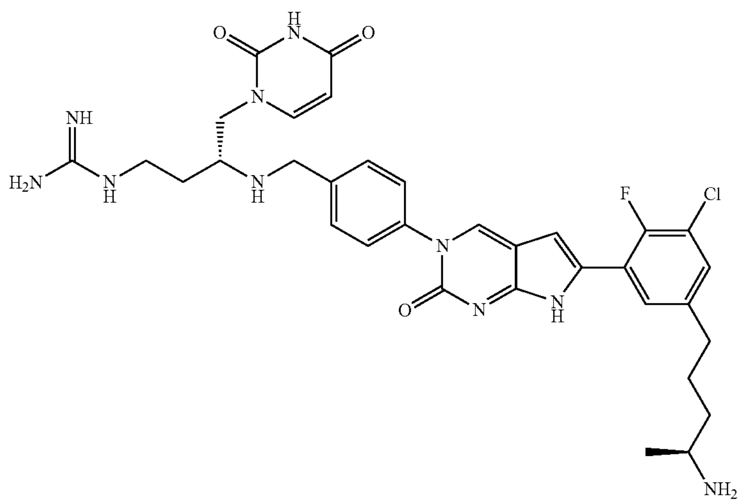 [SMILES: C[C@H](N)CCCc1cc(Cl)c(F)c(-c2cc3cn(-c4ccc(CN[C@H](CCNC(=N)N)Cn5ccc(=O)[nH]c5=O)cc4)c(=O)nc3[nH]2)c1] | 677 |
| 8 | 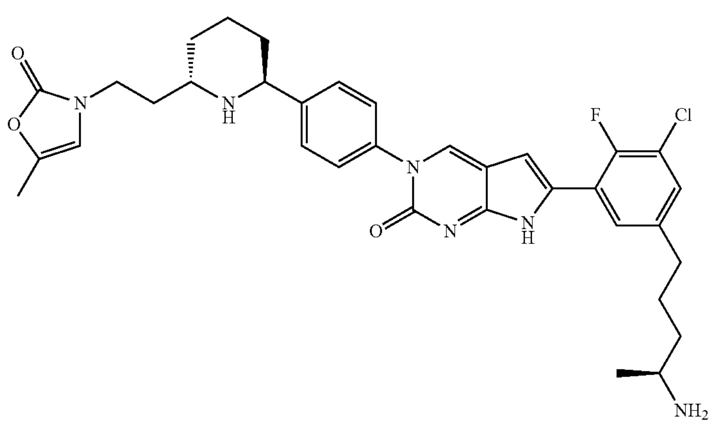 [SMILES: Cc1cn(CC[C@@H]2CCC[C@@H](c3ccc(-n4cc5cc(-c6cc(CCC[C@H](C)N)cc(Cl)c6F)[nH]c5nc4=O)cc3)N2)c(=O)o1] | 633 |
| 9 | 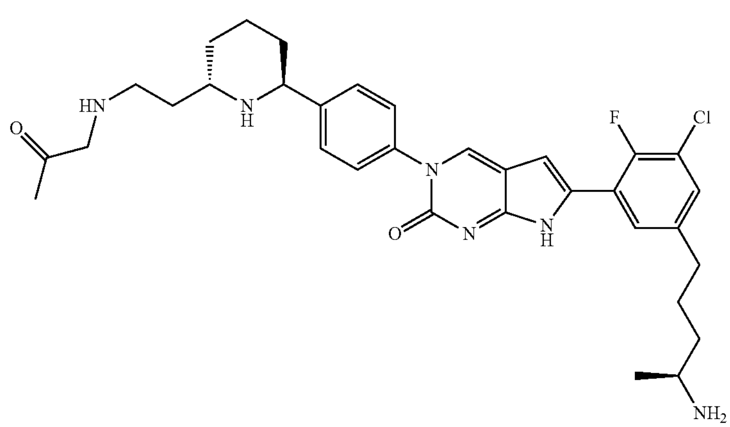 [SMILES: CC(=O)CNCC[C@@H]1CCC[C@@H](c2ccc(-n3cc4cc(-c5cc(CCC[C@H](C)N)cc(Cl)c5F)[nH]c4nc3=O)cc2)N1] | 607 |

TABLE 1-continued

| Cmpd No. | Structure | ESI, m/z [M + H]+ |
|---|---|---|
| 10 | 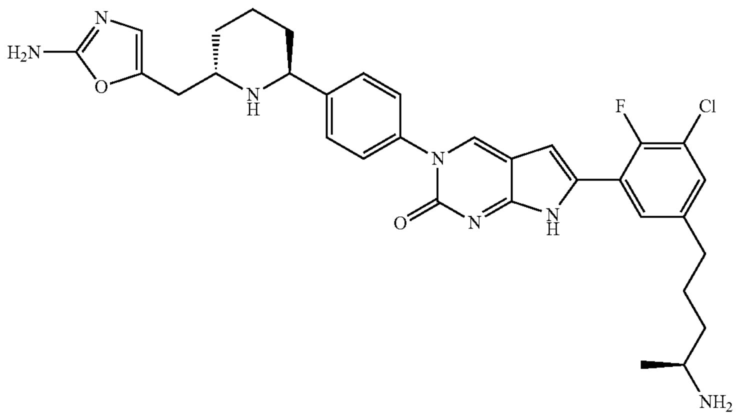 [SMILES: C[C@H](N)CCCc1cc(Cl)c(F)c(-c2cc3cn(-c4ccc([C@@H]5CCC[C@@H](Cc6cnc(N)o6)N5)cc4)c(=O)nc3[nH]2)c1] | 604 |
| 11 | 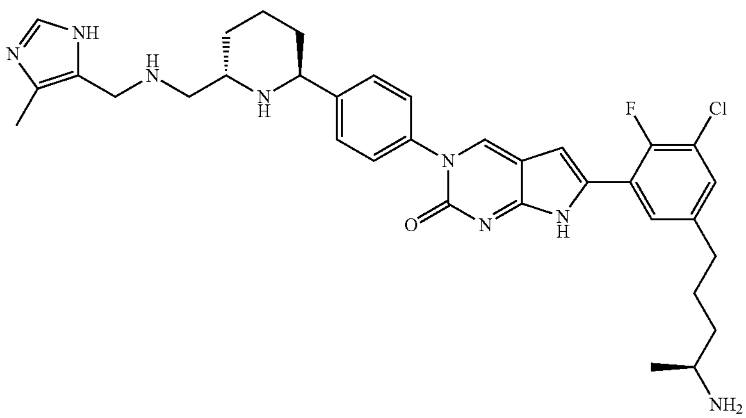 [SMILES: Cc1nc[nH]c1CNC[C@@H]1CCC[C@@H](c2ccc(-n3cc4cc(-c5cc(CCC[C@H](C)N)cc(Cl)c5F)[nH]c4nc3=O)cc2)N1] | 631 |
| 12 | 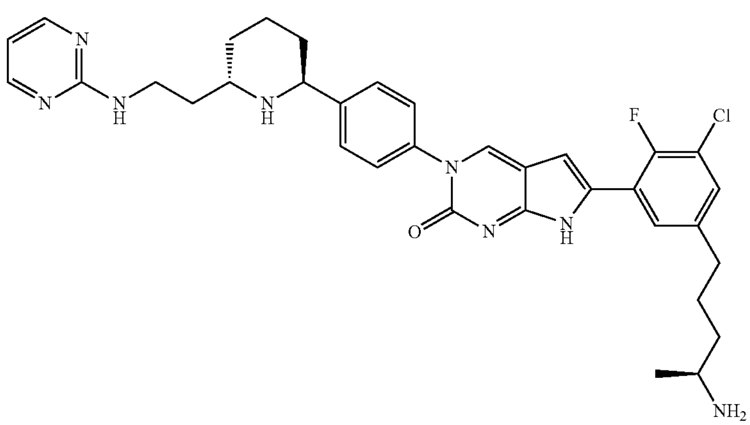 [SMILES: C[C@H](N)CCCc1cc(Cl)c(F)c(-c2cc3cn(-c4ccc([C@@H]5CCC[C@@H](CCNc6ncccn6)N5)cc4)c(=O)nc3[nH]2)c1] | 629.6 |

TABLE 1-continued
| Cmpd No. | Structure | ESI, m/z [M + H]+ |
|---|---|---|
| 13 | 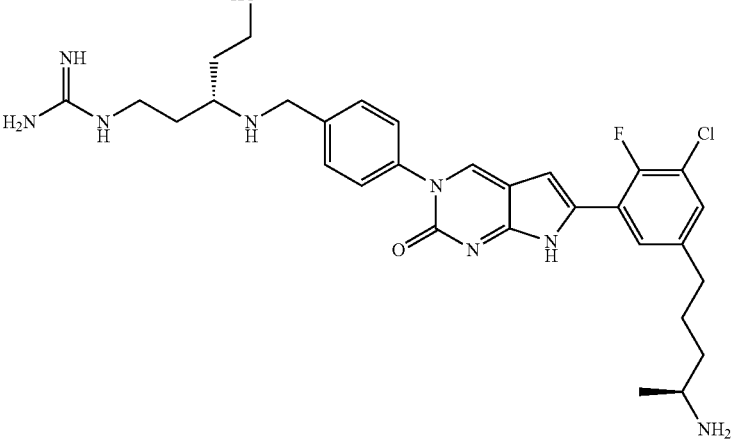 | 598.7 |
| 14 | 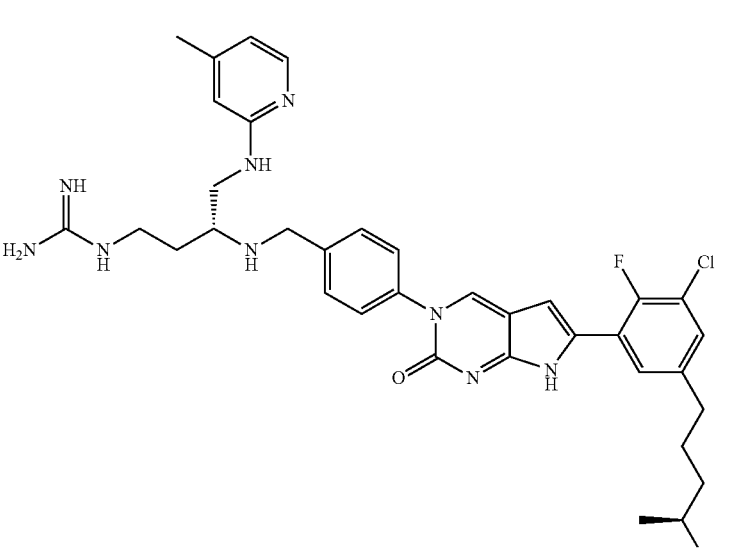 | 673 |
| 15 | 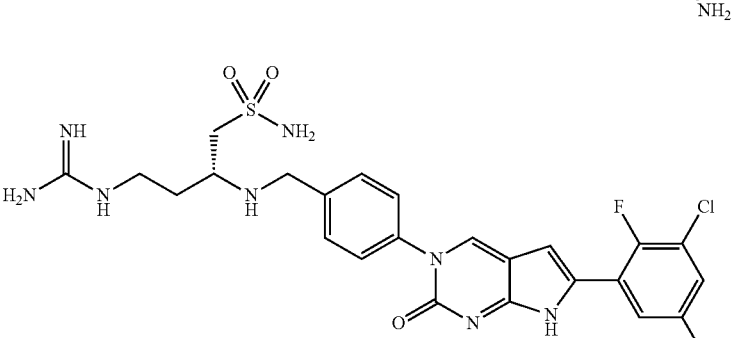 | 646 |

TABLE 1-continued

| Cmpd No. | Structure | ESI, m/z [M + H]+ |
|---|---|---|
| 16 | 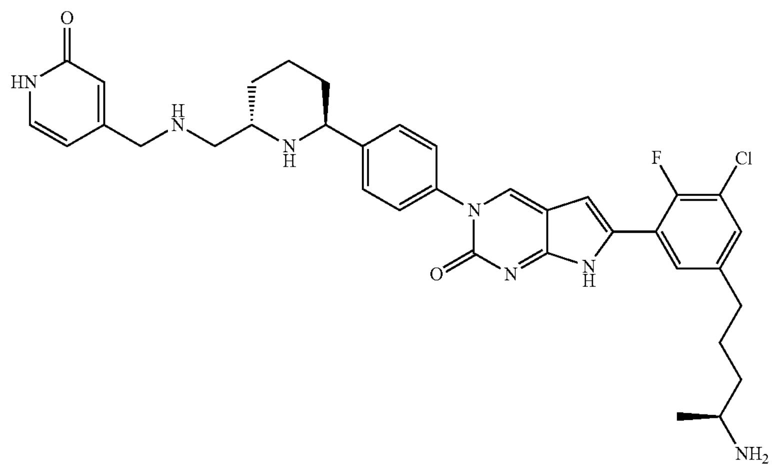 [SMILES: C[C@H](N)CCCc1cc(Cl)c(F)c(-c2cc3cn(-c4ccc([C@@H]5CCC[C@@H](CNCc6cc[nH]c(=O)c6)N5)cc4)c(=O)nc3[nH]2)c1] | 644 |
| 17 | 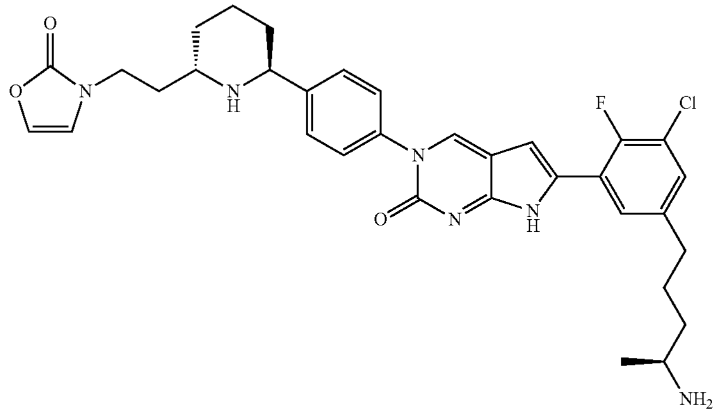 [SMILES: C[C@H](N)CCCc1cc(Cl)c(F)c(-c2cc3cn(-c4ccc([C@@H]5CCC[C@@H](CCn6ccoc6=O)N5)cc4)c(=O)nc3[nH]2)c1] | 619 |
| 18 | 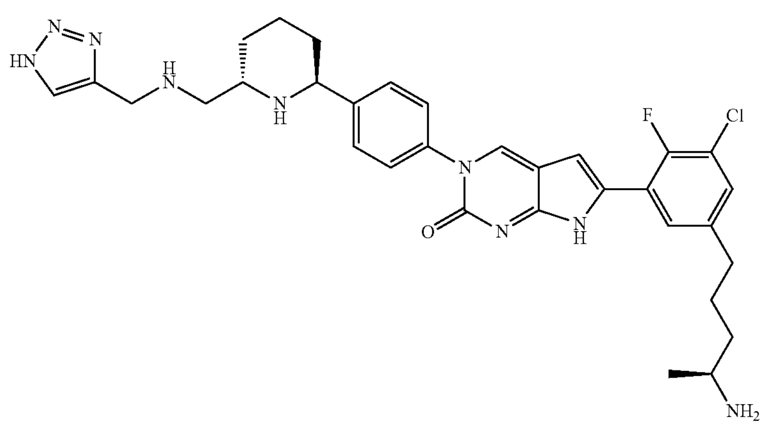 [SMILES: C[C@H](N)CCCc1cc(Cl)c(F)c(-c2cc3cn(-c4ccc([C@@H]5CCC[C@@H](CNCc6c[nH]nn6)N5)cc4)c(=O)nc3[nH]2)c1] | 618 |

TABLE 1-continued

| Cmpd No. | Structure | ESI, m/z [M + H]+ |
|---|---|---|
| 19 | 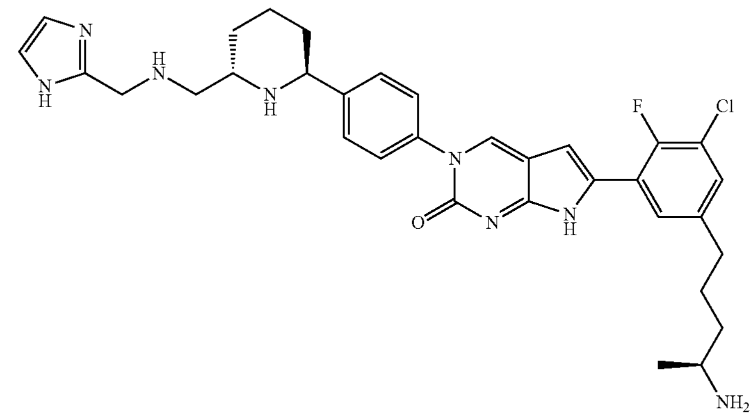 [SMILES: C[C@H](N)CCCc1cc(Cl)c(F)c(-c2cc3cn(-c4ccc([C@@H]5CCC[C@@H](CNCc6ncc[nH]6)N5)cc4)c(=O)nc3[nH]2)c1] | 615 |
| 20 | 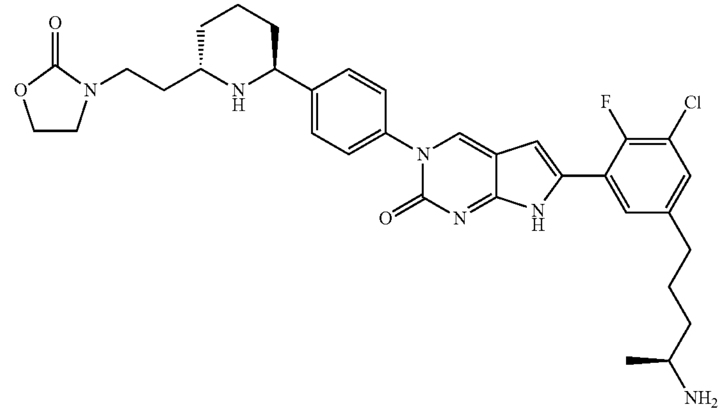 [SMILES: C[C@H](N)CCCc1cc(Cl)c(F)c(-c2cc3cn(-c4ccc([C@@H]5CCC[C@@H](CCN6CCOC6=O)N5)cc4)c(=O)nc3[nH]2)c1] | 621 |
| 21 | 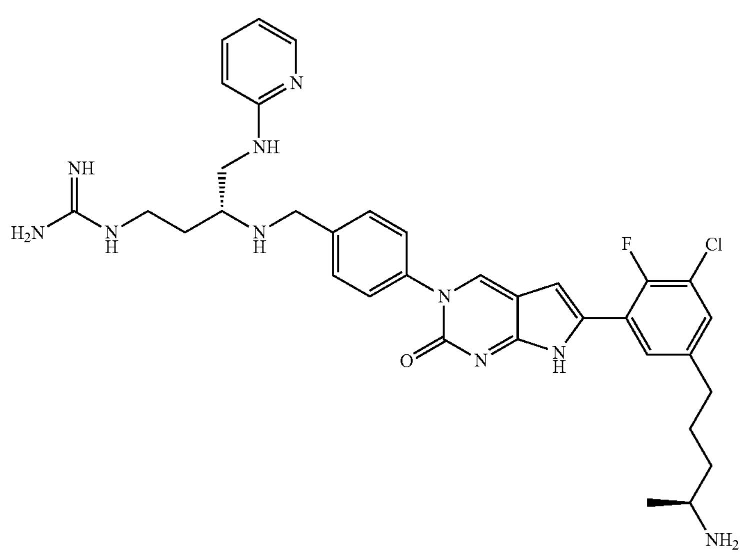 [SMILES: C[C@H](N)CCCc1cc(Cl)c(F)c(-c2cc3cn(-c4ccc(CN[C@H](CCNC(=N)N)CNc5ccccn5)cc4)c(=O)nc3[nH]2)c1] | 659 |

TABLE 1-continued
| Cmpd No. | Structure | ESI, m/z [M + H]+ |
|---|---|---|
| 22 | 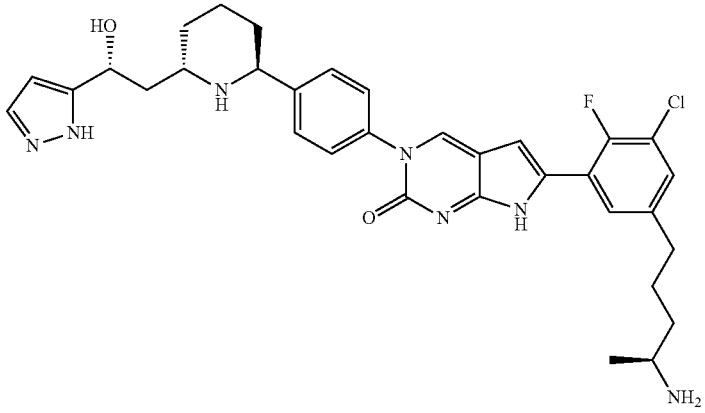 [SMILES: C[C@H](N)CCCc1cc(Cl)c(F)c(-c2cc3cn(-c4ccc([C@@H]5CCC[C@@H](C[C@@H](O)c6ccn[nH]6)N5)cc4)c(=O)nc3[nH]2)c1] | 618 |
| 23 | 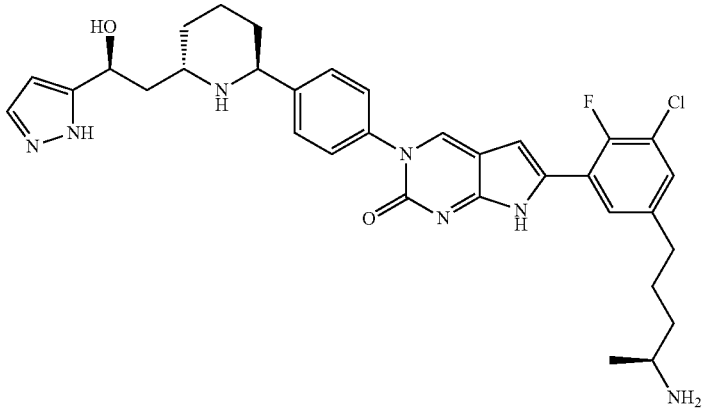 [SMILES: C[C@H](N)CCCc1cc(Cl)c(F)c(-c2cc3cn(-c4ccc([C@@H]5CCC[C@@H](C[C@H](O)c6ccn[nH]6)N5)cc4)c(=O)nc3[nH]2)c1] | 618 |
| 24 | 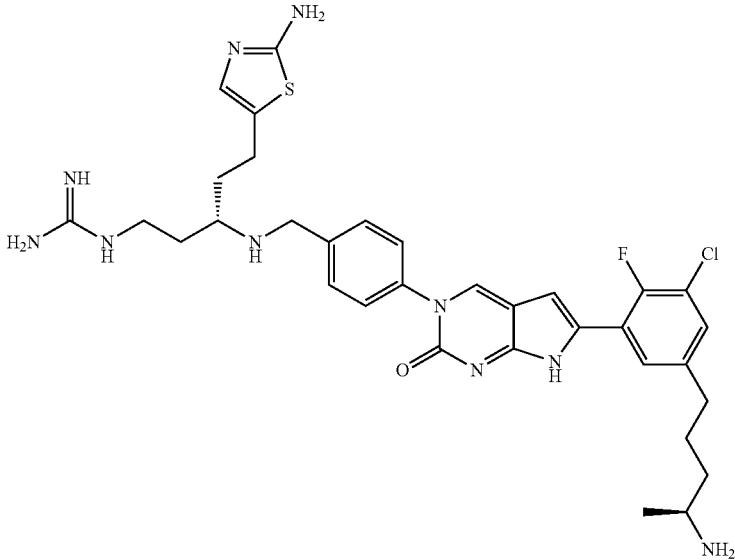 [SMILES: C[C@H](N)CCCc1cc(Cl)c(F)c(-c2cc3cn(-c4ccc(CN[C@H](CCNC(=N)N)CCc5cnc(N)s5)cc4)c(=O)nc3[nH]2)c1] | 679.6 |

TABLE 1-continued

| Cmpd No. | Structure | ESI, m/z [M + H]+ |
|---|---|---|
| 25 | 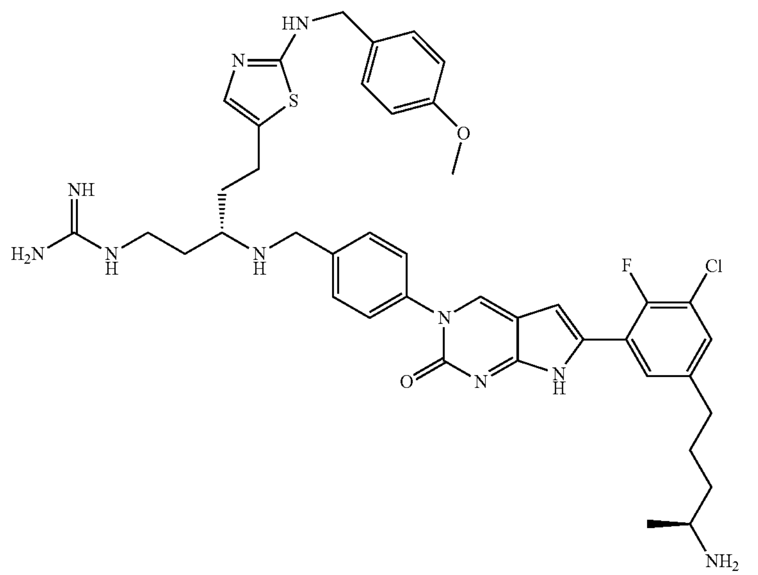 [SMILES: COc1ccc(CNc2ncc(CC[C@@H](CCNC(=N)N)NCc3ccc(-n4cc5cc(-c6cc(CCC[C@H](C)N)cc(Cl)c6F)[nH]c5nc4=O)cc3)s2)cc1] | 799.7 |
| 26 | 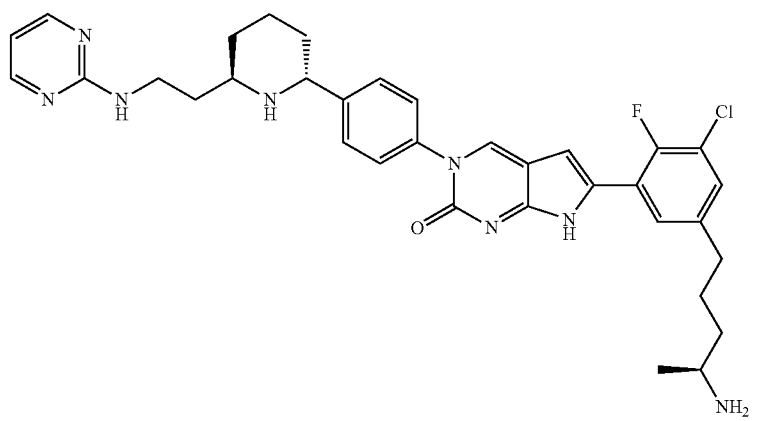 [SMILES: C[C@H](N)CCCc1cc(Cl)c(F)c(-c2cc3cn(-c4ccc([C@H]5CCC[C@H](CCNc6ncccn6)N5)cc4)c(=O)nc3[nH]2)c1] | 629.6 |
| 27 | 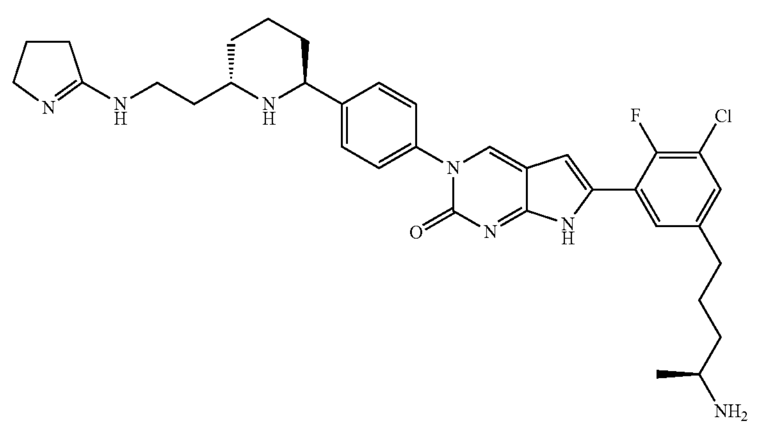 [SMILES: C[C@H](N)CCCc1cc(Cl)c(F)c(-c2cc3cn(-c4ccc([C@@H]5CCC[C@@H](CCNC6=NCCC6)N5)cc4)c(=O)nc3[nH]2)c1] | 618.7 |

TABLE 1-continued
| Cmpd No. | Structure | ESI, m/z [M + H]+ |
|---|---|---|
| 28 | 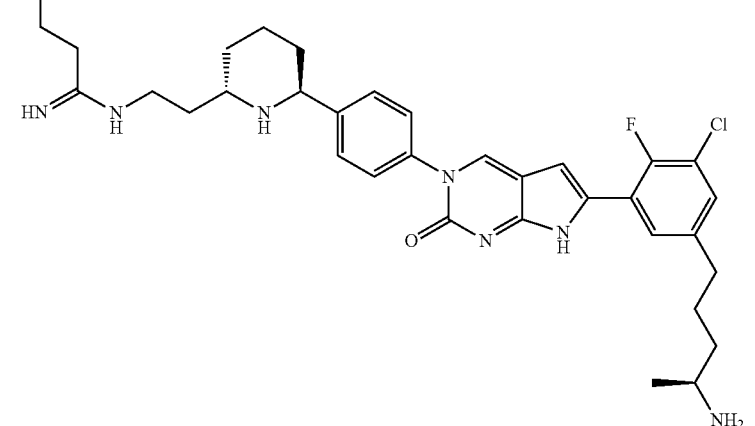 | 654.7 |
| 29 | 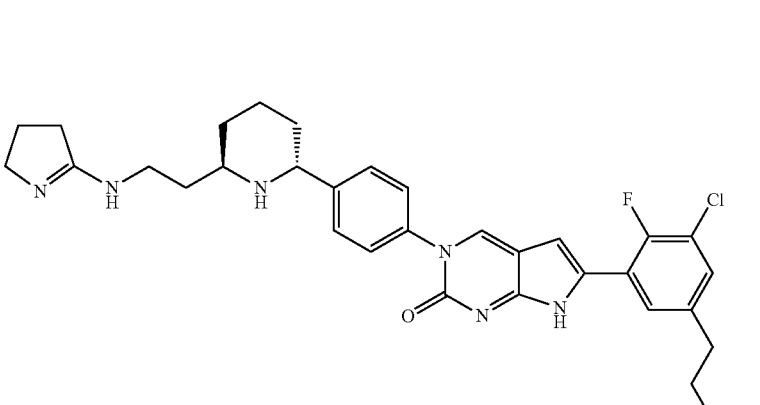 | 618.6 |
| 30 | 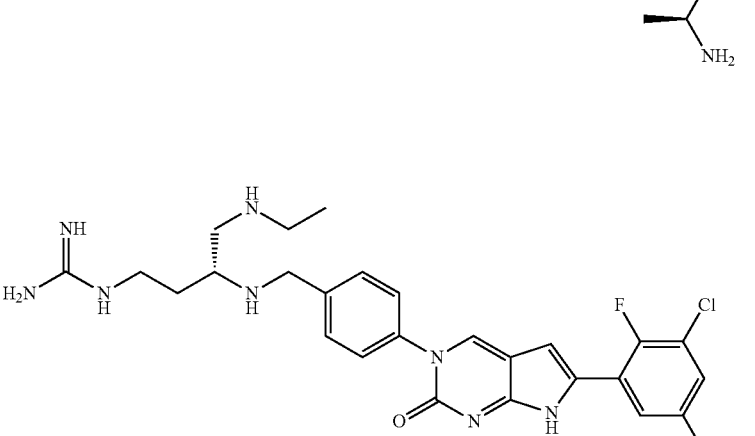 | 610 |

TABLE 1-continued

| Cmpd No. | Structure | ESI, m/z [M + H]+ |
|---|---|---|
| 31 | 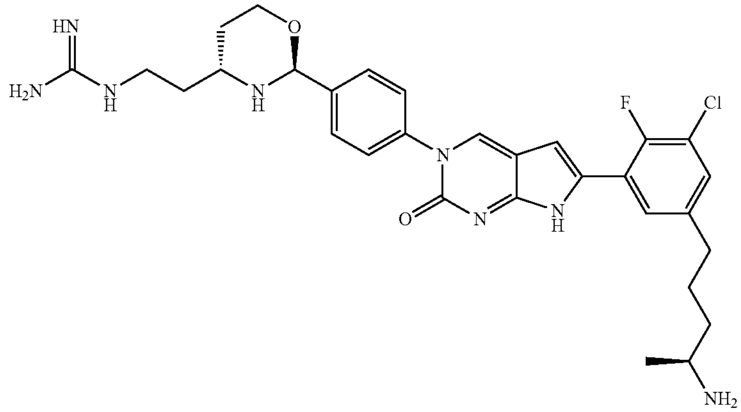 [SMILES: C[C@H](N)CCCc1cc(Cl)c(F)c(-c2cc3cn(-c4ccc([C@H]5N[C@H](CCNC(=N)N)CCO5)cc4)c(=O)nc3[nH]2)c1] | 595.13 |
| 32 | 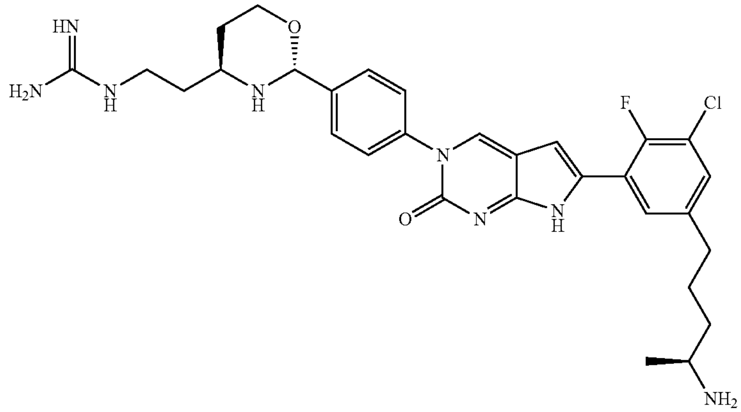 [SMILES: C[C@H](N)CCCc1cc(Cl)c(F)c(-c2cc3cn(-c4ccc([C@@H]5N[C@@H](CCNC(=N)N)CCO5)cc4)c(=O)nc3[nH]2)c1] | 595.13 |
| 33 | 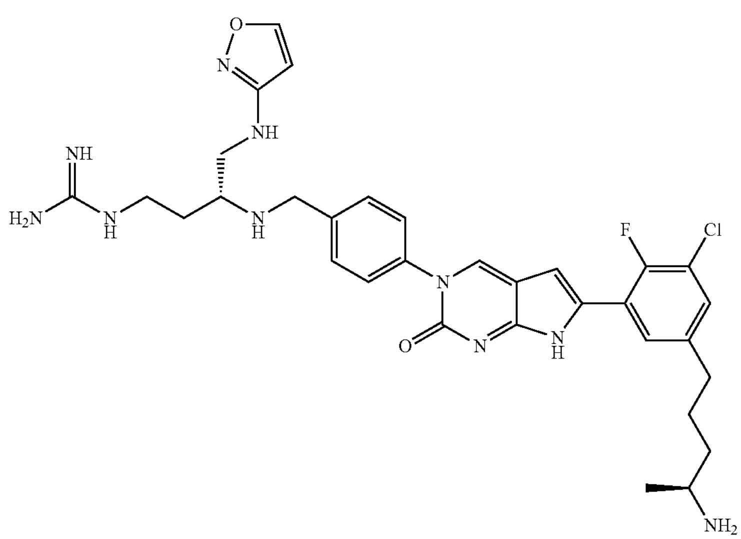 [SMILES: C[C@H](N)CCCc1cc(Cl)c(F)c(-c2cc3cn(-c4ccc(CN[C@H](CCNC(=N)N)CNc5ccon5)cc4)c(=O)nc3[nH]2)c1] | 649 |

TABLE 1-continued

| Cmpd No. | Structure | ESI, m/z [M + H]+ |
|---|---|---|
| 34 | 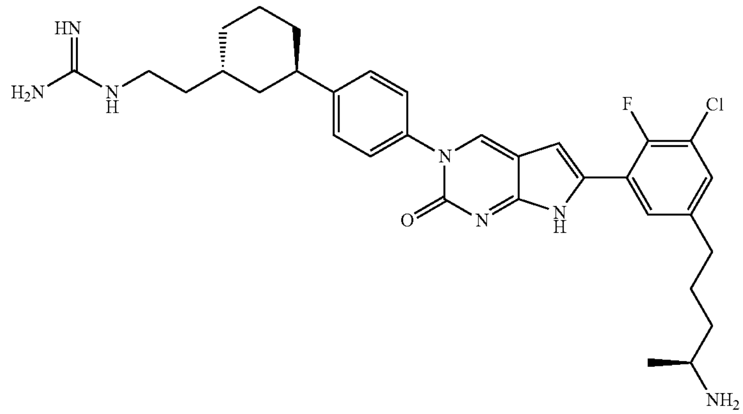 [SMILES: C[C@H](N)CCCc1cc(Cl)c(F)c(-c2cc3cn(-c4ccc([C@@H]5CCC[C@@H](CCNC(=N)N)C5)cc4)c(=O)nc3[nH]2)c1] | 593.16 |
| 35 | 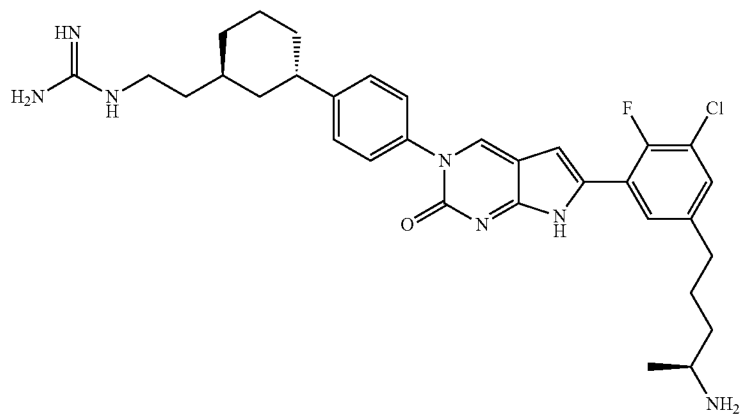 [SMILES: C[C@H](N)CCCc1cc(Cl)c(F)c(-c2cc3cn(-c4ccc([C@H]5CCC[C@H](CCNC(=N)N)C5)cc4)c(=O)nc3[nH]2)c1] | 593.16 |
| 36 | 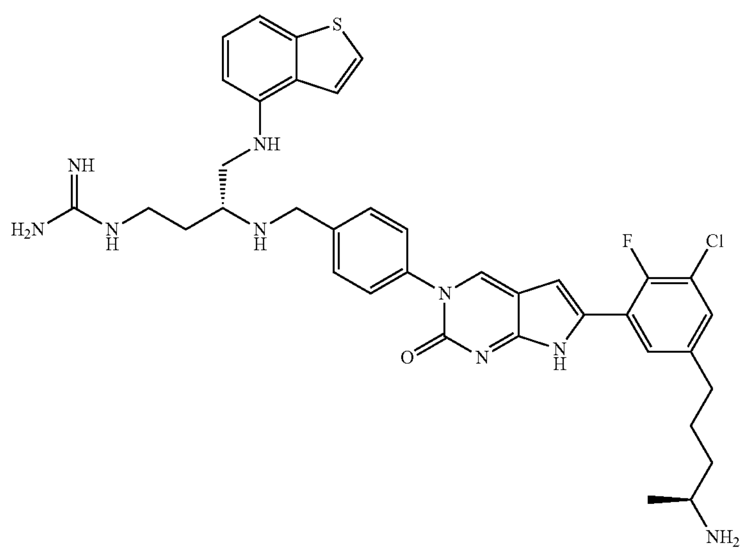 [SMILES: C[C@H](N)CCCc1cc(Cl)c(F)c(-c2cc3cn(-c4ccc(CN[C@H](CCNC(=N)N)CNc5cccc6sccc56)cc4)c(=O)nc3[nH]2)c1] | 714 |

TABLE 1-continued

| Cmpd No. | Structure | ESI, m/z [M + H]+ |
|---|---|---|
| 37 | 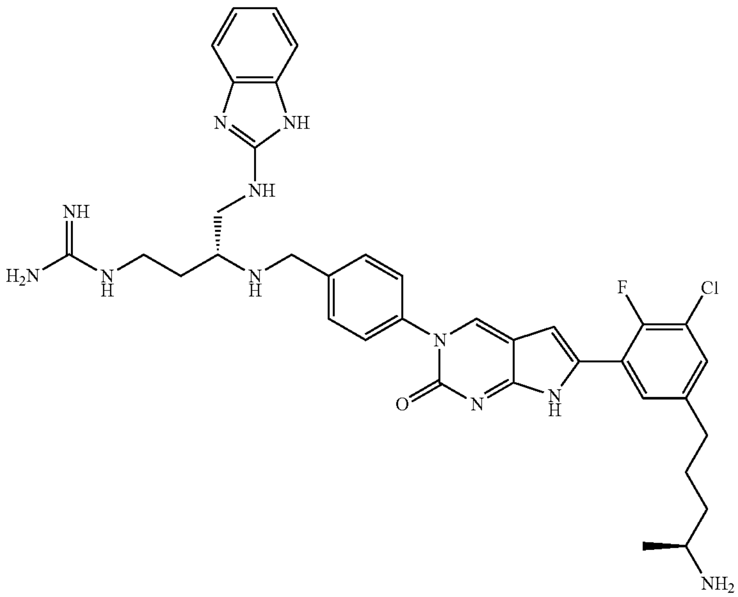 [SMILES: C[C@H](N)CCCc1cc(Cl)c(F)c(-c2cc3cn(-c4ccc(CN[C@H](CCNC(=N)N)CNc5nc6ccccc6[nH]5)cc4)c(=O)nc3[nH]2)c1] | 698 |
| 38 | 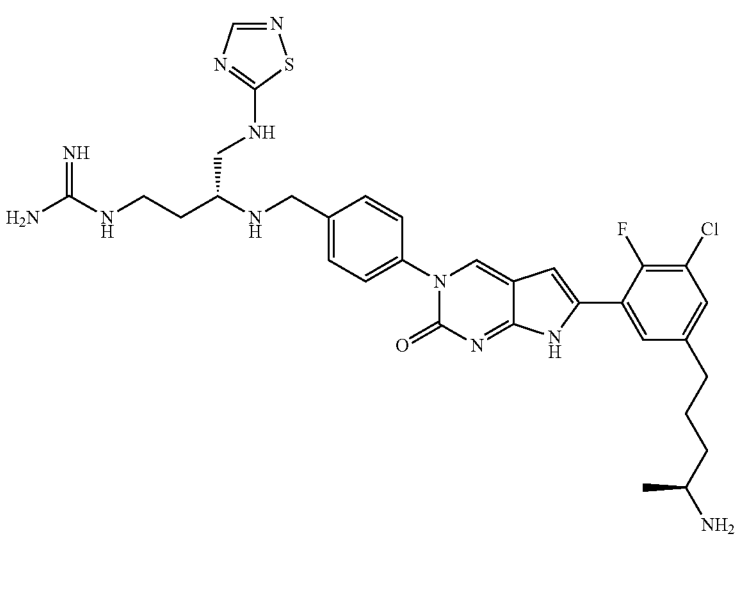 [SMILES: C[C@H](N)CCCc1cc(Cl)c(F)c(-c2cc3cn(-c4ccc(CN[C@H](CCNC(=N)N)CNc5ncns5)cc4)c(=O)nc3[nH]2)c1] | 666 |

TABLE 1-continued
| Cmpd No. | Structure | ESI, m/z [M + H]+ |
|---|---|---|
| 39 | 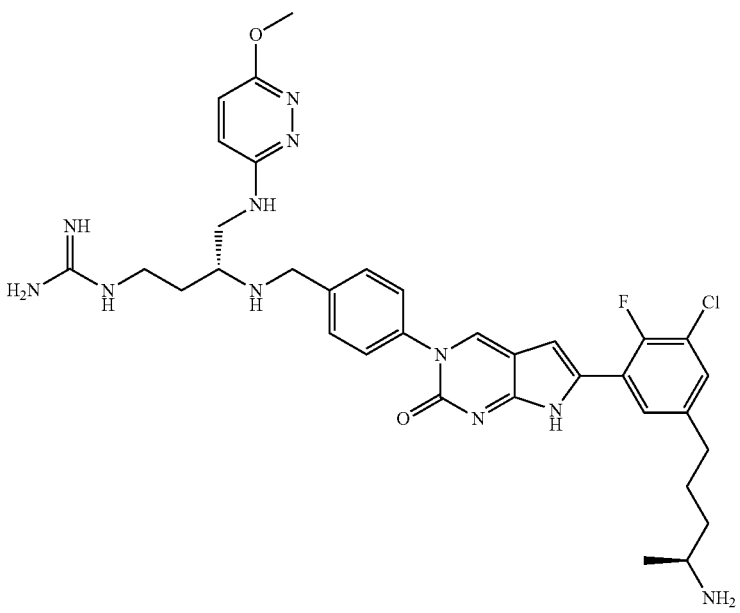 [SMILES: COc1ccc(NC[C@@H](CCNC(=N)N)NCc2ccc(-n3cc4cc(-c5cc(CCC[C@H](C)N)cc(Cl)c5F)[nH]c4nc3=O)cc2)nn1] | 690 |
| 40 | 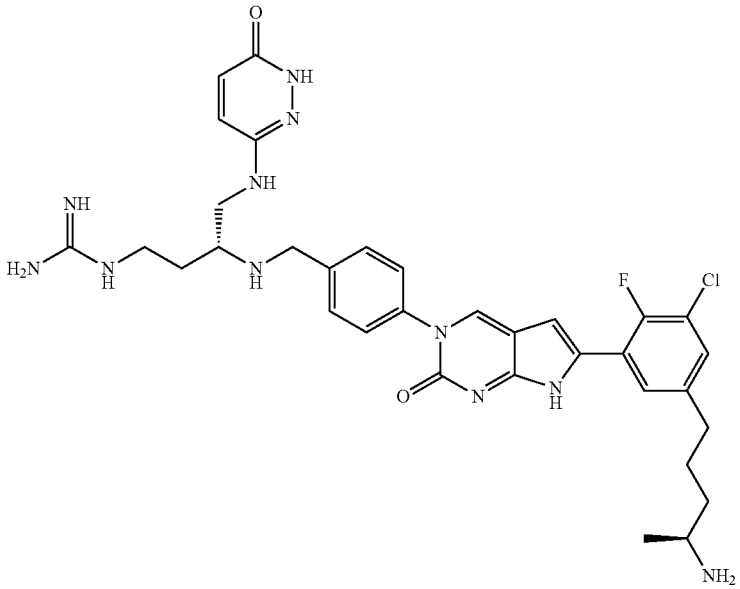 [SMILES: C[C@H](N)CCCc1cc(Cl)c(F)c(-c2cc3cn(-c4ccc(CN[C@H](CCNC(=N)N)CNc5ccc(=O)[nH]n5)cc4)c(=O)nc3[nH]2)c1] | 676 |

TABLE 1-continued
| Cmpd No. | Structure | ESI, m/z [M + H]+ |
|---|---|---|
| 41 | 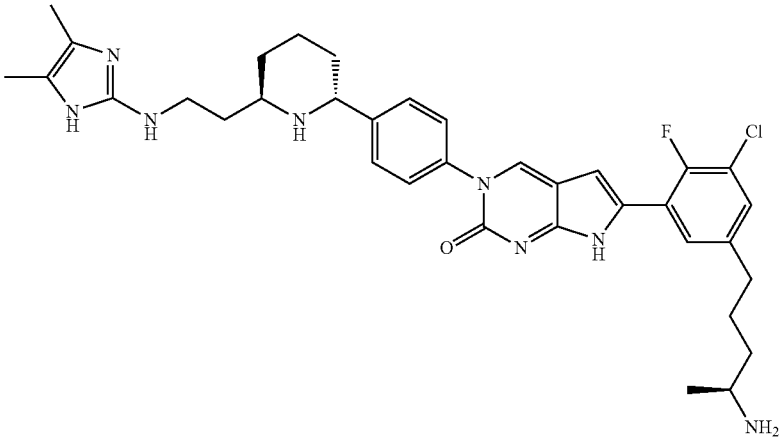 [SMILES: Cc1nc(NCC[C@H]2CCC[C@H](c3ccc(-n4cc5cc(-c6cc(CCC[C@H](C)N)cc(Cl)c6F)[nH]c5nc4=O)cc3)N2)[nH]c1C] | 645.6 |
| 42 | 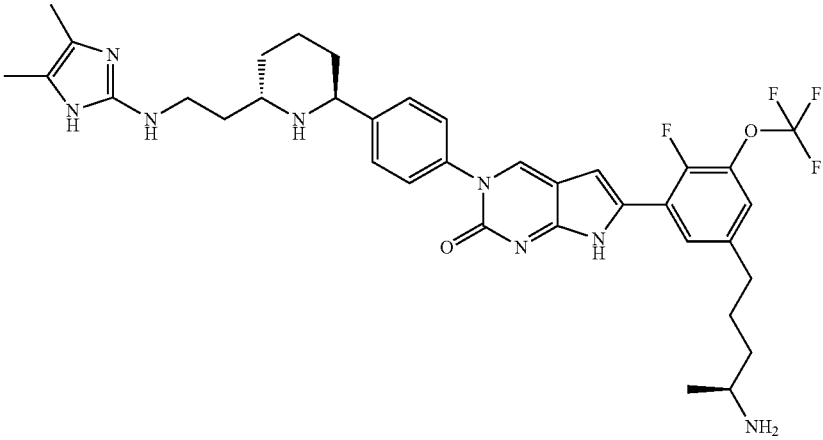 [SMILES: Cc1nc(NCC[C@@H]2CCC[C@@H](c3ccc(-n4cc5cc(-c6cc(CCC[C@H](C)N)cc(OC(F)(F)F)c6F)[nH]c5nc4=O)cc3)N2)[nH]c1C] | 695.7 |
| 43 | 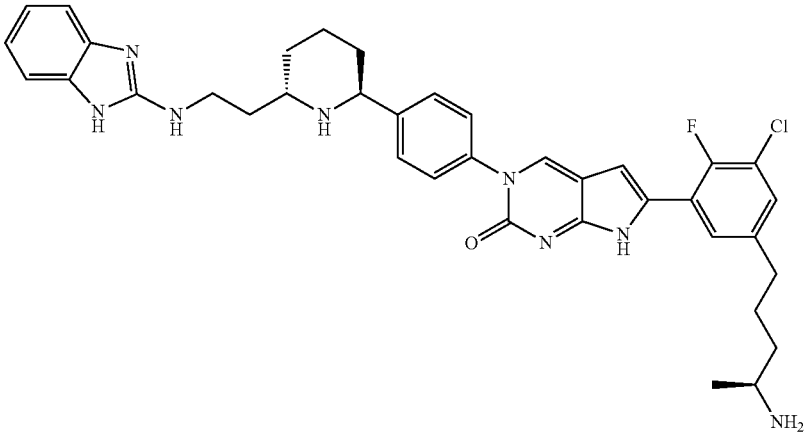 [SMILES: C[C@H](N)CCCc1cc(Cl)c(F)c(-c2cc3cn(-c4ccc([C@@H]5CCC[C@@H](CCNc6nc7ccccc7[nH]6)N5)cc4)c(=O)nc3[nH]2)c1] | 667.6 |

TABLE 1-continued

| Cmpd No. | Structure | ESI, m/z [M + H]+ |
|---|---|---|
| 44 | 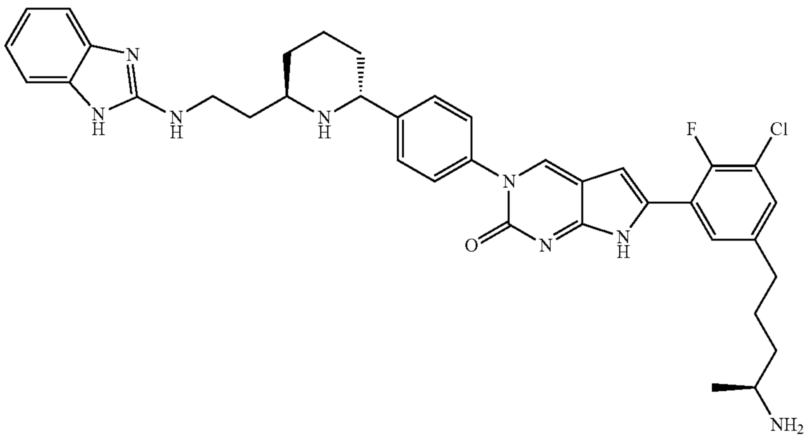 [SMILES: C[C@H](N)CCCc1cc(Cl)c(F)c(-c2cc3cn(-c4ccc([C@H]5CCC[C@H](CCNc6nc7ccccc7[nH]6)N5)cc4)c(=O)nc3[nH]2)c1] | 667.6 |
| 45 | 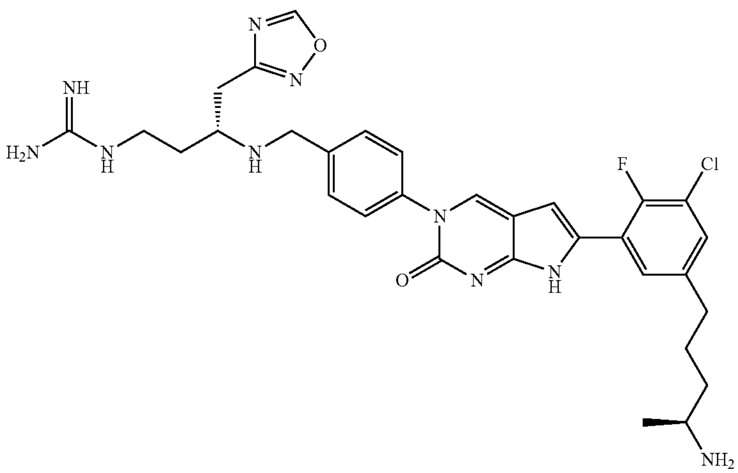 [SMILES: C[C@H](N)CCCc1cc(Cl)c(F)c(-c2cc3cn(-c4ccc(CN[C@H](CCNC(=N)N)Cc5ncon5)cc4)c(=O)nc3[nH]2)c1] | 635 |
| 46 | 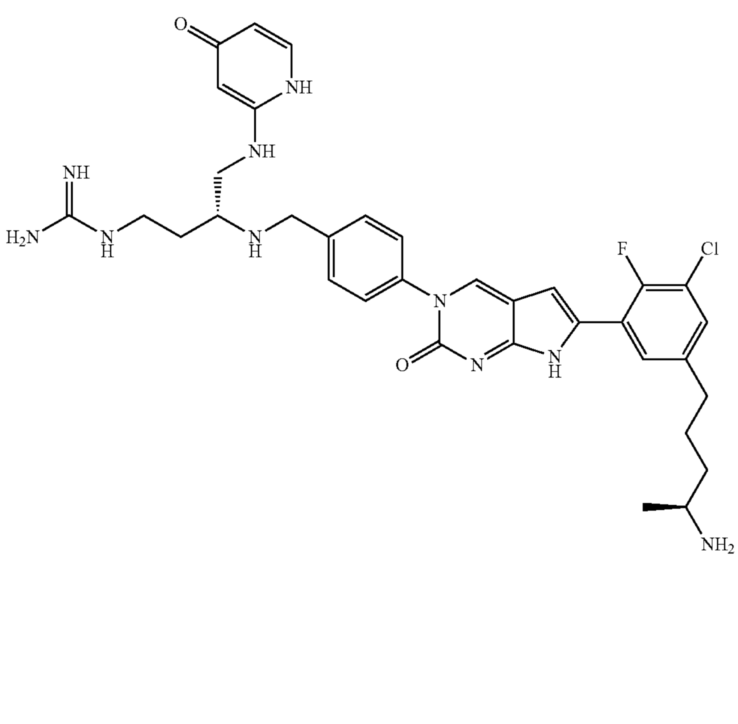 [SMILES: C[C@H](N)CCCc1cc(Cl)c(F)c(-c2cc3cn(-c4ccc(CN[C@H](CCNC(=N)N)CNc5cc(=O)cc[nH]5)cc4)c(=O)nc3[nH]2)c1] | 675 |

TABLE 1-continued
| Cmpd No. | Structure | ESI, m/z [M + H]+ |
|---|---|---|
| 47 | 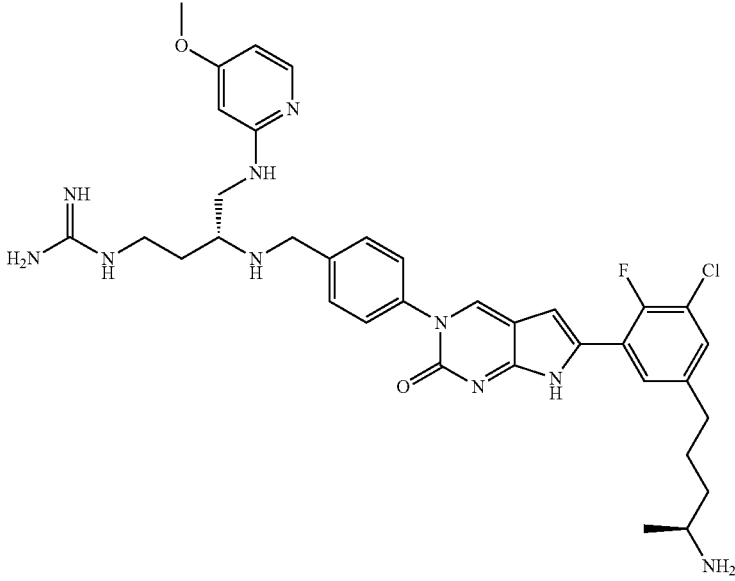 [SMILES: COc1ccnc(NC[C@@H](CCNC(=N)N)NCc2ccc(-n3cc4cc(-c5cc(CCC[C@H](C)N)cc(Cl)c5F)[nH]c4nc3=O)cc2)c1] | 689 |
| 48 | 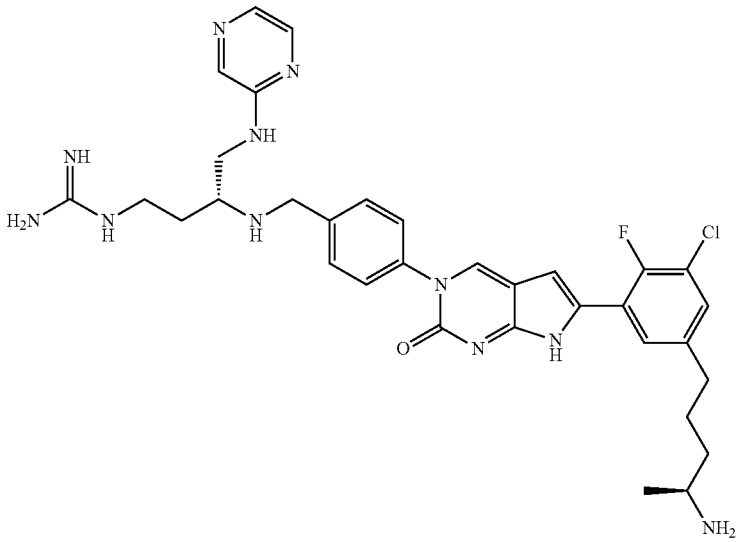 | 660 |

TABLE 1-continued

| Cmpd No. | Structure | ESI, m/z [M + H]+ |
|---|---|---|
| 49 | 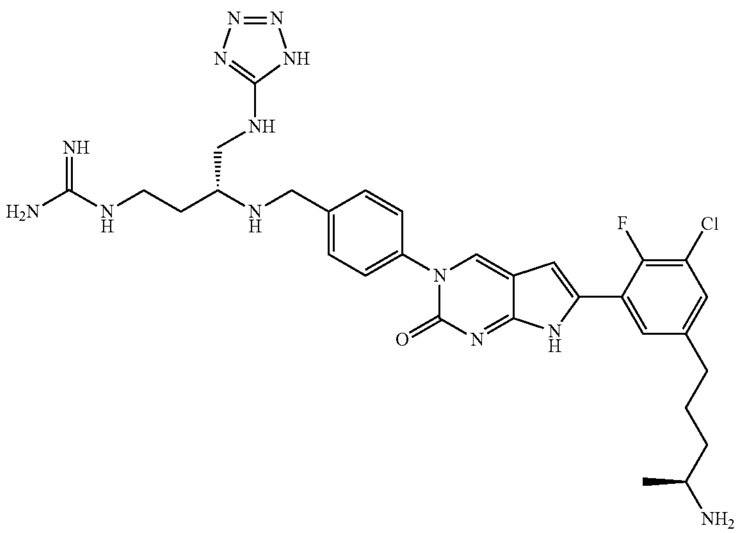 [SMILES: C[C@H](N)CCCc1cc(Cl)c(F)c(-c2cc3cn(-c4ccc(CN[C@H](CCNC(=N)N)CNc5nnn[nH]5)cc4)c(=O)nc3[nH]2)c1] | 650 |
| 50 | 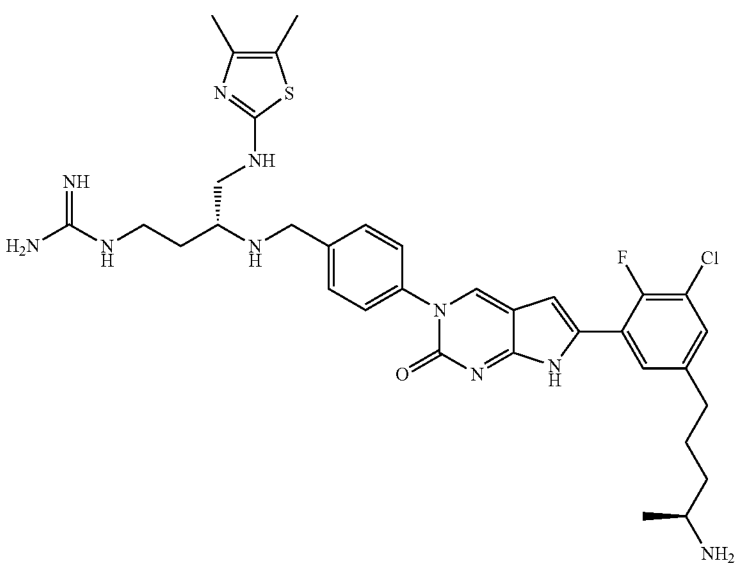 [SMILES: Cc1nc(NC[C@@H](CCNC(=N)N)NCc2ccc(-n3cc4cc(-c5cc(CCC[C@H](C)N)cc(Cl)c5F)[nH]c4nc3=O)cc2)sc1C] | 693 |

TABLE 1-continued

| Cmpd No. | Structure | ESI, m/z [M + H]+ |
|---|---|---|
| 51 | 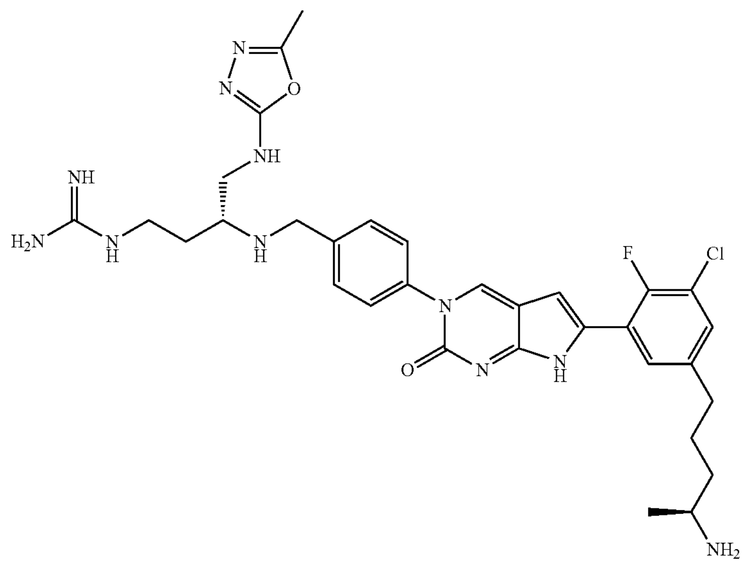 [SMILES: Cc1nnc(NC[C@@H](CCNC(=N)N)NCc2ccc(-n3cc4cc(-c5cc(CCC[C@H](C)N)cc(Cl)c5F)[nH]c4nc3=O)cc2)o1] | 664 |
| 52 | 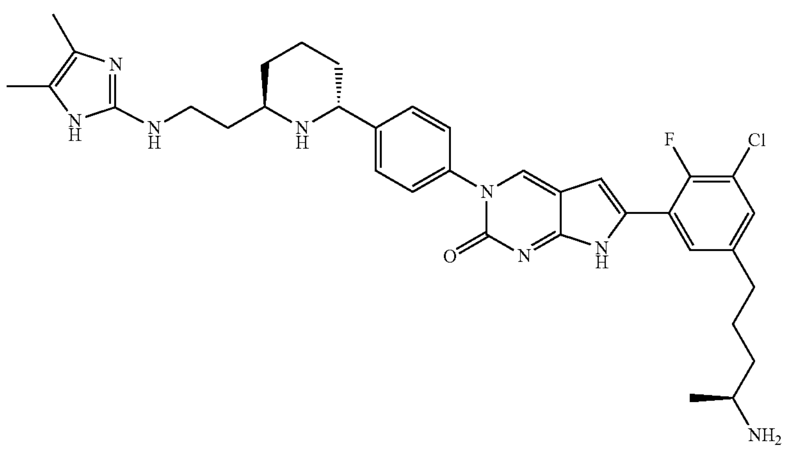 [SMILES: Cc1nc(NCC[C@H]2CCC[C@H](c3ccc(-n4cc5cc(-c6cc(CCC[C@H](C)N)cc(Cl)c6F)[nH]c5nc4=O)cc3)N2)[nH]c1C] | 645.6 |
| 53 | 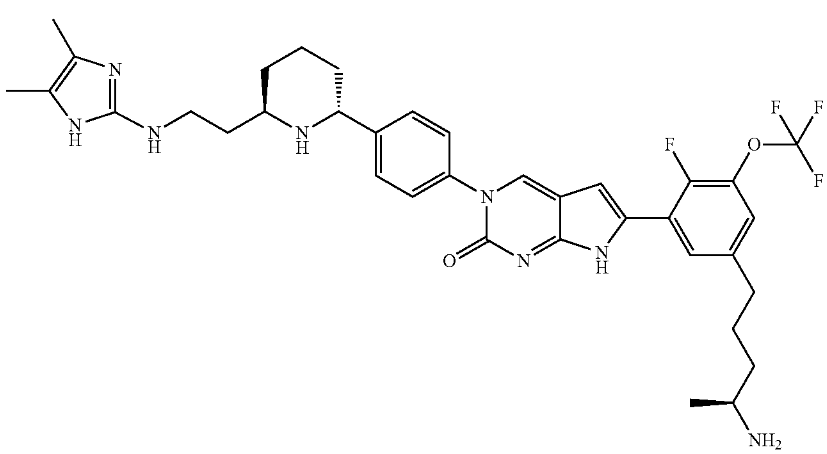 [SMILES: Cc1nc(NCC[C@H]2CCC[C@H](c3ccc(-n4cc5cc(-c6cc(CCC[C@H](C)N)cc(OC(F)(F)F)c6F)[nH]c5nc4=O)cc3)N2)[nH]c1C] | 695.5 |

TABLE 1-continued

| Cmpd No. | Structure | ESI, m/z [M + H]+ |
|---|---|---|
| 54 | 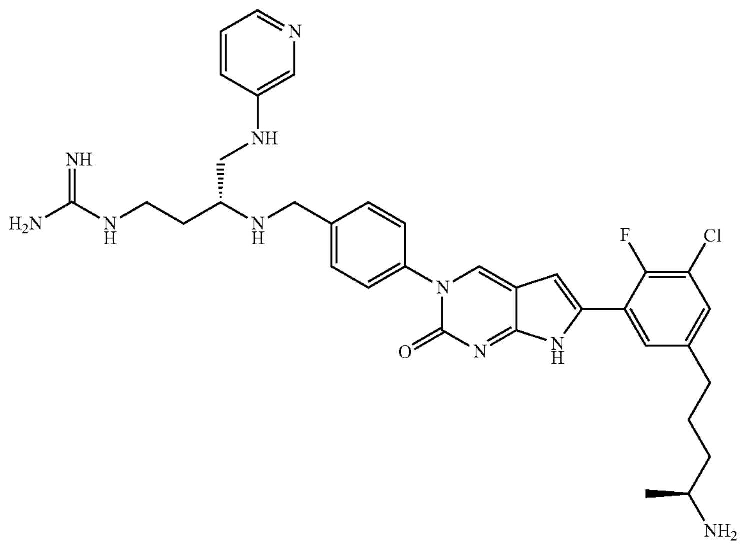 | 659 |
| 55 | 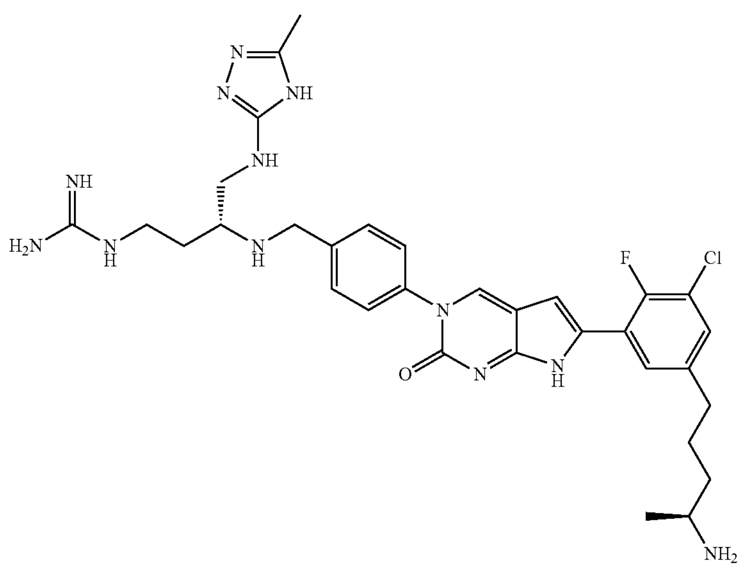 [SMILES: Cc1nnc(NC[C@@H](CCNC(=N)N)NCc2ccc(-n3cc4cc(-c5cc(CCC[C@H](C)N)cc(Cl)c5F)[nH]c4nc3=O)cc2)[nH]1] | 663 |

TABLE 1-continued
| Cmpd No. | Structure | ESI, m/z [M + H]+ |
|---|---|---|
| 56 | 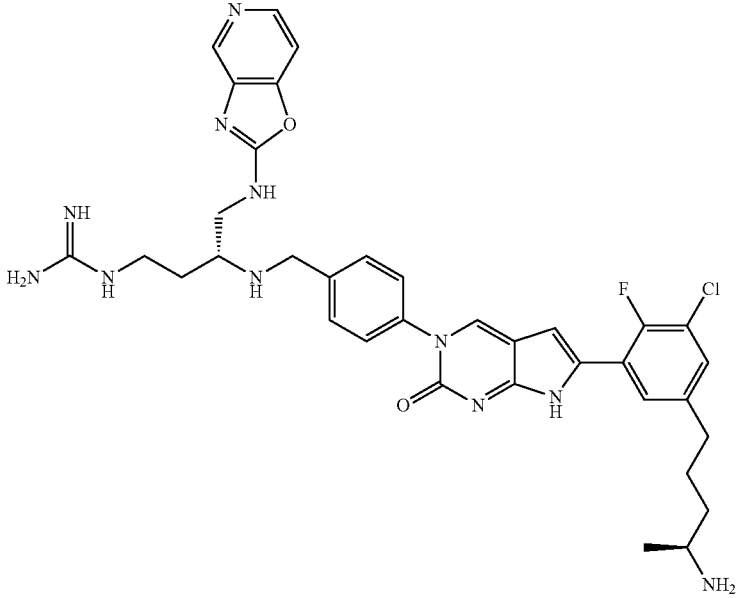 [SMILES: C[C@H](N)CCCc1cc(Cl)c(F)c(-c2cc3cn(-c4ccc(CN[C@H](CCNC(=N)N)CNc5nc6cnccc6o5)cc4)c(=O)nc3[nH]2)c1] | 700 |
| 57 | 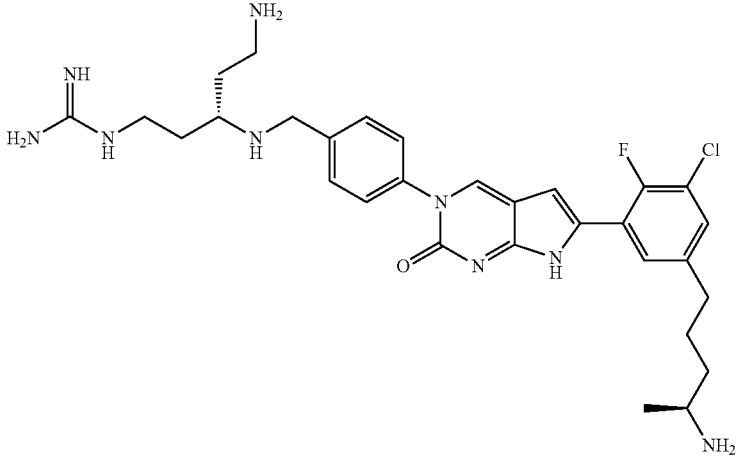 [SMILES: C[C@H](N)CCCc1cc(Cl)c(F)c(-c2cc3cn(-c4ccc(CN[C@@H](CCN)CCNC(=N)N)cc4)c(=O)nc3[nH]2)c1] | 596 |

TABLE 1-continued

| Cmpd No. | Structure | ESI, m/z [M + H]+ |
|---|---|---|
| 58 | 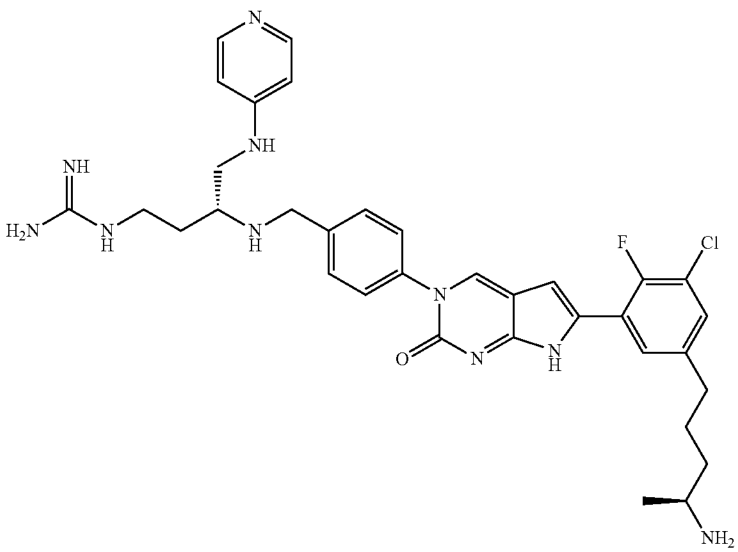 | 659 |
| 59 | 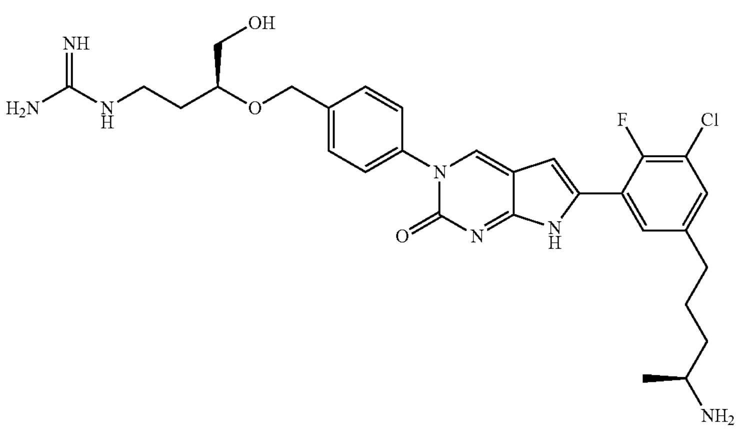 [SMILES: C[C@H](N)CCCc1cc(Cl)c(F)c(-c2cc3cn(-c4ccc(CO[C@H](CO)CCNC(=N)N)cc4)c(=O)nc3[nH]2)c1] | 584.3 |
| 60 | 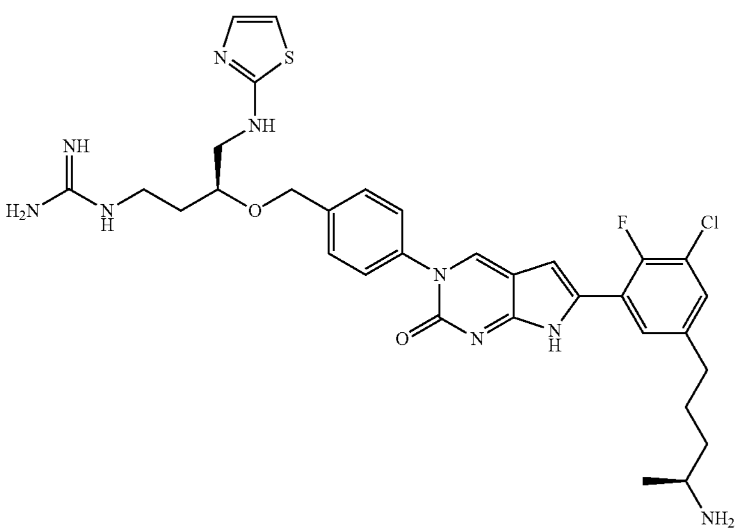 [SMILES: C[C@H](N)CCCc1cc(Cl)c(F)c(-c2cc3cn(-c4ccc(CO[C@@H](CCNC(=N)N)CNc5nccs5)cc4)c(=O)nc3[nH]2)c1] | 666 |

TABLE 1-continued

| Cmpd No. | Structure | ESI, m/z [M + H]+ |
|---|---|---|
| 61 | 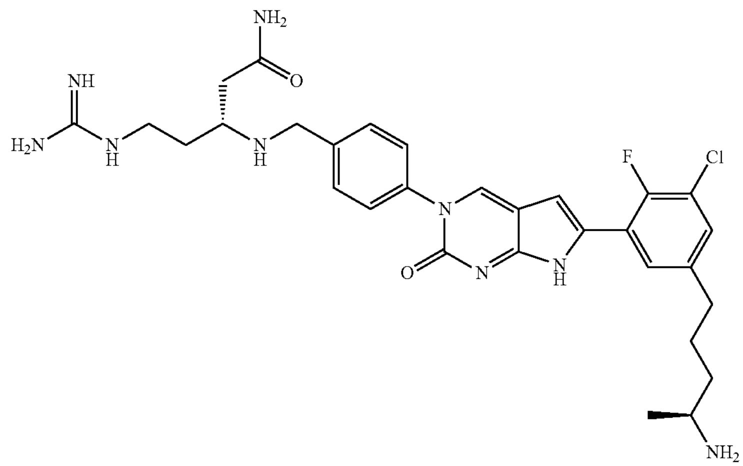 [SMILES: C[C@H](N)CCCc1cc(Cl)c(F)c(-c2cc3cn(-c4ccc(CN[C@H](CCNC(=N)N)CC(N)=O)cc4)c(=O)nc3[nH]2)c1] | 611 |
| 62 | 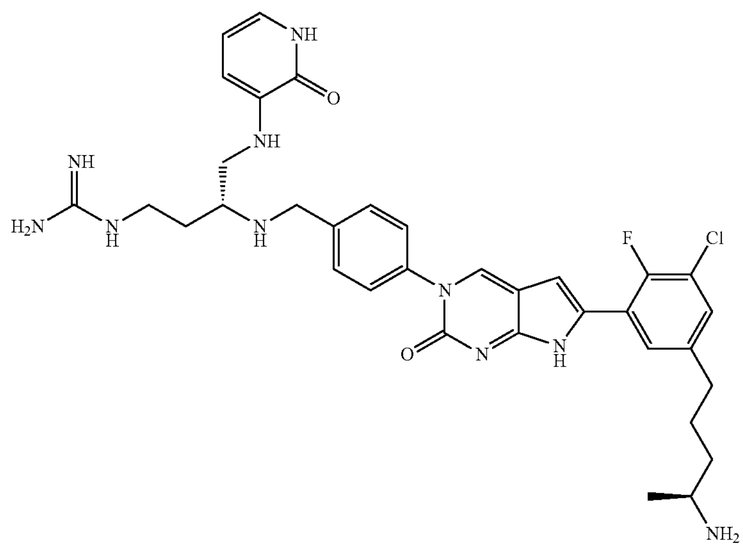 [SMILES: C[C@H](N)CCCc1cc(Cl)c(F)c(-c2cc3cn(-c4ccc(CN[C@H](CCNC(=N)N)CNc5ccc[nH]c5=O)cc4)c(=O)nc3[nH]2)c1] | 675 |
| 63 | 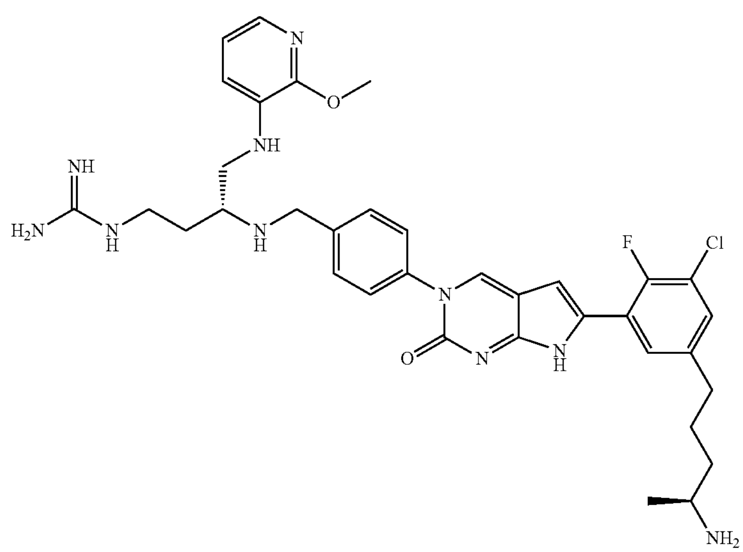 [SMILES: COc1ncccc1NC[C@@H](CCNC(=N)N)NCc1ccc(-n2cc3cc(-c4cc(CCC[C@H](C)N)cc(Cl)c4F)[nH]c3nc2=O)cc1] | 689 |

TABLE 1-continued

| Cmpd No. | Structure | ESI, m/z [M + H]+ |
|---|---|---|
| 64 | 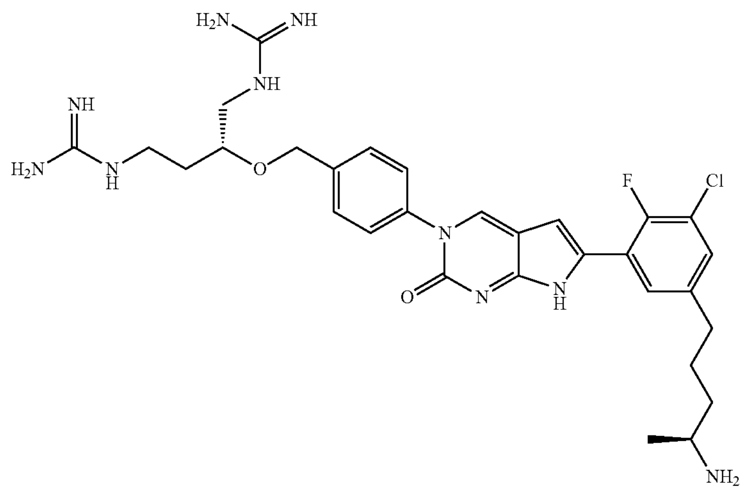 [SMILES: C[C@H](N)CCCc1cc(Cl)c(F)c(-c2cc3cn(-c4ccc(CO[C@H](CCNC(=N)N)CNC(=N)N)cc4)c(=O)nc3[nH]2)c1] | 625 |
| 65 | 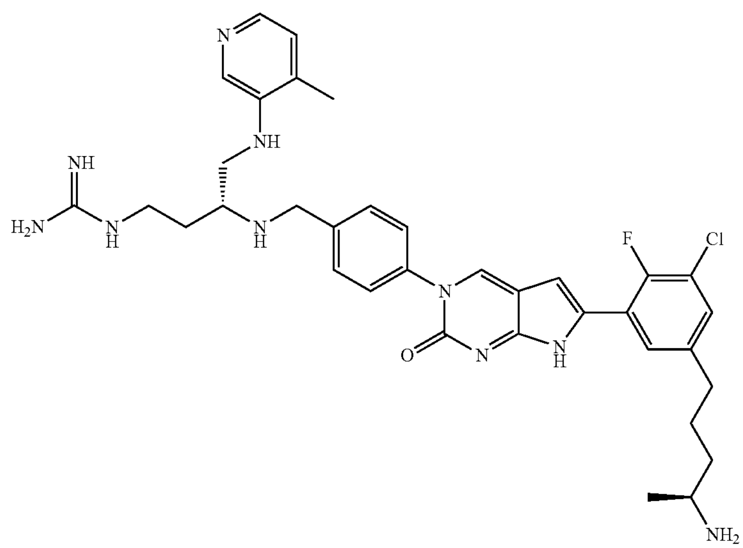 [SMILES: Cc1ccncc1NC[C@@H](CCNC(=N)N)NCc1ccc(-n2cc3cc(-c4cc(CCC[C@H](C)N)cc(Cl)c4F)[nH]c3nc2=O)cc1] | 673 |
| 66 | 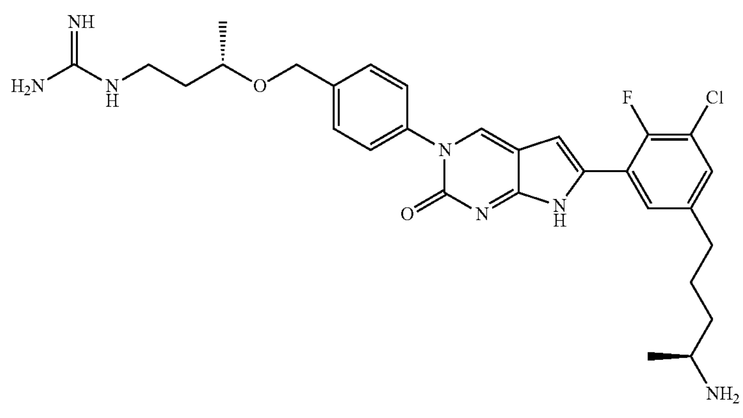 [SMILES: C[C@H](N)CCCc1cc(Cl)c(F)c(-c2cc3cn(-c4ccc(CO[C@@H](C)CCNC(=N)N)cc4)c(=O)nc3[nH]2)c1] | 568 |

TABLE 1-continued
| Cmpd No. | Structure | ESI, m/z [M + H]+ |
|---|---|---|
| 67 | 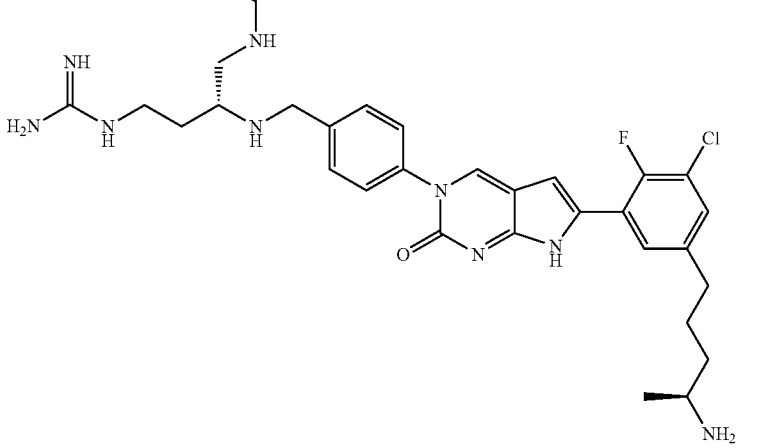 | 623 |
| 68 | 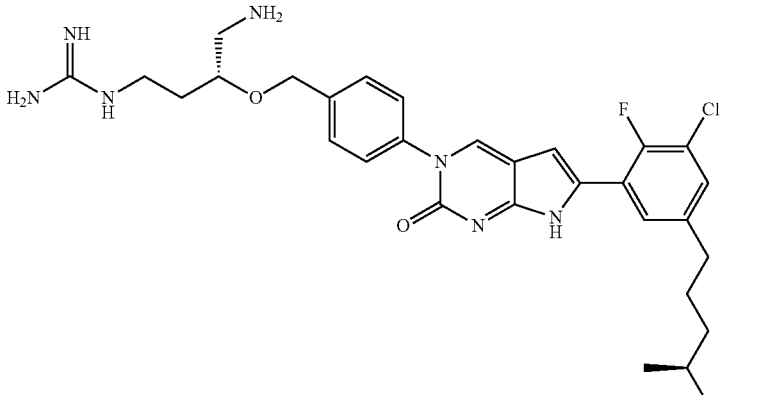 | 583 |
| 69 | 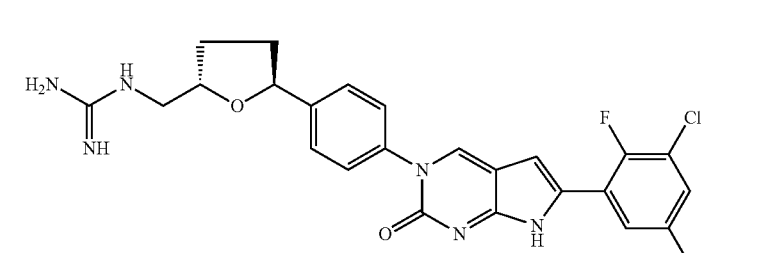 | 566.6 |

TABLE 1-continued

| Cmpd No. | Structure | ESI, m/z [M + H]+ |
|---|---|---|
| 70 | 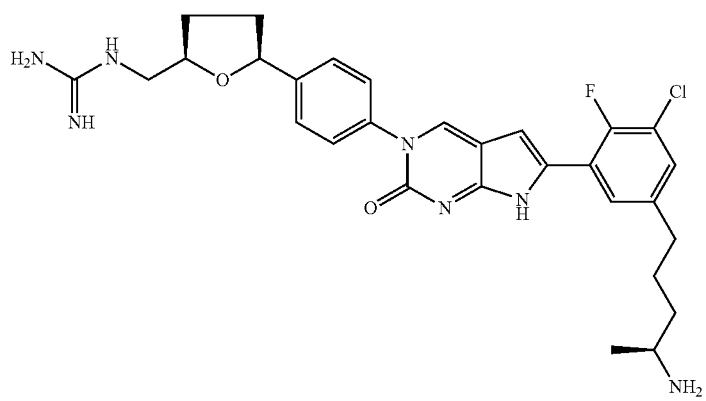 [SMILES: C[C@H](N)CCCc1cc(Cl)c(F)c(-c2cc3cn(-c4ccc([C@@H]5CC[C@H](CNC(=N)N)O5)cc4)c(=O)nc3[nH]2)c1] | 566.6 |
| 71 | 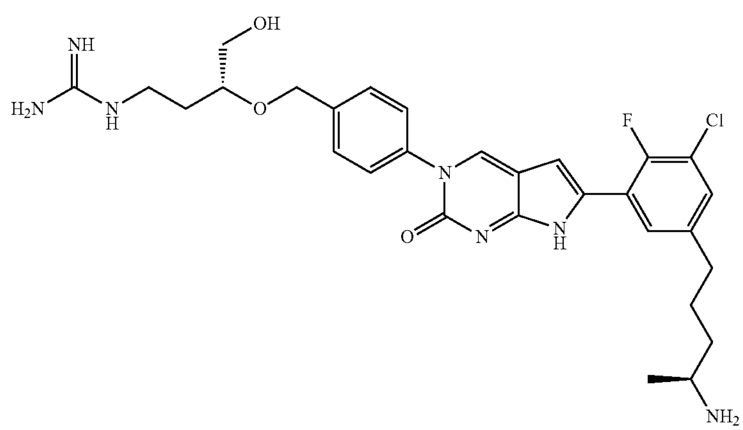 | 584.6 |
| 72 | 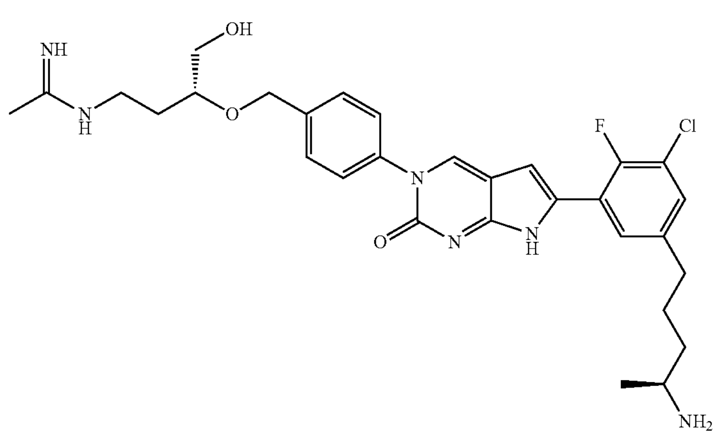 [SMILES: CC(=N)NCC[C@H](CO)OCc1ccc(-n2cc3cc(-c4cc(CCC[C@H](C)N)cc(Cl)c4F)[nH]c3nc2=O)cc1] | 583.6 |

TABLE 1-continued
| Cmpd No. | Structure | ESI, m/z [M + H]+ |
|---|---|---|
| 73 | 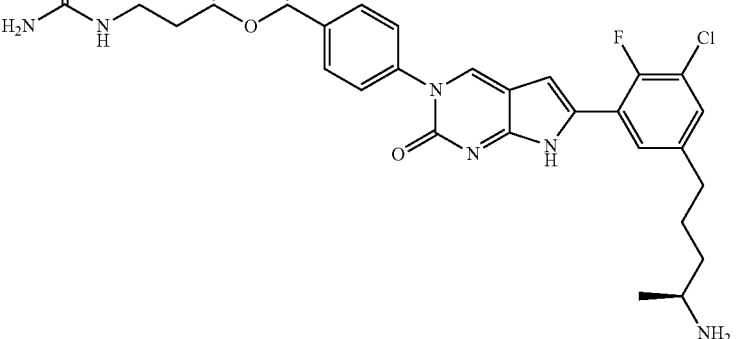 | 580.6 |
| 74 | 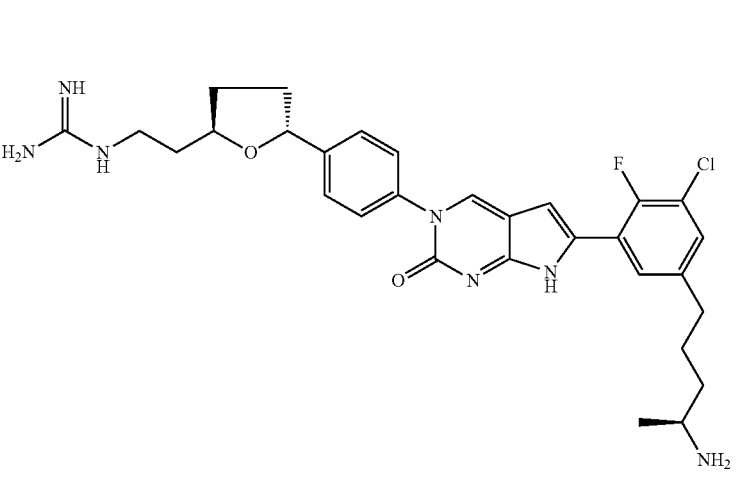 [SMILES: C[C@H](N)CCCc1cc(Cl)c(F)c(-c2cc3cn(-c4ccc([C@H]5CC[C@H](CCNC(=N)N)O5)cc4)c(=O)nc3[nH]2)c1] | 580.6 |
| 75 | 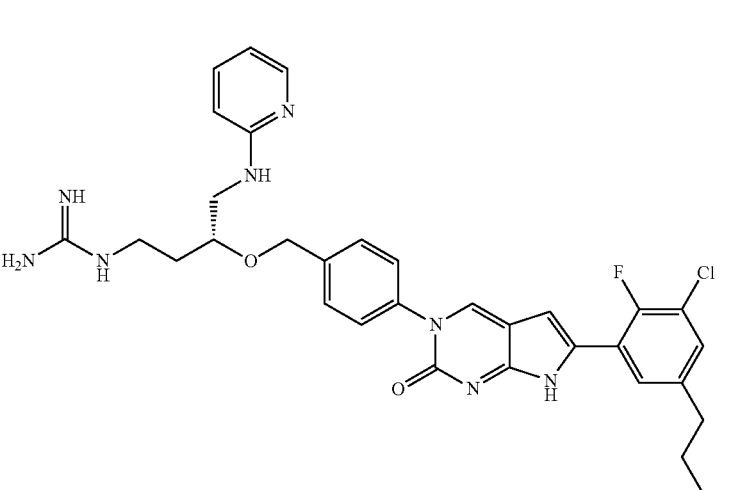 | 660 |

TABLE 1-continued

| Cmpd No. | Structure | ESI, m/z [M + H]+ |
|---|---|---|
| 76 | 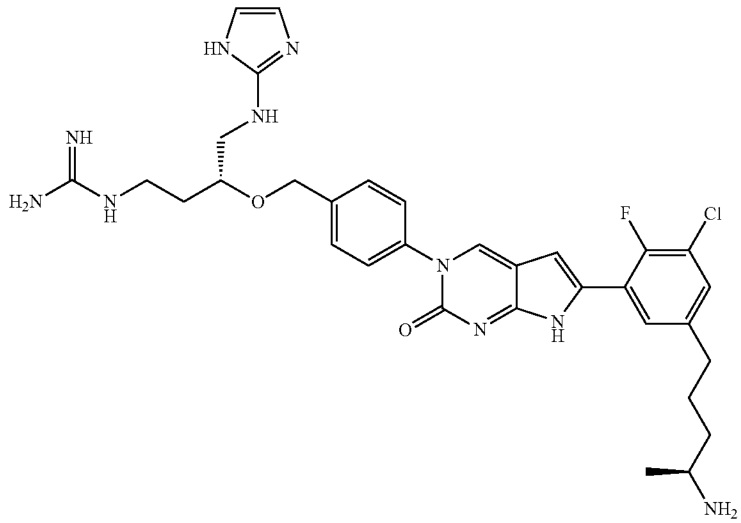 [SMILES: C[C@H](N)CCCc1cc(Cl)c(F)c(-c2cc3cn(-c4ccc(CO[C@H](CCNC(=N)N)CNc5ncc[nH]5)cc4)c(=O)nc3[nH]2)c1] | 649 |
| 77 | 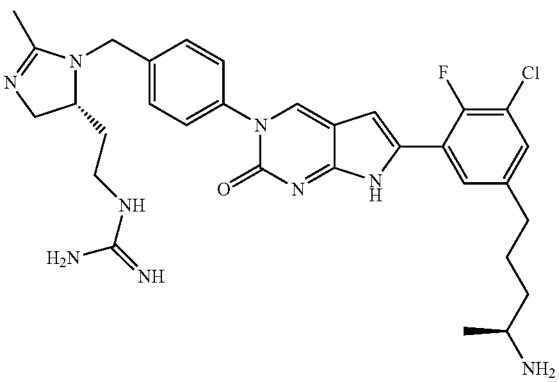 [SMILES: CC1=NC[C@@H](CCNC(=N)N)N1Cc1ccc(-n2cc3cc(-c4cc(CCC[C@H](C)N)cc(Cl)c4F)[nH]c3nc2=O)cc1] | 606 |
| 78 | 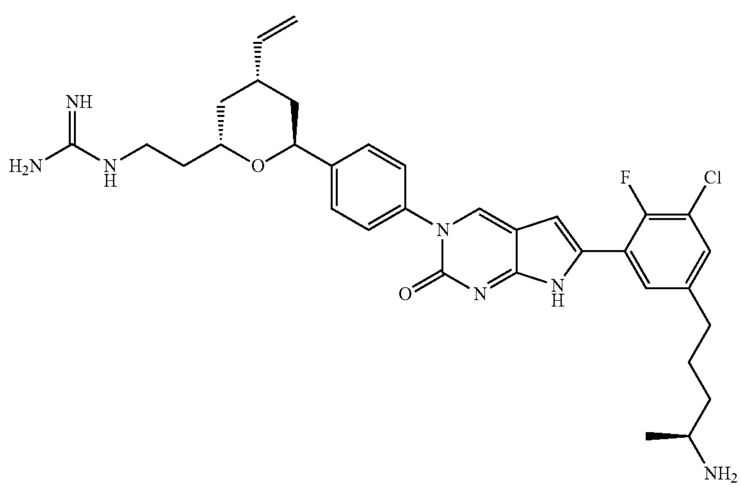 [SMILES: C=C[C@H]1C[C@@H](CCNC(=N)N)O[C@H](c2ccc(-n3cc4cc(-c5cc(CCC[C@H](C)N)cc(Cl)c5F)[nH]c4nc3=O)cc2)C1] | 620.7 |

TABLE 1-continued
| Cmpd No. | Structure | ESI, m/z [M + H]+ |
|---|---|---|
| 79 | 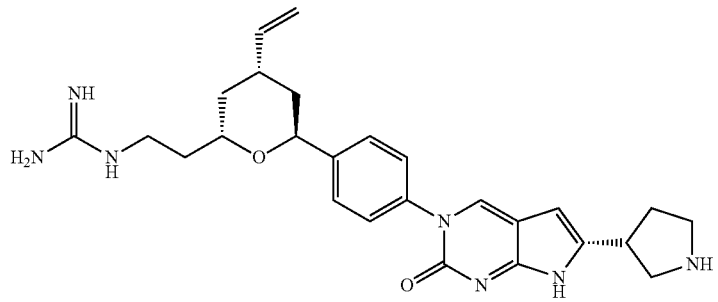 | 476.6 |
| 80 | 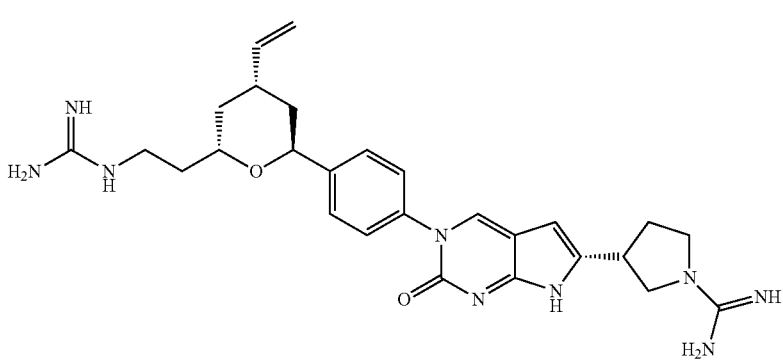 | 518.6 |
| 81 | 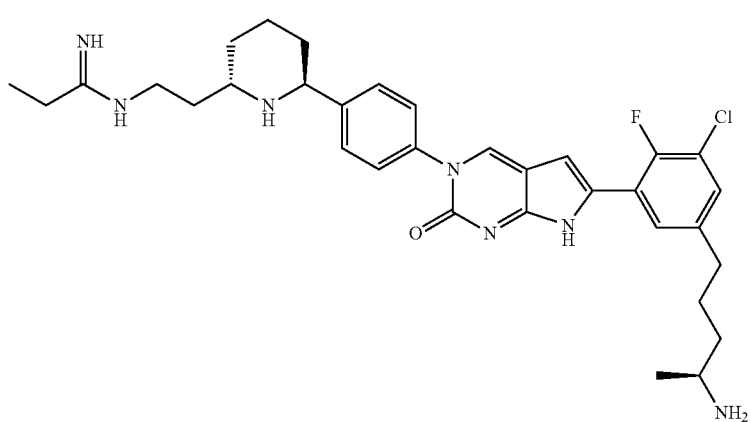 [SMILES: CCC(=N)NCC[C@@H]1CCC[C@@H](c2ccc(-n3cc4cc(-c5cc(CCC[C@H](C)N)cc(Cl)c5F)[nH]c4nc3=O)cc2)N1] | 606.6 |
| 82 | 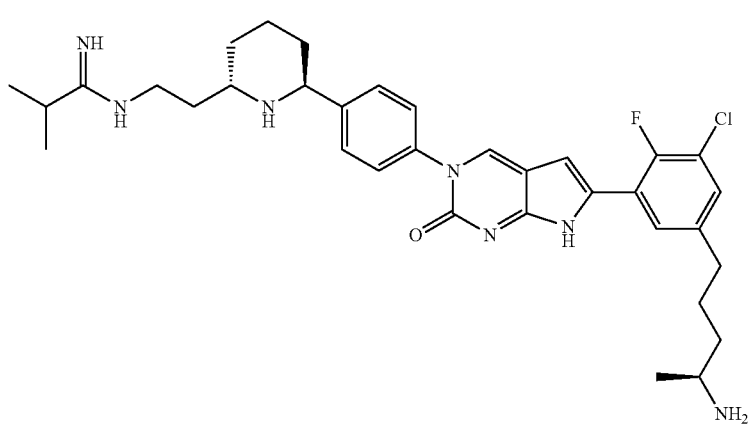 [SMILES: CC(C)C(=N)NCC[C@@H]1CCC[C@@H](c2ccc(-n3cc4cc(-c5cc(CCC[C@H](C)N)cc(Cl)c5F)[nH]c4nc3=O)cc2)N1] | 620.7 |

TABLE 1-continued

| Cmpd No. | Structure | ESI, m/z [M + H]+ |
|---|---|---|
| 83 | 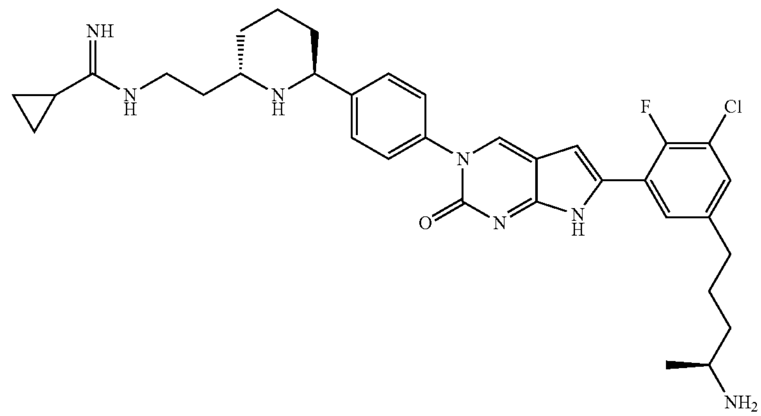 [SMILES: C[C@H](N)CCCc1cc(Cl)c(F)c(-c2cc3cn(-c4ccc([C@@H]5CCC[C@@H](CCNC(=N)C6CC6)N5)cc4)c(=O)nc3[nH]2)c1] | 618.7 |
| 84 | 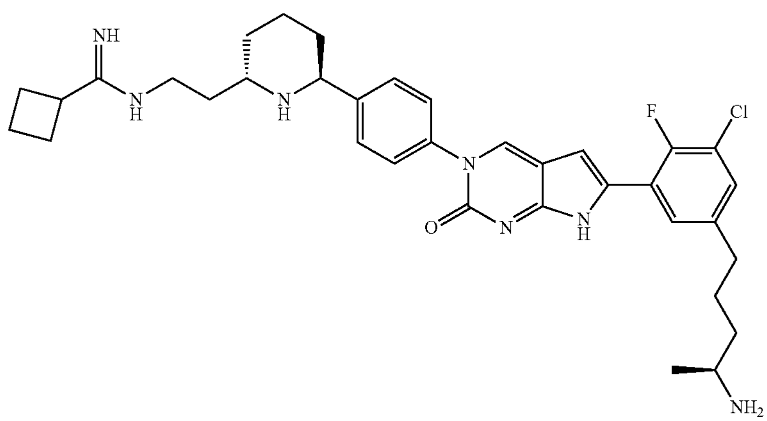 [SMILES: C[C@H](N)CCCc1cc(Cl)c(F)c(-c2cc3cn(-c4ccc([C@@H]5CCC[C@@H](CCNC(=N)C6CCC6)N5)cc4)c(=O)nc3[nH]2)c1] | 632.7 |
| 85 | 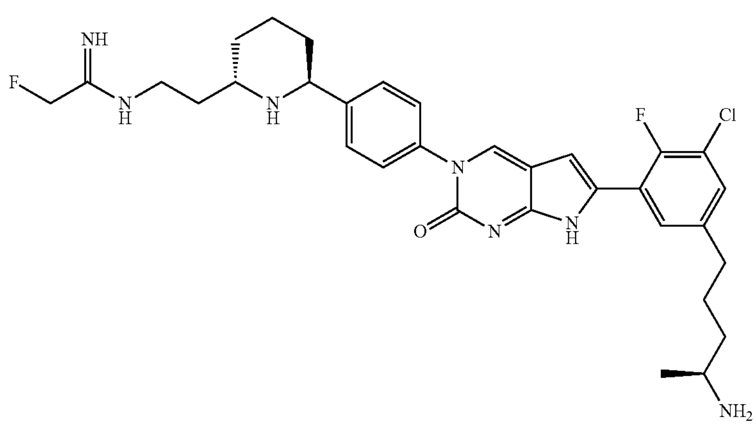 [SMILES: C[C@H](N)CCCc1cc(Cl)c(F)c(-c2cc3cn(-c4ccc([C@@H]5CCC[C@@H](CCNC(=N)CF)N5)cc4)c(=O)nc3[nH]2)c1] | 610.6 |

TABLE 1-continued

| Cmpd No. | Structure | ESI, m/z [M + H]+ |
|---|---|---|
| 86 | 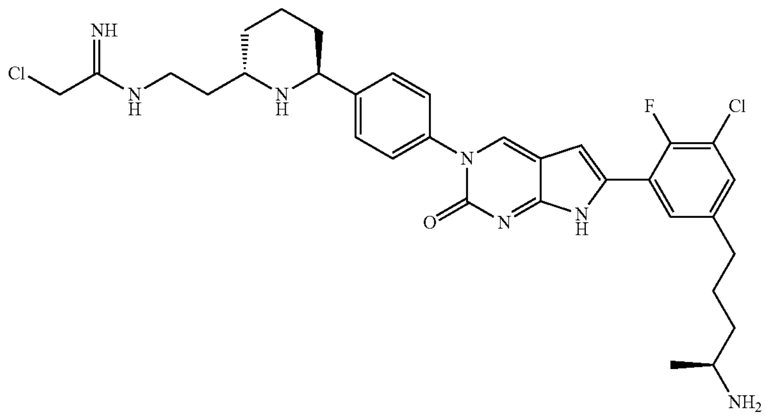 [SMILES: C[C@H](N)CCCc1cc(Cl)c(F)c(-c2cc3cn(-c4ccc([C@@H]5CCC[C@@H](CCNC(=N)CCl)N5)cc4)c(=O)nc3[nH]2)c1] | 626.6 |
| 87 | 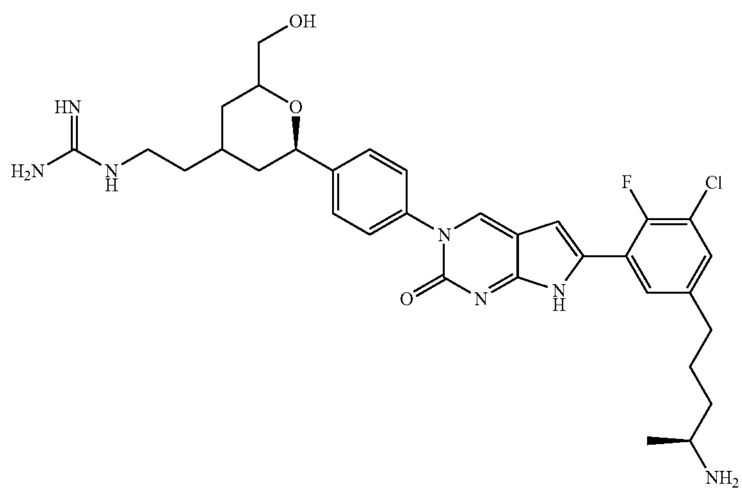 | 625.16 |
| 88 | 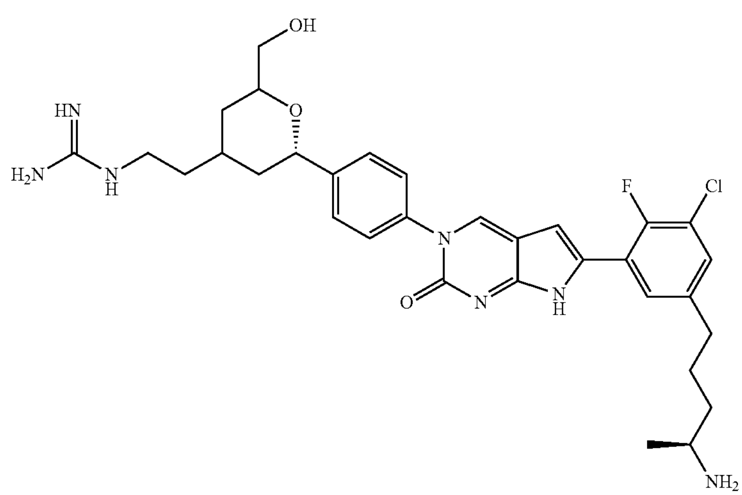 | 625.16 |

TABLE 1-continued
| Cmpd No. | Structure | ESI, m/z [M + H]+ |
|---|---|---|
| 89 | 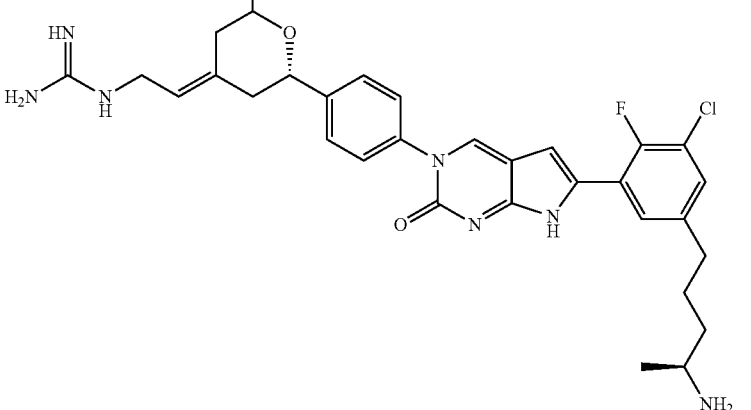 | 623.14 |
| 90 | 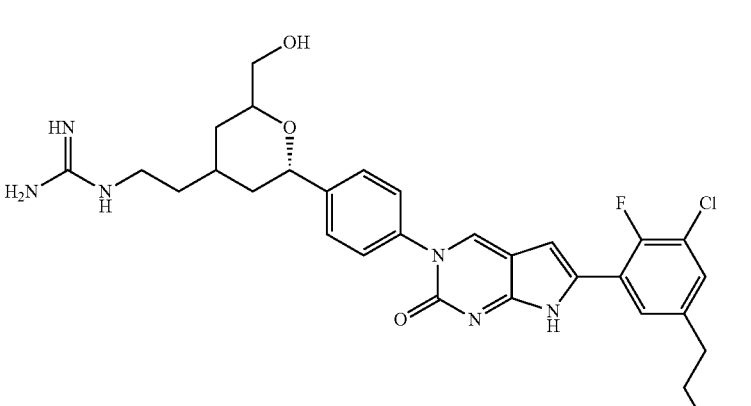 | 625.16 |
| 91 | 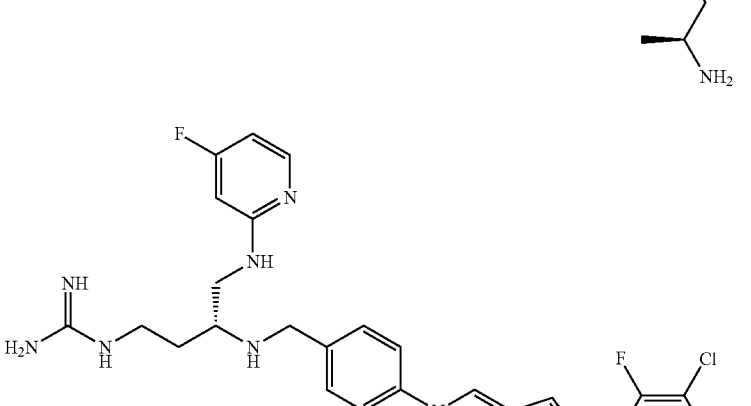 | 677 |

TABLE 1-continued
| Cmpd No. | Structure | ESI, m/z [M + H]+ |
|---|---|---|
| 92 | 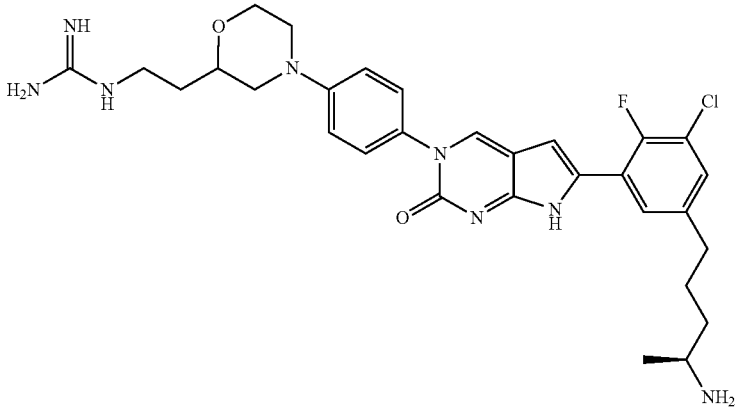 | 595 |
| 93 | 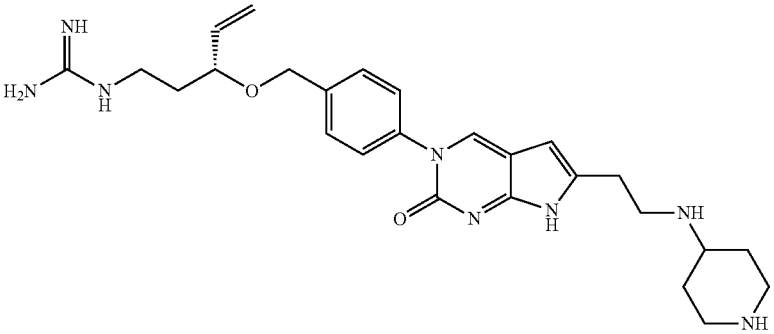 [SMILES: C=C[C@@H](CCNC(=N)N)OCc1ccc(-n2cc3cc(CCNC4CCNCC4)[nH]c3nc2=O)cc1] | 493 |
| 94 | 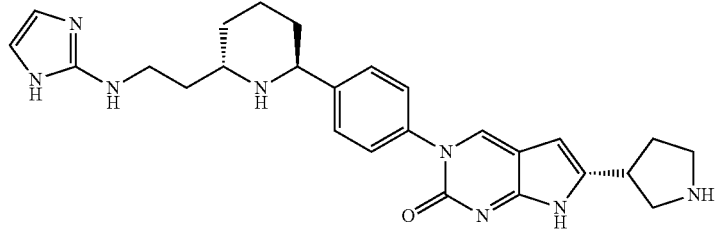 | 473.6 |
| 95 | 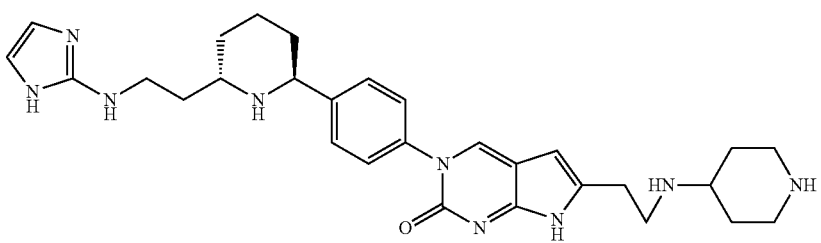 [SMILES: O=c1nc2[nH]c(CCNC3CCNCC3)cc2cn1-c1ccc([C@@H]2CCC[C@@H](CCNc3ncc[nH]3)N2)cc1] | 530.6 |

TABLE 1-continued
| Cmpd No. | Structure | ESI, m/z [M + H]+ |
|---|---|---|
| 96 | 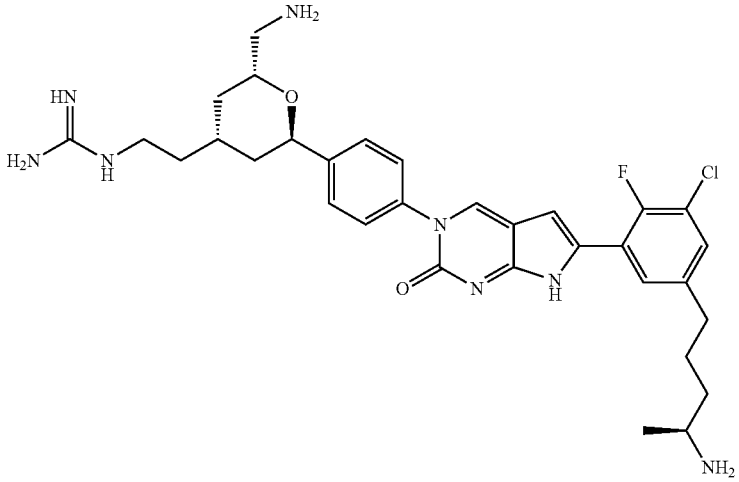 [SMILES: C[C@H](N)CCCc1cc(Cl)c(F)c(-c2cc3cn(-c4ccc([C@H]5C[C@H](CCNC(=N)N)C[C@H](CN)O5)cc4)c(=O)nc3[nH]2)c1] | 623.6 |
| 97 | 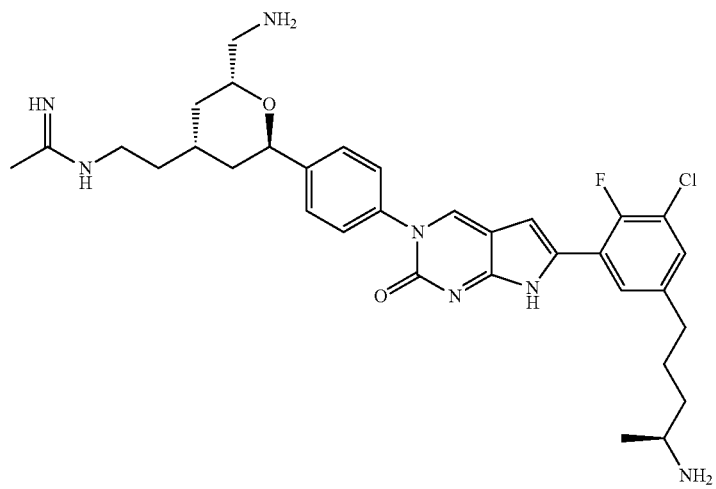 [SMILES: CC(=N)NCC[C@@H]1C[C@H](CN)O[C@@H](c2ccc(-n3cc4cc(-c5cc(CCC[C@H](C)N)cc(Cl)c5F)[nH]c4nc3=O)cc2)C1] | 622.6 |
| 98 | 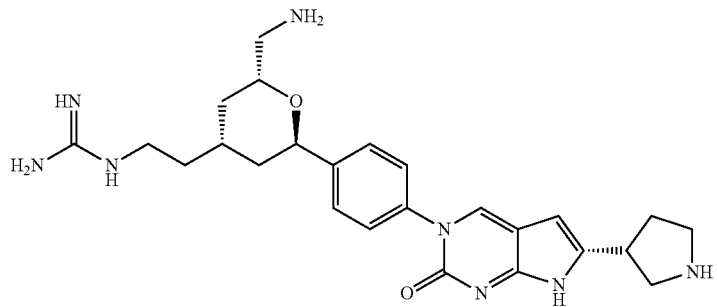 | 479.6 |

TABLE 1-continued

| Cmpd No. | Structure | ESI, m/z [M + H]+ |
|---|---|---|
| 99 | 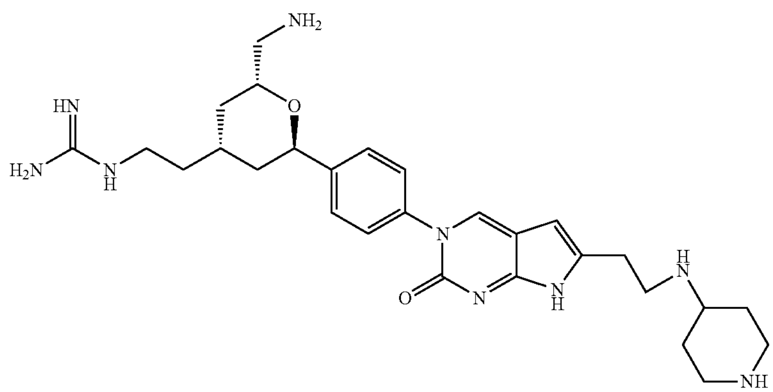 [SMILES: N=C(N)NCC[C@@H]1C[C@H](CN)O[C@@H](c2ccc(-n3cc4cc(CCNC5CCNCC5)[nH]c4nc3=O)cc2)C1] | 536.7 |
| 100 | 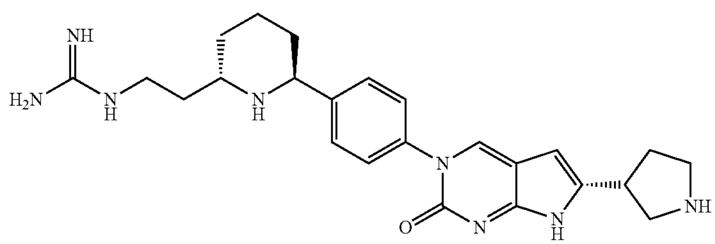 | 449.6 |
| 101 | 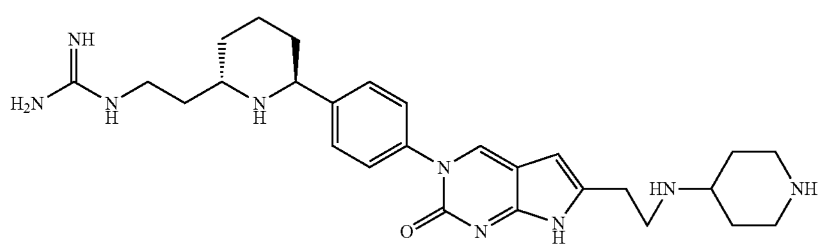 [SMILES: N=C(N)NCC[C@@H]1CCC[C@@H](c2ccc(-n3cc4cc(CCNC5CCNCC5)[nH]c4nc3=O)cc2)N1] | 506.6 |
| 102 | 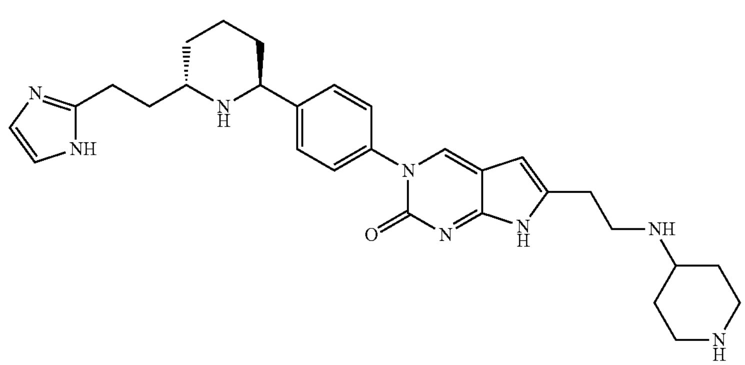 [SMILES: O=c1nc2[nH]c(CCNC3CCNCC3)cc2cn1-c1ccc([C@@H]2CCC[C@@H](CCc3ncc[nH]3)N2)cc1] | 515 |

TABLE 1-continued

| Cmpd No. | Structure | ESI, m/z [M + H]+ |
|---|---|---|
| 103 | 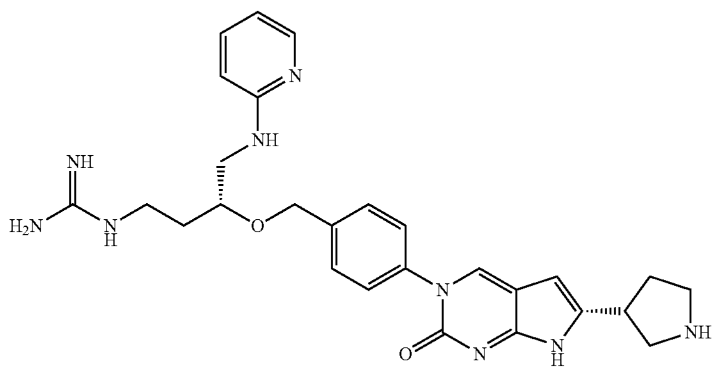 | 516 |
| 104 | 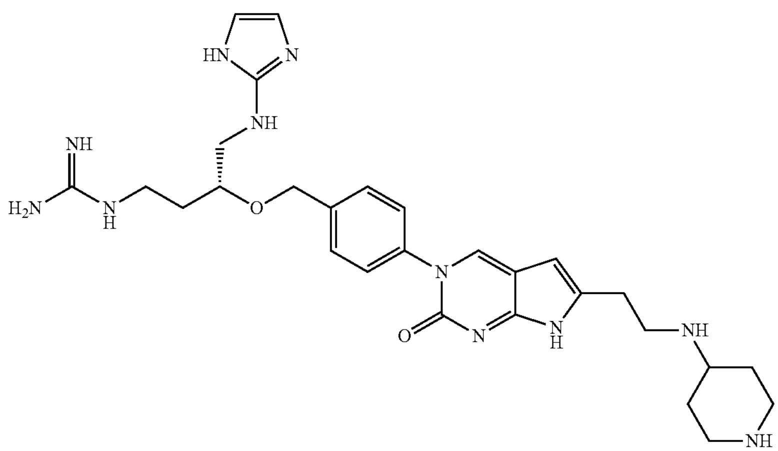 [SMILES: N=C(N)NCC[C@H](CNc1ncc[nH]1)OCc1ccc(-n2cc3cc(CCNC4CCNCC4)[nH]c3nc2=O)cc1] | 562 |
| 105 | 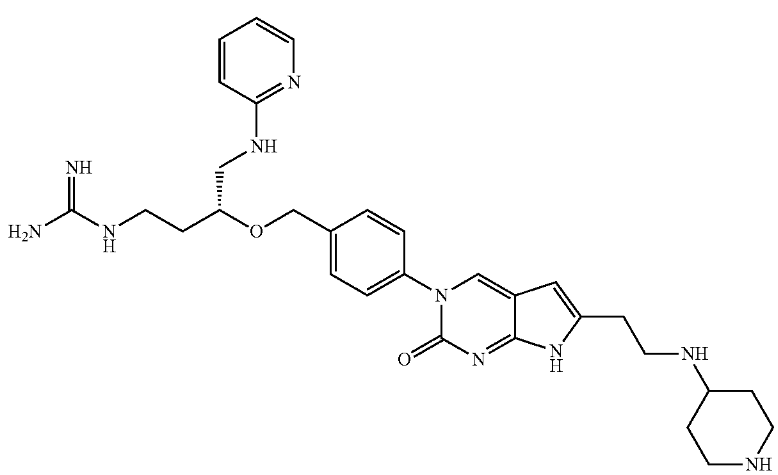 [SMILES: N=C(N)NCC[C@H](CNc1ccccn1)OCc1ccc(-n2cc3cc(CCNC4CCNCC4)[nH]c3nc2=O)cc1] | 573 |

TABLE 1-continued

| Cmpd No. | Structure | ESI, m/z [M + H]+ |
|---|---|---|
| 106 | 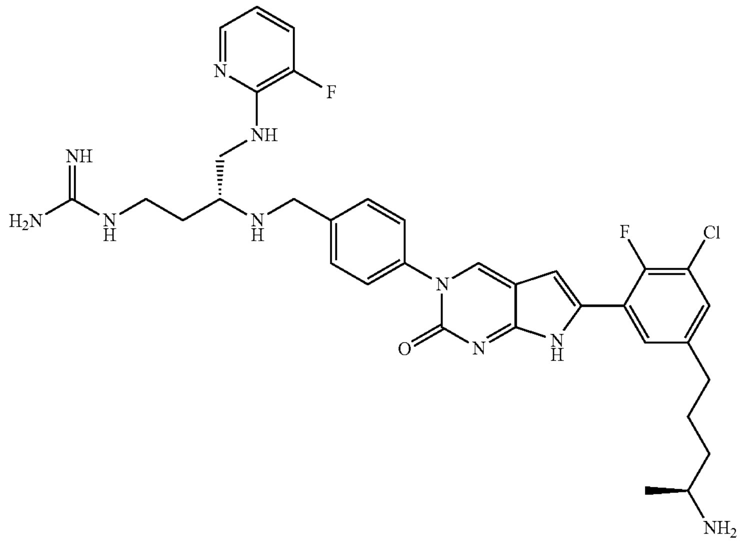 [SMILES: C[C@H](N)CCCc1cc(Cl)c(F)c(-c2cc3cn(-c4ccc(CN[C@H](CCNC(=N)N)CNc5ncccc5F)cc4)c(=O)nc3[nH]2)c1] | 677 |
| 107 | 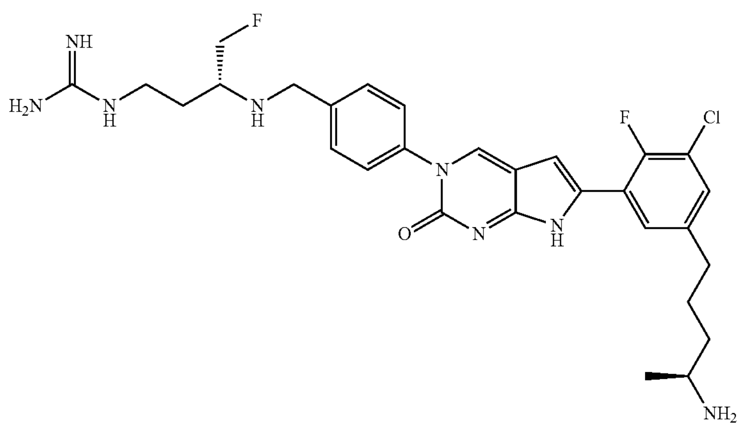 [SMILES: C[C@H](N)CCCc1cc(Cl)c(F)c(-c2cc3cn(-c4ccc(CN[C@@H](CF)CCNC(=N)N)cc4)c(=O)nc3[nH]2)c1] | 585.6 |
| 108 | 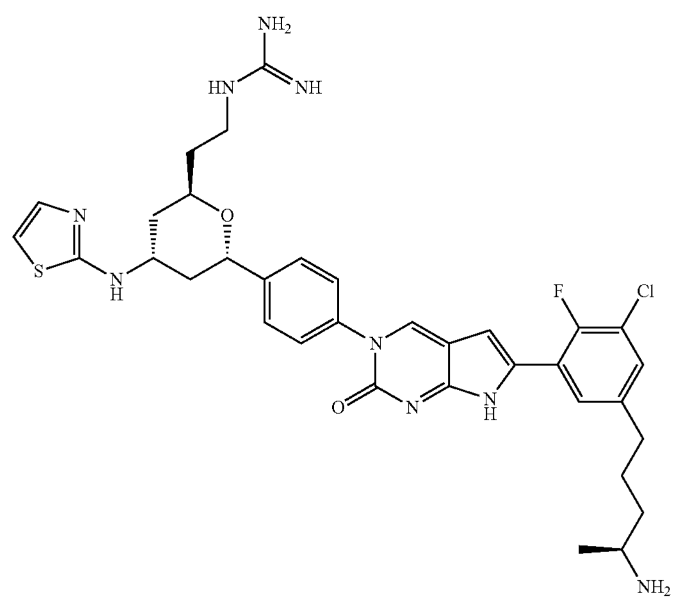 [SMILES: C[C@H](N)CCCc1cc(Cl)c(F)c(-c2cc3cn(-c4ccc([C@@H]5C[C@H](Nc6nccs6)C[C@@H](CCNC(=N)N)O5)cc4)c(=O)nc3[nH]2)c1] | 692.7 |

TABLE 1-continued
| Cmpd No. | Structure | ESI, m/z [M + H]+ |
|---|---|---|
| 109 | 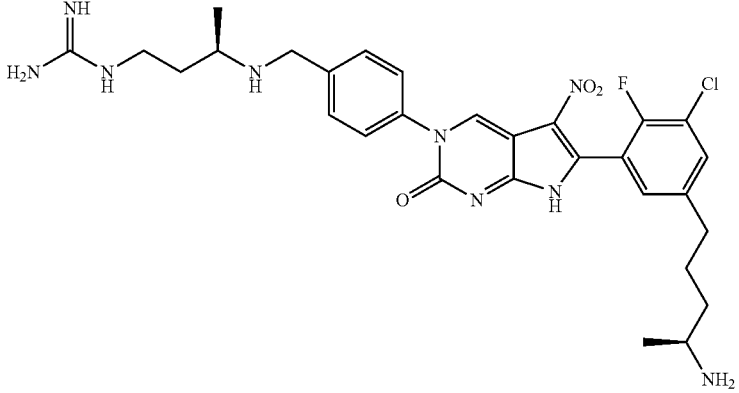 [SMILES: C[C@H](N)CCCc1cc(Cl)c(F)c(-c2[nH]c3nc(=O)n(-c4ccc(CN[C@H](C)CCNC(=N)N)cc4)cc3c2[N+](=O)[O-])c1] | 612.5 |
| 110 | 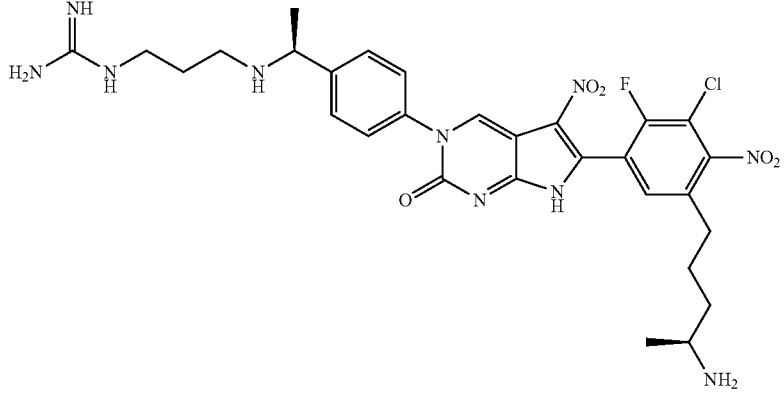 [SMILES: C[C@H](N)CCCc1cc(-c2[nH]c3nc(=O)n(-c4ccc([C@H](C)NCCCNC(=N)N)cc4)cc3c2[N+](=O)[O-])c(F)c(Cl)c1[N+](=O)[O-]] | 657.6 |
| 111 | 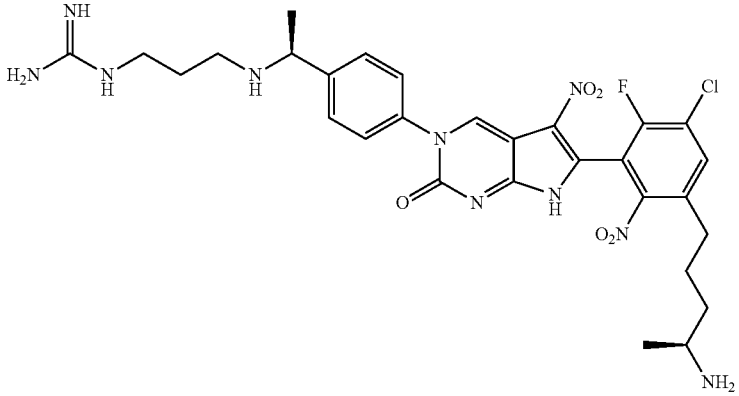 [SMILES: C[C@H](N)CCCc1cc(Cl)c(F)c(-c2[nH]c3nc(=O)n(-c4ccc([C@H](C)NCCCNC(=N)N)cc4)cc3c2[N+](=O)[O-])c1[N+](=O)[O-]] | 657.6 |
| 112 | 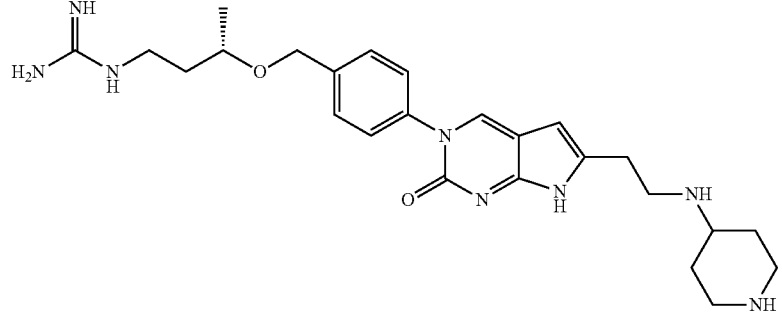 [SMILES: C[C@@H](CCNC(=N)N)OCc1ccc(-n2cc3cc(CCNC4CCNCC4)[nH]c3nc2=O)cc1] | 481 |

| Cmpd No. | Structure | ESI, m/z [M + H]+ |
|---|---|---|
| 113 | 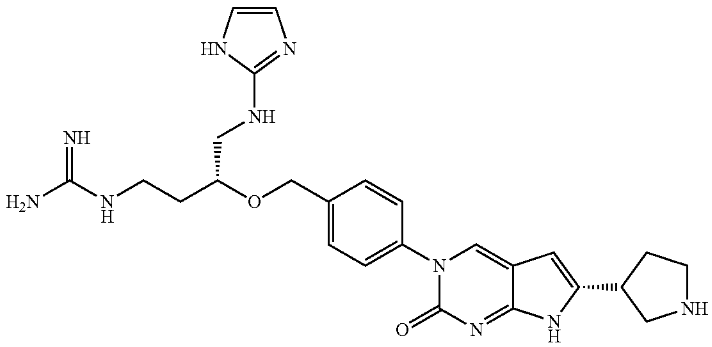 | 505 |
| 114 | 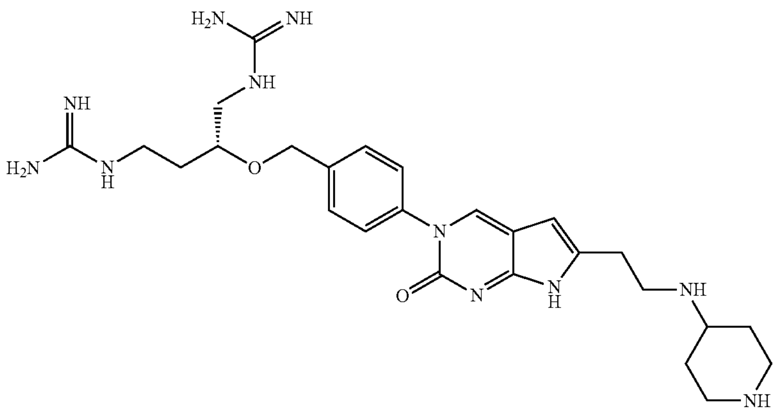 [SMILES: N=C(N)NCC[C@H](CNC(=N)N)OCc1ccc(-n2cc3cc(CCNC4CCNCC4)[nH]c3nc2=O)cc1] | 538 |
| 115 | 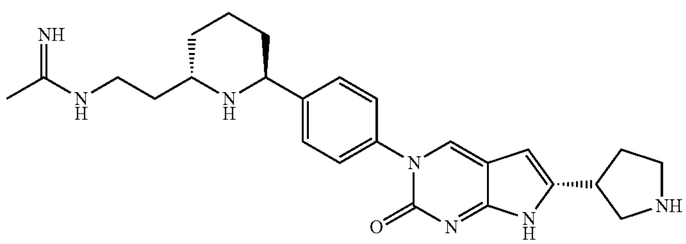 | 448.6 |
| 116 | 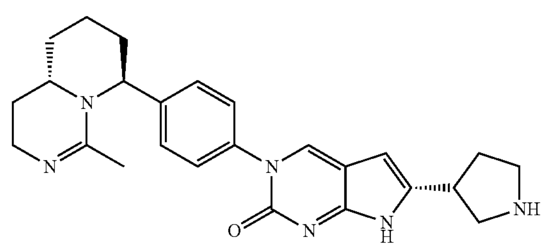 | 431.5 |
| 117 | 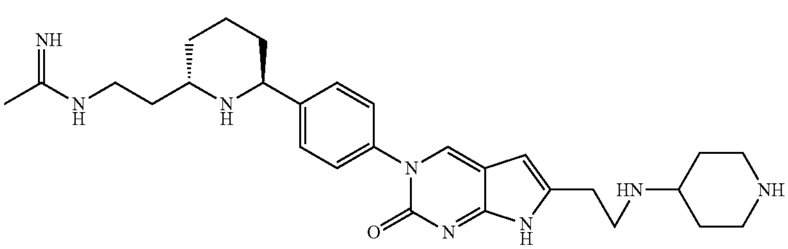 [SMILES: CC(=N)NCC[C@@H]1CCC[C@@H](c2ccc(-n3cc4cc(CCNC5CCNCC5)[nH]c4nc3=O)cc2)N1] | 505.6 |

TABLE 1-continued

| Cmpd No. | Structure | ESI, m/z [M + H]+ |
|---|---|---|
| 118 | 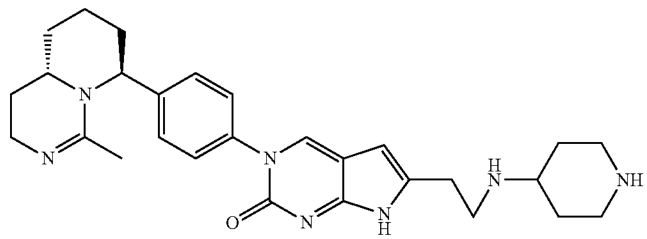 [SMILES: CC1=NCC[C@@H]2CCC[C@@H](c3ccc(-n4cc5cc(CCNC6CCNCC6)[nH]c5nc4=O)cc3)N12] | 488.7 |
| 119 | 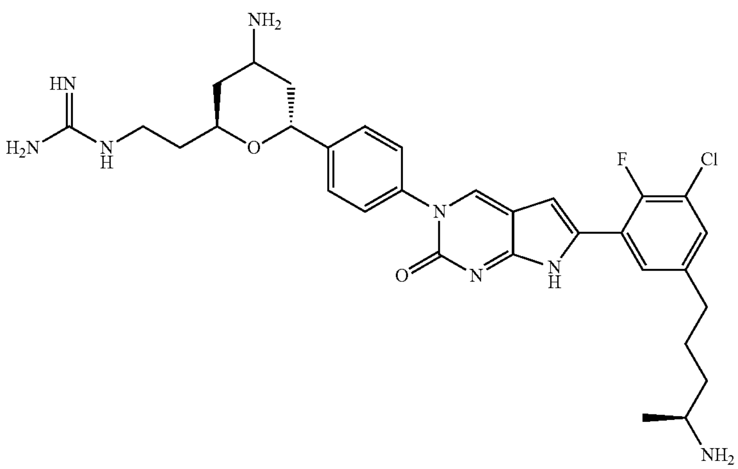 | 609.6 |
| 120 | 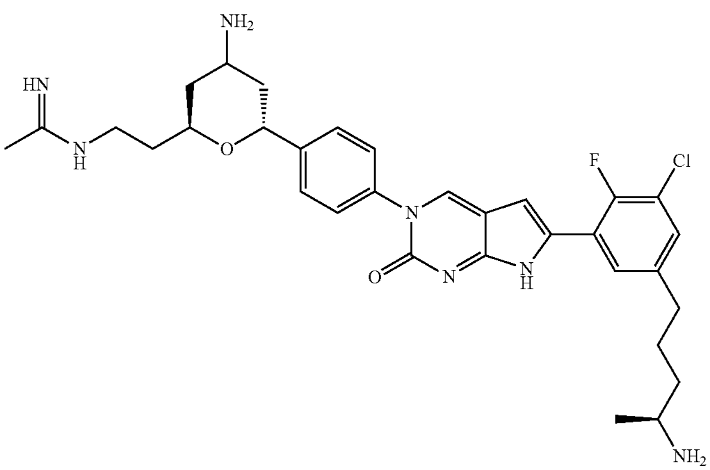 | 608.7 |
| 121 | 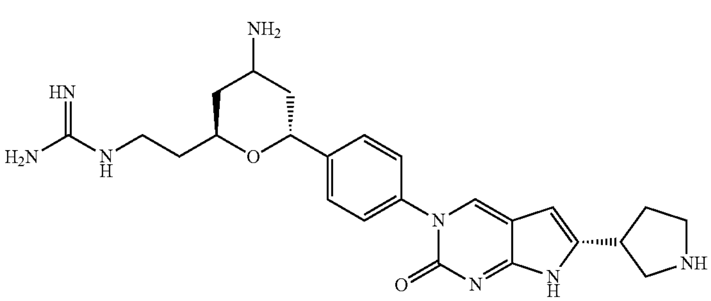 | 465.6 |

TABLE 1-continued
| Cmpd No. | Structure | ESI, m/z [M + H]+ |
|---|---|---|
| 122 | 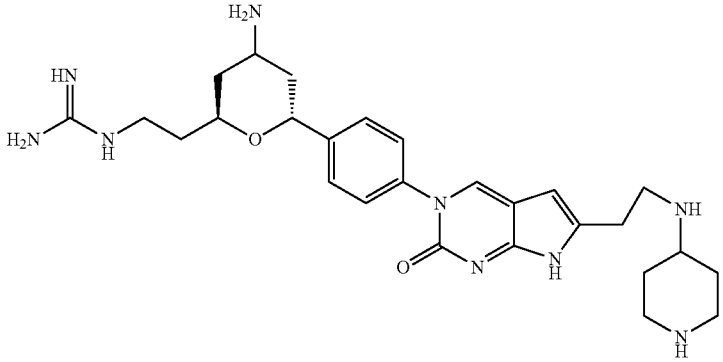 | 522.7 |
| 123 | 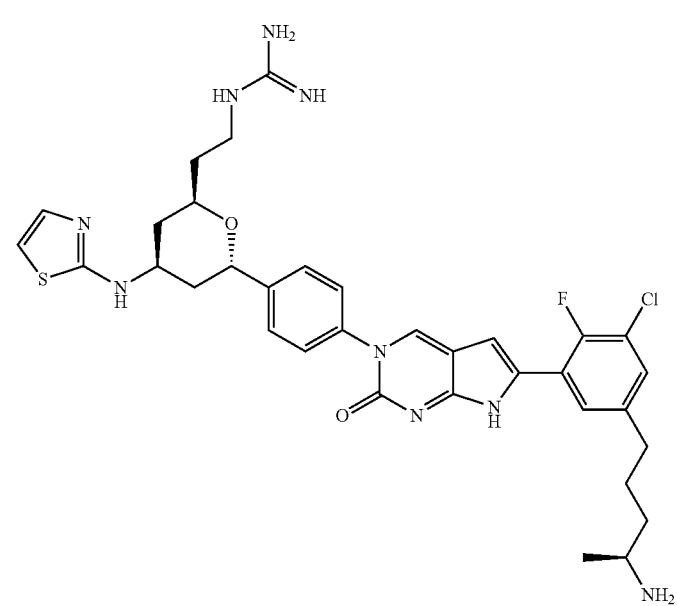 | 692.6 |
| 124 | 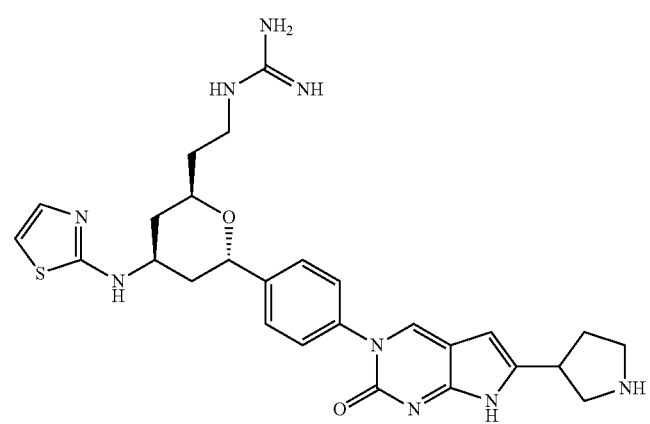 [SMILES: N=C(N)NCC[C@@H]1C[C@H](Nc2nccs2)C[C@@H](c2ccc(-n3cc4cc(C5CCNC5)[nH]c4nc3=O)cc2)O1] | 548.6 |

TABLE 1-continued
| Cmpd No. | Structure | ESI, m/z [M + H]+ |
|---|---|---|
| 125 | 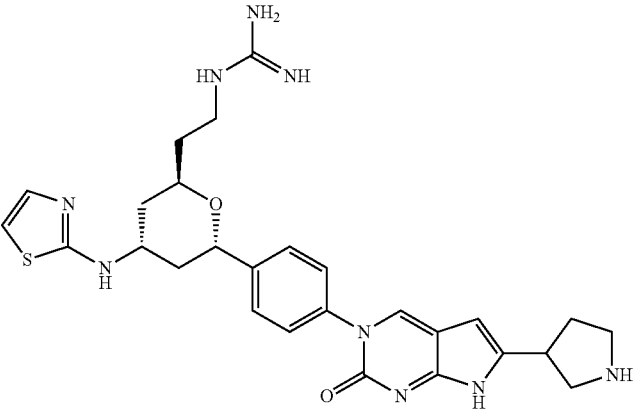 [SMILES: N=C(N)NCC[C@@H]1C[C@@H](Nc2nccs2)C[C@@H](c2ccc(-n3cc4cc(C5CCNC5)[nH]c4nc3=O)cc2)O1] | 548.6 |
| 126 | 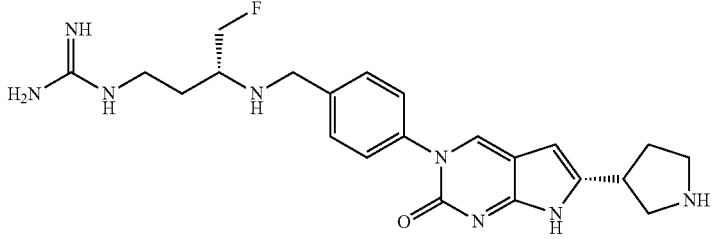 | 441.5 |
| 127 | 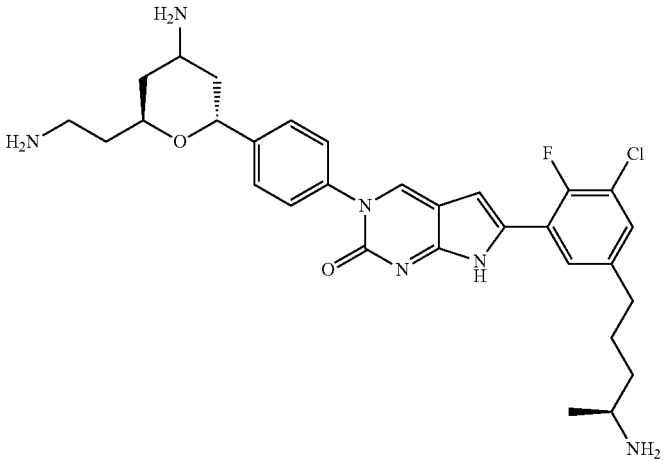 | 567.6 |

TABLE 1-continued

| Cmpd No. | Structure | ESI, m/z [M + H]+ |
|---|---|---|
| 128 | 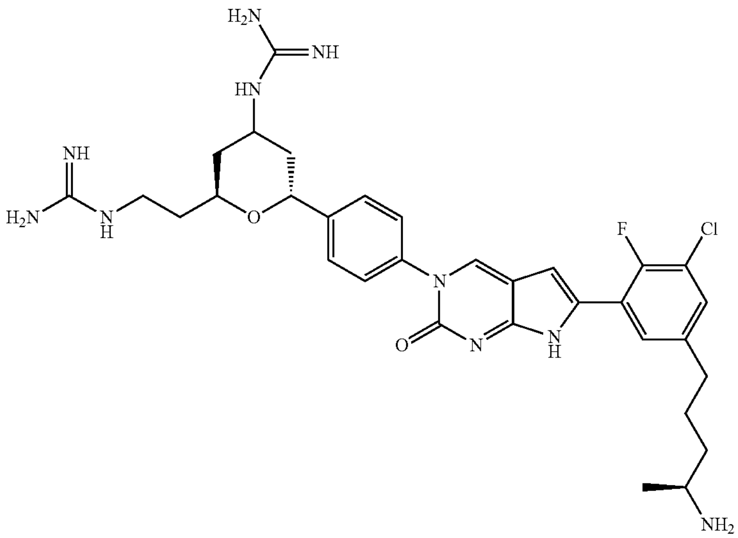 | 651.6 |
| 129 | 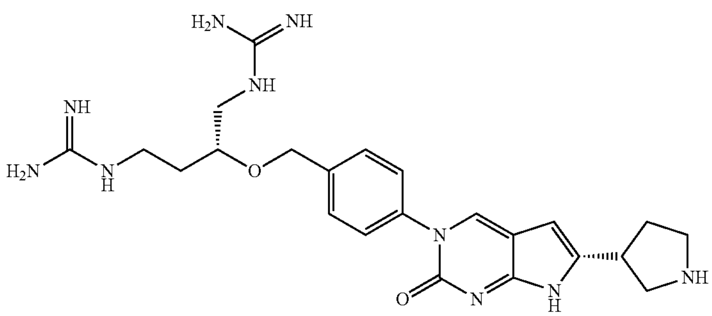 | 481 |
| 130 | 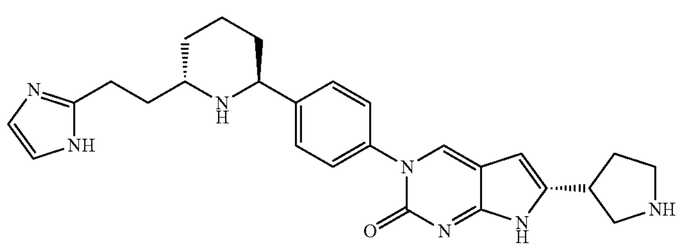 | 458 |
| 131 | 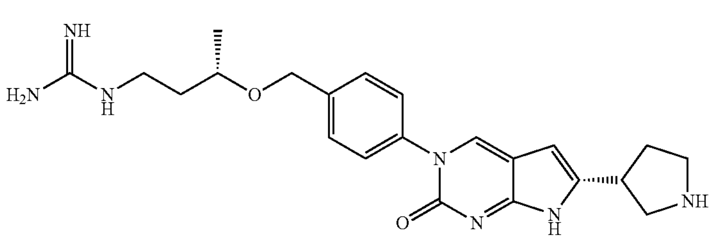 | 424 |

TABLE 1-continued
| Cmpd No. | Structure | ESI, m/z [M + H]+ |
|---|---|---|
| 132 | 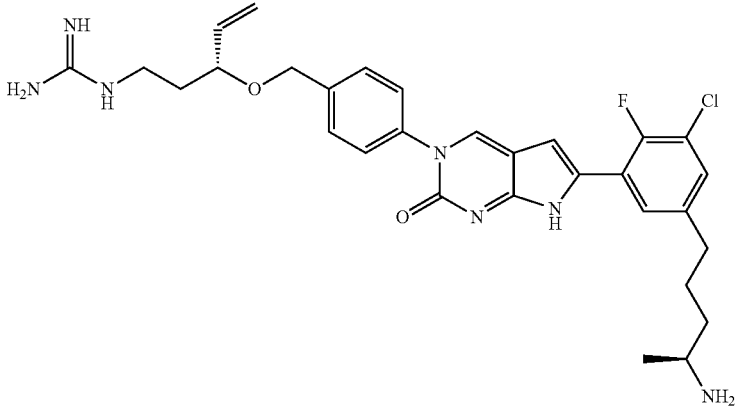 [SMILES: C=C[C@@H](CCNC(=N)N)OCc1ccc(-n2cc3cc(-c4cc(CCC[C@H](C)N)cc(Cl)c4F)[nH]c3nc2=O)cc1] | 580 |
| 133 | 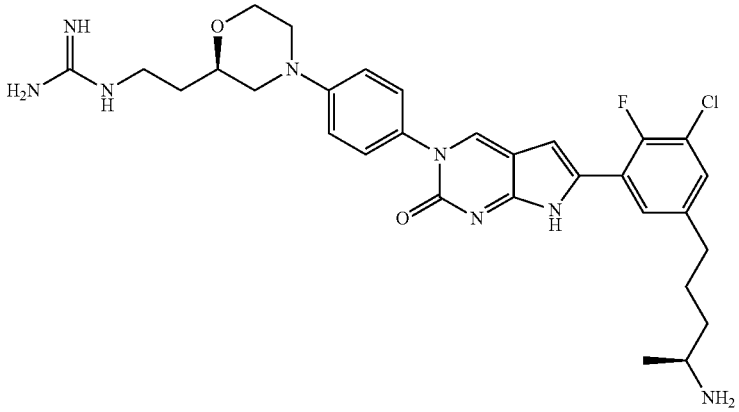 [SMILES: C[C@H](N)CCCc1cc(Cl)c(F)c(-c2cc3cn(-c4ccc(N5CCO[C@H](CCNC(=N)N)C5)cc4)c(=O)nc3[nH]2)c1] | 595 |
| 134 | 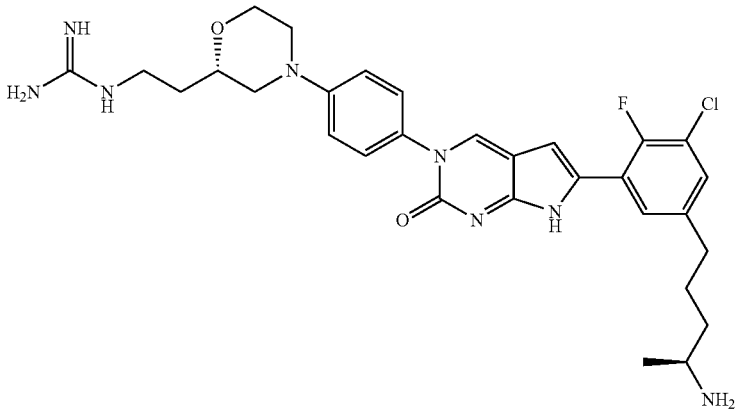 [SMILES: C[C@H](N)CCCc1cc(Cl)c(F)c(-c2cc3cn(-c4ccc(N5CCO[C@@H](CCNC(=N)N)C5)cc4)c(=O)nc3[nH]2)c1] | 595 |

TABLE 1-continued
| Cmpd No. | Structure | ESI, m/z [M + H]+ |
|---|---|---|
| 135 | 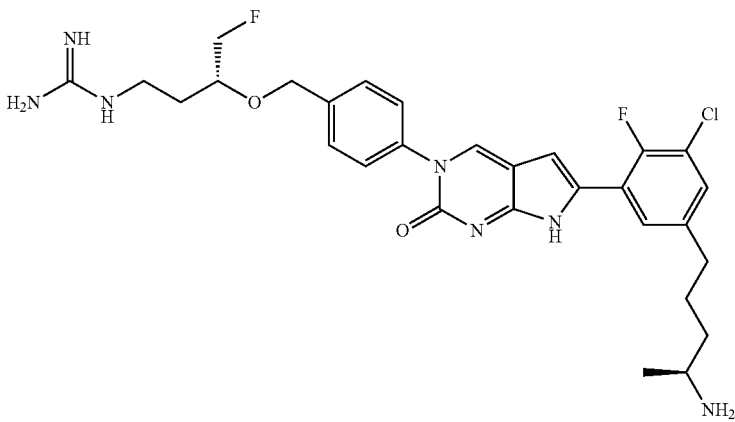 [SMILES: C[C@H](N)CCCc1cc(Cl)c(F)c(-c2cc3cn(-c4ccc(CO[C@@H](CF)CCNC(=N)N)cc4)c(=O)nc3[nH]2)c1] | 586.6 |
| 136 | 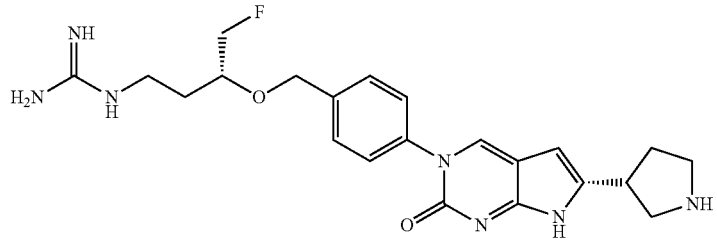 | 442.6 |
| 137 | 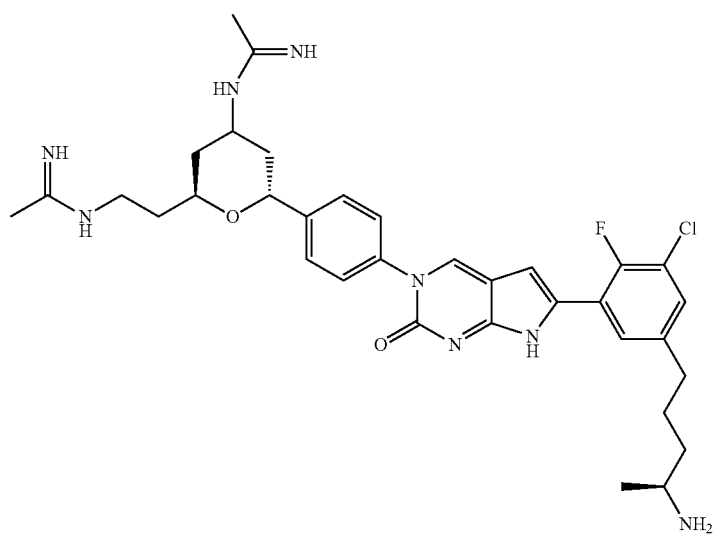 | 649.7 |

TABLE 1-continued

| Cmpd No. | Structure | ESI, m/z [M + H]+ |
|---|---|---|
| 138 | 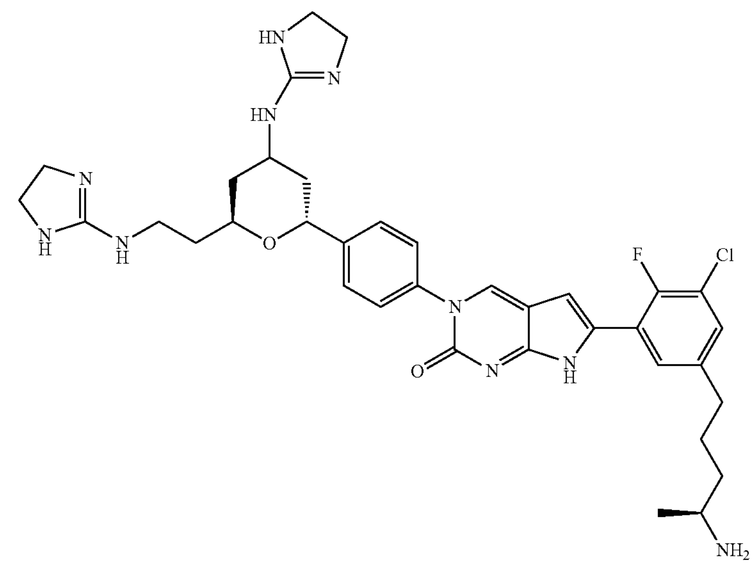 | 703.7 |
| 139 | 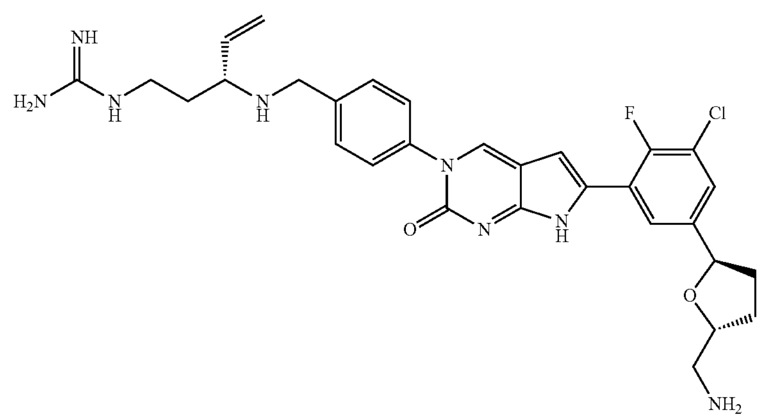 [SMILES: C=C[C@@H](CCNC(=N)N)NCc1ccc(-n2cc3cc(-c4cc([C@H]5CC[C@H](CN)O5)cc(Cl)c4F)[nH]c3nc2=O)cc1] | 593.6 |
| 140 | 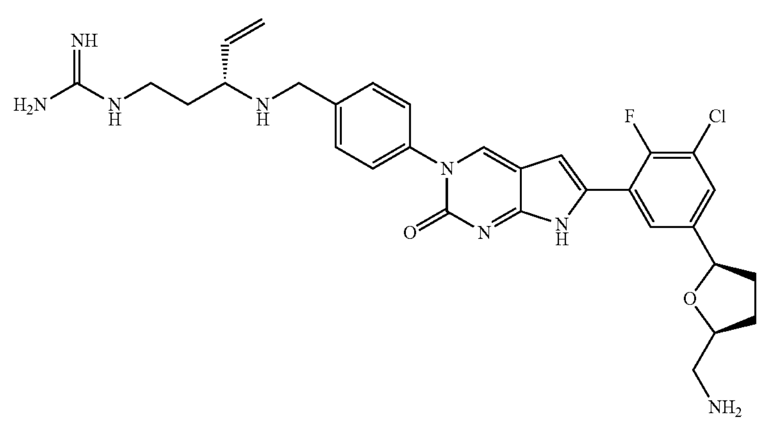 [SMILES: C=C[C@@H](CCNC(=N)N)NCc1ccc(-n2cc3cc(-c4cc([C@H]5CC[C@@H](CN)O5)cc(Cl)c4F)[nH]c3nc2=O)cc1] | 593.6 |

TABLE 1-continued
| Cmpd No. | Structure | ESI, m/z [M + H]+ |
|---|---|---|
| 141 | 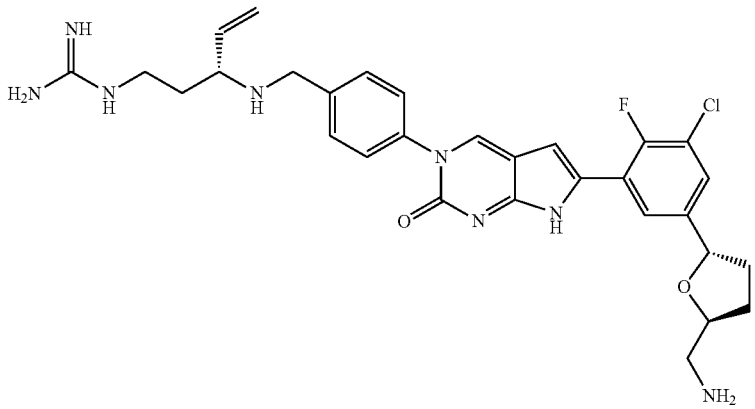 [SMILES: C=C[C@@H](CCNC(=N)N)NCc1ccc(-n2cc3cc(-c4cc([C@@H]5CC[C@@H](CN)O5)cc(Cl)c4F)[nH]c3nc2=O)cc1] | 593.6 |
| 142 | 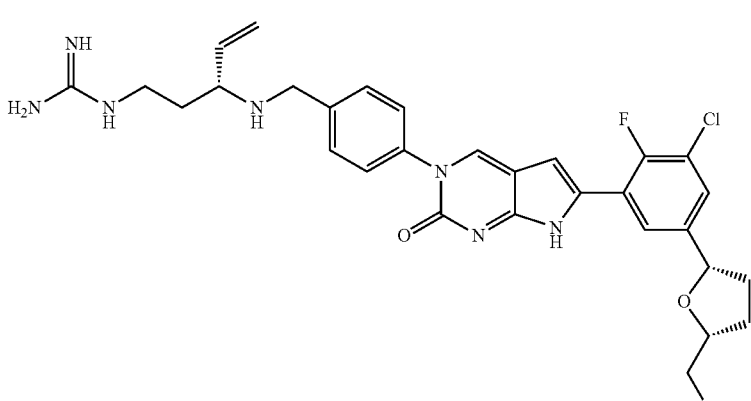 | 593.6 |
| 143 | 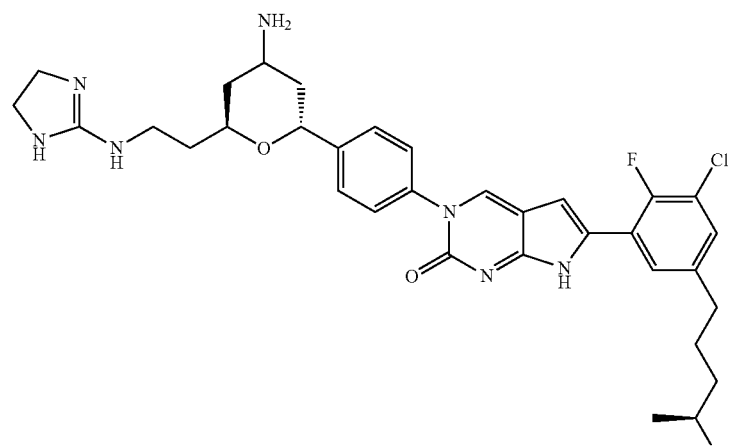 | 635.7 |

TABLE 1-continued
| Cmpd No. | Structure | ESI, m/z [M + H]+ |
|---|---|---|
| 144 | 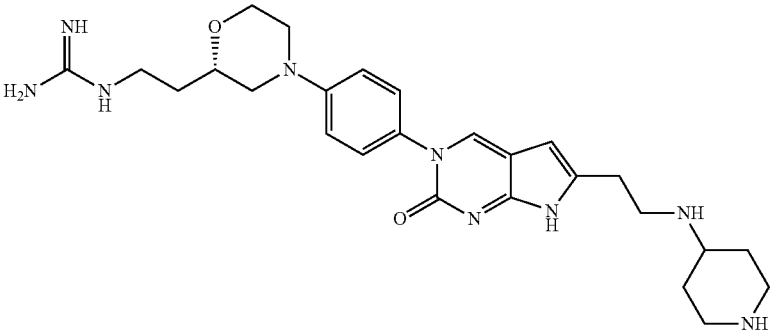 [SMILES: N=C(N)NCC[C@H]1CN(c2ccc(-n3cc4cc(CCNC5CCNCC5)[nH]c4nc3=O)cc2)CCO1] | 508.0 |
| 145 | 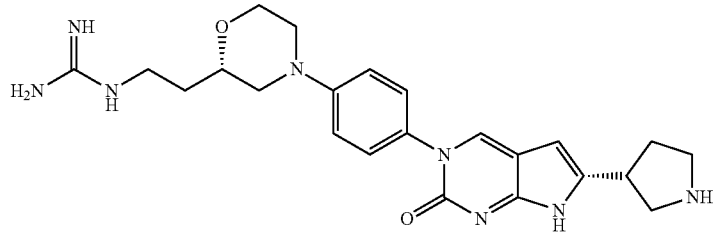 | 451.0 |
| 146 | 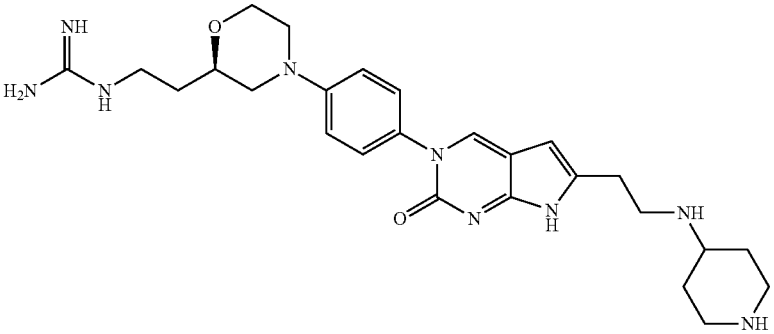 [SMILES: N=C(N)NCC[C@@H]1CN(c2ccc(-n3cc4cc(CCNC5CCNCC5)[nH]c4nc3=O)cc2)CCO1] | 508.0 |
| 147 | 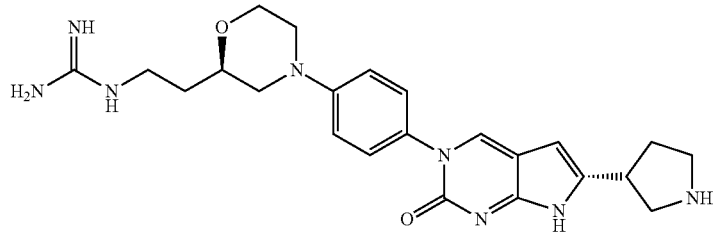 | 451.0 |
| 148 | 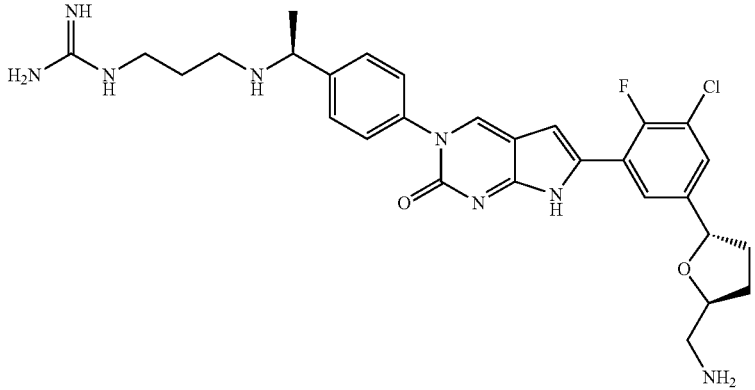 [SMILES: C[C@H](NCCCNC(=N)N)c1ccc(-n2cc3cc(-c4cc([C@@H]5CC[C@@H](CN)O5)cc(Cl)c4F)[nH]c3nc2=O)cc1] | 581.6 |

TABLE 1-continued
| Cmpd No. | Structure | ESI, m/z [M + H]+ |
|---|---|---|
| 149 | 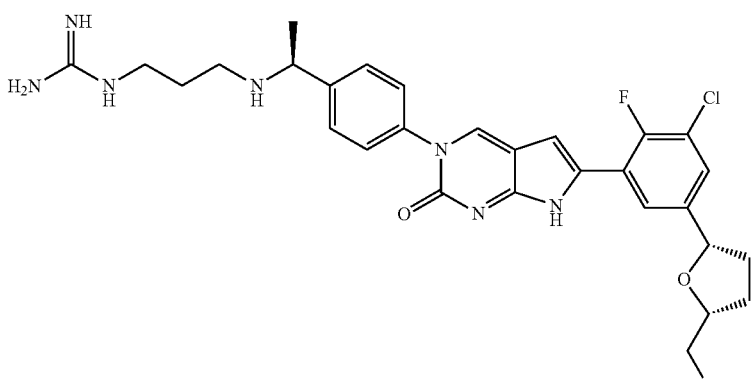 | 581.6 |
| 150 | 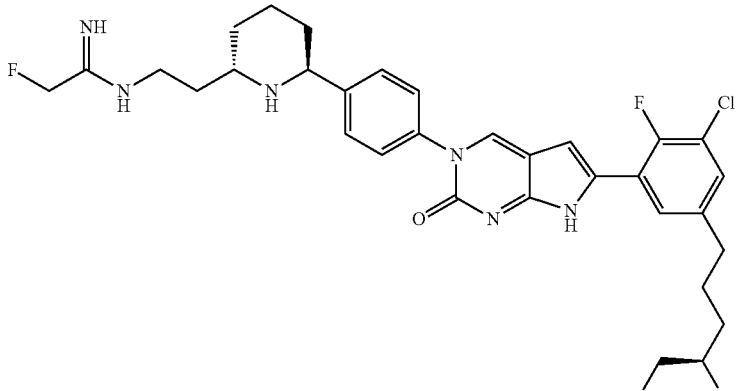 | 626.7 |
| 151 | 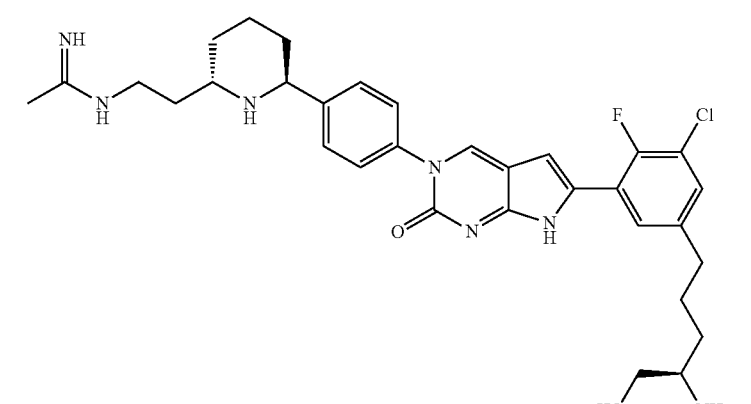 | 608.7 |

TABLE 1-continued
| Cmpd No. | Structure | ESI, m/z [M + H]+ |
|---|---|---|
| 152 | 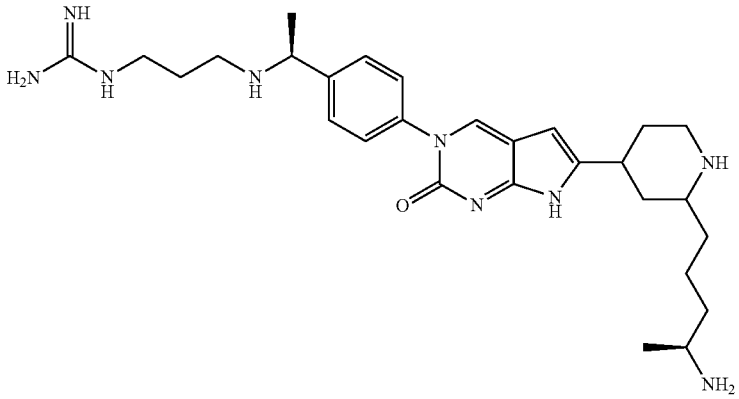 [SMILES: C[C@H](N)CCCC1CC(c2cc3cn(-c4ccc([C@H](C)NCCCNC(=N)N)cc4)c(=O)nc3[nH]2)CCN1] | 522.7 |
| 153 | 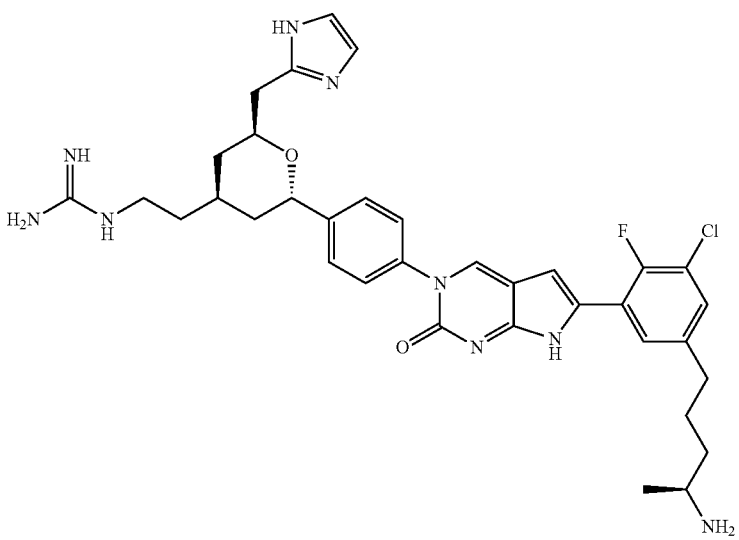 [SMILES: C[C@H](N)CCCc1cc(Cl)c(F)c(-c2cc3cn(-c4ccc([C@@H]5C[C@@H](CCNC(=N)N)C[C@@H](Cc6ncc[nH]6)O5)cc4)c(=O)nc3[nH]2)c1] | 675.2 |

TABLE 1a

| Cmpd No. | Structure | ESI, m/z [M + H]+ |
|---|---|---|
| 159 | 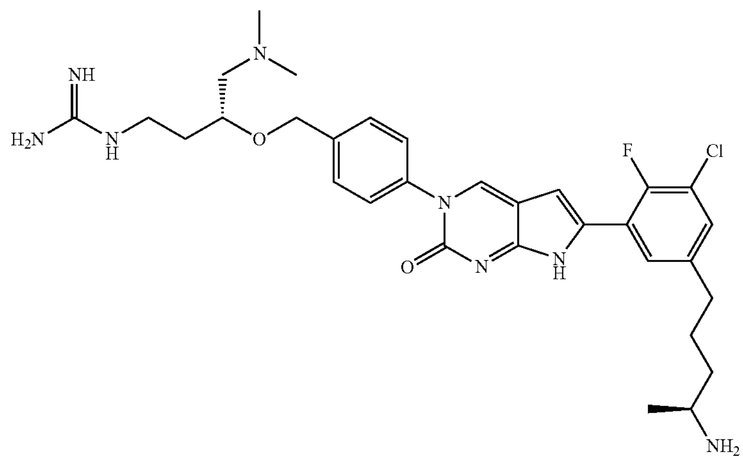 [SMILES: C[C@H](N)CCCc1cc(Cl)c(F)c(-c2cc3cn(-c4ccc(CO[C@H](CCNC(=N)N)CN(C)C)cc4)c(=O)nc3[nH]2)c1] | 611 |
| 160 | 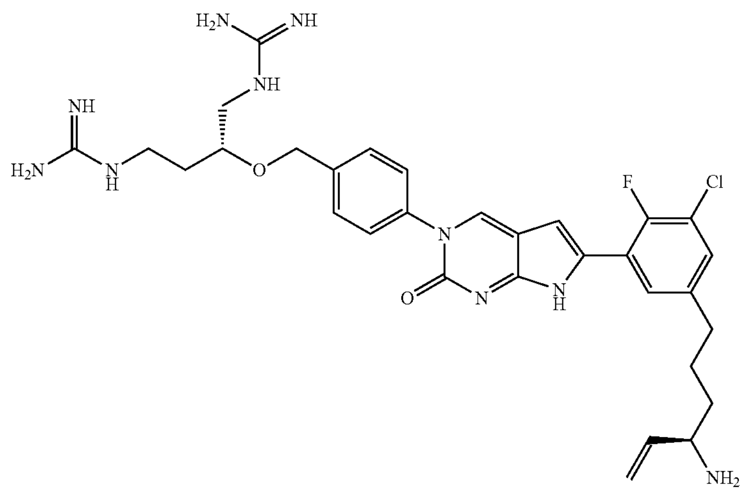 [SMILES: C=C[C@H](N)CCCc1cc(Cl)c(F)c(-c2cc3cn(-c4ccc(CO[C@H](CCNC(=N)N)CNC(=N)N)cc4)c(=O)nc3[nH]2)c1] | 637.5 |
| 161 | 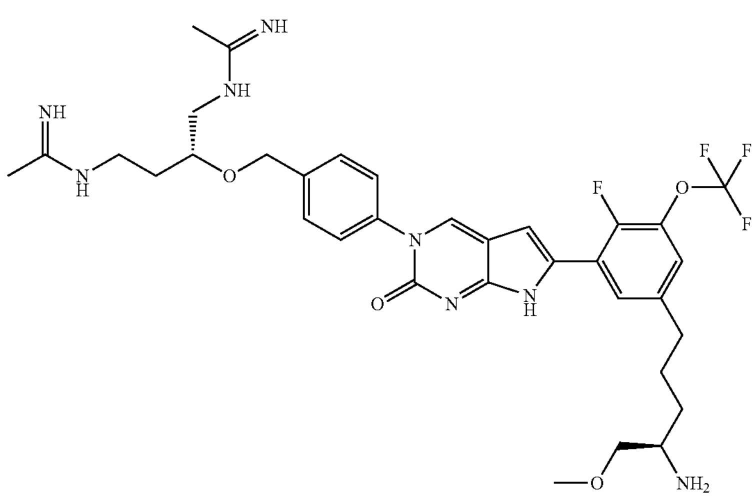 [SMILES: COC[C@H](N)CCCc1cc(OC(F)(F)F)c(F)c(-c2cc3cn(-c4ccc(CO[C@H](CCNC(C)=N)CNC(C)=N)cc4)c(=O)nc3[nH]2)c1] | 703.8 |

TABLE 1a-continued

| Cmpd No. | Structure | ESI, m/z [M + H]+ |
| --- | --- | --- |
| 162 | 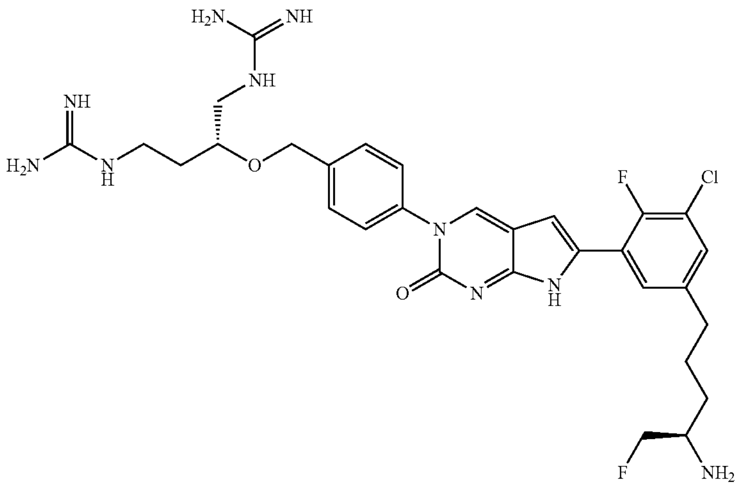 [SMILES: N=C(N)NCC[C@H](CNC(=N)N)OCc1ccc(-n2cc3cc(-c4cc(CCC[C@@H](N)CF)cc(Cl)c4F)[nH]c3nc2=O)cc1] | 643.4 |
| 163 | 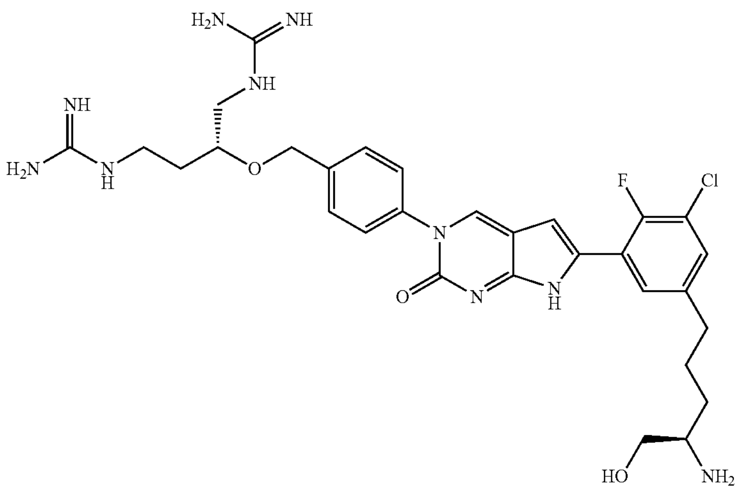 [SMILES: N=C(N)NCC[C@H](CNC(=N)N)OCc1ccc(-n2cc3cc(-c4cc(CCC[C@@H](N)CO)cc(Cl)c4F)[nH]c3nc2=O)cc1] | 641.5 |
| 164 | 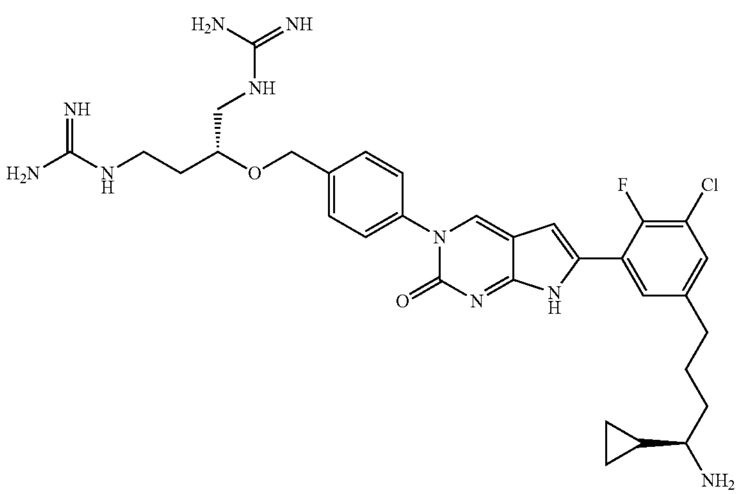 [SMILES: N=C(N)NCC[C@H](CNC(=N)N)OCc1ccc(-n2cc3cc(-c4cc(CCC[C@@H](N)C5CC5)cc(Cl)c4F)[nH]c3nc2=O)cc1] | 651.5 |

TABLE 1a-continued
| Cmpd No. | Structure | ESI, m/z [M + H]+ |
|---|---|---|
| 165 | 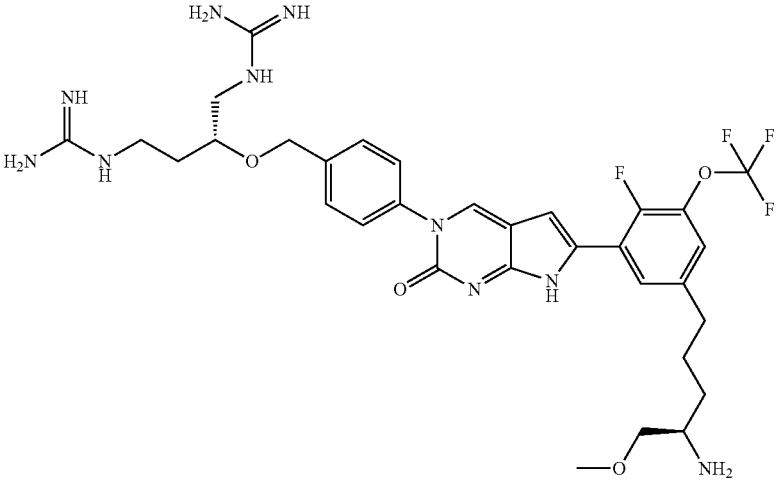 [SMILES: COC[C@H](N)CCCc1cc(OC(F)(F)F)c(F)c(-c2cc3cn(-c4ccc(CO[C@H](CCNC(=N)N)CNC(=N)N)cc4)c(=O)nc3[nH]2)c1] | 705.4 |
| 166 | 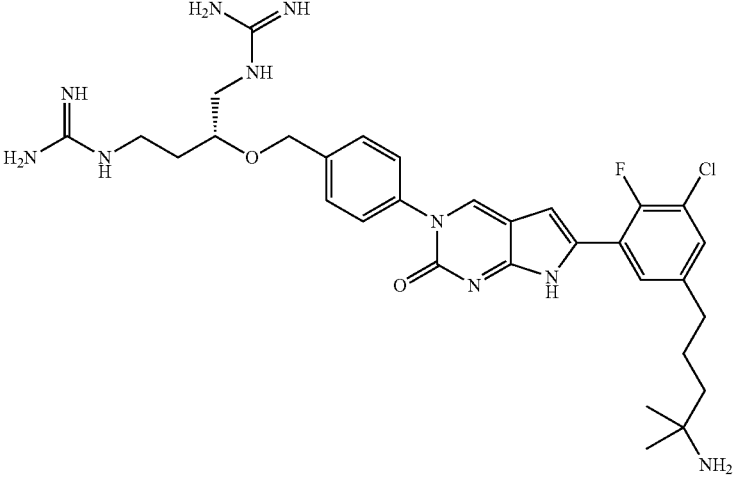 [SMILES: CC(C)(N)CCCc1cc(Cl)c(F)c(-c2cc3cn(-c4ccc(CO[C@H](CCNC(=N)N)CNC(=N)N)cc4)c(=O)nc3[nH]2)c1] | 639.4 |
| 167 | 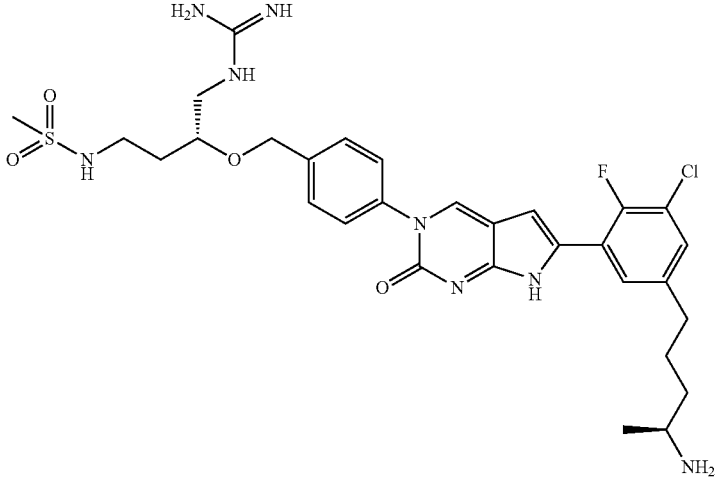 [SMILES: C[C@H](N)CCCc1cc(Cl)c(F)c(-c2cc3cn(-c4ccc(CO[C@H](CCNS(C)(=O)=O)CNC(=N)N)cc4)c(=O)nc3[nH]2)c1] | 661 |

TABLE 1a-continued
| Cmpd No. | Structure | ESI, m/z [M + H]+ |
|---|---|---|
| 168 | 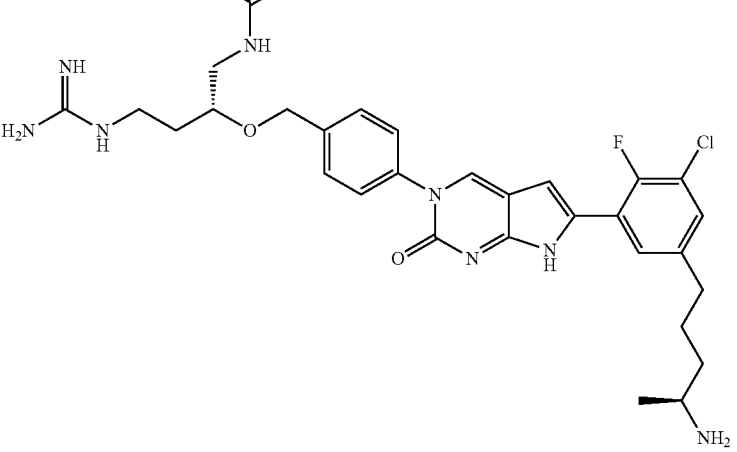 | 624.3 |
| 169 | 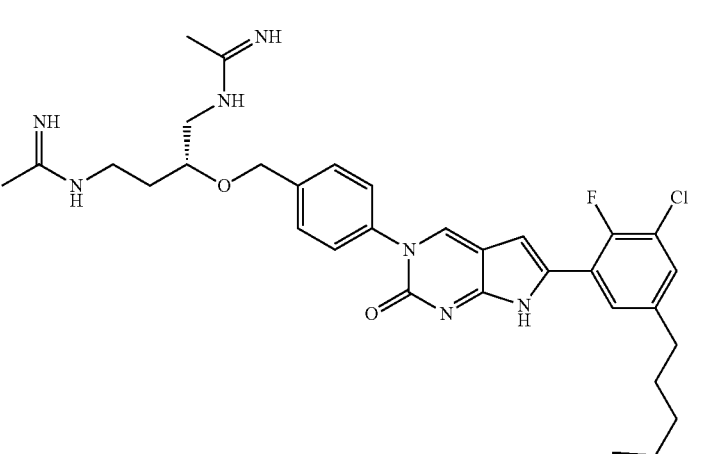 | 624 |
| 170 | 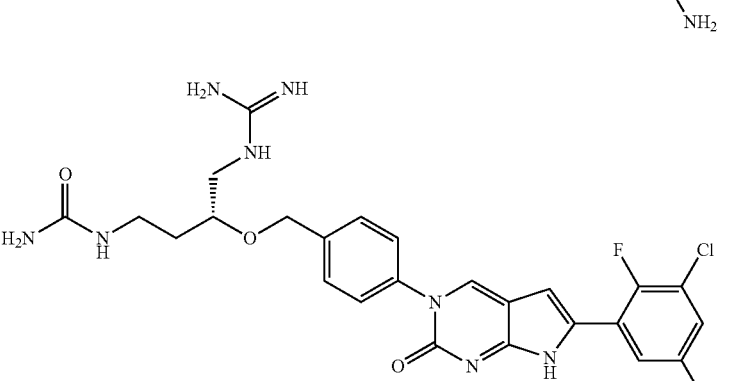 | 626 |

TABLE 1a-continued

| Cmpd No. | Structure | ESI, m/z [M + H]+ |
|---|---|---|
| 171 | 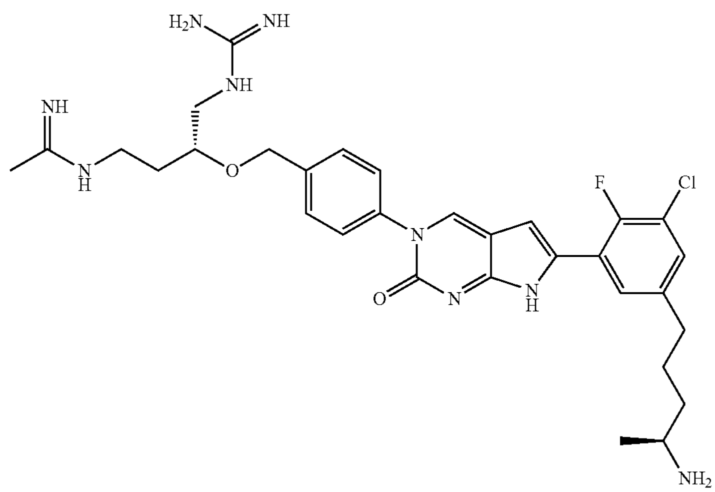 [SMILES: CC(=N)NCC[C@H](CNC(=N)N)OCc1ccc(-n2cc3cc(-c4cc(CCC[C@H](C)N)cc(Cl)c4F)[nH]c3nc2=O)cc1] | 624.7 |
| 172 | 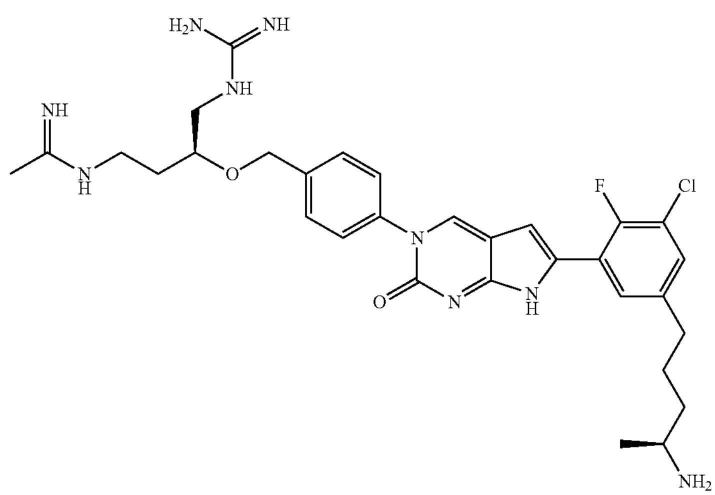 [SMILES: CC(=N)NCC[C@@H](CNC(=N)N)OCc1ccc(-n2cc3cc(-c4cc(CCC[C@H](C)N)cc(Cl)c4F)[nH]c3nc2=O)cc1] | 624.5 |
| 173 | 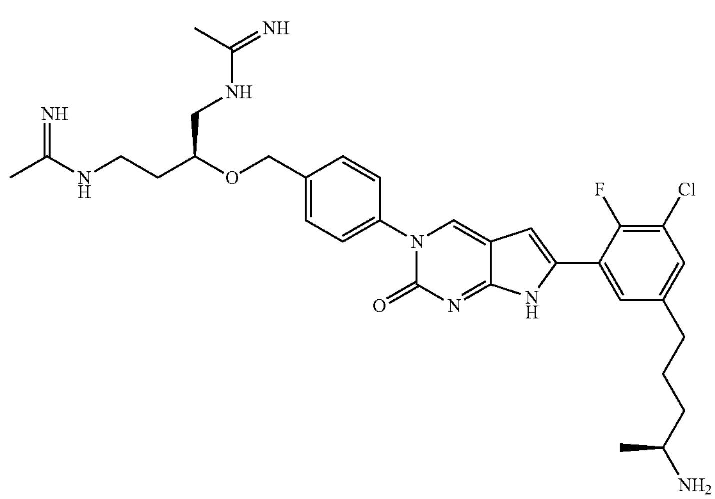 [SMILES: CC(=N)NCC[C@@H](CNC(C)=N)OCc1ccc(-n2cc3cc(-c4cc(CCC[C@H](C)N)cc(Cl)c4F)[nH]c3nc2=O)cc1] | 624.3 |

TABLE 1a-continued

| Cmpd No. | Structure | ESI, m/z [M + H]+ |
|---|---|---|
| 174 | 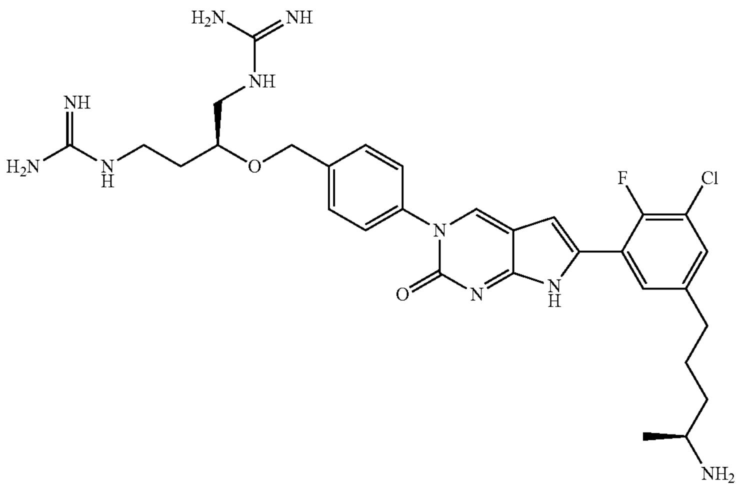 [SMILES: C[C@H](N)CCCc1cc(Cl)c(F)c(-c2cc3cn(-c4ccc(CO[C@@H](CCNC(=N)N)CNC(=N)N)cc4)c(=O)nc3[nH]2)c1] | 625.5 |
| 175 | 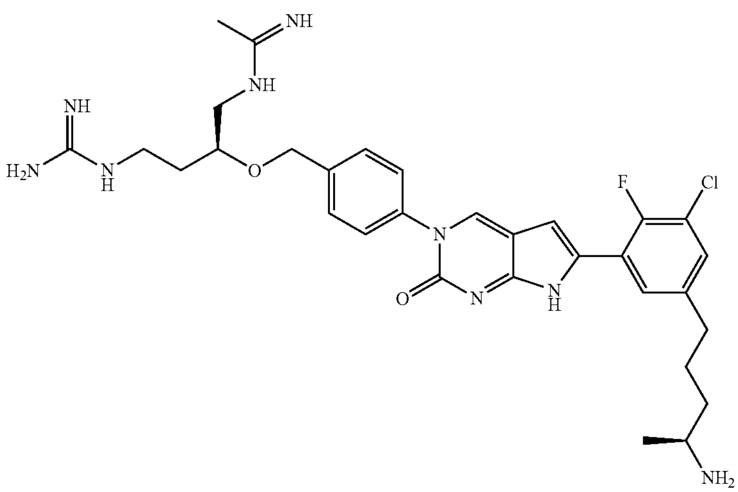 [SMILES: CC(=N)NC[C@H](CCNC(=N)N)OCc1ccc(-n2cc3cc(-c4cc(CCC[C@H](C)N)cc(Cl)c4F)[nH]c3nc2=O)cc1] | 624.4 |
| 176 | 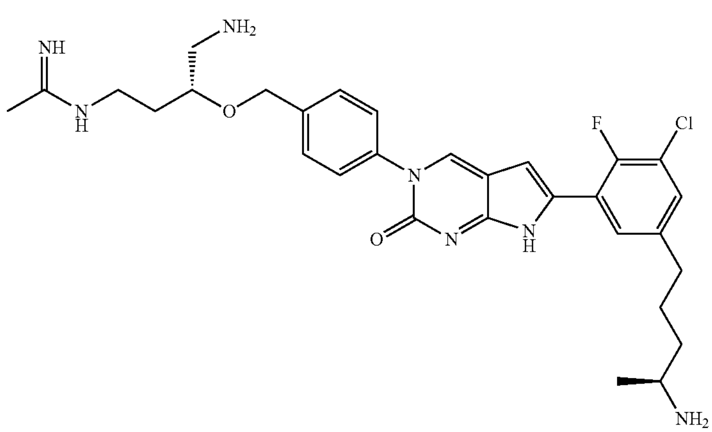 | 582.3 |

TABLE 1a-continued

| Cmpd No. | Structure | ESI, m/z [M + H]+ |
|---|---|---|
| 177 | 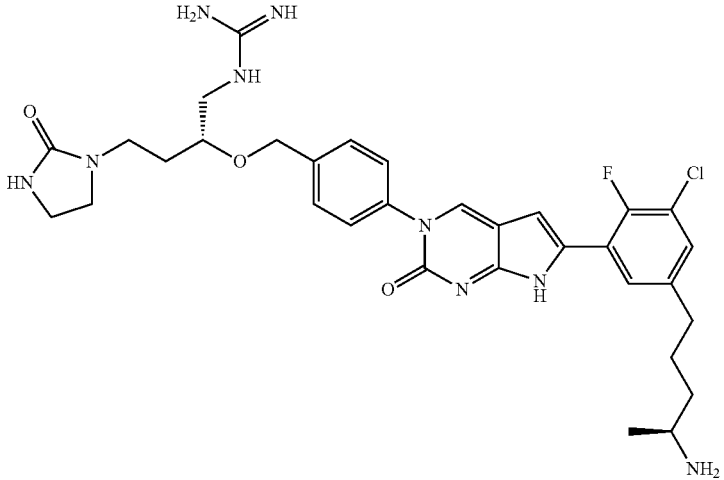 [SMILES: C[C@H](N)CCCc1cc(Cl)c(F)c(-c2cc3cn(-c4ccc(CO[C@H](CCN5CCNC5=O)CNC(=N)N)cc4)c(=O)nc3[nH]2)c1] | 652 |
| 178 | 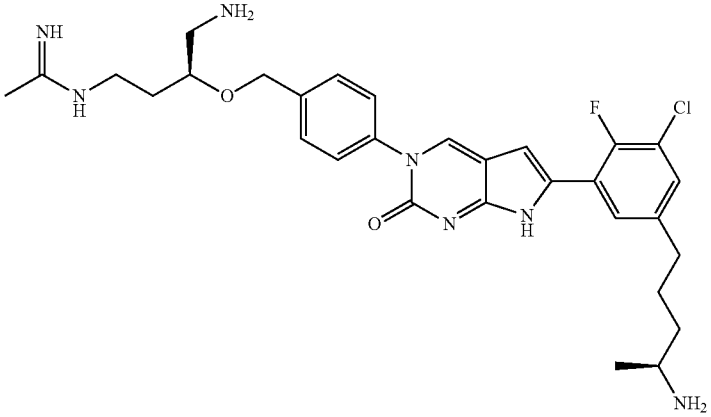 [SMILES: CC(=N)NCC[C@@H](CN)OCc1ccc(-n2cc3cc(-c4cc(CCC[C@H](C)N)cc(Cl)c4F)[nH]c3nc2=O)cc1] | 582 |

In some embodiments, the present disclosure relates to a compound or a tautomer thereof, or a pharmaceutically acceptable salt, ester, or prodrug of said compound or tautomer that binds the ribosome. In some embodiments, the ribosome is a bacterial ribosome.

In some embodiments, the present disclosure relates to a pharmaceutical composition comprising a compound disclosed herein, or a tautomer thereof, or a pharmaceutically acceptable salt, ester, or prodrug of said compound or tautomer, and a pharmaceutically acceptable carrier. In some embodiments, the present disclosure relates to a compound or a tautomer thereof, or a pharmaceutically acceptable salt, ester, or prodrug of said compound or tautomer disclosed herein and a means for delivery of the compound.

In some embodiments, the present disclosure relates to a method of treating, preventing, reducing the risk of or delaying the onset of a disease state in a human or animal comprising administering to the human or animal in need thereof an effective amount of a compound disclosed herein, or a tautomer thereof, or a pharmaceutically acceptable salt, ester, or prodrug of said compound or tautomer.

In some embodiments, the present disclosure relates to a method of treating, preventing, reducing the risk of, or delaying the onset of a microbial infection in a human or animal comprising administering to the human or animal an effective amount of a compound disclosed herein, or a tautomer thereof, or a pharmaceutically acceptable salt, ester, or prodrug of said compound or tautomer.

In some embodiments, the present disclosure relates to use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of, a microbial infection in a human or animal. In another aspect, the present disclosure relates to a compound for use in the manufacture of a medicament for treating a microbial infection in a subject, wherein the compound is selected from a compound of the present disclosure, or a tautomer thereof, or a pharmaceutically acceptable salt, or ester of said compound or tautomer.

In some embodiments, the present disclosure relates to a compound for use in the manufacture of a medicament for preventing a microbial infection in a subject, wherein the compound is selected from a compound of the present disclosure, or a tautomer thereof, or a pharmaceutically acceptable salt, or ester of said compound or tautomer.

In some embodiments, the present disclosure relates to a compound for use in the manufacture of a medicament for reducing the risk of a microbial infection in a subject, wherein the compound is selected from a compound of the present disclosure, or a tautomer thereof, or a pharmaceutically acceptable salt, or ester of said compound or tautomer.

In some embodiments, the present disclosure relates to a compound for use in the manufacture of a medicament for delaying the onset of a microbial infection in a subject, wherein the compound is selected from a compound of the present disclosure, or a tautomer thereof, or a pharmaceutically acceptable salt, or ester of said compound or tautomer.

In some embodiments, the present disclosure relates to a compound disclosed herein, or a tautomer thereof, or a pharmaceutically acceptable salt, ester, or prodrug of said compound or tautomer, for use in treating, preventing, reducing the risk of, or delaying the onset of a microbial infection in a human or animal.

In some embodiments, the present disclosure relates to a compound disclosed herein, or a tautomer thereof, or a pharmaceutically acceptable salt, ester, or prodrug of said compound or tautomer, for use in treating a microbial infection in a human or animal.

In some embodiments, the present disclosure relates to a compound disclosed herein, or a tautomer thereof, or a pharmaceutically acceptable salt, ester, or prodrug of said compound or tautomer, for use in preventing a microbial infection in a human or animal.

In some embodiments, the present disclosure relates to a compound disclosed herein, or a tautomer thereof, or a pharmaceutically acceptable salt, ester, or prodrug of said compound or tautomer, for use in reducing the risk of a microbial infection in a human or animal.

In some embodiments, the present disclosure relates to a compound disclosed herein, or a tautomer thereof, or a pharmaceutically acceptable salt, ester, or prodrug of said compound or tautomer, for use in delaying the onset of a microbial infection in a human or animal.

In some embodiments, the present disclosure relates to a method of treating, preventing, reducing the risk of, or delaying the onset of a microbial infection in a human or animal comprising administering to the human or animal an effective amount of a compound or a tautomer thereof, or a pharmaceutically acceptable salt, ester, or prodrug of said compound or tautomer, wherein said microbial infection is caused by one or more of the following microorganisms: *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *Citrobacter freundii*, *Citrobacter koser*, *Clostridium clostridioforme*, *Clostridium perfringens*, *Enterobacter aerogenes*, *Enterobacter cloacae*, *Enterococcus faecalis*, *Enterococcus* spp. (vancomycin susceptible and resistant isolates), *Escherichia coli* (including ESBL and KPC producing isolates), *Eubacterium lentum*, *Fusobacterium* spp., *Haemophilus influenzae* (including beta-lactamase positive isolates), *Haemophilus parainfluenzae*, *Klebsiella pneumoniae* (including ESBL and KPC producing isolates), *Klebsiella oxytoca* (including ESBL and KPC producing isolates), *Legionella pneumophilia Moraxella catarrhalis*, *Morganella morganii*, *Mycoplasma* spp., *Peptostreptococcus* spp., *Porphyromonas asaccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus* (methicillin susceptible and resistant isolates), *Staphylococcus epidermidis* (methicillin susceptible and resistant isolates), *Stenotrophomonas maltophilia*, *Streptococcus agalactiae*, *Streptococcus constellatus*, *Streptococcus pneumoniae* (penicillin susceptible and resistant isolates), *Streptococcus pyogenes*, or *Streptococcus pyogenes*.

In some embodiments, the present disclosure relates to a method of treating, preventing, reducing the risk of, or delaying the onset of a microbial infection in a human or animal comprising administering to the human or animal an effective amount of a compound or a tautomer thereof, or a pharmaceutically acceptable salt, ester, or prodrug of said compound or tautomer, wherein said infection is caused by or involves one or more microorganisms selected from: *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *Citrobacter freundii*, *Citrobacter koser*, *Clostridium clostridioforme*, *Clostridium perfringens*, *Enterobacter aerogenes*, *Enterobacter cloacae*, *Enterococcus faecalis*, *Enterococcus* spp., *Escherichia coli*, *Eubacterium lentum*, *Fusobacterium* spp., *Haemophilus influenzae*, *Haemophilus parainfluenzae*, *Klebsiella pneumoniae*, *Klebsiella oxytoca*, *Legionella pneumophilia*, *Moraxella catarrhalis*, *Morganella morganii*, *Mycoplasma* spp., *Peptostreptococcus* spp., *Porphyromonas asaccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus*, *Staphylococcus epidermidis*, *Stenotrophomonas maltophilia*, *Streptococcus agalactiae*, *Streptococcus constellatus*, *Streptococcus pneumoniae*, *Streptococcus pyogenes*, and *Streptococcus pyogenes*.

In some embodiments, the present disclosure relates to a method wherein said infection is caused by or involves one or more of aerobic and facultative gram-positive microorganism selected from: *Staphylococcus aureus*, *Streptococcus pneumoniae*, *Enterococcus* spp., *Streptococcus agalactiae*, *Streptococcus pyogenes*, and *Staphylococcus epidermidis*.

In some embodiments, the present disclosure relates to a method wherein said infection is caused by or involves one or more of aerobic and facultative gram-negative microorganism selected from: *Escherichia coli*, *Haemophilus influenzae*, *Klebsiella pneumoniae*, *Citrobacter freundii*, *Enterobacter aerogenes*, *Enterobacter cloacae*, *Morganella morganii*, *Serratia marcescens*, *Pseudomonas aeruginosa*, *Acinetobacter baumanni*, *Moraxella catarrhalis*, *Proteus mirabilis*, *Citrobacter koseri*, *Haemophilus parainfluenzae*, *Klebsiella oxytoca*, *Proteus vulgaris*, *Providencia rettgeri*, and *Providencia stuartii*.

In some embodiments, the present disclosure relates to a method wherein, said infection is caused by or involves one or more anaerobic microorganisms: *Bacteroides fragilis*, *Bacteroides distasonis*, *Bacteroides ovatus*, *Bacteroides thetaiotaomicron*, *Bacteroides uniformis*, *Clostridium clostridioforme*, *Eubacterium lentum*, *Peptostreptococcus* spp., *Porphyromonas asaccharolytica*, *Prevotella bivia*, *Bacteroides vulgatus*, *Clostridium perfringens*, and *Fusobacterium* spp.

In some embodiments, the present disclosure relates to a method, wherein the microorganism *Enterococcus* spp. is selected from vancomycin susceptible isolate and vancomycin resistant isolate.

In some embodiments, the present disclosure relates to a method wherein, the microorganism *Escherichia coli* is selected from extended spectrum beta-lactamase (ESBL) producing isolate and *Klebsiella pneumoniae* carbapenemase (KPC) producing isolate.

In some embodiments, the present disclosure relates to a method wherein, the microorganism *Haemophilus influenzae* is a beta-lactamase positive isolate.

In some embodiments, the present disclosure relates to a method wherein, the microorganism *Klebsiella pneumoniae* is selected from extended spectrum beta-lactamase (ESBL) producing isolate and *Klebsiella pneumoniae* carbapenemase (KPC) producing isolate.

In some embodiments, the present disclosure relates to a method wherein, the microorganism *Klebsiella oxytoca* selected from extended spectrum beta-lactamase (ESBL) producing isolate and *Klebsiella pneumoniae* carbapenemase (KPC) producing isolate.

In some embodiments, the present disclosure relates to a method wherein, the microorganism *Staphylococcus aureus* is selected from methicillin susceptible isolate and methicillin resistant isolate.

In some embodiments, the present disclosure relates to a method wherein, the microorganism *Staphylococcus epidermidis* is selected from methicillin susceptible isolate and methicillin resistant isolate.

In some embodiments, the present disclosure relates to a method wherein, the microorganism *Streptococcus pneumoniae* is selected from penicillin susceptible isolate and penicillin resistant isolate.

In some embodiments, the present disclosure relates to a method of treating, preventing, reducing the risk of, or delaying the onset of a microbial infection in a human or animal comprising administering to the human or animal an effective amount of a compound or a tautomer thereof, or a pharmaceutically acceptable salt, ester, or prodrug of said compound or tautomer, wherein said microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to a method of treating, preventing, reducing the risk of, or delaying the onset of a microbial infection in a human or animal comprising administering to the human or animal an effective amount of a compound or a tautomer thereof, or a pharmaceutically acceptable salt, ester, or prodrug of said compound or tautomer, wherein said microbial infection is caused by one or more of the following microorganisms: *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to a method of treating, preventing, reducing the risk of, or delaying the onset of a microbial infection in a human or animal comprising administering to the human or animal an effective amount of a compound disclosed herein, or a tautomer thereof, or a pharmaceutically acceptable salt, ester, or prodrug of said compound or tautomer, or a pharmaceutical composition thereof, or use of a compound disclosed herein, or a tautomer thereof, or a pharmaceutically acceptable salt, ester, or prodrug of said compound or tautomer, or a pharmaceutical composition thereof, in the manufacture of a medicament for treating, preventing, reducing the risk of, or delaying the onset of a microbial infection in a human or animal, wherein the microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to a method of treating, preventing, reducing the risk of, or delaying the onset of a microbial infection in a human or animal comprising administering to the human or animal an effective amount of a compound disclosed herein, or a tautomer thereof, or a pharmaceutically acceptable salt, ester, or prodrug of said compound or tautomer, or a pharmaceutical composition thereof, wherein the microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to a method of treating a microbial infection in a human or animal comprising administering to the human or animal an effective amount of a compound disclosed herein, or a tautomer thereof, or a pharmaceutically acceptable salt, ester, or prodrug of said compound or tautomer, or a pharmaceutical composition thereof, wherein the microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to a method of preventing a microbial infection in a human or animal comprising administering to the human or animal an effective amount of a compound disclosed herein, or a tautomer thereof, or a pharmaceutically acceptable salt, ester, or prodrug of said compound or tautomer, or a pharmaceutical composition thereof, wherein the microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to a method of reducing the risk of a microbial infection in a human or animal comprising administering to the human or animal an effective amount of a compound disclosed herein, or a tautomer thereof, or a pharmaceutically acceptable salt, ester, or prodrug of said compound or tautomer, or a pharmaceutical composition thereof, wherein the microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to a method of delaying the onset of a microbial infection in a human or animal comprising administering to the human or animal an effective amount of a compound disclosed herein, or a tautomer thereof, or a pharmaceutically acceptable salt, ester, or prodrug of said compound or tautomer, or a pharmaceutical composition thereof, wherein the microbial infection is caused by or involves one or more microorganisms which are capable of being used as biological weapons, e.g., wherein the one or more microorganisms are selected from *Bacillus anthracis* and Multi Drug Resistant (MDR)

anthracis, *Franciscella tularensis, Yersinia pestis, Burkholderia mallei*, and *Burkholderia pseudomallei*.

In some embodiments, the present disclosure relates to the use of one or more compounds disclosed herein, or a tautomer thereof, or a pharmaceutically acceptable salt, ester, or prodrug of said compound or tautomer, or a pharmaceutical composition thereof, in the manufacture of a medicament for treating, preventing, reducing the risk of, or delaying the onset of a microbial infection in a human or animal, wherein the microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to the use of one or more compounds disclosed herein, or a tautomer thereof, or a pharmaceutically acceptable salt, ester, or prodrug of said compound or tautomer, or a pharmaceutical composition thereof, in the manufacture of a medicament for treating a microbial infection in a human or animal, wherein the microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to the use of one or more compounds disclosed herein, or a tautomer thereof, or a pharmaceutically acceptable salt, ester, or prodrug of said compound or tautomer, or a pharmaceutical composition thereof, in the manufacture of a medicament for preventing a microbial infection in a human or animal, wherein the microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to the use of one or more compounds disclosed herein, or a tautomer thereof, or a pharmaceutically acceptable salt, ester, or prodrug of said compound or tautomer, or a pharmaceutical composition thereof, in the manufacture of a medicament for reducing the risk of a microbial infection in a human or animal, wherein the microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to the use of one or more compounds disclosed herein, or a tautomer thereof, or a pharmaceutically acceptable salt, ester, or prodrug of said compound or tautomer, or a pharmaceutical composition thereof, in the manufacture of a medicament for delaying the onset of a microbial infection in a human or animal, wherein the microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure pertains, at least in part, to a compound disclosed herein, or a tautomer thereof, or a pharmaceutically acceptable salt, ester, or prodrug of said compound or tautomer, or a pharmaceutical composition thereof, for use in a method of treating, preventing, reducing the risk of, and/or delaying the onset of a microbial, e.g., bacterial, infection in a subject, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure pertains, at least in part, to a compound disclosed herein, or a tautomer thereof, or a pharmaceutically acceptable salt, ester, or prodrug of said compound or tautomer, or a pharmaceutical composition thereof, for use in a method of treating a microbial, e.g., bacterial, infection in a subject, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure pertains, at least in part, to a compound disclosed herein, or a tautomer thereof, or a pharmaceutically acceptable salt, ester, or prodrug of said compound or tautomer, or a pharmaceutical composition thereof, for use in a method of preventing a microbial, e.g., bacterial, infection in a subject, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure pertains, at least in part, to a compound disclosed herein, or a tautomer thereof, or a pharmaceutically acceptable salt, ester, or prodrug of said compound or tautomer, or a pharmaceutical composition thereof, for use in a method of reducing the risk of a microbial, e.g., bacterial, infection in a subject, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure pertains, at least in part, to a compound disclosed herein, or a tautomer thereof, or a pharmaceutically acceptable salt, ester, or prodrug of said compound or tautomer, or a pharmaceutical composition thereof, for use in a method of delaying the onset of a microbial, e.g., bacterial, infection in a subject, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present disclosure relates to a method of treating, preventing, reducing the risk of, or delaying the onset of a microbial infection in a human or animal comprising administering to the human or animal an effective amount of a compound disclosed herein, or a tautomer thereof, or a pharmaceutically acceptable salt, ester, or prodrug of said compound or tautomer, or use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of a microbial infection in a human or animal, wherein the microbial infection is selected from the group consisting of: a skin infection, a Gram positive infection, a Gram negative infection, nosocomial pneumonia, community acquired pneumonia, post-viral pneumonia, hospital acquired pneumonia/ventilator associated pneumonia, a respiratory tract infection such as chronic respiratory tract infection (CRTI), acute pelvic infection, a complicated skin and skin structure infection, a skin and soft tissue infection (SSTI) including uncomplicated skin and soft tissue infections (uSSTI)s and complicated skin and soft tissue infections, an abdominal infection, a complicated intra-abdominal infection, a urinary tract infection, bacteremia, septicemia, endocarditis, an atrio-ventricular shunt infection, a vascular access infection, meningitis, surgical prophylaxis, a peritoneal infection, a bone infection, a joint infection, a methicillin-resistant *Staphylococcus aureus* infection, a vancomycin-resistant Enterococci infection, a linezolid-resistant organism infection, and tuberculosis.

The compounds of the present disclosure can be used, for example for the treatment of patients with moderate to severe infections, which may be caused by susceptible isolates of the indicated microorganisms.

In some embodiments, the present disclosure relates to a method of treating, preventing, reducing the risk of, or delaying the onset of a complicated intra-abdominal infection in a human or animal comprising administering to the human or animal an effective amount of a compound disclosed herein, or a tautomer thereof, or a pharmaceutically acceptable salt, ester, or prodrug of said compound or tautomer, or to the use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of a complicated intra-abdominal infection in a human or animal.

In some embodiments, the complicated intra-abdominal infection is selected from polymicrobial infections such as abscess due to *Escherichia coli, Clostridium clostridioforme, Eubacterium lentum, Peptostreptococcus* spp., *Bacteroides fragilis, Bacteroides distasonis, Bacteroides ovatus, Bacteroides thetaiotaomicron, Bacteroides uniformis, Streptococcus anginosus, Streptococcus constellatus, Enterococcus faecalis, Proteus mirabilis*, or *Clostridium perfringens*.

In some embodiments, the present disclosure relates to a method of treating, preventing, reducing the risk of, or delaying the onset of a complicated skin and skin structure infection (cSSSI, also known as acute bacterial skin and skin structure infections or ABSSSI) in a human or animal comprising administering to the human or animal an effective amount of a compound disclosed herein, or a tautomer thereof, or a pharmaceutically acceptable salt, ester, or prodrug of said compound or tautomer, or to the use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of a complicated skin and skin structure infection.

In some embodiments, the complicated skin and skin structure infection is selected from diabetic foot infections without osteomyelitis due to *Staphylococcus aureus* (methicillin susceptible and resistant isolates), *Streptococcus agalactiae, Streptococcus pyogenes, Escherichia coli, Klebsiella pneumoniae, Proteus mirabilis, Bacteroides fragilis, Peptostreptococcus species, Porphyromonas asaccharolytica*, or *Prevotella bivia*.

In some embodiments, the present disclosure relates to a method of treating, preventing, reducing the risk of, or delaying the onset of a community acquired pneumonia (CAP) in a human or animal comprising administering to the human or animal an effective amount of a compound disclosed herein, or a tautomer thereof, or a pharmaceutically acceptable salt, ester, or prodrug of said compound or tautomer, or to the use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of community acquired pneumonia.

In some embodiments, the community acquired pneumonia is due to *Streptococcus pneumoniae* (penicillin susceptible and resistant isolates) including cases with concurrent bacteremia, *Haemophilus influenzae* (including beta-lactamase positive isolates), *Moraxella catarrhalis*, or atypical bacteria like *Mycoplasma* spp.

In some embodiments, the present disclosure relates to a method of treating, preventing, reducing the risk of, or delaying the onset of a complicated urinary tract infection (cUTI) in a human or animal comprising administering to the human or animal an effective amount of a compound disclosed herein, or a tautomer thereof, or a pharmaceutically acceptable salt, ester, or prodrug of said compound or tautomer, or to the use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of a complicated urinary tract infection.

In some embodiments, the complicated urinary tract infection is selected from pyelonephritis due to *Escherichia coli*, concurrent bacteremia, or *Klebsiella pneumoniae*.

In some embodiments, the present disclosure relates to a method of treating, preventing, reducing the risk of, or delaying the onset of an acute pelvic infection in a human or animal comprising administering to the human or animal an effective amount of a compound disclosed herein, or a tautomer thereof, or a pharmaceutically acceptable salt, ester, or prodrug of said compound or tautomer, or to the use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of an acute pelvic infection.

In some embodiments, the acute pelvic infection is selected from postpartum endomyometritis, septic abortion and post-surgical gynecologic infections and the infection is due to a microorganism selected from *Streptococcus agalactiae, Escherichia coli, Bacteroides fragilis, Porphyromonas asaccharolytica, Peptostreptococcus* spp., and *Prevotella bivia*.

In some embodiments, the present disclosure relates to a method of treating, preventing, reducing the risk of, or delaying the onset of a hospital acquired pneumonia (HAP)/ventilator associated pneumonia (VAP) in a human or animal comprising administering to the human or animal an effective amount of a compound disclosed herein, or a tautomer thereof, or a pharmaceutically acceptable salt, ester, or prodrug of said compound or tautomer, or to the use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of hospital acquired pneumonia/ventilator associated pneumonia.

In some embodiments, the hospital acquired pneumonia/ventilator associated pneumonia is due to a microorganism selected from *Streptococcus pneumoniae* (penicillin susceptible and resistant isolates), *Staphylococcus aureus* (methicillin susceptible and resistant isolates), *Klebsiella pneumoniae, Pseudomonas aeruginosa, Acinetobacter* spp., *Stenotrophomonas maltophilia, Haemophilus influenzae* (including beta-lactamase positive isolates), and *Legionella pneumophilia*.

The compounds or tautomers or pharmaceutically acceptable salts, esters or prodrugs of said compounds or tautomers of the present disclosure may also be useful for the prevention, prophylaxis, or reduction of surgical site infections. In some embodiments, the compounds or tautomers or pharmaceutically acceptable salts, esters or prodrugs of said compounds or tautomers of the present disclosure are useful following elective colorectal surgery.

Appropriate specimens for bacteriological examination should be obtained in order to isolate and identify the causative organisms and to determine their susceptibility to the compounds of the present disclosure. Therapy with the compounds or tautomers or pharmaceutically acceptable salts, esters or prodrugs of said compounds or tautomers of the present disclosure may be initiated empirically before results of these tests are known; once results become available, antimicrobial therapy should be adjusted accordingly.

To reduce the development of drug-resistant bacteria and maintain the effectiveness of the compounds or tautomers or pharmaceutically acceptable salts, esters or prodrugs of said compounds or tautomers of the present disclosure and other antibacterial drugs, the compounds or tautomers or pharmaceutically acceptable salts, esters or prodrugs of said compounds or tautomers should be used only to treat or prevent infections that are proven or strongly suspected to be caused by susceptible bacteria. When culture and susceptibility information are available, they should be considered in selecting or modifying antibacterial therapy. In the absence of such data, local epidemiology and susceptibility patterns may contribute to the empiric selection of therapy.

In some embodiments, the present disclosure relates to a method of treating, preventing, reducing the risk of, or delaying the onset of a microbial infection due to an aerobic or facultative gram-positive microorganism in a human or animal comprising administering to the human or animal an effective amount of a compound disclosed herein, or a tautomer thereof, or a pharmaceutically acceptable salt, ester, or prodrug of said compound or tautomer, or to the use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of a microbial infection due to an aerobic or facultative gram-positive microorganism.

In some embodiments, the aerobic or facultative gram-positive microorganism is selected from: *Staphylococcus aureus* (methicillin susceptible and resistant isolates), *Streptococcus pneumoniae* (penicillin susceptible and resistant isolates), *Enterococcus* spp. (vancomycin susceptible and resistant isolates), *Streptococcus agalactiae, Streptococcus pyogenes*, and *Staphylococcus epidermidis* (methicillin susceptible and resistant isolates).

In some embodiments, the present disclosure relates to a method of treating, preventing, reducing the risk of, or delaying the onset of a microbial infection due to an aerobic and facultative gram-negative microorganism in a human or animal comprising administering to the human or animal an effective amount of a compound disclosed herein, or a tautomer thereof, or a pharmaceutically acceptable salt, ester, or prodrug of said compound or tautomer, or to the use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of a microbial infection due to an aerobic or facultative gram-positive microorganism.

In some embodiments, the aerobic and facultative gram-negative microorganism is selected from: *Escherichia coli* [including extended spectrum beta-lactamase (ESBL) and *Klebsiella pneumonia* (KPC) producing isolates), *Haemophilus influenzae* (including Beta-lactamase positive isolates), *Klebsiella pneumoniae* (including ESBL and KPC producing isolates), *Citrobacter freundii, Enterobacter aerogenes, Enterobacter cloacae, Morganella morganii, Serratia marcescens, Pseudomonas aeruginosa, Acinetobacter baumanni, Moraxella catarrhalis, Proteus mirabilis, Citrobacter koseri, Haemophilus parainfluenzae, Klebsiella oxytoca* (including ESBL and KPC producing isolates), *Proteus vulgaris, Providencia rettgeri*, and *Providencia stuartii*.

In some embodiments, the present disclosure relates to a method of treating, preventing, reducing the risk of, or delaying the onset of a microbial infection due to an anaerobic microorganism in a human or animal comprising administering to the human or animal an effective amount of a compound disclosed herein, or a tautomer thereof, or a pharmaceutically acceptable salt, ester, or prodrug of said compound or tautomer, or to the use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of a microbial infection due to an anaerobic microorganism.

In some embodiments, the anaerobic microorganism is selected from: *Bacteroides fragilis, Bacteroides distasonis, Bacteroides ovatus, Bacteroides thetaiotaomicron, Bacteroides uniformis, Clostridium clostridioforme, Eubacterium lentum, Peptostreptococcus species, Porphyromonas asaccharolytica, Prevotella bivia, Bacteroides vulgates, Clostridium perfringens*, and *Fusobacterium* spp.

In some embodiments, the present disclosure relates to a method of treating or reducing the risk of a microbial infection in a human or animal comprising administering to the human or animal an effective amount of a compound disclosed herein, or a tautomer thereof, or a pharmaceutically acceptable salt, ester, or prodrug of said compound or tautomer, or to the use of a compound disclosed herein, or a tautomer thereof, or a pharmaceutically acceptable salt, ester, or prodrug of said compound or tautomer, in the manufacture of a medicament for treating, preventing, reducing the risk of, or delaying the onset of a microbial infection.

In some embodiments, the microorganism is *Legionella pneumophilia*.

In some embodiments, the microorganism *Enterococcus* spp. is selected from vancomycin susceptible isolate and vancomycin resistant isolate. In some embodiments, the microorganism *Escherichia coli* is selected from extended spectrum beta-lactamase (ESBL) producing isolate and *Klebsiella pneumoniae* carbapenemase (KPC) producing isolate. In some embodiments, the microorganism *Haemophilus influenzae* is a beta-lactamase positive isolate. In some embodiments, the microorganism *Klebsiella pneumoniae* is selected from extended spectrum beta-lactamase (ESBL) producing isolate and *Klebsiella pneumoniae* carbapenemase (KPC) producing isolate. In some embodiments, the microorganism *Klebsiella oxytoca* selected from extended spectrum beta-lactamase (ESBL) producing isolate and *Klebsiella pneumoniae* carbapenemase (KPC) producing isolate. In some embodiments, the microorganism *Staphylococcus aureus* is selected from methicillin susceptible isolate and methicillin resistant isolate. In some embodiments, the microorganism *Staphylococcus epidermidis* is selected from methicillin susceptible isolate and methicillin resistant isolate. In some embodiments, the microorganism *Streptococcus pneumoniae* is selected from penicillin susceptible isolate and penicillin resistant isolate.

In some embodiments, the present disclosure relates to a method, use, or compound disclosed herein, wherein the amount of compound or a tautomer thereof, or a pharmaceutically acceptable salt, ester, or prodrug of said compound or tautomer comprises from 0.1 mg to 1500 mg.

In some embodiments, the present disclosure relates to a method, use, or compound disclosed herein wherein the amount of compound or a tautomer thereof, or a pharmaceutically acceptable salt, ester, or prodrug of said compound or tautomer comprises about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325, or about 350 mg, or about 375 mg, or about 400 mg, or about 425 mg, or about 450 mg, or about 475 mg, or about 500 mg, or about 525 mg, or about 550 mg, or about 575 mg, or about 600 mg, or about 625 mg, or about 650 mg, or about 675 mg, or about 700 mg, or about 725 mg, or about 750 mg, or about 775 mg, or about 800 mg, or about 825 mg, or about 850 mg, or about 875 mg, or about 900 mg, or about 925 mg, or about 950 mg, or about 975 mg, or about 1000 mg, or about 1025 mg, or about 1050, mg, or about 1075 mg, or about 1100 mg, or about 1125 mg, or about 1150 mg, or about 1175 mg, or about 1200 mg, or about 1225 mg, or about 1250 mg, or about 1275 mg, or about 1300 mg, or about 1325 mg, or about 1350 mg, or about 1375 mg, or about 1400 mg, or about 1425 mg, or about 1450 mg, or about 1475 mg, or about 1500 mg.

In some embodiments, the present disclosure relates to a method, use, or compound disclosed herein wherein the compound, or a tautomer thereof, or a pharmaceutically acceptable salt, ester, or prodrug of said compound or tautomer, is administered otically, ophthalmically, nasally, orally, parenterally, topically, or intravenously.

In some embodiments, the present disclosure relates to a method of synthesizing a compound disclosed herein, or a tautomer thereof, or a pharmaceutically acceptable salt, ester, or prodrug of said compound or tautomer.

In some embodiments, the present disclosure relates to a medical device containing a compound disclosed herein or a tautomer thereof, or a pharmaceutically acceptable salt, ester, or prodrug of said compound or tautomer. In some embodiments, the device is a stent.

3. Synthesis of the Compounds of the Disclosure

The compounds of the present disclosure can be synthesized by using art recognized techniques, such as those described in US 2012-0220566, WO 2012/173689, or PCT/US2014/054869, the contents of each of which are incorporated herein by reference in their entireties. The compounds thus obtained can be further purified, for example, by flash column chromatography, high performance liquid chromatography, crystallization, or any known purification method.

In one embodiment, the compounds of the present disclosure can be synthesized according to the synthetic Schemes 1-3 below:

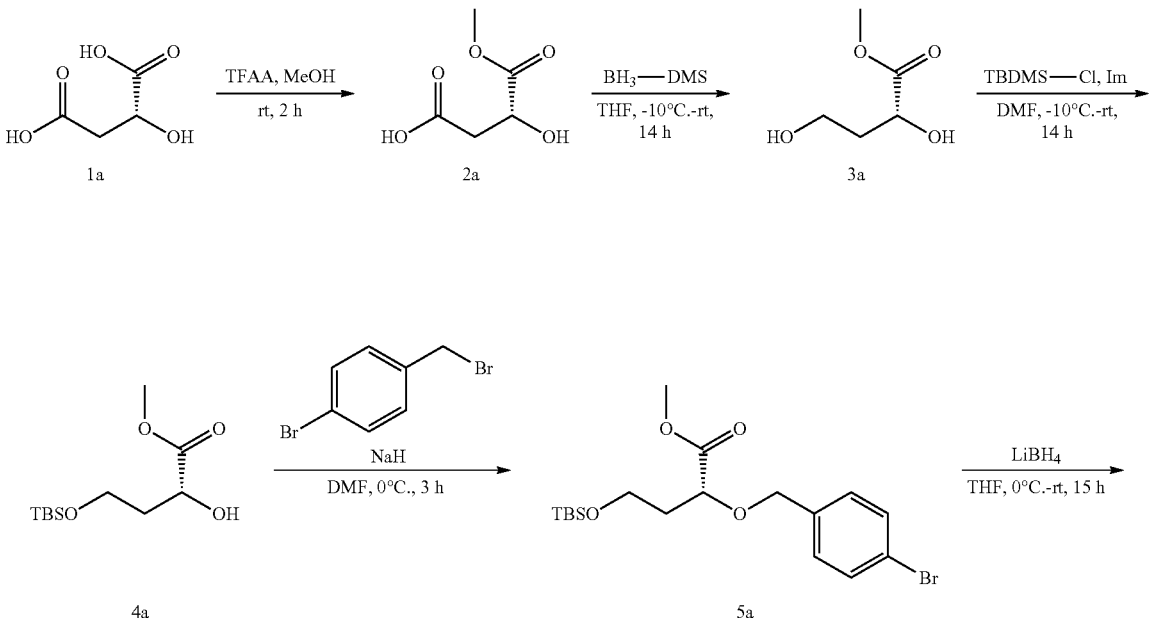

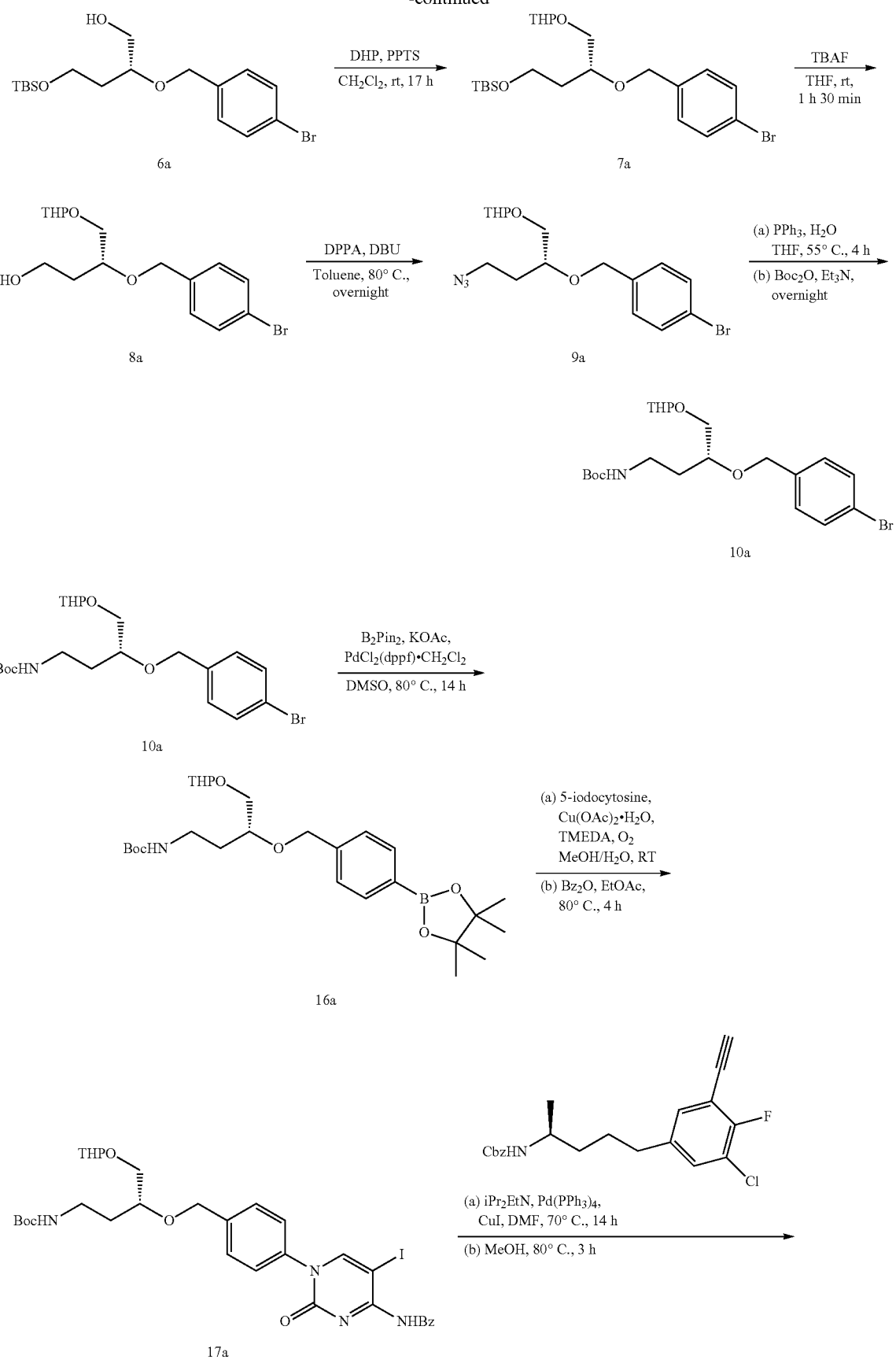

-continued

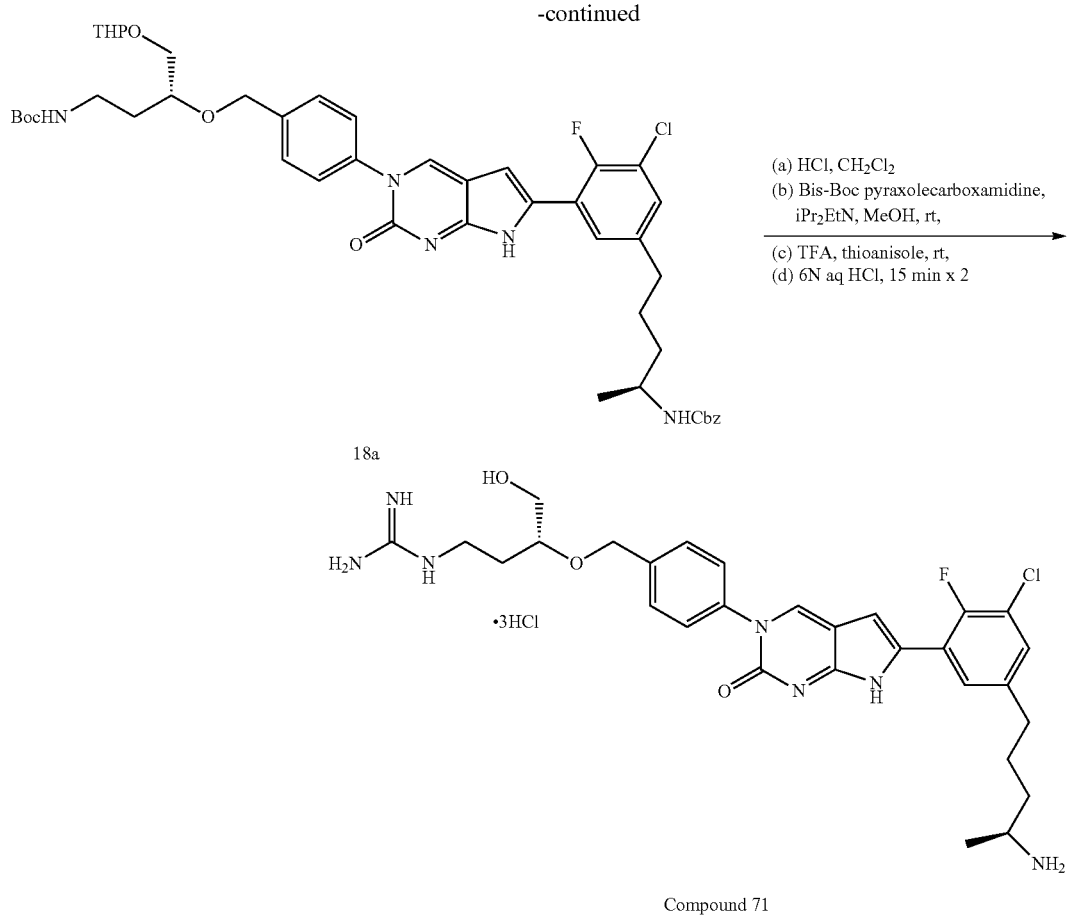

Compound 71

Referring to Scheme 1, esterification of D-Malic acid (1a) is accomplished by adding trifluoroacetic anhydride to and the carboxylic acid e.g., (1a), and stirring the resulting mixture at e.g., room temperature under an inert atmosphere e.g., argon atmosphere for e.g., 40 min. Volatiles are removed, an anhydrous alcohol, e.g., methanol is added, and the mixture is stirred at e.g., room temperature for e.g., 1 h 30 min. The resulting mixture is then concentrated and the residue is crystallized from e.g., diethyl ether/hexanes to obtain 2a.

Reduction of intermediate 2a using a reducing agent e.g., $BH_3$-DMS in a solvent e.g., anhydrous THF at low temperature e.g., −10° C. under an inert atmosphere, e.g., argon atmosphere provides intermediate 3a. Intermediate 4a is obtained by treating 3a with TBDMS-Cl and imidazole in a solvent e.g., anhydrous DMF at low temperature e.g., −10° C. Alkylation of intermediate 4a using a base, e.g., sodium hydride and 4-bromobenzaldehyde in a solvent e.g., anhydrous DMF provides 5a. Reduction of ester 5a with e.g., $LiBH_4$ in a solvent, e.g., anhydrous THF at low temperature, e.g., 0° C. under an inert atmosphere, e.g., argon atmosphere, followed by the addition of e.g., a solution of $LiEt_3BH$ in THF yields 6a.

Intermediate 7a is prepared by treating 6a with dihydropyran in a solvent, e.g., anhydrous methylene chloride, followed by pyridinium p-toluenesulfonate (PPTS) under an inert atmosphere, e.g., argon atmosphere for e.g., 14 h. Deprotection of 7a using a solution of e.g., tetrabutylammonium fluoride in a solvent, e.g., THF yields 8a. Treatment of 8a with diphenylphosphoryl azide in a solvent, e.g., anhydrous toluene under an inert atmosphere, e.g., argon atmosphere and at an elevated temperature, e.g., 80° C., yields 9a. Intermediate 10a is obtained by treating 9a with triphenylphosphine in a solvent, e.g., THF and water at an elevated temperature, e.g., 60° C. for e.g., 3 h.

Treatment of 10a with bispinacolatodiborane, potassium acetate, and $PdCl_2$ (dppf).$CH_2Cl_2$ in a solvent, e.g., anhydrous DMSO under an inert atmosphere, e.g., argon atmosphere and at an elevated temperature e.g., 80° C. yields 16a. Arylation of 16a with 5-iodocytosine in the presence of copper acetate monohydrate, tetramethylethylenediamine, water, and a solvent, e.g., in methanol provides 17a. Coupling of 17a with an alkyne using standard Sonogashira coupling conditions e.g., treatment of 17a and an alkyne with N—N-diisopropylethylamine, $Pd(PPh_3)_4$, and CuI in a solvent, e.g., anhydrous DMF under an inert atmosphere, e.g., argon atmosphere and at an elevated temperature e.g., 70° C. for e.g., 12 h yields 18a.

HCl is added to a solution of 18a in a solvent, e.g., dichloromethane, and stirred at e.g., room temperature for e.g., 1 h. The resulting mixture is concentrated and the residue is dissolved in a solvent, e.g., anhydrous methanol. Bis-boc-1-pyrazolecarboxamide and N—N-diisopropylethylamine are added to the residue and the resulting mixture is stirred at e.g., room temperature for e.g., 12 h. The solvent is removed and the resulting crude mixture is treated with thioanisole in trifluoroacetic acid at e.g., room temperature for e.g., 17 h to provide compounds disclosed herein e.g., Compound 71.

Scheme 2
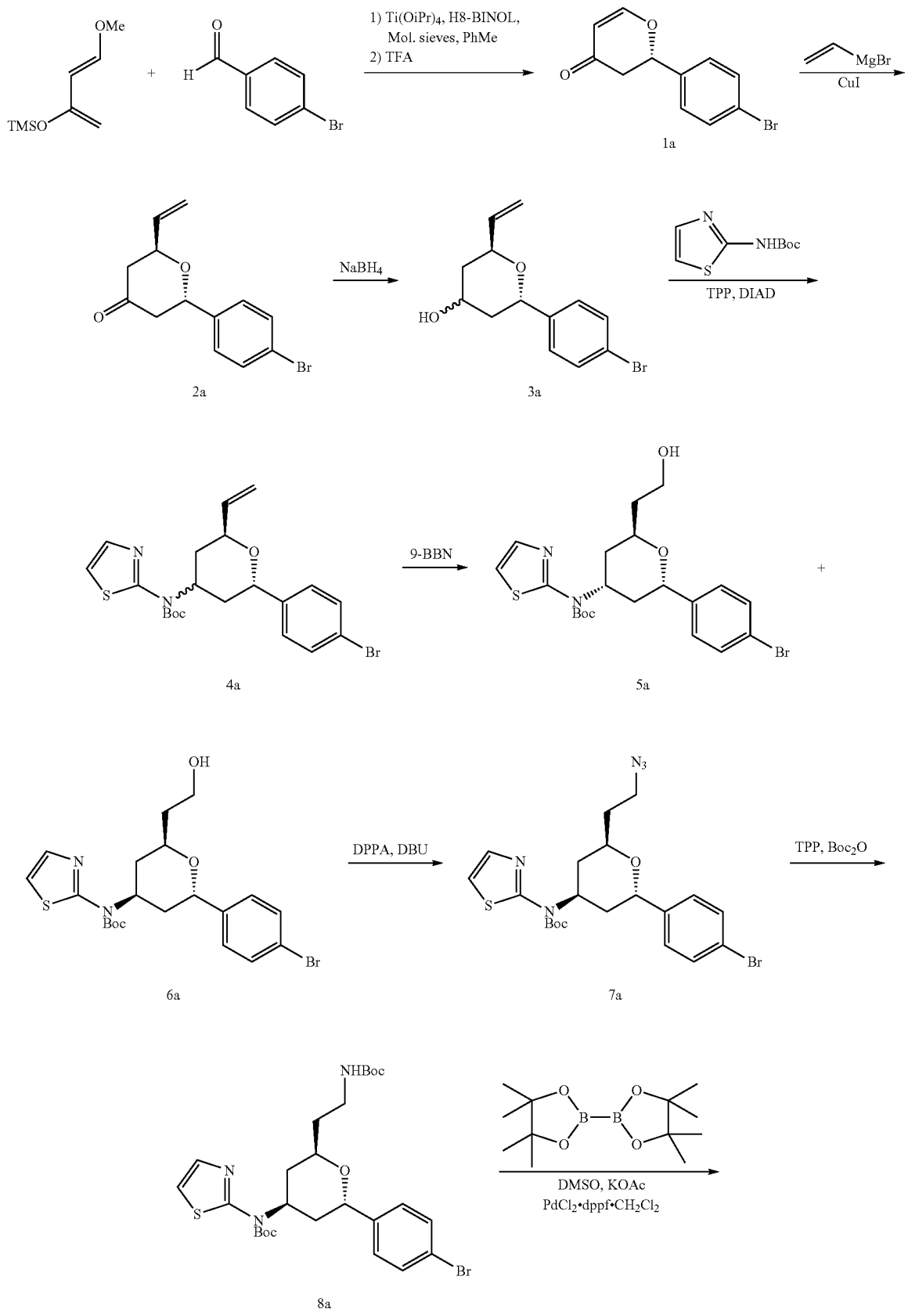

-continued
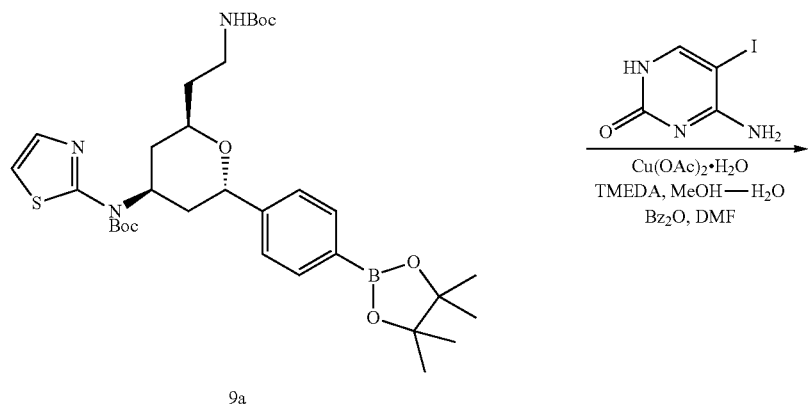
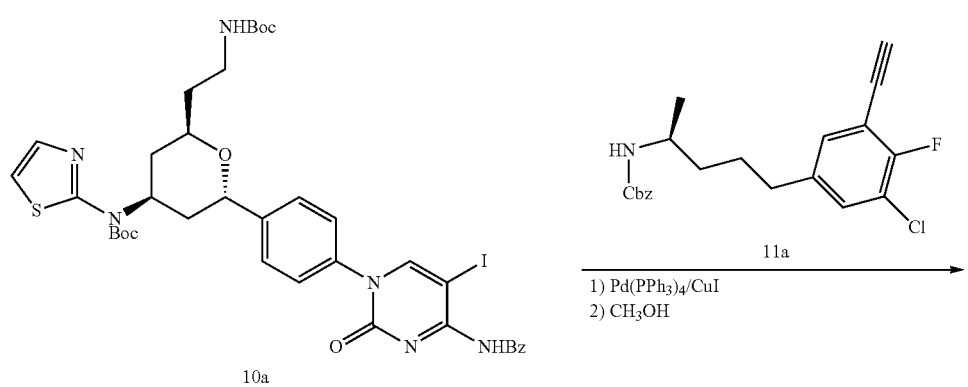
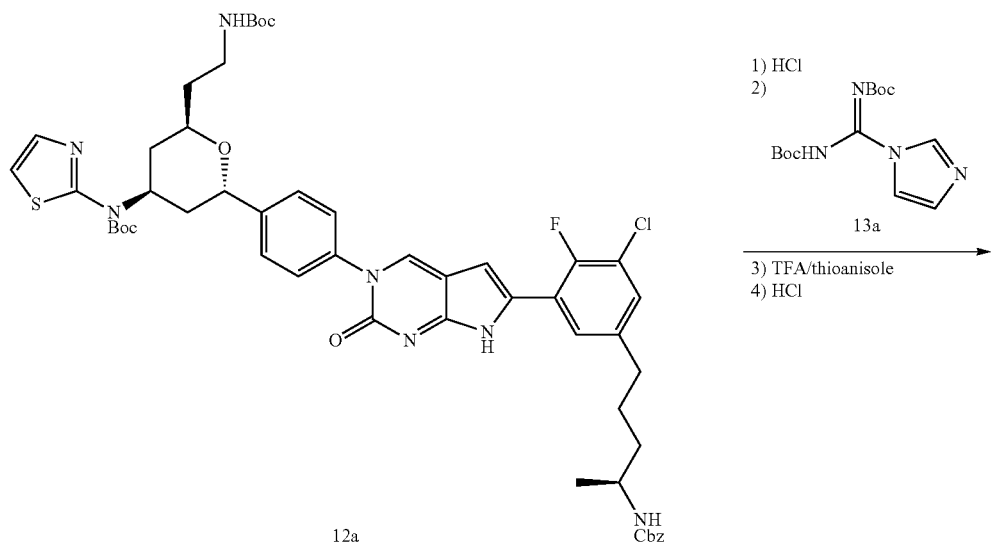

-continued

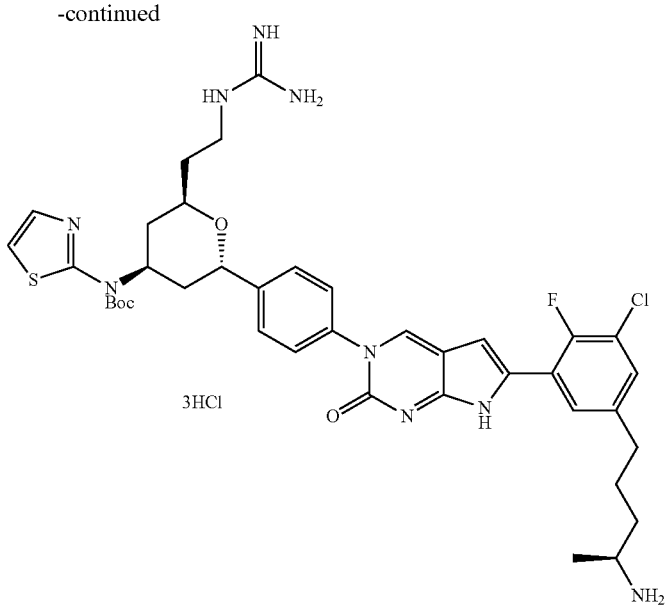

Compound 108

Referring to Scheme 2, cyclization of 4-bromobenzaldehyde and Danishefsky's diene in the presence of (S)-H8-BINOL, 4 Å powdered molecular sieves, and Ti(OiPr)$_4$ in a solvent, e.g., toluene under an inert atmosphere, e.g., argon atmosphere provides 1a. Alkylation of 1a using CuI, vinyl magnesium bromide, DMPU, and TMS-Cl in a solvent, e.g., THF at low temperature, e.g., 0° C. yields 2a. Reduction of 2a using e.g., NaBH$_4$ in a solvent, e.g., methanol provides 3a. Intermediate 4a is prepared by amination of 3a with N-Boc-2-aminothiazole, diisopropyl azodicarboxylate (DIAD), and triphenylphosphine in a solvent, e.g., THF. Treatment of 4a with 9-BBN dimer in a solvent, e.g., anhydrous THF under an inert atmosphere, e.g., argon for e.g., 16 hr yields a mixture of diastereomers 5a and 6a. Intermediate 7a is then prepared by treating 6a with DPPA and DBU in a solvent, e.g., toluene.

Reduction and protection of 7a is accomplished by treatment of 7a with triphenylphosphine in a solvent, e.g., THF and water heating to e.g., 60-65° C. for e.g., 21 hr. The resulting mixture is then cooled to e.g., RT, and treated with triethylamine and (Boc)$_2$O at e.g., RT to yield 8a. Treatment of 8a with bispinacalatodiborane and KOAc followed by PdCl$_2$(dppf)CH$_2$Cl$_2$ in a solvent, e.g., DMSO at elevated temperature e.g., 80-85° C. for e.g., 19 hr provides 9a. Arylation of 9a using Iodocytosine, Cu(OAc)$_2$, and TMEDA in a solvent, e.g., MeOH and/or water at e.g., RT for e.g., 16 hr yields 10a. Coupling of 10a with 11a in the presence of DIPEA, Pd(PPh$_3$)$_4$, and CuI in a solvent, e.g., DMF at an elevated temperature e.g., 70-75° C. for e.g., 13 hr followed by treatment with methanol provides 12a.

12a is then treated with 4N HCl solution in dioxane in a solvent, e.g., CH$_2$Cl$_2$ (5.0 ml) at e.g., RT for e.g., 4 hr. The reaction mixture is then concentrated and treated with N,N'-BisBocgunylpyrazole (13a) and DIPEA in a solvent, e.g., methanol at e.g., RT for e.g., 18 hr. The resulting product is treated with thioanisole in TFA at elevated temperature e.g., 40-45° C. for e.g., 3.5 hr to provide compounds disclosed herein e.g., Compound 108.

Scheme 3

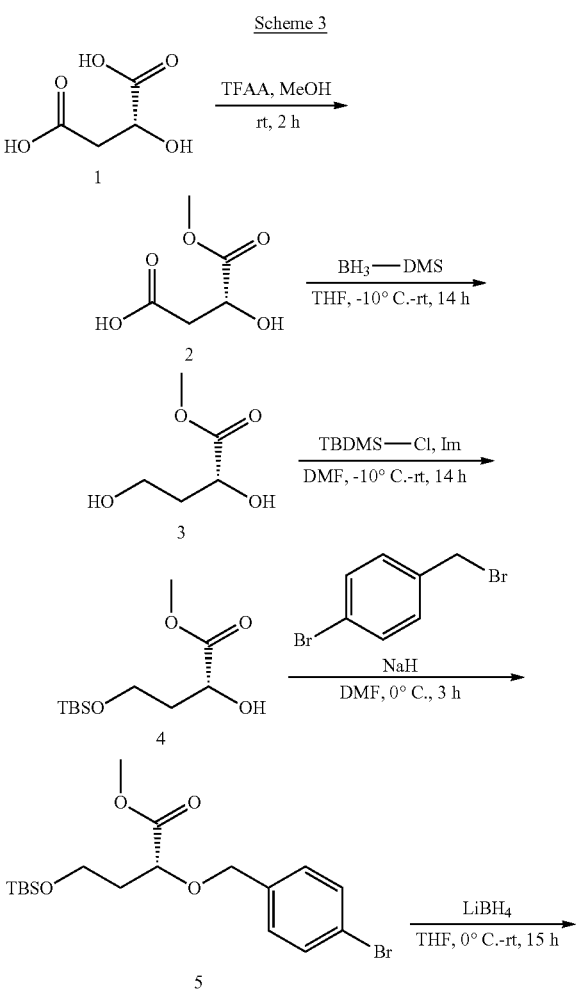

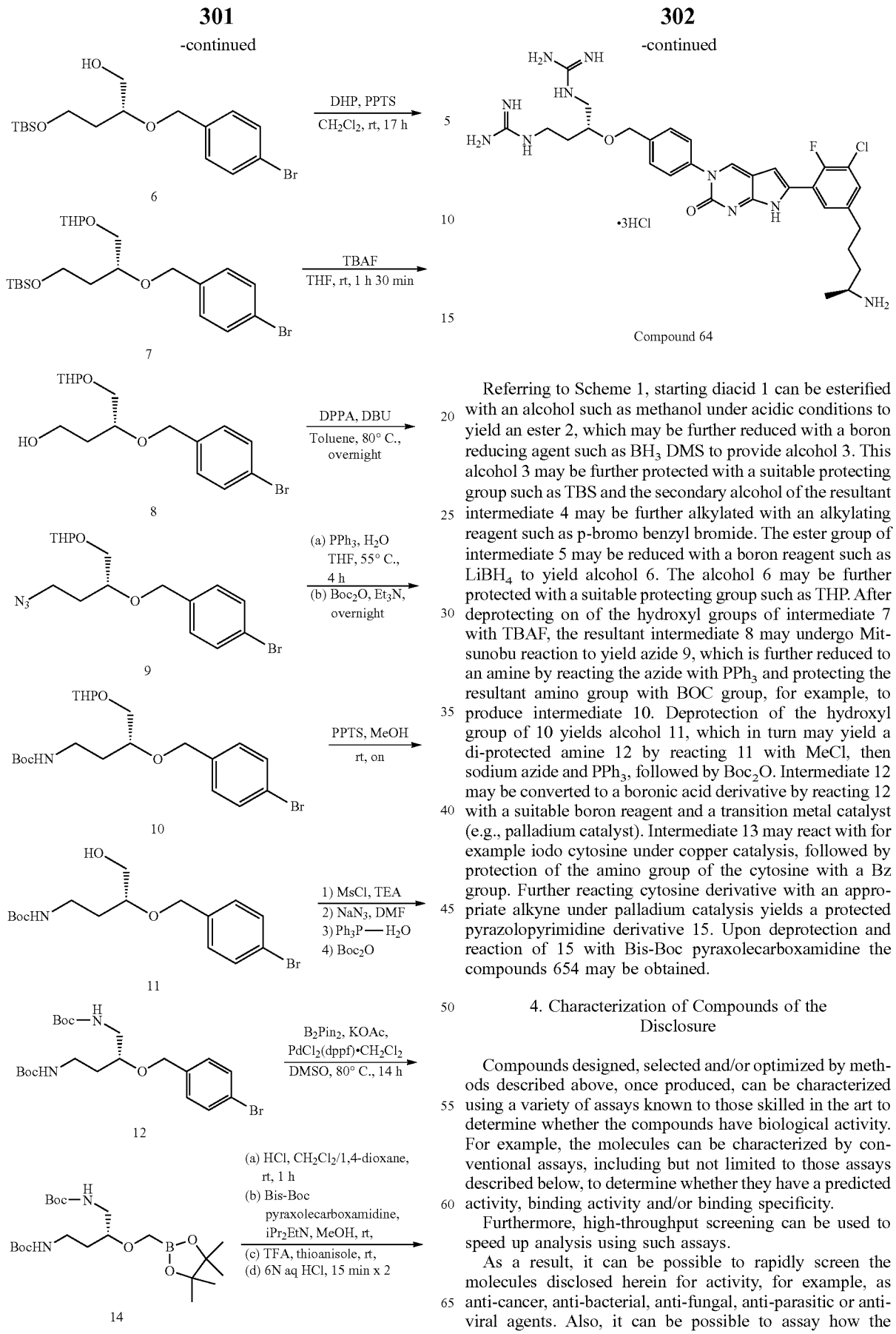

Compound 64

Referring to Scheme 1, starting diacid 1 can be esterified with an alcohol such as methanol under acidic conditions to yield an ester 2, which may be further reduced with a boron reducing agent such as $BH_3$ DMS to provide alcohol 3. This alcohol 3 may be further protected with a suitable protecting group such as TBS and the secondary alcohol of the resultant intermediate 4 may be further alkylated with an alkylating reagent such as p-bromo benzyl bromide. The ester group of intermediate 5 may be reduced with a boron reagent such as $LiBH_4$ to yield alcohol 6. The alcohol 6 may be further protected with a suitable protecting group such as THP. After deprotecting on of the hydroxyl groups of intermediate 7 with TBAF, the resultant intermediate 8 may undergo Mitsunobu reaction to yield azide 9, which is further reduced to an amine by reacting the azide with $PPh_3$ and protecting the resultant amino group with BOC group, for example, to produce intermediate 10. Deprotection of the hydroxyl group of 10 yields alcohol 11, which in turn may yield a di-protected amine 12 by reacting 11 with MeCl, then sodium azide and $PPh_3$, followed by $Boc_2O$. Intermediate 12 may be converted to a boronic acid derivative by reacting 12 with a suitable boron reagent and a transition metal catalyst (e.g., palladium catalyst). Intermediate 13 may react with for example iodo cytosine under copper catalysis, followed by protection of the amino group of the cytosine with a Bz group. Further reacting cytosine derivative with an appropriate alkyne under palladium catalysis yields a protected pyrazolopyrimidine derivative 15. Upon deprotection and reaction of 15 with Bis-Boc pyraxolecarboxamidine the compounds 654 may be obtained.

4. Characterization of Compounds of the Disclosure

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays.

As a result, it can be possible to rapidly screen the molecules disclosed herein for activity, for example, as anti-cancer, anti-bacterial, anti-fungal, anti-parasitic or anti-viral agents. Also, it can be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

(1) Surface Binding Studies.

A variety of binding assays can be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor RTM from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization.

Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis.

It is contemplated that, in addition to characterization by the foregoing biochemical assays, the compound of interest can also be characterized as a modulator (for example, an inhibitor of protein synthesis) of the functional activity of the ribosome or ribosomal subunit.

Furthermore, more specific protein synthesis inhibition assays can be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3$H leucine or $^{35}$S methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is an inhibitor of protein synthesis.

(4) Antimicrobial Assays and Other Evaluation.

Furthermore, the compounds can be assayed for anti-proliferative or anti-infective properties on a cellular level. For example, where the target organism is a microorganism, the activity of compounds of interest can be assayed by growing the microorganisms of interest in media either containing or lacking the compound. Growth inhibition can be indicative that the molecule can be acting as a protein synthesis inhibitor. More specifically, the activity of the compounds of interest against bacterial pathogens can be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms.

The in vitro activity of the compounds of the present disclosure can be determined. Antimicrobial testing is typically performed to determine the minimum inhibitory concentration (MIC). Minimum inhibitory concentrations (MICs) are determined by the microdilution method in a final volume of 100 µl according to protocols outlined by The Clinical and Laboratory Standards Institute (CLSI). Performance standards for reference strains are assessed within the same experimental design to maintain quality control. See, for example, Clinical Laboratory Standards Institute: Methods for dilution antimicrobial susceptibility tests for bacteria that grow aerobically M7-A8. Approved Standard-Eighth Edition. Wayne, Pa.: CLSI; December 2008; and Clinical Laboratory Standards Institute: Performance Standards for Antimicrobial Susceptibility Testing M100-S20; Approved Standard-Twentieth Edition. Wayne, Pa.: CLSI; June 2010.

The antimicrobial and other drug properties of the compounds can further be evaluated in various in vivo mammalian assays, such as a mouse or rat peritonitis infectious models, skin and soft tissue models (often referred to as the thigh model), or a mouse pneumonia model. There are septicemia or organ infection models known to those skilled in the art. These efficacy models can be used as part of the evaluation process and can be used as a guide of potential efficacy in humans. Endpoints can vary from reduction in bacterial burden to lethality. For the latter endpoint, results are often expressed as a $PD_{50}$ value, or the dose of drug that protects 50% of the animals from mortality.

To further assess a compound's drug-like properties, measurements of inhibition of cytochrome P450 enzymes and phase II metabolizing enzyme activity can also be measured either using recombinant human enzyme systems or more complex systems like human liver microsomes.

Further, compounds can be assessed as substrates of these metabolic enzyme activities as well. These activities are useful in determining the potential of a compound to cause drug-drug interactions or generate metabolites that retain or have no useful antimicrobial activity.

To get an estimate of the potential of the compound to be orally bioavailable, one can also perform solubility and Caco-2 assays. The latter is a cell line from human epithelium that allows measurement of drug uptake and passage through a Caco-2 cell monolayer often growing within wells of a 24-well microtiter plate equipped with a 1 micron membrane. Free drug concentrations can be measured on the basolateral side of the monolayer, assessing the amount of drug that can pass through the intestinal monolayer. Appropriate controls to ensure monolayer integrity and tightness of gap junctions are needed. Using this same system one can get an estimate of P-glycoprotein mediated efflux. P-glycoprotein is a pump that localizes to the apical membrane of cells, forming polarized monolayers. This pump can abrogate the active or passive uptake across the Caco-2 cell membrane, resulting in less drug passing through the intestinal epithelial layer. These results are often done in conjunction with solubility measurements and both of these factors are known to contribute to oral bioavailability in mammals. Measurements of oral bioavailability in animals and ultimately in man using traditional pharmacokinetic experiments will determine the absolute oral bioavailability.

Experimental results can also be used to build models that help predict physical-chemical parameters that contribute to drug-like properties. When such a model is verified, experimental methodology can be reduced, with increased reliance on the model predictability.

(5) Animal Pharmacology and Toxicology.

The compounds of the present disclosure can be evaluated for efficacy in well-known animal models. The following table provides representative animal models for various infection indications.

| Target Infection Indication | Animal Model of Efficacy |
|---|---|
| HAP/VAP | Efficacy in mouse and/or rat pneumoniae model vs. respiratory tract infection pathogens of interest (*Streptococcus pneumoniae*, including multi-drug resistant *Streptococcus pneumoniae*, *H. influenzae*, methicillin resistant *Staphylococcus aureus* (MRSA), and *Pseudomonas. aeruginosa*) |
| cSSSI | Efficacy in mouse model against pathogens of interest (MRSA, *K. pneumoniae*) |
| Sepsis | Efficacy in mouse peritonitis model vs. pathogens of interest (*E. coli*, *K. pneumoniae*, *E. faecalis*, MRSA) |
| cUTI | Efficacy in mouse model against *E. coli*, *K. pneumoniae* and/or MRSA) |
| Febrile neutropenia | Efficacy in mouse peritonitis model against *S. aureus*, *S. epidermidis*, *S. pneumoniae*, *S. pyogenes*, *P. aeruginosa* |

Animal Model for Complicated Skin and Skin Structure Infections (cSSSI):
Murine Skin and Soft Tissue Infection Model of *Klebsiella pneumoniae* 1705966 in Thighs of Neutropenic Female CD-1 Mice This model is useful to assess the efficacy of compounds of the present disclosure in a *Klebsiella pneumoniae* 1705966 neutropenic mouse thigh infection model using female ICR (CD-1) mice.

Study Design:
Species: Female ICR (CD-1) Mice, 8 to 9 weeks old, weighting 25-29 g.
Inoculum: *Klebsiella pneumoniae* 17059663 was streaked from frozen stock onto Blood agar (Tryptic Soy Agar+5% Sheep Blood), BD, #221261) and incubated overnight at 35° C. After overnight incubation, enough bacteria (approx. 1 full loop) to measure $OD_{625}$=0.990 was transferred from plate and diluted into 10 ml pre-warmed Mueller-Hinton broth. This culture was further diluted 1:1000 into pre-warmed MH broth and grown for approximately 2 hours at 35° C. with shaking. Each mouse was given 0.1 mL of 1:1000 dilution culture injected into both caudal thigh muscles under isoflurane inhalation anesthesia.

| Dilution | Initial O.D. | Final O.D. (after ~2 hr. incubation) |
|---|---|---|
| 1:10 | 0.135 | 0.424 |
| 1:100 | 0.014 | 0.215 |
| 1:1000 | 0.001 | 0.035 |

Neutropenia is induced by intraperitoneal (I.P.) administration of Cyclophosphamide monohydrate on Day −4 (150 mg/kg) and Day −1 (100 mg/kg).

Vehicle: 0.9% sodium chloride
Dosing: Each mouse in the treated groups was given the appropriate dose of the compound to be tested in a volume of 0.2 ml, 2 and 8 hrs. post bacterial inoculation.
Time points:
Controls: 0, 2, 6, and 24 hrs.
Treated: 24 hrs.
Sampling: 2 or 3 mice/time point were euthanized via $CO_2$, and their caudal thigh muscles excised and homogenized. The thigh muscles were placed in 5 ml sterile PBS in Stomacher Filter bag and homogenized with MicroBiomaster80 (Brinkmann) for 60 seconds, normal setting and 1:10 dilutions were made per standard protocol in a 96-well plate. Aliquots of 25 ul for each dilution, as well as the homogenate, were plated on blood agar plates and incubated at 35° C. to determine the CFU/mL over the time course. After overnight incubation, colonies were counted.

Animal Model for Sepsis:
Murine Peritonitis Model (*E. coli*, *K. Pneumoniae*, *E. Faecalis*, MRSA)

This model is used to evaluate the effect of subcutaneous (SC) treatment with compounds of the present disclosure on growth of *Escherichia coli* ATCC 25922 in a mouse peritonitis model using female Swiss Webster mice.

Controls:
Negative: Inoculum only
Inoculum Vehicle Intraperitoneal
Positive: Ciprofloxacin
Study Design:
Species: Female Swiss Webster Mice
Inoculation: *Escherichia coli* ATCC 25922 is made by adding 1 ml (4/6/07) stock to 9 ml 0.25% Brewer's Yeast to make (1:10), then 1 ml of the (1:10) will be added to 9 ml 0.25% Brewer's Yeast to make (1:100), then 1 ml of the (1:100) will be added to 9 ml 0.25% Brewer's Yeast to make (1:1000), then 2.5 ml of the (1:1000) will be added to 122.5 ml 0.25% Brewer's Yeast to make (1:50,000), 1 ml/mouse will be inoculated intraperitoneally (IP).
Route of Administration: SC
Dosing: Vehicle for compounds of the present disclosure: Saline or 50 mM Sodium phosphate buffer in 10% Captisol in water, pH=7.2.
Dose Administration: Q3H×3 beginning at 30 min post bacterial inoculation
Study Duration: 24 hrs. 0.25% Brewer's Yeast Extract (BYE): Dilute 2% prepared on 11/12/09 (Lot.2158K, MP Biomedicals) 25 ml 2%+175 ml 1×PBS.
Outcome Measures: Colony Forming Unit's from peritoneal wash and spleen homogenate and drug levels from wash, spleen homogenate, and plasma.

Blood is collected via cardiac puncture while mouse is under $CO_2$ narcosis. The whole blood sample is placed in heparinized eppendorf tubes and kept on wet ice until centrifuged (4 min @ 14,000 rpm). Plasma is transferred to 96 deep-well block on dry ice and stored at −20° C. Immediately following blood collection, 2 ml of sterile PBS (phosphate buffered saline) was injected into the peritoneal cavity with a 25G needle. The abdomen was gently massaged, and a small incision was made to allow access to the peritoneal cavity. The peritoneal wash fluid was collected using sterile technique, serially diluted 1:10, plated on blood agar plates, and incubated overnight at 35° C.

Spleens were harvested and placed in 1 ml sterile PBS in Stomacher bag and homogenized with MicroBiomaster80 (Brinkmann) for 60 seconds, normal setting and 1:10 dilutions were made. 25 µl of each dilution, as well as the homogenate, was plated on blood agar plates and incubated at 35° C. to determine the CFU/mL over the time course. After overnight incubation, colonies were counted.
Other Animal Models
Similarly, other animal infection models can be used for hospital acquired pneumonia (HAP)/ventilator acquired pneumonia (VAP), complicated urinary tract infections (cUTI), and febrile neutropenia.

5. Formulation and Administration

The compositions and methods of the present disclosure can be practiced by delivering the compounds of the present disclosure using a means for delivery e.g., any suitable carrier. The dose of active compound, mode of administration and use of suitable carrier will depend upon the intended patient or subject and the targeted microorganism, e.g., the target bacterial organism. The formulations, both for human medical use and veterinary use, of compounds according to the present disclosure typically include such compounds in association with a pharmaceutically acceptable carrier.

The carrier(s) should be "acceptable" in the sense of being compatible with compounds of the present disclosure and not deleterious to the recipient. Pharmaceutically acceptable carriers, in this regard, are intended to include any and all solvents, dispersion media, coatings, absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the disclosure and/or known in the art) also can be incorporated into the compositions. The formulations can conveniently be presented in dosage unit form and can be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the disclosure should be formulated to be compatible with its intended route of administration. Solutions or suspensions can include the following components: a sterile diluent such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

A wide variety of formulations and administration methods, including, e.g., intravenous formulations and administration methods can be found in S. K. Niazi, ed., Handbook of Pharmaceutical Formulations, Vols. 1-6 [Vol. 1 Compressed Solid Products, Vol. 2 Uncompressed Drug Products, Vol. 3 Liquid Products, Vol. 4 Semi-Solid Products, Vol. 5 Over the Counter Products, and Vol. 6 Sterile Products], CRC Press, Apr. 27, 2004.

Useful solutions for oral or parenteral administration can be prepared by any of the methods well known in the pharmaceutical art, described, for example, in *Remington's Pharmaceutical Sciences*, 18th ed. (Mack Publishing Company, 1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present disclosure suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems also be used to present the drug for both intra-articular and ophthalmic administration. Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations disclosed herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

In conjunction with the methods of the present disclosure, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

Generally, an effective amount of dosage of active compound will be in the range of from about 0.1 to about 100 mg/kg of body weight/day, more preferably from about 1.0 to about 50 mg/kg of body weight/day. The amount administered will also likely depend on such variables as the type of surgery or invasive medical procedure, the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

Nonlimiting doses of active compound comprise from about 0.1 to about 1500 mg per dose. Nonlimiting examples of doses, which can be formulated as a unit dose for convenient administration to a patient include: about 25 mg, about 50 mg, about 75 mg, about 100 mg, about 125 mg, about 150 mg, about 175 mg, about 200 mg, about 225 mg, about 250 mg, about 275 mg, about 300 mg, about 325, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050, mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, and about 1500 mg. The foregoing doses are useful for administering the compounds of the present disclosure according to the methods of the present disclosure.

As is understood by one of ordinary skill in the art, generally, when dosages are described for a pharmaceutical active, the dosage is given on the basis of the parent or active moiety. Therefore, if a salt, hydrate, or another form of the parent or active moiety is used, a corresponding adjustment in the weight of the compound is made, although the dose is still referred to on the basis of the parent or active moiety delivered. As a nonlimiting example, if the parent or active moiety of interest is a monocarboxylic acid having a molecular weight of 250, and if the monosodium salt of the acid is desired to be delivered to be delivered at the same dosage, then an adjustment is made recognizing that the monosodium salt would have a molecular weight of approximately 272 (i.e., minus 1H or 1.008 atomic mass units and plus 1 Na or 22.99 atomic mass units). Therefore, a 250 mg dosage of the parent or active compound would correspond to about 272 mg of the monosodium salt, which would also deliver 250 mg of the parent or active compound. Said another way, about 272 mg of the monosodium salt would be equivalent to a 250 mg dosage of the parent or active compound.

Formulation Examples

I. Formulation for Intravenous Administration

| Ingredients | Amount |
| --- | --- |
| Antimicrobial Compound of the present disclosure | 0.1-1500 total mg |
| Dextrose, USP | 50 mg/ml |
| Sodium citrate, USP | 1.60-1.75 mg/ml |
| Citric Acid, USP | 0.80-0.90 mg/ml |
| Water, USP | q.s |

This formulation for intravenous administration is formulated by heating water for injection to about 60° C. Next the sodium citrate, citric acid and dextrose are added and stirred until dissolved. A solution or aqueous slurry of the antimicrobial compound is added to the previous mixture and stirred until dissolved. The mixture is cooled to 25° C. with stirring. The pH is measured and adjusted if necessary. Lastly the mixture is brought to the desired volume, if necessary, with water for injection. The mixture is filtered, filled into the desired container (vial, syringe, infusion container, etc.), over wrapped and terminally moist heat sterilized.

This formulation is useful for intravenous administration, either bolus or infusion, to a patient for treating, preventing, reducing the risk of, or delaying the onset of infection.

II. Lyophilisate for Reconstitution

Alternatively, the antimicrobial compound can be provided as a lyophilisate which can be reconstituted before intravenous or intramuscular administration.

| Ingredient | mg per injection vial |
| --- | --- |
| Antimicrobial Compound of the present disclosure | 0.1-1500 |
| Cyclodextrin | 1500 |

Reconstitution solution for a volume to be administered of 50 ml (infusion): 5% aqueous glucose solution.

Reconstitution solution for a volume to be administered of 15 ml (bolus): 3.3% aqueous glucose solution.

The foregoing lyophilisate is useful for reconstitution and intravenous administration, either bolus or infusion, to a patient for treating, preventing, reducing the risk of, or delaying the onset of infection.

III. Lyophilisate for Reconstitution

| Ingredient | mg per injection vial |
| --- | --- |
| Antimicrobial Compound of the present disclosure | 0.1-1500 |
| soya lecithin | 2250 |
| Sodium cholate | 1500 |

Reconstitution solution for a volume to be administered of 50 ml (infusion): 4% aqueous glucose solution.

Reconstitution solution for a volume to be administered of 15 ml (bolus): 2% aqueous glucose solution.

The foregoing lyophilisate is useful for reconstitution and intravenous administration, either bolus or infusion, to a patient for treating, preventing, reducing the risk of, or delaying the onset of infection.

IV. Lyophilisate for Reconstitution

| Ingredient | mg per injection vial |
| --- | --- |
| Antimicrobial Compound of the present disclosure | 0.1-1500 |
| soya lecithin | 900 |
| Sodium glycocholate | 540 |

Reconstitution solution for a volume to be administered of 15 ml (bolus): 3.3% aqueous glucose solution.

The foregoing lyophilisate is useful for reconstitution and intravenous administration, either bolus or infusion, to a patient for treating, preventing, reducing the risk of, or delaying the onset of infection.

V. Tablet for Oral Administration

| Ingredients | Per Tablet | Per 4000 Tablets |
| --- | --- | --- |
| Antimicrobial Compound of the present disclosure | 0.1-1500 mg | 0.4-6000 g |
| Anhydrous Lactose, NF | 110.45 mg | 441.8 g |
| Microcrystalline Cellulose NF | 80.0 mg | 320.0 g |
| Magnesium Stearate Impalpable Powder NF | 1.00 mg | 4.0 g |
| Croscarmellose Sodium NF Type A | 2.00 mg | 8.0 g |

The antimicrobial compound (any of the compounds equivalent to the desired delivery strength, e.g., 50 to 1500 mg per tablet) is premixed with ⅓ of the microcrystalline cellulose NF and ½ of the anhydrous lactose NF in a ribbon blender for 5 minutes at 20 RPM. To the premix is added the remaining ⅔ of the microcrystalline cellulose NF and the remaining ½ of the anhydrous lactose NF. This is blended for 10 minutes at 20 RPM. Croscarmellose sodium is added to the blended powders and mixed for 5 minutes at 20 RPM. Finally the magnesium stearate is added to the mixture by passing through a 90 mesh screen and blended for an additional 5 minutes at 20 RPM. The lubricated mixture is compressed to provide tablets of 500 mg active ingredient.

These tablets are useful for oral administration to a patient for treating, prevention, reducing the risk of, or delaying the onset of infection.

6. Examples

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

The compounds or tautomers thereof, or pharmaceutically acceptable salts, esters or prodrugs of said compounds or tautomers of the present disclosure can be prepared using known chemical transformations adapted to the particular situation at hand.

Some of the abbreviations used in the following experimental details of the synthesis of the examples are defined below: h or hr=hour(s); min=minute(s); mol=mole(s); mmol=millimole(s); M=molar; µM=micromolar; g=gram(s); µg=microgram(s); rt=room temperature; L=liter(s); mL=milliliter(s); $Et_2O$=diethyl ether; THF=tetrahydrofuran; DMSO=dimethyl sulfoxide; EtOAc=ethyl acetate; $Et_3N$=triethylamine; i-$Pr_2NEt$ or DIPEA=diisopropylethylamine; $CH_2Cl_2$=methylene chloride; $CHCl_3$=chloroform; $CDCl_3$=deuterated chloroform; $CCl_4$=carbon tetrachloride; MeOH=methanol; $CD_3OD$=deuterated methanol; EtOH=ethanol; DMF=dimethylformamide; BOC=t-butoxycarbonyl; CBZ=benzyloxycarbonyl; TBS=t-butyldimethylsilyl; TBSCl=t-butyldimethylsilyl chloride; TFA=trifluoroacetic acid; DBU=diazabicycloundecene; TBDPSCl=t-butyldiphenylchlorosilane; Hunig's Base=N,N-diisopropylethylamine; DMAP=4-dimethylaminopyridine; CuI=copper (I) iodide; MsCl=methanesulfonyl chloride; $NaN_3$=sodium azide; $Na_2SO_4$=sodium sulfate; $NaHCO_3$=sodium bicarbonate; NaOH=sodium hydroxide; $MgSO_4$=magnesium sulfate; $K_2CO_3$=potassium carbonate; KOH=potassium hydroxide; $NH_4OH$=ammonium hydroxide; $NH_4Cl$=ammonium chloride; $SiO_2$=silica; Pd—C=palladium on carbon; Pd(dppf)$Cl_2$=dichloro[1,1'-bis(diphenylphosphino)ferrocene] palladium (II).

Exemplary compounds synthesized in accordance with the disclosure are listed in Table 1. A bolded or dashed bond is shown to indicate a particular stereochemistry at a chiral center, whereas a wavy bond indicates that the substituent can be in either orientation or that the compound is a mixture thereof.

The compounds of the present disclosure can be prepared, formulated, and delivered as salts, esters, and prodrugs. For convenience, the compounds are generally shown without indicating a particular salt, ester, or prodrug form.

The compounds of the present disclosure can be made using synthetic chemical techniques well known to those of skill in the art.

Example 1: Syntheses of Compounds 1-153 and 159-178

Compounds 1-153 and 159-178 were synthesized according to the methods described in US 2012-0220566, WO 2012/173689, or PCT/US2014/054869, and according to the methods and procedures similar to those described for compounds 64, 71, 76, 108, and 125. Compounds 64, 71, 76, 108, and 125 were synthesized according to the methods described below.

Synthetic Scheme for Compound 64

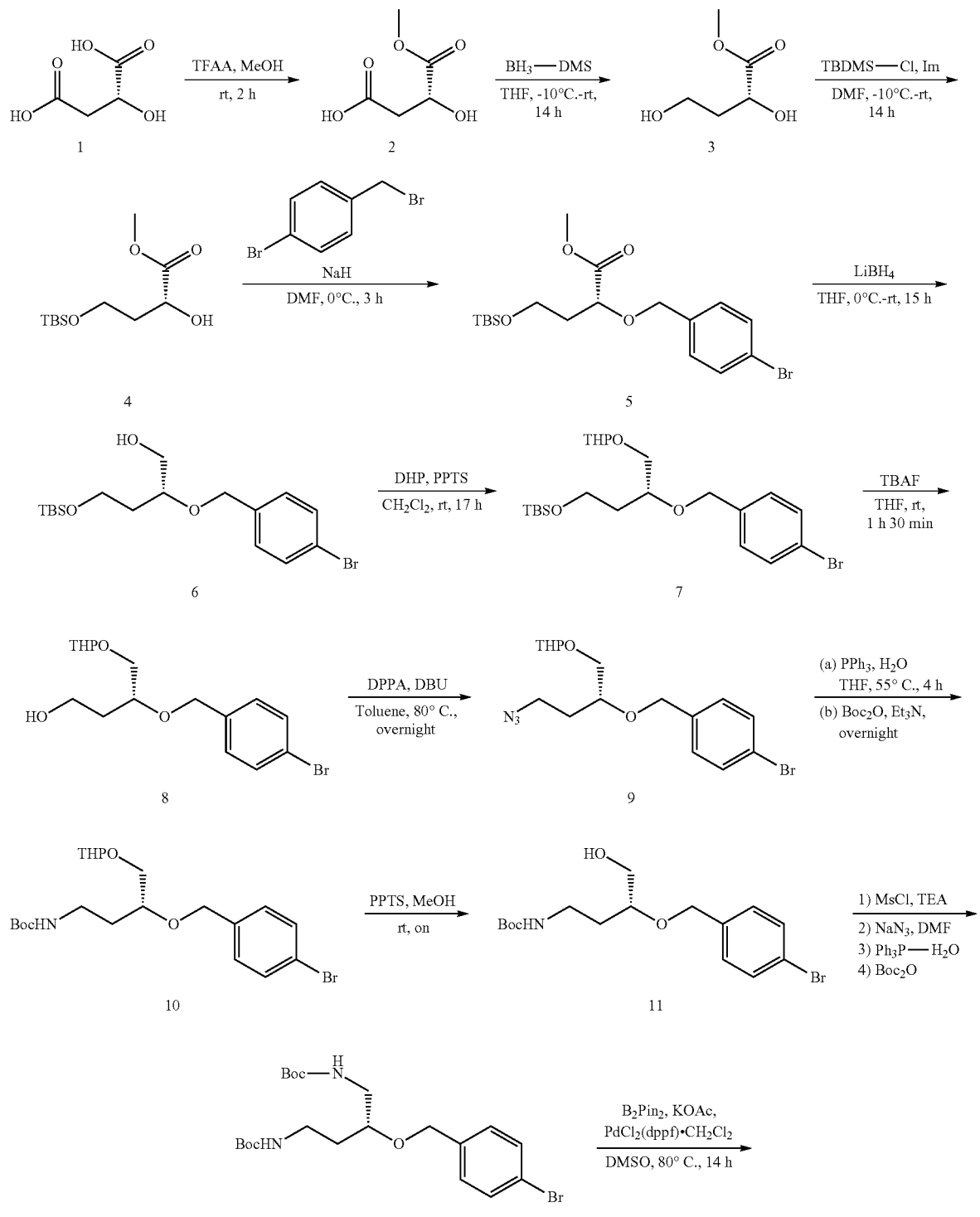

317

-continued

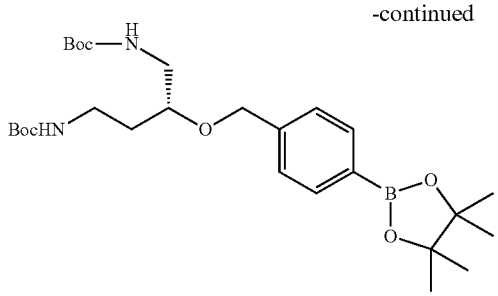

13

(a) HCl, CH$_2$Cl$_2$/1,4-dioxane, rt, 1 h
(b) Bis-Boc pyraxolecarboxamidine, iPr$_2$EtN, MeOH, rt,
(c) TFA, thioanisole, rt,
(d) 6N aq HCl, 15 min × 2

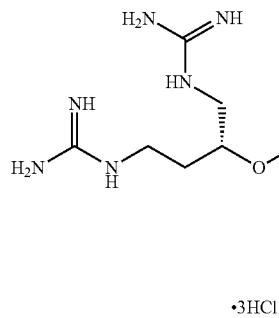

·3HCl

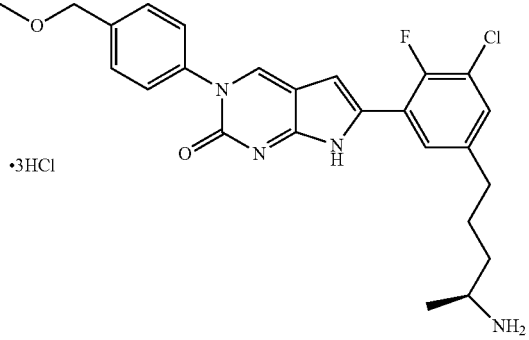

Compound 64

318

Experimental (referring to synthetic scheme for compound 64):

Synthesis of Intermediate 2

Trifluoroacetic anhydride (55 ml) was added to D-Malic acid (1) (13.4 g, 100 mmol), and stirred at room temperature under argon atmosphere for 40 min. Volatiles were removed, 80 ml of anhydrous methanol was added and stirred at room temperature for 1 h 30 min. Concentrated and the residue was crystallized from diethyl ether/hexanes to obtain 14.7 g (yield, 99%) of 2 as a white solid. This material was used for the next without further processing.

Synthesis of Intermediate 3

BH$_3$-DMS (1M in THF, 200 ml, 200 mmol) was added drop wise to a stirring solution of 2 (14.85, 100 mmol) in anhydrous THF (334 ml) at −10° C. under argon atmosphere. After stirring for 2 h at the same temperature, cooling bath was removed and stirred at room temperature for 14 h. The reaction was quenched by dropwise addition of 200 ml of methanol. Stirred for 20 min, solvent was evaporated. Another 100 ml of methanol was added stirred for 20 min and solvent was evaporated. The residue was dissolved in 200 ml of diethyl ether, passed through a plug of celite and concentrated to dryness to obtain 13 g (yield 96%) of 3 as a colorless liquid.

Synthesis of Intermediate 4

To a stirring solution of 3 (8.9 g, 60 mmol) in anhydrous DMF (75 ml) at −10° C. TBDMS-Cl (9.59 g, 63 mmol) was added followed by imidazole (4.95, 72 mmol). The solution was stirred overnight and quenched with water (150 ml), product was extracted with ethyl acetate (100 ml×3). Combined organic phases was washed with water (100 ml×2) and brine (150 ml), dried over sodium sulfate, concentrated and purified by flash silica gel chromatography (heptane/ethyl acetate gradient) to obtain 10.62 g (yield, 71%) of 4 as a colorless liquid.

Synthesis of Intermediate 5

Sodium Hydride (1.7 g 60% in mineral oil, 42.7 mmol) was added to a cold solution of 4 (10.60 g, 42.7 mmol) and 4-bromobenzaldehyde (11.26 g, 44.8 mmol) in anhydrous DMF (85 ml). After 3 h, the reaction was quenched with water (5 ml). After 5 min, another 100 ml of water was added. Product was extracted by ethyl acetate (50 ml×2). Combined organic phases was washed with water (100 ml) and brine (100 ml), dried over sodium sulfate and purified by flash silica gel chromatography (Heptane/Ethyl acetate gradient) to obtain 15.7 g (yield, 88%) of 5 as brownish liquid.

Synthesis of Intermediate 6

To the stirring solution of 5 (10.42 g, 25 mmol) in anhydrous THF (125 ml) at 0° C. under argon atmosphere, LiBH$_4$ (95%, 0.80 g, 35 mmol) was added in two portions followed by solution of LiEt$_3$BH in THF (1 M, 2.5 ml, 2.5 mmol) and stirred for 17 h. Cooled to 0° C., 10 ml of water was added slowly followed by another 100 ml of water. After 1 h cooling bath was removed and stirred at room temperature for 5 h. Product was extracted by ethyl acetate (50 ml×2). Combined organic phases was washed with brine (100 ml), dried over sodium sulfate, concentrated and purified by flash silica gel chromatography (Heptane/Ethyl acetate gradient) to obtain 7.4 g (yield, 76%) of 6 as colorless viscous liquid.

Synthesis of Intermediates 7 and 8

Didhydropyran (4.67 ml, 51 mmol) was added to a solution of 6 (6.61 g, 17 mmol) in anhydrous methylene chloride (24 ml), followed by PPTS (0.43 g, 1.7 mmol) and stirred at under argon atmosphere for 14 h. The reaction mixture was washed with water (25 ml×2), dried over sodium sulfate and concentrated to dryness to obtain 6.9 g of 7 as colorless viscous liquid. To this crude liquid, the solution of tetrabutylammonium fluoride in THF (1M, 20.4 ml, 20.4 mmol) was added and stirred for 1 h and 30 min. LCMS showed completion of TBS removal. The crude reaction mixture was concentrated and purified by flash silica gel chromatography (Heptane/Ethyl acetate gradient) to obtain 5.05 g (yield, 98%, MS, ESI, m/z 381.4 [M+H]$^+$) of 8, as colorless viscous liquid.

Synthesis of Intermediate 9

To the stirring solution of 8 (5.35 g, 17 mmol) in anhydrous toluene (100 ml) under argon atmosphere diphenylphosphoryl azide (5.77 g, 21 mmol) was added followed by dropwise addition of DBU (3.19 g, 21 mmol). After 30 min, it was placed in 80° C. temperature oil bath and stirred for 14 h. LCMS shows the completion of the reaction. Cooled down to room temperature, 100 ml of water is added and the product is extracted by ethyl acetate (75 ml×2). Combined organic phases was washed with water (75 ml) and brine (75 ml), dried over sodium sulfate, concentrated and purified by flash silica gel chromatography (Heptane/Ethyl acetate gradient) to obtain 5.37 g (yield, 93%, MS, ESI, m/z 406.4 [M+Na]$^+$) of 9 as colorless liquid.

Synthesis of Intermediate 10

A solution of 9 (5.37 g, 14 mmol) in THF (130 ml), triphenylphosphine (5.50 g, 21 mmol) and water (11 ml) was stirred at 60° C. for 3 h. The reaction mixture was cooled down to 0° C., Boc anhydride (3.67 g, 16.8 mmol) was added followed by triethylamine (2.83 g, 28 mmol). The reaction mixture was left stirring in same bath overnight. LCMS shows complete consumption of intermediate amine. It was concentrated and purified by flash silica gel chromatography (Heptane/Ethyl acetate gradient) to obtain 6.3 g (yield, 98%, MS, ESI, m/z 480.5 [M+Na]$^+$) of 10 as colorless viscous liquid.

Synthesis of Intermediate 11

To the stirring solution of 10 (Ig, 1.8 mmol) in anhydrous methanol (3.6 ml) PPTS (0.46 g, 1.8 mmol) was added and stirred under argon atmosphere for 14 h. TLC shows completion of reaction. Methanol was evaporated; the residue was dissolved in 20 ml of dichloromethane, washed with water (20 ml), concentrated and purified by flash silica gel chromatography (Heptane/Ethyl acetate gradient) to obtain 0.61 g (yield, 93%, MS, ESI, m/z 374.7 [M+H]$^+$) of 11 as colorless viscous liquid.

Synthesis of Intermediate 12

To a stirring solution of 11 (5.47 g, 14.6 mmol) and TEA (6 mL, 43.8 mmol) in DCM (200 ml) was added MsCl (methanesulfonyl acid chloride, 2 g, 17.5 mmol) at 0° C. and stirred overnight. It was concentrated and re-dissolved in hexane (400 mL), washed with sodium bicarbonate solution (5%, 100 mL×3), dried to afford clear oil (6.7 g). This mesylate derivative was treated with NaN$_3$ (1.42 g, 21.9 mmol) in DMF (100 mL) and heated at 80° C. overnight. Diluted with ether (300 mL) and washed with water (100 mL×3), dried and concentrated to yield 5.56 g of azide derivative. A mixture of azide derivative (13.93 mmol) and Ph$_3$P (7.3 g, 27.5 mmol) in THF-H$_2$O (120+20 mL) was heated to reflux for 3 hours. It was cooled, Boc$_2$O (3.69 g, 16.7 mmol) was added and stirred overnight at ambient temperature. Concentrated and extracted with ethyl acetate, dried, evaporated and purified by flash chromatography (ethyl acetate-hexane) to yield 12 (5.94 g, 95%).

Synthesis of Intermediate 13

To the solution of 12 (5.94 g, 12.53 mmol) in anhydrous DMF (130 mL), bispinacolatodiborane (15.94 g, 62.75 mmol), potassium acetate (3.69 g, 37.65 mmol) and PdCl$_2$ (dppf).CH$_2$Cl$_2$ (1.54 g, 1.88 mmol) were added. The mixture was degassed, purged with argon twice and stirred at 80° C. for 14 h. LCMS shows complete consumption of 12 and formation of 13. Cooled down to room temperature, 200 ml of water was added. Product was extracted with ethyl acetate (100 ml×3). Combined organic phases were washed with water (200 ml), 14% ammonium hydroxide (100 ml), water (100 ml) and brine (200 ml). It was dried over sodium sulfate, concentrated and purified by flash silica gel chromatography (Heptane/Ethyl acetate gradient) to obtain 6.31 g (96%) of 13 as a colorless sticky solid.

Synthesis of Intermediate 14

To the solution of 13 (6.31 g, 12.1 mmol) in methanol (360 ml) and water (40 ml) was added 5-iodocytosine (4.31 g, 18.2 mmol), copper acetate monohydrate (3.64 g, 18.2 mmol) followed my tetramethylehtylenediamine (5.4 ml, 36.3 mmol). The mixture was stirred at room temperature under open air. After 17 h the mixture was concentrated. 200 ml of water was added. Product was extracted by ethyl acetate (200 ml×3). Combined organic phase was washed with water (200 ml), 14% ammonium hydroxide (200 ml), water (200 ml) and brine (200 ml), dried over sodium sulfate and concentrated to dryness to obtain 8 g (12 mmol) of off-white solid. This solid was dissolved in 250 ml of ethyl acetate, benzoic anhydride (4.12 g, 18.2 mmol) was added and the mixture was stirred at 80° C. for 4 h. Solvent was evaporated and purified by flash silica gel chromatography (Heptane/Ethyl acetate gradient) to yield 7.5 g (yield 85%) of 14 as white solid.

Synthesis of Intermediate 15 and Compound 64

The solution of 14 (2.94 g, 4 mmol) and alkyne (1.65 g, 4.4 mmol) in anhydrous DMF (40 ml) was degassed and purged with argon twice. To this solution were added N—N-diisopropylethylamine (2.09 ml, 12 mmol) followed by Pd(PPh$_3$)$_4$ (232 mg, 0.2 mmol) and CuI (76 mg, 0.4 mmol). The mixture was stirred at 70° C. for 12 h. Cooled down to room temperature, 70 ml of methanol was added and stirred at 80° C. for 3 h. Cooled to room temperature, methanol was evaporated; 200 ml of water was added. Product was extracted by ethyl acetate (200 ml×2). Combined organic phase was washed with water (200 ml), 14% ammonium hydroxide (200 ml), water (200 ml) and brine (200 ml). It was dried over sodium sulfate, concentrated and purified by flash chromatography over silica gel to yield 1.7 g of 15 as yellow solid. HCl (65 ml of 4N in dioxane) was added to a solution of 15 in dichloromethane (50 ml), and stirred at room temperature for 1 h. Concentrated and the residue (1.95 mmol) was dissolved in anhydrous methanol (50 ml). Bis-boc-1-pyrazolecarboxamide (1.51 g, 4.89 mmol) and N—N-diisopropylethylamine (3.4 ml, 19.5 mmol) were added and stirred at room temperature for 12 h. Solvent was removed, dissolved in trifluoroacetic acid (100 ml), 100 drops of thioanisole were added and stirred at room temperature for 17 h. LCMS showed complete removal of Boc and Cbz groups. It was then concentrated and purified by HPLC. Desired fractions were concentrated to dryness, TFA was exchanged with HCl (6N aq., 100 ml×2 in 15 min interval) and lyophilized to obtain 416 mg (yield 60%), MS, ESI, m/z 625 [M+H]$^+$) of Compound 64 as yellow solid.

Synthetic scheme for Compound 71

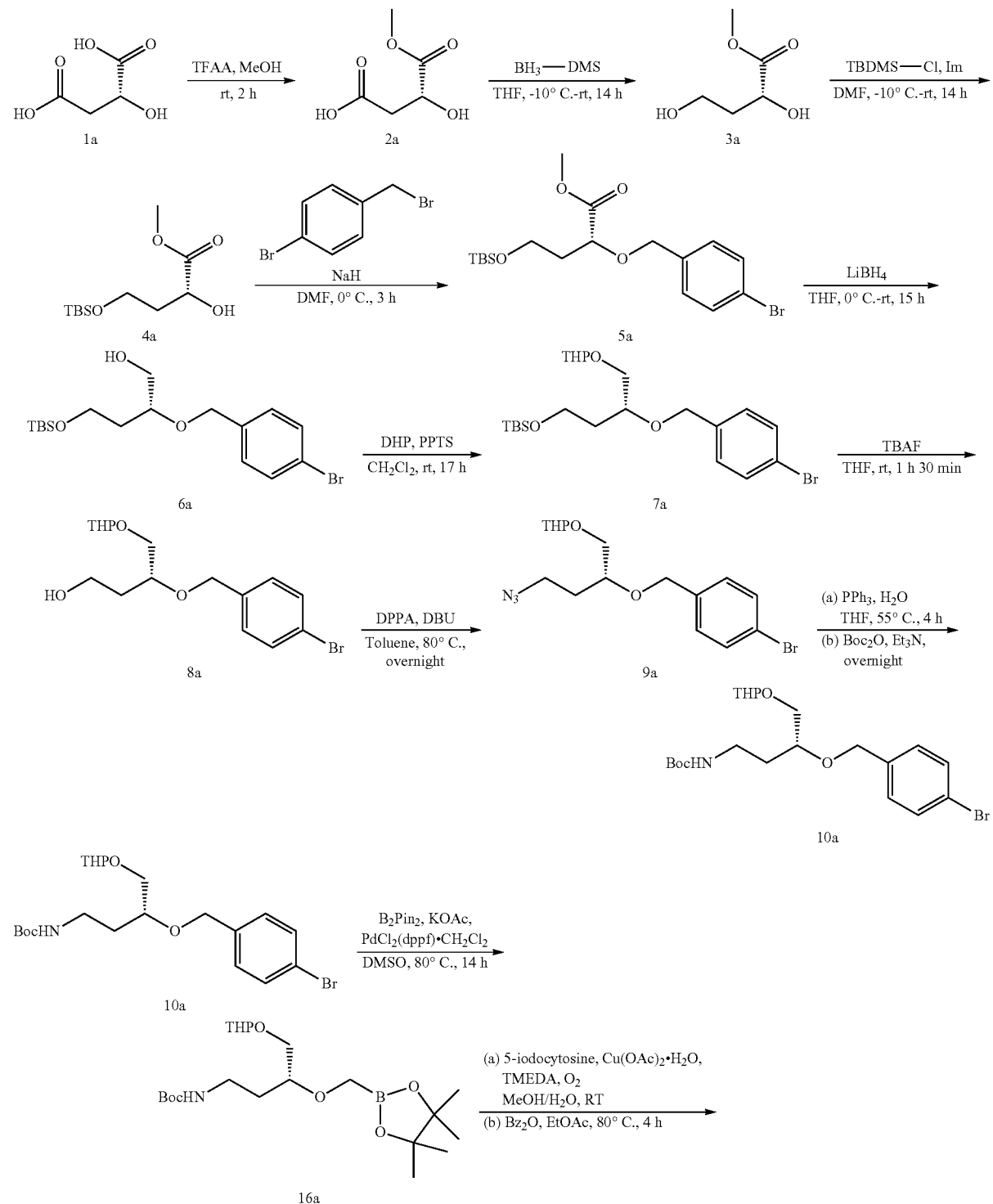

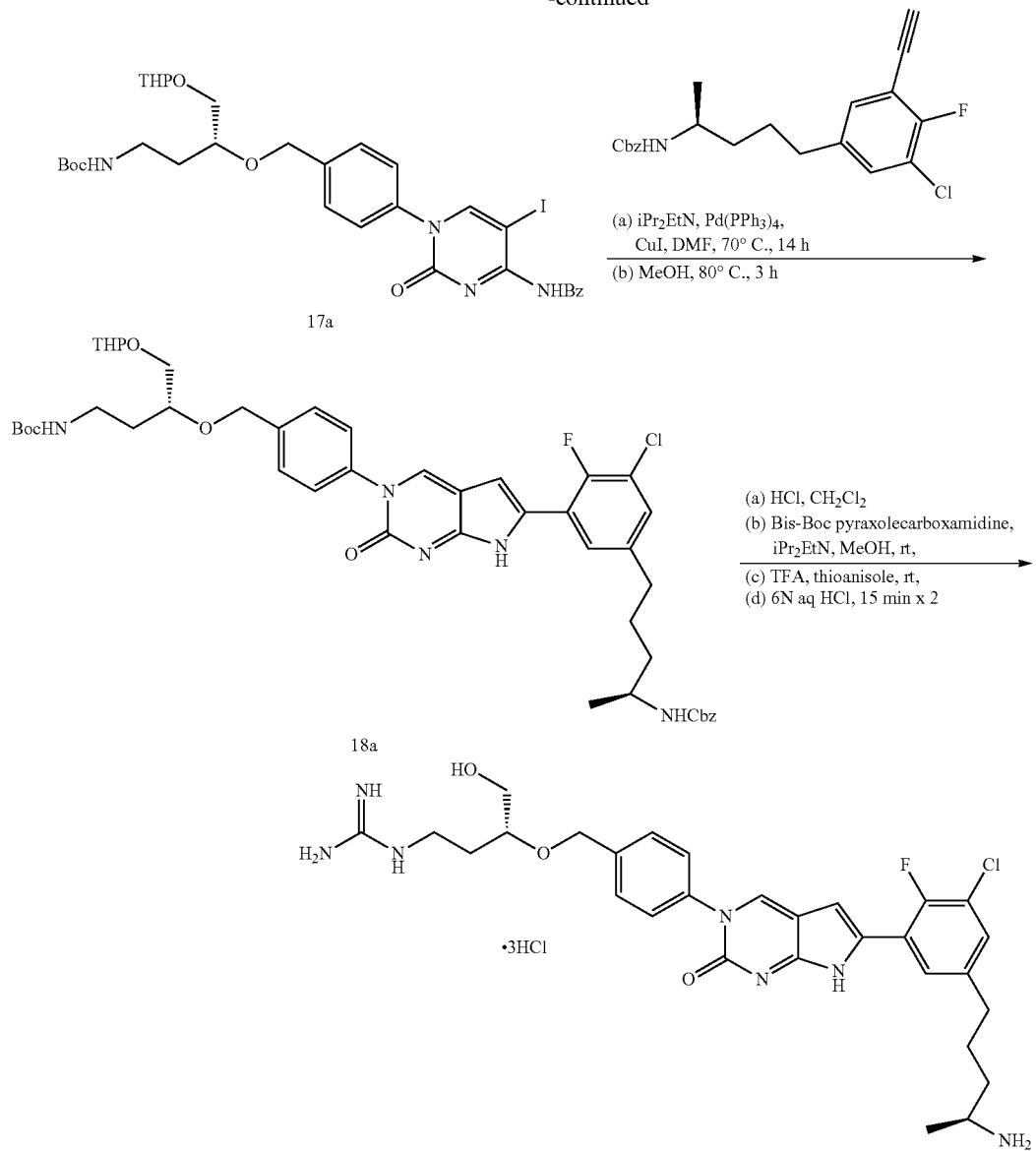

Compound 71

Experimental (referring to synthetic scheme for compound 71):

Synthesis of Intermediate 2a

Trifluoroacetic anhydride (55 ml) was added to D-Malic acid (1a) (13.4 g, 100 mmol), and stirred at room temperature under argon atmosphere for 40 min. Volatiles were removed, 80 ml of anhydrous methanol was added and the resulting mixture was stirred at room temperature for 1 h 30 min. The mixture was then concentrated and the resulting residue was crystallized from diethyl ether/hexanes to obtain 14.7 g (yield, 99%) of 2a as a white solid. This material was used in the next step without further purification or processing.

Synthesis of Intermediate 3a

BH$_3$-DMS (1M in THF, 200 ml, 200 mmol) was added drop wise to a stirring solution of 2a (14.85, 100 mmol) in anhydrous THF (334 ml) at −10° C. under argon atmosphere. After stirring for 2 h at the same temperature, the cooling bath was removed and the reaction was stirred at room temperature for 14 h. The reaction was quenched by dropwise addition of 200 ml of methanol. The resulting mixture was stirred for 20 min and the solvent was then evaporated. Another 100 ml of methanol was added and the mixture was stirred for 20 min. The solvent was then evaporated. The residue was dissolved in 200 ml of diethyl ether, passed through a plug of celite and concentrated to dryness to provide 13 g (yield 96%) of 3a as a colorless liquid.

Synthesis of Intermediate 4a

To a stirring solution of 3a (8.9 g, 60 mmol) in anhydrous DMF (75 ml) at −10° C. was added TBDMS-Cl (9.59 g, 63 mmol) followed by imidazole (4.95, 72 mmol). The solution was stirred overnight and quenched with water (150 ml). The resulting mixture was extracted with ethyl acetate (100 ml×3). The combined organic phases were washed with water (100 ml×2) and brine (150 ml), dried over sodium sulfate, concentrated, and purified by flash silica gel chromatography (heptane/ethyl acetate gradient) to provide 10.62 g (yield, 71%) of 4a as a colorless liquid.

Synthesis of Intermediate 5a

Sodium Hydride (1.7 g 60% in mineral oil, 42.7 mmol) was added to a cold solution of 4a (10.60 g, 42.7 mmol) and 4-bromobenzaldehyde (11.26 g, 44.8 mmol) in anhydrous DMF (85 ml). After 3 h, the reaction was quenched with water (5 ml). After an additional 5 min of stirring, another 100 ml of water was added. The resulting reaction mixture was washed with ethyl acetate (50 ml×2). The combined organic phases were washed with water (100 ml) and brine (100 ml), dried over sodium sulfate, and purified by flash silica gel chromatography (Heptane/Ethyl acetate gradient) to provide 15.7 g (yield, 88%) of 5a as brownish liquid.

Synthesis of Intermediate 6a

To the stirring solution of 5a (10.42 g, 25 mmol) in anhydrous THF (125 ml) at 0° C. under argon atmosphere, was added LiBH$_4$ (95%, 0.80 g, 35 mmol) in two portions followed by a solution of LiEt$_3$BH in THF (1 M, 2.5 ml, 2.5 mmol). The resulting reaction mixture was stirred for 17 h. The mixture was then cooled to 0° C. and 10 ml of water was added slowly followed by another 100 ml of water. After 1 h, the cooling bath was removed and the mixture was stirred at room temperature for 5 h. The product was extracted from the mixture with ethyl acetate (50 ml×2). The combined organic phases were washed with brine (100 ml), dried over sodium sulfate, concentrated, and purified by flash silica gel chromatography (Heptane/Ethyl acetate gradient) to provide 7.4 g (yield, 76%) of 6a as colorless viscous liquid.

Synthesis of Intermediate 8a

Dihydropyran (4.67 ml, 51 mmol) was added to a solution of 6a (6.61 g, 17 mmol) in anhydrous methylene chloride (24 ml), followed by PPTS (0.43 g, 1.7 mmol) and stirred at under argon atmosphere for 14 h. The reaction mixture was washed with water (25 ml×2), dried over sodium sulfate, and concentrated to dryness to obtain 6.9 g of 7a as colorless viscous liquid. To this crude liquid, a solution of tetrabutylammonium fluoride in THF (1M, 20.4 ml, 20.4 mmol) was added and the reaction mixture was stirred for 1 h and 30 min. Once LCMS showed complete of TBS removal, the crude reaction mixture was concentrated and purified by flash silica gel chromatography (Heptane/Ethyl acetate gradient) to provide 5.05 g (yield, 98%, MS, ESI, m/z 381.4 [M+H]$^+$) of 8a, as colorless viscous liquid.

Synthesis of Intermediate 9a

To a stirring solution of 8a (5.35 g, 17 mmol) in anhydrous toluene (100 ml) under argon atmosphere was added diphenylphosphoryl azide (5.77 g, 21 mmol) followed by dropwise addition of DBU (3.19 g, 21 mmol). After 30 min, the mixture was heated to 80° C. temperature in an oil bath and then stirred at that temperature for 14 h. Once LCMS showed reaction completion, the reaction was cooled down to room temperature. Once at room temperature, 100 ml of water was added and the resulting mixture was washed with ethyl acetate (75 ml×2). The combined organic phases were washed with water (75 ml) and brine (75 ml), dried over sodium sulfate, concentrated, and purified by flash silica gel chromatography (Heptane/Ethyl acetate gradient) to provide 5.37 g (yield, 93%, MS, ESI, m/z 406.4 [M+Na]$^+$) of 9a as colorless liquid.

Synthesis of Intermediate 10a

A solution of 9a (5.37 g, 14 mmol) in THF (130 ml), triphenylphosphine (5.50 g, 21 mmol) and water (11 ml) was stirred at 60° C. for 3 h. The reaction mixture was cooled down to 0° C. and Boc anhydride (3.67 g, 16.8 mmol) was then added followed by triethylamine (2.83 g, 28 mmol). The reaction mixture was stirring in the same bath overnight. Once LCMS showed complete consumption of intermediate amine, the reaction mixture was concentrated and purified by flash silica gel chromatography (Heptane/Ethyl acetate gradient) to provide 6.3 g (yield, 98%, MS, ESI, m/z 480.5 [M+Na]$^+$) of 10a as colorless viscous liquid.

Synthesis of Intermediate 16a

To the solution of 10a (1.00 g, 2.2 mmol) in anhydrous DMSO (14.6 ml), bispinacolatodiborane (1.41 g, 5.5 mmol), potassium acetate (0.65 g, 6.6 mmol) and PdCl$_2$ (dppf) .CH$_2$Cl$_2$ (0.090 g, 0.011 mmol) were added. The mixture was degassed, purged with argon twice and stirred at 80° C. for 14 h. Once LCMS shows complete consumption of 10a and formation of 16a, the reaction mixture was cooled down to room temperature and 20 ml of water is added. Product was extracted with ethyl acetate (20 ml×2). Combined organic phases were washed with water (20 ml), 14% ammonium hydroxide (20 ml), water (20 ml) and brine (20 ml). It was dried over sodium sulfate, concentrated and purified by flash silica gel chromatography (Heptane/Ethyl acetate gradient) to obtain 1.0 g (yield 90%, MS, ESI, m/z 528.7 [M+Na]$^+$) of 16a as a colorless sticky solid.

Synthesis of Intermediate 17a

To the solution of 16a (1.21 g, 2.4 mmol) in methanol (35 ml), was added 9 ml of water. To this mixture was then added 5-iodocytosine (0.8 g, 3.36 mmol) and copper acetate monohydrate (0.47 g, 2.4 mmol) followed by tetramethylethylenediamine (0.55 g, 4.8 mmol). The mixture was stirred at room temperature under open air for 19 h. After 19 h the mixture was concentrated and 20 ml of water was added. The product was extracted using ethyl acetate (25 ml×2). The combined organic phases were washed with water (25 ml), 14% ammonium hydroxide (25 ml), water (25 ml) and brine (25 ml), dried over sodium sulfate and concentrated to dryness to provide an off-white solid. This solid was dissolved in 43 ml of ethyl acetate, benzoic anhydride (0.65 g, 2.88 mmol) was added, and the mixture was stirred at 80° C. for 4 h. The reaction mixture was concentrated and purified by flash silica gel chromatography (Heptane/Ethyl acetate gradient) to yield 1.1 g (yield 64%, MS, ESI, m/z 719.7 [M+H]$^+$) of 17a as white solid.

Synthesis of Intermediate 18a

A solution of 17a (0.35 g, 0.49 mmol) and the alkyne (0.182 g, 0.49 mmol) in anhydrous DMF (4.9 ml) was degassed and purged with argon twice. To this solution were then added N—N-diisopropylethylamine (0.19 g, 1.47 mmol) followed by Pd (PPh$_3$)$_4$ (0.028 g, 0.024 mmol) and CuI (0.0094 g, 0.049 mmol). The mixture was stirred at 70° C. for 12 h. Once LCMS showed completion of the Sonogashira coupling, the mixture was cooled down to room temperature, 7 ml of methanol was added, and the resulting mixture was then stirred at 80° C. for 3 h. The mixture was cooled to room temperature and concentrated. 25 ml of water was added and the product was extracted with ethyl acetate (25 ml×2). The combined organic phases were washed with water (25 ml), 14% ammonium hydroxide (25 ml), water (25 ml) and brine (25 ml), dried over sodium sulfate, concentrated, and purified by flash silica gel chromatography using a gradient of Methanol (containing 0.2% saturated ammonium hydroxide) in dichloromethane from 0% to 10% in 16 CV. The desired product fractions were concentrated to obtain 0.35 g (yield 83%, MS, ESI, m/z 860.90 [M+H]$^+$) of 18a as a solid.

Synthesis of Compound 71

HCl (3.87 ml of 4N in dioxane, 15.5 mmol) was added to a solution of 18a (0.26 g, 0.31 mmol) in dichloromethane (10 ml), and the resulting mixture was stirred at room temperature for 1 h. The mixture was then concentrated and the residue was dissolved in anhydrous methanol (10 ml). Bis-boc-1-pyrazolecarboxamide (0.19 g, 0.62 mmol) and N—N-diisopropylethylamine (0.40 g, 3.1 mmol) were added and mixture was stirred at room temperature for 12 h. After 12 h, the solvent was removed in vacuo. To the resulting residue was added trifluoroacetic acid (10 ml) and 10 drops of thioanisole and the resulting reaction mixture was stirred at room temperature for 17 h. Once LCMS showed complete removal of Boc and Cbz groups, the mixture was concentrated and purified by HPLC. The desired fractions were concentrated to dryness. TFA was exchanged with HCl (6N aq., 10 ml×2 in 15 min interval), and the product was lyophilized to obtain 0.107 g (yield 52% over four steps, MS, ESI, m/z 584.7 [M+H]$^+$) of 71 as yellow solid.

Synthetic scheme for Compound 76

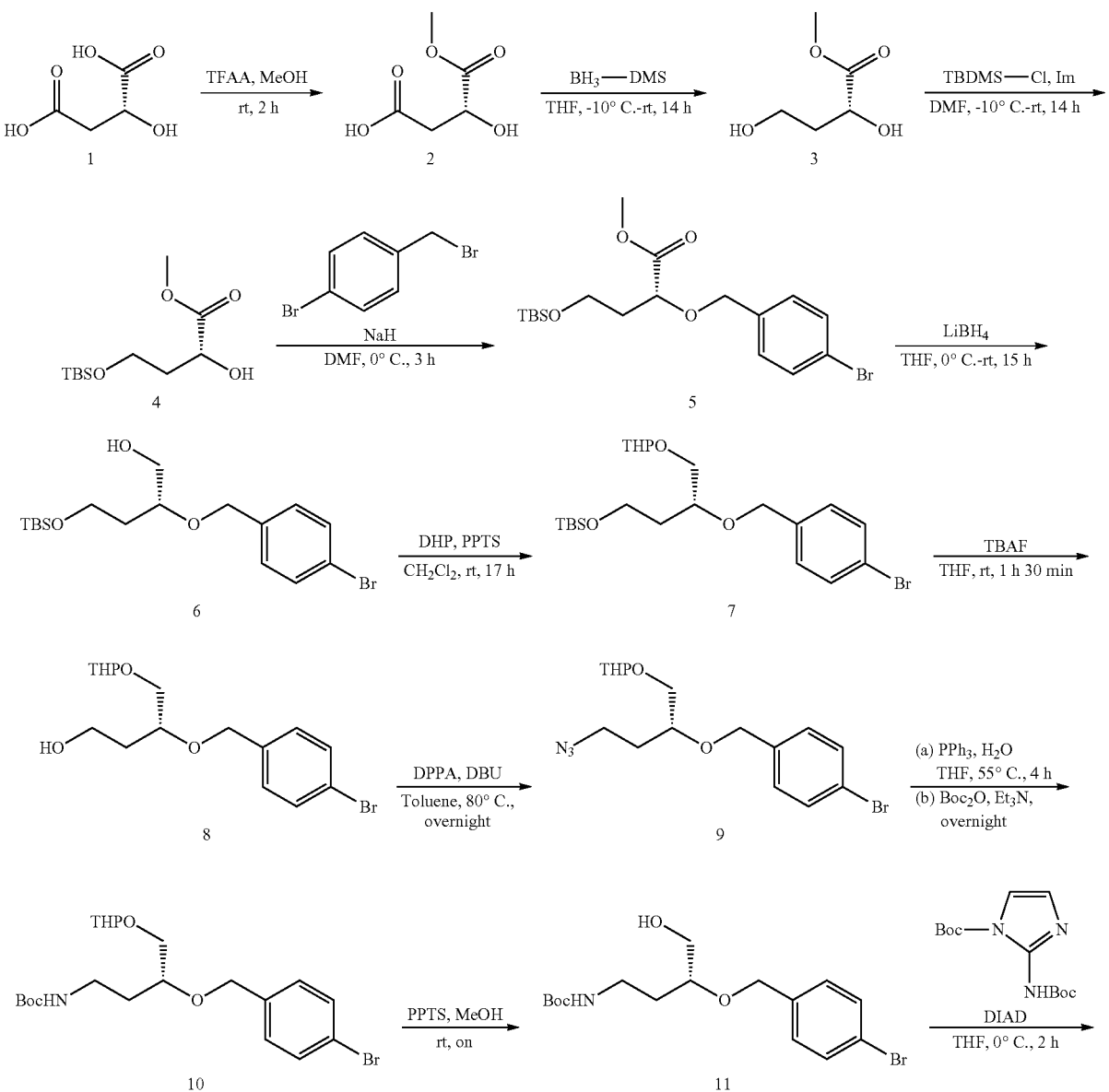

-continued
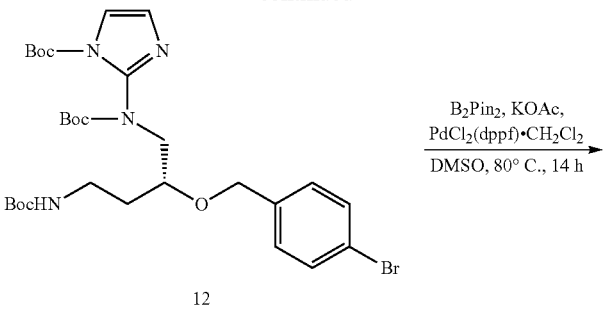
12
B₂Pin₂, KOAc,
PdCl₂(dppf)·CH₂Cl₂
―――――――――――――→
DMSO, 80° C., 14 h
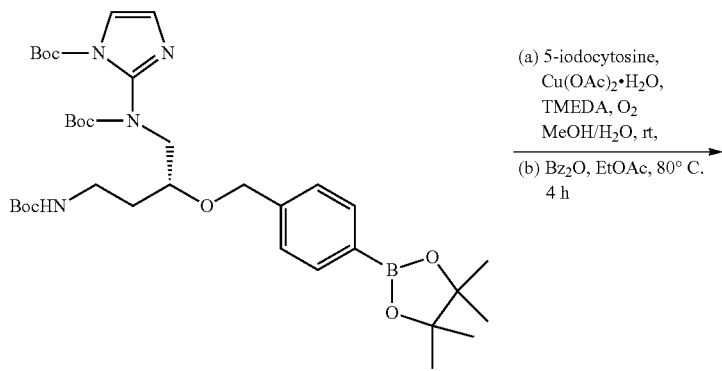
13
(a) 5-iodocytosine,
Cu(OAc)₂·H₂O,
TMEDA, O₂
MeOH/H₂O, rt,
―――――――――――――→
(b) Bz₂O, EtOAc, 80° C.
4 h
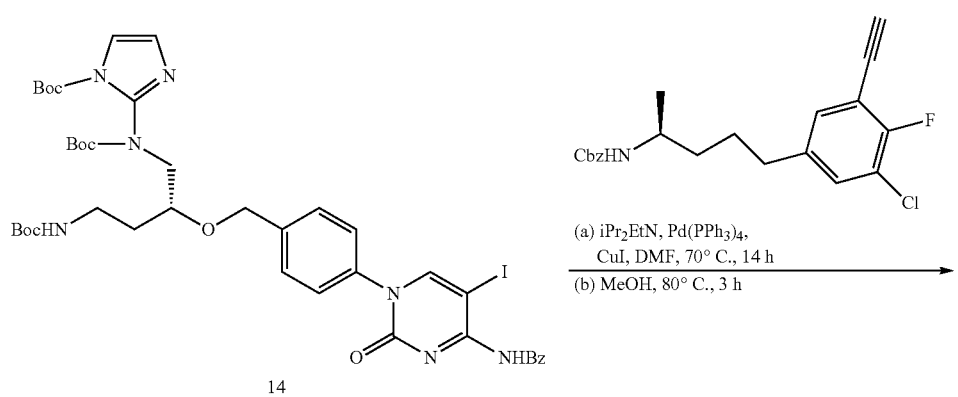
14
(a) iPr₂EtN, Pd(PPh₃)₄,
CuI, DMF, 70° C., 14 h
―――――――――――――→
(b) MeOH, 80° C., 3 h
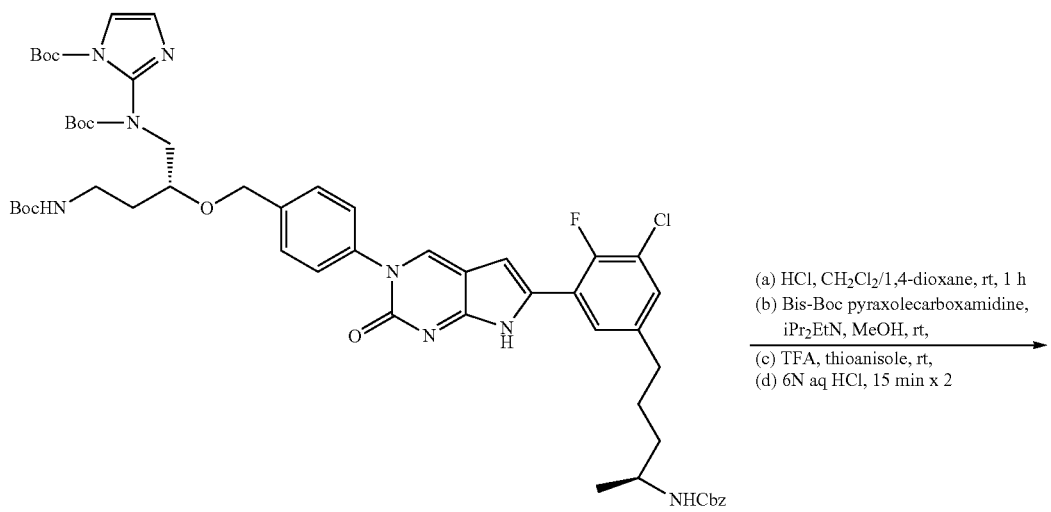
15
(a) HCl, CH₂Cl₂/1,4-dioxane, rt, 1 h
(b) Bis-Boc pyraxolecarboxamidine,
iPr₂EtN, MeOH, rt,
―――――――――――――→
(c) TFA, thioanisole, rt,
(d) 6N aq HCl, 15 min x 2

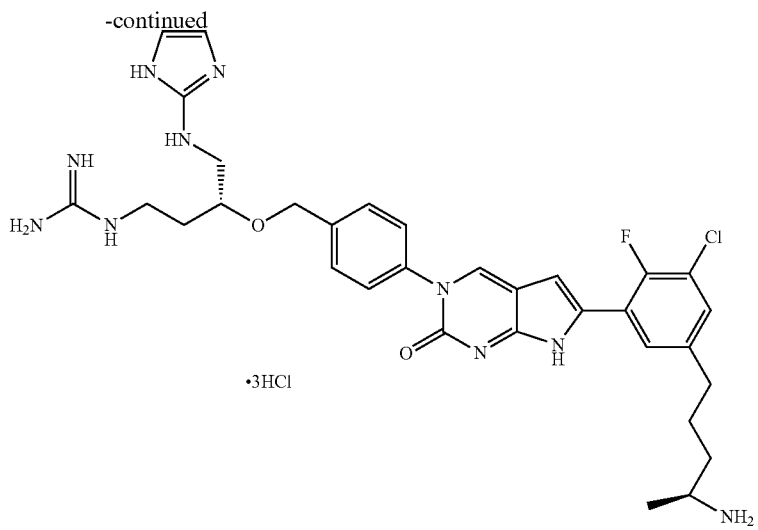

Compound 76

Experimental (referring to synthetic scheme for compound 76):

Synthesis of Intermediate 2

Trifluoroacetic anhydride (55 ml) was added to D-Malic acid (1) (13.4 g, 100 mmol), and stirred at room temperature under argon atmosphere for 40 min. Volatiles were removed, 80 ml of anhydrous methanol was added and stirred at room temperature for 1 h 30 min. Concentrated and the residue was crystallized from diethyl ether/hexanes to obtain 14.7 g (yield, 99%) of 2 as a white solid. This material was used for the next without further processing.

Synthesis of Intermediate 3

BH$_3$-DMS (1M in THF, 200 ml, 200 mmol) was added drop wise to a stirring solution of 2 (14.85, 100 mmol) in anhydrous THF (334 ml) at −10° C. under argon atmosphere. After stirring for 2 h at the same temperature, cooling bath was removed and stirred at room temperature for 14 h. The reaction was quenched by dropwise addition of 200 ml of methanol. Stirred for 20 min, solvent was evaporated. Another 100 ml of methanol was added stirred for 20 min and solvent was evaporated. The residue was dissolved in 200 ml of diethyl ether, passed through a plug of celite and concentrated to dryness to obtain 13 g (yield 96%) of 3 as a colorless liquid.

Synthesis of Intermediate 4

To a stirring solution of 3 (8.9 g, 60 mmol) in anhydrous DMF (75 ml) at −10° C. TBDMS-Cl (9.59 g, 63 mmol) was added followed by imidazole (4.95, 72 mmol).

The solution was stirred overnight and quenched with water (150 ml), product was extracted with ethyl acetate (100 ml×3). Combined organic phases was washed with water (100 ml×2) and brine (150 ml), dried over sodium sulfate, concentrated and purified by flash silica gel chromatography (heptane/ethyl acetate gradient) to obtain 10.62 g (yield, 71%) of 4 as a colorless liquid.

Synthesis of Intermediate 5

Sodium Hydride (1.7 g 60% in mineral oil, 42.7 mmol) was added to a cold solution of 4 (10.60 g, 42.7 mmol) and 4-bromobenzaldehyde (11.26 g, 44.8 mmol) in anhydrous DMF (85 ml). After 3 h, the reaction was quenched with water (5 ml). After 5 min, another 100 ml of water was added. Product was extracted by ethyl acetate (50 ml×2). Combined organic phases was washed with water (100 ml) and brine (100 ml), dried over sodium sulfate and purified by flash silica gel chromatography (Heptane/Ethyl acetate gradient) to obtain 15.7 g (yield, 88%) of 5 as brownish liquid.

Synthesis of Intermediate 6

To the stirring solution of 5 (10.42 g, 25 mmol) in anhydrous THF (125 ml) at 0° C. under argon atmosphere, LiBH$_4$ (95%, 0.80 g, 35 mmol) was added in two portions followed by solution of LiEt$_3$BH in THF (1 M, 2.5 ml, 2.5 mmol) and stirred for 17 h. Cooled to 0° C., 10 ml of water was added slowly followed by another 100 ml of water. After 1 h cooling bath was removed and stirred at room temperature for 5 h. Product was extracted by ethyl acetate (50 ml×2). Combined organic phases was washed with brine (100 ml), dried over sodium sulfate, concentrated and purified by flash silica gel chromatography (Heptane/Ethyl acetate gradient) to obtain 7.4 g (yield, 76%) of 6 as colorless viscous liquid.

Synthesis of Intermediates 7 and 8

Didhydropyran (4.67 ml, 51 mmol) was added to a solution of 6 (6.61 g, 17 mmol) in anhydrous methylene chloride (24 ml), followed by PPTS (0.43 g, 1.7 mmol) and stirred at under argon atmosphere for 14 h. The reaction mixture was washed with water (25 ml×2), dried over sodium sulfate and concentrated to dryness to obtain 6.9 g of 7 as colorless viscous liquid. To this crude liquid, the solution of tetrabutylammonium fluoride in THF (1M, 20.4 ml, 20.4 mmol) was added and stirred for 1 h and 30 min. LCMS showed completion of TBS removal. The crude reaction mixture was concentrated and purified by flash silica gel chromatography (Heptane/Ethyl acetate gradient)

to obtain 5.05 g (yield, 98%, MS, ESI, m/z 381.4 [M+H]$^+$) of 8, as colorless viscous liquid.

Synthesis of Intermediate 9

To the stirring solution of 8 (5.35 g, 17 mmol) in anhydrous toluene (100 ml) under argon atmosphere diphenylphosphoryl azide (5.77 g, 21 mmol) was added followed by dropwise addition of DBU (3.19 g, 21 mmol). After 30 min, it was placed in 80° C. temperature oil bath and stirred for 14 h. LCMS shows the completion of the reaction. Cooled down to room temperature, 100 ml of water is added and the product is extracted by ethyl acetate (75 ml×2). Combined organic phases was washed with water (75 ml) and brine (75 ml), dried over sodium sulfate, concentrated and purified by flash silica gel chromatography (Heptane/Ethyl acetate gradient) to obtain 5.37 g (yield, 93%, MS, ESI, m/z 406.4 [M+Na]$^+$) of 9 as colorless liquid.

Synthesis of Intermediate 10

A solution of 9 (5.37 g, 14 mmol) in THF (130 ml), triphenylphosphine (5.50 g, 21 mmol) and water (11 ml) was stirred at 60° C. for 3 h. The reaction mixture was cooled down to 0° C., Boc anhydride (3.67 g, 16.8 mmol) was added followed by triethylamine (2.83 g, 28 mmol). The reaction mixture was left stirring in same bath overnight. LCMS shows complete consumption of intermediate amine. It was concentrated and purified by flash silica gel chromatography (Heptane/Ethyl acetate gradient) to obtain 6.3 g (yield, 98%, MS, ESI, m/z 480.5 [M+Na]$^+$) of 10 as colorless viscous liquid.

Synthesis of Intermediate 11

To the stirring solution of 10 (Ig, 1.8 mmol) in anhydrous methanol (3.6 ml) PPTS (0.46 g, 1.8 mmol) was added and stirred under argon atmosphere for 14 h. TLC shows completion of reaction. Methanol was evaporated; the residue was dissolved in 20 ml of dichloromethane, washed with water (20 ml), concentrated and purified by flash silica gel chromatography (Heptane/Ethyl acetate gradient) to obtain 0.61 g (yield, 93%, MS, ESI, m/z 374.7 [M+H]$^+$) of 11 as colorless viscous liquid.

Synthesis of Intermediate 12

To the stirring solution of 11 (0.25 g, 0.7 mmol) in anhydrous THF (7 ml) at 0° C. under argon atmosphere, PPh$_3$ (0.26 g, 1 mmol) is added followed by dropwise addition of DIAD (0.22 g, 1 mmol) followed by Boc-2-aminoboc imidazole (0.23 g, 0.8 mmol). After stirring overnight at ambient temperature the solution was concentrated and purified by flash silica gel chromatography (Heptane/Ethyl acetate gradient) to obtain 0.3 g (yield 91%) of 12 as colorless sticky solid.

Synthesis of Intermediate 13

To the solution of 12 (0.58 g, 0.91 mmol) in anhydrous DMF (12 ml), bispinacolatodiborane (1.16 g, 4.55 mmol), potassium acetate (0.27 g, 2.73 mmol) and PdCl$_2$ (dppf) .CH$_2$Cl$_2$ (0.114 g, 0.14 mmol) were added. The mixture was degassed, purged with argon twice and stirred at 80° C. for 14 h. Cooled down to room temperature, 20 ml of water was added. Product was extracted with ethyl acetate (20 ml×2). Combined organic phases were washed with water (20 ml), 14% ammonium hydroxide (20 ml), water (20 ml) and brine (20 ml). It was dried over sodium sulfate, concentrated and purified by flash silica gel chromatography (Heptane/Ethyl acetate gradient) to obtain 0.430 g (yield 68%) of 13 as a colorless sticky solid. From this reaction mono-boc protected 13 was also isolated (0.14 g, yield 25%).

Synthesis of Intermediate 14

To the solution of 13 (0.43 g, 0.63 mmol) in methanol (18 ml), 2 ml of water was added. To this mixture were added 5-iodocytosine (0.23 g, 0.94 mmol), copper acetate monohydrate (0.19 g, 0.93 mmol) followed by tetramethylehtylenediamine (0.28 g, 1.9 mmol). The mixture was stirred at room temperature under open air. After 17 h the mixture was concentrated. 20 ml of water was added. Product was extracted by ethyl acetate (25 ml×2). Combined organic phase was washed with water (25 ml), 14% ammonium hydroxide (25 ml), water (25 ml) and brine (25 ml), dried over sodium sulfate and concentrated to dryness to obtain 0.5 g of off-white solid. This solid was dissolved in 50 ml of ethyl acetate, benzoic anhydride (0.22 g, 0.94 mmol) was added and the mixture was stirred at 80° C. for 4 h. Solvent was evaporated and purified by flash silica gel chromatography (Heptane/Ethyl acetate gradient) to yield 0.34 g (yield, 60%) of 14 as white solid.

Synthesis of Intermediate 15

The solution of 14 (0.34 g, 0.4 mmol) and alkyne (0.16 g, 0.42 mmol) in anhydrous DMF (4 ml) was degassed and purged with argon twice. To this solution were added N—N-diisopropylethylamine (197 ul, 1.1 mmol) followed by Pd(PPh$_3$)$_4$ (0.023 g, 0.02 mmol) and CuI (0.076 g, 0.04 mmol). The mixture was stirred at 70° C. for 12 h. LCMS showed completion of Sonogashira coupling. Cooled down to room temperature, 7 ml of methanol was added and stirred at 80° C. for 3 h. Cooled to room temperature, methanol was evaporated; 25 ml of water was added. Product was extracted by ethyl acetate (25 ml×2). Combined organic phase was washed with water (25 ml), 14% ammonium hydroxide (25 ml), water (25 ml) and brine (25 ml). It was dried over sodium sulfate, concentrated and purified by flash silica gel chromatography using a gradient of Methanol (containing 0.2% saturated ammonium hydroxide) in dichloromethane from 0% to 10% in 16 CV. Desired product fractions were concentrated to obtain 0.15 g (yield 38%) of 15 as yellow solid.

Synthesis of Compound 76

HCl (6.5 ml of 4N in dioxane) was added to a solution of 15 (0.192 g, 0.2 mmol) in dichloromethane (15 ml), and stirred at room temperature for 1 h. Concentrated and the residue was dissolved in anhydrous methanol (5 ml). Bis-boc-1-pyrazolecarboxamide (0.065 g, 0.2 mmol) and N—N-diisopropylethylamine (230 ul, 1.2 mmol) were added and stirred at room temperature for 12 h. Solvent was removed, dissolved in trifluoroacetic acid (17 ml), 17 drops of thioanisole were added and stirred at room temperature for 17 h. It was then concentrated and purified by HPLC. Desired fractions were concentrated to dryness, TFA was exchanged with HCl (6N aq., 17 ml×2 in 15 min interval) and lyophilized to obtain 0.055 g (yield 60, MS, ESI, m/z 649 [M+H]$^+$) of Compound 76 as yellow solid.

Scheme 4
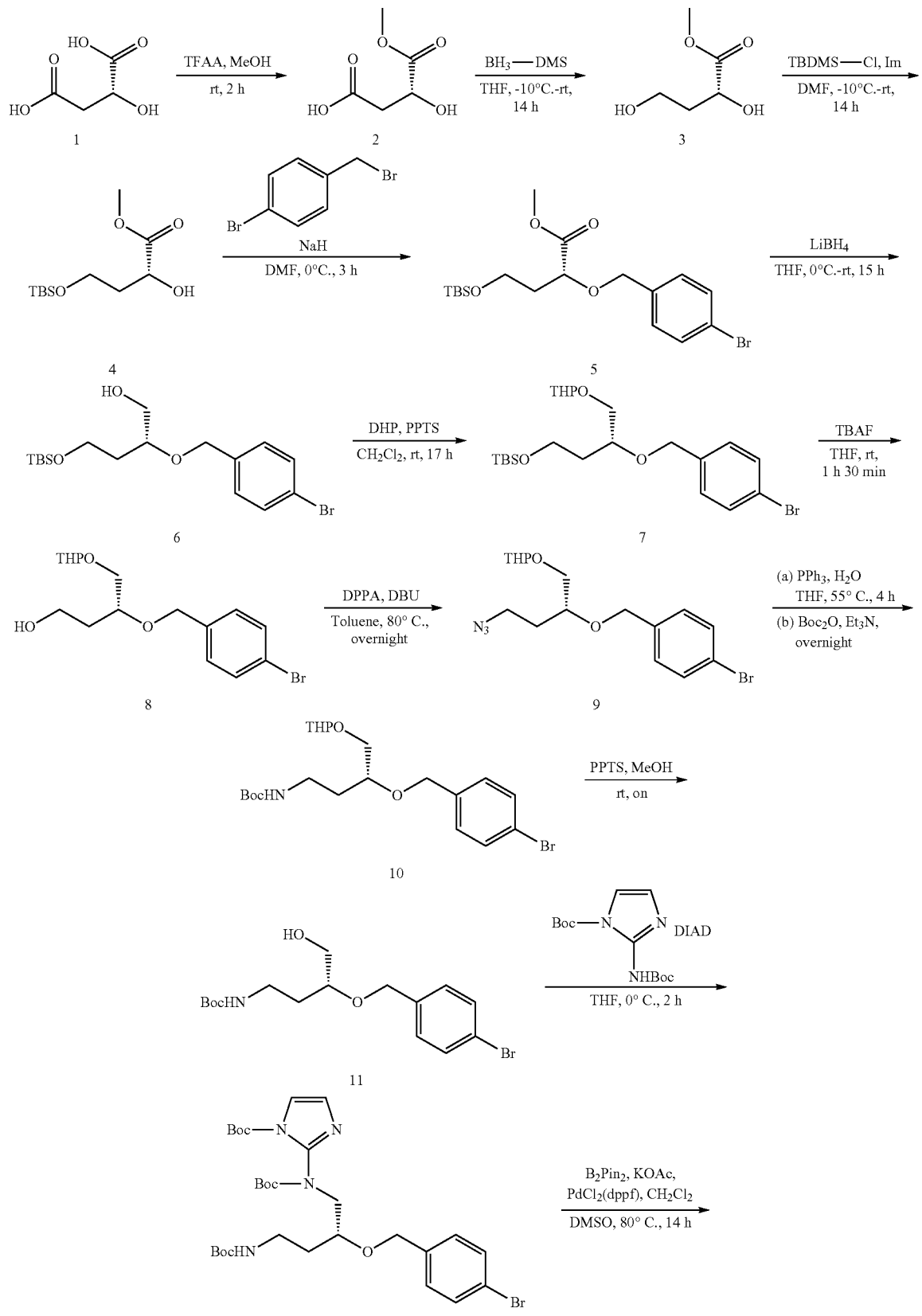

-continued
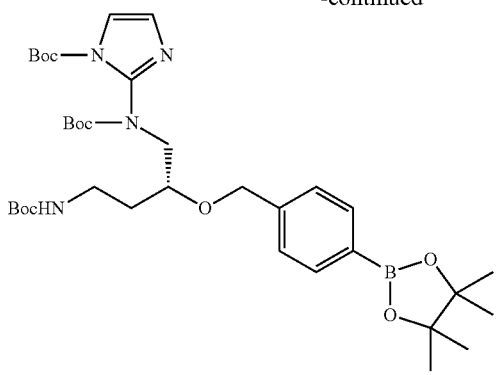
13
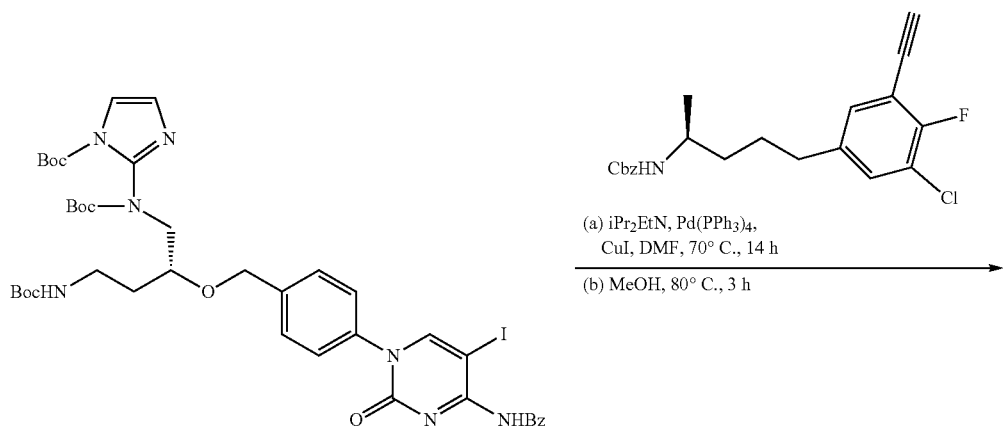
14
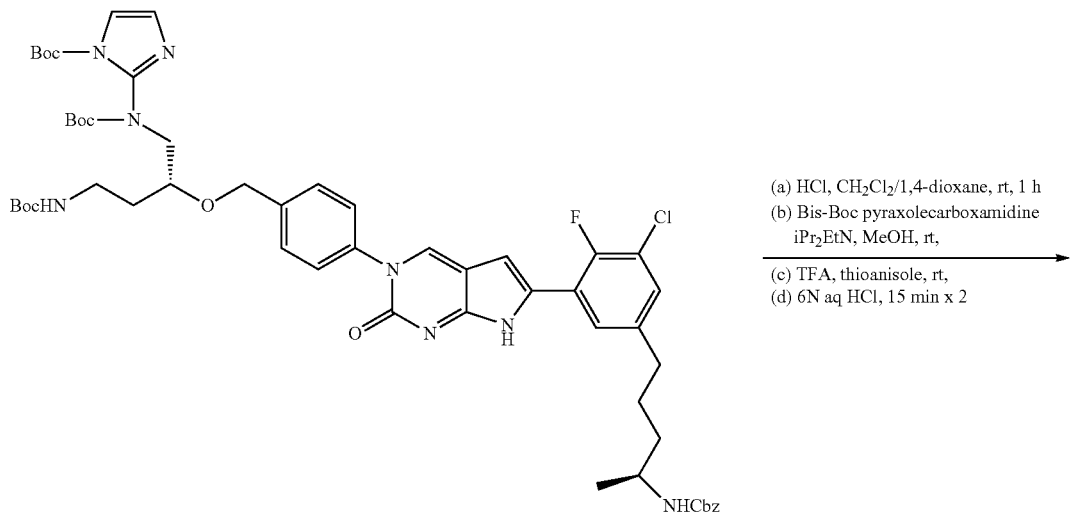
15

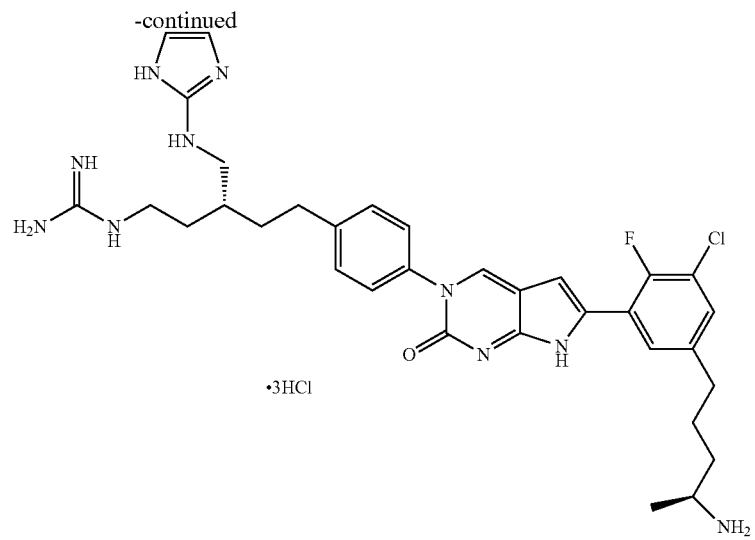

Compound 76

Referring to Scheme 4, starting diacid 1 can be esterified with an alcohol such as methanol under acidic conditions to yield an ester 2, which may be further reduced with a boron reducing agent such as $BH_3$ DMS to provide alcohol 3. This alcohol 3 may be further protected with a suitable protecting group such as TBS and the secondary alcohol of the resultant intermediate 4 may be further alkylated with an alkylating reagent such as p-bromo benzyl bromide. The ester group of intermediate 5 may be reduced with a boron reagent such as $LiBH_4$ to yield alcohol 6. The alcohol 6 may be further protected with a suitable protecting group such as THP. After deprotecting on of the hydroxyl groups of intermediate 7 with TBAF, the resultant intermediate 8 may undergo Mitsunobu reaction to yield azide 9, which is further reduced to an amine by reacting the azide with $PPh_3$ and protecting the resultant amino group with BOC group, for example, to produce intermediate 10. Deprotection of the hydroxyl group of 10 yields alcohol 11, which in turn may yield intermediate 12 by reacting 11 with di-BOC protected aminoimidazole. Intermediate 12 may be converted to a boronic acid derivative by reacting 12 with a suitable boron reagent and a transition metal catalyst (e.g., palladium catalyst). Intermediate 13 may react with for example iodo cytosine under copper catalysis, followed by protection of the amino group of the cytosine with a Bz group. Further reacting cytosine derivative with an appropriate alkyne under palladium catalysis yields a protected pyrazolopyrimidine derivative 15. Upon deprotection and reaction of 15 with Bis-Boc pyraxolecarboxamidine the compound 76 may be obtained.

Synthetic scheme for Compound 108

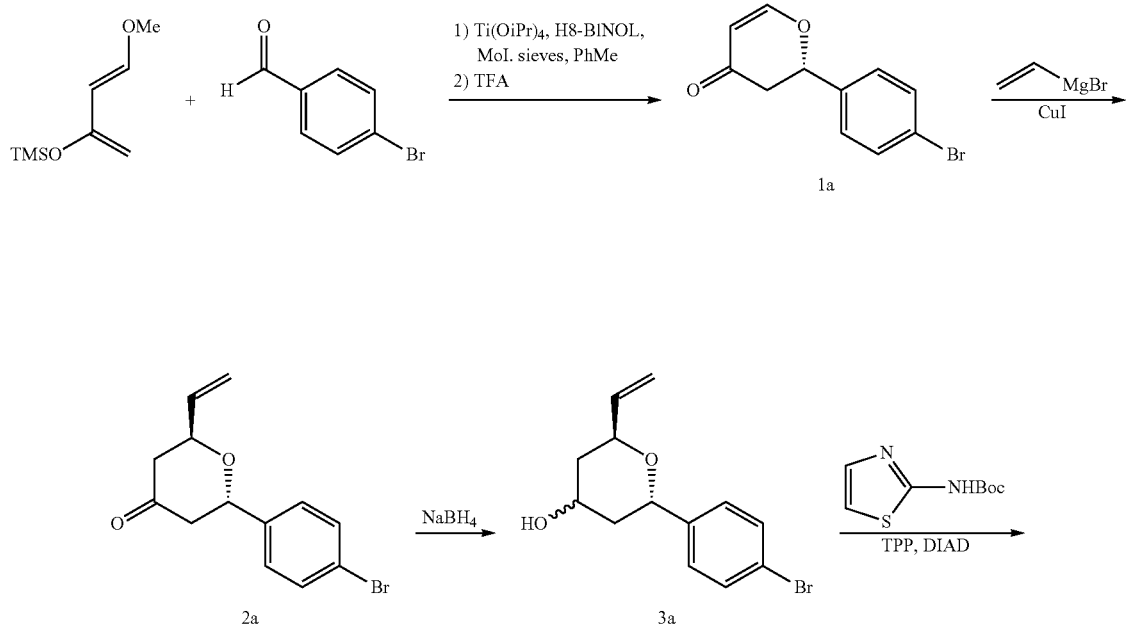

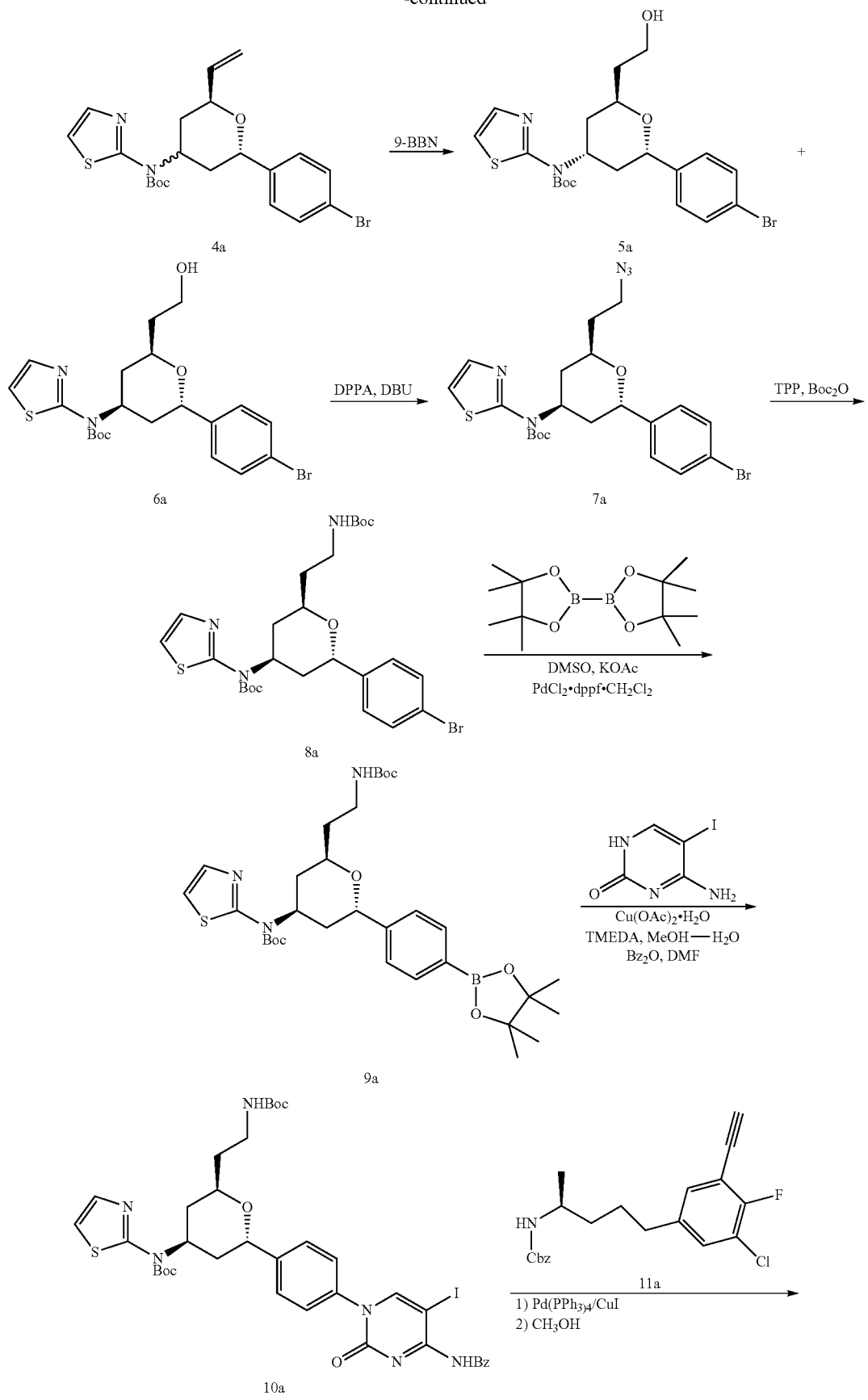

-continued

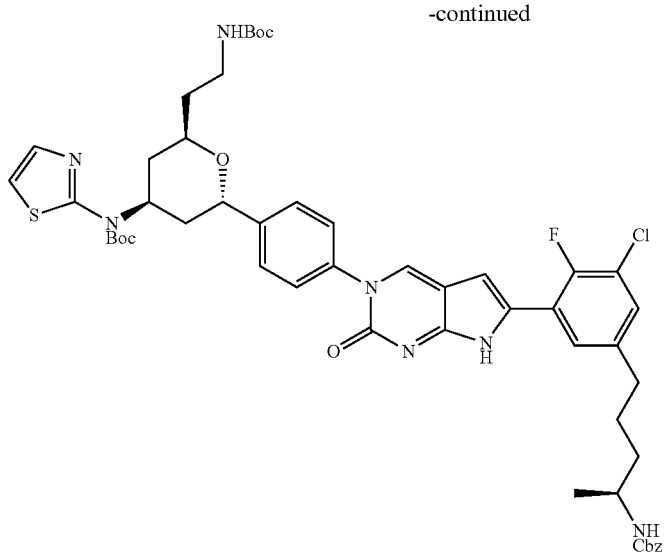

12a

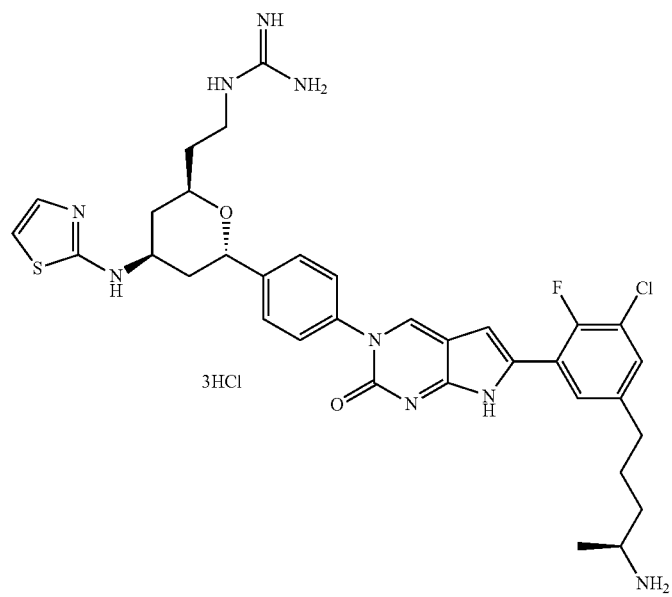

Compound 108

Experimental (referring to synthetic scheme for compound 108):

Synthesis of Intermediate 1a

To a solution of (S)-H8-BINOL (1.8 g, 6.1 mmol) in toluene (96.0 ml) was added anhydrous 4 Å powdered molecular sieves (10.0 g) followed by Ti(OiPr)$_4$ (1.4 g, 4.8 mmol) at RT (Ref: *J Org. Chem.* 2002, 67, 2175-2182). The resulting pale yellow emulsion was then heated at 35° C. in oil bath under argon atmosphere for 90 minutes. Heating was discontinued and the solution was allowed to cool to RT. To this reaction mixture was added 4-bromobenzaldehyde (4.5 g, 24.2 mmol) in one portion, the resulting mixture was stirred at RT for 30 minutes. The mixture was then cooled in ice bath (0° C.), Danishefsky's diene (5.0 g, 29 mmol) was added drop wise, and the resulting reaction mixture was stirred at 0° C. for 24 hrs. After 24 h, 6N HCl solution in water (8.0 ml, 48 mmol) was added at 0° C. (reaction mixture turns dark brown). After 50 minutes, 10.0 ml of a saturated solution of NaHCO$_3$ was added and the resulting mixture was filtered through a cintered funnel to remove solids. The layers were separated and the aqueous layer was washed with EtOAc. The combined organic layers were concentrated and purified by Combiflash (80 gm column) using 0-75% EtOAc in heptane as eluent to afford 3.4 gm (55%) of 1a [90% ee by HPLC, LC-MS-M+: 253.3].

Synthesis of Intermediate 2a

To a suspension of CuI (15.23 g, 80 mmol) in THF (115.0 ml) at −78° C. was added vinyl magnesium bromide (1N, 80.0 ml, 80 mmol). The resulting mixture was warmed to 0° C. and stirred at 0° C. for 1 hr. To this solution, DMPU (23.2 ml, 192 mmol) was added followed by TMS-Cl (10.15 ml, 80 mmol). The resulting thick paste was cooled to −78° C. in a dry-ice acetone bath and stirred for 10 mins. To this mixture, a solution of 1a (3.4 g, 13.44 mmol) in THF (27.0 ml) was added drop wise. The resulting thick paste was stirred at −78° C. in a dry ice-acetone bath for 3 hr and then allowed to warm to RT for 2 hrs. The reaction was quenched with crushed ice and saturated NH$_4$Cl solution. Water and EtOAc were added in reaction mixture and the layers were separated (filter through celite if necessary to remove emulsion). The combined organic layers concentrated and purified using Combiflash to get 1.41 g of 2a (37% and 1.95 g of 1a (57%) [LC-MS: M+: 283.4].

Synthesis of Intermediate 3a

To a solution of 2a (1.4 g, 5 mmol) in methanol (15.0 ml) cooled to 0° C. in ice bath, was added NaBH$_4$ (0.38 g, 10 mmol) single lot. After 30 minutes, the ice bath was removed and reaction mixture was warmed to RT and stirred at RT for 1 hr. The reaction was then quenched with ice and sat. NH$_4$Cl solution and extracted with EtOAc. The combined organic layers were concentrated and purified by Combiflash (40 g) to provide 1.4 g of 3a (quantitative) [LC-MS: M+: 285.3].

Synthesis of Intermediate 4a

To an ice cooled solution of 3a (0.693 g, 2.45 mmol), N-Boc-2-aminothiazole (0.6 g, 2.94 mmol) and triphenylphosphine (0.96 g, 3.7 mmol) in THF (10.0 ml), DIAD was added drop wise. The ice bath was removed after 15 minutes and the reaction mixture was allowed to warm to RT. Slight turbidity develops in the reaction mixture after ~30 mins and some solid precipitates out after ~1 hr. After 2 hr, the reaction mixture was concentrated and purified by combiflash (40 g) to obtain 0.825 g (72%) of 4a [LC-MS: M+: 465.4].

Synthesis of Intermediate 5a and 6a

To a solution of 4a (0.825 g, 1.8 mmol) in dry THF was added 9-BBN dimer (0.44 g, 1.8 mmol) at RT and the resulting solution was stirred under argon for 16 hr. The reaction mixture was then cooled in ice bath and methanol (2.0 ml) was added followed by 4 N aqueous NaOH solution and 30% H$_2$O$_2$ (3.0 ml). The reaction mixture was then stirred at RT for 1 hr and then heated to 50-55° C. for 3 hrs. After cooling to RT, the reaction mixture was extracted with EtOAc, and the combined organic layers were concentrated and purified using Combiflash (40 g) to obtain 0.213 g of 5a (24%) [LC-MS: M+: 485.4] and 0.26 g of 6a (30%) [LC-MS: M+: 485.4].

Synthesis of Intermediate 7a

To a solution of 6a (0.26 g, 0.54 mmol) in toluene (5.0 ml) was added DPPA (0.3 g, 1.08 mmol) followed by DBU (0.16 g, 1.08 mmol) (bubbles after DBU addition and solution becomes turbid). The resulting reaction mixture was heated under argon at 80-85° C. for 18 hr. After 18 hr, the mixture was cooled to RT, concentrated, and purified by combiflash (40 g) to provide 0.26 g of 7a (95%) [LC-MS: M+: 508.5].

Synthesis of Intermediate 8a

To a solution of 7a (0.26 g, 0.51 mmol) in THF (10.0 ml) and water (1.0 ml) was added triphenylphosphine (0.27 g, 1.02 mmol) and the resulting reaction mixture was heated with stirring at 60-65° C. in an oil bath for 21 hr. The reaction mixture was then cooled to RT, triethylamine (0.35 ml, 2.55 mmol) and (Boc)$_2$O (0.2 g, 1.0 mmol) were added and resulting mixture was stirred at RT for 48-72 h. The reaction mixture was then concentrated in vacuo and purified by Combiflash to obtain 0.2 g (67%) of 8a [LC-MS: M+: 584.5].

Synthesis of Intermediate 9a

To a degassed solution of 8a (0.2 g, 0.34 mmol) in DMSO (6.0 ml) was added bispinacalatodiborane (0.104 g, 0.41 mmol) and KOAc (0.10 g, 1.02 mmol) followed by PdCl$_2$ (dppf)CH$_2$Cl$_2$ (0.028 g, 0.034 mmol). The resulting reaction mixture was then heated under argon at 80-85° C. for 19 hr. After completion of reaction, the reaction mixture was cooled to RT, diluted with water and EtOAc, and aqueous layer was extracted with EtOAc (*filter through celite to remove emulsion if necessary). The combined organic layers were concentrated and purified using Combiflash to provide 0.188 g (88%) of 9a [LC-MS: M+: 630.7].

Synthesis of Intermediate 10a

To a solution of 9a (0.188 g, 0.3 mmol) in MeOH:water (10.0 ml, 4:1) was added Iodocytosine (0.09 g, 0.36 mmol), Cu(OAc)$_2$ (0.06 g (0.3 mmol) and TMEDA (0.09 ml (0.6 mmol) and the resulting reaction mixture was stirred at RT open to air for 16 hr. The reaction mixture was then concentrated and diluted with water and CH$_2$Cl$_2$. The layers were separated and the aqueous layer was washed with CH$_2$Cl$_2$. The combined organic layers were concentrated to obtain greenish blue foam (−0.275 g) which was dissolved in EtOAc (6.0 ml). Bz$_2$O (0.09 g (0.4 mmol) was then added and the resulting mixture was heated under argon at 75-80° C. for 5 hrs. The reaction mixture was cooled to RT, diluted with NaHCO$_3$ solution and the layers were separated. The organic layer was concentrated and purified by using Combiflash to afford 0.16 g (63%) of 10a [LC-MS: M+: 843.6].

Synthesis of Intermediate 12a

To a solution of 10a (0.16 g, 0.19 mmol) in DMF (5.0 ml) was added 11a (0.09 g, 0.23 mmol). This mixture was degassed, DIPEA (0.1 ml, 0.6 mmol), Pd(PPh$_3$)$_4$ (0.023 g, 0.02 mmol), CuI (0.008 g, 0.04 mmol) were then added and the resulting reaction mixture was heated under argon at 70-75° C. for 13 hr. After 13 hrs, methanol (4.0 ml) was added to the reaction mixture and it was heated for an additional 3 hrs at 75-80° C. The reaction mixture was then cooled, concentrated on rotavap, and diluted with water and EtOAc. The layers were separated and the aqueous layer was washed with EtOAc. The combined organic layers were washed with 14% NH$_4$OH solution and water, concentrated, and purified by preparatory TLC (100% EtOAc as solvent) to afford 0.09 g (48%) of 12a [LC-MS: M+: 984.8].

Synthesis of Compound 108

To a solution of 12a (0.09 g, 0.09 mmol) in CH$_2$Cl$_2$ (5.0 ml) was added 4N HCl solution in dioxane (0.5 ml). The resulting reaction mixture was stirred at RT for 4 hr. The reaction mixture was then concentrated and dried under vacuum to provide crude product [LC-MS: M+: 884.8]. This crude viscous liquid was dissolved in methanol (5.0 ml) and DIPEA (0.17 ml, 1.0 mmol) was added followed by N,N'-BisBocgunylpyrazole (13a, 0.04 g, 0.12 mmol). The reaction mixture was stirred at RT for 18 hr, then concentrated and dried under vacuum to obtain the product as a viscous liquid [LC-MS: M+: 1026.8]. This viscous liquid was dissolved in TFA (5.0 ml) and thioanisole (2-3 drops) was added. The resulting solution was heated at 40-45° C. for 3.5 hr. After 3.5 h, the mixture was concentrated and purified using preparatory HPLC (30-65% MeOH in water with 0.15% TFA). Pure HPLC fractions were concentrated and treated with 6.0 N HCl twice to make HCl salt of final compound. Lyophilization afforded 0.022 g of Compound 108 [LC-MS: M+: 692.7].

Synthetic scheme for Compound 125

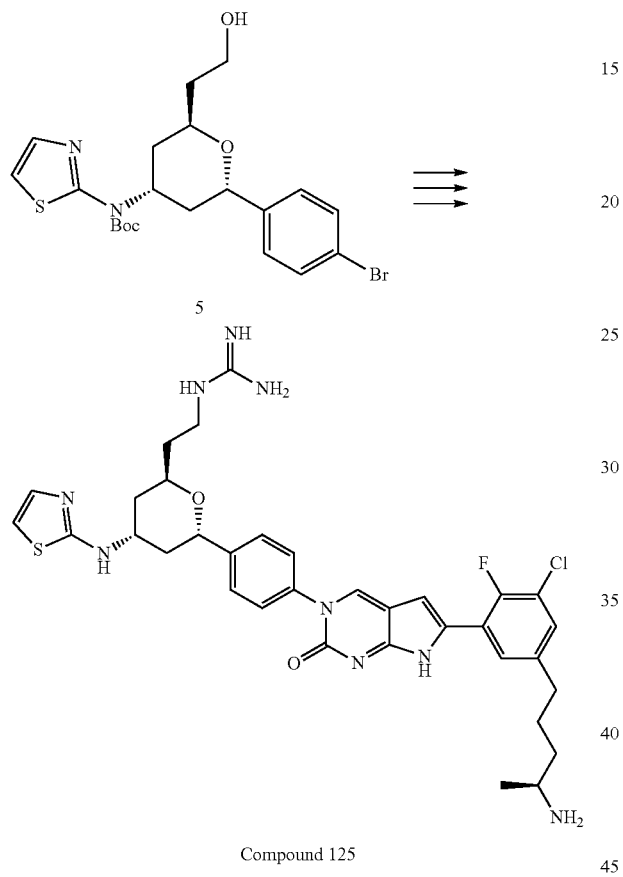

Compound 125

Compound 125 was using a similar synthetic protocol as described for Compound 109 starting from Intermediate 5a (Compound 125, 0.05 g) [LC-MS: M+: 692.6].

Compounds of the present disclosure are shown in Table 1. ESI-LCMS (electrospray ionization-liquid chromatography mass spectral) data are provided, where available. When data is not available this is indicated by "NA". The LCMS data are provided using the convention for m/z in the format, [M+H]+, except where otherwise indicated.

Example 2—Antimicrobial Activity

The compounds of the present disclosure were tested for antimicrobial activity. These data are presented in Table 2. The Compounds 1-149 were run against *Escherichia coli* (*E. Coli*) strain ATCC25922 and against *Staphylococcus aureus* (*S. aureus*) 11540 strain using a standard microdilution assay to determine minimum inhibitory concentrations (MICs). The data is presented whereby a "+" indicates that the compound has an MIC value of 16 micrograms/mL or less and a "−" indicates that the compound has an MIC value greater than 16 micrograms/mL. It will be recognized by one skilled in the art that the compounds can be assessed against other bacterial organisms and that the presentation of data for activity against *Eschericia coli* and *Staphylococcus aureus* are illustrative and in no way is intended to limit the scope of the present disclosure. The compounds of the present disclosure can be assayed against a range of other microorganisms depending upon the performance activity desired to be gathered. Furthermore, the "+" and "−" representation and the selection of a cutoff value of 16 micrograms/mL is also illustrative and in no way is intended to limit the scope of the present disclosure. For example, a "−" is not meant to indicate that the compound necessarily lacks activity or utility, but rather that its MIC value against the indicated microorganism is greater than 16 micrograms/mL.

TABLE 2

| Compound No. | MIC *E. Coli* | MIC *S. aureus* |
| --- | --- | --- |
| 1 | + | + |
| 2 | + | + |
| 3 | + | + |
| 4 | + | + |
| 5 | + | + |
| 6 | + | + |
| 7 | + | + |
| 8 | + | + |
| 9 | + | + |
| 10 | − | − |
| 11 | + | + |
| 12 | − | − |
| 13 | + | + |
| 14 | + | + |
| 15 | + | + |
| 16 | + | + |
| 17 | + | + |
| 18 | − | − |
| 19 | + | + |
| 20 | − | − |
| 21 | + | + |
| 22 | + | + |
| 23 | − | + |
| 24 | + | + |
| 25 | + | + |
| 26 | − | + |
| 27 | + | + |
| 28 | + | + |
| 29 | + | + |
| 30 | + | + |
| 31 | + | + |
| 32 | + | + |
| 33 | + | + |
| 34 | + | + |
| 35 | + | + |
| 36 | + | + |
| 37 | + | + |
| 38 | + | + |
| 39 | + | + |
| 40 | + | + |
| 41 | + | + |
| 42 | + | + |
| 43 | + | + |
| 44 | + | + |
| 45 | + | + |
| 46 | + | + |
| 47 | + | + |
| 48 | + | + |
| 49 | + | + |
| 50 | + | + |
| 51 | + | + |
| 52 | + | + |
| 53 | + | + |
| 54 | + | + |
| 55 | + | + |
| 56 | + | + |
| 57 | + | + |
| 58 | + | + |

TABLE 2-continued

| Compound No. | MIC E. Coli | MIC S. aureus |
|---|---|---|
| 59 | + | + |
| 60 | + | + |
| 61 | + | + |
| 62 | + | + |
| 63 | + | + |
| 64 | + | + |
| 65 | + | + |
| 66 | + | + |
| 67 | + | + |
| 68 | + | + |
| 69 | + | + |
| 70 | + | + |
| 71 | + | + |
| 72 | + | + |
| 73 | + | + |
| 74 | + | + |
| 75 | + | + |
| 76 | + | + |
| 77 | + | + |
| 78 | + | + |
| 79 | − | − |
| 80 | − | − |
| 81 | + | + |
| 82 | + | + |
| 83 | + | + |
| 84 | + | + |
| 85 | + | + |
| 86 | + | + |
| 87 | + | + |
| 88 | + | + |
| 89 | + | + |
| 90 | + | + |
| 91 | + | + |
| 92 | + | + |
| 93 | − | − |
| 94 | + | − |
| 95 | + | + |
| 96 | + | + |
| 97 | + | + |
| 98 | − | − |
| 99 | + | − |
| 100 | + | + |
| 101 | + | + |
| 102 | + | + |
| 103 | − | − |
| 104 | + | + |
| 105 | − | − |
| 106 | + | + |
| 107 | + | + |
| 108 | + | + |
| 109 | − | + |
| 110 | − | − |
| 111 | − | + |
| 112 | − | − |
| 113 | + | − |
| 114 | + | + |
| 115 | + | + |
| 116 | − | − |
| 117 | + | + |
| 118 | − | − |
| 119 | + | + |
| 120 | + | + |
| 121 | + | − |
| 122 | + | + |
| 123 | − | + |
| 124 | − | − |
| 125 | − | − |
| 126 | − | − |
| 127 | + | + |
| 128 | + | + |
| 129 | + | + |
| 130 | + | − |
| 131 | − | − |
| 132 | + | + |
| 133 | + | + |
| 134 | + | + |
| 135 | + | + |
| 136 | − | − |
| 137 | + | + |
| 138 | + | + |
| 139 | + | + |
| 140 | + | + |
| 141 | + | + |
| 142 | + | + |
| 143 | + | + |
| 144 | + | − |
| 145 | − | − |
| 146 | − | − |
| 147 | − | − |
| 148 | + | + |
| 149 | + | + |
| 150 | + | + |
| 151 | + | + |
| 152 | + | + |
| 153 | n/a | n/a |

TABLE 2a

| Compound No. | MIC E. Coli | MIC S. aureus |
|---|---|---|
| 159 | + | + |
| 160 | + | + |
| 161 | + | + |
| 162 | + | + |
| 163 | + | + |
| 164 | + | + |
| 165 | + | + |
| 166 | + | + |
| 167 | + | + |
| 168 | + | + |
| 169 | + | + |
| 170 | + | + |
| 171 | + | + |
| 172 | + | + |
| 173 | + | + |
| 174 | + | + |
| 175 | + | + |
| 176 | + | + |
| 177 | + | + |
| 178 | + | + |

INCORPORATION BY REFERENCE

The entire disclosure of each of the patent documents and scientific articles referred to herein is incorporated by reference for all purposes.

EQUIVALENTS

The disclosure can be embodied in other specific forms without departing from the spirit or essential characteristics thereof. The foregoing embodiments are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

What is claimed is:
1. A compound of Formula (A):

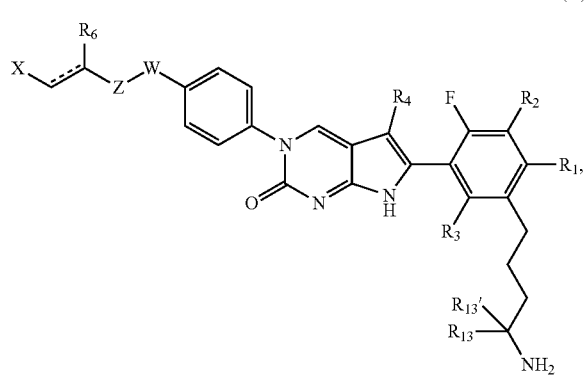

(A)

or a tautomer thereof, or a pharmaceutically acceptable salt of said compound or tautomer
wherein:
----- is a single or a double bond;
X is —NHC(NH)NH$_2$, —CH$_2$NH$_2$, —CH$_2$NHC(NH)NH$_2$, —CH$_2$NHCH$_2$C(O)CH$_3$, —CH$_2$NHC(NH)(C$_1$-C$_4$)alkyl, —CH$_2$NHC(NH)(C$_3$-C$_7$)cycloalkyl, —CH$_2$NHC(NH)heteroaryl, heteroaryl, —CH$_2$heteroaryl, —NHCH$_2$heteroaryl, —CH$_2$NHheteroaryl, —CH(OH)heteroaryl, —CH$_2$heterocycloalkyl, —NHCH$_2$heterocycloalkyl, or —CH$_2$NHheterocycloalkyl, wherein the (C$_1$-C$_4$)alkyl, cycloalkyl, heterocycloalkyl and heteroaryl are optionally substituted with one or more R$_7$;
Z is O, CH$_2$, NR$_{11}$, or S(O)$_p$;
W is N(R$_5$) or C(R$_5$)(R$_{5'}$);
R$_1$ is H, (C$_1$-C$_4$)alkyl, (C$_2$-C$_4$)alkenyl, (C$_2$-C$_4$)alkynyl, (C$_1$-C$_3$)alkoxy, (C$_1$-C$_3$)haloalkyl, —O(C$_1$-C$_3$)haloalkyl, heterocycloalkyl, halogen, —NO$_2$, wherein the (C$_1$-C$_4$)alkyl, (C$_2$-C$_4$)alkenyl, and heterocycloalkyl are optionally substituted with one or more R$_{12}$; or
R$_1$ and R$_2$ together with the carbon atoms to which they are attached form a (C$_3$-C$_7$)cycloalkyl or heterocycloalkyl;
R$_2$ is —F, —Cl, —CF$_3$, —SCF$_3$, or —OCF$_3$;
R$_3$ is H or —NO$_2$;
R$_4$ is H, (C$_1$-C$_3$)alkyl, (C$_2$-C$_3$)alkenyl, halogen, or —NO$_2$;
R$_5$ is H or —CH$_3$;
R$_{5'}$ is H; or
R$_6$ is H, (C$_1$-C$_3$)alkyl, (C$_2$-C$_3$)alkenyl, (C$_1$-C$_3$)haloalkyl, CH$_2$NHC(NH)NH$_2$, —CH$_2$NHC(NH)(C$_1$-C$_3$)alkyl, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NHheterocycloalkyl, —(CH$_2$)$_n$heteroaryl, or —CH$_2$NHheteroaryl, wherein the heteroaryl and heterocycloalkyl is optionally substituted with one or more R$_8$; or
R$_5$ and R$_6$ together with the carbon atoms to which they are attached and the Z atom connecting said two carbon atoms, form a (C$_5$-C$_6$)cycloalkyl or a 5- to 6-membered heterocycloalkyl ring containing 1-3 heteroatoms optionally substituted with one or more R$_9$; or
when W is N(R$_5$), R$_6$ and W together with the Z atom connecting W and the carbon atom to which R$_6$ is attached, form a 5- to 6-membered heterocycloalkyl ring containing 1-3 heteroatoms optionally substituted with one or more R$_9$;
at least one of R$_5$ and R$_6$ is not H;
each R$_7$ is independently (C$_1$-C$_3$)alkyl, halogen, oxo, —OH, or —NH$_2$;
each R$_8$ is independently (C$_1$-C$_3$)alkyl, (C$_1$-C$_3$)alkoxy, halogen, oxo, —NH$_2$, or —NHR$_{10}$;
each R$_9$ is independently (C$_1$-C$_3$)alkyl, (C$_2$-C$_4$)alkenyl, —NH$_2$, —NHC(NH)NH$_2$, —NHC(NH)(C$_1$-C$_3$)alkyl, —CH$_2$heteroaryl, —NHheterocycloalkyl, or —NHheteroaryl, wherein the (C$_1$-C$_3$)alkyl is optionally substituted with one or more substituents independently selected from —NHC(NH)NH$_2$, —OH and —NH$_2$;
each R$_{10}$ is independently —CH$_2$aryl optionally substituted with (C$_1$-C$_3$)alkoxy or halogen;
R$_{11}$ is H, —NHC(NH)NH$_2$, —C(O)H, —C(O)(C$_1$-C$_4$)alkyl, —C(O)O(C$_1$-C$_4$)alkyl, (C$_1$-C$_4$)alkyl, (C$_3$-C$_6$)cycloalkyl, or heterocycloalkyl, wherein the (C$_1$-C$_4$)alkyl is optionally substituted with one or more substituents independently selected from —OH, (C$_1$-C$_3$)alkoxy, —NH$_2$, and —NHC(NH)NH$_2$;
each R$_{12}$ is independently selected from (C$_1$-C$_3$)alkoxy, (C$_1$-C$_3$)haloalkyl, (C$_1$-C$_3$) hydroxyalkyl, halogen, —OH, —NH$_2$, —NH(C$_1$-C$_4$)alkyl, —N((C$_1$-C$_4$)alkyl)$_2$, and oxo;
R$_{13}$ is —CH$_3$, —CH=CH$_2$, —CF$_3$, —CH$_2$F, or —CH$_2$OH;
R$_{13'}$ is H or —CH$_3$;
n is 1 or 2;
each p is independently 0, 1, or 2; and
provided that when Z is NH, X is —CH$_2$NHC(NH)NH$_2$ or —CH$_2$NH$_2$, R$_1$ is H or F, R$_3$ is H, R$_5$ is methyl, and R$_6$ is H, then R$_4$ is (C$_1$-C$_3$)alkyl, (C$_2$-C$_3$)alkenyl, F, I, or —NO$_2$;
provided that when Z is NH, W is not CH(CH$_3$), and X is not CH$_2$NHC(NH)NH$_2$, and R$_2$ is not Cl, and R$_{13}$ is not CH$_3$, and R$_6$, R$_1$, R$_3$, R$_4$, and R$_{13'}$ are not H.

2. The compound of claim 1, wherein when Z is NH, X is —NHC(NH)NH$_2$, —CH$_2$NHC(NH)NH$_2$, —CH$_2$NHC(NH)(C$_1$-C$_3$ alkyl) or —CH$_2$NH$_2$, and R$_5$ is H or CH$_3$, then R$_6$ is not CH$_3$, —CH=CH$_2$, —(CH$_2$)$_n$NH$_2$, —(CH$_2$)$_n$OH or a group of Formula:

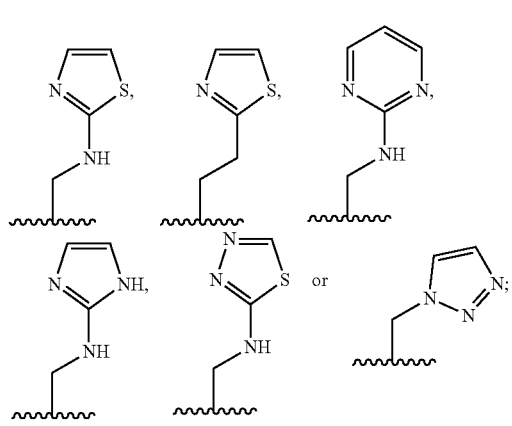

and when Z is NH, X is —NHC(NH)NH$_2$, —CH$_2$NHC(NH)CH$_3$, —CH$_2$NHC(NH)NH$_2$, —CH$_2$NH$_2$ or a group of Formula:

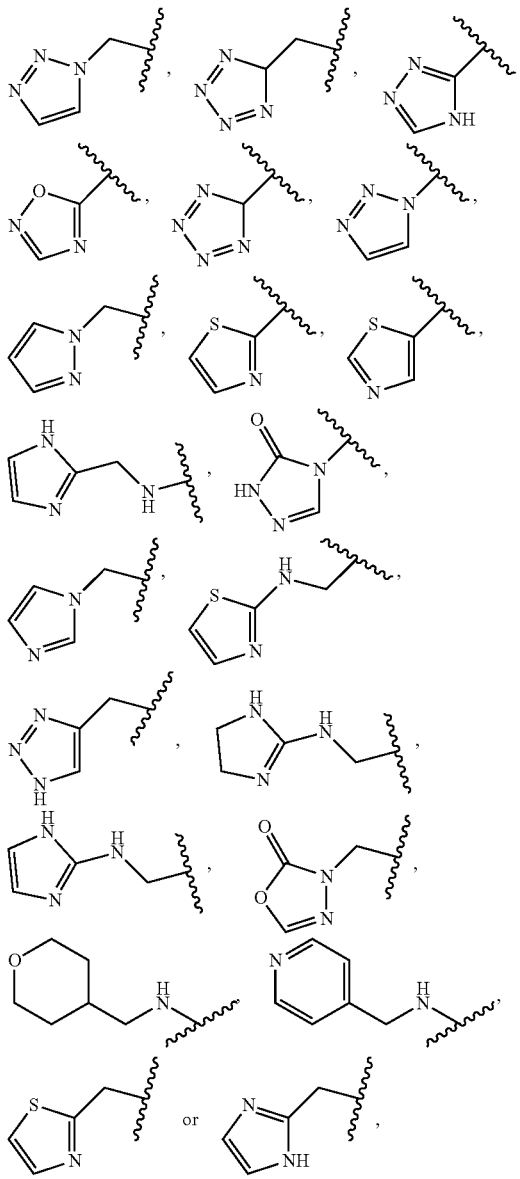

then R$_5$ and R$_6$ do not from a ring of Formula:

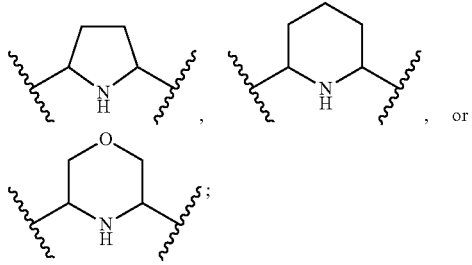

and when Z is O, X is —CH$_2$NHC(NH)NH$_2$, and R$_5$ is H, then R$_6$ is not a group of Formula:

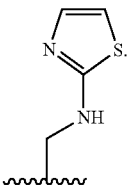

3. The compound of claim 1, wherein:
Z is O, CH$_2$, or NH;
R$_1$ is H or —NO$_2$;
R$_2$ is —Cl or —OCF$_3$;
R$_4$ is H or —NO$_2$;
R$_{11}$ is H;
R$_{13}$ is —CH$_3$; and
R$_{13'}$ is H.

4. The compound of claim 1, wherein:
R$_6$ is H, (C$_1$-C$_3$)alkyl, (C$_2$-C$_3$)alkenyl, (C$_1$-C$_3$)haloalkyl, —CH$_2$NHC(NH)NH$_2$, —CH$_2$NHC(NH)CH$_3$, —(CH$_2$)$_n$OH, —CH$_2$S(O)$_2$NH$_2$, —CH$_2$NHCH$_2$CH$_3$, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more R$_8$.

5. The compound of claim 1, wherein:
R$_6$ is H, (C$_1$-C$_3$)alkyl, (C$_2$-C$_3$)alkenyl, (C$_1$-C$_3$)haloalkyl, —CH$_2$NHC(NH)NH$_2$, —(CH$_2$)$_n$OH, —CH$_2$S(O)$_p$NH$_2$, —CH$_2$NH(C$_1$-C$_3$)alkyl, —CH$_2$C(O)NH$_2$, —(CH$_2$)$_n$NH$_2$, —CH$_2$heterocycloalkyl, —CH$_2$NH$_2$heterocycloalkyl, —(CH$_2$)$_n$heteroaryl, or —CH$_2$NH$_2$heteroaryl, wherein the heteroaryl and heterocycloalkyl is optionally substituted with one or more R$_8$; and
provided that when Z is NH, X is —CH$_2$NHC(NH)NH$_2$ or —CH$_2$NH$_2$, R$_1$ is H, R$_3$ is H, R$_4$ is H, then R$_6$ is not H, —CH$_3$, —CH$_2$OH, —CH$_2$NH$_2$NH$_2$, or —CH=CH$_2$.

6. The compound of claim 1, wherein:
R$_6$ is (C$_1$-C$_3$)alkyl, (C$_2$-C$_3$)alkenyl, (C$_1$-C$_3$)haloalkyl, —CH$_2$NHC(NH)NH$_2$, CH$_2$NHC(NH)CH$_3$, —CH$_2$CH$_2$OH, —CH$_2$OH, —CH$_2$S(O)$_2$NH$_2$, CH$_2$NHCH$_2$CH$_3$, —CH$_2$C(O)NH$_2$, —CH$_2$CH$_2$NH$_2$, —CH$_2$NH$_2$, or a group of Formulae:

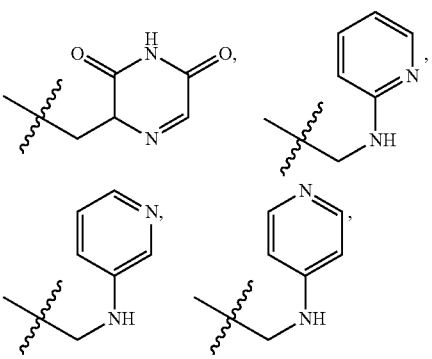

-continued
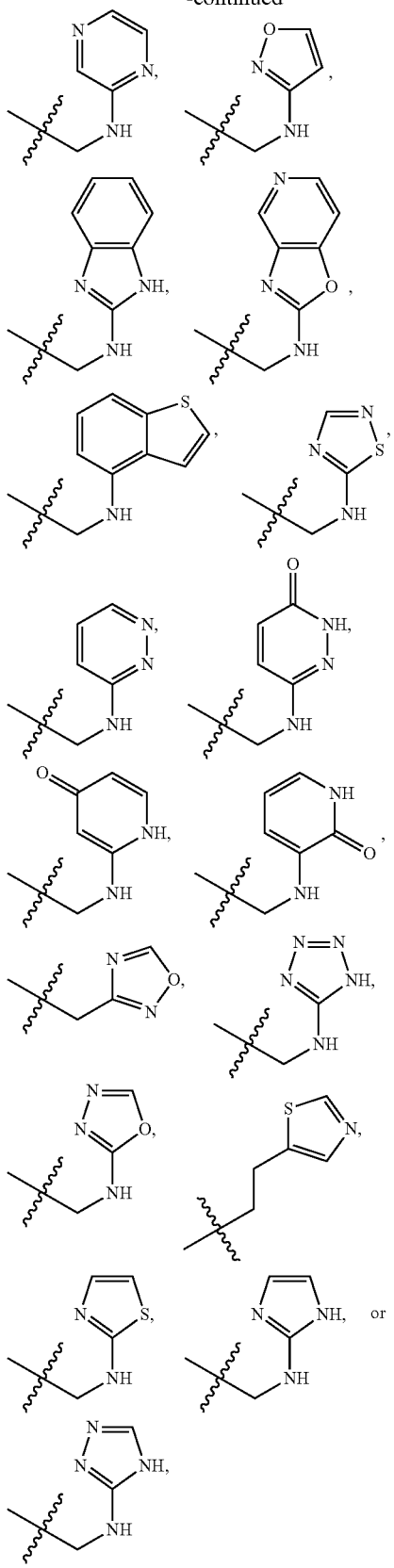
wherein any one of the Formulae is optionally substituted with one or more $R_8$.
7. The compound of claim 1, wherein:
$R_6$ is $(C_1-C_3)$alkyl, $(C_2-C_3)$alkenyl, $(C_1-C_3)$haloalkyl, —$CH_2NHC(NH)NH_2$, —$(CH_2)_nOH$, —$CH_2S(O)_pNH_2$, —$CH_2NH(C_1-C_3)$alkyl, —$CH_2C(O)NH_2$, —$(CH_2)_nNH_2$,
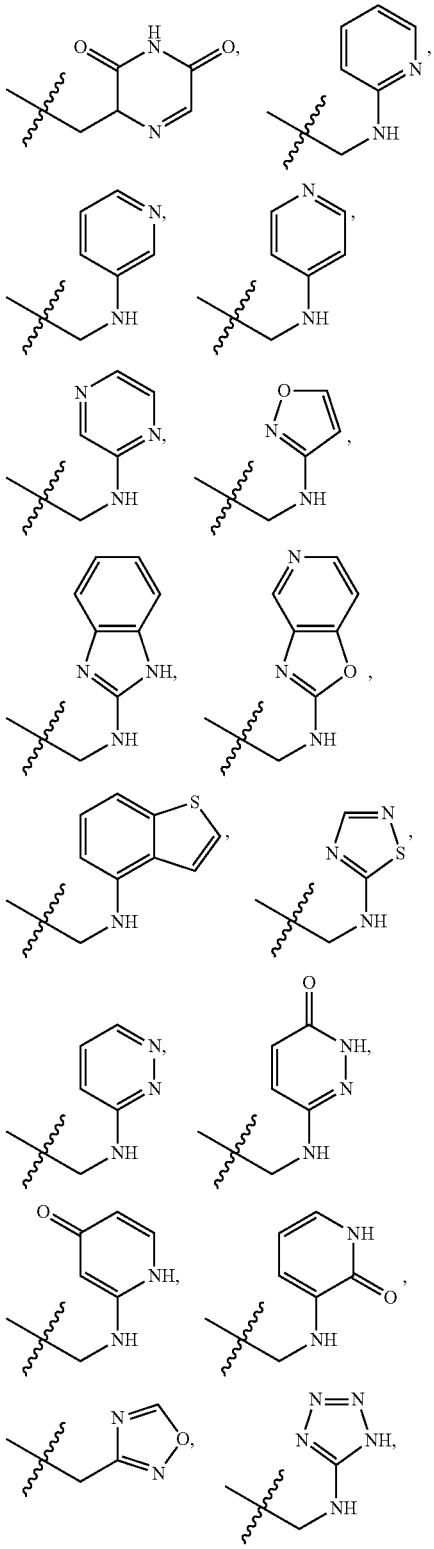

-continued

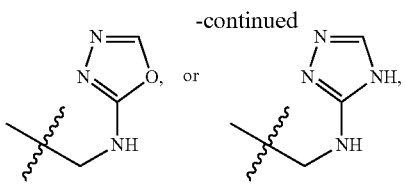

wherein the heteroaryl and heterocycloalkyl are optionally substituted with one or more $R_8$; and provided that when Z is NH, X is —$CH_2NHC(NH)NH_2$ or —$CH_2NH_2$, $R_1$ is H, $R_3$ is H, $R_4$ is H, then $R_6$ is not ($C_1$-$C_3$)alkyl or ($C_2$-$C_3$)alkenyl.

8. The compound of claim 1, wherein:
$R_6$ is

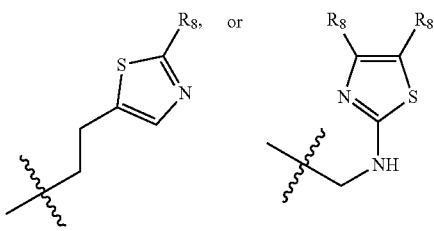

and provided that when Z is NH, X is —$CH_2NHC(NH)NH_2$ or —$CH_2NH_2$, $R_1$ is H, $R_3$ is H, $R_4$ is H, then $R_6$ is not ($C_1$-$C_3$)alkyl or ($C_2$-$C_3$)alkenyl.

9. The compound of claim 1, wherein:
X is —$CH_2NHCH_2C(O)CH_3$, —$CH_2NHC(NH)(C_1$-$C_4)$ alkyl, —$CH_2NHC(NH)(C_3$-$C_7)$cycloalkyl, —$CH_2NHC(NH)$heteroaryl, heteroaryl, —$NHCH_2$heteroaryl, —$CH_2NH$heteroaryl, —$CH(OH)$ heteroaryl, —$CH_2$heterocycloalkyl, —$NHCH_2$heterocycloalkyl, or —$CH_2NH$heterocycloalkyl, wherein the ($C_1$-$C_4$)alkyl, cycloalkyl, heterocycloalkyl and heteroaryl are optionally substituted with one or more $R_7$;
$R_1$ is H;
$R_3$ is H;
$R_4$ is H;
$R_5$ and $R_6$ together with the carbon atoms to which they are attached and the Z atom connecting said two carbon atoms, form a ($C_5$-$C_6$)cycloalkyl or a 5- to 6-membered heterocycloalkyl ring containing 1-3 heteroatoms optionally substituted with one or more $R_9$;
provided that when Z is NH, $R_1$ is H, $R_2$ is H, $R_3$ is H and $R_4$ is H, then X is not —$CH_2NHC(NH)CH_3$.

10. The compound of claim 1, wherein:
X is —$CH_2NHCH_2C(O)CH_3$, —$CH_2NHC(NH)(C_1$-$C_4)$ alkyl, —$CH_2NHC(NH)(C_3$-$C_7)$cycloalkyl, —$CH_2NHC(NH)$heteroaryl, or —$CH(OH)$heteroaryl, wherein the ($C_1$-$C_4$)alkyl, cycloalkyl, and heteroaryl are optionally substituted with one or more $R_7$;
$R_1$ is H;
$R_3$ is H;
$R_4$ is H;
$R_5$ and $R_6$ together with the carbon atoms to which they are attached and the Z atom connecting said two carbon atoms, form a ($C_5$-$C_6$)cycloalkyl or a 5- to 6-membered heterocycloalkyl ring containing 1-3 heteroatoms optionally substituted with one or more $R_9$; and provided that when Z is NH, $R_1$ is H, $R_2$ is H, $R_3$ is H and $R_4$ is H, then X is not —$CH_2NHC(NH)CH_3$.

11. The compound of claim 1, wherein:
X is —$CH_2NHCH_2C(O)CH_3$, —$CH_2NHC(NH)(C_1$-$C_4)$ alkyl, —$CH_2NHC(NH)(C_1$-$C_4)$haloalkyl, —$CH_2NHC(NH)(C_3$-$C_7)$cycloalkyl, or a group selected from:

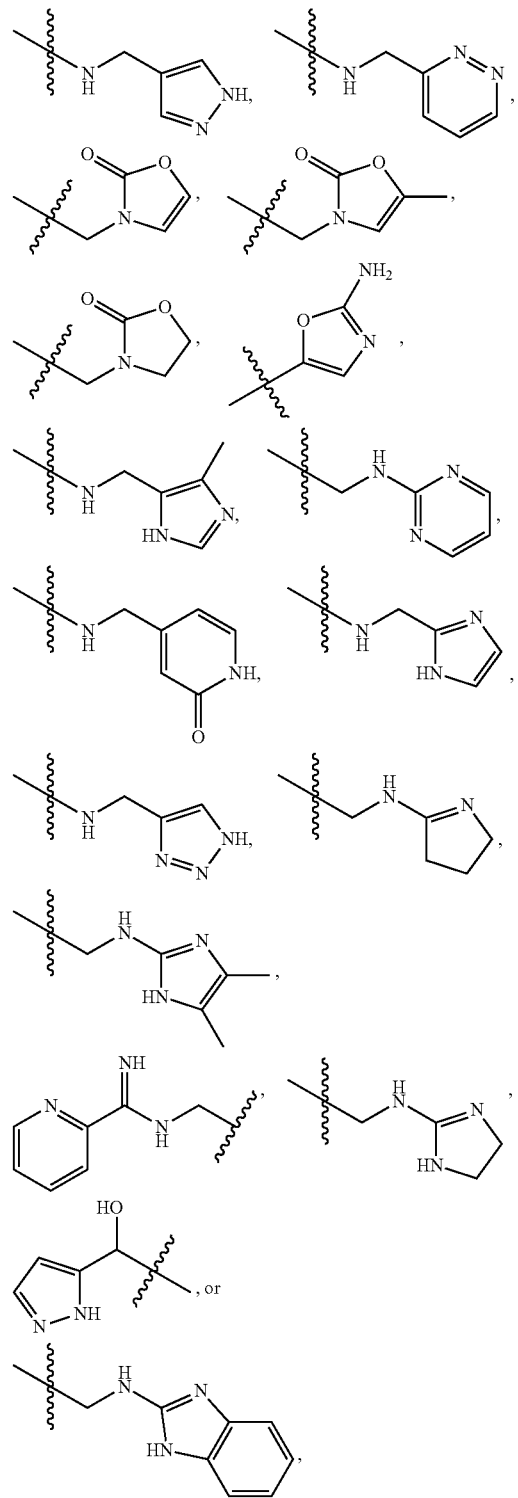

wherein the $(C_1-C_4)$alkyl, cycloalkyl, and any one of the above structures are optionally substituted with one or more $R_7$.

12. The compound of claim 1, wherein
when Z is NH and X is —NHC(NH)NH$_2$, —CH$_2$NHC(NH)NH$_2$, or —CH$_2$NH$_2$,
then $R_5$ and $R_6$ do not from a ring of Formula:

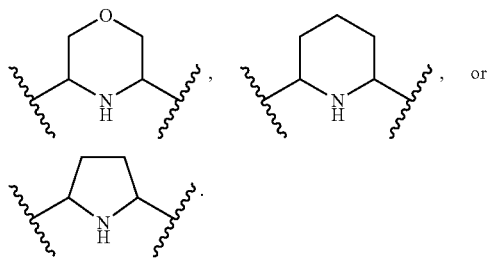

13. The compound of claim 11, wherein the compound is not:

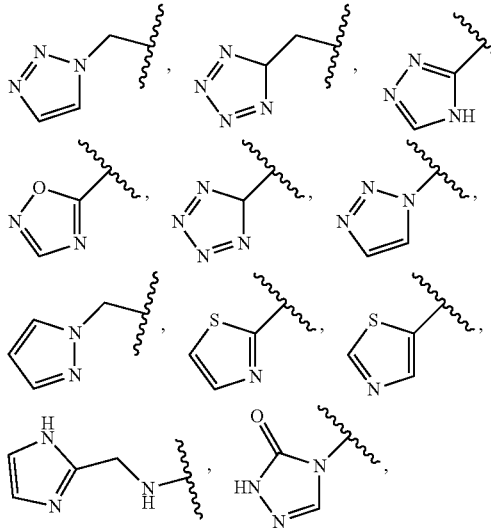

14. The compound of claim 1, wherein
when Z is NH and X is any one of the following Formulae:

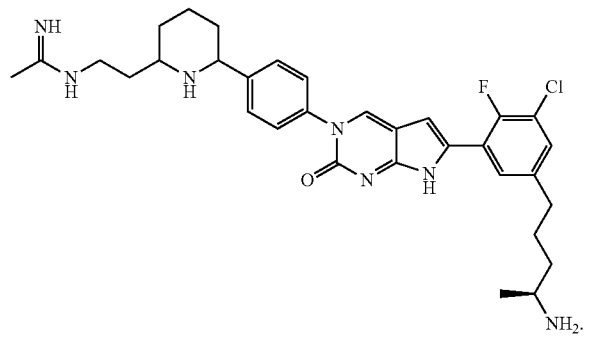

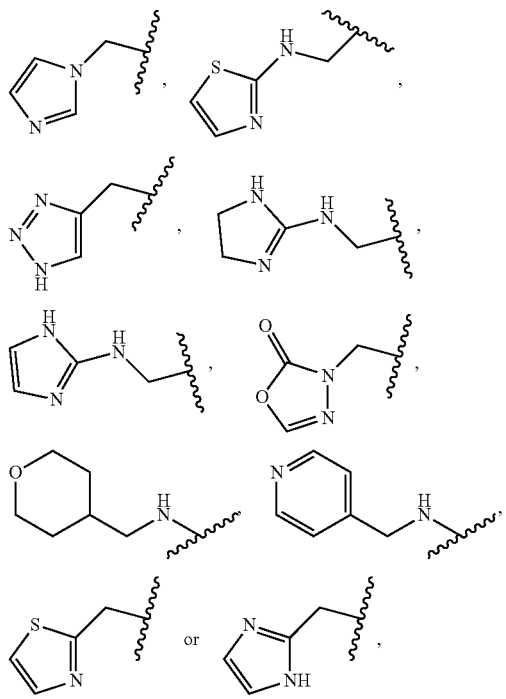

then $R_5$ and $R_6$ do not from a ring of Formula:

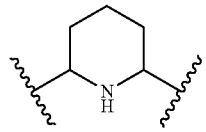

15. The compound of claim 1, wherein:
$R_5$ and $R_6$ form a ring of Formula:

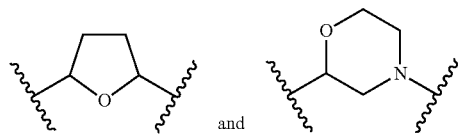

and

16. The compound of claim 1, wherein:
X is

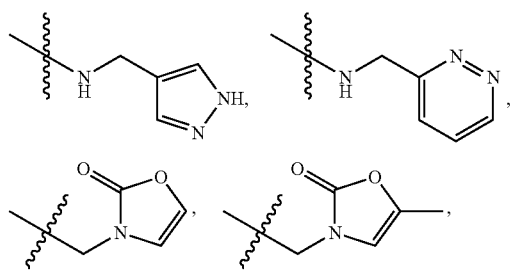

-continued

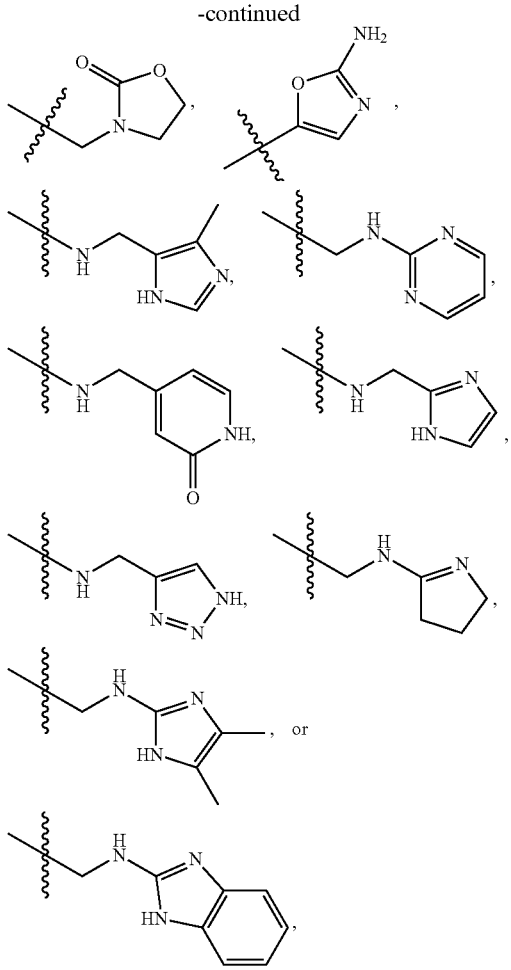

wherein each heterocycloalkyl and heteroaryl in the above structures is optionally substituted with one or more $R_7$;

$R_1$ is H;

$R_3$ is H;

$R_4$ is H;

$R_5$ and $R_6$ together with the carbon atoms to which they are attached and the Z atom connecting said two carbon atoms, form a $(C_5$-$C_6)$cycloalkyl or a 5- to 6-membered heterocycloalkyl ring containing 1-3 heteroatoms optionally substituted with one or more $R_9$; and provided that when Z is NH, $R_1$ is H, $R_2$ is H, $R_3$ is H and $R_4$ is H, then X is not —$CH_2NHC(NH)CH_3$.

17. The compound of claim 1, wherein

Z is O;

W is $CH_2$; and $R_6$ is $(C_1$-$C_3)$alkyl, $(C_2$-$C_3)$alkenyl, $(C_1$-$C_3)$haloalkyl, —$(CH_2)_n$OH, —$CH_2NHC(NH)NH_2$, $CH_2NH_2$, $CH_2NH$heteroaryl, or —$CH_2NHC(=NH)$ $(C_1$-$C_3)$alkyl.

18. The compound of claim 1, wherein

Z is O;

W is $CH_2$; and $R_6$ is $CH_3$, —$CH=CH_2$, $CH_2F$, —$CH_2NHC(NH)NH_2$, —$CH_2NHC(=NH)CH_3$, —$CH_2OH$, or —$CH_2NH_2$.

19. The compound of claim 17, wherein when X is —$CH_2NHC(NH)NH_2$, then $R_6$ is not a group of Formula:

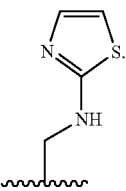

20. The compound of claim 1, wherein:

Z is O;

$R_6$ is H, $(C_1$-$C_3)$alkyl, $(C_2$-$C_3)$alkenyl, $(C_1$-$C_3)$haloalkyl, —$CH_2NHC(NH)NH_2$, —$(CH_2)_n$OH, —$CH_2S(O)_pNH_2$, —$CH_2NH(C_1$-$C_3)$alkyl, —$CH_2C(O)NH_2$, —$(CH_2)_nNH_2$, —$CH_2$heterocycloalkyl, —$CH_2NH_2$heterocycloalkyl, —$(CH_2)_n$heteroaryl, or —$CH_2NH_2$heteroaryl, wherein the heteroaryl and heterocycloalkyl is optionally substituted with one or more $R_8$; and at least one of $R_5$ and $R_6$ is not H.

21. The compound of claim 1, wherein:

Z is $CH_2$;

$R_6$ is H, $(C_1$-$C_3)$alkyl, $(C_2$-$C_3)$alkenyl, $(C_1$-$C_3)$haloalkyl, —$CH_2NHC(NH)NH_2$, —$(CH_2)_n$OH, —$CH_2S(O)_pNH_2$, —$CH_2NH(C_1$-$C_3)$alkyl, —$CH_2C(O)NH_2$, —$(CH_2)_nNH_2$, —$CH_2$heterocycloalkyl, —$CH_2NH_2$heterocycloalkyl, $(CH_2)_n$heteroaryl, or —$CH_2NH_2$heteroaryl, wherein the heteroaryl and heterocycloalkyl is optionally substituted with one or more $R_8$; and at least one of $R_5$ and $R_6$ is not H.

22. The compound of claim 1, wherein:

Z is NH;

$R_6$ is H, $(C_1$-$C_3)$alkyl, $(C_2$-$C_3)$alkenyl, $(C_1$-$C_3)$haloalkyl, —$CH_2NHC(NH)NH_2$, —$(CH_2)_n$OH, —$CH_2S(O)_pNH_2$, —$CH_2NH(C_1$-$C_3)$alkyl, —$CH_2C(O)NH_2$, —$(CH_2)_nNH_2$, —$CH_2$heterocycloalkyl, —$CH_2NH_2$heterocycloalkyl, —$(CH_2)_n$heteroaryl, or —$CH_2NH_2$heteroaryl, wherein the heteroaryl and heterocycloalkyl is optionally substituted with one or more $R_8$;

at least one of $R_5$ and $R_6$ is not H; and provided that when X is —$CH_2NHC(NH)NH_2$ or —$CH_2NH_2$, $R_1$ is H, $R_3$ is H, $R_4$ is H, then $R_6$ is not H, $(C_1$-$C_3)$alkyl or $(C_2$-$C_3)$alkenyl.

23. The compound of claim 1, wherein:

X is —$CH_2NH_2$ or —$CH_2NHC(NH)NH_2$;

Z is NH;

$R_1$ is H or —$NO_2$;

$R_2$ is —Cl or —$OCF_3$;

$R_3$ is H or —$NO_2$;

$R_4$ is —$NO_2$;

$R_5$ is H or —$CH_3$;

and $R_6$ is H.

24. The compound of claim 1, wherein X is —NHC(NH)$NH_2$, —$CH_2NH_2$, or —$CH_2NHC(NH)NH_2$.

25. The compound of claim 1, wherein X is —$CH_2NHCH_2C(O)CH_3$, —$CH_2NHC(NH)(C_1$-$C_4)$alkyl, —$CH_2NHC(NH)(C_3$-$C_7)$cycloalkyl, or —$CH_2NHC(NH)$heteroaryl, wherein the $(C_1$-$C_4)$alkyl, cycloalkyl, and heteroaryl optionally substituted with one or more $R_7$.

26. The compound of claim 1, wherein X is —CH(OH) heteroaryl optionally substituted with one or more $R_7$.

27. The compound of claim 1, wherein X is

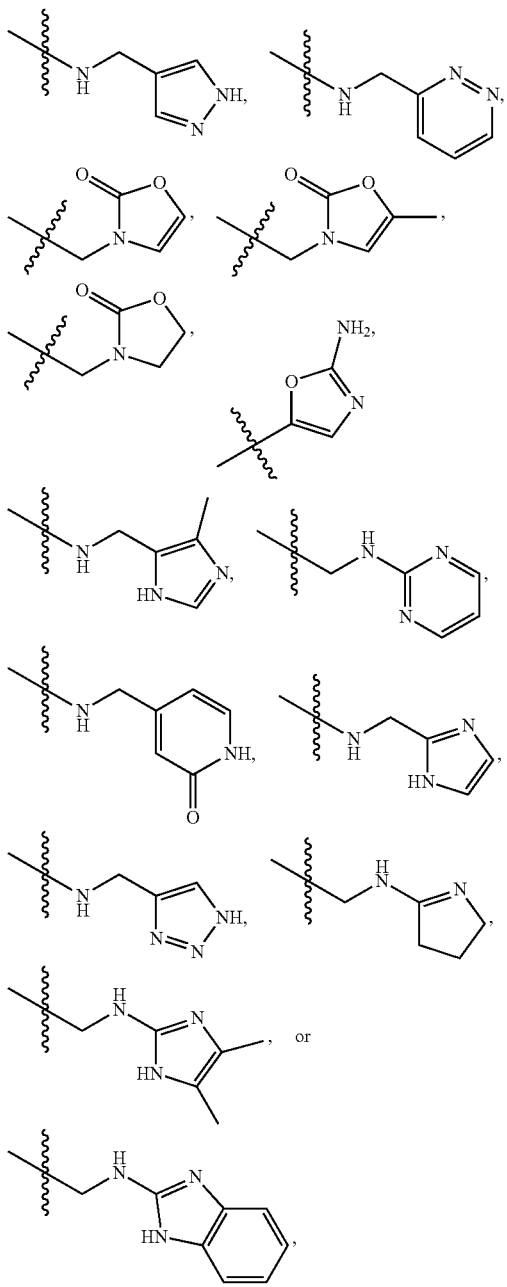

wherein each is optionally substituted with one or more $R_7$.

28. The compound of claim 1, wherein $R_2$ is —Cl.
29. The compound of claim 1, wherein $R_1$ is H, $R_3$ is H and $R_4$ is H.
30. The compound of claim 1, wherein Z is NH.
31. The compound of claim 1, wherein Z is O.
32. The compound of claim 1, wherein Z is $CH_2$.
33. The compound of claim 1, wherein $R_5$ is H.
34. The compound of claim 1, wherein W is $NR_5$.
35. The compound of claim 1, wherein W is $CHR_5$.
36. The compound of claim 1, wherein $R_6$ is $(C_1$-$C_3)$alkyl, $(C_2$-$C_3)$alkenyl, or $(C_1$-$C_3)$haloalkyl.

37. The compound of claim 1, wherein $R_6$ is $(C_1$-$C_3)$alkyl, $(C_2$-$C_3)$alkenyl, or $(C_1$-$C_3)$haloalkyl and X is —$CH_2NHCH_2C(O)CH_3$, —$CH_2NHC(NH)(C_1$-$C_4)$alkyl, —$CH_2NHC(NH)(C_3$-$C_7)$cycloalkyl, or —$CH_2NHC(NH)$ heteroaryl, or —CH(OH)heteroaryl, wherein the $(C_1$-$C_4)$ alkyl, cycloalkyl and heteroaryl is optionally substituted with one or more $R_7$.

38. The compound of claim 1, wherein $R_6$ is —$CH_2NHC(NH)NH_2$, —$(CH_2)_nOH$, —$CH_2S(O)_pNH_2$, —$CH_2NH(C_1$-$C_3)$alkyl, —$CH_2C(O)NH_2$, or —$(CH_2)_nNH_2$.

39. The compound of claim 1, wherein $R_6$ is

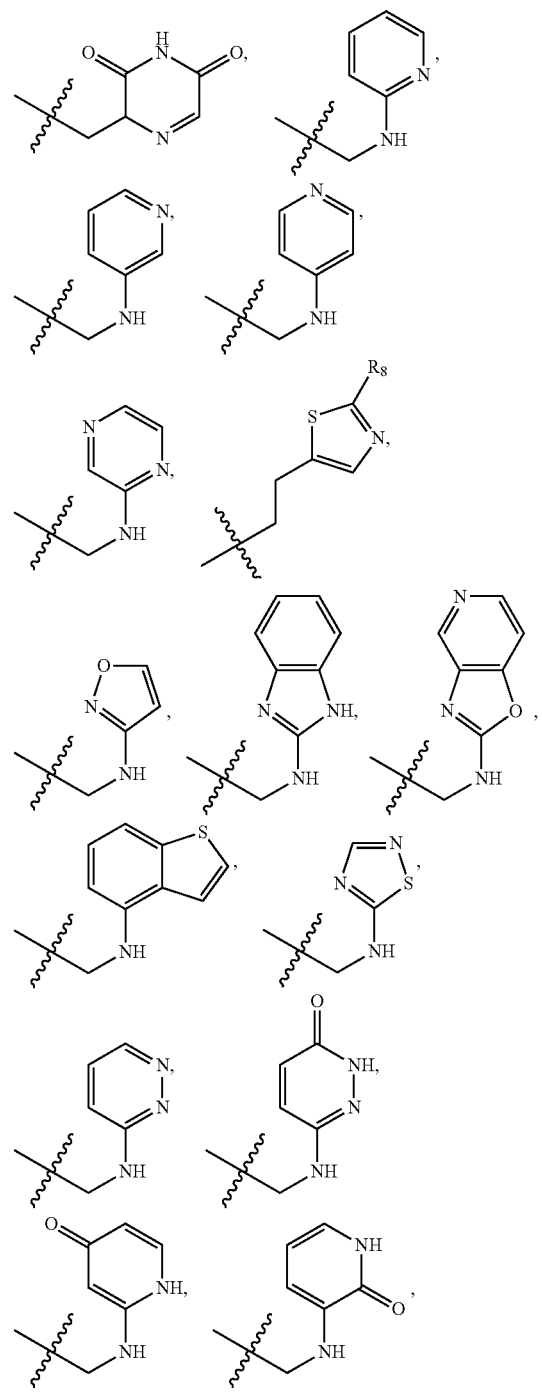

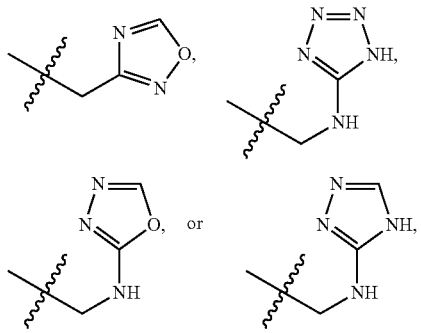
wherein each heteroaryl and heterocycloalkyl is optionally substituted with one or more $R_8$.
40. The compound of claim 1, wherein $R_6$ is
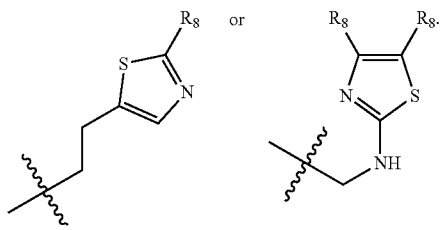
41. The compound of claim 1 having any one of the following Formulae:
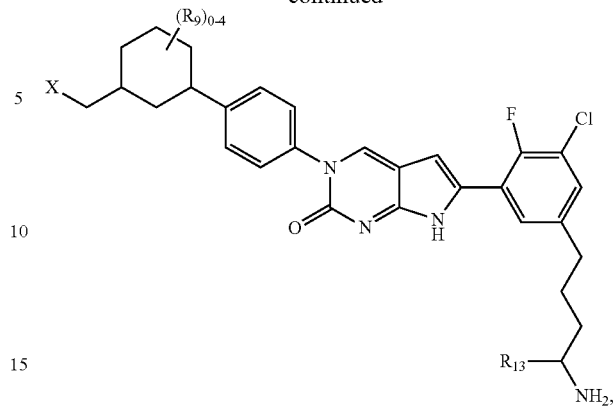
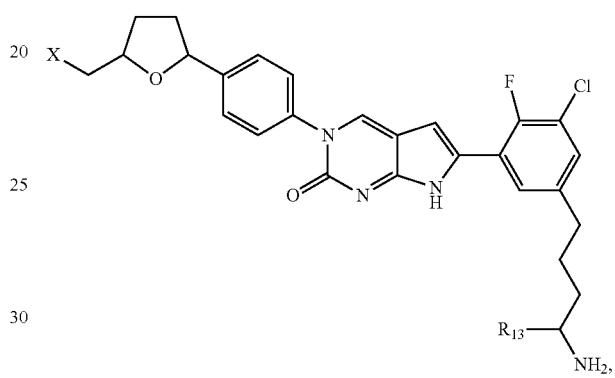
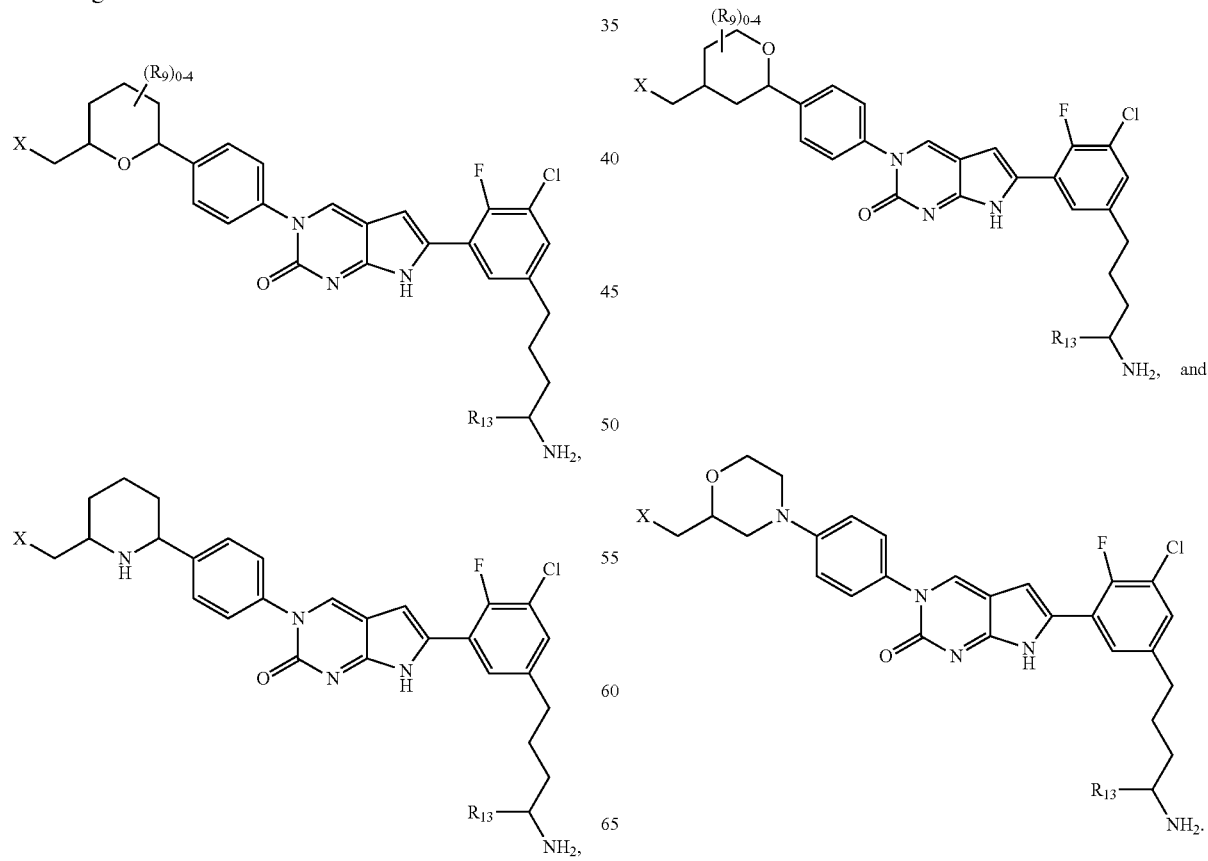

42. The compound of claim 1, wherein the compound of Formula A is selected from any one of compounds 1, 3-76, 78, 81-89, 91, 92, 96, 97, 106, 107, 109-111, 119, 120, 127, 128, 132-135, 137, 138, 143, 150, 151, and 153:
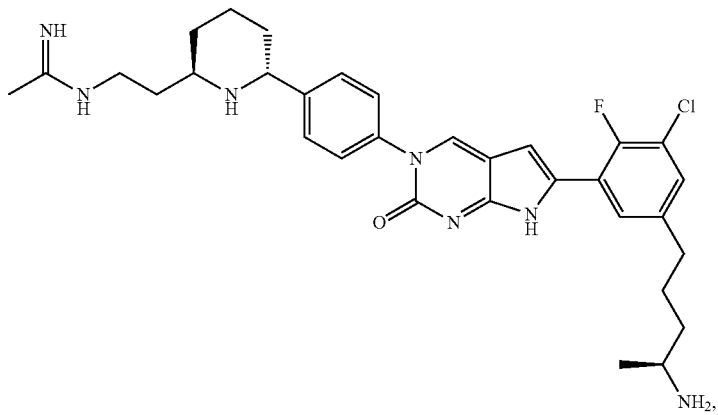
1
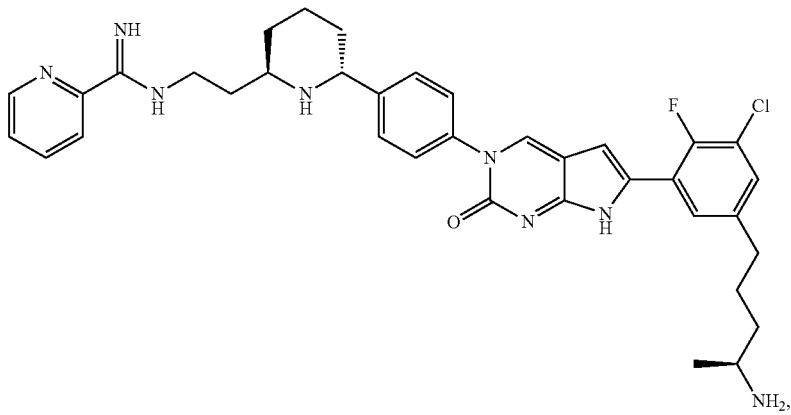
3
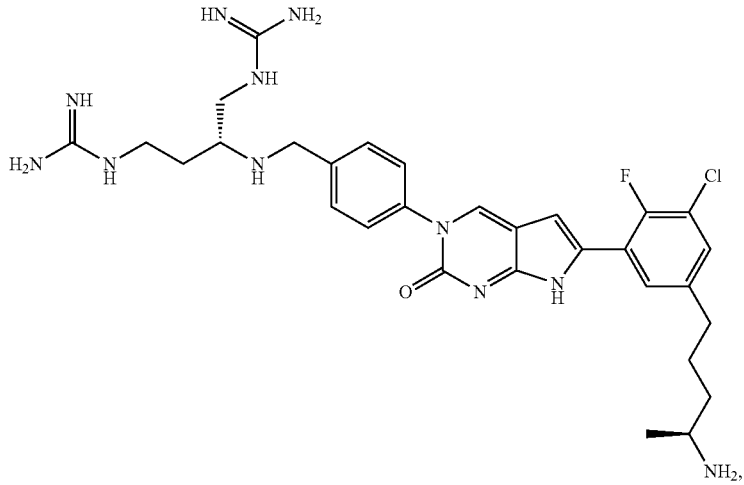
4

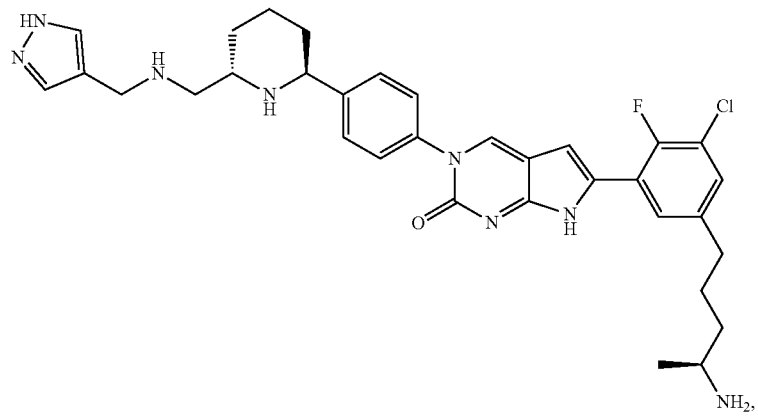
5
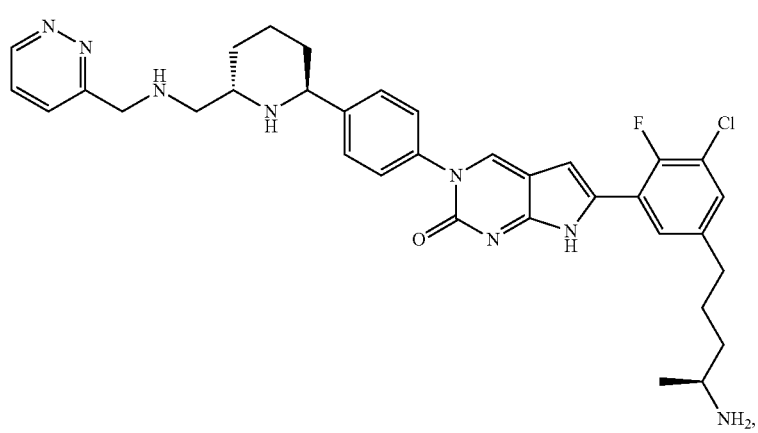
6
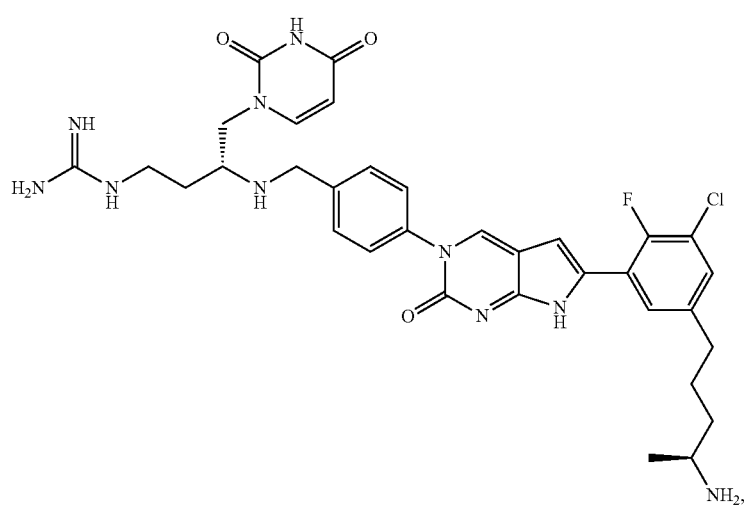
7

8
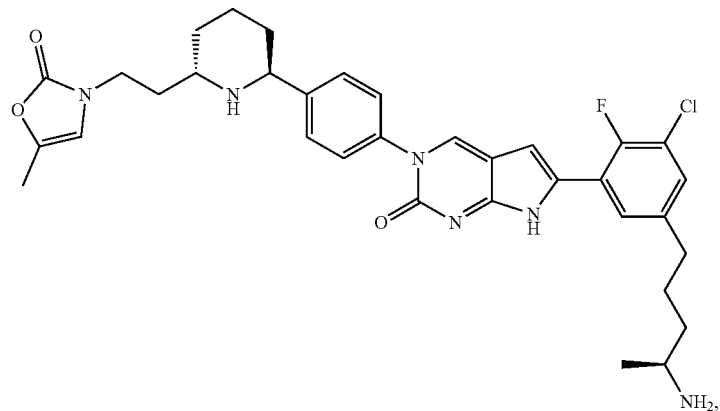
9
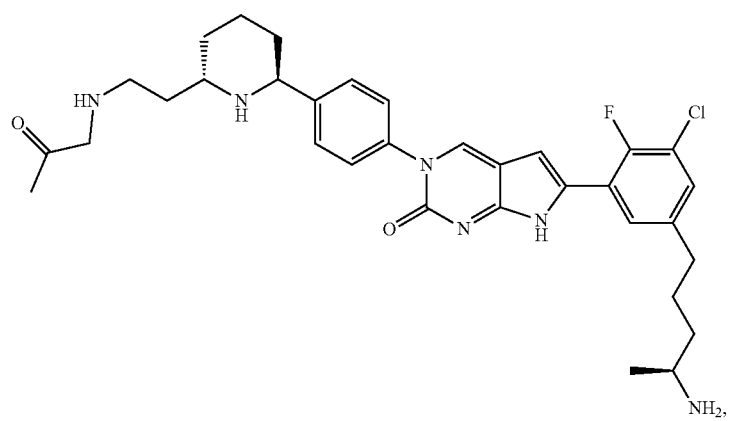
10
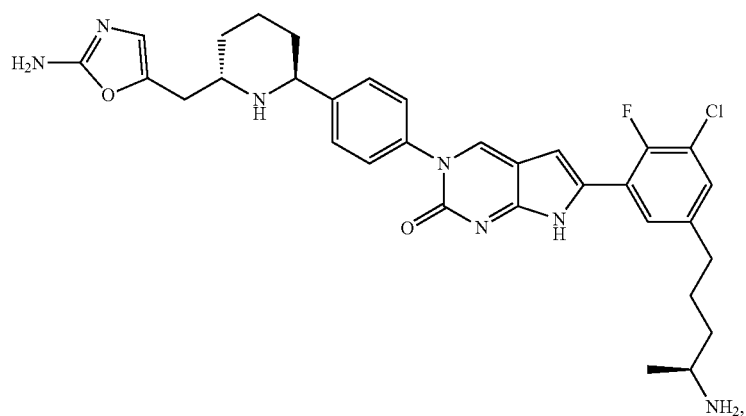
11
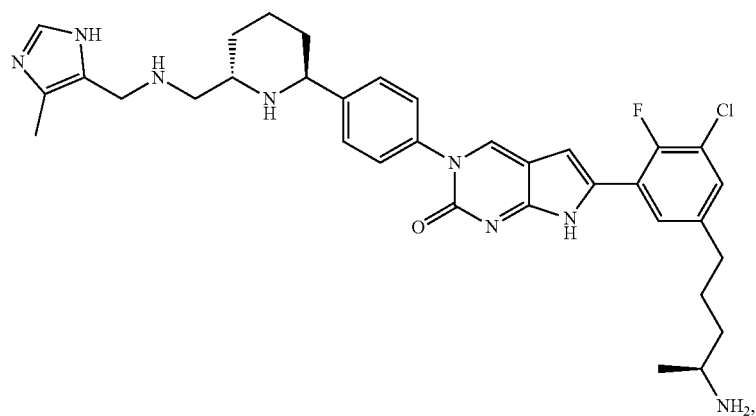

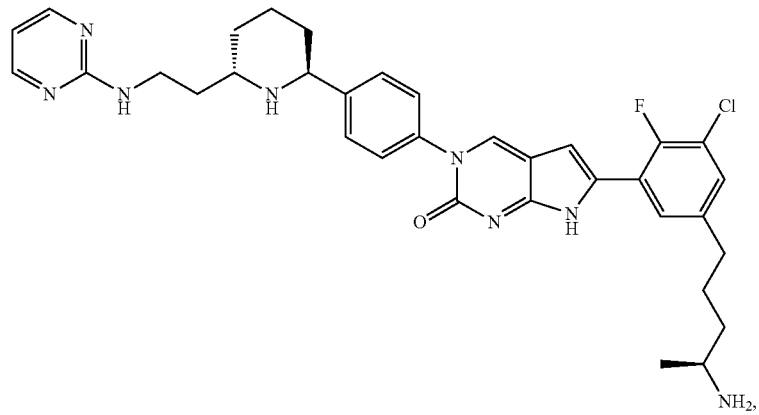
12
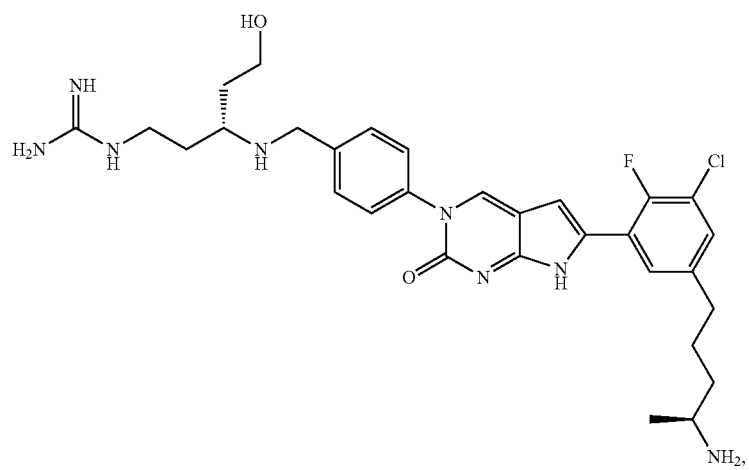
13
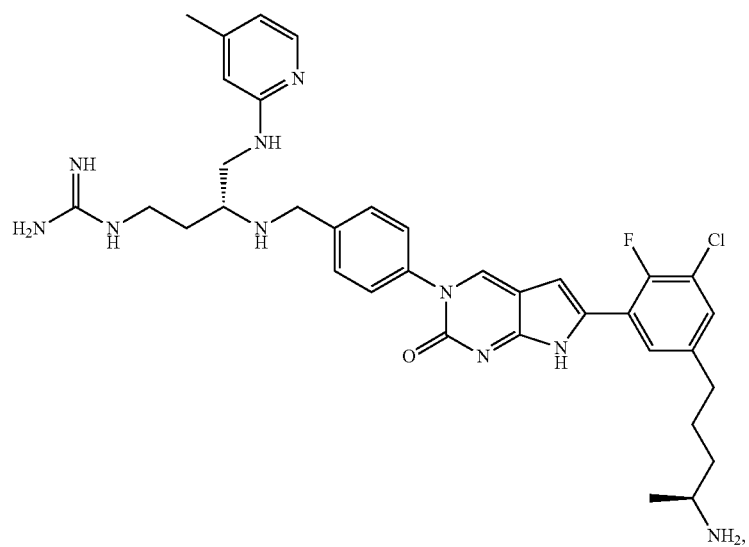
14

-continued
15
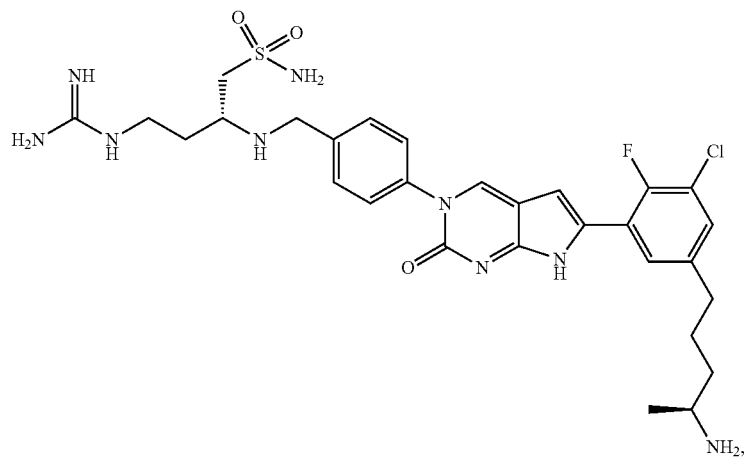
16
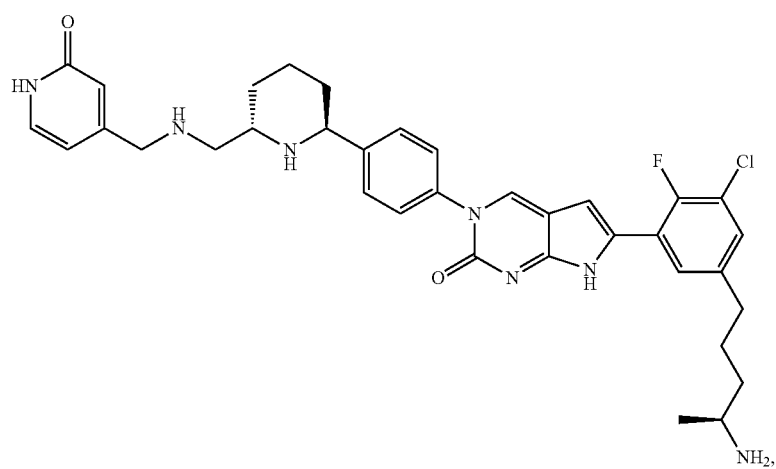
17
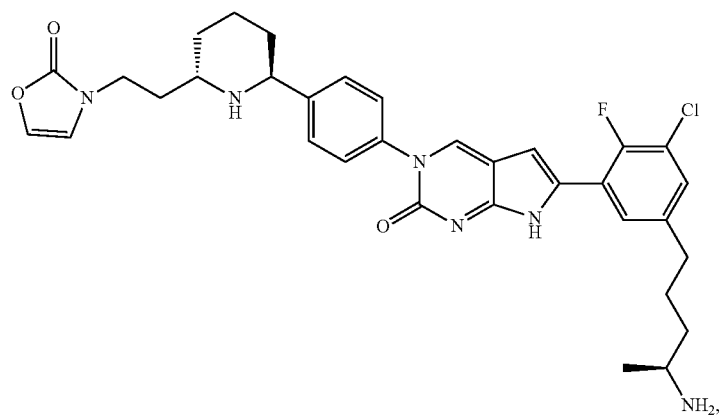

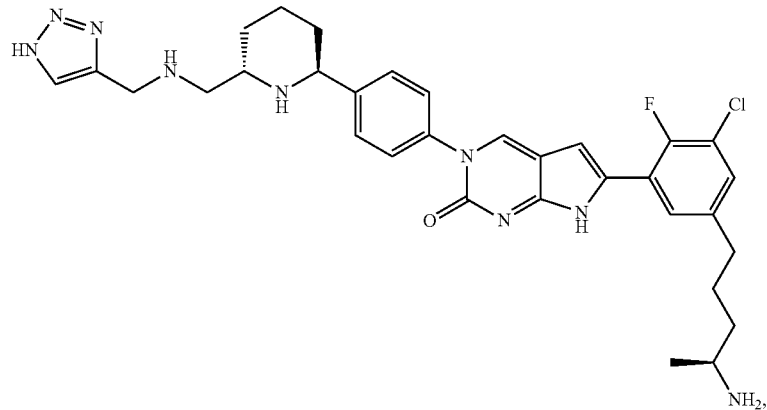
18
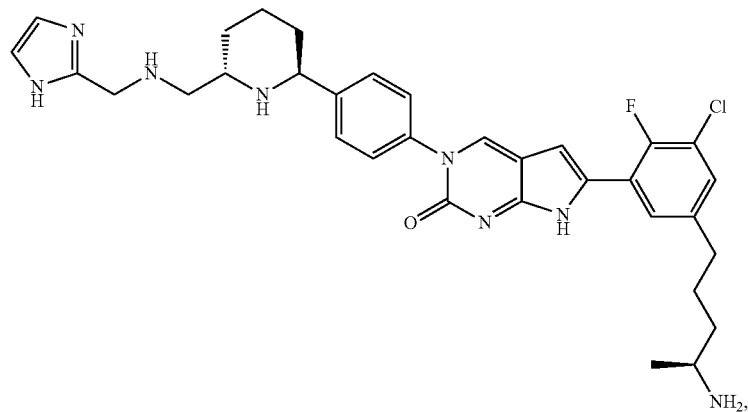
19
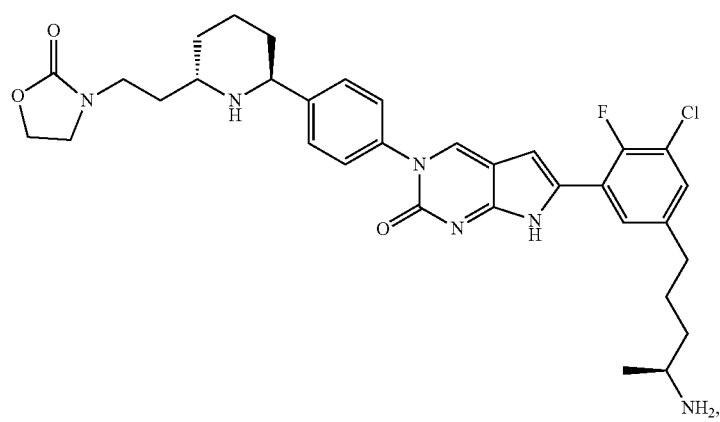
20

21
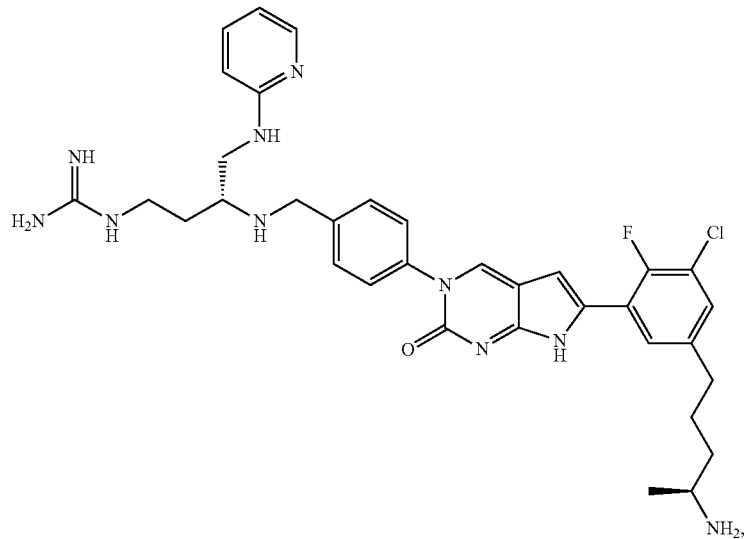
22
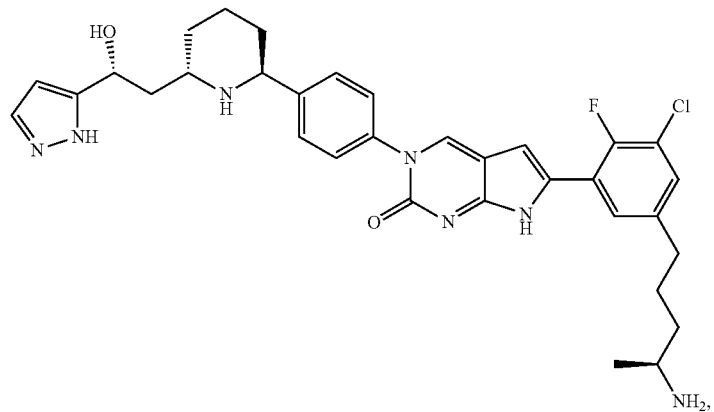
23
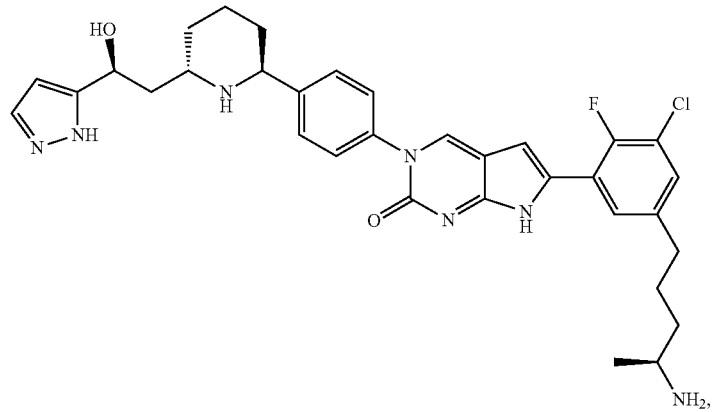

24
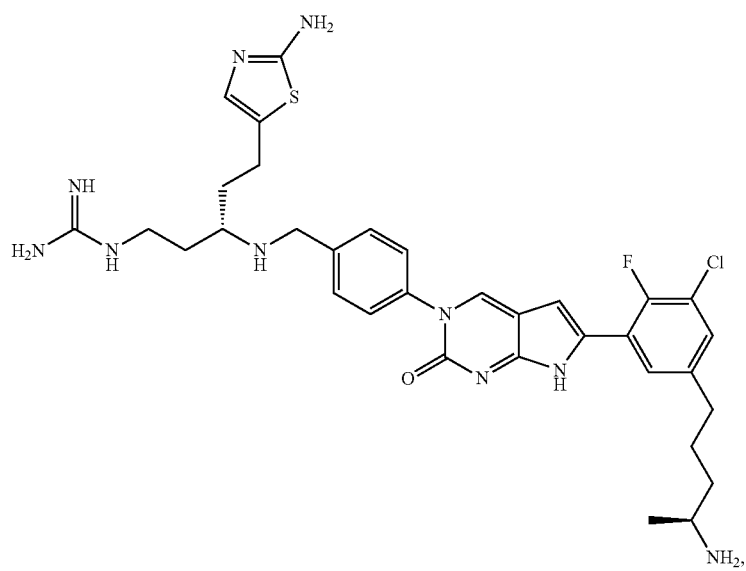
25
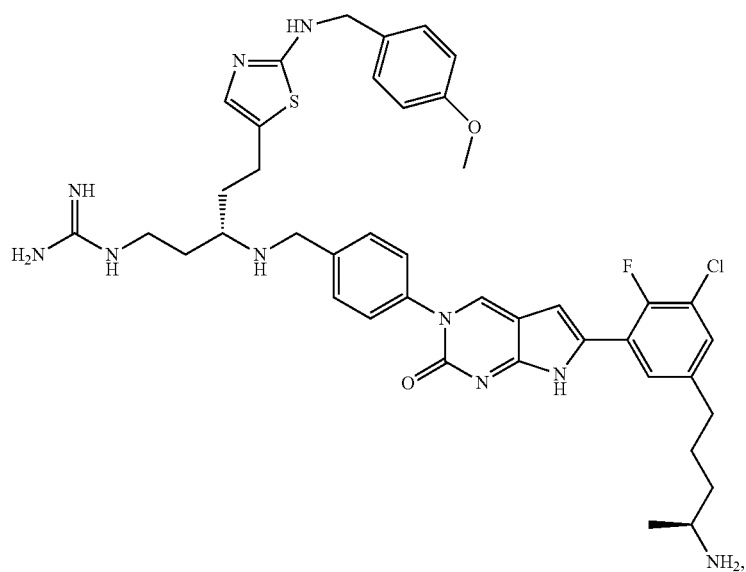
26
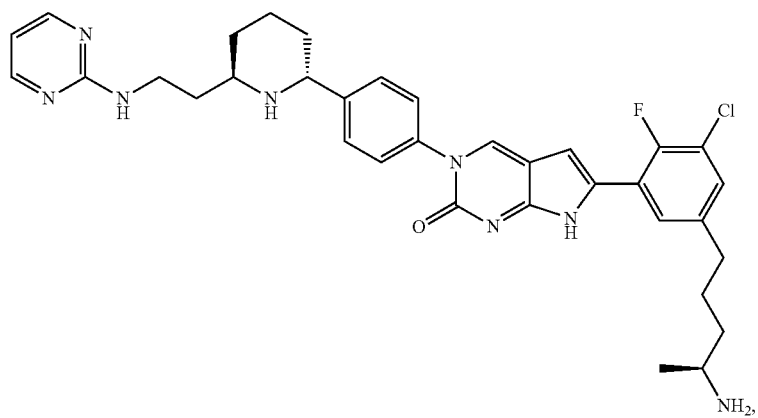

27
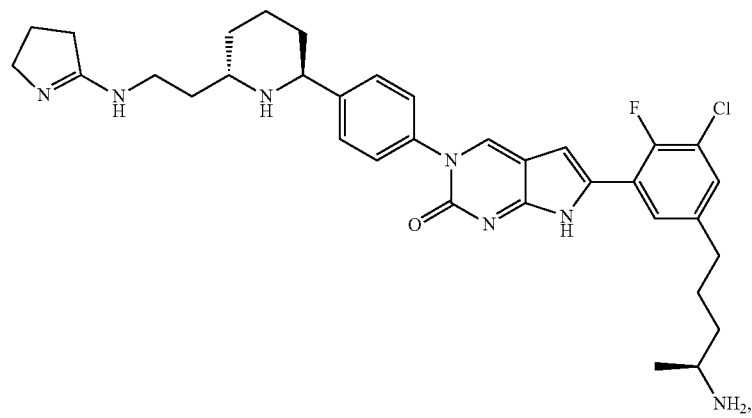
28
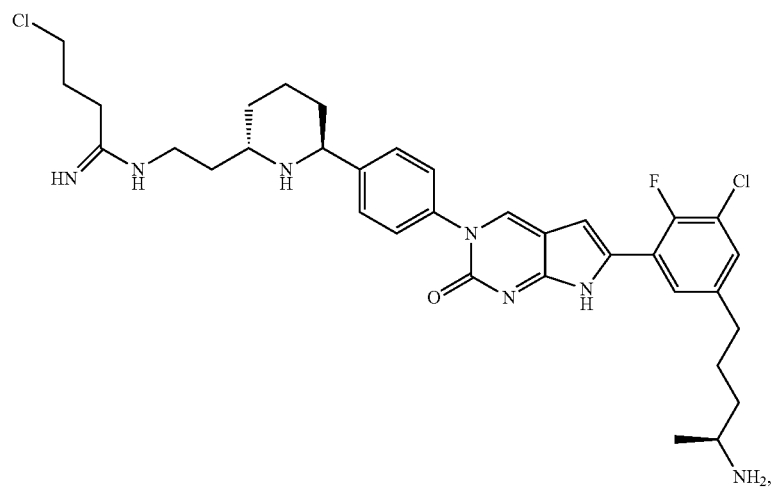
29
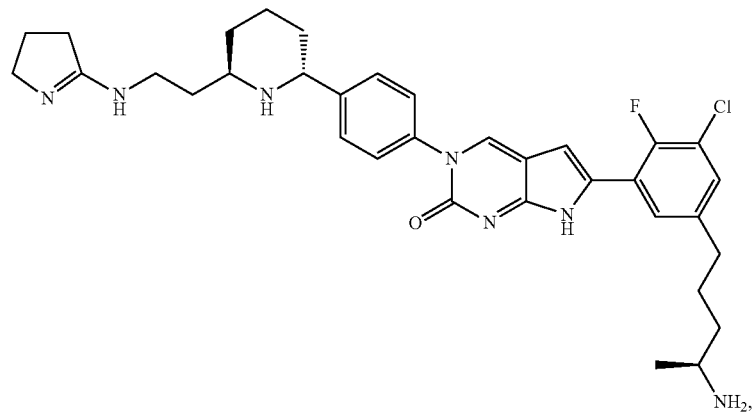

-continued
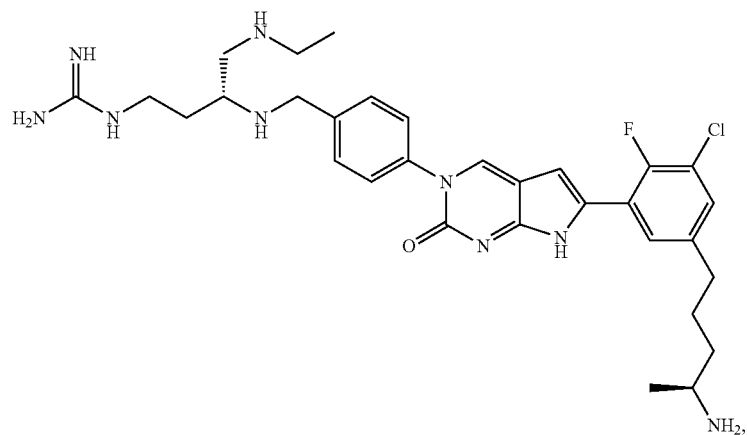
30
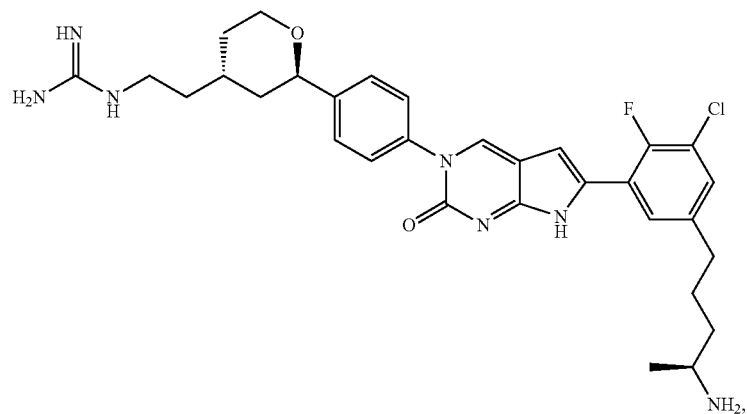
31
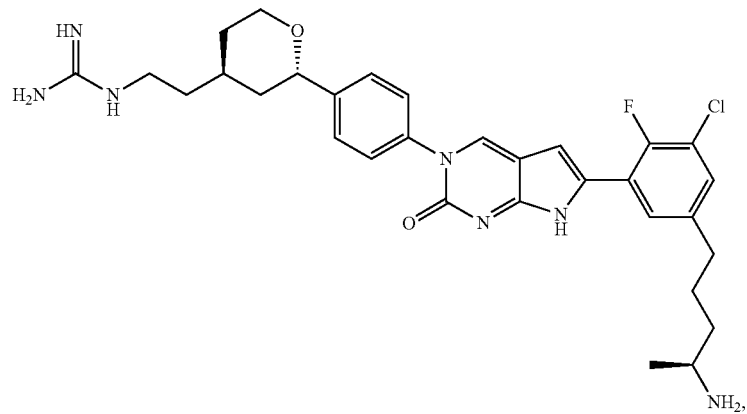
32

-continued
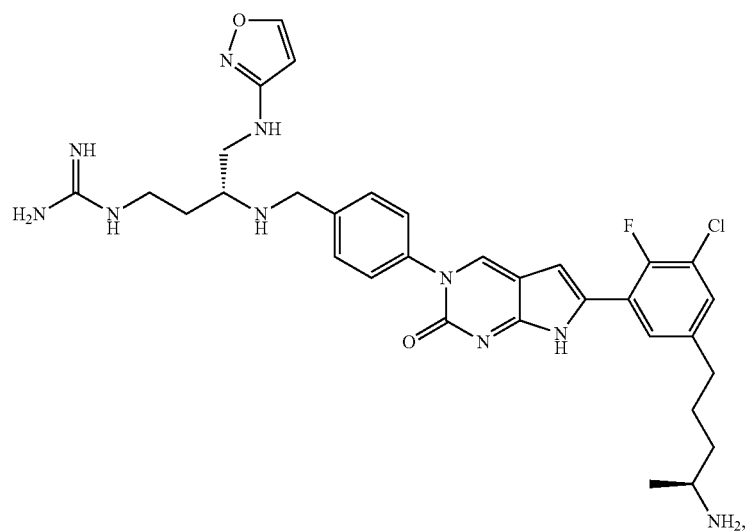
33
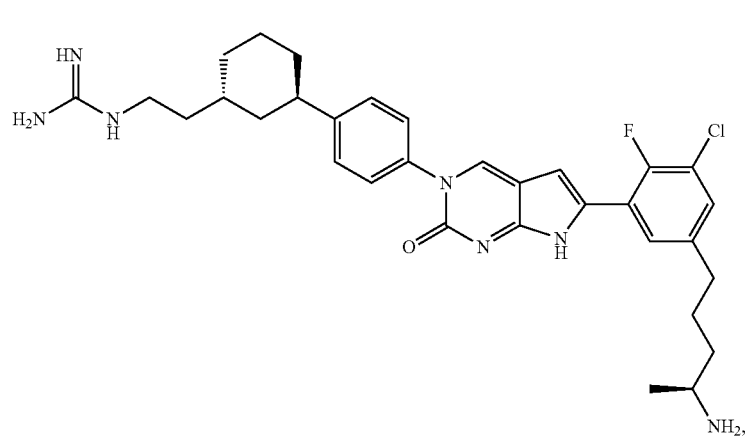
34
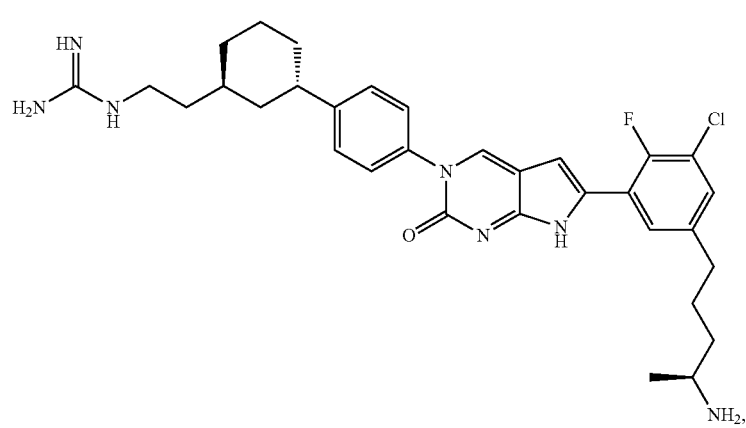
35

36
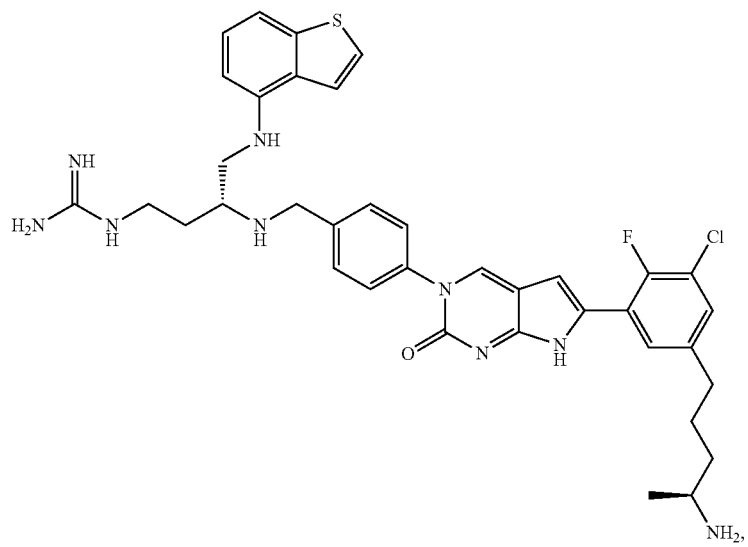
37
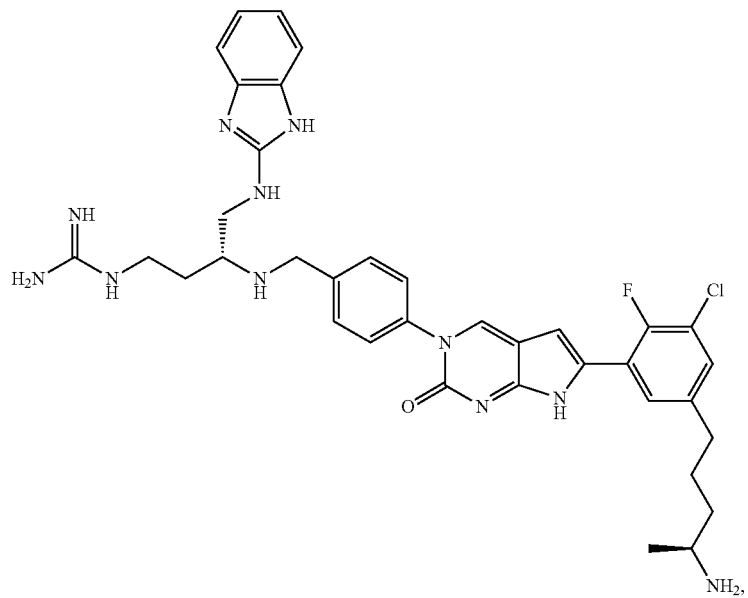
38
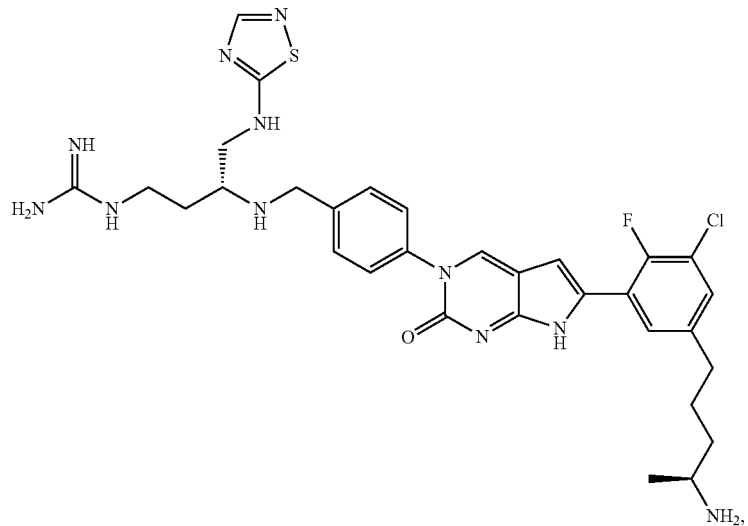

39
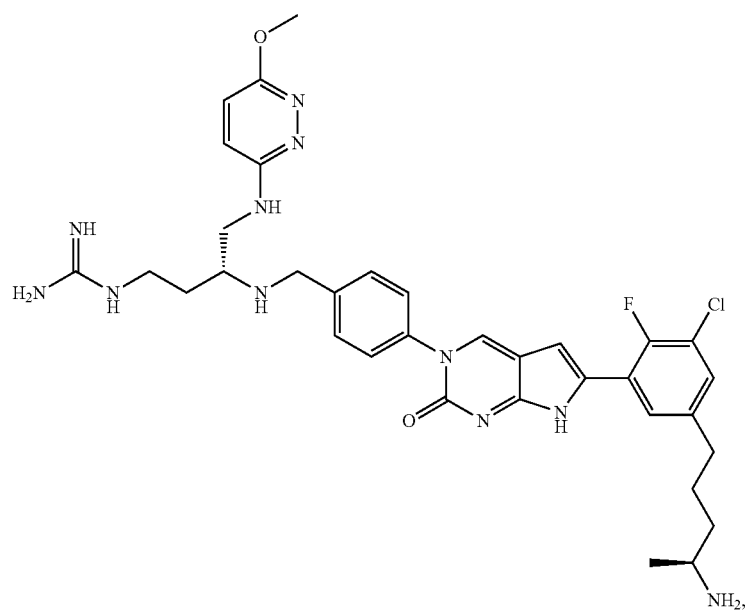
40
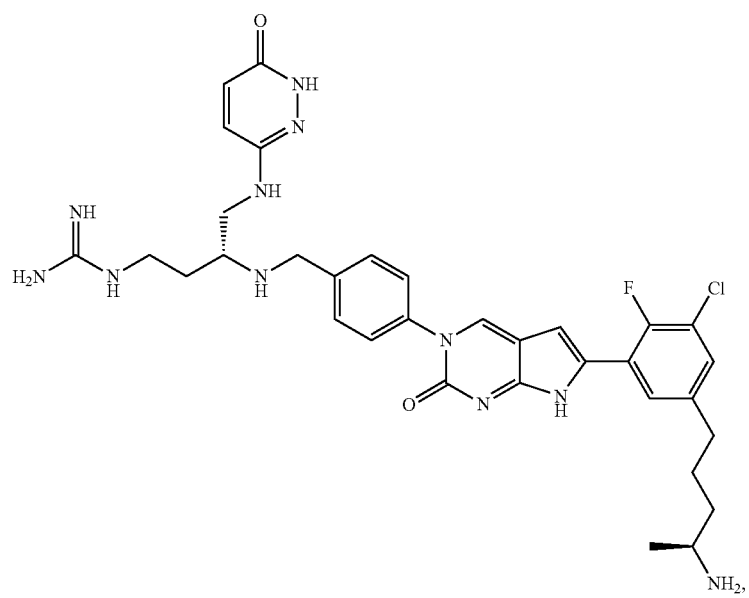
41
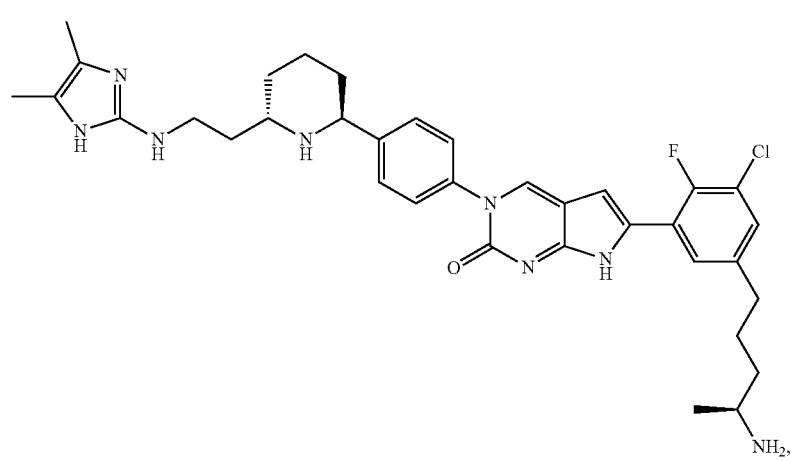

42
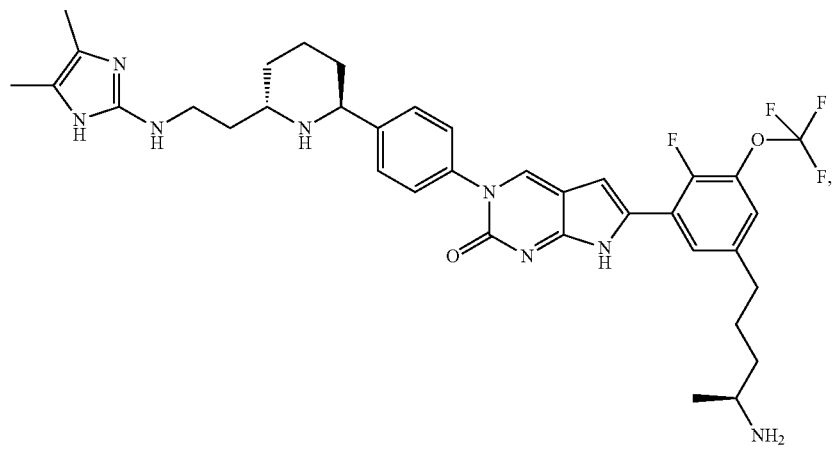
43
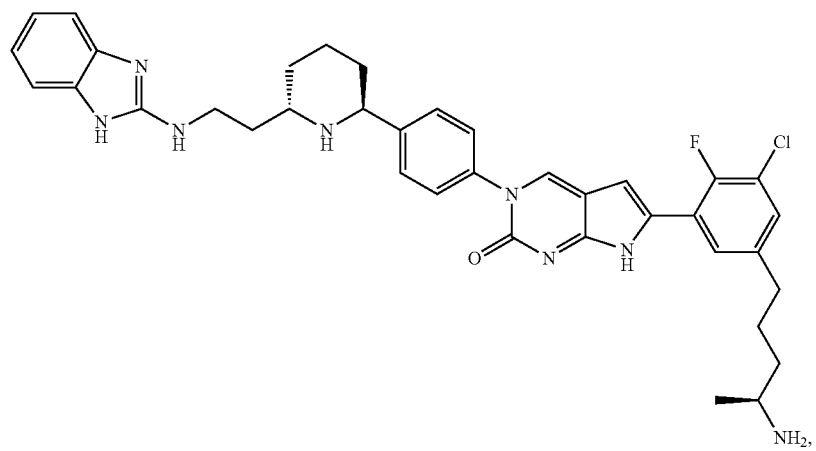
44
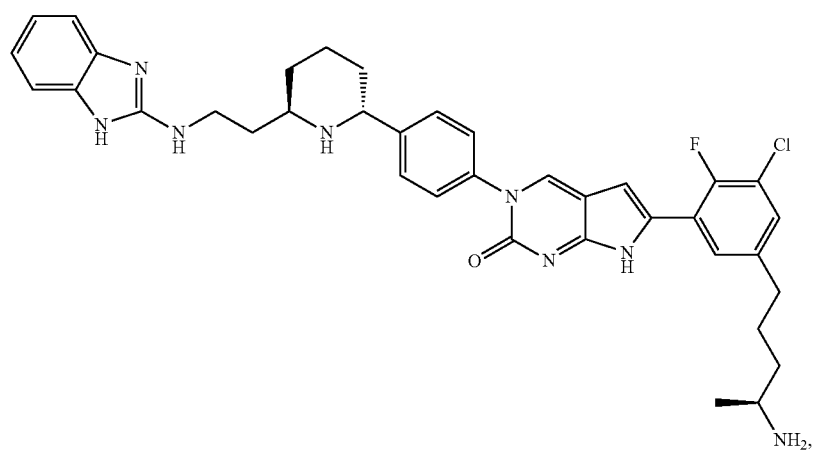

45
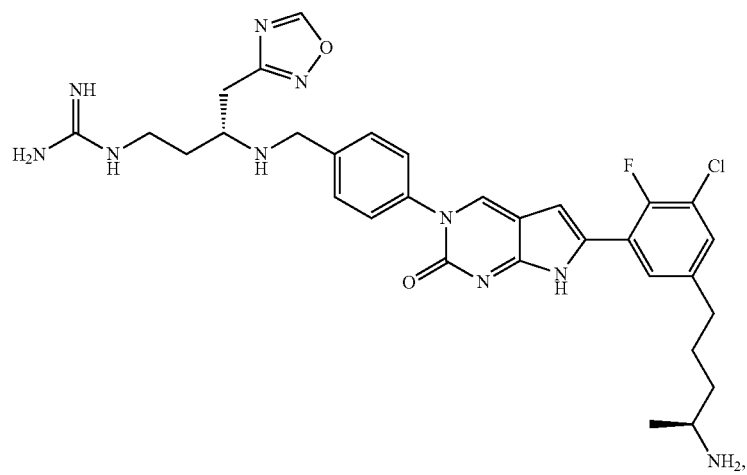
46
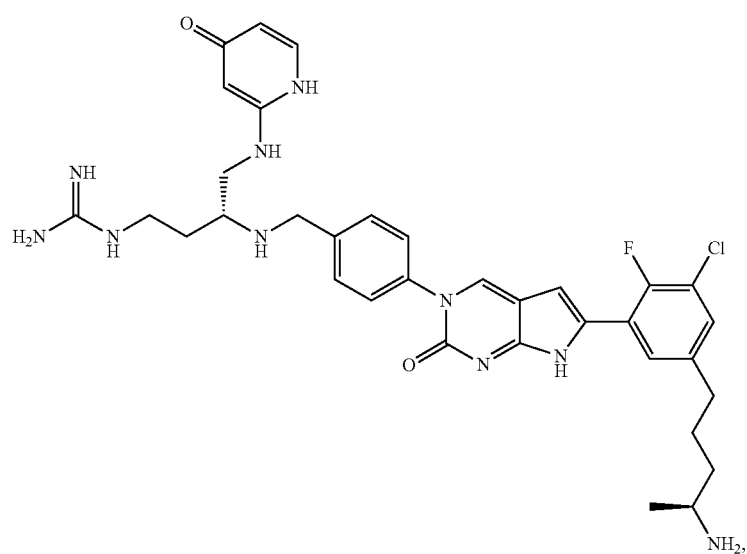
47
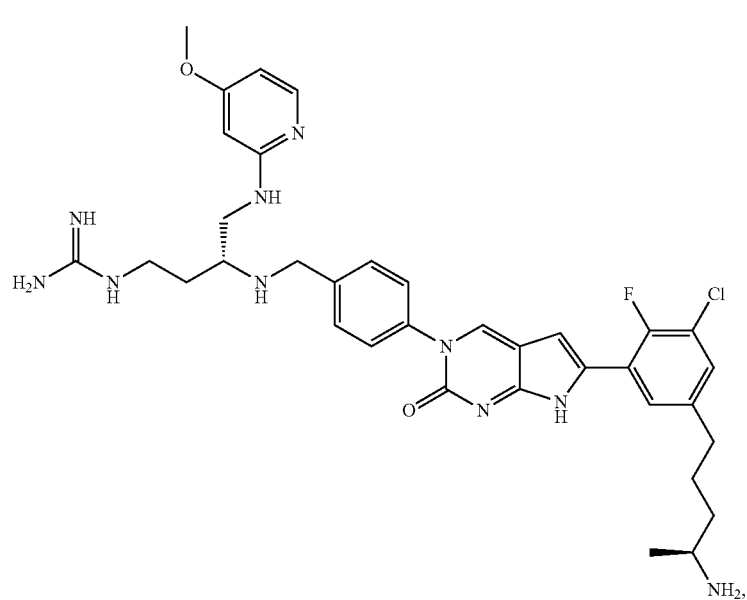

48
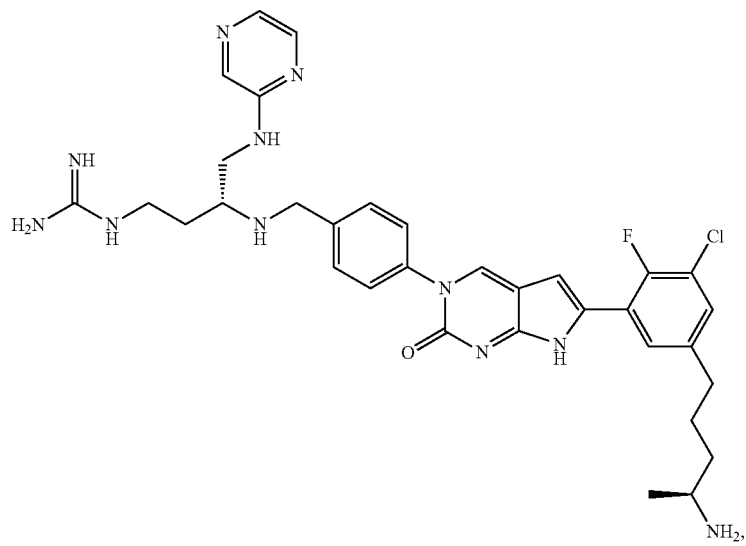
49
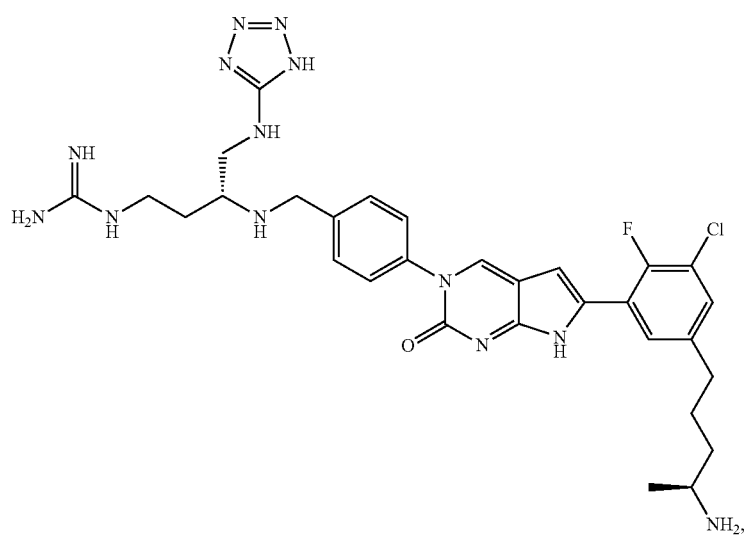
50
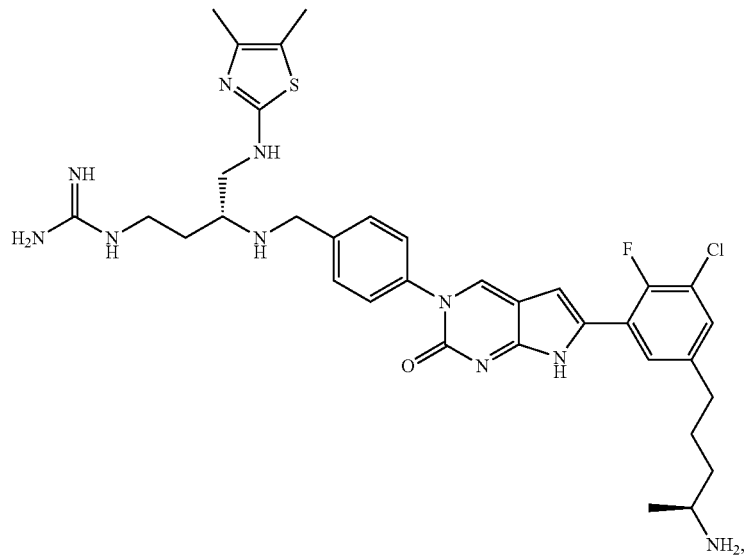

51
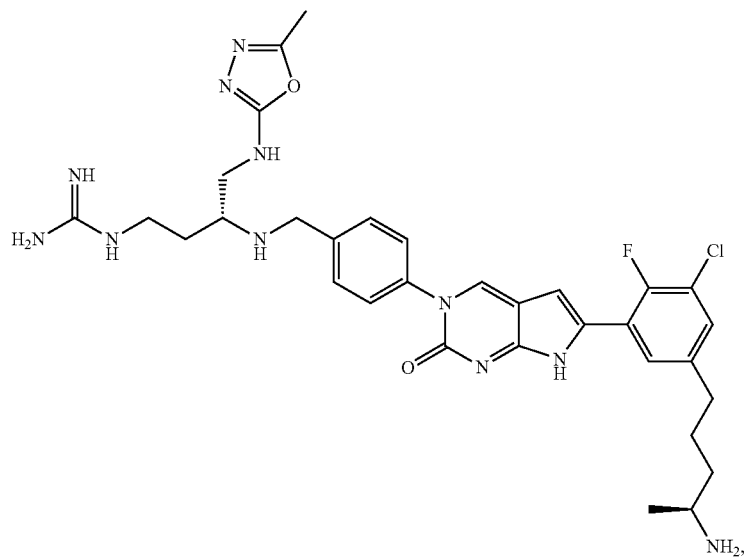
52
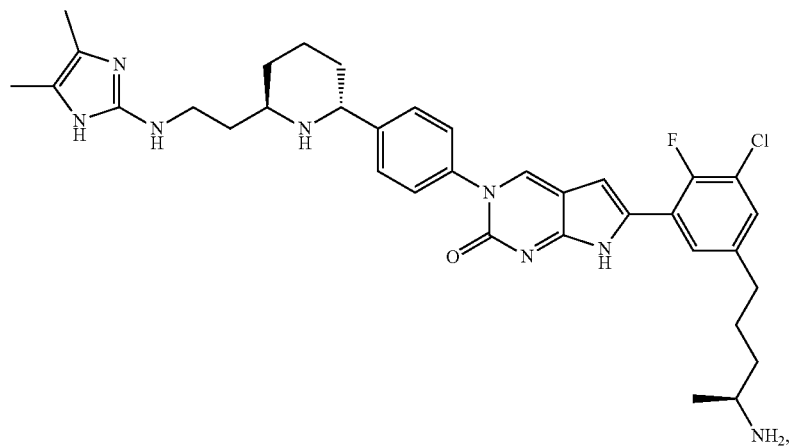
53
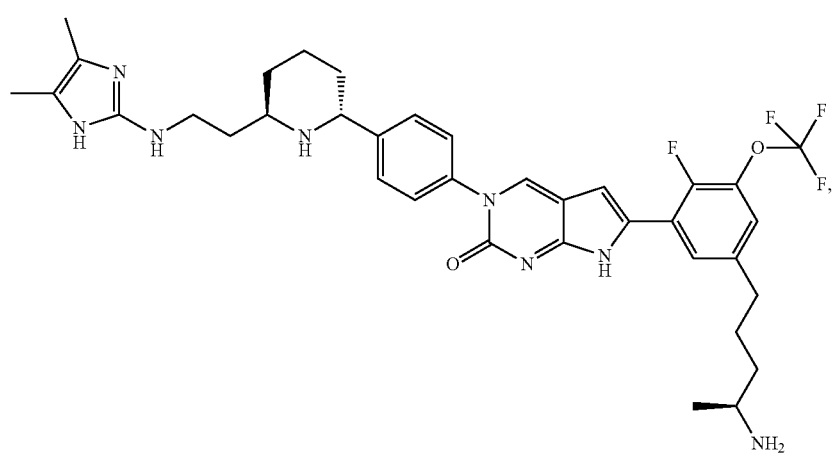

54
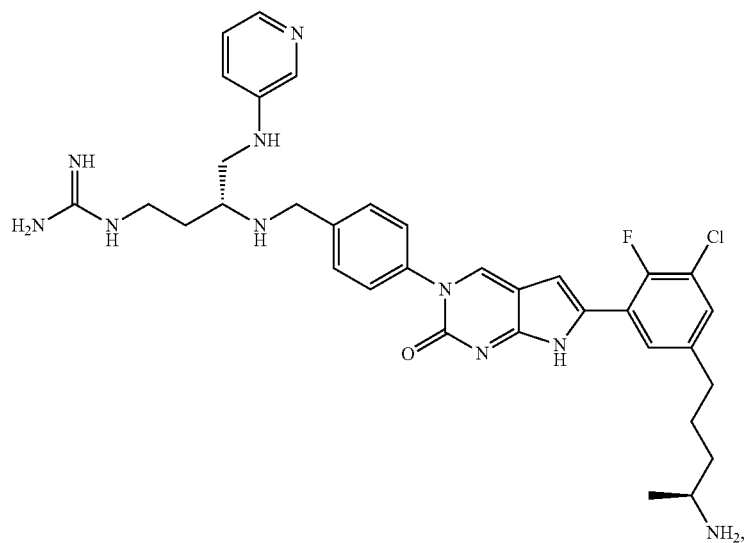
55
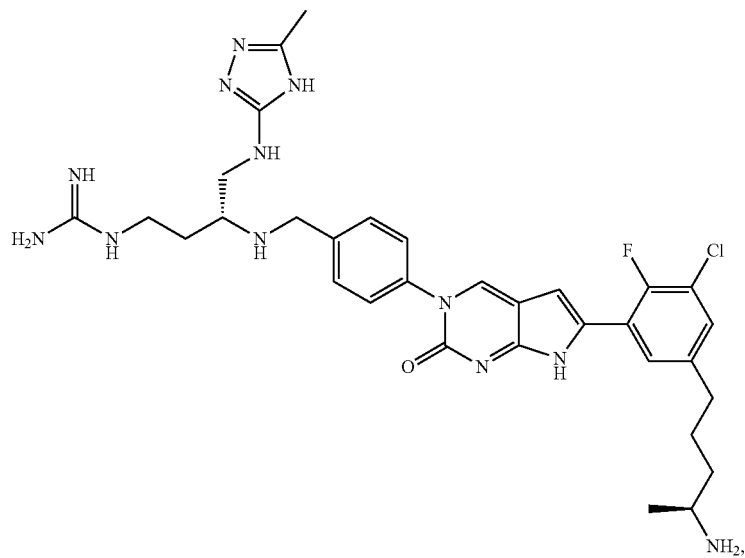
56
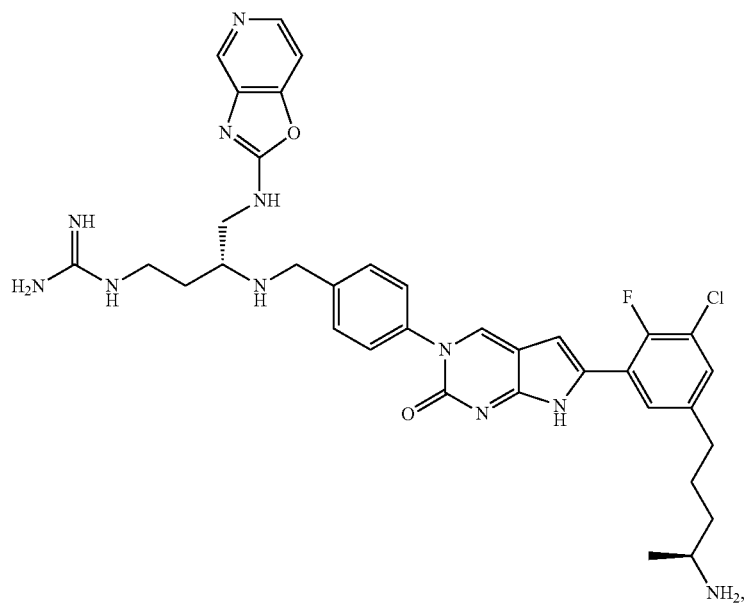

57
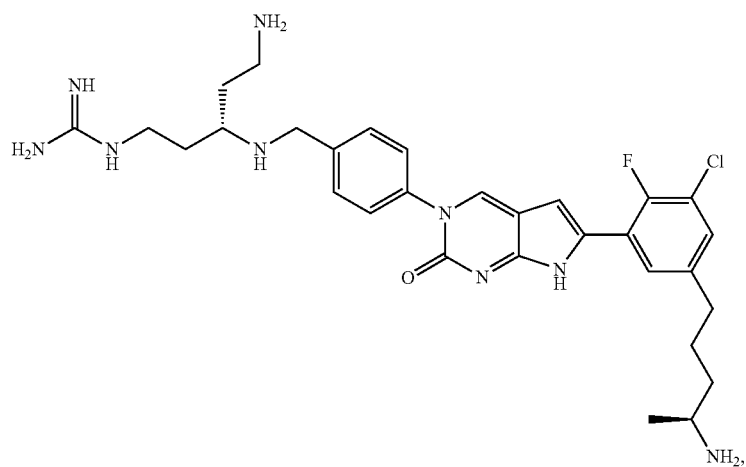
58
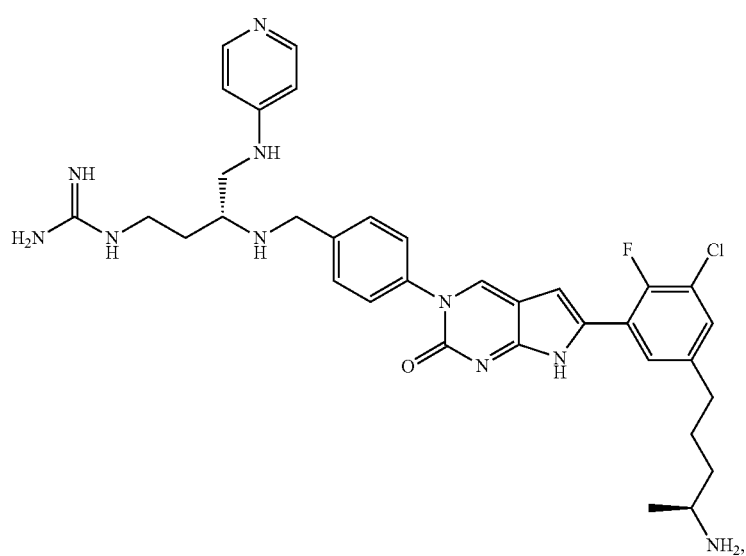
59
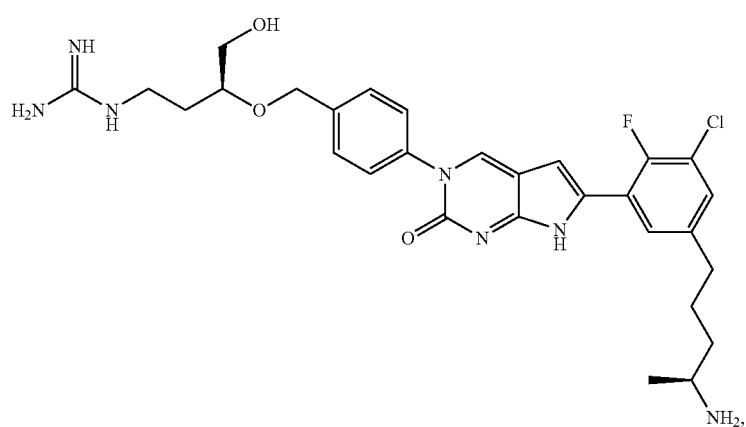

60
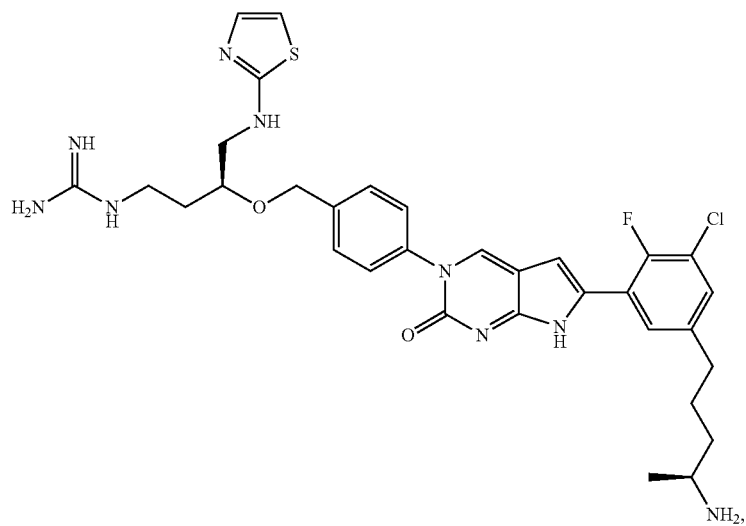
61
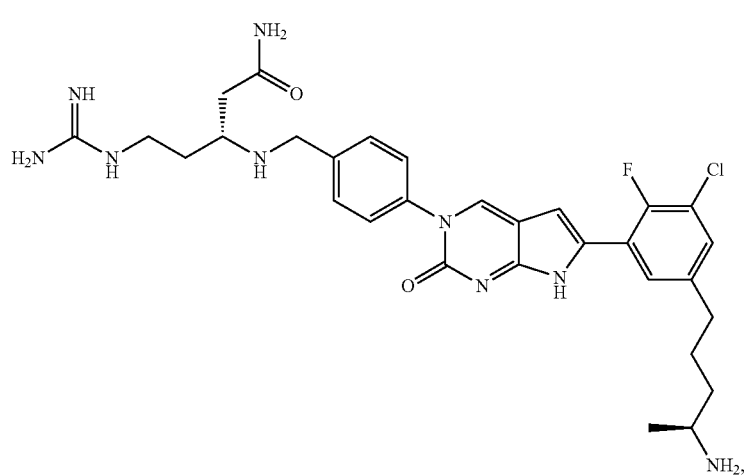
62
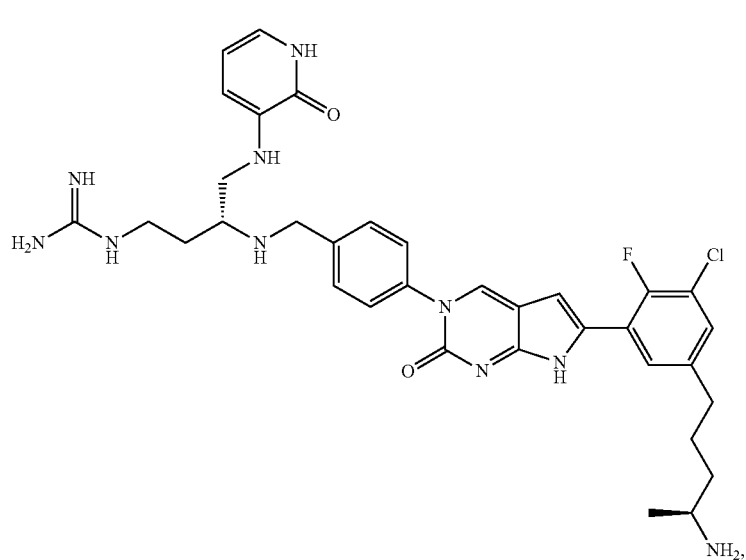

63
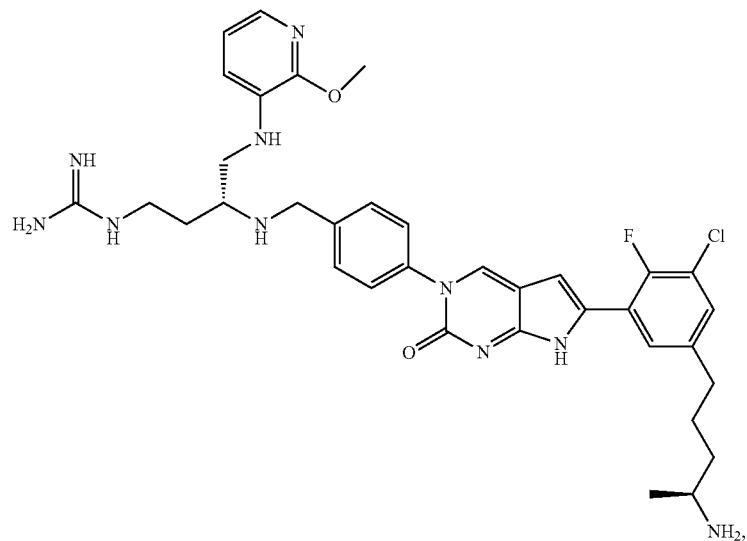
64
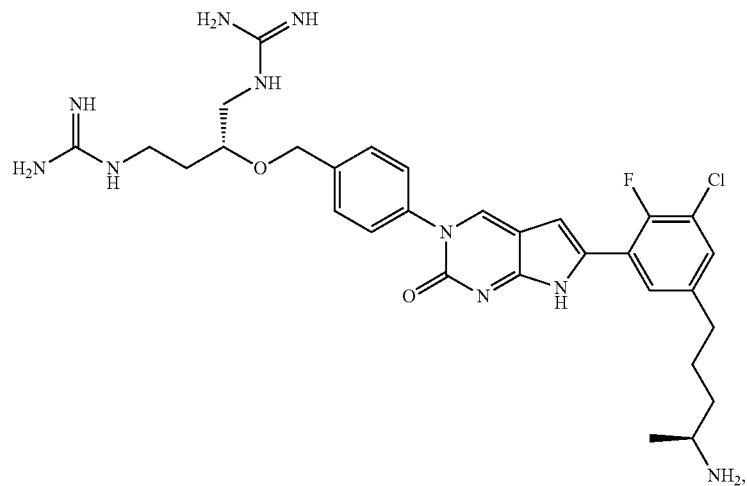
65
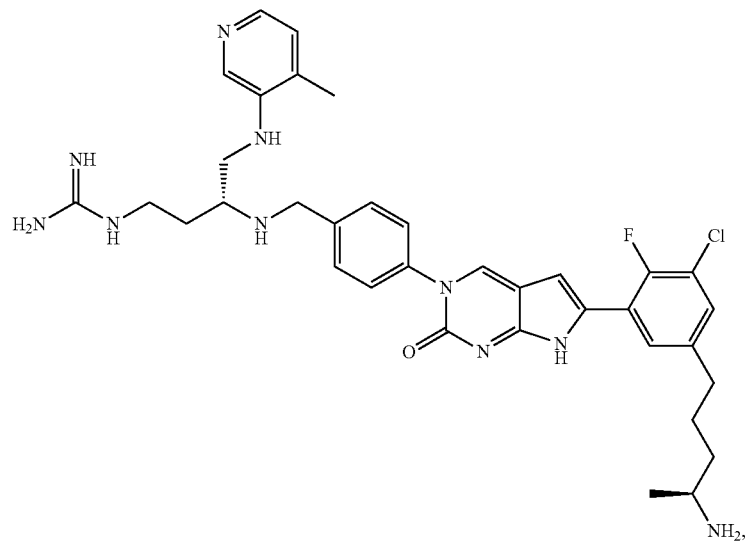

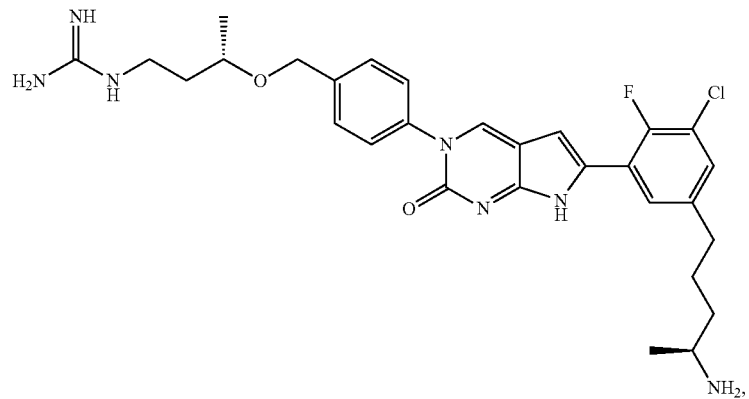
66
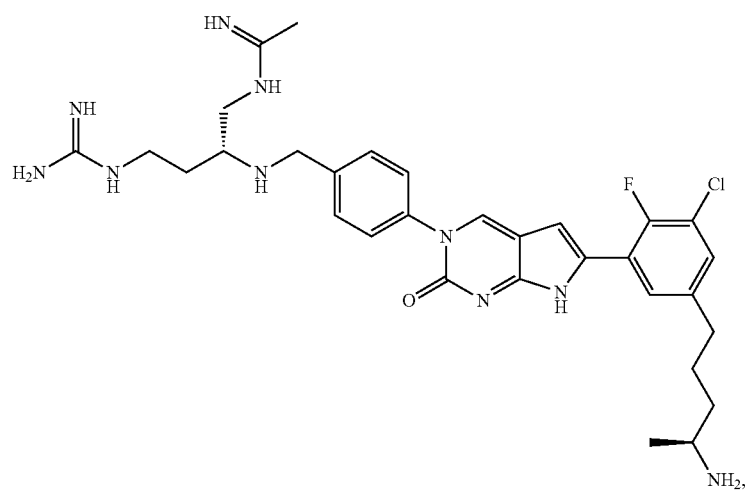
67
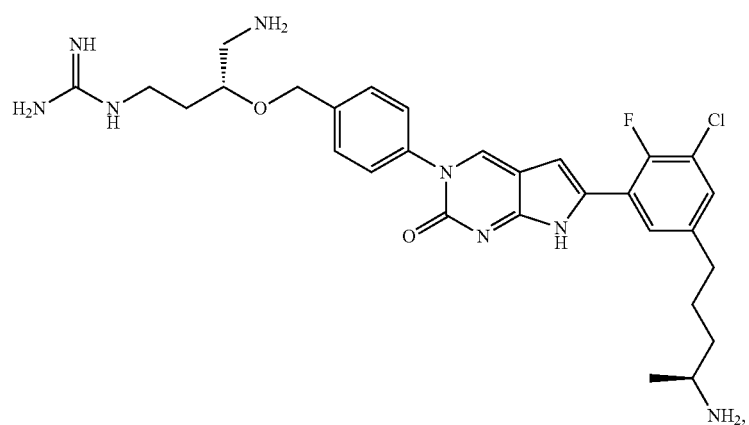
68

-continued
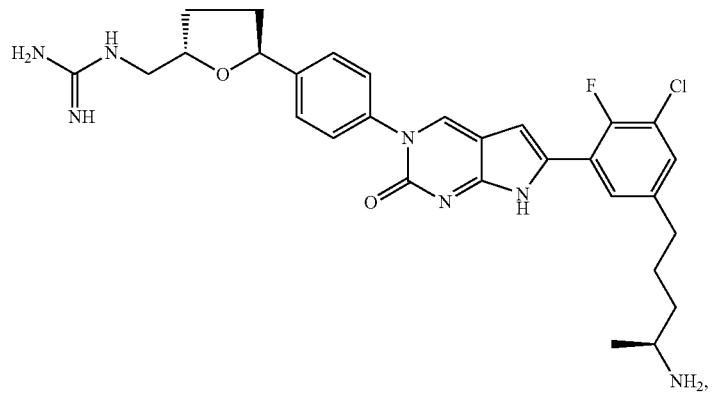
69
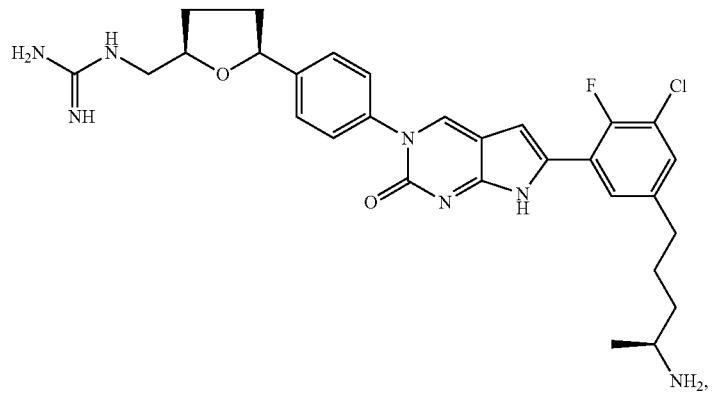
70
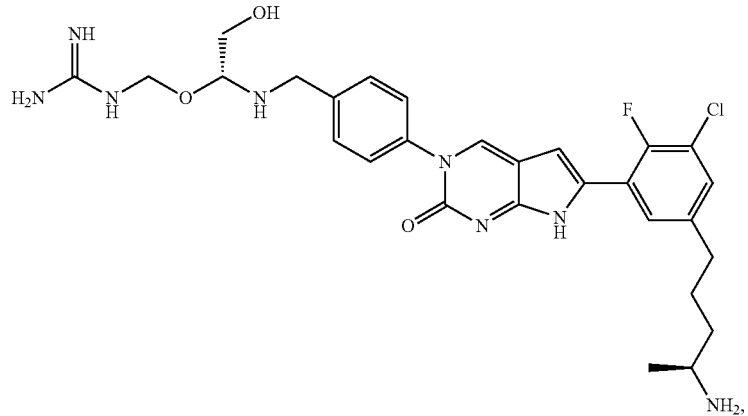
71
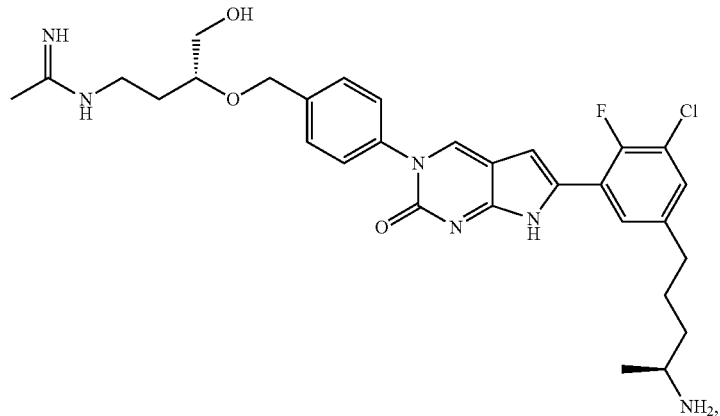
72

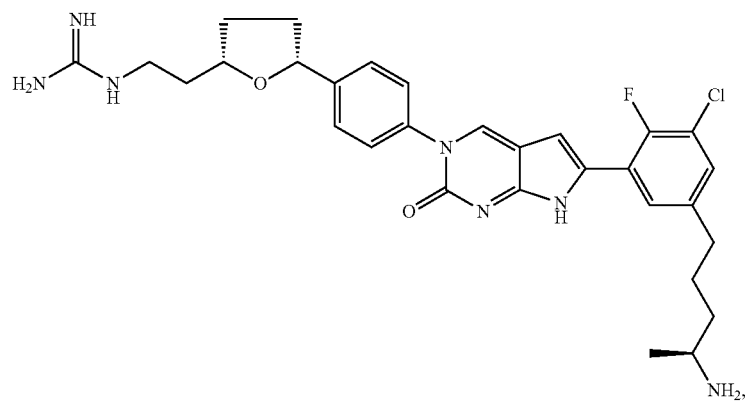
73
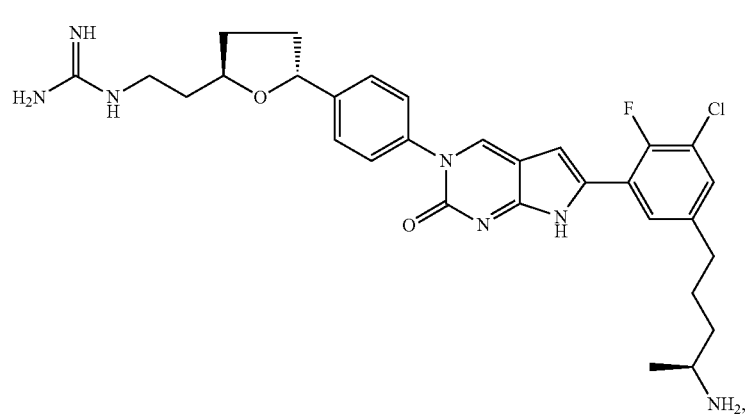
74
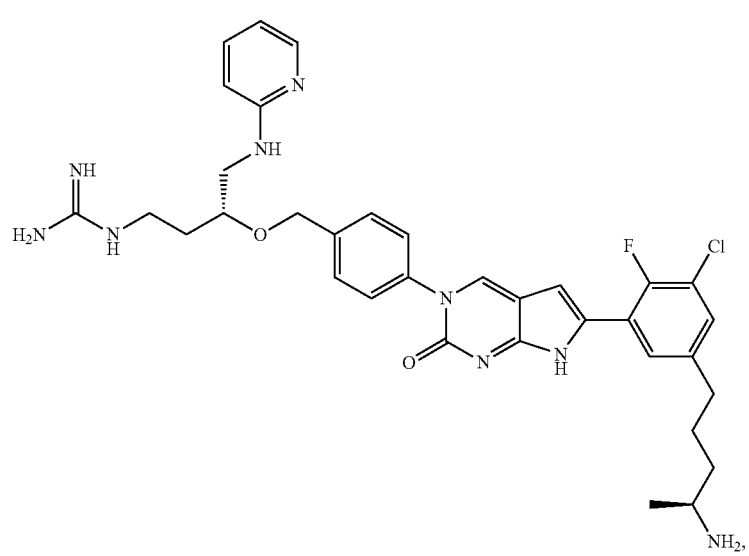
75

76
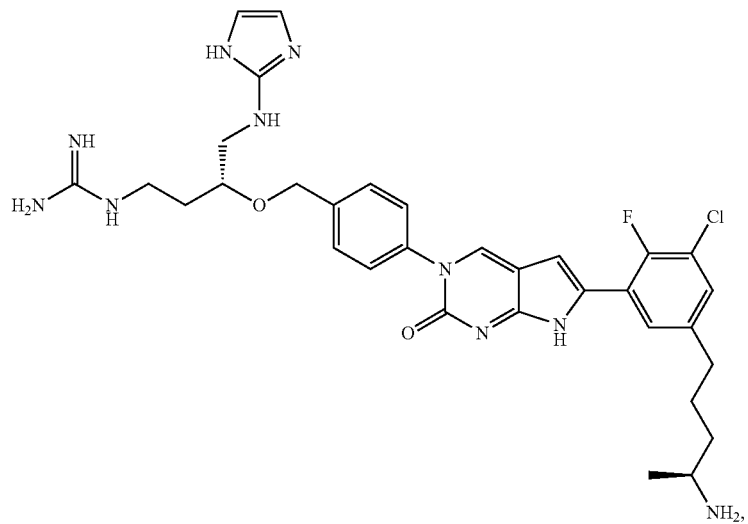
78
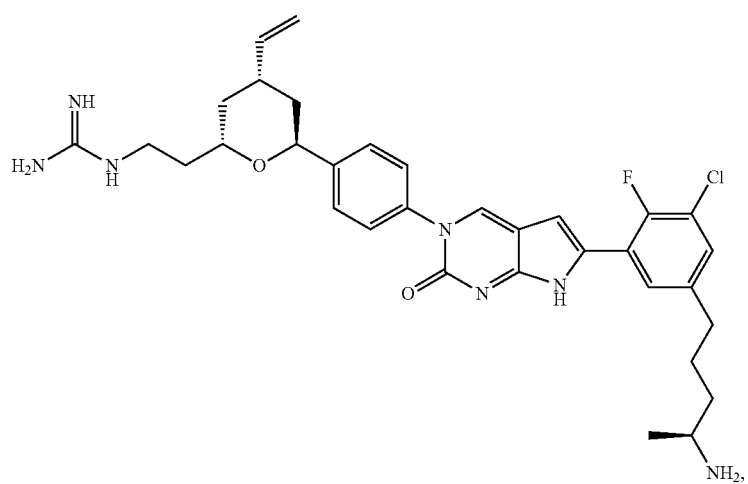
81
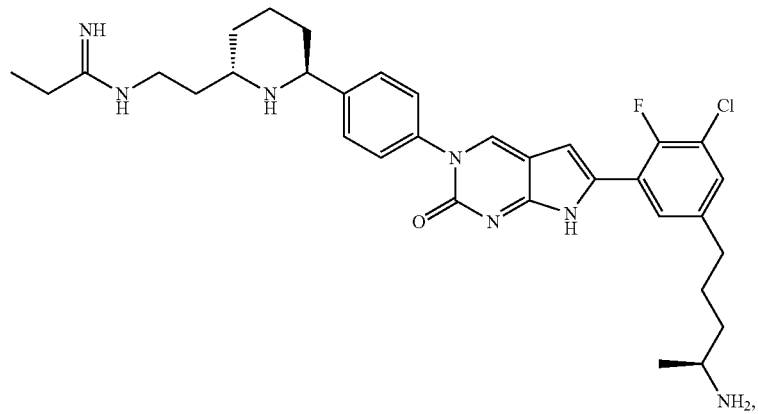

82
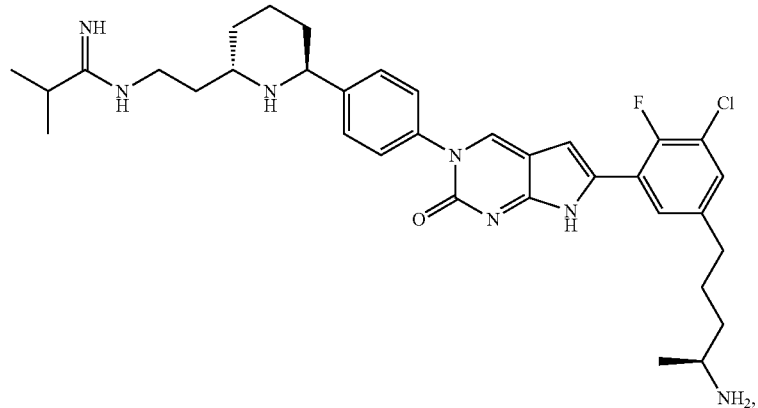
83
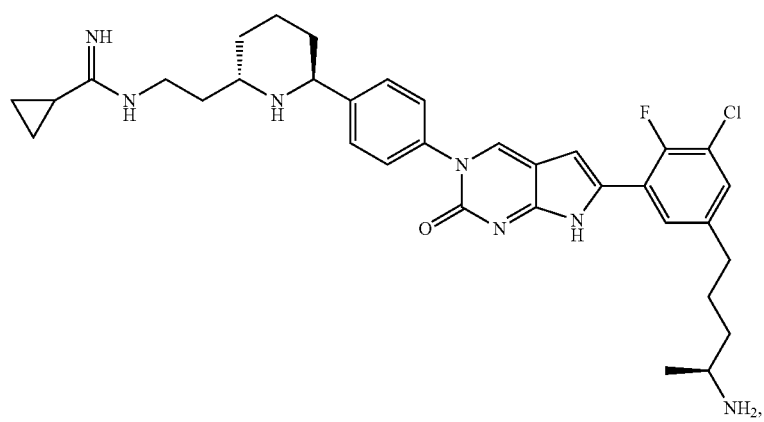
84
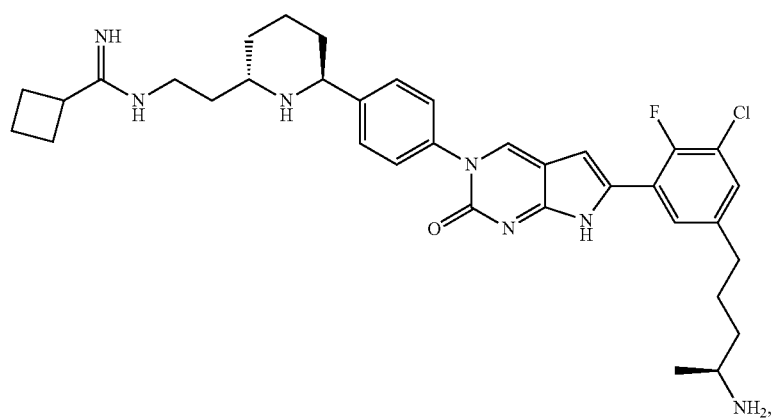

85
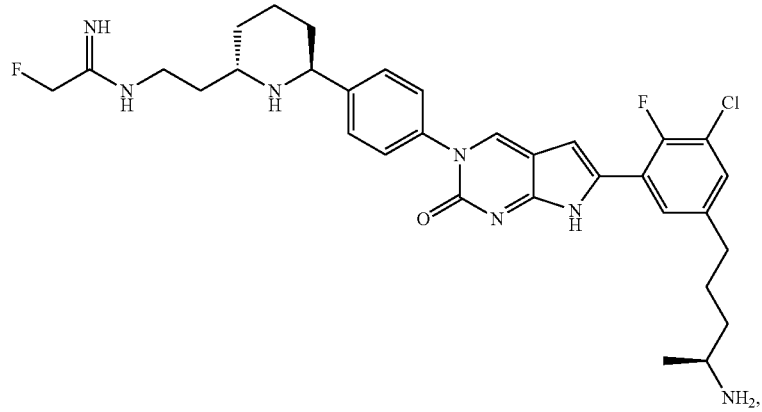
86
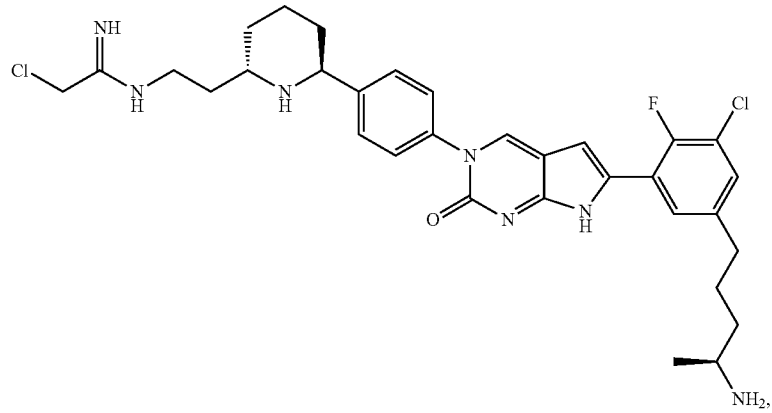
87
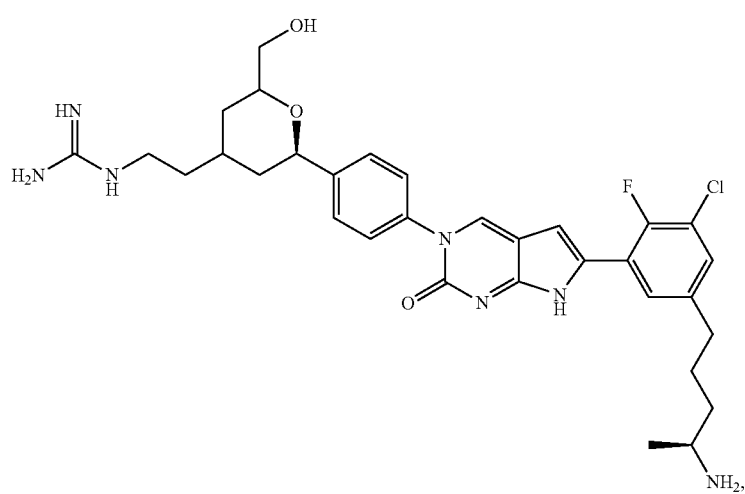

88
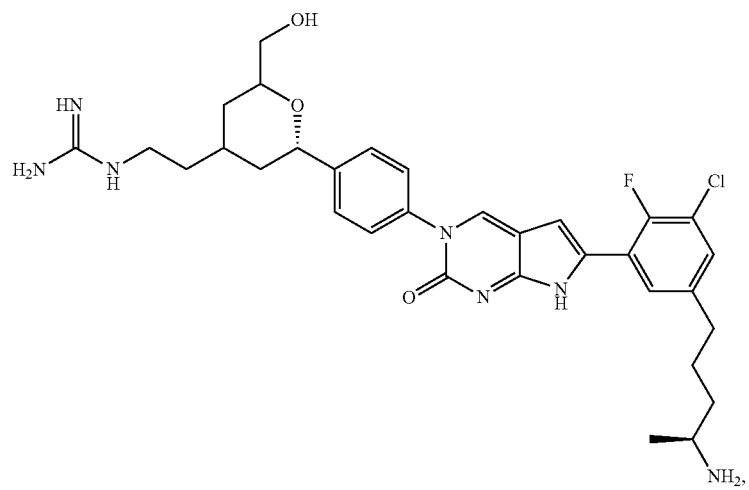
89
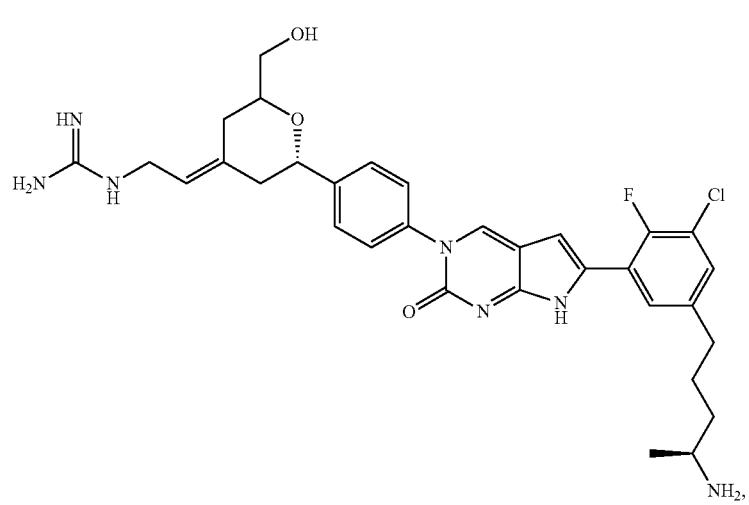
91
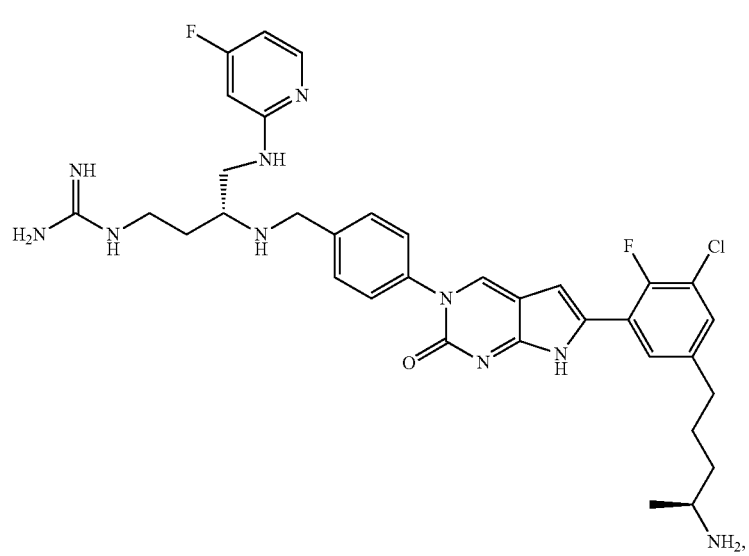

92
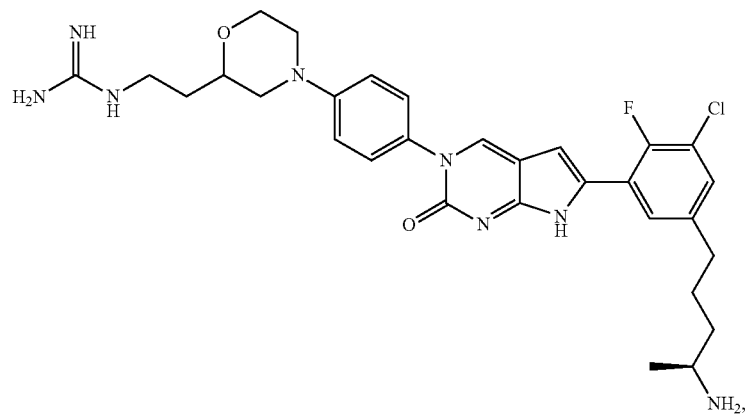
96
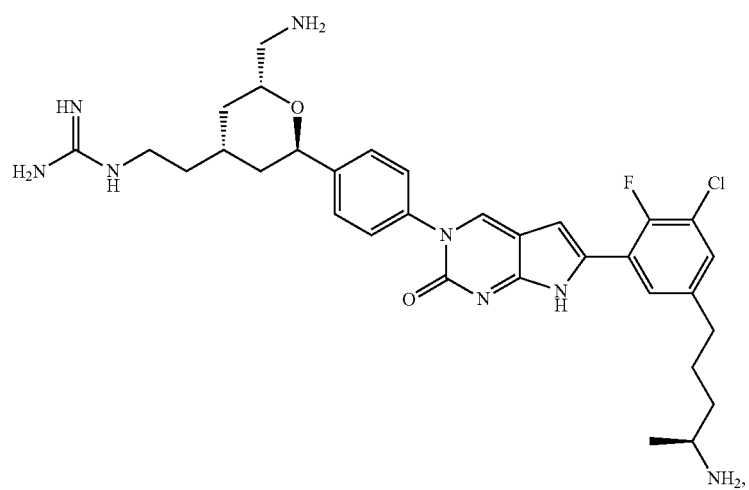
97
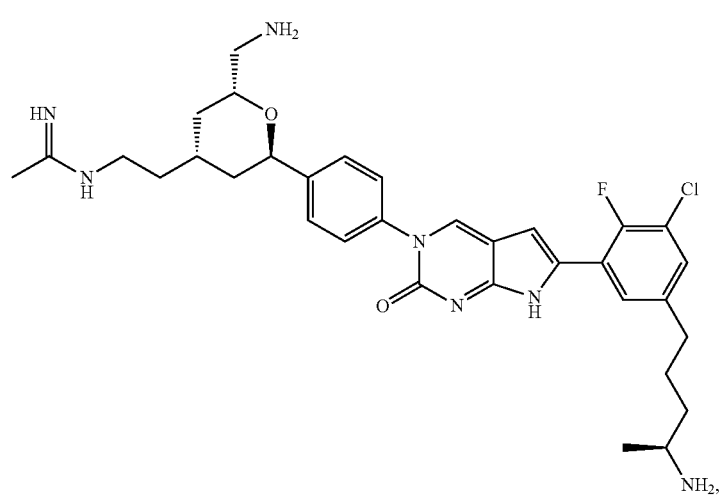

106
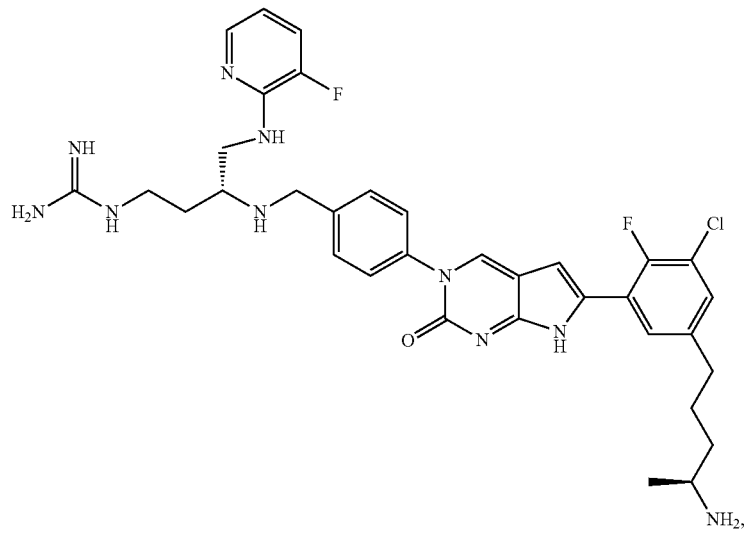
107
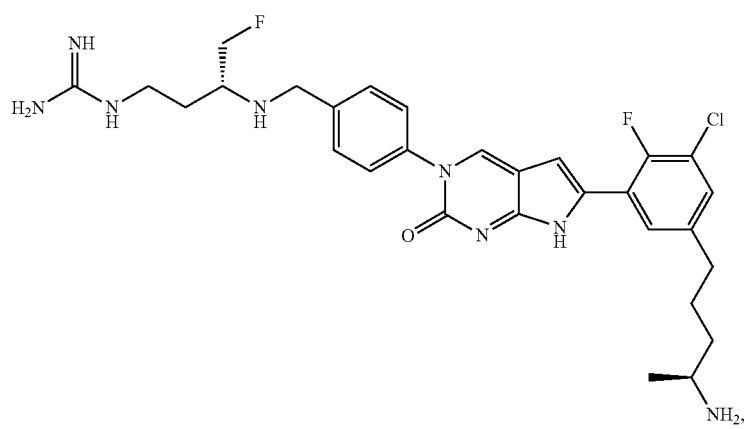
109
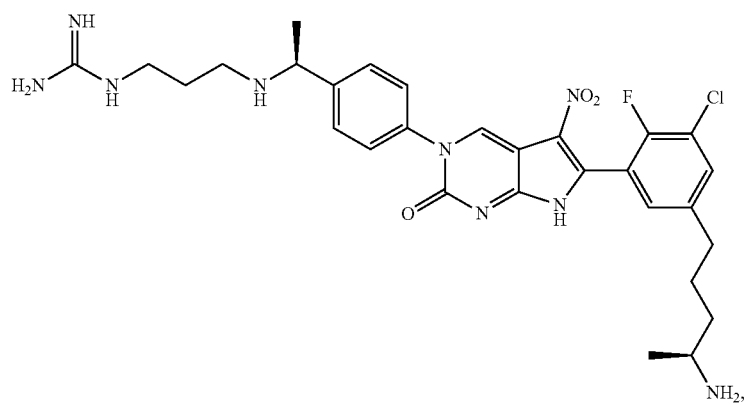

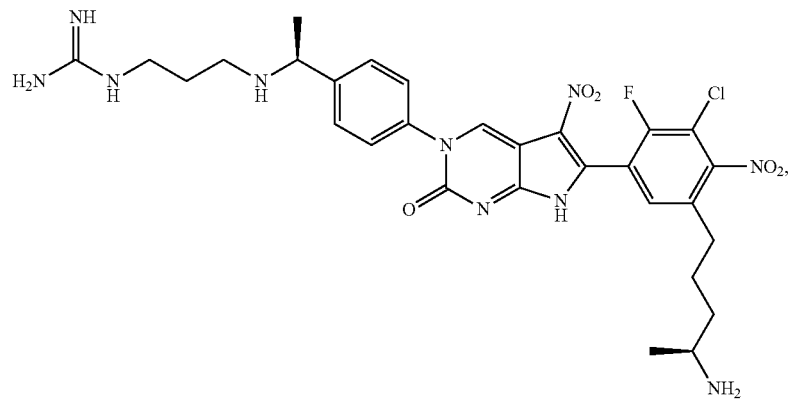
110
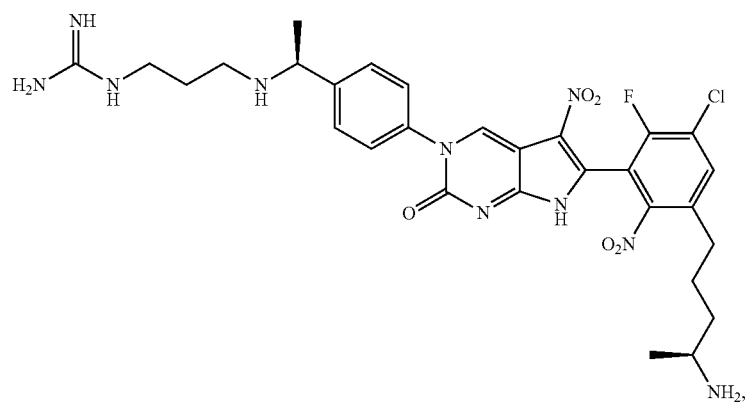
111
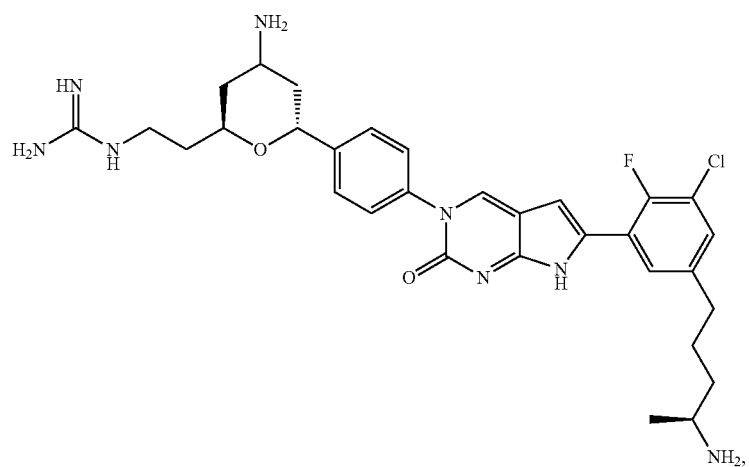
119

120
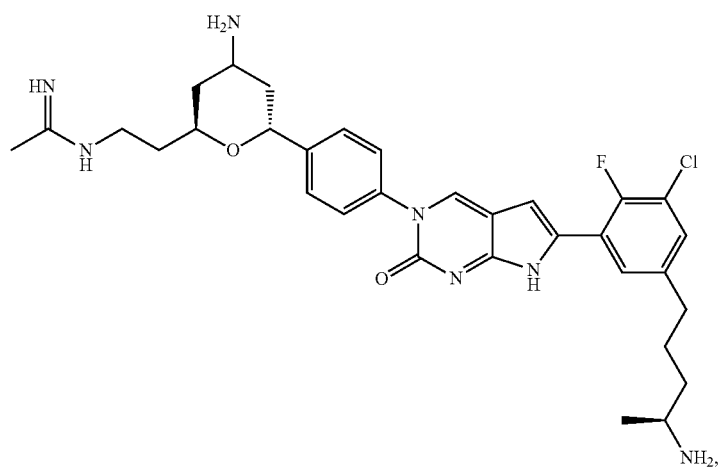
127
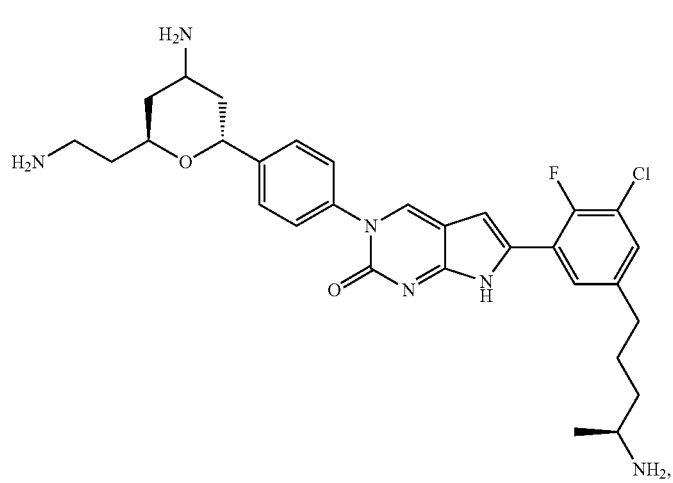
128
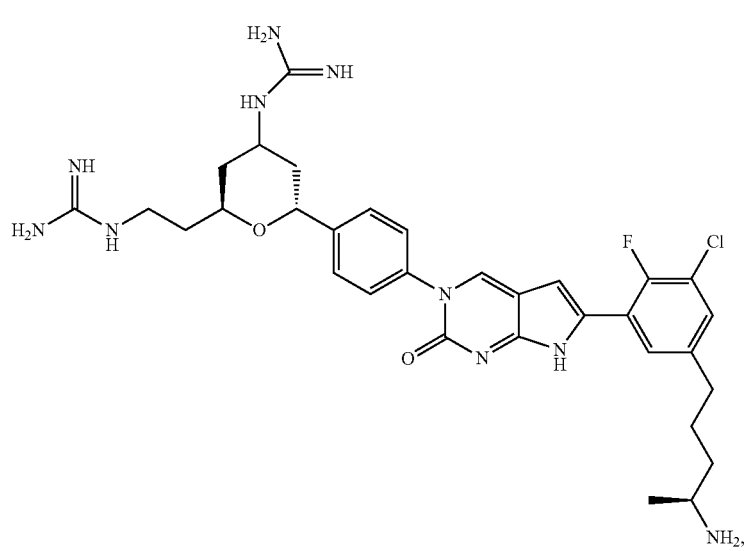

132
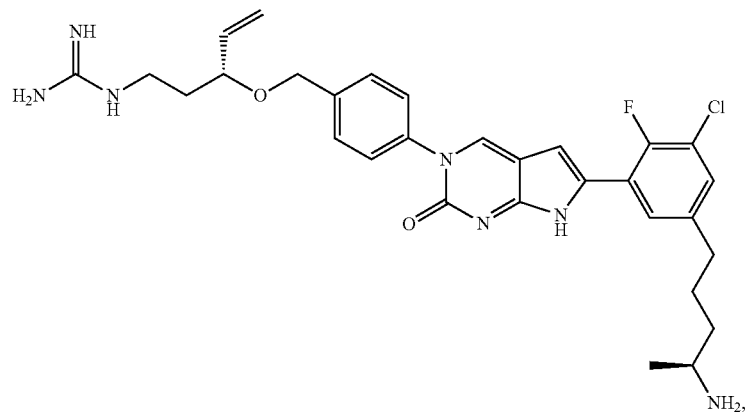
133
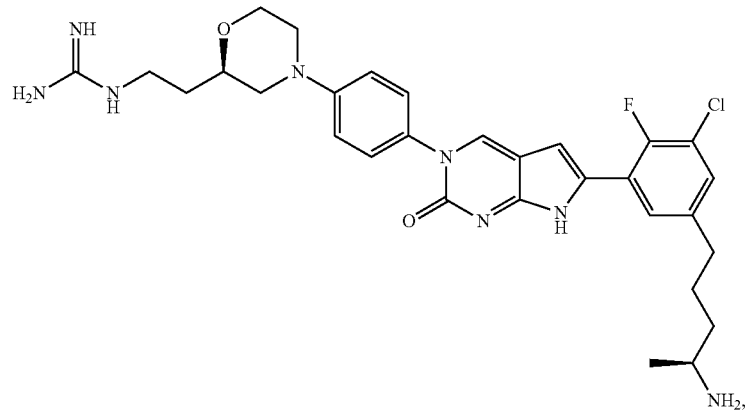
134
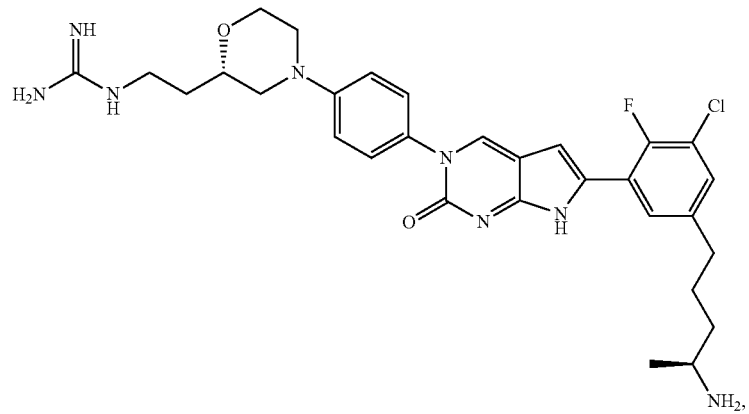

135
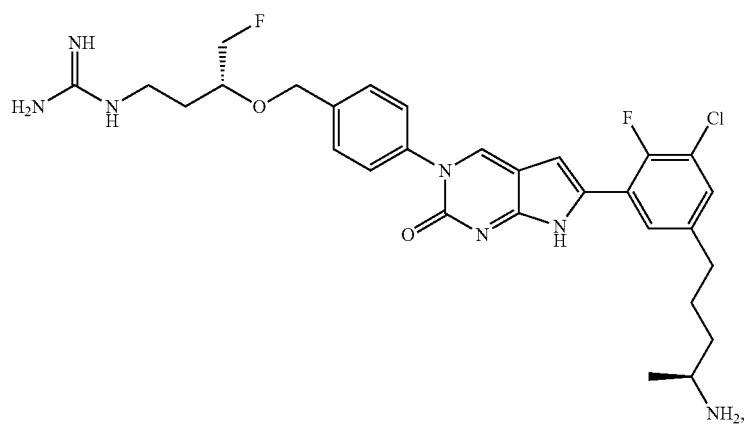
137
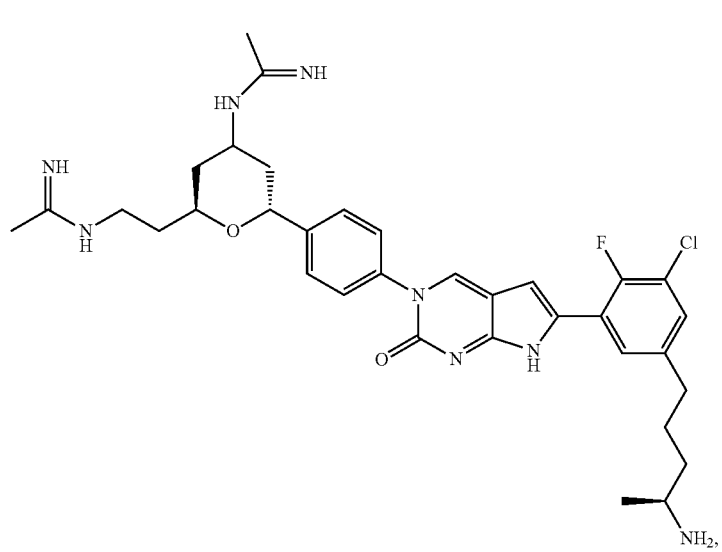
138
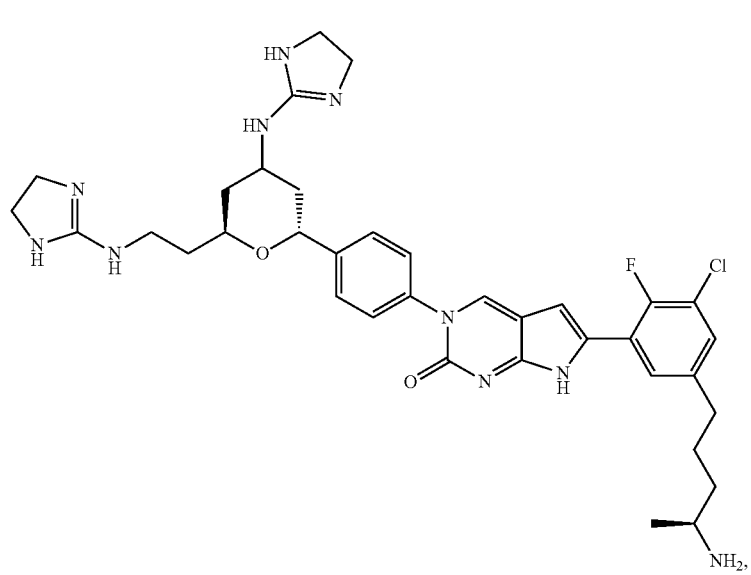

-continued
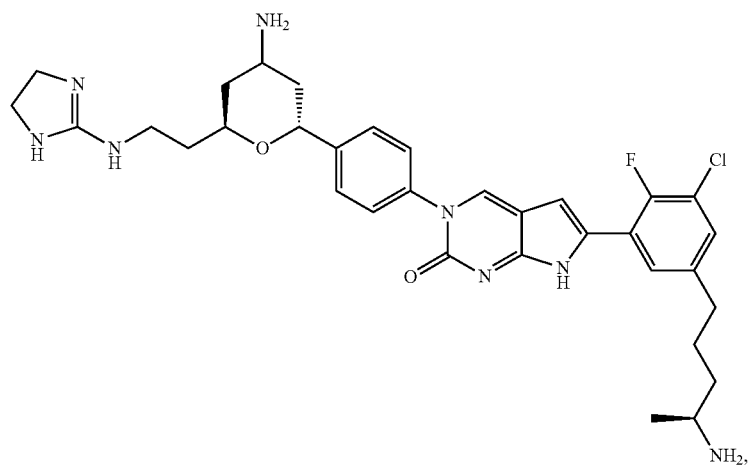
143
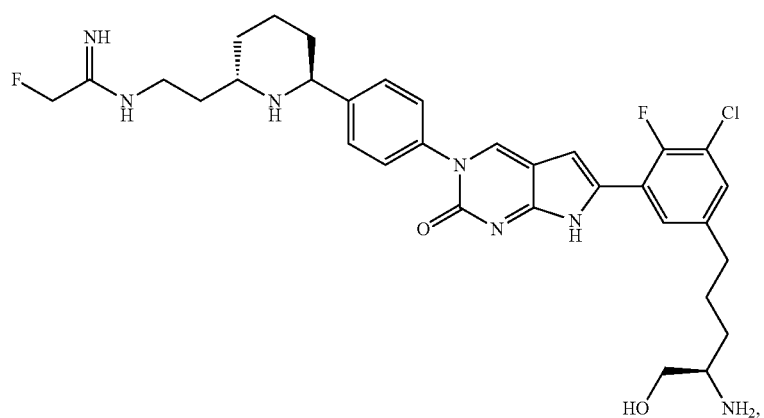
150
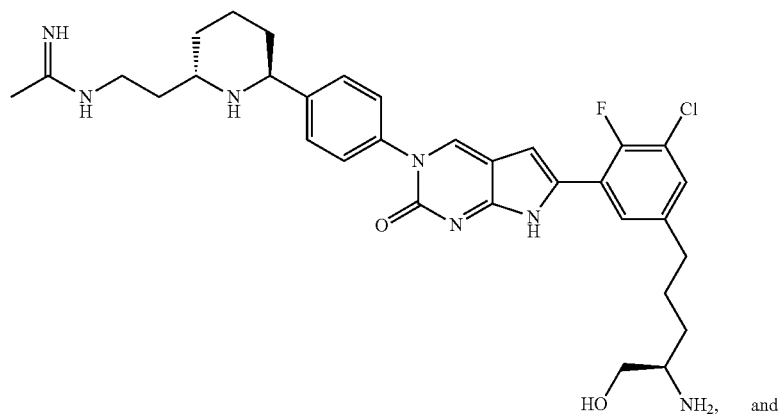
151

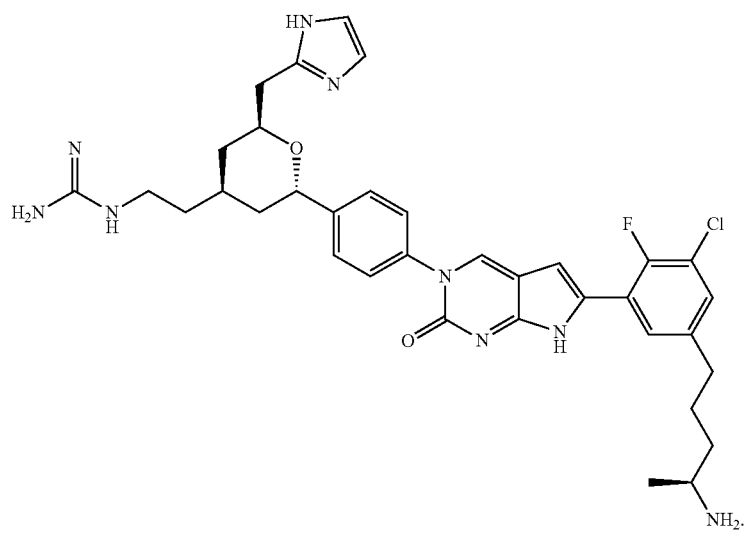

153

43. A pharmaceutical composition comprising a pharmaceutically acceptable carrier and a compound of claim 1, or a tautomer thereof, or a pharmaceutically acceptable salt of said compound or tautomer.

44. A method of treating a microbial infection comprising administering to a subject in need thereof an effective amount of a compound of claim 1, or a tautomer thereof, or a pharmaceutically acceptable salt of said compound or tautomer.

45. A method of reducing the risk of a microbial infection comprising administering to a subject in need thereof an effective amount of a compound of claim 1, or a tautomer thereof, or a pharmaceutically acceptable salt of said compound or tautomer.

46. A method of delaying the onset of a microbial infection comprising administering to a subject in need thereof an effective amount of a compound of claim 1, or a tautomer thereof, or a pharmaceutically acceptable salt of said compound or tautomer.

* * * * *